US009416146B2

(12) United States Patent
Akama

(10) Patent No.: US 9,416,146 B2
(45) Date of Patent: *Aug. 16, 2016

(54) BORON-CONTAINING SMALL MOLECULES AS ANTI-INFLAMMATORY AGENTS

(71) Applicant: ANACOR PHARMACEUTICALS, INC., Palo Alto, CA (US)

(72) Inventor: Tsutomu Akama, Sunnyvale, CA (US)

(73) Assignee: Anacor Pharmaceuticals, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/666,075

(22) Filed: Mar. 23, 2015

(65) Prior Publication Data

US 2015/0291629 A1    Oct. 15, 2015

Related U.S. Application Data

(63) Continuation of application No. 13/915,494, filed on Jun. 11, 2013, now Pat. No. 9,012,431, which is a continuation of application No. 13/236,543, filed on Sep. 19, 2011, now Pat. No. 8,461,135, which is a continuation of application No. 12/399,015, filed on Mar. 5, 2009, now Pat. No. 8,039,450.

(60) Provisional application No. 61/148,731, filed on Jan. 30, 2009, provisional application No. 61/143,700, filed on Jan. 9, 2009, provisional application No. 61/110,903, filed on Nov. 3, 2008, provisional application No. 61/105,990, filed on Oct. 16, 2008, provisional application No. 61/094,406, filed on Sep. 4, 2008, provisional application No. 61/052,637, filed on May 12, 2008, provisional application No. 61/034,371, filed on Mar. 6, 2008.

(51) Int. Cl.
*A61K 31/69* (2006.01)
*C07F 5/04* (2006.01)
*C07F 5/02* (2006.01)

(52) U.S. Cl.
CPC .............. *C07F 5/025* (2013.01); *A61K 31/69* (2013.01); *C07F 5/04* (2013.01)

(58) Field of Classification Search
USPC .............................. 546/13; 558/288; 514/64
See application file for complete search history.

(56) References Cited

U.S. PATENT DOCUMENTS

| 2,260,336 | A | 10/1941 | Prescott et al. |
| 3,686,398 | A | 8/1972 | Kohn et al. |
| 3,873,279 | A | 3/1975 | Singer |
| 4,602,011 | A | 7/1986 | West et al. |
| 4,716,035 | A | 12/1987 | Sampathkamar |
| 4,766,113 | A | 8/1988 | West et al. |
| 4,894,220 | A | 1/1990 | Nabi et al. |
| 4,919,934 | A | 4/1990 | Deckner et al. |
| 5,348,947 | A | 9/1994 | Patel et al. |
| 5,348,948 | A | 9/1994 | Patel et al. |
| 5,591,731 | A | 1/1997 | Kennedy et al. |
| 5,668,258 | A | 9/1997 | Stolowitz |
| 5,688,928 | A | 11/1997 | Stolowitz |
| 5,831,045 | A | 11/1998 | Stolowitz et al. |
| 5,880,188 | A | 3/1999 | Austin et al. |
| 5,962,498 | A | 10/1999 | Driedger et al. |
| 6,083,903 | A | 7/2000 | Adams et al. |
| 6,221,640 | B1 | 4/2001 | Tao et al. |
| 6,306,628 | B1 | 10/2001 | Rothschild et al. |
| 6,369,098 | B1 | 4/2002 | Pershadsingh et al. |
| 6,521,619 | B2 | 2/2003 | Link et al. |
| 6,800,645 | B1 | 10/2004 | Cox et al. |
| 6,855,848 | B2 | 2/2005 | Scherer et al. |
| 7,169,603 | B2 | 1/2007 | Hedley et al. |
| 7,205,425 | B2 | 4/2007 | Shibasaki et al. |
| 7,217,701 | B2 | 5/2007 | Mikoshiba et al. |
| 7,390,806 | B2 | 6/2008 | Lee et al. |
| 7,446,236 | B2 | 11/2008 | Naud et al. |
| 7,465,836 | B2 | 12/2008 | Lee et al. |
| 7,582,621 | B2 | 9/2009 | Baker et al. |
| 7,767,657 | B2 | 8/2010 | Baker et al. |
| 7,816,344 | B2 | 10/2010 | Baker et al. |
| 8,039,450 | B2 * | 10/2011 | Akama et al. ................... 514/64 |
| 8,168,614 | B2 | 5/2012 | Baker et al. |
| 2002/0028831 | A1 | 3/2002 | Manley |
| 2002/0161230 | A1 | 10/2002 | Meudt et al. |
| 2003/0032673 | A1 | 2/2003 | Nagy |
| 2004/0077601 | A1 | 4/2004 | Adams et al. |
| 2004/0224923 | A1 | 11/2004 | Lee et al. |
| 2004/0259842 | A1 | 12/2004 | Mikoshiba et al. |
| 2005/0054644 | A1 | 3/2005 | Lee et al. |
| 2005/0125852 | A1 | 6/2005 | Caenepeel et al. |

(Continued)

FOREIGN PATENT DOCUMENTS

EP    0969531        1/2000
EP    1155698 A1    11/2001

(Continued)

OTHER PUBLICATIONS

Adamczyk-Wozniac, et al., "Benzoxaboroles-Old Compounds with new applications", Journal of Organometalic Chemistry 694;3533-3541 (2009).

Akama, et al., "Discovery and structure-activity study of novel benzoxaborole anti-inflammatory agent (AN2728) for the potential topical treatment of psoriasis and atopic dermatitis", Bioorganic & Medicinal Chemistry Letters, (2009) 19: 2129-2132.

Alley, et al., "Recent Progress on Topical Therapy of Onychomycosis", Expert Opinion Investigate Drugs(Feb. 2007) 16(2): 157-67.

Austin, et al., "Oxaboroles and Salts and their Use of Biocides for Plastics", CAS, vol. 124, pp. 234-024, (1996).

(Continued)

*Primary Examiner* — Charanjit Aulakh
(74) *Attorney, Agent, or Firm* — Morgan, Lewis & Bockius LLP

(57) ABSTRACT

Compounds and methods of treating anti-inflammatory conditions are disclosed.

43 Claims, 141 Drawing Sheets

(56) References Cited

U.S. PATENT DOCUMENTS

| | | | |
|---|---|---|---|
| 2005/0239170 | A1 | 10/2005 | Hedley et al. |
| 2006/0009386 | A1 | 1/2006 | Stossel et al. |
| 2006/0222671 | A1 | 10/2006 | Weidner |
| 2006/0234981 | A1 | 10/2006 | Baker et al. |
| 2007/0155699 | A1 | 7/2007 | Baker et al. |
| 2007/0286822 | A1 | 12/2007 | Sanders et al. |
| 2007/0293457 | A1 | 12/2007 | Baker et al. |
| 2009/0227541 | A1 | 9/2009 | Baker et al. |
| 2010/0048570 | A1 | 2/2010 | Kim et al. |
| 2010/0256092 | A1 | 10/2010 | Xia et al. |

FOREIGN PATENT DOCUMENTS

| | | |
|---|---|---|
| EP | 1 444 981 A1 | 8/2004 |
| WO | WO 9533754 | 5/1995 |
| WO | WO 9622023 A1 | 7/1996 |
| WO | WO 9812206 A1 | 3/1998 |
| WO | WO 0027822 | 5/2000 |
| WO | WO 0044387 A1 | 8/2000 |
| WO | WO 0075142 A2 | 12/2000 |
| WO | WO 0114578 A1 | 3/2001 |
| WO | WO 0149303 A1 | 7/2001 |
| WO | WO 0187846 A2 | 11/2001 |
| WO | WO 0244184 | 6/2002 |
| WO | WO 03033002 A1 | 4/2003 |
| WO | WO 03059916 A2 | 7/2003 |
| WO | WO 2004056322 A2 | 7/2004 |
| WO | WO 2005013892 A3 | 2/2005 |
| WO | WO 2005123094 A2 | 12/2005 |
| WO | WO 2006007384 | 1/2006 |
| WO | WO 2006062731 A1 | 6/2006 |
| WO | WO 2006079843 A1 | 8/2006 |
| WO | WO 2006089067 A2 | 8/2006 |
| WO | WO 2006096131 A1 | 9/2006 |
| WO | WO 2007022437 A2 | 2/2007 |
| WO | WO 2007078340 A2 | 7/2007 |
| WO | WO 2007095638 A2 | 8/2007 |
| WO | WO 2007146965 A2 | 12/2007 |
| WO | WO 2008157726 A1 | 12/2008 |
| WO | WO 2009111676 A2 | 9/2009 |
| WO | WO 2009140309 A2 | 11/2009 |
| WO | WO 2010028005 A1 | 3/2010 |
| WO | WO 2010045503 A | 4/2010 |
| WO | WO 2010045505 A1 | 4/2010 |

OTHER PUBLICATIONS

Bailey, et al., "Boron-Containing Antibacterial Agents: Effects on Growth and Morphology of Bacteria Under Various Culture Conditions," Antimicrobial Agents and Chemotherapy, 17(04):549-553, (Apr. 1980).
Baker, et al., "Discovery of New Boron-Containing Antifungal Agent, 5-Fluoro-1,3-dihydro-1-hydroxy-2, 1-benzoxaborole (AN2690) for Potential Treatment of Onychomoycosis", Journal of Medicinal Chemistry, vol. 49, No. 15; pp. 4447-4450, (Jul. 27, 2006).
Baker, et al., "Identification of a Novel Boron-Containing Antibacterial Agent (AN0128) with Anti-inflammatory activity, for the Potential Treatment of Cutaneous Diseases", Bioorganic & Medicinal Chemistry Letters (2006) 16: 5963-5937.
Baker, et al., "Progress on New Therapeutics for Fungal Nail Infections", Annual Reports in Medicinal Chemistry, vol. 40: pp. 323-335, (2005).
Baker, et al., "Synthesis of Isotopically labelled (3-$^{14}$C)- and (3,3-$^2$H$_2$)-5-fluoro-1,3-dihydro-1-hydroxy-2,1-benzoxaborole (AN2690), a new antifugal agent for the potential treatment of onychomycosis", J. Label Compd Radiopharm, (2007) 50:245-250.
Bessis, N., "Gene Therapy for Rheumatoid Arthritis," J. Gene Med, vol. 4; pp. 581-591 (2002).
Brown, et al., "Chiral Synthesis Via Organoboranes. 35. Simple Procedures for the Efficient Recycling of the Terpenyl Chiral Auxiliaries and Convenient Isolation of the Homoallylic Alcohols in Asymmetric Allyl- and Crotylboration of Aldehydes," J. Org. Chem., vol. 57, No. 24; pp. 6608-6614, (1992).

Cairns, et al., "Derivatives of 1,4-Xylene-2,5-diboronic acid and 1,4-xylene-2-boronic acid", J. Org. Chem. vol. 29; pp. 2810-2812, (1964).
Chander, et al. "Prevalence of Fungal Corneal Ulcers in Northern India", Infections, vol. 22, No. 3; pp. 207-209, (1994).
Chemical Abstracts Registry No. 845302-09-2, Entered STN Mar. 11, 2005.
Cui, et al., "Organoboron Compounds with an 8-Hydroxyquinolato Chelate and Its Derivatives: Substituent Effects on Structures and Luminescence," Inorganic Chemistry, vol. 44, No. 03; pp. 601-609, (Feb. 7, 2005).
Cusack, S., et al., "The 2 A Crystal Structure of leucyl-tRNA Synthetase and its Complex with a Leucyl-Adenylate Analogue." EMBO Journal, vol. 19; pp. 2351-2361, (2000).
Dale, et al., "Substituted Styrenes VIII Syntheses and some Reactions of the Vinylbenzeneboronic Acids" J. Org. Chem. vol. 27; pp. 2598-2603, (Jan. 1, 1962).
Denis, "Pharmacology 1104 Lecture: Drug Classifications & Characteristics of Antimicrobials" (2003).
Dian, "International Nomenclature of Organics", China Petrochemical Press, 1st Edition; 50-51 (Jan. 21, 2004).
Farfan, et al., "Through-Bond Modulation on N-B Ring Formation Shown by NMR and X-Ray Diffraction Studies of Borate Derivatives of Pyridyl Alcohols," J. Chem. Soc. Perkin Trans., vol. 2; pp. 527-532 (1992).
Ferrer, "Targeting Aminocytl-tRNA Synthetases for the Treatment of Fungal Infections", Drug News Perspective, vol. 19, No. 6; pp. 347-348, (Jul./Aug. 2006).
Fungicide: Definition from Answer.com, (1998).
Goodman, et al., "Goodman & Gilman's Manual of Pharmacology and Therapeutics" Chapter 40;681-694 (2008).
Grassberger, et al., "Degradation of 1,2-dihydro-1-hydroxy-2-(organosulfonyl)2,3,1-benzodiasaborines and -thieno[3,2-d][1,,3]diazaborines in Alkaline Aqueous Solutions", Liebigs Annalen Der Chemie, vol. 4; pp. 683-688, (1985).
Guo-Zheng, et al., "Single Site Transarylation of 2,2'-Dimetalized-1,1'-Binaphthyl to Aminocloroborates and Synthesis of 2-Binaphthyl Boron Compounds," Youji Huaxue/Organic Chemistry, Science Press, vol. 16, No. 02; pp. 139-144, (1996) (English Abstract).
Haynes, et al., "Arylboronic Acids VIII. Reactions of boronphthalide" J. Org. Chem. vol. 29, No. 11; pp. 3229-3233, (1964).
Hauck, et al., "Preparation and Anticonvulsant Activity of Some Arydialkkylsuccinimides" Research Lab of Parke Davis Co. (1967).
He, et al., "Small-Molecule Inhibition of TNF-alpha", Science, vol. 310, No. 5750; pp. 1022-1025, (Nov. 11, 2005).
Hui, et al., "In Vitro Penetration of a Novel Oxaborole Antifungal (AN2690) into the Human Nail Plate", Journal of Pharmaceutical Sciences (2007) 96(10): 2622-2631.
Lampe, et al., "Synthesis and Protien Kinase Inhibitory Activity of Balanol Analogues with Modified Benzophenone Subunits", J. Med. Chem., vol. 45(12); pp. 2624-2643, (2002).
Lee, K., et al., "Molecular Study of the Editing Active Site of Escherichia coli Leucyl-tRNA Synthetase: Two Amino Acid Binding Site in the Editing Domain", vol. 54; pp. 693-704, (2004).
Lennarz, et al., "Arylboronic Acids. IV. Reactions of Boronophthalide" J. Am. Chem. Soc. vol. 82; pp. 2172-2175, (1960).
Li, et al., "An Improved Protocol for Preparation of 3-Pyridyl- and Some Arylboronic Acids", J. Org. Chem., vol. 67; pp. 5394-5397, (2002).
Luan, et al., "Inhibition of Experimental Periodontitis by a topical boron-base antimicrobial" J Dent. Res, 87(2):148-152 (2008).
Koster, et al., "Cyclisierugen von Bor-Stickstoff-Verbindugen in der Hietz" Liebigs Ann. Chem., vol. 720; pp. 23-31, (1968).
Koster, et al., "Boron Compounds, XXXIX. Alkenoxy(diorgany)boranes Substituted at the Alkeonxy Group from 2-methylacrolein and triorganylboranes," Justus Liebigs Annalen Der Chemie, No. 06; pp. 1116-1134, (1976).
McMillin, et al., "Systemic Aspects of Psoriasis: An Integrative Model Based on Intestinal Etiology", Int. Med. vol. 2, Issue 2/3, (1999).

(56) References Cited

OTHER PUBLICATIONS

Moeder, et al., "Kinetic Analysis of the Asymmetric Amplification exhibited by B-chlorodiisopinocampheylborane," Journal of Physical Organic Chemistry, vol. 17, No. 4; pp. 317-324, (Apr. 2004).
Morissette, et al., "High-throughput Crystallization: Polymorphs, Salts, Co-Crystals and Solvates of Pharmaceutical Solids", Advanced Drug Delivery Reviews, vol. 56; pp. 273-300, (2004).
Mudran, "Drug Delivery to the Nail Following Topical Application", International Journal of Pharmaceutics, vol. 236: pp. 1-26, (2002).
Patani, et al., "Bioisosterism: A Rational Approach to Drug Design", Chem. Rev., vol. 96; pp. 3147-3176 (1996).
Perola, E., et al., "Successful Virtual Screening of a Chemical Database for Farnesltransferase Inhibitor Leads." vol. 43; pp. 401-4008, (2000).
Qin, et al., "Luminescent Organoboron Quinolate Polymers," Journal of the American Chemical Society, vol. 126, No. 22; pp. 7015-7018, (Jun. 9, 2004).
Qin, Clinical Mycology, Fudan Press, Shanghai Medical University Press, pp. 92, 111, 340-341, 365, 437 and 487 (2001) With English Translation.
Rock, et al., "An Antifungal Agents Inhibits Aminoacyl-tRNA Synthetase by Trapping tRNA in the Editing Site", Science, vol. 316, No. 5832; pp. 1759-1761, (Jun. 22, 2007).
Silverman, "The Organic Chemistry of Drug Design and Drug Action", 2nd Edition, Northwestern University, Department of Chemistry, Evanston, Illinois, Section 2: 29-32 (2004).
Snyder, et al. "Common Bacteria Whose Susceptibility to Antimicrobials in no longer Predictable" J. Med. Liban, vol. 48 No. 4; pp. 208-214, (2000).
Sugar, et al., "Comparison of Three Methods of Antifungal Susceptibility Testing with the Proposed NCCLS Standard Broth Macrodilution Assay: Lack of Effect of Phenol Red" Diagn. Microbiol. Infect. Dis. vol. 21; pp. 129-133, (1995).
Tabuchi, et al., "Anticoccidial Activity of some Azacyclo Organoborinates," Heterocycles, vol. 60, No. 01; pp. 177-182, (2003).
Tatsumi, et al., "Therapeutic Efficacy of Topically applied KP-103 against Experimental Tinea Uguium in Guinea Pigs in Comparison with Amorolfine and Terbinafine", Antimicrobial Agents and Chemotherapy, vol. 46, No. 12; pp. 3797-3801 (2002).
Toporcer, et al., "Preparation and Properties of some Tetracoordinate Boron Compounds. The Pseudo-metal Ion Concept," Inorganic Chemistry, vol. 4, No. 11; pp. 649-1655, (Nov. 1965).
Trujillo, et al., "X-Ray Crystallographic Study of Boroxazolidones, Obtained from L-ornithine, L-methionine, Kainic acid and 2,6-pyridinedicarboxylic acid", Journal of Organometallic Chemistry, vol. 571; pp. 21-29, (1998).
Tschampel, et al., "Arylboronic Acids. VII. Some Reactions to o-Formybenzeneboronic Acids", J. Org. Chem. vol. 29, No. 8; pp. 2168-2172, (1964).
Turner, et al., Current Pharmaceutical Design, vol. 2; pp. 209-224 (1996).
Vippagunta, "Crystalline Solids", Advanced Drug Delivery Reviews, vol. 48; pp. 3-26, (2001).
Wang, et al., "Expression, Purification and Characterization of Human cAMP-Specific Phosphodiesterase (PDE4) Subtypes A, B, C, and D", Biochemical and Biophysical Research Communications, vol. 234; pp. 320-324, (1997).
Ye, et al., "Convenient and Versatile Syntheis of formyl-substituted Benzoxaboroles", Tetrahedron, vol. 65; pp. 8738-8744, (2009).
Williams, et al., "Foye's Principles of Medicinal Chemistry", 5th Edition, 2002, Lippincoot Williams & Wilkins, p. 59.
Zhdankin, et al., "Synthesis and Structure of Benzoboroxoles: Novel Organboron Heterocycles," Tetrahedron Letters, vol. 40; pp. 6705-6708, (1999).
Zhou, et al., "Hemodextrin: a Self-assembled Cyclodextrin-Porphyrin Construct That Binds Dioxygen," Biophysical Chemistry, 105:639-648 (2003).
Zhou, et al., "Structure-activity Studies on a Library of Potent Calix[4]arene-based PDGF Antagonists that Inhibit PDGF-stimulated PDGFR Tyrosine Phosphorylation," Org. Biomol. Chem., 4:2376-2386 (2006).
Zhou, et al., "Pattern Recognition of Proteins Based on an Array of Functionalized Porphyrins," J. Am. Chem. Soc., 128:2421-2425 (2006).
Zixing, et al., "Synthesis of Aromatic Nitrogen-containing Heterocyclic Derivatives of Asymmetric Diarylborinic Acids," Wuhan Daxue Xuebo-Wuhan University Journal, vol. 3; pp. 67-71, (1990), (English Abstract).
"Structure-Activity Studies led to the Discovery of AN2898 in Development for Topical Treatment of Psoriasis and Atopic Dermatitis", Scientific Presentation at the American Academy of Dermatology Annual Meeting, San Francisco, CA Mar. 6-10, 2009.
"AN2898 Inhibits Cytokines Relevant to Topical Treatment of Psoriasis and Atopic Dermatitis", Scientific Presentation at the American Academy of Dermatology Annual Meeting, San Francisco, CA Mar. 6-10, 2009.
"AN2718 has Broad Spectrum Antifungal Activity Necessary for the Topical Treatment of Skin and Nail Fungal Infections", Scientific Presentation at the American Academy of Dermatology Annual Meeting, San Francisco, CA Mar. 6-10, 2009.
"AN2718 Demonstrates Significant Efficacy in Three Phase Ib Psoriasis Microplaque Trials" Scientific Presentation at the American Academy of Dermatology Annual Meeting, San Francisco, CA Mar. 6-10, 2009.
"AN2728 Demonstrates Significant Safety and Efficacy in Phase IIa Double Blind Trial in Plaque Type Psoriasis", Scientific Presentation at the American Academy of Dermatology Annual Meeting, San Francisco, CA Mar. 6-10, 2009.
"AN2728 Preclinical Studies Demonstrate an Acceptable Safety Profile for the Topical Treatment of Psoriasis and Atopic Dermatitis", Scientific Presentation at the American Academy of Dermatology Annual Meeting, San Francisco, CA May 6-10, 2009.
"A New Class of Benzoxaborole-based Potent Antitrypanosomal Agents: Probing Effect of Different Linkage Groups in *Trypanosoma brucei* Growth Inhibition", Scientific Presentation at the American Society of Tropical Medicine and Hygiene Conference, New Orleans, LA Dec. 7-11, 2008.
"AN2920, A Novel Oxaborole, Shows in Vitro and in Vivo Activity Against *Trypanosomal brucei*", Scientific Presentation at the American Society of Tropical Medicine and Hygiene Conference, New Orleans, LA Dec. 7-11, 2008.
"A Novel Oxaborole, AN3520, Show Efficacy against Human African Trypanomiasis in Vitro and in Vivo, Including Promise in a Murine CNS Model of *T. brucei* Infection", Scientific Presentation at the American Society of Tropical Medicine and Hygiene Conference, New Orleans, LA Dec. 7-11, 2008.
"Antifungal Activity and Mechanism of Action of a Benzoxaborole, AN2718, which is in Development for the Treatment of Tinea Pedis", Scientific Presentation at the 48th Interscience Conference on Antimicrobial Agents and Chemotherapy, Washington, D.C. Oct. 25-28, 2008.
"AN2728 Ointment, a Novel Oxaborole with Anti-Inflammatory Activity, Demonstrates Safety and Significant Efficacy in a Phase Ib Psoriasis Plaque Test", Scientific Presentation at Montagna Symposium on Biology of Skin, Gleneden Beach, OR, Oct. 2-6, 2008.
"Preclinical Toxicology of AN2728, a Novel Oxaborole in Development for the Topical Treatment of Psoriasis", Scientific Presentation at the International Investigative Dermatology Conference, Kyoto, Japan, May 14-18, 2008.
"AN2898, a Novel Oxaborole Compound with Anti-Inflammatory Activity: Mechanism of Action and in vitro Cytokine Inhibition", Scientific Presentation at the International Investigative Dermatology Conference, Kyoto, Japan, May 14-18, 2008.
"Structure-Activity Studies of AN2728 and AN2898, Novel Oxaborole Compounds with Anti-Inflammatory Activity", Scientific Presentation at the International Investigative Dermatology Conference, Kyoto, Japan, May 14-18, 2008.
"In Vitro Activity and Mechanism of Action of AN2728, a Novel Oxaborole in Development for Treatment of Psoriasis", Scientific

(56) References Cited

OTHER PUBLICATIONS

Presentation at the International Investigative Dermatology Conference, Kyoto, Japan, May 14-18, 2008.
"AN2898, a Novel Oxaborole Compound with Anti-Inflammatory Activity: Results of In Vivo Efficacy and Preclinical Safety Studies", Scientific Presentation at the International Investigative Dermatology Conference, Kyoto, Japan, May 14-18, 2008.
"AN2728, a Novel Oxaborole in Development for Treatment of Psoriasis, Demonstrates Significant Activity in a Micro Plaque Study", Scientific Presentation at the International Investigative Dermatology Conference, Kyoto, Japan, May 14-18, 2008.
"Preclinical Toxicology of AN2728, a Novel Borinic Acid Ester with Anti-Inflammatory Activity", American Academy of Dermatology, 65th Annual Meeting, Washington, DC, Feb. 2-6, 2007.
"AN2728, a Novel Oxaborole with Broad-Spectrum In Vitro Anti-Inflammatory Activity", American Academy of Dermatology, 65th Annual Meeting, Washington, DC, Feb. 2-6, 2007.
"In Vitro Nail Penetration of AN2690, Effect of Vehicle and Co-Efficient of Efficacy", American Academy of Dermatology, 65th Annual Meeting, Washington, DC, Feb. 2-6, 2007.
"Interim Results of a Multi-Center Study to Evaluate the Safety and Efficacy of Topically Applied AN2690 5.0% and 7.5% Solutions for the Treatment of Onychomycosis of the Great Toenail", American Academy of Dermatology, 65th Annual Meeting, Washington, DC, Feb. 2-6, 2007.
"In vivo Nail Residence Time of AN2690, a Novel Broad-Spectrum Antifungal Agent in Development for the Topical Treatment of Onychomycosis", American Academy of Dermatology, 65th Annual Meeting, Washington, DC, Feb. 2-6, 2007.
"An Open-Label, Multi-dose Study of Absorption and Systemic Pharmacokinetics of AN2690 Applied as a 7.5% Solution to All Toenails of Adult Patients with Moderate to Severe Onychomycosis", American Academy of Dermatology, 65th Annual Meeting, Washington, DC, Feb. 2-6, 2007.
"Medicinal Chemistry Development of AN2728, A Novel Oxaborole in Development for the Topical Treatment of Psoriasis", American Academy of Dermatology, 65th Annual Meeting, Washington, DC, Feb. 2-6, 2007.
"Skin Penetration and Anti-Inflammatory Activity of AN2728, a Novel Oxaborole", American Academy of Dermatology, 65th Annual Meeting, Washington, DC, Feb. 2-6, 2007.
"Nail Penetration and Nail Concentration of AN2690, a Novel Broad-Spectrum Antifungal Agent in Development for the Topical Treatment of Onychomycosis", Scientific Presentation at the American Associate of Pharmaceutical Scientist, Annual Meeting, San Antonio, TX, Oct. 29-Nov. 2, 2006.

* cited by examiner

| No. | $R^{9a}$ | $R^{10a}$ | $R^{11a}$ | $R^{12a}$ |
|---|---|---|---|---|
| 1 | F | H | H | H |
| 2 | H | F | H | H |
| 3 | H | H | F | H |
| 4 | H | H | H | F |
| 5 | F | F | H | H |
| 6 | H | F | F | H |
| 7 | H | H | F | F |
| 8 | F | H | F | H |
| 9 | H | F | H | F |
| 10 | F | H | H | F |
| 11 | H | F | F | F |
| 12 | F | H | F | F |
| 13 | F | F | H | F |
| 14 | F | F | F | H |
| 15 | F | F | F | F |
| 16 | Cl | H | H | H |
| 17 | H | Cl | H | H |
| 18 | H | H | Cl | H |
| 19 | H | H | H | Cl |
| 20 | Cl | Cl | H | H |
| 21 | H | Cl | Cl | H |
| 22 | H | H | Cl | Cl |
| 23 | Cl | H | Cl | H |
| 24 | H | Cl | H | Cl |
| 25 | Cl | H | H | Cl |
| 26 | H | Cl | Cl | Cl |
| 27 | Cl | H | Cl | Cl |
| 28 | Cl | Cl | H | Cl |
| 29 | Cl | Cl | Cl | H |
| 30 | Cl | Cl | Cl | Cl |
| 31 | Br | H | H | H |
| 32 | H | Br | H | H |
| 33 | H | H | Br | H |
| 34 | H | H | H | Br |
| 35 | Br | Br | H | H |
| 36 | H | Br | Br | H |

Figure 1B

| No. | $R^{9a}$ | $R^{10a}$ | $R^{11a}$ | $R^{12a}$ |
|---|---|---|---|---|
| 37 | H | H | Br | Br |
| 38 | Br | H | Br | H |
| 39 | H | Br | H | Br |
| 40 | Br | H | H | Br |
| 41 | H | Br | Br | Br |
| 42 | Br | H | Br | Br |
| 43 | Br | Br | H | Br |
| 44 | Br | Br | Br | H |
| 45 | Br | Br | Br | Br |
| 46 | -CN | H | H | H |
| 47 | H | -CN | H | H |
| 48 | H | H | -CN | H |
| 49 | H | H | H | -CN |
| 50 | -CN | -CN | H | H |
| 51 | H | -CN | -CN | H |
| 52 | H | H | -CN | -CN |
| 53 | -CN | H | -CN | H |
| 54 | H | -CN | H | -CN |
| 55 | -CN | H | H | -CN |
| 56 | H | -CN | -CN | -CN |
| 57 | -CN | H | -CN | -CN |
| 58 | -CN | -CN | H | -CN |
| 59 | -CN | -CN | -CN | H |
| 60 | -CN | -CN | -CN | -CN |
| 61 | -Me | H | H | H |
| 62 | H | -Me | H | H |
| 63 | H | H | -Me | H |
| 64 | H | H | H | -Me |
| 65 | -Me | -Me | H | H |
| 66 | H | -Me | -Me | H |
| 67 | H | H | -Me | -Me |
| 68 | -Me | H | -Me | H |
| 69 | H | -Me | H | -Me |
| 70 | -Me | H | H | -Me |
| 71 | H | -Me | -Me | -Me |
| 72 | -Me | H | -Me | -Me |
| 73 | -Me | -Me | H | -Me |
| 74 | -Me | -Me | -Me | H |
| 75 | -Me | -Me | -Me | -Me |
| 76 | -CH$_2$OH | H | H | H |
| 77 | H | -CH$_2$OH | H | H |
| 78 | H | H | -CH$_2$OH | H |

Figure 1C

| No. | $R^{9a}$ | $R^{10a}$ | $R^{11a}$ | $R^{12a}$ |
|---|---|---|---|---|
| 79 | H | H | H | -CH$_2$OH |
| 80 | -CH$_2$OH | -CH$_2$OH | H | H |
| 81 | H | -CH$_2$OH | -CH$_2$OH | H |
| 82 | H | H | -CH$_2$OH | -CH$_2$OH |
| 83 | -CH$_2$OH | H | -CH$_2$OH | H |
| 84 | H | -CH$_2$OH | H | -CH$_2$OH |
| 85 | -CH$_2$OH | H | H | -CH$_2$OH |
| 86 | H | -CH$_2$OH | -CH$_2$OH | -CH$_2$OH |
| 87 | -CH$_2$OH | H | -CH$_2$OH | -CH$_2$OH |
| 88 | -CH$_2$OH | -CH$_2$OH | H | -CH$_2$OH |
| 89 | -CH$_2$OH | -CH$_2$OH | -CH$_2$OH | H |
| 90 | -CH$_2$OH | -CH$_2$OH | -CH$_2$OH | -CH$_2$OH |
| 91 | -benzyl | H | H | H |
| 92 | H | -benzyl | H | H |
| 93 | H | H | -benzyl | H |
| 94 | H | H | H | -benzyl |
| 95 | -benzyl | -benzyl | H | H |
| 96 | H | -benzyl | -benzyl | H |
| 97 | H | H | -benzyl | -benzyl |
| 98 | -benzyl | H | -benzyl | H |
| 99 | H | -benzyl | H | -benzyl |
| 100 | -benzyl | H | H | -benzyl |
| 101 | H | -benzyl | -benzyl | -benzyl |
| 102 | -benzyl | H | -benzyl | -benzyl |
| 103 | -benzyl | -benzyl | H | -benzyl |
| 104 | -benzyl | -benzyl | -benzyl | H |
| 105 | -benzyl | -benzyl | -benzyl | -benzyl |
| 106 | -OMe | H | H | H |
| 107 | H | -OMe | H | H |
| 108 | H | H | -OMe | H |
| 109 | H | H | H | -OMe |
| 110 | -OMe | -OMe | H | H |
| 111 | H | -OMe | -OMe | H |
| 112 | H | H | -OMe | -OMe |
| 113 | -OMe | H | -OMe | H |
| 114 | -OMe | H | H | -OMe |
| 115 | H | -OMe | -OMe | -OMe |
| 116 | -OMe | H | -OMe | -OMe |
| 117 | -OMe | -OMe | H | -OMe |
| 118 | -OMe | -OMe | -OMe | H |
| 119 | -OMe | -OMe | -OMe | -OMe |
| 120 | -4-cyanophenoxy | H | H | H |

Figure 1D

| No. | $R^{9a}$ | $R^{10a}$ | $R^{11a}$ | $R^{12a}$ |
|---|---|---|---|---|
| 121 | H | -4-cyanophenoxy | H | H |
| 122 | H | H | -4-cyanophenoxy | H |
| 123 | H | H | H | -4-cyanophenoxy |
| 124 | -4-cyanophenoxy | -4-cyanophenoxy | H | H |
| 125 | H | -4-cyanophenoxy | -4-cyanophenoxy | H |
| 126 | H | H | -4-cyanophenoxy | -4-cyanophenoxy |
| 127 | -4-cyanophenoxy | H | -4-cyanophenoxy | H |
| 128 | H | -4-cyanophenoxy | H | -4-cyanophenoxy |
| 129 | -4-cyanophenoxy | H | H | -4-cyanophenoxy |
| 130 | H | -4-cyanophenoxy | -4-cyanophenoxy | -4-cyanophenoxy |
| 131 | -4-cyanophenoxy | H | -4-cyanophenoxy | -4-cyanophenoxy |
| 132 | -4-cyanophenoxy | -4-cyanophenoxy | H | -4-cyanophenoxy |
| 133 | -4-cyanophenoxy | -4-cyanophenoxy | -4-cyanophenoxy | H |
| 134 | -4-cyanophenoxy | -4-cyanophenoxy | -4-cyanophenoxy | -4-cyanophenoxy |
| 135 | -3-cyanophenoxy | H | H | H |
| 136 | H | -3-cyanophenoxy | H | H |
| 137 | H | H | -3-cyanophenoxy | H |
| 138 | H | H | H | -3-cyanophenoxy |
| 139 | -3-cyanophenoxy | -3-cyanophenoxy | H | H |
| 140 | H | -3-cyanophenoxy | -3-cyanophenoxy | H |
| 141 | H | H | -3-cyanophenoxy | -3-cyanophenoxy |
| 142 | -3-cyanophenoxy | H | -3-cyanophenoxy | H |
| 143 | H | -3-cyanophenoxy | H | -3-cyanophenoxy |
| 144 | -3-cyanophenoxy | H | H | -3-cyanophenoxy |
| 145 | H | -3-cyanophenoxy | -3-cyanophenoxy | -3-cyanophenoxy |
| 146 | -3-cyanophenoxy | H | -3-cyanophenoxy | -3-cyanophenoxy |
| 147 | -3-cyanophenoxy | -3-cyanophenoxy | H | -3-cyanophenoxy |
| 148 | -3-cyanophenoxy | -3-cyanophenoxy | -3-cyanophenoxy | H |
| 149 | -3-cyanophenoxy | -3-cyanophenoxy | -3-cyanophenoxy | -3-cyanophenoxy |
| 150 | -2-cyanophenoxy | H | H | H |
| 151 | H | -2-cyanophenoxy | H | H |
| 152 | H | H | -2-cyanophenoxy | H |
| 153 | H | H | H | -2-cyanophenoxy |
| 154 | -2-cyanophenoxy | -2-cyanophenoxy | H | H |
| 155 | H | -2-cyanophenoxy | -2-cyanophenoxy | H |
| 156 | H | H | -2-cyanophenoxy | -2-cyanophenoxy |
| 157 | -2-cyanophenoxy | H | -2-cyanophenoxy | H |
| 158 | H | -2-cyanophenoxy | H | -2-cyanophenoxy |
| 159 | -2-cyanophenoxy | H | H | -2-cyanophenoxy |
| 160 | H | -2-cyanophenoxy | -2-cyanophenoxy | -2-cyanophenoxy |
| 161 | -2-cyanophenoxy | H | -2-cyanophenoxy | -2-cyanophenoxy |
| 162 | -2-cyanophenoxy | -2-cyanophenoxy | H | -2-cyanophenoxy |

Figure 1E

| No. | $R^{9a}$ | $R^{10a}$ | $R^{11a}$ | $R^{12a}$ |
|---|---|---|---|---|
| 163 | -2-cyanophenoxy | -2-cyanophenoxy | -2-cyanophenoxy | H |
| 164 | -2-cyanophenoxy | -2-cyanophenoxy | -2-cyanophenoxy | -2-cyanophenoxy |
| 165 | -4-chlorophenoxy | H | H | H |
| 166 | H | -4-chlorophenoxy | H | H |
| 167 | H | H | -4-chlorophenoxy | H |
| 168 | H | H | H | -4-chlorophenoxy |
| 169 | -4-chlorophenoxy | -4-chlorophenoxy | H | H |
| 170 | H | -4-chlorophenoxy | -4-chlorophenoxy | H |
| 171 | H | H | -4-chlorophenoxy | -4-chlorophenoxy |
| 172 | -4-chlorophenoxy | H | -4-chlorophenoxy | H |
| 173 | H | -4-chlorophenoxy | H | -4-chlorophenoxy |
| 174 | -4-chlorophenoxy | H | H | -4-chlorophenoxy |
| 175 | H | -4-chlorophenoxy | -4-chlorophenoxy | -4-chlorophenoxy |
| 176 | -4-chlorophenoxy | H | -4-chlorophenoxy | -4-chlorophenoxy |
| 177 | -4-chlorophenoxy | -4-chlorophenoxy | H | -4-chlorophenoxy |
| 178 | -4-chlorophenoxy | -4-chlorophenoxy | -4-chlorophenoxy | H |
| 179 | -4-chlorophenoxy | -4-chlorophenoxy | -4-chlorophenoxy | -4-chlorophenoxy |
| 180 | -3-chlorophenoxy | H | H | H |
| 181 | H | -3-chlorophenoxy | H | H |
| 182 | H | H | -3-chlorophenoxy | H |
| 183 | H | H | H | -3-chlorophenoxy |
| 184 | -3-chlorophenoxy | -3-chlorophenoxy | H | H |
| 185 | H | -3-chlorophenoxy | -3-chlorophenoxy | H |
| 186 | H | H | -3-chlorophenoxy | -3-chlorophenoxy |
| 187 | -3-chlorophenoxy | H | -3-chlorophenoxy | H |
| 188 | H | -3-chlorophenoxy | H | -3-chlorophenoxy |
| 189 | -3-chlorophenoxy | H | H | -3-chlorophenoxy |
| 190 | H | -3-chlorophenoxy | -3-chlorophenoxy | -3-chlorophenoxy |
| 191 | -3-chlorophenoxy | H | -3-chlorophenoxy | -3-chlorophenoxy |
| 192 | -3-chlorophenoxy | -3-chlorophenoxy | H | -3-chlorophenoxy |
| 193 | -3-chlorophenoxy | -3-chlorophenoxy | -3-chlorophenoxy | H |
| 194 | -3-chlorophenoxy | -3-chlorophenoxy | -3-chlorophenoxy | -3-chlorophenoxy |
| 195 | -2-chlorophenoxy | H | H | H |
| 196 | H | -2-chlorophenoxy | H | H |
| 197 | H | H | -2-chlorophenoxy | H |
| 198 | H | H | H | -2-chlorophenoxy |
| 199 | -2-chlorophenoxy | -2-chlorophenoxy | H | H |
| 200 | H | -2-chlorophenoxy | -2-chlorophenoxy | H |
| 201 | H | H | -2-chlorophenoxy | -2-chlorophenoxy |
| 202 | -2-chlorophenoxy | H | -2-chlorophenoxy | H |
| 203 | H | -2-chlorophenoxy | H | -2-chlorophenoxy |
| 204 | -2-chlorophenoxy | H | H | -2-chlorophenoxy |

Figure 1F

| No. | $R^{9a}$ | $R^{10a}$ | $R^{11a}$ | $R^{12a}$ |
|-----|----------|-----------|-----------|-----------|
| 205 | H | -2-chlorophenoxy | -2-chlorophenoxy | -2-chlorophenoxy |
| 206 | -2-chlorophenoxy | H | -2-chlorophenoxy | -2-chlorophenoxy |
| 207 | -2-chlorophenoxy | -2-chlorophenoxy | H | -2-chlorophenoxy |
| 208 | -2-chlorophenoxy | -2-chlorophenoxy | -2-chlorophenoxy | H |
| 209 | -2-chlorophenoxy | -2-chlorophenoxy | -2-chlorophenoxy | -2-chlorophenoxy |
| 210 | -phenoxy | H | H | H |
| 211 | H | -phenoxy | H | H |
| 212 | H | H | -phenoxy | H |
| 213 | H | H | H | -phenoxy |
| 214 | -phenoxy | -phenoxy | H | H |
| 215 | H | -phenoxy | -phenoxy | H |
| 216 | H | H | -phenoxy | -phenoxy |
| 217 | -phenoxy | H | -phenoxy | H |
| 218 | H | -phenoxy | H | -phenoxy |
| 219 | -phenoxy | H | H | -phenoxy |
| 220 | H | -phenoxy | -phenoxy | -phenoxy |
| 221 | -phenoxy | H | -phenoxy | -phenoxy |
| 222 | -phenoxy | -phenoxy | H | -phenoxy |
| 223 | -phenoxy | -phenoxy | -phenoxy | H |
| 224 | -phenoxy | -phenoxy | -phenoxy | -phenoxy |
| 225 | -4-cyanophenylthio | H | H | H |
| 226 | H | -4-cyanophenylthio | H | H |
| 227 | H | H | -4-cyanophenylthio | H |
| 228 | H | H | H | -4-cyanophenylthio |
| 229 | -4-cyanophenylthio | -4-cyanophenylthio | H | H |
| 230 | H | -4-cyanophenylthio | -4-cyanophenylthio | H |
| 231 | H | H | -4-cyanophenylthio | -4-cyanophenylthio |
| 232 | -4-cyanophenylthio | H | -4-cyanophenylthio | H |
| 233 | H | -4-cyanophenylthio | H | -4-cyanophenylthio |
| 234 | -4-cyanophenylthio | H | H | -4-cyanophenylthio |
| 235 | H | -4-cyanophenylthio | -4-cyanophenylthio | -4-cyanophenylthio |
| 236 | -4-cyanophenylthio | H | -4-cyanophenylthio | -4-cyanophenylthio |
| 237 | -4-cyanophenylthio | -4-cyanophenylthio | H | -4-cyanophenylthio |
| 238 | -4-cyanophenylthio | -4-cyanophenylthio | -4-cyanophenylthio | H |
| 239 | -4-cyanophenylthio | -4-cyanophenylthio | -4-cyanophenylthio | -4-cyanophenylthio |
| 240 | -3-cyanophenylthio | H | H | H |
| 241 | H | 3-cyanophenylthio | H | H |
| 242 | H | H | -3-cyanophenylthio | H |
| 243 | H | H | H | -3-cyanophenylthio |
| 244 | -3-cyanophenylthio | -3-cyanophenylthio | H | H |
| 245 | H | -3-cyanophenylthio | -3-cyanophenylthio | H |

Figure 1G

| No. | $R^{9a}$ | $R^{10a}$ | $R^{11a}$ | $R^{12a}$ |
|---|---|---|---|---|
| 246 | H | H | -3-cyanophenylthio | -3-cyanophenylthio |
| 247 | -3-cyanophenylthio | H | -3-cyanophenylthio | H |
| 248 | H | -3-cyanophenylthio | H | -3-cyanophenylthio |
| 249 | -3-cyanophenylthio | H | H | -3-cyanophenylthio |
| 250 | H | -3-cyanophenylthio | -3-cyanophenylthio | -3-cyanophenylthio |
| 251 | -3-cyanophenylthio | H | -3-cyanophenylthio | -3-cyanophenylthio |
| 252 | -3-cyanophenylthio | -3-cyanophenylthio | H | -3-cyanophenylthio |
| 253 | -3-cyanophenylthio | -3-cyanophenylthio | -3-cyanophenylthio | H |
| 254 | -3-cyanophenylthio | -3-cyanophenylthio | -3-cyanophenylthio | -3-cyanophenylthio |
| 255 | -2-cyanophenylthio | H | H | H |
| 256 | H | -2-cyanophenylthio | H | H |
| 257 | H | H | -2-cyanophenylthio | H |
| 258 | H | H | H | -2-cyanophenylthio |
| 259 | -2-cyanophenylthio | -2-cyanophenylthio | H | H |
| 260 | H | -2-cyanophenylthio | -2-cyanophenylthio | H |
| 261 | H | H | -2-cyanophenylthio | -2-cyanophenylthio |
| 262 | -2-cyanophenylthio | H | -2-cyanophenylthio | H |
| 263 | H | -2-cyanophenylthio | H | -2-cyanophenylthio |
| 264 | -2-cyanophenylthio | H | H | -2-cyanophenylthio |
| 265 | H | -2-cyanophenylthio | -2-cyanophenylthio | -2-cyanophenylthio |
| 266 | 2-cyanophenylthio | H | -2-cyanophenylthio | -2-cyanophenylthio |
| 267 | 2-cyanophenylthio | -2-cyanophenylthio | H | -2-cyanophenylthio |
| 268 | 2-cyanophenylthio | -2-cyanophenylthio | -2-cyanophenylthio | H |
| 269 | 2-cyanophenylthio | -2-cyanophenylthio | -2-cyanophenylthio | -2-cyanophenylthio |
| 270 | -OCH$_2$C(O)OH | H | H | H |
| 271 | H | -OCH$_2$C(O)OH | H | H |
| 272 | H | H | -OCH$_2$C(O)OH | H |
| 273 | H | H | H | -OCH$_2$C(O)OH |
| 274 | F | -OCH$_2$C(O)OH | H | H |
| 275 | H | -OCH$_2$C(O)OH | F | H |
| 276 | H | -OCH$_2$C(O)OH | H | F |
| 277 | F | -OCH$_2$C(O)OH | F | H |
| 278 | H | -OCH$_2$C(O)OH | F | F |
| 279 | F | -OCH$_2$C(O)OH | F | F |
| 280 | -NMeS(O)$_2$Ph | H | H | H |
| 281 | H | -NMeS(O)$_2$Ph | H | H |
| 282 | H | H | -NMeS(O)$_2$Ph | H |
| 283 | H | H | H | -NMeS(O)$_2$Ph |
| 284 | F | -NMeS(O)$_2$Ph | H | H |
| 285 | H | -NMeS(O)$_2$Ph | F | H |
| 286 | H | -NMeS(O)$_2$Ph | H | F |

Figure 1H

| No. | $R^{9a}$ | $R^{10a}$ | $R^{11a}$ | $R^{12a}$ |
| --- | --- | --- | --- | --- |
| 287 | F | -NMeS(O)$_2$Ph | F | H |
| 288 | H | -NMeS(O)$_2$Ph | F | F |
| 289 | F | -NMeS(O)$_2$Ph | F | F |
| 290 | -CH$_2$OH | H | H | H |
| 291 | H | -CH$_2$OH | H | H |
| 292 | H | H | -CH$_2$OH | H |
| 293 | H | H | H | -CH$_2$OH |
| 294 | -CH$_2$OH | F | H | H |
| 295 | -CH$_2$OH | H | F | H |
| 296 | -CH$_2$OH | H | H | F |
| 297 | -CH$_2$OH | Cl | H | H |
| 298 | -CH$_2$OH | H | Cl | H |
| 299 | -CH$_2$OH | H | H | Cl |
| 300 | F | -CH$_2$OH | H | H |
| 301 | H | -CH$_2$OH | F | H |
| 302 | H | -CH$_2$OH | H | F |
| 303 | Cl | -CH$_2$OH | H | H |
| 304 | H | -CH$_2$OH | Cl | H |
| 305 | H | -CH$_2$OH | H | Cl |
| 306 | F | H | -CH$_2$OH | H |
| 307 | H | F | -CH$_2$OH | H |
| 308 | H | H | -CH$_2$OH | F |
| 309 | Cl | H | -CH$_2$OH | H |
| 310 | H | Cl | -CH$_2$OH | H |
| 311 | H | H | -CH$_2$OH | Cl |
| 312 | F | H | H | -CH$_2$OH |
| 313 | H | F | H | -CH$_2$OH |
| 314 | H | H | F | -CH$_2$OH |
| 315 | Cl | H | H | -CH$_2$OH |
| 316 | H | Cl | H | -CH$_2$OH |
| 317 | H | H | Cl | -CH$_2$OH |
| 318 | F | -CH$_2$OH | F | H |
| 319 | H | -CH$_2$OH | F | F |
| 320 | F | -CH$_2$OH | F | F |
| 321 | H | -NH$_2$ | H | H |
| 322 | H | H | -NH$_2$ | H |
| 323 | H | H | H | -NH$_2$ |
| 324 | -NH$_2$ | F | H | H |
| 325 | -NH$_2$ | H | F | H |
| 326 | -NH$_2$ | H | H | F |
| 327 | -NH$_2$ | Cl | H | H |
| 328 | -NH$_2$ | H | Cl | H |

Figure 1I

| No. | $R^{9a}$ | $R^{10a}$ | $R^{11a}$ | $R^{12a}$ |
|---|---|---|---|---|
| 329 | -NH$_2$ | H | H | Cl |
| 330 | F | -NH$_2$ | H | H |
| 331 | H | -NH$_2$ | F | H |
| 332 | H | -NH$_2$ | H | F |
| 333 | Cl | -NH$_2$ | H | H |
| 334 | H | -NH$_2$ | Cl | H |
| 335 | H | -NH$_2$ | H | Cl |
| 336 | F | H | -NH$_2$ | H |
| 337 | H | F | -NH$_2$ | H |
| 338 | H | H | -NH$_2$ | F |
| 339 | Cl | H | -NH$_2$ | H |
| 340 | H | Cl | -NH$_2$ | H |
| 341 | H | H | -NH$_2$ | Cl |
| 342 | F | H | H | -NH$_2$ |
| 343 | H | F | H | -NH$_2$ |
| 344 | H | H | F | -NH$_2$ |
| 345 | Cl | H | H | -NH$_2$ |
| 346 | H | Cl | H | -NH$_2$ |
| 347 | H | H | Cl | -NH$_2$ |
| 348 | F | -NH$_2$ | F | H |
| 349 | H | -NH$_2$ | F | F |
| 350 | F | -NH$_2$ | F | F |
| 351 | -O(4-CN-Ph) | H | H | H |
| 352 | H | -O(4-CN-Ph) | H | H |
| 353 | H | H | -O(4-CN-Ph) | H |
| 354 | H | H | H | -O(4-CN-Ph) |
| 355 | F | -O(4-CN-Ph) | H | H |
| 356 | H | -O(4-CN-Ph) | F | H |
| 357 | H | -O(4-CN-Ph) | H | F |
| 358 | F | -O(4-CN-Ph) | F | H |
| 359 | H | -O(4-CN-Ph) | F | F |
| 360 | F | -O(4-CN-Ph) | F | F |
| 361 | 3-(phenylthio)-1H-indol-1-yl | H | H | H |
| 362 | H | 3-(phenylthio)-1H-indol-1-yl | H | H |
| 363 | H | H | 3-(phenylthio)-1H-indol-1-yl | H |
| 364 | H | H | H | 3-(phenylthio)-1H-indol-1-yl |
| 365 | F | 3-(phenylthio)-1H-indol-1-yl | H | H |
| 366 | H | 3-(phenylthio)-1H- | F | H |

Figure 1J

| No. | $R^{9a}$ | $R^{10a}$ | $R^{11a}$ | $R^{12a}$ |
|---|---|---|---|---|
| 367 | H | 3-(phenylthio)-1H-indol-1-yl | H | F |
| 368 | F | 3-(phenylthio)-1H-indol-1-yl | F | H |
| 369 | H | 3-(phenylthio)-1H-indol-1-yl | F | F |
| 370 | F | 3-(phenylthio)-1H-indol-1-yl | F | F |
| 371 | dibenzylamino | H | H | H |
| 372 | H | dibenzylamino | H | H |
| 373 | H | H | dibenzylamino | H |
| 374 | H | H | H | dibenzylamino |
| 375 | F | dibenzylamino | H | H |
| 376 | H | dibenzylamino | F | H |
| 377 | H | dibenzylamino | H | F |
| 378 | F | dibenzylamino | F | H |
| 379 | H | dibenzylamino | F | F |
| 380 | F | dibenzylamino | F | F |
| 381 | -S(O)$_2$(4-Cl-Ph) | H | H | H |
| 382 | H | -S(O)$_2$(4-Cl-Ph) | H | H |
| 383 | H | H | -S(O)$_2$(4-Cl-Ph) | H |
| 384 | H | H | H | -S(O)$_2$(4-Cl-Ph) |
| 385 | F | -S(O)$_2$(4-Cl-Ph) | H | H |
| 386 | H | -S(O)$_2$(4-Cl-Ph) | F | H |
| 387 | H | -S(O)$_2$(4-Cl-Ph) | H | F |
| 388 | F | -S(O)$_2$(4-Cl-Ph) | F | H |
| 389 | H | -S(O)$_2$(4-Cl-Ph) | F | F |
| 390 | F | -S(O)$_2$(4-Cl-Ph) | F | F |
| 391 | -S(4-pyridyl) | H | H | H |
| 392 | H | -S(4-pyridyl) | H | H |
| 393 | H | H | -S(4-pyridyl) | H |
| 394 | H | H | H | -S(4-pyridyl) |
| 395 | F | -S(4-pyridyl) | H | H |
| 396 | H | -S(4-pyridyl) | F | H |
| 397 | H | -S(4-pyridyl) | H | F |
| 398 | F | -S(4-pyridyl) | F | H |
| 399 | H | -S(4-pyridyl) | F | F |
| 400 | F | -S(4-pyridyl) | F | F |
| 401 | -NHCH$_2$Ph | H | H | H |
| 402 | H | -NHCH$_2$Ph | H | H |
| 403 | H | H | -NHCH$_2$Ph | H |
| 404 | H | H | H | -NHCH$_2$Ph |

Figure 1K

| No. | $R^{9a}$ | $R^{10a}$ | $R^{11a}$ | $R^{12a}$ |
|-----|----------|-----------|-----------|-----------|
| 405 | F | -NHCH$_2$Ph | H | H |
| 406 | H | -NHCH$_2$Ph | F | H |
| 407 | H | -NHCH$_2$Ph | H | F |
| 408 | F | -NHCH$_2$Ph | F | H |
| 409 | H | -NHCH$_2$Ph | F | F |
| 410 | F | -NHCH$_2$Ph | F | F |

FIGURE 2A

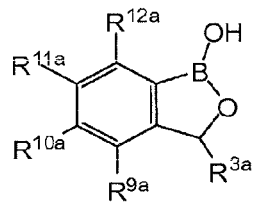

| No. | R³ᵃ | R⁹ᵃ | R¹⁰ᵃ | R¹¹ᵃ | R¹²ᵃ |
|---|---|---|---|---|---|
| 1 | -CH₂Ph | F | H | H | H |
| 2 | -CH₂Ph | H | F | H | H |
| 3 | -CH₂Ph | H | H | F | H |
| 4 | -CH₂Ph | H | H | H | F |
| 5 | -CH₂Ph | F | F | H | H |
| 6 | -CH₂Ph | H | F | F | H |
| 7 | -CH₂Ph | H | H | F | F |
| 8 | -CH₂Ph | F | H | F | H |
| 9 | -CH₂Ph | H | F | H | F |
| 10 | -CH₂Ph | F | H | H | F |
| 11 | -CH₂Ph | H | F | F | F |
| 12 | -CH₂Ph | F | H | F | F |
| 13 | -CH₂Ph | F | F | H | F |
| 14 | -CH₂Ph | F | F | F | H |
| 15 | -CH₂Ph | F | F | F | F |
| 16 | -CH₂Ph | -OCH₂C(O)OH | H | H | H |
| 17 | -CH₂Ph | H | -OCH₂C(O)OH | H | H |
| 18 | -CH₂Ph | H | H | -OCH₂C(O)OH | H |
| 19 | -CH₂Ph | H | H | H | -OCH₂C(O)OH |
| 20 | -CH₂Ph | F | -OCH₂C(O)OH | H | H |
| 21 | -CH₂Ph | H | -OCH₂C(O)OH | F | H |
| 22 | -CH₂Ph | H | -OCH₂C(O)OH | H | F |
| 23 | -CH₂Ph | F | -OCH₂C(O)OH | F | H |
| 24 | -CH₂Ph | H | -OCH₂C(O)OH | F | F |
| 25 | -CH₂Ph | F | -OCH₂C(O)OH | F | F |
| 26 | -CH₂Ph | -NMeS(O)₂Ph | H | H | H |
| 27 | -CH₂Ph | H | -NMeS(O)₂Ph | H | H |
| 28 | -CH₂Ph | H | H | -NMeS(O)₂Ph | H |
| 29 | -CH₂Ph | H | H | H | -NMeS(O)₂Ph |
| 30 | -CH₂Ph | F | -NMeS(O)₂Ph | H | H |
| 31 | -CH₂Ph | H | -NMeS(O)₂Ph | F | H |
| 32 | -CH₂Ph | H | -NMeS(O)₂Ph | H | F |
| 33 | -CH₂Ph | F | -NMeS(O)₂Ph | F | H |
| 34 | -CH₂Ph | H | -NMeS(O)₂Ph | F | F |
| 35 | -CH₂Ph | F | -NMeS(O)₂Ph | F | F |
| 36 | -CH₂Ph | H | -CH₂OH | H | H |
| 37 | -CH₂Ph | H | H | -CH₂OH | H |

FIGURE 2B

| No. | $R^{3a}$ | $R^{9a}$ | $R^{10a}$ | $R^{11a}$ | $R^{12a}$ |
|---|---|---|---|---|---|
| 38 | -CH$_2$Ph | H | H | H | -CH$_2$OH |
| 39 | -CH$_2$Ph | -CH$_2$OH | F | H | H |
| 40 | -CH$_2$Ph | -CH$_2$OH | H | F | H |
| 41 | -CH$_2$Ph | -CH$_2$OH | H | H | F |
| 42 | -CH$_2$Ph | -CH$_2$OH | Cl | H | H |
| 43 | -CH$_2$Ph | -CH$_2$OH | H | Cl | H |
| 44 | -CH$_2$Ph | -CH$_2$OH | H | H | Cl |
| 45 | -CH$_2$Ph | F | -CH$_2$OH | H | H |
| 46 | -CH$_2$Ph | H | -CH$_2$OH | F | H |
| 47 | -CH$_2$Ph | H | -CH$_2$OH | H | F |
| 48 | -CH$_2$Ph | Cl | -CH$_2$OH | H | H |
| 49 | -CH$_2$Ph | H | -CH$_2$OH | Cl | H |
| 50 | -CH$_2$Ph | H | -CH$_2$OH | H | Cl |
| 51 | -CH$_2$Ph | F | H | -CH$_2$OH | H |
| 52 | -CH$_2$Ph | H | F | -CH$_2$OH | H |
| 53 | -CH$_2$Ph | H | H | -CH$_2$OH | F |
| 54 | -CH$_2$Ph | Cl | H | -CH$_2$OH | H |
| 55 | -CH$_2$Ph | H | Cl | -CH$_2$OH | H |
| 56 | -CH$_2$Ph | H | H | -CH$_2$OH | Cl |
| 57 | -CH$_2$Ph | F | H | H | -CH$_2$OH |
| 58 | -CH$_2$Ph | H | F | H | -CH$_2$OH |
| 59 | -CH$_2$Ph | H | H | F | -CH$_2$OH |
| 60 | -CH$_2$Ph | Cl | H | H | -CH$_2$OH |
| 61 | -CH$_2$Ph | H | Cl | H | -CH$_2$OH |
| 62 | -CH$_2$Ph | H | H | Cl | -CH$_2$OH |
| 63 | -CH$_2$Ph | F | -CH$_2$OH | F | H |
| 64 | -CH$_2$Ph | H | -CH$_2$OH | F | F |
| 65 | -CH$_2$Ph | F | -CH$_2$OH | F | F |
| 66 | -CH$_2$Ph | H | -NH$_2$ | H | H |
| 67 | -CH$_2$Ph | H | H | -NH$_2$ | H |
| 68 | -CH$_2$Ph | H | H | H | -NH$_2$ |
| 69 | -CH$_2$Ph | -NH$_2$ | F | H | H |
| 70 | -CH$_2$Ph | -NH$_2$ | H | F | H |
| 71 | -CH$_2$Ph | -NH$_2$ | H | H | F |
| 72 | -CH$_2$Ph | -NH$_2$ | Cl | H | H |
| 73 | -CH$_2$Ph | -NH$_2$ | H | Cl | H |
| 74 | -CH$_2$Ph | -NH$_2$ | H | H | Cl |
| 75 | -CH$_2$Ph | F | -NH$_2$ | H | H |
| 76 | -CH$_2$Ph | H | -NH$_2$ | F | H |
| 77 | -CH$_2$Ph | H | -NH$_2$ | H | F |
| 78 | -CH$_2$Ph | Cl | -NH$_2$ | H | H |
| 79 | -CH$_2$Ph | H | -NH$_2$ | Cl | H |
| 80 | -CH$_2$Ph | H | -NH$_2$ | H | Cl |

FIGURE 2C

| No. | $R^{3a}$ | $R^{9a}$ | $R^{10a}$ | $R^{11a}$ | $R^{12a}$ |
|---|---|---|---|---|---|
| 81 | -CH$_2$Ph | F | H | -NH$_2$ | H |
| 82 | -CH$_2$Ph | H | F | -NH$_2$ | H |
| 83 | -CH$_2$Ph | H | H | -NH$_2$ | F |
| 84 | -CH$_2$Ph | Cl | H | -NH$_2$ | H |
| 85 | -CH$_2$Ph | H | Cl | -NH$_2$ | H |
| 86 | -CH$_2$Ph | H | H | -NH$_2$ | Cl |
| 87 | -CH$_2$Ph | F | H | H | -NH$_2$ |
| 88 | -CH$_2$Ph | H | F | H | -NH$_2$ |
| 89 | -CH$_2$Ph | H | H | F | -NH$_2$ |
| 90 | -CH$_2$Ph | Cl | H | H | -NH$_2$ |
| 91 | -CH$_2$Ph | H | Cl | H | -NH$_2$ |
| 92 | -CH$_2$Ph | H | H | Cl | -NH$_2$ |
| 93 | -CH$_2$Ph | F | -NH$_2$ | F | H |
| 94 | -CH$_2$Ph | H | -NH$_2$ | F | F |
| 95 | -CH$_2$Ph | F | -NH$_2$ | F | F |
| 96 | -CH$_2$Ph | -O(4-CN-Ph) | H | H | H |
| 97 | -CH$_2$Ph | H | -O(4-CN-Ph) | H | H |
| 98 | -CH$_2$Ph | H | H | -O(4-CN-Ph) | H |
| 99 | -CH$_2$Ph | H | H | H | -O(4-CN-Ph) |
| 100 | -CH$_2$Ph | F | -O(4-CN-Ph) | H | H |
| 101 | -CH$_2$Ph | H | -O(4-CN-Ph) | F | H |
| 102 | -CH$_2$Ph | H | -O(4-CN-Ph) | H | F |
| 103 | -CH$_2$Ph | F | -O(4-CN-Ph) | F | H |
| 104 | -CH$_2$Ph | H | -O(4-CN-Ph) | F | F |
| 105 | -CH$_2$Ph | F | -O(4-CN-Ph) | F | F |
| 106 | -CH$_2$Ph | 3-(phenylthio)-1H-indol-1-yl | H | H | H |
| 107 | -CH$_2$Ph | H | 3-(phenylthio)-1H-indol-1-yl | H | H |
| 108 | -CH$_2$Ph | H | H | 3-(phenylthio)-1H-indol-1-yl | H |
| 109 | -CH$_2$Ph | H | H | H | 3-(phenylthio)-1H-indol-1-yl |
| 110 | -CH$_2$Ph | F | 3-(phenylthio)-1H-indol-1-yl | H | H |
| 111 | -CH$_2$Ph | H | 3-(phenylthio)-1H-indol-1-yl | F | H |
| 112 | -CH$_2$Ph | H | 3-(phenylthio)-1H-indol-1-yl | H | F |
| 113 | -CH$_2$Ph | F | 3-(phenylthio)-1H-indol-1-yl | F | H |
| 114 | -CH$_2$Ph | H | 3-(phenylthio)-1H-indol-1-yl | F | F |
| 115 | -CH$_2$Ph | F | 3-(phenylthio)-1H-indol-1-yl | F | F |

FIGURE 2D

| No. | $R^{3a}$ | $R^{9a}$ | $R^{10a}$ | $R^{11a}$ | $R^{12a}$ |
|---|---|---|---|---|---|
| 116 | -CH$_2$Ph | dibenzylamino | H | H | H |
| 117 | -CH$_2$Ph | H | dibenzylamino | H | H |
| 118 | -CH$_2$Ph | H | H | dibenzylamino | H |
| 119 | -CH$_2$Ph | H | H | H | dibenzylamino |
| 120 | -CH$_2$Ph | F | dibenzylamino | H | H |
| 121 | -CH$_2$Ph | H | dibenzylamino | F | H |
| 122 | -CH$_2$Ph | H | dibenzylamino | H | F |
| 123 | -CH$_2$Ph | F | dibenzylamino | F | H |
| 124 | -CH$_2$Ph | H | dibenzylamino | F | F |
| 125 | -CH$_2$Ph | F | dibenzylamino | F | F |
| 126 | -CH$_2$Ph | -S(O)$_2$(4-Cl-Ph) | H | H | H |
| 127 | -CH$_2$Ph | H | -S(O)$_2$(4-Cl-Ph) | H | H |
| 128 | -CH$_2$Ph | H | H | -S(O)$_2$(4-Cl-Ph) | H |
| 129 | -CH$_2$Ph | H | H | H | -S(O)$_2$(4-Cl-Ph) |
| 130 | -CH$_2$Ph | F | -S(O)$_2$(4-Cl-Ph) | H | H |
| 131 | -CH$_2$Ph | H | -S(O)$_2$(4-Cl-Ph) | F | H |
| 132 | -CH$_2$Ph | H | -S(O)$_2$(4-Cl-Ph) | H | F |
| 133 | -CH$_2$Ph | F | -S(O)$_2$(4-Cl-Ph) | F | H |
| 134 | -CH$_2$Ph | H | -S(O)$_2$(4-Cl-Ph) | F | F |
| 135 | -CH$_2$Ph | F | -S(O)$_2$(4-Cl-Ph) | F | F |
| 136 | -CH$_2$Ph | -S(4-pyridyl) | H | H | H |
| 137 | -CH$_2$Ph | H | -S(4-pyridyl) | H | H |
| 138 | -CH$_2$Ph | H | H | -S(4-pyridyl) | H |
| 139 | -CH$_2$Ph | H | H | H | -S(4-pyridyl) |
| 140 | -CH$_2$Ph | F | -S(4-pyridyl) | H | H |
| 141 | -CH$_2$Ph | H | -S(4-pyridyl) | F | H |
| 142 | -CH$_2$Ph | H | -S(4-pyridyl) | H | F |
| 143 | -CH$_2$Ph | F | -S(4-pyridyl) | F | H |
| 144 | -CH$_2$Ph | H | -S(4-pyridyl) | F | F |
| 145 | -CH$_2$Ph | F | -S(4-pyridyl) | F | F |
| 146 | -CH$_2$Ph | -NHCH$_2$Ph | H | H | H |
| 147 | -CH$_2$Ph | H | -NHCH$_2$Ph | H | H |
| 148 | -CH$_2$Ph | H | H | -NHCH$_2$Ph | H |
| 149 | -CH$_2$Ph | H | H | H | -NHCH$_2$Ph |
| 150 | -CH$_2$Ph | F | -NHCH$_2$Ph | H | H |
| 151 | -CH$_2$Ph | H | -NHCH$_2$Ph | F | H |
| 152 | -CH$_2$Ph | H | -NHCH$_2$Ph | H | F |
| 153 | -CH$_2$Ph | F | -NHCH$_2$Ph | F | H |
| 154 | -CH$_2$Ph | H | -NHCH$_2$Ph | F | F |
| 155 | -CH$_2$Ph | F | -NHCH$_2$Ph | F | F |
| 156 | Me | F | H | H | H |
| 157 | Me | H | F | H | H |
| 158 | Me | H | H | F | H |

FIGURE 2E

| No. | $R^{3a}$ | $R^{9a}$ | $R^{10a}$ | $R^{11a}$ | $R^{12a}$ |
|---|---|---|---|---|---|
| 159 | Me | H | H | H | F |
| 160 | Me | F | F | H | H |
| 161 | Me | H | F | F | H |
| 162 | Me | H | H | F | F |
| 163 | Me | F | H | F | H |
| 164 | Me | H | F | H | F |
| 165 | Me | F | H | H | F |
| 166 | Me | H | F | F | F |
| 167 | Me | F | H | F | F |
| 168 | Me | F | F | H | F |
| 169 | Me | F | F | F | H |
| 170 | Me | F | F | F | F |
| 171 | Me | -OCH$_2$C(O)OH | H | H | H |
| 172 | Me | H | -OCH$_2$C(O)OH | H | H |
| 173 | Me | H | H | -OCH$_2$C(O)OH | H |
| 174 | Me | H | H | H | -OCH$_2$C(O)OH |
| 175 | Me | F | -OCH$_2$C(O)OH | H | H |
| 176 | Me | H | -OCH$_2$C(O)OH | F | H |
| 177 | Me | H | -OCH$_2$C(O)OH | H | F |
| 178 | Me | F | -OCH$_2$C(O)OH | F | H |
| 179 | Me | H | -OCH$_2$C(O)OH | F | F |
| 180 | Me | F | -OCH$_2$C(O)OH | F | F |
| 181 | Me | -NMeS(O)$_2$Ph | H | H | H |
| 182 | Me | H | -NMeS(O)$_2$Ph | H | H |
| 183 | Me | H | H | -NMeS(O)$_2$Ph | H |
| 184 | Me | H | H | H | -NMeS(O)$_2$Ph |
| 185 | Me | F | -NMeS(O)$_2$Ph | H | H |
| 186 | Me | H | -NMeS(O)$_2$Ph | F | H |
| 187 | Me | H | -NMeS(O)$_2$Ph | H | F |
| 188 | Me | F | -NMeS(O)$_2$Ph | F | H |
| 189 | Me | H | -NMeS(O)$_2$Ph | F | F |
| 190 | Me | F | -NMeS(O)$_2$Ph | F | F |
| 191 | Me | H | -CH$_2$OH | H | H |
| 192 | Me | H | H | -CH$_2$OH | H |
| 193 | Me | H | H | H | -CH$_2$OH |
| 194 | Me | -CH$_2$OH | F | H | H |
| 195 | Me | -CH$_2$OH | H | F | H |
| 196 | Me | -CH$_2$OH | H | H | F |
| 197 | Me | -CH$_2$OH | Cl | H | H |
| 198 | Me | -CH$_2$OH | H | Cl | H |
| 199 | Me | -CH$_2$OH | H | H | Cl |
| 200 | Me | F | -CH$_2$OH | H | H |

FIGURE 2F

| No. | $R^{3a}$ | $R^{9a}$ | $R^{10a}$ | $R^{11a}$ | $R^{12a}$ |
|---|---|---|---|---|---|
| 201 | Me | H | -CH$_2$OH | F | H |
| 202 | Me | H | -CH$_2$OH | H | F |
| 203 | Me | Cl | -CH$_2$OH | H | H |
| 204 | Me | H | -CH$_2$OH | Cl | H |
| 205 | Me | H | -CH$_2$OH | H | Cl |
| 206 | Me | F | H | -CH$_2$OH | H |
| 207 | Me | H | F | -CH$_2$OH | H |
| 208 | Me | H | H | -CH$_2$OH | F |
| 209 | Me | Cl | H | -CH$_2$OH | H |
| 210 | Me | H | Cl | -CH$_2$OH | H |
| 211 | Me | H | H | -CH$_2$OH | Cl |
| 212 | Me | F | H | H | -CH$_2$OH |
| 213 | Me | H | F | H | -CH$_2$OH |
| 214 | Me | H | H | F | -CH$_2$OH |
| 215 | Me | Cl | H | H | -CH$_2$OH |
| 216 | Me | H | Cl | H | -CH$_2$OH |
| 217 | Me | H | H | Cl | -CH$_2$OH |
| 218 | Me | F | -CH$_2$OH | F | H |
| 219 | Me | H | -CH$_2$OH | F | F |
| 220 | Me | F | -CH$_2$OH | F | F |
| 221 | Me | H | -NH$_2$ | H | H |
| 222 | Me | H | H | -NH$_2$ | H |
| 223 | Me | H | H | H | -NH$_2$ |
| 224 | Me | -NH$_2$ | F | H | H |
| 225 | Me | -NH$_2$ | H | F | H |
| 226 | Me | -NH$_2$ | H | H | F |
| 227 | Me | -NH$_2$ | Cl | H | H |
| 228 | Me | -NH$_2$ | H | Cl | H |
| 229 | Me | -NH$_2$ | H | H | Cl |
| 230 | Me | F | -NH$_2$ | H | H |
| 231 | Me | H | -NH$_2$ | F | H |
| 232 | Me | H | -NH$_2$ | H | F |
| 233 | Me | Cl | -NH$_2$ | H | H |
| 234 | Me | H | -NH$_2$ | Cl | H |
| 235 | Me | H | -NH$_2$ | H | Cl |
| 236 | Me | F | H | -NH$_2$ | H |
| 237 | Me | H | F | -NH$_2$ | H |
| 238 | Me | H | H | -NH$_2$ | F |
| 239 | Me | Cl | H | -NH$_2$ | H |
| 240 | Me | H | Cl | -NH$_2$ | H |
| 241 | Me | H | H | -NH$_2$ | Cl |
| 242 | Me | F | H | H | -NH$_2$ |
| 243 | Me | H | F | H | -NH$_2$ |

FIGURE 2G

| No. | $R^{3a}$ | $R^{9a}$ | $R^{10a}$ | $R^{11a}$ | $R^{12a}$ |
|---|---|---|---|---|---|
| 244 | Me | H | H | F | -NH$_2$ |
| 245 | Me | Cl | H | H | -NH$_2$ |
| 246 | Me | H | Cl | H | -NH$_2$ |
| 247 | Me | H | H | Cl | -NH$_2$ |
| 248 | Me | F | -NH$_2$ | F | H |
| 249 | Me | H | -NH$_2$ | F | F |
| 250 | Me | F | -NH$_2$ | F | F |
| 251 | Me | -O(4-CN-Ph) | H | H | H |
| 252 | Me | H | -O(4-CN-Ph) | H | H |
| 253 | Me | H | H | -O(4-CN-Ph) | H |
| 254 | Me | H | H | H | -O(4-CN-Ph) |
| 255 | Me | F | -O(4-CN-Ph) | H | H |
| 256 | Me | H | -O(4-CN-Ph) | F | H |
| 257 | Me | H | -O(4-CN-Ph) | H | F |
| 258 | Me | F | -O(4-CN-Ph) | F | H |
| 259 | Me | H | -O(4-CN-Ph) | F | F |
| 260 | Me | F | -O(4-CN-Ph) | F | F |
| 261 | Me | 3-(phenylthio)-1H-indol-1-yl | H | H | H |
| 262 | Me | H | 3-(phenylthio)-1H-indol-1-yl | H | H |
| 263 | Me | H | H | 3-(phenylthio)-1H-indol-1-yl | H |
| 264 | Me | H | H | H | 3-(phenylthio)-1H-indol-1-yl |
| 265 | Me | F | 3-(phenylthio)-1H-indol-1-yl | H | H |
| 266 | Me | H | 3-(phenylthio)-1H-indol-1-yl | F | H |
| 267 | Me | H | 3-(phenylthio)-1H-indol-1-yl | H | F |
| 268 | Me | F | 3-(phenylthio)-1H-indol-1-yl | F | H |
| 269 | Me | H | 3-(phenylthio)-1H-indol-1-yl | F | F |
| 270 | Me | F | 3-(phenylthio)-1H-indol-1-yl | F | F |
| 271 | Me | dibenzylamino | H | H | H |
| 272 | Me | H | dibenzylamino | H | H |
| 273 | Me | H | H | dibenzylamino | H |
| 274 | Me | H | H | H | dibenzylamino |
| 275 | Me | F | dibenzylamino | H | H |
| 276 | Me | H | dibenzylamino | F | H |
| 277 | Me | H | dibenzylamino | H | F |
| 278 | Me | F | dibenzylamino | F | H |

FIGURE 2H

| No. | $R^{3a}$ | $R^{9a}$ | $R^{10a}$ | $R^{11a}$ | $R^{12a}$ |
|---|---|---|---|---|---|
| 279 | Me | H | dibenzylamino | F | F |
| 280 | Me | F | dibenzylamino | F | F |
| 281 | Me | -S(O)$_2$(4-Cl-Ph) | H | H | H |
| 282 | Me | H | -S(O)$_2$(4-Cl-Ph) | H | H |
| 283 | Me | H | H | -S(O)$_2$(4-Cl-Ph) | H |
| 284 | Me | H | H | H | -S(O)$_2$(4-Cl-Ph) |
| 285 | Me | F | -S(O)$_2$(4-Cl-Ph) | H | H |
| 286 | Me | H | -S(O)$_2$(4-Cl-Ph) | F | H |
| 287 | Me | H | -S(O)$_2$(4-Cl-Ph) | H | F |
| 288 | Me | F | -S(O)$_2$(4-Cl-Ph) | F | H |
| 289 | Me | H | -S(O)$_2$(4-Cl-Ph) | F | F |
| 290 | Me | F | -S(O)$_2$(4-Cl-Ph) | F | F |
| 291 | Me | -S(4-pyridyl) | H | H | H |
| 292 | Me | H | -S(4-pyridyl) | H | H |
| 293 | Me | H | H | -S(4-pyridyl) | H |
| 294 | Me | H | H | H | -S(4-pyridyl) |
| 295 | Me | F | -S(4-pyridyl) | H | H |
| 296 | Me | H | -S(4-pyridyl) | F | H |
| 297 | Me | H | -S(4-pyridyl) | H | F |
| 298 | Me | F | -S(4-pyridyl) | F | H |
| 299 | Me | H | -S(4-pyridyl) | F | F |
| 300 | Me | F | -S(4-pyridyl) | F | F |
| 301 | Me | -NHCH$_2$Ph | H | H | H |
| 302 | Me | H | -NHCH$_2$Ph | H | H |
| 303 | Me | H | H | -NHCH$_2$Ph | H |
| 304 | Me | H | H | H | -NHCH$_2$Ph |
| 305 | Me | F | -NHCH$_2$Ph | H | H |
| 306 | Me | H | -NHCH$_2$Ph | F | H |
| 307 | Me | H | -NHCH$_2$Ph | H | F |
| 308 | Me | F | -NHCH$_2$Ph | F | H |
| 309 | Me | H | -NHCH$_2$Ph | F | F |
| 310 | Me | F | -NHCH$_2$Ph | F | F |

FIGURE 3A

| Structure | X | R$^b$ | R |
|---|---|---|---|
| NC—[ring with R$^b$, X, O]—[benzoxaborole with OH] | CH | F | |
| | | Cl | |
| | | CH$_3$ | |
| | | CH$_2$CH$_3$ | |
| | | C$_3$-alkyl | |
| | | C$_4$-alkyl | |
| | | C$_5$-alkyl | |
| | | C$_6$-alkyl | |
| | | C$_3$-cycloalkyl | |
| | | C$_4$-cycloalkyl | |
| | | C$_5$-cycloalkyl | |
| | | C$_6$-cycloalkyl | |
| | | CH$_2$R | OH |
| | | | NH$_2$ |
| | | | N(CH$_3$)$_2$ |
| | | | —N(morpholine) |
| | | | —N(N-methylpiperazine) |
| | | | —N(piperidine) |
| | | | NHCHO |
| | | CHO | |
| | | CH=N-OH | |
| | | COOR | H |
| | | | CH$_3$ |
| | | | CH$_2$CH$_3$ |
| | | CF$_3$ | |
| | | NHR | H |
| | | | CH$_3$ |
| | | | C(CH$_3$)$_3$ |
| | | | CH$_2$Ph |
| | | | CH$_2$CH$_2$OH |
| | | | CH$_2$CH$_2$OCH$_3$ |
| | | | CH$_2$CH$_2$OCH$_2$Ph |
| | | N(CH$_3$)R | CH$_3$ |
| | | | CH$_2$CH$_2$OH |
| | | | CH$_2$CH$_2$OCH$_3$ |
| | | —N(pyrrolidine) | |
| | | —N(morpholine) | |
| | | —N(piperidine) | |
| | | OH | |
| | | C$_1$-alkoxy | |

FIGURE 3B

| Structure | X | R^b | R |
|---|---|---|---|
| (NC-pyridine/benzene-O-benzoxaborole structure with R^b) | CH | C_2-alkoxy | |
| | | C_3-alkoxy | |
| | | C_4-alkoxy | |
| | | -O-CH_2-cyclopropyl | |
| | | -O-cyclopentyl | |
| | | -O-CH_2-cyclopentyl | |
| | | -O-CH_2-cyclohexyl | |
| | | OCH_2CH_2R | F |
| | | | N(CH_3)_2 |
| | | | OH |
| | | | OCH_3 |
| | | | OC(O)CH_3 |
| | | | -O-tetrahydropyran-2-yl |
| | | | -OCH(CH_3)_2 |
| | | | -CH_2COCH_3 |
| | | OCH_2CF_3 | |
| | | OCH_2CHF_2 | |
| | | -O-CH_2-(2-pyridyl) | |
| | | OC(O)CH_3 | |
| | | OCH_2C(O)R | OH |
| | | | OCH_2CH_3 |
| | | | OC(CH_3)_3 |
| | | | N(CH_2CH_3)_2 |
| | | | -N(4-methylpiperidinyl) |
| | | | -N(4-methylpiperazinyl)-CH_3 |
| | | | -N-morpholinyl |
| | N | F | |
| | | Cl | |
| | | CH_3 | |
| | | CH_2CH_3 | |
| | | C_3-alkyl | |
| | | C_4-alkyl | |
| | | C_5-alkyl | |

FIGURE 3C
| Structure | X | R$^b$ | R |
|---|---|---|---|
| 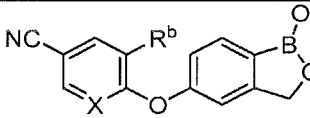 | N | C$_6$-alkyl | |
| | | C$_3$-cycloalkyl | |
| | | C$_4$-cycloalkyl | |
| | | C$_5$-cycloalkyl | |
| | | C$_6$-cycloalkyl | |
| | | C$_7$-cycloalkyl | |
| | | C$_8$-cycloalkyl | |
| | | CH$_2$R | OH |
| | | | NH$_2$ |
| | | | N(CH$_3$)$_2$ |
| | | | 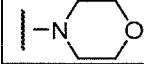 |
| | | |  |
| | | | NHCHO |
| | | CHO | |
| | | CH=N-OH | |
| | | COOR | H |
| | | | CH$_3$ |
| | | | CH$_2$CH$_3$ |
| | | CF$_3$ | |
| | | NHR | H |
| | | | CH$_3$ |
| | | | C(CH$_3$)$_3$ |
| | | | CH$_2$Ph |
| | | | CH$_2$CH$_2$OH |
| | | | CH$_2$CH$_2$OCH$_3$ |
| | | | CH$_2$CH$_2$OCH$_2$Ph |
| | | N(CH$_3$)R | CH$_3$ |
| | | | CH$_2$CH$_2$OH |
| | | | CH$_2$CH$_2$OCH$_3$ |
| | | 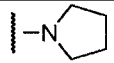 | |
| | | 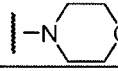 | |
| | | OH | |
| | | C$_1$-alkoxy | |
| | | C$_2$-alkoxy | |
| | | C$_3$-alkoxy | |
| | | C$_4$-alkoxy | |
| | | 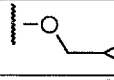 | |
| | | 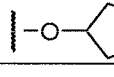 | |

FIGURE 3D

| Structure | X | R$^b$ | R |
|---|---|---|---|
| 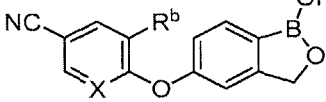 | N | -O-CH₂-cyclopentyl | |
| | | OCH₂CH₂R | F |
| | | | N(CH₃)₂ |
| | | | OH |
| | | | OCH₃ |
| | | | OC(O)CH₃ |
| | | | -O-tetrahydropyranyl |
| | | | -OCH(CH₃)₂ |
| | | | -CH₂COCH₃ |
| | | OCH₂CF₃ | |
| | | OCH₂CHF₂ | |
| | | -O-CH₂-(2-pyridyl) | |
| | | OC(O)CH₃ | |
| | | OCH₂C(O)R | OH |
| | | | OCH₂CH₃ |
| | | | OC(CH₃)₃ |
| | | | N(CH₂CH₃)₂ |
| | | | -N(4-methylpiperidinyl) |
| | | | -N(4-methylpiperazinyl) |
| | | | -N(morpholinyl) |
| 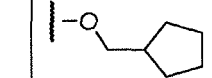 | CH | F | |
| | | Cl | |
| | | CH₃ | |
| | | CH₂CH₃ | |
| | | C₃-alkyl | |
| | | C₄-alkyl | |
| | | C₅-alkyl | |
| | | C₆-alkyl | |
| | | C₃-cycloalkyl | |
| | | C₄-cycloalkyl | |
| | | C₅-cycloalkyl | |
| | | C₆-cycloalkyl | |
| | | C₇-cycloalkyl | |
| | | C₈-cycloalkyl | |
| | | CH₂R | OH |
| | | | NH₂ |
| | | | N(CH₃)₂ |

FIGURE 3E

| Structure | X | R$^b$ | R |
|---|---|---|---|
| (structure shown: NC-pyridine-O-benzoxaborole with R$^b$ substituent) | CH | CH$_2$R | -N(morpholine) |
| | | | -N(N-methylpiperazine) |
| | | | NHCHO |
| | | CHO | |
| | | CH=N-OH | |
| | | COOR | H |
| | | | CH$_3$ |
| | | | CH$_2$CH$_3$ |
| | | CF$_3$ | |
| | | NHR | H |
| | | | CH$_3$ |
| | | | C(CH$_3$)$_3$ |
| | | | CH$_2$Ph |
| | | | CH$_2$CH$_2$OH |
| | | | CH$_2$CH$_2$OCH$_3$ |
| | | | CH$_2$CH$_2$OCH$_2$Ph |
| | | N(CH$_3$)R | CH$_3$ |
| | | | CH$_2$CH$_2$OH |
| | | | CH$_2$CH$_2$OCH$_3$ |
| | | -N(pyrrolidine) | |
| | | -N(morpholine) | |
| | | OH | |
| | | C$_1$-alkoxy | |
| | | C$_2$-alkoxy | |
| | | C$_3$-alkoxy | |
| | | C$_4$-alkoxy | |
| | | -O-CH$_2$-cyclopropyl | |
| | | -O-cyclopentyl | |
| | | -O-CH$_2$-cyclopentyl | |
| | | OCH$_2$CH$_2$R | F |
| | | | N(CH$_3$)$_2$ |
| | | | OH |
| | | | OCH$_3$ |
| | | | OC(O)CH$_3$ |
| | | | -O-tetrahydropyran |
| | | OCH$_2$CF$_3$ | |

FIGURE 3F

| Structure | X | R^b | R |
|---|---|---|---|
| (structure shown: NC-pyridyl(R^b)-X-O-benzoxaborole-OH) | CH | -O-CH₂-(2-pyridyl) | |
| | | OC(O)CH₃ | |
| | | OCH₂C(O)R | OH |
| | | | OCH₂CH₃ |
| | | | OC(CH₃)₃ |
| | | | N(CH₂CH₃)₂ |
| | | | -N(piperidinyl)-CH₃ |
| | | | -N(piperazinyl)N-CH₃ |
| | | | -N(morpholinyl)O |
| | N | F | |
| | | Cl | |
| | | CH₃ | |
| | | CH₂CH₃ | |
| | | C₃-alkyl | |
| | | C₄-alkyl | |
| | | C₅-alkyl | |
| | | C₆-alkyl | |
| | | C₃-cycloalkyl | |
| | | C₄-cycloalkyl | |
| | | C₅-cycloalkyl | |
| | | C₆-cycloalkyl | |
| | | C₇-cycloalkyl | |
| | | C₈-cycloalkyl | |
| | | CH₂R | OH |
| | | | NH₂ |
| | | | N(CH₃)₂ |
| | | | -N(morpholinyl)O |
| | | | -N(piperazinyl)N-CH₃ |
| | | | NHCHO |
| | | CHO | |
| | | CH=N-OH | |
| | | COOR | H |
| | | | CH₃ |
| | | | CH₂CH₃ |
| | | CF₃ | |
| | | NHR | H |
| | | | CH₃ |
| | | | C(CH₃)₃ |
| | | | CH₂Ph |

FIGURE 3G

| Structure | X | R$^b$ | R |
|---|---|---|---|
| (structure shown: NC-pyridine with R$^b$, X, linked via O to benzoxaborole with OH) | N | NHR | CH$_2$CH$_2$OH |
| | | | CH$_2$CH$_2$OCH$_3$ |
| | | | CH$_2$CH$_2$OCH$_2$Ph |
| | | N(CH$_3$)R | CH$_3$ |
| | | | CH$_2$CH$_2$OH |
| | | | CH$_2$CH$_2$OCH$_3$ |
| | | –N(pyrrolidine) | |
| | | –N(morpholine) | |
| | | OH | |
| | | C$_1$-alkoxy | |
| | | C$_2$-alkoxy | |
| | | C$_3$-alkoxy | |
| | | C$_4$-alkoxy | |
| | | –O–CH$_2$-cyclopropyl | |
| | | –O–cyclopentyl | |
| | | –O–CH$_2$-cyclopentyl | |
| | | OCH$_2$CH$_2$R | F |
| | | | N(CH$_3$)$_2$ |
| | | | OH |
| | | | OCH$_3$ |
| | | | OC(O)CH$_3$ |
| | | | O-tetrahydropyranyl |
| | | OCH$_2$CF$_3$ | |
| | | –O–CH$_2$-pyridyl | |
| | | OC(O)CH$_3$ | |
| | | OCH$_2$C(O)R | OH |
| | | | OCH$_2$CH$_3$ |
| | | | OC(CH$_3$)$_3$ |
| | | | N(CH$_2$CH$_3$)$_2$ |
| | | | –N(4-methylpiperidine)–CH$_3$ |
| | | | –N(piperazine)N–CH$_3$ |
| | | | –N(morpholine) |

FIGURE 3H
| Structure | X | R^b | R |
|---|---|---|---|
| 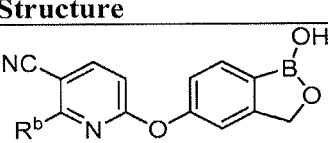 | [n/a] | F | |
| | | Cl | |
| | | $CH_3$ | |
| | | $CH_2CH_3$ | |
| | | $C_3$-alkyl | |
| | | $C_4$-alkyl | |
| | | $C_5$-alkyl | |
| | | $C_6$-alkyl | |
| | | $C_3$-cycloalkyl | |
| | | $C_4$-cycloalkyl | |
| | | $C_5$-cycloalkyl | |
| | | $C_6$-cycloalkyl | |
| | | $C_7$-cycloalkyl | |
| | | $C_8$-cycloalkyl | |
| | | $CH_2R$ | OH |
| | | | $NH_2$ |
| | | | $N(CH_3)_2$ |
| | | | 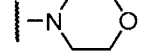 |
| | | | 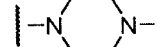 |
| | | | NHCHO |
| | | CHO | |
| | | CH=N-OH | |
| | | COOR | H |
| | | | $CH_3$ |
| | | | $CH_2CH_3$ |
| | | $CF_3$ | |
| | | NHR | H |
| | | | $CH_3$ |
| | | | $C(CH_3)_3$ |
| | | | $CH_2Ph$ |
| | | | $CH_2CH_2OH$ |
| | | | $CH_2CH_2OCH_3$ |
| | | | $CH_2CH_2OCH_2Ph$ |
| | | $N(CH_3)R$ | $CH_3$ |
| | | | $CH_2CH_2OH$ |
| | | | $CH_2CH_2OCH_3$ |
| | | 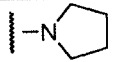 | |
| | |  | |
| | | OH | |
| | | $C_1$-alkoxy | |
| | | $C_2$-alkoxy | |
| | | $C_3$-alkoxy | |

FIGURE 3I
| Structure | X | R$^b$ | R |
|---|---|---|---|
| 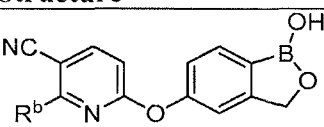 | [n/a] | C$_4$-alkoxy | |
| | | 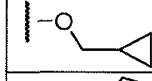 | |
| | | 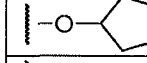 | |
| | | 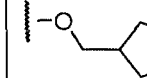 | |
| | | OCH$_2$CH$_2$R | F |
| | | | N(CH$_3$)$_2$ |
| | | | OH |
| | | | OCH$_3$ |
| | | | OC(O)CH$_3$ |
| | | | 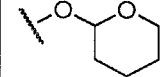 |
| | | OCH$_2$CF$_3$ | |
| | | 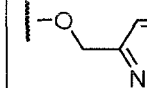 | |
| | | OC(O)CH$_3$ | |
| | | OCH$_2$C(O)R | OH |
| | | | OCH$_2$CH$_3$ |
| | | | OC(CH$_3$)$_3$ |
| | | | N(CH$_2$CH$_3$)$_2$ |
| | | | 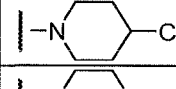 |
| | | | 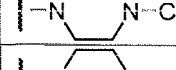 |
| | | | 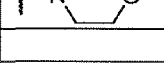 |
| 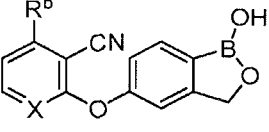 | CH | F | |
| | | Cl | |
| | | CH$_3$ | |
| | | CH$_2$CH$_3$ | |
| | | C$_3$-alkyl | |
| | | C$_4$-alkyl | |
| | | C$_5$-alkyl | |
| | | C$_6$-alkyl | |
| | | C$_3$-cycloalkyl | |
| | | C$_4$-cycloalkyl | |
| | | C$_5$-cycloalkyl | |
| | | C$_6$-cycloalkyl | |
| | | C$_7$-cycloalkyl | |
| | | C$_8$-cycloalkyl | |
| | | CH$_2$R | OH |
| | | | NH$_2$ |

FIGURE 3J

| Structure | X | R^b | R |
|---|---|---|---|
| ![structure with R^b, CN, OH, B, O, X] | CH | CH₂R | N(CH₃)₂ |
| | | | −N⟨O⟩ (morpholine) |
| | | | −N⟨N−CH₃⟩ (N-methylpiperazine) |
| | | | NHCHO |
| | | CHO | |
| | | CH=N-OH | |
| | | COOR | H |
| | | | CH₃ |
| | | | CH₂CH₃ |
| | | CF₃ | |
| | | NHR | H |
| | | | CH₃ |
| | | | C(CH₃)₃ |
| | | | CH₂Ph |
| | | | CH₂CH₂OH |
| | | | CH₂CH₂OCH₃ |
| | | | CH₂CH₂OCH₂Ph |
| | | N(CH₃)R | CH₃ |
| | | | CH₂CH₂OH |
| | | | CH₂CH₂OCH₃ |
| | | −N⟨⟩ (pyrrolidine) | |
| | | −N⟨O⟩ (morpholine) | |
| | | OH | |
| | | C₁-alkoxy | |
| | | C₂-alkoxy | |
| | | C₃-alkoxy | |
| | | C₄-alkoxy | |
| | | −O-CH₂-cyclopropyl | |
| | | −O-cyclopentyl | |
| | | −O-CH₂-cyclopentyl | |
| | | OCH₂CH₂R | F |
| | | | N(CH₃)₂ |
| | | | OH |
| | | | OCH₃ |
| | | | OC(O)CH₃ |
| | | | −O-tetrahydropyranyl |
| | | OCH₂CF₃ | |

FIGURE 3K

| Structure | X | Rᵇ | R |
|---|---|---|---|
| 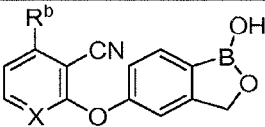 | CH | -O-CH₂-(2-pyridyl) | |
| | | OC(O)CH₃ | |
| | | OCH₂C(O)R | OH |
| | | | OCH₂CH₃ |
| | | | OC(CH₃)₃ |
| | | | N(CH₂CH₃)₂ |
| | | | -N(4-methylpiperidinyl) |
| | | | -N(4-methylpiperazinyl) |
| | | | -N(morpholinyl) |
| | N | F | |
| | | Cl | |
| | | CH₃ | |
| | | CH₂CH₃ | |
| | | C₃-alkyl | |
| | | C₄-alkyl | |
| | | C₅-alkyl | |
| | | C₆-alkyl | |
| | | C₃-cycloalkyl | |
| | | C₄-cycloalkyl | |
| | | C₅-cycloalkyl | |
| | | C₆-cycloalkyl | |
| | | C₇-cycloalkyl | |
| | | C₈-cycloalkyl | |
| | | CH₂R | OH |
| | | | NH₂ |
| | | | N(CH₃)₂ |
| | | | -N(morpholinyl) |
| | | | -N(4-methylpiperazinyl) |
| | | | NHCHO |
| | | CHO | |
| | | CH=N-OH | |
| | | COOR | H |
| | | | CH₃ |
| | | | CH₂CH₃ |
| | | CF₃ | |
| | | NHR | H |
| | | | CH₃ |
| | | | C(CH₃)₃ |
| | | | CH₂Ph |

FIGURE 3L

| Structure | X | R$^b$ | R |
|---|---|---|---|
| ![structure with R$^b$, CN, OH, B, O, X] | N | NHR | CH$_2$CH$_2$OH |
| | | | CH$_2$CH$_2$OCH$_3$ |
| | | | CH$_2$CH$_2$OCH$_2$Ph |
| | | N(CH$_3$)R | CH$_3$ |
| | | | CH$_2$CH$_2$OH |
| | | | CH$_2$CH$_2$OCH$_3$ |
| | | -N(pyrrolidine) | |
| | | -N(morpholine) | |
| | | OH | |
| | | C$_1$-alkoxy | |
| | | C$_2$-alkoxy | |
| | | C$_3$-alkoxy | |
| | | C$_4$-alkoxy | |
| | | -O-cyclopropyl | |
| | | -O-cyclopentyl | |
| | | -O-CH$_2$-cyclopentyl | |
| | | OCH$_2$CH$_2$R | F |
| | | | N(CH$_3$)$_2$ |
| | | | OH |
| | | | OCH$_3$ |
| | | | OC(O)CH$_3$ |
| | | | -O-tetrahydropyran |
| | | OCH$_2$CF$_3$ | |
| | | -O-CH$_2$-pyridyl | |
| | | OC(O)CH$_3$ | |
| | | OCH$_2$C(O)R | OH |
| | | | OCH$_2$CH$_3$ |
| | | | OC(CH$_3$)$_3$ |
| | | | N(CH$_2$CH$_3$)$_2$ |
| | | | -N(4-methylpiperidine) |
| | | | -N(N-methylpiperazine) |
| | | | -N(morpholine) |

FIGURE 3M

| Structure | X | R^b | R |
|---|---|---|---|
| 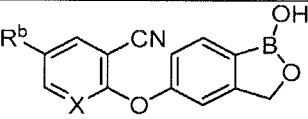 | CH | F | |
| | | Cl | |
| | | CH$_3$ | |
| | | CH$_2$CH$_3$ | |
| | | C$_3$-alkyl | |
| | | C$_4$-alkyl | |
| | | C$_5$-alkyl | |
| | | C$_6$-alkyl | |
| | | C$_3$-cycloalkyl | |
| | | C$_4$-cycloalkyl | |
| | | C$_5$-cycloalkyl | |
| | | C$_6$-cycloalkyl | |
| | | C$_7$-cycloalkyl | |
| | | C$_8$-cycloalkyl | |
| | | CH$_2$R | OH |
| | | | NH$_2$ |
| | | | N(CH$_3$)$_2$ |
| | | |  |
| | | |  |
| | | | NHCHO |
| | | CHO | |
| | | CH=N-OH | |
| | | COOR | H |
| | | | CH$_3$ |
| | | | CH$_2$CH$_3$ |
| | | CF$_3$ | |
| | | NHR | H |
| | | | CH$_3$ |
| | | | C(CH$_3$)$_3$ |
| | | | CH$_2$Ph |
| | | | CH$_2$CH$_2$OH |
| | | | CH$_2$CH$_2$OCH$_3$ |
| | | | CH$_2$CH$_2$OCH$_2$Ph |
| | | N(CH$_3$)R | CH$_3$ |
| | | | CH$_2$CH$_2$OH |
| | | | CH$_2$CH$_2$OCH$_3$ |
| | |  | |
| | |  | |
| | | OH | |
| | | C$_1$-alkoxy | |
| | | C$_2$-alkoxy | |
| | | C$_3$-alkoxy | |

FIGURE 3N
| Structure | X | R^b | R |
|---|---|---|---|
| 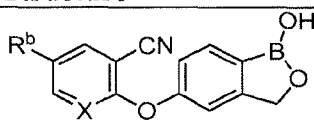 | CH | C_4-alkoxy | |
| | | 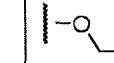 | |
| | | 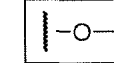 | |
| | | 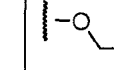 | |
| | | OCH_2CH_2R | F |
| | | | N(CH_3)_2 |
| | | | OH |
| | | | OCH_3 |
| | | | OC(O)CH_3 |
| | | | 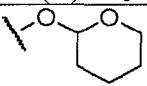 |
| | | OCH_2CF_3 | |
| | | 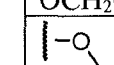 | |
| | | OC(O)CH_3 | |
| | | OCH_2C(O)R | OH |
| | | | OCH_2CH_3 |
| | | | OC(CH_3)_3 |
| | | | N(CH_2CH_3)_2 |
| | | | 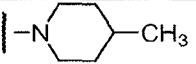 |
| | | | 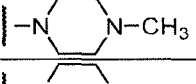 |
| | | |  |
| | N | F | |
| | | Cl | |
| | | CH_3 | |
| | | CH_2CH_3 | |
| | | C_3-alkyl | |
| | | C_4-alkyl | |
| | | C_5-alkyl | |
| | | C_6-alkyl | |
| | | C_3-cycloalkyl | |
| | | C_4-cycloalkyl | |
| | | C_5-cycloalkyl | |
| | | C_6-cycloalkyl | |
| | | C_7-cycloalkyl | |
| | | C_8-cycloalkyl | |
| | | CH_2R | OH |
| | | | NH_2 |

FIGURE 3O

| Structure | X | R$^b$ | R |
|---|---|---|---|
| 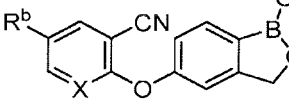 | N | CH$_2$R | N(CH$_3$)$_2$ |
| | | | 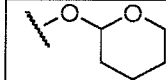 -N⟨O⟩ (morpholine) |
| | | | -N⟨N-CH$_3$⟩ (N-methylpiperazine) |
| | | | NHCHO |
| | | CHO | |
| | | CH=N-OH | |
| | | COOR | H |
| | | | CH$_3$ |
| | | | CH$_2$CH$_3$ |
| | | CF$_3$ | |
| | | NHR | H |
| | | | CH$_3$ |
| | | | C(CH$_3$)$_3$ |
| | | | CH$_2$Ph |
| | | | CH$_2$CH$_2$OH |
| | | | CH$_2$CH$_2$OCH$_3$ |
| | | | CH$_2$CH$_2$OCH$_2$Ph |
| | | N(CH$_3$)R | CH$_3$ |
| | | | CH$_2$CH$_2$OH |
| | | | CH$_2$CH$_2$OCH$_3$ |
| | | -N⟩ (pyrrolidine) | |
| | | -N⟨O⟩ (morpholine) | |
| | | OH | |
| | | C$_1$-alkoxy | |
| | | C$_2$-alkoxy | |
| | | C$_3$-alkoxy | |
| | | C$_4$-alkoxy | |
| | | -O-CH$_2$-cyclopropyl | |
| | | -O-cyclopentyl | |
| | | -O-CH$_2$-cyclopentyl | |
| | | OCH$_2$CH$_2$R | F |
| | | | N(CH$_3$)$_2$ |
| | | | OH |
| | | | OCH$_3$ |
| | | | OC(O)CH$_3$ |
| | | | -O-tetrahydropyranyl |
| | | OCH$_2$CF$_3$ | |

FIGURE 3P
| Structure | X | R$^b$ | R |
|---|---|---|---|
| 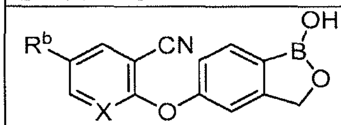 | N | 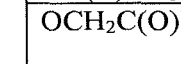 | |
| | | OC(O)CH$_3$ | |
| | | OCH$_2$C(O)R | OH |
| | | | OCH$_2$CH$_3$ |
| | | | OC(CH$_3$)$_3$ |
| | | | N(CH$_2$CH$_3$)$_2$ |
| | | | 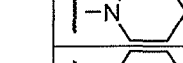 |
| | | | 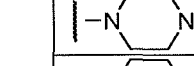 |
| | | | 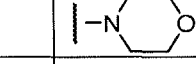 |
| 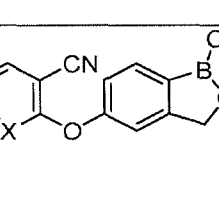 | CH | F | |
| | | Cl | |
| | | CH$_3$ | |
| | | CH$_2$CH$_3$ | |
| | | C$_3$-alkyl | |
| | | C$_4$-alkyl | |
| | | C$_5$-alkyl | |
| | | C$_6$-alkyl | |
| | | C$_3$-cycloalkyl | |
| | | C$_4$-cycloalkyl | |
| | | C$_5$-cycloalkyl | |
| | | C$_6$-cycloalkyl | |
| | | C$_7$-cycloalkyl | |
| | | C$_8$-cycloalkyl | |
| | | CH$_2$R | OH |
| | | | NH$_2$ |
| | | | N(CH$_3$)$_2$ |
| | | | 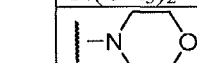 |
| | | | 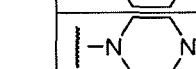 |
| | | | NHCHO |
| | | CHO | |
| | | CH=N-OH | |
| | | COOR | H |
| | | | CH$_3$ |
| | | | CH$_2$CH$_3$ |
| | | CF$_3$ | |
| | | NHR | H |
| | | | CH$_3$ |
| | | | C(CH$_3$)$_3$ |
| | | | CH$_2$Ph |

FIGURE 3Q
| Structure | X | R$^b$ | R |
|---|---|---|---|
| 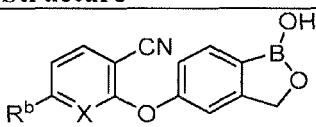 | CH | NHR | CH$_2$CH$_2$OH |
| | | | CH$_2$CH$_2$OCH$_3$ |
| | | | CH$_2$CH$_2$OCH$_2$Ph |
| | | N(CH$_3$)R | CH$_3$ |
| | | | CH$_2$CH$_2$OH |
| | | | CH$_2$CH$_2$OCH$_3$ |
| | | 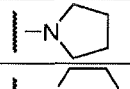 | |
| | | 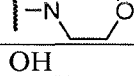 | |
| | | OH | |
| | | C$_1$-alkoxy | |
| | | C$_2$-alkoxy | |
| | | C$_3$-alkoxy | |
| | | C$_4$-alkoxy | |
| | | 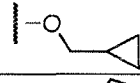 | |
| | | 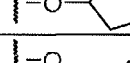 | |
| | | 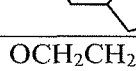 | |
| | | OCH$_2$CH$_2$R | F |
| | | | N(CH$_3$)$_2$ |
| | | | OH |
| | | | OCH$_3$ |
| | | | OC(O)CH$_3$ |
| | | | 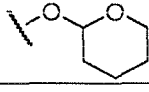 |
| | | OCH$_2$CF$_3$ | |
| | | 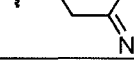 | |
| | | OC(O)CH$_3$ | |
| | | OCH$_2$C(O)R | OH |
| | | | OCH$_2$CH$_3$ |
| | | | OC(CH$_3$)$_3$ |
| | | | N(CH$_2$CH$_3$)$_2$ |
| | | | 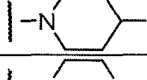 |
| | | | 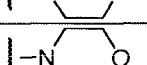 |
| | | |  |
| | N | F | |
| | | Cl | |

FIGURE 3R
| Structure | X | R^b | R |
|---|---|---|---|
| 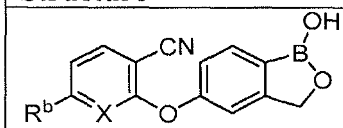 | N | CH₃ | |
| | | CH₂CH₃ | |
| | | C₃-alkyl | |
| | | C₄-alkyl | |
| | | C₅-alkyl | |
| | | C₆-alkyl | |
| | | C₃-cycloalkyl | |
| | | C₄-cycloalkyl | |
| | | C₅-cycloalkyl | |
| | | C₆-cycloalkyl | |
| | | C₇-cycloalkyl | |
| | | C₈-cycloalkyl | |
| | | CH₂R | OH |
| | | | NH₂ |
| | | | N(CH₃)₂ |
| | | |  |
| | | |  |
| | | | NHCHO |
| | | CHO | |
| | | CH=N-OH | |
| | | COOR | H |
| | | | CH₃ |
| | | | CH₂CH₃ |
| | | CF₃ | |
| | | NHR | H |
| | | | CH₃ |
| | | | C(CH₃)₃ |
| | | | CH₂Ph |
| | | | CH₂CH₂OH |
| | | | CH₂CH₂OCH₃ |
| | | | CH₂CH₂OCH₂Ph |
| | | N(CH₃)R | CH₃ |
| | | | CH₂CH₂OH |
| | | | CH₂CH₂OCH₃ |
| | |  | |
| | | 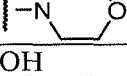 | |
| | | OH | |
| | | C₁-alkoxy | |
| | | C₂-alkoxy | |
| | | C₃-alkoxy | |
| | | C₄-alkoxy | |

FIGURE 3S
| Structure | X | R$^b$ | R |
|---|---|---|---|
| 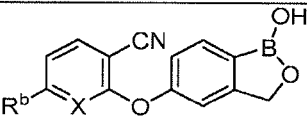 | N | 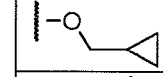 | |
| | | 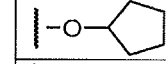 | |
| | | 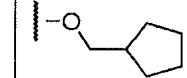 | |
| | | OCH$_2$CH$_2$R | F |
| | | | N(CH$_3$)$_2$ |
| | | | OH |
| | | | OCH$_3$ |
| | | | OC(O)CH$_3$ |
| | | | 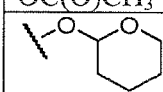 |
| | | OCH$_2$CF$_3$ | |
| | | 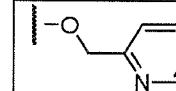 | |
| | | OC(O)CH$_3$ | |
| | | OCH$_2$C(O)R | OH |
| | | | OCH$_2$CH$_3$ |
| | | | OC(CH$_3$)$_3$ |
| | | | N(CH$_2$CH$_3$)$_2$ |
| | | | 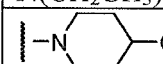 |
| | | | 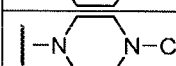 |
| | | | 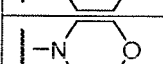 |
| (second structure) | [n/a] | F | |
| | | Cl | |
| | | CH$_3$ | |
| | | CH$_2$CH$_3$ | |
| | | C$_3$-alkyl | |
| | | C$_4$-alkyl | |
| | | C$_5$-alkyl | |
| | | C$_6$-alkyl | |
| | | C$_3$-cycloalkyl | |
| | | C$_4$-cycloalkyl | |
| | | C$_5$-cycloalkyl | |
| | | C$_6$-cycloalkyl | |
| | | C$_7$-cycloalkyl | |
| | | C$_8$-cycloalkyl | |
| | | CH$_2$R | OH |
| | | | NH$_2$ |
| | | | N(CH$_3$)$_2$ |

FIGURE 3T
| Structure | X | R^b | R |
|---|---|---|---|
| 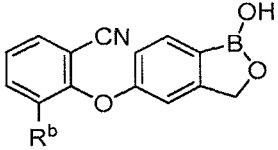 | [n/a] | CH$_2$R | 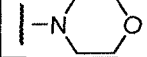 |
| | | | 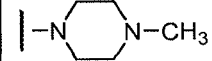 |
| | | | NHCHO |
| | | CHO | |
| | | CH=N-OH | |
| | | COOR | H |
| | | | CH$_3$ |
| | | | CH$_2$CH$_3$ |
| | | CF$_3$ | |
| | | NHR | H |
| | | | CH$_3$ |
| | | | C(CH$_3$)$_3$ |
| | | | CH$_2$Ph |
| | | | CH$_2$CH$_2$OH |
| | | | CH$_2$CH$_2$OCH$_3$ |
| | | | CH$_2$CH$_2$OCH$_2$Ph |
| | | N(CH$_3$)R | CH$_3$ |
| | | | CH$_2$CH$_2$OH |
| | | | CH$_2$CH$_2$OCH$_3$ |
| | | 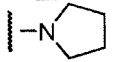 | |
| | | 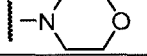 | |
| | | OH | |
| | | C$_1$-alkoxy | |
| | | C$_2$-alkoxy | |
| | | C$_3$-alkoxy | |
| | | C$_4$-alkoxy | |
| | | 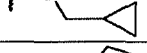 | |
| | |  | |
| | |  | |
| | | OCH$_2$CH$_2$R | F |
| | | | N(CH$_3$)$_2$ |
| | | | OH |
| | | | OCH$_3$ |
| | | | OC(O)CH$_3$ |
| | | | 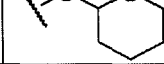 |
| | | OCH$_2$CF$_3$ | |

FIGURE 3U

| Structure | X | R$^b$ | R |
|---|---|---|---|
| (structure with CN, O-B-OH, R$^b$) | [n/a] | -O-CH$_2$-(2-pyridyl) | |
| | | OC(O)CH$_3$ | |
| | | OCH$_2$C(O)R | OH |
| | | | OCH$_2$CH$_3$ |
| | | | OC(CH$_3$)$_3$ |
| | | | N(CH$_2$CH$_3$)$_2$ |
| | | | -N(4-methylpiperidinyl) |
| | | | -N(N'-methylpiperazinyl) |
| | | | -N(morpholinyl) |
| (structure with CN, X, R$^b$, O-B-OH) | CH | F | |
| | | Cl | |
| | | CH$_3$ | |
| | | CH$_2$CH$_3$ | |
| | | C$_3$-alkyl | |
| | | C$_4$-alkyl | |
| | | C$_5$-alkyl | |
| | | C$_6$-alkyl | |
| | | C$_3$-cycloalkyl | |
| | | C$_4$-cycloalkyl | |
| | | C$_5$-cycloalkyl | |
| | | C$_6$-cycloalkyl | |
| | | C$_7$-cycloalkyl | |
| | | C$_8$-cycloalkyl | |
| | | CH$_2$R | OH |
| | | | NH$_2$ |
| | | | N(CH$_3$)$_2$ |
| | | | -N(morpholinyl) |
| | | | -N(N'-methylpiperazinyl) |
| | | | NHCHO |
| | | CHO | |
| | | CH=N-OH | |
| | | COOR | H |
| | | | CH$_3$ |
| | | | CH$_2$CH$_3$ |
| | | CF$_3$ | |
| | | NHR | H |
| | | | CH$_3$ |
| | | | C(CH$_3$)$_3$ |
| | | | CH$_2$Ph |

FIGURE 3V
| Structure | X | R^b | R |
|---|---|---|---|
| 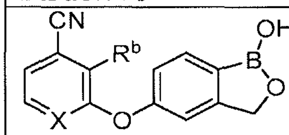 | CH | NHR | CH$_2$CH$_2$OH |
| | | | CH$_2$CH$_2$OCH$_3$ |
| | | | CH$_2$CH$_2$OCH$_2$Ph |
| | | N(CH$_3$)R | CH$_3$ |
| | | | CH$_2$CH$_2$OH |
| | | | CH$_2$CH$_2$OCH$_3$ |
| | |  | |
| | |  | |
| | | OH | |
| | | C$_1$-alkoxy | |
| | | C$_2$-alkoxy | |
| | | C$_3$-alkoxy | |
| | | C$_4$-alkoxy | |
| | |  | |
| | |  | |
| | |  | |
| | | OCH$_2$CH$_2$R | F |
| | | | N(CH$_3$)$_2$ |
| | | | OH |
| | | | OCH$_3$ |
| | | | OC(O)CH$_3$ |
| | | |  |
| | | OCH$_2$CF$_3$ | |
| | |  | |
| | | OC(O)CH$_3$ | |
| | | OCH$_2$C(O)R | OH |
| | | | OCH$_2$CH$_3$ |
| | | | OC(CH$_3$)$_3$ |
| | | | N(CH$_2$CH$_3$)$_2$ |
| | | |  |
| | | |  |
| | | |  |
| | N | F | |
| | | Cl | |

FIGURE 3W
| Structure | X | Rᵇ | R |
|---|---|---|---|
| 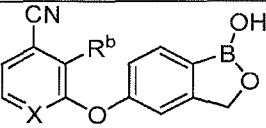 | N | CH₃ | |
| | | CH₂CH₃ | |
| | | C₃-alkyl | |
| | | C₄-alkyl | |
| | | C₅-alkyl | |
| | | C₆-alkyl | |
| | | C₃-cycloalkyl | |
| | | C₄-cycloalkyl | |
| | | C₅-cycloalkyl | |
| | | C₆-cycloalkyl | |
| | | C₇-cycloalkyl | |
| | | C₈-cycloalkyl | |
| | | CH₂R | OH |
| | | | NH₂ |
| | | | N(CH₃)₂ |
| | | | 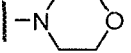 |
| | | | 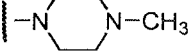 |
| | | | NHCHO |
| | | CHO | |
| | | CH=N-OH | |
| | | COOR | H |
| | | | CH₃ |
| | | | CH₂CH₃ |
| | | CF₃ | |
| | | NHR | H |
| | | | CH₃ |
| | | | C(CH₃)₃ |
| | | | CH₂Ph |
| | | | CH₂CH₂OH |
| | | | CH₂CH₂OCH₃ |
| | | | CH₂CH₂OCH₂Ph |
| | | N(CH₃)R | CH₃ |
| | | | CH₂CH₂OH |
| | | | CH₂CH₂OCH₃ |
| | | 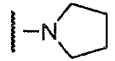 | |
| | | 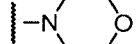 | |
| | | OH | |
| | | C₁-alkoxy | |
| | | C₂-alkoxy | |
| | | C₃-alkoxy | |
| | | C₄-alkoxy | |

FIGURE 3X

| Structure | X | R^b | R |
|---|---|---|---|
| ![structure with CN, R^b, B(OH)O, X] | N | -O-cyclopropylmethyl | |
| | | -O-cyclopentyl | |
| | | -O-cyclopentylmethyl | |
| | | OCH₂CH₂R | F |
| | | | N(CH₃)₂ |
| | | | OH |
| | | | OCH₃ |
| | | | OC(O)CH₃ |
| | | | -O-tetrahydropyranyl |
| | | OCH₂CF₃ | |
| | | -O-CH₂-(2-pyridyl) | |
| | | OC(O)CH₃ | |
| | | OCH₂C(O)R | OH |
| | | | OCH₂CH₃ |
| | | | OC(CH₃)₃ |
| | | | N(CH₂CH₃)₂ |
| | | | -N(4-methylpiperidinyl) |
| | | | -N(4-methylpiperazinyl) |
| | | | -N-morpholinyl |
| ![structure with CN, R^b, B(OH)O, X] | CH | F | |
| | | Cl | |
| | | CH₃ | |
| | | CH₂CH₃ | |
| | | C₃-alkyl | |
| | | C₄-alkyl | |
| | | C₅-alkyl | |
| | | C₆-alkyl | |
| | | C₃-cycloalkyl | |
| | | C₄-cycloalkyl | |
| | | C₅-cycloalkyl | |
| | | C₆-cycloalkyl | |
| | | C₇-cycloalkyl | |
| | | C₈-cycloalkyl | |
| | | CH₂R | OH |
| | | | NH₂ |
| | | | N(CH₃)₂ |

FIGURE 3Y
| Structure | X | R$^b$ | R |
|---|---|---|---|
| 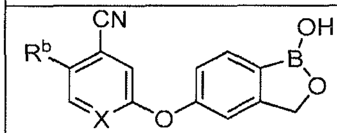 | CH | CH$_2$R | 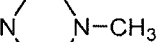 |
| | | |  |
| | | | NHCHO |
| | | CHO | |
| | | CH=N-OH | |
| | | COOR | H |
| | | | CH$_3$ |
| | | | CH$_2$CH$_3$ |
| | | CF$_3$ | |
| | | NHR | H |
| | | | CH$_3$ |
| | | | C(CH$_3$)$_3$ |
| | | | CH$_2$Ph |
| | | | CH$_2$CH$_2$OH |
| | | | CH$_2$CH$_2$OCH$_3$ |
| | | | CH$_2$CH$_2$OCH$_2$Ph |
| | | N(CH$_3$)R | CH$_3$ |
| | | | CH$_2$CH$_2$OH |
| | | | CH$_2$CH$_2$OCH$_3$ |
| | |  | |
| | |  | |
| | | OH | |
| | | C$_1$-alkoxy | |
| | | C$_2$-alkoxy | |
| | | C$_3$-alkoxy | |
| | | C$_4$-alkoxy | |
| | |  | |
| | |  | |
| | |  | |
| | | OCH$_2$CH$_2$R | F |
| | | | N(CH$_3$)$_2$ |
| | | | OH |
| | | | OCH$_3$ |
| | | | OC(O)CH$_3$ |
| | | |  |
| | | OCH$_2$CF$_3$ | |

FIGURE 3Z
| Structure | X | R^b | R |
|---|---|---|---|
| 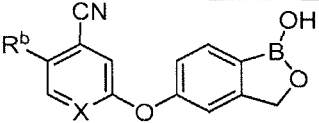 | CH | 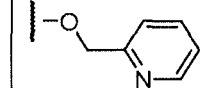 | |
| | | OC(O)CH₃ | |
| | | OCH₂C(O)R | OH |
| | | | OCH₂CH₃ |
| | | | OC(CH₃)₃ |
| | | | N(CH₂CH₃)₂ |
| | | |  |
| | | | 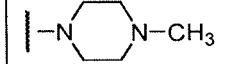 |
| | | | 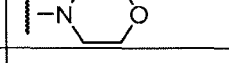 |
| | N | F | |
| | | Cl | |
| | | CH₃ | |
| | | CH₂CH₃ | |
| | | C₃-alkyl | |
| | | C₄-alkyl | |
| | | C₅-alkyl | |
| | | C₆-alkyl | |
| | | C₃-cycloalkyl | |
| | | C₄-cycloalkyl | |
| | | C₅-cycloalkyl | |
| | | C₆-cycloalkyl | |
| | | C₇-cycloalkyl | |
| | | C₈-cycloalkyl | |
| | | CH₂R | OH |
| | | | NH₂ |
| | | | N(CH₃)₂ |
| | | | 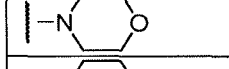 |
| | | | 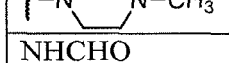 |
| | | | NHCHO |
| | | CHO | |
| | | CH=N-OH | |
| | | COOR | H |
| | | | CH₃ |
| | | | CH₂CH₃ |
| | | CF₃ | |
| | | NHR | H |
| | | | CH₃ |
| | | | C(CH₃)₃ |
| | | | CH₂Ph |

FIGURE 3AA

| Structure | X | R$^b$ | R |
|---|---|---|---|
| ![structure with CN, R$^b$, X, O, B, OH] | N | NHR | CH$_2$CH$_2$OH |
| | | | CH$_2$CH$_2$OCH$_3$ |
| | | | CH$_2$CH$_2$OCH$_2$Ph |
| | | N(CH$_3$)R | CH$_3$ |
| | | | CH$_2$CH$_2$OH |
| | | | CH$_2$CH$_2$OCH$_3$ |
| | | -N(pyrrolidine) | |
| | | -N(morpholine) | |
| | | OH | |
| | | C$_1$-alkoxy | |
| | | C$_2$-alkoxy | |
| | | C$_3$-alkoxy | |
| | | C$_4$-alkoxy | |
| | | -O-cyclopropyl | |
| | | -O-cyclopentyl | |
| | | -O-CH$_2$-cyclopentyl | |
| | | OCH$_2$CH$_2$R | F |
| | | | N(CH$_3$)$_2$ |
| | | | OH |
| | | | OCH$_3$ |
| | | | OC(O)CH$_3$ |
| | | | -O-tetrahydropyranyl |
| | | OCH$_2$CF$_3$ | |
| | | -O-CH$_2$-pyridyl | |
| | | OC(O)CH$_3$ | |
| | | OCH$_2$C(O)R | OH |
| | | | OCH$_2$CH$_3$ |
| | | | OC(CH$_3$)$_3$ |
| | | | N(CH$_2$CH$_3$)$_2$ |
| | | | -N(4-methylpiperidine) |
| | | | -N(4-methylpiperazine) |
| | | | -N(morpholine) |

FIGURE 3BB

| Structure | X | R$^b$ | R |
|---|---|---|---|
| (structure shown: benzoxaborole with CN, OH, R$^b$, X, O linker) | CH | F | |
| | | Cl | |
| | | CH$_3$ | |
| | | CH$_2$CH$_3$ | |
| | | C$_3$-alkyl | |
| | | C$_4$-alkyl | |
| | | C$_5$-alkyl | |
| | | C$_6$-alkyl | |
| | | C$_3$-cycloalkyl | |
| | | C$_4$-cycloalkyl | |
| | | C$_5$-cycloalkyl | |
| | | C$_6$-cycloalkyl | |
| | | C$_7$-cycloalkyl | |
| | | C$_8$-cycloalkyl | |
| | | CH$_2$R | OH |
| | | | NH$_2$ |
| | | | N(CH$_3$)$_2$ |
| | | | –N(morpholine) |
| | | | –N(N-methylpiperazine)–CH$_3$ |
| | | | NHCHO |
| | | CHO | |
| | | CH=N-OH | |
| | | COOR | H |
| | | | CH$_3$ |
| | | | CH$_2$CH$_3$ |
| | | CF$_3$ | |
| | | NHR | H |
| | | | CH$_3$ |
| | | | C(CH$_3$)$_3$ |
| | | | CH$_2$Ph |
| | | | CH$_2$CH$_2$OH |
| | | | CH$_2$CH$_2$OCH$_3$ |
| | | | CH$_2$CH$_2$OCH$_2$Ph |
| | | N(CH$_3$)R | CH$_3$ |
| | | | CH$_2$CH$_2$OH |
| | | | CH$_2$CH$_2$OCH$_3$ |
| | | –N(pyrrolidine) | |
| | | –N(morpholine) | |
| | | OH | |
| | | C$_1$-alkoxy | |
| | | C$_2$-alkoxy | |
| | | C$_3$-alkoxy | |

FIGURE 3CC

| Structure | X | R$^b$ | R |
|---|---|---|---|
| [structure with CN, R$^b$, X, O, benzoxaborole-OH] | CH | C$_4$-alkoxy | |
| | | -O-cyclopropylmethyl | |
| | | -O-cyclopentyl | |
| | | -O-cyclopentylmethyl | |
| | | OCH$_2$CH$_2$R | F |
| | | | N(CH$_3$)$_2$ |
| | | | OH |
| | | | OCH$_3$ |
| | | | OC(O)CH$_3$ |
| | | | tetrahydropyranyloxy |
| | | OCH$_2$CF$_3$ | |
| | | -O-CH$_2$-pyridin-2-yl | |
| | | OC(O)CH$_3$ | |
| | | OCH$_2$C(O)R | OH |
| | | | OCH$_2$CH$_3$ |
| | | | OC(CH$_3$)$_3$ |
| | | | N(CH$_2$CH$_3$)$_2$ |
| | | | -N(4-methylpiperidinyl) |
| | | | -N(4-methylpiperazinyl) |
| | | | -N(morpholinyl) |
| | N | F | |
| | | Cl | |
| | | CH$_3$ | |
| | | CH$_2$CH$_3$ | |
| | | C$_3$-alkyl | |
| | | C$_4$-alkyl | |
| | | C$_5$-alkyl | |
| | | C$_6$-alkyl | |
| | | C$_3$-cycloalkyl | |
| | | C$_4$-cycloalkyl | |
| | | C$_5$-cycloalkyl | |
| | | C$_6$-cycloalkyl | |
| | | C$_7$-cycloalkyl | |
| | | C$_8$-cycloalkyl | |
| | | CH$_2$R | OH |
| | | | NH$_2$ |

FIGURE 3DD

| Structure | X | R$^b$ | R |
|---|---|---|---|
| (structure with CN, Rb, X, O-benzoxaborole-OH) | N | CH₂R | N(CH₃)₂ |
| | | | −N(morpholine) |
| | | | −N(N-methylpiperazine)−CH₃ |
| | | | NHCHO |
| | | CHO | |
| | | CH=N-OH | |
| | | COOR | H |
| | | | CH₃ |
| | | | CH₂CH₃ |
| | | CF₃ | |
| | | NHR | H |
| | | | CH₃ |
| | | | C(CH₃)₃ |
| | | | CH₂Ph |
| | | | CH₂CH₂OH |
| | | | CH₂CH₂OCH₃ |
| | | | CH₂CH₂OCH₂Ph |
| | | N(CH₃)R | CH₃ |
| | | | CH₂CH₂OH |
| | | | CH₂CH₂OCH₃ |
| | | −N(pyrrolidine) | |
| | | −N(morpholine) | |
| | | OH | |
| | | C₁-alkoxy | |
| | | C₂-alkoxy | |
| | | C₃-alkoxy | |
| | | C₄-alkoxy | |
| | | −O-CH₂-cyclopropyl | |
| | | −O-cyclopentyl | |
| | | −O-CH₂-cyclopentyl | |
| | | OCH₂CH₂R | F |
| | | | N(CH₃)₂ |
| | | | OH |
| | | | OCH₃ |
| | | | OC(O)CH₃ |
| | | | −O-tetrahydropyran-O |
| | | OCH₂CF₃ | |

FIGURE 3EE

| Structure | X | R^b | R |
|---|---|---|---|
| [structure: CN-pyridine with X, R^b, O-benzoxaborole-OH] | N | -O-CH2-(2-pyridyl) | |
| | | OC(O)CH3 | |
| | | OCH2C(O)R | OH |
| | | | OCH2CH3 |
| | | | OC(CH3)3 |
| | | | N(CH2CH3)2 |
| | | | -N(4-methylpiperidine) |
| | | | -N(N'-methylpiperazine) |
| | | | -N(morpholine) |
| [structure: CN-phenyl with R^b, O-benzoxaborole-OH] | [n/a] | F | |
| | | Cl | |
| | | CH3 | |
| | | CH2CH3 | |
| | | C3-alkyl | |
| | | C4-alkyl | |
| | | C5-alkyl | |
| | | C6-alkyl | |
| | | C3-cycloalkyl | |
| | | C4-cycloalkyl | |
| | | C5-cycloalkyl | |
| | | C6-cycloalkyl | |
| | | C7-cycloalkyl | |
| | | C8-cycloalkyl | |
| | | CH2R | OH |
| | | | NH2 |
| | | | N(CH3)2 |
| | | | -N(morpholine) |
| | | | -N(N'-methylpiperazine) |
| | | | NHCHO |
| | | CHO | |
| | | CH=N-OH | |
| | | COOR | H |
| | | | CH3 |
| | | | CH2CH3 |
| | | CF3 | |
| | | NHR | H |
| | | | CH3 |
| | | | C(CH3)3 |
| | | | CH2Ph |

FIGURE 3FF

| Structure | X | R^b | R |
|---|---|---|---|
| (structure: benzonitrile-O-benzoxaborole with R^b) | [n/a] | NHR | CH₂CH₂OH |
| | | | CH₂CH₂OCH₃ |
| | | | CH₂CH₂OCH₂Ph |
| | | N(CH₃)R | CH₃ |
| | | | CH₂CH₂OH |
| | | | CH₂CH₂OCH₃ |
| | | -N(pyrrolidine) | |
| | | -N(morpholine) | |
| | | OH | |
| | | C₁-alkoxy | |
| | | C₂-alkoxy | |
| | | C₃-alkoxy | |
| | | C₄-alkoxy | |
| | | -O-CH₂-cyclopropyl | |
| | | -O-cyclopentyl | |
| | | -O-CH₂-cyclopentyl | |
| | | OCH₂CH₂R | F |
| | | | N(CH₃)₂ |
| | | | OH |
| | | | OCH₃ |
| | | | OC(O)CH₃ |
| | | | -O-tetrahydropyran |
| | | OCH₂CF₃ | |
| | | -O-CH₂-(2-pyridyl) | |
| | | OC(O)CH₃ | |
| | | OCH₂C(O)R | OH |
| | | | OCH₂CH₃ |
| | | | OC(CH₃)₃ |
| | | | N(CH₂CH₃)₂ |
| | | | -N(4-methylpiperidine) |
| | | | -N(4-methylpiperazine) |
| | | | -N(morpholine) |

FIGURE 4A

| Structure | X | R$^b$ | R |
|---|---|---|---|
| (methyl pyridine carboxylate with O-linked benzoxaborole, R$^b$ substituent) | CH | F | |
| | | Cl | |
| | | CH$_3$ | |
| | | CH$_2$CH$_3$ | |
| | | C$_3$-alkyl | |
| | | C$_4$-alkyl | |
| | | C$_5$-alkyl | |
| | | C$_6$-alkyl | |
| | | C$_3$-cycloalkyl | |
| | | C$_4$-cycloalkyl | |
| | | C$_5$-cycloalkyl | |
| | | C$_6$-cycloalkyl | |
| | | CH$_2$R | OH |
| | | | NH$_2$ |
| | | | N(CH$_3$)$_2$ |
| | | | –N(morpholine) |
| | | | –N(N-methylpiperazine) |
| | | | –N(piperidine) |
| | | | NHCHO |
| | | CHO | |
| | | CH=N-OH | |
| | | COOR | H |
| | | | CH$_3$ |
| | | | CH$_2$CH$_3$ |
| | | CF$_3$ | |
| | | NHR | H |
| | | | CH$_3$ |
| | | | C(CH$_3$)$_3$ |
| | | | CH$_2$Ph |
| | | | CH$_2$CH$_2$OH |
| | | | CH$_2$CH$_2$OCH$_3$ |
| | | | CH$_2$CH$_2$OCH$_2$Ph |
| | | N(CH$_3$)R | CH$_3$ |
| | | | CH$_2$CH$_2$OH |
| | | | CH$_2$CH$_2$OCH$_3$ |
| | | –N(pyrrolidine) | |
| | | –N(morpholine) | |
| | | –N(piperidine) | |
| | | OH | |
| | | C$_1$-alkoxy | |

FIGURE 4B

| Structure | X | R$^b$ | R |
|---|---|---|---|
| (methyl ester-pyridine-O-benzoxaborole structure with R$^b$) | CH | C$_2$-alkoxy | |
| | | C$_3$-alkoxy | |
| | | C$_4$-alkoxy | |
| | | –O–CH$_2$-cyclopropyl | |
| | | –O-cyclopentyl | |
| | | –O–CH$_2$-cyclopentyl | |
| | | –O–CH$_2$-cyclohexyl | |
| | | OCH$_2$CH$_2$R | F |
| | | | N(CH$_3$)$_2$ |
| | | | OH |
| | | | OCH$_3$ |
| | | | OC(O)CH$_3$ |
| | | | –O-tetrahydropyranyl |
| | | | –OCH(CH$_3$)$_2$ |
| | | | –CH$_2$COCH$_3$ |
| | | OCH$_2$CF$_3$ | |
| | | OCH$_2$CHF$_2$ | |
| | | –O–CH$_2$-pyridyl | |
| | | OC(O)CH$_3$ | |
| | | OCH$_2$C(O)R | OH |
| | | | OCH$_2$CH$_3$ |
| | | | OC(CH$_3$)$_3$ |
| | | | N(CH$_2$CH$_3$)$_2$ |
| | | | –N-(4-methylpiperidinyl) |
| | | | –N-(4-methylpiperazinyl) |
| | | | –N-morpholinyl |
| | N | F | |
| | | Cl | |
| | | CH$_3$ | |
| | | CH$_2$CH$_3$ | |
| | | C$_3$-alkyl | |
| | | C$_4$-alkyl | |
| | | C$_5$-alkyl | |

FIGURE 4C

| Structure | X | R^b | R |
|---|---|---|---|
| (methyl benzoate-pyridine-O-benzoxaborole structure with R^b substituent) | N | C_6-alkyl | |
| | | C_3-cycloalkyl | |
| | | C_4-cycloalkyl | |
| | | C_5-cycloalkyl | |
| | | C_6-cycloalkyl | |
| | | C_7-cycloalkyl | |
| | | C_8-cycloalkyl | |
| | | CH_2R | OH |
| | | | NH_2 |
| | | | N(CH_3)_2 |
| | | | −N(morpholine) |
| | | | −N(N-methylpiperazine)−CH_3 |
| | | | NHCHO |
| | | CHO | |
| | | CH=N-OH | |
| | | COOR | H |
| | | | CH_3 |
| | | | CH_2CH_3 |
| | | CF_3 | |
| | | NHR | H |
| | | | CH_3 |
| | | | C(CH_3)_3 |
| | | | CH_2Ph |
| | | | CH_2CH_2OH |
| | | | CH_2CH_2OCH_3 |
| | | | CH_2CH_2OCH_2Ph |
| | | N(CH_3)R | CH_3 |
| | | | CH_2CH_2OH |
| | | | CH_2CH_2OCH_3 |
| | | −N(pyrrolidine) | |
| | | −N(morpholine) | |
| | | OH | |
| | | C_1-alkoxy | |
| | | C_2-alkoxy | |
| | | C_3-alkoxy | |
| | | C_4-alkoxy | |
| | | −O−CH_2-cyclopropyl | |
| | | −O−cyclopentyl | |

FIGURE 4D

| Structure | X | R$^b$ | R |
|---|---|---|---|
| 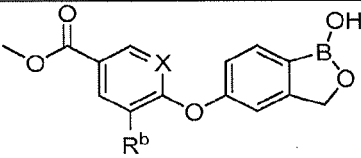 | N | 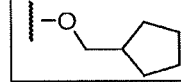 (-O-CH₂-cyclopentyl) | |
| | | OCH₂CH₂R | F |
| | | | N(CH₃)₂ |
| | | | OH |
| | | | OCH₃ |
| | | | OC(O)CH₃ |
| | | | 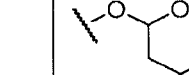 (-O-tetrahydropyranyl) |
| | | | -OCH(CH₃)₂ |
| | | | -CH₂COCH₃ |
| | | OCH₂CF₃ | |
| | | OCH₂CHF₂ | |
| | | 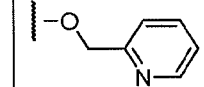 (-O-CH₂-pyridyl) | |
| | | OC(O)CH₃ | |
| | | OCH₂C(O)R | OH |
| | | | OCH₂CH₃ |
| | | | OC(CH₃)₃ |
| | | | N(CH₂CH₃)₂ |
| | | | 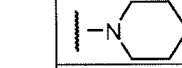 (-N-4-methylpiperidinyl) |
| | | | 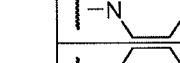 (-N-methylpiperazinyl) |
| | | | 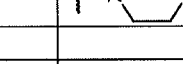 (-N-morpholinyl) |
| 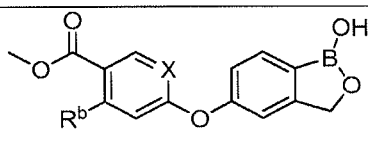 | CH | F | |
| | | Cl | |
| | | CH₃ | |
| | | CH₂CH₃ | |
| | | C₃-alkyl | |
| | | C₄-alkyl | |
| | | C₅-alkyl | |
| | | C₆-alkyl | |
| | | C₃-cycloalkyl | |
| | | C₄-cycloalkyl | |
| | | C₅-cycloalkyl | |
| | | C₆-cycloalkyl | |
| | | C₇-cycloalkyl | |
| | | C₈-cycloalkyl | |
| | | CH₂R | OH |
| | | | NH₂ |
| | | | N(CH₃)₂ |

FIGURE 4E
| Structure | X | R^b | R |
|---|---|---|---|
| 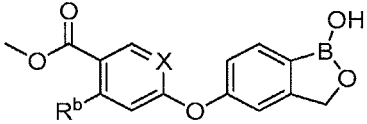 | CH | CH$_2$R |  |
| | | | 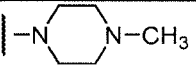 |
| | | | NHCHO |
| | | CHO | |
| | | CH=N-OH | |
| | | COOR | H |
| | | | CH$_3$ |
| | | | CH$_2$CH$_3$ |
| | | CF$_3$ | |
| | | NHR | H |
| | | | CH$_3$ |
| | | | C(CH$_3$)$_3$ |
| | | | CH$_2$Ph |
| | | | CH$_2$CH$_2$OH |
| | | | CH$_2$CH$_2$OCH$_3$ |
| | | | CH$_2$CH$_2$OCH$_2$Ph |
| | | N(CH$_3$)R | CH$_3$ |
| | | | CH$_2$CH$_2$OH |
| | | | CH$_2$CH$_2$OCH$_3$ |
| | |  | |
| | |  | |
| | | OH | |
| | | C$_1$-alkoxy | |
| | | C$_2$-alkoxy | |
| | | C$_3$-alkoxy | |
| | | C$_4$-alkoxy | |
| | |  | |
| | | 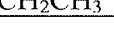 | |
| | |  | |
| | | OCH$_2$CH$_2$R | F |
| | | | N(CH$_3$)$_2$ |
| | | | OH |
| | | | OCH$_3$ |
| | | | OC(O)CH$_3$ |
| | | |  |
| | | OCH$_2$CF$_3$ | |

FIGURE 4F
| Structure | X | R^b | R |
|---|---|---|---|
| 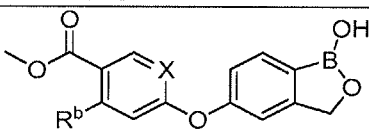 | CH | 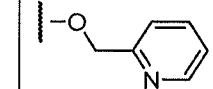 | |
| | | OC(O)CH₃ | |
| | | OCH₂C(O)R | OH |
| | | | OCH₂CH₃ |
| | | | OC(CH₃)₃ |
| | | | N(CH₂CH₃)₂ |
| | | |  |
| | | |  |
| | | | 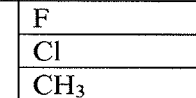 |
| | N | F | |
| | | Cl | |
| | | CH₃ | |
| | | CH₂CH₃ | |
| | | C₃-alkyl | |
| | | C₄-alkyl | |
| | | C₅-alkyl | |
| | | C₆-alkyl | |
| | | C₃-cycloalkyl | |
| | | C₄-cycloalkyl | |
| | | C₅-cycloalkyl | |
| | | C₆-cycloalkyl | |
| | | C₇-cycloalkyl | |
| | | C₈-cycloalkyl | |
| | | CH₂R | OH |
| | | | NH₂ |
| | | | N(CH₃)₂ |
| | | |  |
| | | |  |
| | | | NHCHO |
| | | CHO | |
| | | CH=N-OH | |
| | | COOR | H |
| | | | CH₃ |
| | | | CH₂CH₃ |
| | | CF₃ | |
| | | NHR | H |
| | | | CH₃ |
| | | | C(CH₃)₃ |
| | | | CH₂Ph |

FIGURE 4G
| Structure | X | R^b | R |
|---|---|---|---|
| 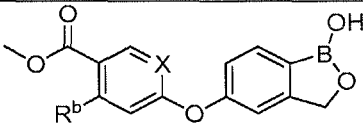 | N | NHR | CH$_2$CH$_2$OH |
| | | | CH$_2$CH$_2$OCH$_3$ |
| | | | CH$_2$CH$_2$OCH$_2$Ph |
| | | N(CH$_3$)R | CH$_3$ |
| | | | CH$_2$CH$_2$OH |
| | | | CH$_2$CH$_2$OCH$_3$ |
| | | 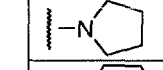 | |
| | | 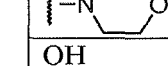 | |
| | | OH | |
| | | C$_1$-alkoxy | |
| | | C$_2$-alkoxy | |
| | | C$_3$-alkoxy | |
| | | C$_4$-alkoxy | |
| | | 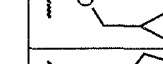 | |
| | | 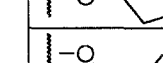 | |
| | |  | |
| | | OCH$_2$CH$_2$R | F |
| | | | N(CH$_3$)$_2$ |
| | | | OH |
| | | | OCH$_3$ |
| | | | OC(O)CH$_3$ |
| | | | 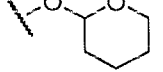 |
| | | OCH$_2$CF$_3$ | |
| | | 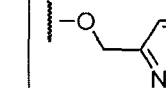 | |
| | | OC(O)CH$_3$ | |
| | | OCH$_2$C(O)R | OH |
| | | | OCH$_2$CH$_3$ |
| | | | OC(CH$_3$)$_3$ |
| | | | N(CH$_2$CH$_3$)$_2$ |
| | | |  |
| | | | 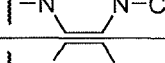 |
| | | | 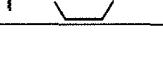 |

FIGURE 4H

| Structure | X | R$^b$ | R |
|---|---|---|---|
| (structure shown) | [n/a] | F | |
| | | Cl | |
| | | CH$_3$ | |
| | | CH$_2$CH$_3$ | |
| | | C$_3$-alkyl | |
| | | C$_4$-alkyl | |
| | | C$_5$-alkyl | |
| | | C$_6$-alkyl | |
| | | C$_3$-cycloalkyl | |
| | | C$_4$-cycloalkyl | |
| | | C$_5$-cycloalkyl | |
| | | C$_6$-cycloalkyl | |
| | | C$_7$-cycloalkyl | |
| | | C$_8$-cycloalkyl | |
| | | CH$_2$R | OH |
| | | | NH$_2$ |
| | | | N(CH$_3$)$_2$ |
| | | | -N(morpholine) |
| | | | -N(N-methylpiperazine) |
| | | | NHCHO |
| | | CHO | |
| | | CH=N-OH | |
| | | COOR | H |
| | | | CH$_3$ |
| | | | CH$_2$CH$_3$ |
| | | CF$_3$ | |
| | | NHR | H |
| | | | CH$_3$ |
| | | | C(CH$_3$)$_3$ |
| | | | CH$_2$Ph |
| | | | CH$_2$CH$_2$OH |
| | | | CH$_2$CH$_2$OCH$_3$ |
| | | | CH$_2$CH$_2$OCH$_2$Ph |
| | | N(CH$_3$)R | CH$_3$ |
| | | | CH$_2$CH$_2$OH |
| | | | CH$_2$CH$_2$OCH$_3$ |
| | | -N(pyrrolidine) | |
| | | -N(morpholine) | |
| | | OH | |
| | | C$_1$-alkoxy | |
| | | C$_2$-alkoxy | |
| | | C$_3$-alkoxy | |

FIGURE 4I
| Structure | X | R$^b$ | R |
|---|---|---|---|
| 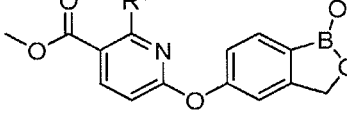 | [n/a] | C$_4$-alkoxy | |
| | | 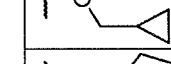 | |
| | | 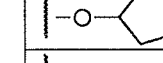 | |
| | | 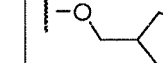 | |
| | | OCH$_2$CH$_2$R | F |
| | | | N(CH$_3$)$_2$ |
| | | | OH |
| | | | OCH$_3$ |
| | | | OC(O)CH$_3$ |
| | | | 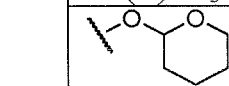 |
| | | OCH$_2$CF$_3$ | |
| | | 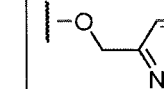 | |
| | | OC(O)CH$_3$ | |
| | | OCH$_2$C(O)R | OH |
| | | | OCH$_2$CH$_3$ |
| | | | OC(CH$_3$)$_3$ |
| | | | N(CH$_2$CH$_3$)$_2$ |
| | | | 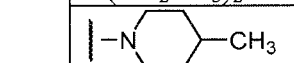 |
| | | | 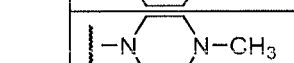 |
| | | | 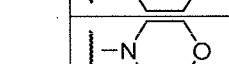 |
| 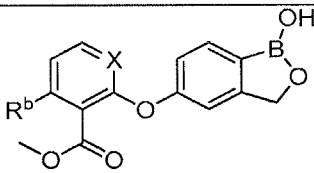 | CH | F | |
| | | Cl | |
| | | CH$_3$ | |
| | | CH$_2$CH$_3$ | |
| | | C$_3$-alkyl | |
| | | C$_4$-alkyl | |
| | | C$_5$-alkyl | |
| | | C$_6$-alkyl | |
| | | C$_3$-cycloalkyl | |
| | | C$_4$-cycloalkyl | |
| | | C$_5$-cycloalkyl | |
| | | C$_6$-cycloalkyl | |
| | | C$_7$-cycloalkyl | |
| | | C$_8$-cycloalkyl | |
| | | CH$_2$R | OH |
| | | | NH$_2$ |

FIGURE 4J

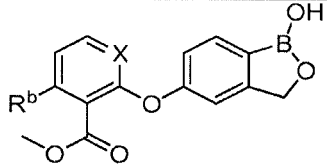

| Structure | X | R$^b$ | R |
|---|---|---|---|
| 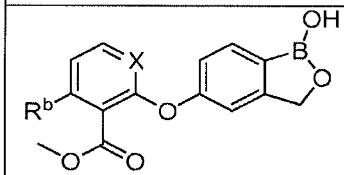 | CH | CH$_2$R | N(CH$_3$)$_2$ |
| | | | -N(morpholine) |
| | | | -N(N-methylpiperazine)-CH$_3$ |
| | | | NHCHO |
| | | CHO | |
| | | CH=N-OH | |
| | | COOR | H |
| | | | CH$_3$ |
| | | | CH$_2$CH$_3$ |
| | | CF$_3$ | |
| | | NHR | H |
| | | | CH$_3$ |
| | | | C(CH$_3$)$_3$ |
| | | | CH$_2$Ph |
| | | | CH$_2$CH$_2$OH |
| | | | CH$_2$CH$_2$OCH$_3$ |
| | | | CH$_2$CH$_2$OCH$_2$Ph |
| | | N(CH$_3$)R | CH$_3$ |
| | | | CH$_2$CH$_2$OH |
| | | | CH$_2$CH$_2$OCH$_3$ |
| | | -N(pyrrolidine) | |
| | | -N(morpholine) | |
| | | OH | |
| | | C$_1$-alkoxy | |
| | | C$_2$-alkoxy | |
| | | C$_3$-alkoxy | |
| | | C$_4$-alkoxy | |
| | | -O-CH$_2$-cyclopropyl | |
| | | -O-cyclopentyl | |
| | | -O-CH$_2$-cyclopentyl | |
| | | OCH$_2$CH$_2$R | F |
| | | | N(CH$_3$)$_2$ |
| | | | OH |
| | | | OCH$_3$ |
| | | | OC(O)CH$_3$ |
| | | | -O-tetrahydropyranyl |
| | | OCH$_2$CF$_3$ | |

FIGURE 4K

| Structure | X | R$^b$ | R |
|---|---|---|---|
| 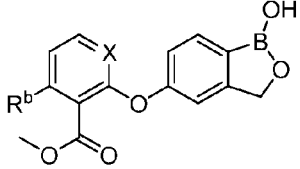 | CH | -O-CH$_2$-(2-pyridyl) | |
| | | OC(O)CH$_3$ | |
| | | OCH$_2$C(O)R | OH |
| | | | OCH$_2$CH$_3$ |
| | | | OC(CH$_3$)$_3$ |
| | | | N(CH$_2$CH$_3$)$_2$ |
| | | | -N(4-methylpiperidinyl) |
| | | | -N(4-methylpiperazinyl) |
| | | | -N(morpholinyl) |
| | N | F | |
| | | Cl | |
| | | CH$_3$ | |
| | | CH$_2$CH$_3$ | |
| | | C$_3$-alkyl | |
| | | C$_4$-alkyl | |
| | | C$_5$-alkyl | |
| | | C$_6$-alkyl | |
| | | C$_3$-cycloalkyl | |
| | | C$_4$-cycloalkyl | |
| | | C$_5$-cycloalkyl | |
| | | C$_6$-cycloalkyl | |
| | | C$_7$-cycloalkyl | |
| | | C$_8$-cycloalkyl | |
| | | CH$_2$R | OH |
| | | | NH$_2$ |
| | | | N(CH$_3$)$_2$ |
| | | | -N(morpholinyl) |
| | | | -N(4-methylpiperazinyl) |
| | | | NHCHO |
| | | CHO | |
| | | CH=N-OH | |
| | | COOR | H |
| | | | CH$_3$ |
| | | | CH$_2$CH$_3$ |
| | | CF$_3$ | |
| | | NHR | H |
| | | | CH$_3$ |
| | | | C(CH$_3$)$_3$ |
| | | | CH$_2$Ph |

FIGURE 4L

| Structure | X | R$^b$ | R |
|---|---|---|---|
| (structure shown: methyl ester pyridine linked via O to benzoxaborole with OH) | N | NHR | CH$_2$CH$_2$OH |
| | | | CH$_2$CH$_2$OCH$_3$ |
| | | | CH$_2$CH$_2$OCH$_2$Ph |
| | | N(CH$_3$)R | CH$_3$ |
| | | | CH$_2$CH$_2$OH |
| | | | CH$_2$CH$_2$OCH$_3$ |
| | | -N(pyrrolidine) | |
| | | -N(morpholine) | |
| | | OH | |
| | | C$_1$-alkoxy | |
| | | C$_2$-alkoxy | |
| | | C$_3$-alkoxy | |
| | | C$_4$-alkoxy | |
| | | -O-CH$_2$-cyclopropyl | |
| | | -O-cyclopentyl | |
| | | -O-CH$_2$-cyclopentyl | |
| | | OCH$_2$CH$_2$R | F |
| | | | N(CH$_3$)$_2$ |
| | | | OH |
| | | | OCH$_3$ |
| | | | OC(O)CH$_3$ |
| | | | O-tetrahydropyran-2-yl |
| | | OCH$_2$CF$_3$ | |
| | | -O-CH$_2$-(2-pyridyl) | |
| | | OC(O)CH$_3$ | |
| | | OCH$_2$C(O)R | OH |
| | | | OCH$_2$CH$_3$ |
| | | | OC(CH$_3$)$_3$ |
| | | | N(CH$_2$CH$_3$)$_2$ |
| | | | -N(4-methylpiperidine) |
| | | | -N(4-methylpiperazine) |
| | | | -N(morpholine) |

FIGURE 4M

| Structure | X | R$^b$ | R |
|---|---|---|---|
| 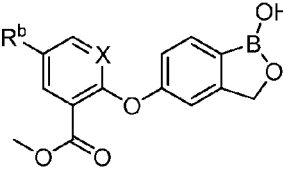 | CH | F | |
| | | Cl | |
| | | CH$_3$ | |
| | | CH$_2$CH$_3$ | |
| | | C$_3$-alkyl | |
| | | C$_4$-alkyl | |
| | | C$_5$-alkyl | |
| | | C$_6$-alkyl | |
| | | C$_3$-cycloalkyl | |
| | | C$_4$-cycloalkyl | |
| | | C$_5$-cycloalkyl | |
| | | C$_6$-cycloalkyl | |
| | | C$_7$-cycloalkyl | |
| | | C$_8$-cycloalkyl | |
| | | CH$_2$R | OH |
| | | | NH$_2$ |
| | | | N(CH$_3$)$_2$ |
| | | | 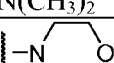 |
| | | | 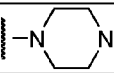 |
| | | | NHCHO |
| | | CHO | |
| | | CH=N-OH | |
| | | COOR | H |
| | | | CH$_3$ |
| | | | CH$_2$CH$_3$ |
| | | CF$_3$ | |
| | | NHR | H |
| | | | CH$_3$ |
| | | | C(CH$_3$)$_3$ |
| | | | CH$_2$Ph |
| | | | CH$_2$CH$_2$OH |
| | | | CH$_2$CH$_2$OCH$_3$ |
| | | | CH$_2$CH$_2$OCH$_2$Ph |
| | | N(CH$_3$)R | CH$_3$ |
| | | | CH$_2$CH$_2$OH |
| | | | CH$_2$CH$_2$OCH$_3$ |
| | | 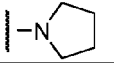 | |
| | | 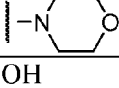 | |
| | | OH | |
| | | C$_1$-alkoxy | |
| | | C$_2$-alkoxy | |
| | | C$_3$-alkoxy | |

FIGURE 4N
| Structure | X | R$^b$ | R |
|---|---|---|---|
| 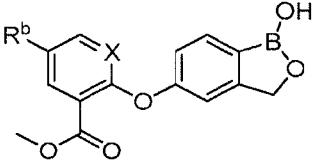 | CH | C$_4$-alkoxy | |
| | | 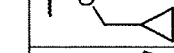 | |
| | | 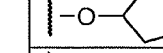 | |
| | | 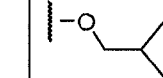 | |
| | | OCH$_2$CH$_2$R | F |
| | | | N(CH$_3$)$_2$ |
| | | | OH |
| | | | OCH$_3$ |
| | | | OC(O)CH$_3$ |
| | | | 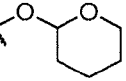 |
| | | OCH$_2$CF$_3$ | |
| | | 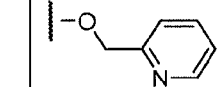 | |
| | | OC(O)CH$_3$ | |
| | | OCH$_2$C(O)R | OH |
| | | | OCH$_2$CH$_3$ |
| | | | OC(CH$_3$)$_3$ |
| | | | N(CH$_2$CH$_3$)$_2$ |
| | | | 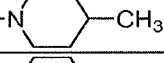 |
| | | | 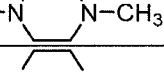 |
| | | |  |
| | N | F | |
| | | Cl | |
| | | CH$_3$ | |
| | | CH$_2$CH$_3$ | |
| | | C$_3$-alkyl | |
| | | C$_4$-alkyl | |
| | | C$_5$-alkyl | |
| | | C$_6$-alkyl | |
| | | C$_3$-cycloalkyl | |
| | | C$_4$-cycloalkyl | |
| | | C$_5$-cycloalkyl | |
| | | C$_6$-cycloalkyl | |
| | | C$_7$-cycloalkyl | |
| | | C$_8$-cycloalkyl | |
| | | CH$_2$R | OH |
| | | | NH$_2$ |

FIGURE 4O

| Structure | X | R$^b$ | R |
|---|---|---|---|
| (structure: R$^b$ substituted pyridine with X, linked via O to benzoxaborole with OH; methyl ester substituent) | N | CH$_2$R | N(CH$_3$)$_2$ |
| | | | −N(morpholine) |
| | | | −N(N-methylpiperazine) |
| | | | NHCHO |
| | | CHO | |
| | | CH=N-OH | |
| | | COOR | H |
| | | | CH$_3$ |
| | | | CH$_2$CH$_3$ |
| | | CF$_3$ | |
| | | NHR | H |
| | | | CH$_3$ |
| | | | C(CH$_3$)$_3$ |
| | | | CH$_2$Ph |
| | | | CH$_2$CH$_2$OH |
| | | | CH$_2$CH$_2$OCH$_3$ |
| | | | CH$_2$CH$_2$OCH$_2$Ph |
| | | N(CH$_3$)R | CH$_3$ |
| | | | CH$_2$CH$_2$OH |
| | | | CH$_2$CH$_2$OCH$_3$ |
| | | −N(pyrrolidine) | |
| | | −N(morpholine) | |
| | | OH | |
| | | C$_1$-alkoxy | |
| | | C$_2$-alkoxy | |
| | | C$_3$-alkoxy | |
| | | C$_4$-alkoxy | |
| | | −O−CH$_2$-cyclopropyl | |
| | | −O-cyclopentyl | |
| | | −O-CH$_2$-cyclopentyl | |
| | | OCH$_2$CH$_2$R | F |
| | | | N(CH$_3$)$_2$ |
| | | | OH |
| | | | OCH$_3$ |
| | | | OC(O)CH$_3$ |
| | | | −O-tetrahydropyranyl |
| | | OCH$_2$CF$_3$ | |

FIGURE 4P

| Structure | X | R$^b$ | R |
|---|---|---|---|
| (structure with R$^b$, X, methyl ester, benzoxaborole) | N | -O-CH$_2$-pyridine | |
| | | OC(O)CH$_3$ | |
| | | OCH$_2$C(O)R | OH |
| | | | OCH$_2$CH$_3$ |
| | | | OC(CH$_3$)$_3$ |
| | | | N(CH$_2$CH$_3$)$_2$ |
| | | | -N(4-methylpiperidine)-CH$_3$ |
| | | | -N(piperazine)N-CH$_3$ |
| | | | -N-morpholine |
| (structure with R$^b$, X, methyl ester, benzoxaborole) | CH | F | |
| | | Cl | |
| | | CH$_3$ | |
| | | CH$_2$CH$_3$ | |
| | | C$_3$-alkyl | |
| | | C$_4$-alkyl | |
| | | C$_5$-alkyl | |
| | | C$_6$-alkyl | |
| | | C$_3$-cycloalkyl | |
| | | C$_4$-cycloalkyl | |
| | | C$_5$-cycloalkyl | |
| | | C$_6$-cycloalkyl | |
| | | C$_7$-cycloalkyl | |
| | | C$_8$-cycloalkyl | |
| | | CH$_2$R | OH |
| | | | NH$_2$ |
| | | | N(CH$_3$)$_2$ |
| | | | -N-morpholine |
| | | | -N(piperazine)N-CH$_3$ |
| | | | NHCHO |
| | | CHO | |
| | | CH=N-OH | |
| | | COOR | H |
| | | | CH$_3$ |
| | | | CH$_2$CH$_3$ |
| | | CF$_3$ | |
| | | NHR | H |
| | | | CH$_3$ |
| | | | C(CH$_3$)$_3$ |
| | | | CH$_2$Ph |

FIGURE 4Q

| Structure | X | R$^b$ | R |
|---|---|---|---|
| (structure shown with R$^b$, X, and methyl ester benzoxaborole ether) | CH | NHR | CH$_2$CH$_2$OH |
| | | | CH$_2$CH$_2$OCH$_3$ |
| | | | CH$_2$CH$_2$OCH$_2$Ph |
| | | N(CH$_3$)R | CH$_3$ |
| | | | CH$_2$CH$_2$OH |
| | | | CH$_2$CH$_2$OCH$_3$ |
| | | -N(pyrrolidine) | |
| | | -N(morpholine) | |
| | | OH | |
| | | C$_1$-alkoxy | |
| | | C$_2$-alkoxy | |
| | | C$_3$-alkoxy | |
| | | C$_4$-alkoxy | |
| | | -O-CH$_2$-cyclopropyl | |
| | | -O-cyclopentyl | |
| | | -O-CH$_2$-cyclopentyl | |
| | | OCH$_2$CH$_2$R | F |
| | | | N(CH$_3$)$_2$ |
| | | | OH |
| | | | OCH$_3$ |
| | | | OC(O)CH$_3$ |
| | | | -O-tetrahydropyranyl |
| | | OCH$_2$CF$_3$ | |
| | | -O-CH$_2$-pyridyl | |
| | | OC(O)CH$_3$ | |
| | | OCH$_2$C(O)R | OH |
| | | | OCH$_2$CH$_3$ |
| | | | OC(CH$_3$)$_3$ |
| | | | N(CH$_2$CH$_3$)$_2$ |
| | | | -N(4-methylpiperidine) |
| | | | -N(4-methylpiperazine) |
| | | | -N(morpholine) |
| | N | F | |
| | | Cl | |

FIGURE 4R

| Structure | X | R$^b$ | R |
|---|---|---|---|
| (structure shown) | N | CH$_3$ | |
| | | CH$_2$CH$_3$ | |
| | | C$_3$-alkyl | |
| | | C$_4$-alkyl | |
| | | C$_5$-alkyl | |
| | | C$_6$-alkyl | |
| | | C$_3$-cycloalkyl | |
| | | C$_4$-cycloalkyl | |
| | | C$_5$-cycloalkyl | |
| | | C$_6$-cycloalkyl | |
| | | C$_7$-cycloalkyl | |
| | | C$_8$-cycloalkyl | |
| | | CH$_2$R | OH |
| | | | NH$_2$ |
| | | | N(CH$_3$)$_2$ |
| | | | -N(morpholine) |
| | | | -N(N-methylpiperazine)-CH$_3$ |
| | | | NHCHO |
| | | CHO | |
| | | CH=N-OH | |
| | | COOR | H |
| | | | CH$_3$ |
| | | | CH$_2$CH$_3$ |
| | | CF$_3$ | |
| | | NHR | H |
| | | | CH$_3$ |
| | | | C(CH$_3$)$_3$ |
| | | | CH$_2$Ph |
| | | | CH$_2$CH$_2$OH |
| | | | CH$_2$CH$_2$OCH$_3$ |
| | | | CH$_2$CH$_2$OCH$_2$Ph |
| | | N(CH$_3$)R | CH$_3$ |
| | | | CH$_2$CH$_2$OH |
| | | | CH$_2$CH$_2$OCH$_3$ |
| | | -N(pyrrolidine) | |
| | | -N(morpholine) | |
| | | OH | |
| | | C$_1$-alkoxy | |
| | | C$_2$-alkoxy | |
| | | C$_3$-alkoxy | |
| | | C$_4$-alkoxy | |

FIGURE 4S
| Structure | X | R$^b$ | R |
|---|---|---|---|
| 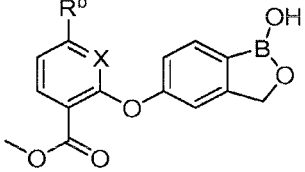 | N | 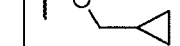 | |
| | | 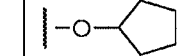 | |
| | | 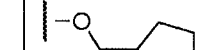 | |
| | | OCH$_2$CH$_2$R | F |
| | | | N(CH$_3$)$_2$ |
| | | | OH |
| | | | OCH$_3$ |
| | | | OC(O)CH$_3$ |
| | | |  |
| | | OCH$_2$CF$_3$ | |
| | |  | |
| | | OC(O)CH$_3$ | |
| | | OCH$_2$C(O)R | OH |
| | | | OCH$_2$CH$_3$ |
| | | | OC(CH$_3$)$_3$ |
| | | | N(CH$_2$CH$_3$)$_2$ |
| | | |  |
| | | | -N⌒N-CH$_3$ |
| | | | -N⌒O |
| 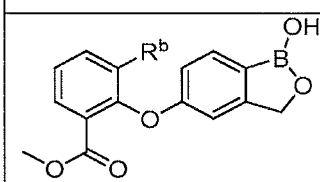 | [n/a] | F | |
| | | Cl | |
| | | CH$_3$ | |
| | | CH$_2$CH$_3$ | |
| | | C$_3$-alkyl | |
| | | C$_4$-alkyl | |
| | | C$_5$-alkyl | |
| | | C$_6$-alkyl | |
| | | C$_3$-cycloalkyl | |
| | | C$_4$-cycloalkyl | |
| | | C$_5$-cycloalkyl | |
| | | C$_6$-cycloalkyl | |
| | | C$_7$-cycloalkyl | |
| | | C$_8$-cycloalkyl | |
| | | CH$_2$R | OH |
| | | | NH$_2$ |
| | | | N(CH$_3$)$_2$ |

FIGURE 4T

| Structure | X | R$^b$ | R |
|---|---|---|---|
| [structure: methyl benzoate with Rb substituent, linked via O to benzoxaborole with OH] | [n/a] | CH$_2$R | -N(morpholine) |
| | | | -N(N-methylpiperazine) |
| | | | NHCHO |
| | | CHO | |
| | | CH=N-OH | |
| | | COOR | H |
| | | | CH$_3$ |
| | | | CH$_2$CH$_3$ |
| | | CF$_3$ | |
| | | NHR | H |
| | | | CH$_3$ |
| | | | C(CH$_3$)$_3$ |
| | | | CH$_2$Ph |
| | | | CH$_2$CH$_2$OH |
| | | | CH$_2$CH$_2$OCH$_3$ |
| | | | CH$_2$CH$_2$OCH$_2$Ph |
| | | N(CH$_3$)R | CH$_3$ |
| | | | CH$_2$CH$_2$OH |
| | | | CH$_2$CH$_2$OCH$_3$ |
| | | -N(pyrrolidine) | |
| | | -N(morpholine) | |
| | | OH | |
| | | C$_1$-alkoxy | |
| | | C$_2$-alkoxy | |
| | | C$_3$-alkoxy | |
| | | C$_4$-alkoxy | |
| | | -O-CH$_2$-cyclopropyl | |
| | | -O-cyclopentyl | |
| | | -O-CH$_2$-cyclopentyl | |
| | | OCH$_2$CH$_2$R | F |
| | | | N(CH$_3$)$_2$ |
| | | | OH |
| | | | OCH$_3$ |
| | | | OC(O)CH$_3$ |
| | | | -O-tetrahydropyran |
| | | OCH$_2$CF$_3$ | |

FIGURE 4U
| Structure | X | R^b | R |
|---|---|---|---|
| 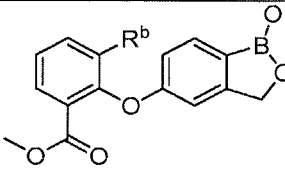 | [n/a] | 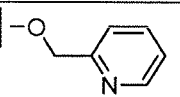 | |
| | | OC(O)CH$_3$ | |
| | | OCH$_2$C(O)R | OH |
| | | | OCH$_2$CH$_3$ |
| | | | OC(CH$_3$)$_3$ |
| | | | N(CH$_2$CH$_3$)$_2$ |
| | | | 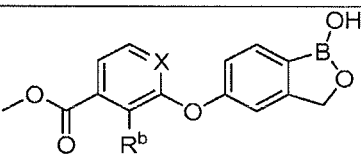 |
| | | |  |
| | | |  |
| 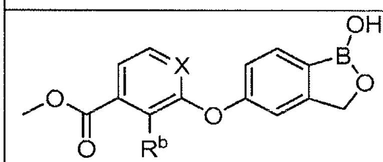 | CH | F | |
| | | Cl | |
| | | CH$_3$ | |
| | | CH$_2$CH$_3$ | |
| | | C$_3$-alkyl | |
| | | C$_4$-alkyl | |
| | | C$_5$-alkyl | |
| | | C$_6$-alkyl | |
| | | C$_3$-cycloalkyl | |
| | | C$_4$-cycloalkyl | |
| | | C$_5$-cycloalkyl | |
| | | C$_6$-cycloalkyl | |
| | | C$_7$-cycloalkyl | |
| | | C$_8$-cycloalkyl | |
| | | CH$_2$R | OH |
| | | | NH$_2$ |
| | | | N(CH$_3$)$_2$ |
| | | |  |
| | | |  |
| | | | NHCHO |
| | | CHO | |
| | | CH=N-OH | |
| | | COOR | H |
| | | | CH$_3$ |
| | | | CH$_2$CH$_3$ |
| | | CF$_3$ | |
| | | NHR | H |
| | | | CH$_3$ |
| | | | C(CH$_3$)$_3$ |
| | | | CH$_2$Ph |

FIGURE 4V
| Structure | X | R$^b$ | R |
|---|---|---|---|
| 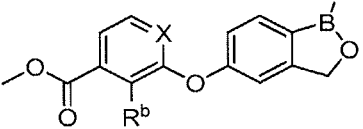 | CH | NHR | CH$_2$CH$_2$OH |
| | | | CH$_2$CH$_2$OCH$_3$ |
| | | | CH$_2$CH$_2$OCH$_2$Ph |
| | | N(CH$_3$)R | CH$_3$ |
| | | | CH$_2$CH$_2$OH |
| | | | CH$_2$CH$_2$OCH$_3$ |
| | | 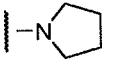 | |
| | | 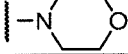 | |
| | | OH | |
| | | C$_1$-alkoxy | |
| | | C$_2$-alkoxy | |
| | | C$_3$-alkoxy | |
| | | C$_4$-alkoxy | |
| | | 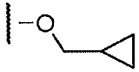 | |
| | | 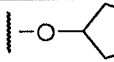 | |
| | | 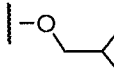 | |
| | | OCH$_2$CH$_2$R | F |
| | | | N(CH$_3$)$_2$ |
| | | | OH |
| | | | OCH$_3$ |
| | | | OC(O)CH$_3$ |
| | | | 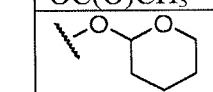 |
| | | OCH$_2$CF$_3$ | |
| | | 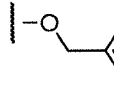 | |
| | | OC(O)CH$_3$ | |
| | | OCH$_2$C(O)R | OH |
| | | | OCH$_2$CH$_3$ |
| | | | OC(CH$_3$)$_3$ |
| | | | N(CH$_2$CH$_3$)$_2$ |
| | | |  |
| | | | 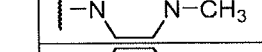 |
| | | | 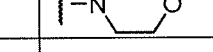 |
| | N | F | |
| | | Cl | |

FIGURE 4W

| Structure | X | R$^b$ | R |
|---|---|---|---|
| (structure shown with methyl ester, X, R$^b$, O-linked benzoxaborole-OH) | N | CH$_3$ | |
| | | CH$_2$CH$_3$ | |
| | | C$_3$-alkyl | |
| | | C$_4$-alkyl | |
| | | C$_5$-alkyl | |
| | | C$_6$-alkyl | |
| | | C$_3$-cycloalkyl | |
| | | C$_4$-cycloalkyl | |
| | | C$_5$-cycloalkyl | |
| | | C$_6$-cycloalkyl | |
| | | C$_7$-cycloalkyl | |
| | | C$_8$-cycloalkyl | |
| | | CH$_2$R | OH |
| | | | NH$_2$ |
| | | | N(CH$_3$)$_2$ |
| | | | -N(morpholine) |
| | | | -N(N-methylpiperazine) |
| | | | NHCHO |
| | | CHO | |
| | | CH=N-OH | |
| | | COOR | H |
| | | | CH$_3$ |
| | | | CH$_2$CH$_3$ |
| | | CF$_3$ | |
| | | NHR | H |
| | | | CH$_3$ |
| | | | C(CH$_3$)$_3$ |
| | | | CH$_2$Ph |
| | | | CH$_2$CH$_2$OH |
| | | | CH$_2$CH$_2$OCH$_3$ |
| | | | CH$_2$CH$_2$OCH$_2$Ph |
| | | N(CH$_3$)R | CH$_3$ |
| | | | CH$_2$CH$_2$OH |
| | | | CH$_2$CH$_2$OCH$_3$ |
| | | -N(pyrrolidine) | |
| | | -N(morpholine) | |
| | | OH | |
| | | C$_1$-alkoxy | |
| | | C$_2$-alkoxy | |
| | | C$_3$-alkoxy | |
| | | C$_4$-alkoxy | |

FIGURE 4X

| Structure | X | R$^b$ | R |
|---|---|---|---|
| (structure 1) | N | –O–cyclopropylmethyl | |
| | | –O–cyclopentyl | |
| | | –O–cyclopentylmethyl | |
| | | OCH$_2$CH$_2$R | F |
| | | | N(CH$_3$)$_2$ |
| | | | OH |
| | | | OCH$_3$ |
| | | | OC(O)CH$_3$ |
| | | | –O–tetrahydropyranyl |
| | | OCH$_2$CF$_3$ | |
| | | –O–CH$_2$–(2-pyridyl) | |
| | | OC(O)CH$_3$ | |
| | | OCH$_2$C(O)R | OH |
| | | | OCH$_2$CH$_3$ |
| | | | OC(CH$_3$)$_3$ |
| | | | N(CH$_2$CH$_3$)$_2$ |
| | | | –N(4-methylpiperidinyl) |
| | | | –N(4-methylpiperazinyl) |
| | | | –N-morpholinyl |
| (structure 2) | CH | F | |
| | | Cl | |
| | | CH$_3$ | |
| | | CH$_2$CH$_3$ | |
| | | C$_3$-alkyl | |
| | | C$_4$-alkyl | |
| | | C$_5$-alkyl | |
| | | C$_6$-alkyl | |
| | | C$_3$-cycloalkyl | |
| | | C$_4$-cycloalkyl | |
| | | C$_5$-cycloalkyl | |
| | | C$_6$-cycloalkyl | |
| | | C$_7$-cycloalkyl | |
| | | C$_8$-cycloalkyl | |
| | | CH$_2$R | OH |
| | | | NH$_2$ |
| | | | N(CH$_3$)$_2$ |

FIGURE 4Y
| Structure | X | $R^b$ | R |
|---|---|---|---|
| 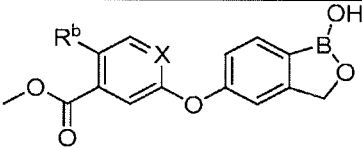 | CH | CH$_2$R |  |
| | | | 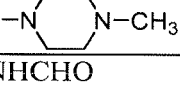 |
| | | | NHCHO |
| | | CHO | |
| | | CH=N-OH | |
| | | COOR | H |
| | | | CH$_3$ |
| | | | CH$_2$CH$_3$ |
| | | CF$_3$ | |
| | | NHR | H |
| | | | CH$_3$ |
| | | | C(CH$_3$)$_3$ |
| | | | CH$_2$Ph |
| | | | CH$_2$CH$_2$OH |
| | | | CH$_2$CH$_2$OCH$_3$ |
| | | | CH$_2$CH$_2$OCH$_2$Ph |
| | | N(CH$_3$)R | CH$_3$ |
| | | | CH$_2$CH$_2$OH |
| | | | CH$_2$CH$_2$OCH$_3$ |
| | |  | |
| | |  | |
| | | OH | |
| | | C$_1$-alkoxy | |
| | | C$_2$-alkoxy | |
| | | C$_3$-alkoxy | |
| | | C$_4$-alkoxy | |
| | |  | |
| | |  | |
| | |  | |
| | | OCH$_2$CH$_2$R | F |
| | | | N(CH$_3$)$_2$ |
| | | | OH |
| | | | OCH$_3$ |
| | | | OC(O)CH$_3$ |
| | | |  |
| | | OCH$_2$CF$_3$ | |

FIGURE 4Z

| Structure | X | R^b | R |
|---|---|---|---|
| ![structure with R^b, X, B-OH, methyl ester] | CH | -O-CH2-(2-pyridyl) | |
| | | OC(O)CH3 | |
| | | OCH2C(O)R | OH |
| | | | OCH2CH3 |
| | | | OC(CH3)3 |
| | | | N(CH2CH3)2 |
| | | | -N(piperidine-4-CH3) |
| | | | -N(piperazine-N-CH3) |
| | | | -N(morpholine) |
| | N | F | |
| | | Cl | |
| | | CH3 | |
| | | CH2CH3 | |
| | | C3-alkyl | |
| | | C4-alkyl | |
| | | C5-alkyl | |
| | | C6-alkyl | |
| | | C3-cycloalkyl | |
| | | C4-cycloalkyl | |
| | | C5-cycloalkyl | |
| | | C6-cycloalkyl | |
| | | C7-cycloalkyl | |
| | | C8-cycloalkyl | |
| | | CH2R | OH |
| | | | NH2 |
| | | | N(CH3)2 |
| | | | -N(morpholine) |
| | | | -N(piperazine-N-CH3) |
| | | | NHCHO |
| | | CHO | |
| | | CH=N-OH | |
| | | COOR | H |
| | | | CH3 |
| | | | CH2CH3 |
| | | CF3 | |
| | | NHR | H |
| | | | CH3 |
| | | | C(CH3)3 |
| | | | CH2Ph |

FIGURE 4AA

| Structure | X | R$^b$ | R |
|---|---|---|---|
| [structure with R$^b$, X, methyl ester, O, benzoxaborole-OH] | N | NHR | CH$_2$CH$_2$OH |
| | | | CH$_2$CH$_2$OCH$_3$ |
| | | | CH$_2$CH$_2$OCH$_2$Ph |
| | | N(CH$_3$)R | CH$_3$ |
| | | | CH$_2$CH$_2$OH |
| | | | CH$_2$CH$_2$OCH$_3$ |
| | | -N(pyrrolidinyl) | |
| | | -N(morpholinyl) | |
| | | OH | |
| | | C$_1$-alkoxy | |
| | | C$_2$-alkoxy | |
| | | C$_3$-alkoxy | |
| | | C$_4$-alkoxy | |
| | | -O-CH$_2$-cyclopropyl | |
| | | -O-cyclopentyl | |
| | | -O-CH$_2$-cyclopentyl | |
| | | OCH$_2$CH$_2$R | F |
| | | | N(CH$_3$)$_2$ |
| | | | OH |
| | | | OCH$_3$ |
| | | | OC(O)CH$_3$ |
| | | | O-tetrahydropyranyl |
| | | OCH$_2$CF$_3$ | |
| | | -O-CH$_2$-pyridyl | |
| | | OC(O)CH$_3$ | |
| | | OCH$_2$C(O)R | OH |
| | | | OCH$_2$CH$_3$ |
| | | | OC(CH$_3$)$_3$ |
| | | | N(CH$_2$CH$_3$)$_2$ |
| | | | -N(methylpiperidinyl) |
| | | | -N(N-methylpiperazinyl) |
| | | | -N(morpholinyl) |

FIGURE 4BB
| Structure | X | R<sup>b</sup> | R |
|---|---|---|---|
| 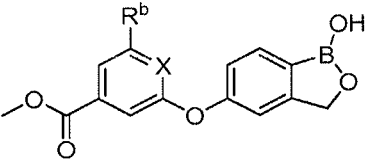 | CH | F | |
| | | Cl | |
| | | CH₃ | |
| | | CH₂CH₃ | |
| | | C₃-alkyl | |
| | | C₄-alkyl | |
| | | C₅-alkyl | |
| | | C₆-alkyl | |
| | | C₃-cycloalkyl | |
| | | C₄-cycloalkyl | |
| | | C₅-cycloalkyl | |
| | | C₆-cycloalkyl | |
| | | C₇-cycloalkyl | |
| | | C₈-cycloalkyl | |
| | | CH₂R | OH |
| | | | NH₂ |
| | | | N(CH₃)₂ |
| | | | 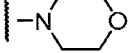 |
| | | | 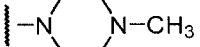 |
| | | | NHCHO |
| | | CHO | |
| | | CH=N-OH | |
| | | COOR | H |
| | | | CH₃ |
| | | | CH₂CH₃ |
| | | CF₃ | |
| | | NHR | H |
| | | | CH₃ |
| | | | C(CH₃)₃ |
| | | | CH₂Ph |
| | | | CH₂CH₂OH |
| | | | CH₂CH₂OCH₃ |
| | | | CH₂CH₂OCH₂Ph |
| | | N(CH₃)R | CH₃ |
| | | | CH₂CH₂OH |
| | | | CH₂CH₂OCH₃ |
| | |  | |
| | | 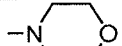 | |
| | | OH | |
| | | C₁-alkoxy | |
| | | C₂-alkoxy | |
| | | C₃-alkoxy | |

FIGURE 4CC
| Structure | X | R$^b$ | R |
|---|---|---|---|
| 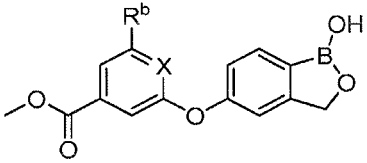 | CH | C$_4$-alkoxy | |
| | | 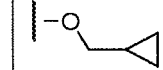 | |
| | | 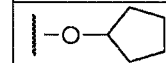 | |
| | | 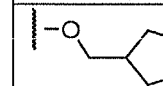 | |
| | | OCH$_2$CH$_2$R | F |
| | | | N(CH$_3$)$_2$ |
| | | | OH |
| | | | OCH$_3$ |
| | | | OC(O)CH$_3$ |
| | | |  |
| | | OCH$_2$CF$_3$ | |
| | |  | |
| | | OC(O)CH$_3$ | |
| | | OCH$_2$C(O)R | OH |
| | | | OCH$_2$CH$_3$ |
| | | | OC(CH$_3$)$_3$ |
| | | | N(CH$_2$CH$_3$)$_2$ |
| | | |  |
| | | |  |
| | | |  |
| | N | F | |
| | | Cl | |
| | | CH$_3$ | |
| | | CH$_2$CH$_3$ | |
| | | C$_3$-alkyl | |
| | | C$_4$-alkyl | |
| | | C$_5$-alkyl | |
| | | C$_6$-alkyl | |
| | | C$_3$-cycloalkyl | |
| | | C$_4$-cycloalkyl | |
| | | C$_5$-cycloalkyl | |
| | | C$_6$-cycloalkyl | |
| | | C$_7$-cycloalkyl | |
| | | C$_8$-cycloalkyl | |
| | | CH$_2$R | OH |
| | | | NH$_2$ |

FIGURE 4DD

| Structure | X | R$^b$ | R |
|---|---|---|---|
| [structure: methyl ester - pyridine (X) with R$^b$ - O - benzoxaborole-OH] | N | CH$_2$R | N(CH$_3$)$_2$ |
| | | | -N(morpholine) |
| | | | -N(N-methylpiperazine)-CH$_3$ |
| | | | NHCHO |
| | | CHO | |
| | | CH=N-OH | |
| | | COOR | H |
| | | | CH$_3$ |
| | | | CH$_2$CH$_3$ |
| | | CF$_3$ | |
| | | NHR | H |
| | | | CH$_3$ |
| | | | C(CH$_3$)$_3$ |
| | | | CH$_2$Ph |
| | | | CH$_2$CH$_2$OH |
| | | | CH$_2$CH$_2$OCH$_3$ |
| | | | CH$_2$CH$_2$OCH$_2$Ph |
| | | N(CH$_3$)R | CH$_3$ |
| | | | CH$_2$CH$_2$OH |
| | | | CH$_2$CH$_2$OCH$_3$ |
| | | -N(pyrrolidine) | |
| | | -N(morpholine) | |
| | | OH | |
| | | C$_1$-alkoxy | |
| | | C$_2$-alkoxy | |
| | | C$_3$-alkoxy | |
| | | C$_4$-alkoxy | |
| | | -O-CH$_2$-cyclopropyl | |
| | | -O-cyclopentyl | |
| | | -O-CH$_2$-cyclopentyl | |
| | | OCH$_2$CH$_2$R | F |
| | | | N(CH$_3$)$_2$ |
| | | | OH |
| | | | OCH$_3$ |
| | | | OC(O)CH$_3$ |
| | | | -O-(tetrahydropyran-2-yloxy) |
| | | OCH$_2$CF$_3$ | |

FIGURE 4EE

| Structure | X | R$^b$ | R |
|---|---|---|---|
| [structure: methyl ester-pyridine(X)-O-benzoxaborole with R$^b$] | N | -O-CH$_2$-(2-pyridyl) | |
| | | OC(O)CH$_3$ | |
| | | OCH$_2$C(O)R | OH |
| | | | OCH$_2$CH$_3$ |
| | | | OC(CH$_3$)$_3$ |
| | | | N(CH$_2$CH$_3$)$_2$ |
| | | | -N(4-methylpiperidinyl) |
| | | | -N(4-methylpiperazinyl) |
| | | | -N(morpholinyl) |
| [structure: methyl ester-phenyl(R$^b$)-O-benzoxaborole] | [n/a] | F | |
| | | Cl | |
| | | CH$_3$ | |
| | | CH$_2$CH$_3$ | |
| | | C$_3$-alkyl | |
| | | C$_4$-alkyl | |
| | | C$_5$-alkyl | |
| | | C$_6$-alkyl | |
| | | C$_3$-cycloalkyl | |
| | | C$_4$-cycloalkyl | |
| | | C$_5$-cycloalkyl | |
| | | C$_6$-cycloalkyl | |
| | | C$_7$-cycloalkyl | |
| | | C$_8$-cycloalkyl | |
| | | CH$_2$R | OH |
| | | | NH$_2$ |
| | | | N(CH$_3$)$_2$ |
| | | | -N(morpholinyl) |
| | | | -N(4-methylpiperazinyl) |
| | | | NHCHO |
| | | CHO | |
| | | CH=N-OH | |
| | | COOR | H |
| | | | CH$_3$ |
| | | | CH$_2$CH$_3$ |
| | | CF$_3$ | |
| | | NHR | H |
| | | | CH$_3$ |
| | | | C(CH$_3$)$_3$ |
| | | | CH$_2$Ph |

FIGURE 4FF

| Structure | X | R$^b$ | R |
|---|---|---|---|
| ![structure with Rb, methyl ester, benzoxaborole OH] | [n/a] | NHR | CH$_2$CH$_2$OH |
| | | | CH$_2$CH$_2$OCH$_3$ |
| | | | CH$_2$CH$_2$OCH$_2$Ph |
| | | N(CH$_3$)R | CH$_3$ |
| | | | CH$_2$CH$_2$OH |
| | | | CH$_2$CH$_2$OCH$_3$ |
| | | −N(pyrrolidine) | |
| | | −N(morpholine) | |
| | | OH | |
| | | C$_1$-alkoxy | |
| | | C$_2$-alkoxy | |
| | | C$_3$-alkoxy | |
| | | C$_4$-alkoxy | |
| | | −O−CH$_2$-cyclopropyl | |
| | | −O−cyclopentyl | |
| | | −O−CH$_2$-cyclopentyl | |
| | | OCH$_2$CH$_2$R | F |
| | | | N(CH$_3$)$_2$ |
| | | | OH |
| | | | OCH$_3$ |
| | | | OC(O)CH$_3$ |
| | | | −O-tetrahydropyranyl |
| | | OCH$_2$CF$_3$ | |
| | | −O−CH$_2$-(2-pyridyl) | |
| | | OC(O)CH$_3$ | |
| | | OCH$_2$C(O)R | OH |
| | | | OCH$_2$CH$_3$ |
| | | | OC(CH$_3$)$_3$ |
| | | | N(CH$_2$CH$_3$)$_2$ |
| | | | −N(4-methylpiperidine)−CH$_3$ |
| | | | −N(piperazine)N−CH$_3$ |
| | | | −N(morpholine) |

FIGURE 5A
| Structure | X | R^b | R |
|---|---|---|---|
| 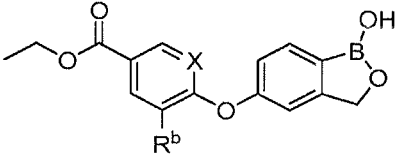 | CH | F | |
| | | Cl | |
| | | CH$_3$ | |
| | | CH$_2$CH$_3$ | |
| | | C$_3$-alkyl | |
| | | C$_4$-alkyl | |
| | | C$_5$-alkyl | |
| | | C$_6$-alkyl | |
| | | C$_3$-cycloalkyl | |
| | | C$_4$-cycloalkyl | |
| | | C$_5$-cycloalkyl | |
| | | C$_6$-cycloalkyl | |
| | | CH$_2$R | OH |
| | | | NH$_2$ |
| | | | N(CH$_3$)$_2$ |
| | | | 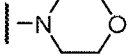 |
| | | | 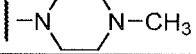 |
| | | |  |
| | | | NHCHO |
| | | CHO | |
| | | CH=N-OH | |
| | | COOR | H |
| | | | CH$_3$ |
| | | | CH$_2$CH$_3$ |
| | | CF$_3$ | |
| | | NHR | H |
| | | | CH$_3$ |
| | | | C(CH$_3$)$_3$ |
| | | | CH$_2$Ph |
| | | | CH$_2$CH$_2$OH |
| | | | CH$_2$CH$_2$OCH$_3$ |
| | | | CH$_2$CH$_2$OCH$_2$Ph |
| | | N(CH$_3$)R | CH$_3$ |
| | | | CH$_2$CH$_2$OH |
| | | | CH$_2$CH$_2$OCH$_3$ |
| | | 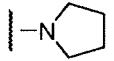 | |
| | | 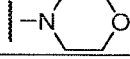 | |
| | | 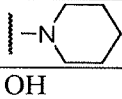 | |
| | | OH | |
| | | C$_1$-alkoxy | |

FIGURE 5B
| Structure | X | R^b | R |
|---|---|---|---|
| 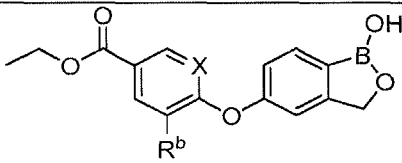 | CH | C$_2$-alkoxy | |
| | | C$_3$-alkoxy | |
| | | C$_4$-alkoxy | |
| | | 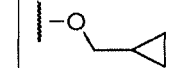 | |
| | | 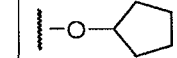 | |
| | | 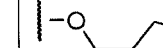 | |
| | | 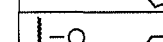 | |
| | | OCH$_2$CH$_2$R | F |
| | | | N(CH$_3$)$_2$ |
| | | | OH |
| | | | OCH$_3$ |
| | | | OC(O)CH$_3$ |
| | | | 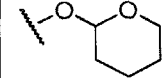 |
| | | | –OCH(CH$_3$)$_2$ |
| | | | –CH$_2$COCH$_3$ |
| | | OCH$_2$CF$_3$ | |
| | | OCH$_2$CHF$_2$ | |
| | | 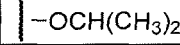 | |
| | | OC(O)CH$_3$ | |
| | | OCH$_2$C(O)R | OH |
| | | | OCH$_2$CH$_3$ |
| | | | OC(CH$_3$)$_3$ |
| | | | N(CH$_2$CH$_3$)$_2$ |
| | | | 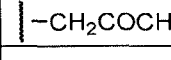 |
| | | | 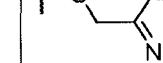 |
| | | | 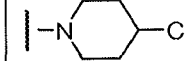 |
| | N | F | |
| | | Cl | |
| | | CH$_3$ | |
| | | CH$_2$CH$_3$ | |
| | | C$_3$-alkyl | |
| | | C$_4$-alkyl | |
| | | C$_5$-alkyl | |

FIGURE 5C

| Structure | X | R$^b$ | R |
|---|---|---|---|
| (ethyl pyridine-carboxylate with boronic ester phenoxy group, R$^b$ substituent) | N | C$_6$-alkyl | |
| | | C$_3$-cycloalkyl | |
| | | C$_4$-cycloalkyl | |
| | | C$_5$-cycloalkyl | |
| | | C$_6$-cycloalkyl | |
| | | C$_7$-cycloalkyl | |
| | | C$_8$-cycloalkyl | |
| | | CH$_2$R | OH |
| | | | NH$_2$ |
| | | | N(CH$_3$)$_2$ |
| | | | -N(morpholino) |
| | | | -N(N-methylpiperazino)-CH$_3$ |
| | | | NHCHO |
| | | CHO | |
| | | CH=N-OH | |
| | | COOR | H |
| | | | CH$_3$ |
| | | | CH$_2$CH$_3$ |
| | | CF$_3$ | |
| | | NHR | H |
| | | | CH$_3$ |
| | | | C(CH$_3$)$_3$ |
| | | | CH$_2$Ph |
| | | | CH$_2$CH$_2$OH |
| | | | CH$_2$CH$_2$OCH$_3$ |
| | | | CH$_2$CH$_2$OCH$_2$Ph |
| | | N(CH$_3$)R | CH$_3$ |
| | | | CH$_2$CH$_2$OH |
| | | | CH$_2$CH$_2$OCH$_3$ |
| | | -N(pyrrolidino) | |
| | | -N(morpholino) | |
| | | OH | |
| | | C$_1$-alkoxy | |
| | | C$_2$-alkoxy | |
| | | C$_3$-alkoxy | |
| | | C$_4$-alkoxy | |
| | | -O-CH$_2$-cyclopropyl | |
| | | -O-cyclopentyl | |

FIGURE 5D
| Structure | X | R<sup>b</sup> | R |
|---|---|---|---|
| 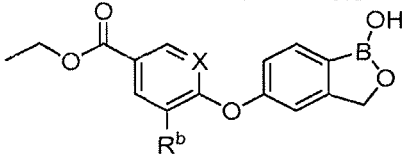 | N | 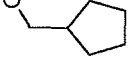 | |
| | | OCH₂CH₂R | F |
| | | | N(CH₃)₂ |
| | | | OH |
| | | | OCH₃ |
| | | | OC(O)CH₃ |
| | | | 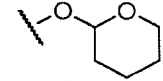 |
| | | | -OCH(CH₃)₂ |
| | | | -CH₂COCH₃ |
| | | OCH₂CF₃ | |
| | | OCH₂CHF₂ | |
| | | 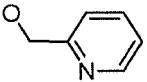 | |
| | | OC(O)CH₃ | |
| | | OCH₂C(O)R | OH |
| | | | OCH₂CH₃ |
| | | | OC(CH₃)₃ |
| | | | N(CH₂CH₃)₂ |
| | | |  |
| | | | 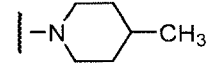 |
| | | | 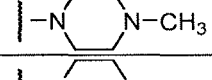 |
| 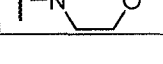 | CH | F | |
| | | Cl | |
| | | CH₃ | |
| | | CH₂CH₃ | |
| | | C₃-alkyl | |
| | | C₄-alkyl | |
| | | C₅-alkyl | |
| | | C₆-alkyl | |
| | | C₃-cycloalkyl | |
| | | C₄-cycloalkyl | |
| | | C₅-cycloalkyl | |
| | | C₆-cycloalkyl | |
| | | C₇-cycloalkyl | |
| | | C₈-cycloalkyl | |
| | | CH₂R | OH |
| | | | NH₂ |
| | | | N(CH₃)₂ |

FIGURE 5E

| Structure | X | R$^b$ | R |
|---|---|---|---|
| (ethyl ester pyridine-B(OH)-benzoxaborole structure with R$^b$ and X) | CH | CH$_2$R | -N(morpholine) |
| | | | -N(N-methylpiperazine) |
| | | | NHCHO |
| | | CHO | |
| | | CH=N-OH | |
| | | COOR | H |
| | | | CH$_3$ |
| | | | CH$_2$CH$_3$ |
| | | CF$_3$ | |
| | | NHR | H |
| | | | CH$_3$ |
| | | | C(CH$_3$)$_3$ |
| | | | CH$_2$Ph |
| | | | CH$_2$CH$_2$OH |
| | | | CH$_2$CH$_2$OCH$_3$ |
| | | | CH$_2$CH$_2$OCH$_2$Ph |
| | | N(CH$_3$)R | CH$_3$ |
| | | | CH$_2$CH$_2$OH |
| | | | CH$_2$CH$_2$OCH$_3$ |
| | | -N(pyrrolidine) | |
| | | -N(morpholine) | |
| | | OH | |
| | | C$_1$-alkoxy | |
| | | C$_2$-alkoxy | |
| | | C$_3$-alkoxy | |
| | | C$_4$-alkoxy | |
| | | -O-CH$_2$-cyclopropyl | |
| | | -O-cyclopentyl | |
| | | -O-CH$_2$-cyclopentyl | |
| | | OCH$_2$CH$_2$R | F |
| | | | N(CH$_3$)$_2$ |
| | | | OH |
| | | | OCH$_3$ |
| | | | OC(O)CH$_3$ |
| | | | -O-tetrahydropyranyl |
| | | OCH$_2$CF$_3$ | |

FIGURE 5F
| Structure | X | R$^b$ | R |
|---|---|---|---|
| 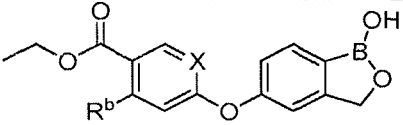 | CH | 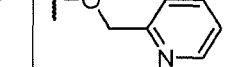 | |
| | | OC(O)CH$_3$ | |
| | | OCH$_2$C(O)R | OH |
| | | | OCH$_2$CH$_3$ |
| | | | OC(CH$_3$)$_3$ |
| | | | N(CH$_2$CH$_3$)$_2$ |
| | | |  |
| | | | 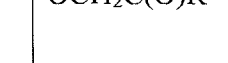 |
| | | |  |
| | N | F | |
| | | Cl | |
| | | CH$_3$ | |
| | | CH$_2$CH$_3$ | |
| | | C$_3$-alkyl | |
| | | C$_4$-alkyl | |
| | | C$_5$-alkyl | |
| | | C$_6$-alkyl | |
| | | C$_3$-cycloalkyl | |
| | | C$_4$-cycloalkyl | |
| | | C$_5$-cycloalkyl | |
| | | C$_6$-cycloalkyl | |
| | | C$_7$-cycloalkyl | |
| | | C$_8$-cycloalkyl | |
| | | CH$_2$R | OH |
| | | | NH$_2$ |
| | | | N(CH$_3$)$_2$ |
| | | |  |
| | | |  |
| | | | NHCHO |
| | | CHO | |
| | | CH=N-OH | |
| | | COOR | H |
| | | | CH$_3$ |
| | | | CH$_2$CH$_3$ |
| | | CF$_3$ | |
| | | NHR | H |
| | | | CH$_3$ |
| | | | C(CH$_3$)$_3$ |
| | | | CH$_2$Ph |

FIGURE 5G
| Structure | X | R^b | R |
|---|---|---|---|
| 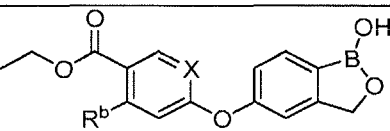 | N | NHR | CH$_2$CH$_2$OH |
| | | | CH$_2$CH$_2$OCH$_3$ |
| | | | CH$_2$CH$_2$OCH$_2$Ph |
| | | N(CH$_3$)R | CH$_3$ |
| | | | CH$_2$CH$_2$OH |
| | | | CH$_2$CH$_2$OCH$_3$ |
| | |  | |
| | |  | |
| | | OH | |
| | | C$_1$-alkoxy | |
| | | C$_2$-alkoxy | |
| | | C$_3$-alkoxy | |
| | | C$_4$-alkoxy | |
| | |  | |
| | |  | |
| | |  | |
| | | OCH$_2$CH$_2$R | F |
| | | | N(CH$_3$)$_2$ |
| | | | OH |
| | | | OCH$_3$ |
| | | | OC(O)CH$_3$ |
| | | 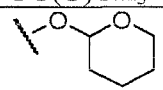 | |
| | | OCH$_2$CF$_3$ | |
| | | 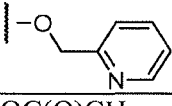 | |
| | | OC(O)CH$_3$ | |
| | | OCH$_2$C(O)R | OH |
| | | | OCH$_2$CH$_3$ |
| | | | OC(CH$_3$)$_3$ |
| | | | N(CH$_2$CH$_3$)$_2$ |
| | | |  |
| | | | 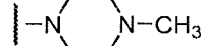 |
| | | | 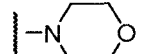 |

FIGURE 5H

| Structure | X | R$^b$ | R |
|---|---|---|---|
| 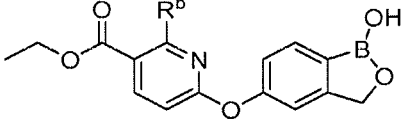 | [n/a] | F | |
| | | Cl | |
| | | CH$_3$ | |
| | | CH$_2$CH$_3$ | |
| | | C$_3$-alkyl | |
| | | C$_4$-alkyl | |
| | | C$_5$-alkyl | |
| | | C$_6$-alkyl | |
| | | C$_3$-cycloalkyl | |
| | | C$_4$-cycloalkyl | |
| | | C$_5$-cycloalkyl | |
| | | C$_6$-cycloalkyl | |
| | | C$_7$-cycloalkyl | |
| | | C$_8$-cycloalkyl | |
| | | CH$_2$R | OH |
| | | | NH$_2$ |
| | | | N(CH$_3$)$_2$ |
| | | | 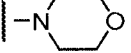 |
| | | | 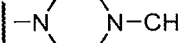 |
| | | | NHCHO |
| | | CHO | |
| | | CH=N-OH | |
| | | COOR | H |
| | | | CH$_3$ |
| | | | CH$_2$CH$_3$ |
| | | CF$_3$ | |
| | | NHR | H |
| | | | CH$_3$ |
| | | | C(CH$_3$)$_3$ |
| | | | CH$_2$Ph |
| | | | CH$_2$CH$_2$OH |
| | | | CH$_2$CH$_2$OCH$_3$ |
| | | | CH$_2$CH$_2$OCH$_2$Ph |
| | | N(CH$_3$)R | CH$_3$ |
| | | | CH$_2$CH$_2$OH |
| | | | CH$_2$CH$_2$OCH$_3$ |
| | | 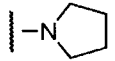 | |
| | | 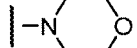 | |
| | | OH | |
| | | C$_1$-alkoxy | |
| | | C$_2$-alkoxy | |
| | | C$_3$-alkoxy | |

FIGURE 5I
| Structure | X | R<sup>b</sup> | R |
|---|---|---|---|
| 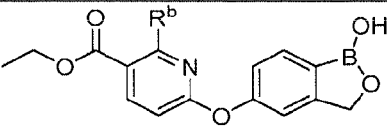 | [n/a] | C$_4$-alkoxy | |
| | | 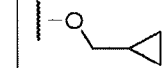 | |
| | | 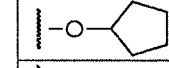 | |
| | | 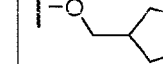 | |
| | | OCH$_2$CH$_2$R | F |
| | | | N(CH$_3$)$_2$ |
| | | | OH |
| | | | OCH$_3$ |
| | | | OC(O)CH$_3$ |
| | | | 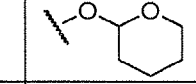 |
| | | OCH$_2$CF$_3$ | |
| | | 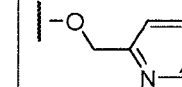 | |
| | | OC(O)CH$_3$ | |
| | | OCH$_2$C(O)R | OH |
| | | | OCH$_2$CH$_3$ |
| | | | OC(CH$_3$)$_3$ |
| | | | N(CH$_2$CH$_3$)$_2$ |
| | | | 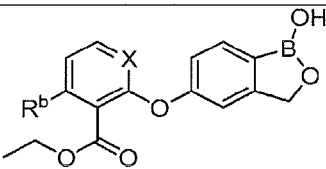 |
| | | | 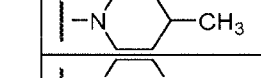 |
| | | | 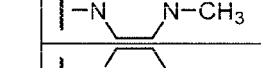 |
| 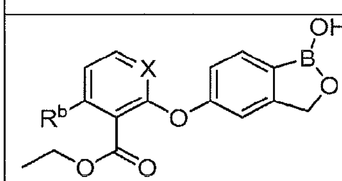 | CH | F | |
| | | Cl | |
| | | CH$_3$ | |
| | | CH$_2$CH$_3$ | |
| | | C$_3$-alkyl | |
| | | C$_4$-alkyl | |
| | | C$_5$-alkyl | |
| | | C$_6$-alkyl | |
| | | C$_3$-cycloalkyl | |
| | | C$_4$-cycloalkyl | |
| | | C$_5$-cycloalkyl | |
| | | C$_6$-cycloalkyl | |
| | | C$_7$-cycloalkyl | |
| | | C$_8$-cycloalkyl | |
| | | CH$_2$R | OH |
| | | | NH$_2$ |

FIGURE 5J

| Structure | X | R$^b$ | R |
|---|---|---|---|
| ![structure] | CH | CH$_2$R | N(CH$_3$)$_2$ |
| | | | −N(morpholine) |
| | | | −N(N-methylpiperazine)−CH$_3$ |
| | | | NHCHO |
| | | CHO | |
| | | CH=N-OH | |
| | | COOR | H |
| | | | CH$_3$ |
| | | | CH$_2$CH$_3$ |
| | | CF$_3$ | |
| | | NHR | H |
| | | | CH$_3$ |
| | | | C(CH$_3$)$_3$ |
| | | | CH$_2$Ph |
| | | | CH$_2$CH$_2$OH |
| | | | CH$_2$CH$_2$OCH$_3$ |
| | | | CH$_2$CH$_2$OCH$_2$Ph |
| | | N(CH$_3$)R | CH$_3$ |
| | | | CH$_2$CH$_2$OH |
| | | | CH$_2$CH$_2$OCH$_3$ |
| | | −N(pyrrolidine) | |
| | | −N(morpholine) | |
| | | OH | |
| | | C$_1$-alkoxy | |
| | | C$_2$-alkoxy | |
| | | C$_3$-alkoxy | |
| | | C$_4$-alkoxy | |
| | | −O−CH$_2$-cyclopropyl | |
| | | −O−cyclopentyl | |
| | | −O−CH$_2$-cyclopentyl | |
| | | OCH$_2$CH$_2$R | F |
| | | | N(CH$_3$)$_2$ |
| | | | OH |
| | | | OCH$_3$ |
| | | | OC(O)CH$_3$ |
| | | | −O−tetrahydropyranyl |
| | | OCH$_2$CF$_3$ | |

FIGURE 5K
| Structure | X | R$^b$ | R |
|---|---|---|---|
| 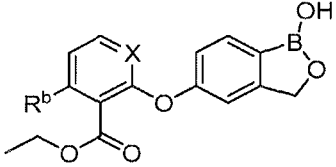 | CH | 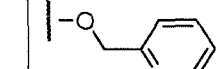 | |
| | | OC(O)CH$_3$ | |
| | | OCH$_2$C(O)R | OH |
| | | | OCH$_2$CH$_3$ |
| | | | OC(CH$_3$)$_3$ |
| | | | N(CH$_2$CH$_3$)$_2$ |
| | | |  |
| | | |  |
| | | |  |
| | N | F | |
| | | Cl | |
| | | CH$_3$ | |
| | | CH$_2$CH$_3$ | |
| | | C$_3$-alkyl | |
| | | C$_4$-alkyl | |
| | | C$_5$-alkyl | |
| | | C$_6$-alkyl | |
| | | C$_3$-cycloalkyl | |
| | | C$_4$-cycloalkyl | |
| | | C$_5$-cycloalkyl | |
| | | C$_6$-cycloalkyl | |
| | | C$_7$-cycloalkyl | |
| | | C$_8$-cycloalkyl | |
| | | CH$_2$R | OH |
| | | | NH$_2$ |
| | | | N(CH$_3$)$_2$ |
| | | | 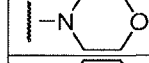 |
| | | |  |
| | | | NHCHO |
| | | CHO | |
| | | CH=N-OH | |
| | | COOR | H |
| | | | CH$_3$ |
| | | | CH$_2$CH$_3$ |
| | | CF$_3$ | |
| | | NHR | H |
| | | | CH$_3$ |
| | | | C(CH$_3$)$_3$ |
| | | | CH$_2$Ph |

FIGURE 5L
| Structure | X | R$^b$ | R |
|---|---|---|---|
| 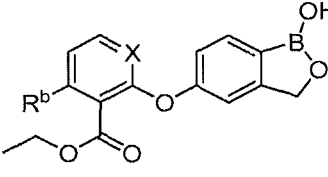 | N | NHR | CH$_2$CH$_2$OH |
| | | | CH$_2$CH$_2$OCH$_3$ |
| | | | CH$_2$CH$_2$OCH$_2$Ph |
| | | N(CH$_3$)R | CH$_3$ |
| | | | CH$_2$CH$_2$OH |
| | | | CH$_2$CH$_2$OCH$_3$ |
| | |  | |
| | | 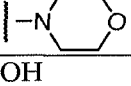 | |
| | | OH | |
| | | C$_1$-alkoxy | |
| | | C$_2$-alkoxy | |
| | | C$_3$-alkoxy | |
| | | C$_4$-alkoxy | |
| | | 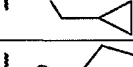 | |
| | | 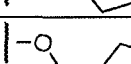 | |
| | |  | |
| | | OCH$_2$CH$_2$R | F |
| | | | N(CH$_3$)$_2$ |
| | | | OH |
| | | | OCH$_3$ |
| | | | OC(O)CH$_3$ |
| | | | 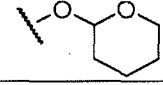 |
| | | OCH$_2$CF$_3$ | |
| | | 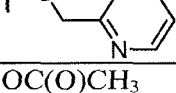 | |
| | | OC(O)CH$_3$ | |
| | | OCH$_2$C(O)R | OH |
| | | | OCH$_2$CH$_3$ |
| | | | OC(CH$_3$)$_3$ |
| | | | N(CH$_2$CH$_3$)$_2$ |
| | | | 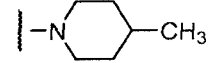 |
| | | | 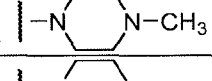 |
| | | | 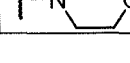 |

FIGURE 5M
| Structure | X | R^b | R |
|---|---|---|---|
| 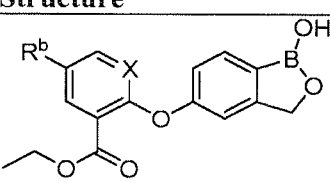 | CH | F | |
| | | Cl | |
| | | $CH_3$ | |
| | | $CH_2CH_3$ | |
| | | $C_3$-alkyl | |
| | | $C_4$-alkyl | |
| | | $C_5$-alkyl | |
| | | $C_6$-alkyl | |
| | | $C_3$-cycloalkyl | |
| | | $C_4$-cycloalkyl | |
| | | $C_5$-cycloalkyl | |
| | | $C_6$-cycloalkyl | |
| | | $C_7$-cycloalkyl | |
| | | $C_8$-cycloalkyl | |
| | | $CH_2R$ | OH |
| | | | $NH_2$ |
| | | | $N(CH_3)_2$ |
| | | | 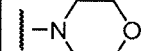 |
| | | | 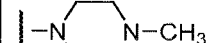 |
| | | | NHCHO |
| | | CHO | |
| | | CH=N-OH | |
| | | COOR | H |
| | | | $CH_3$ |
| | | | $CH_2CH_3$ |
| | | $CF_3$ | |
| | | NHR | H |
| | | | $CH_3$ |
| | | | $C(CH_3)_3$ |
| | | | $CH_2Ph$ |
| | | | $CH_2CH_2OH$ |
| | | | $CH_2CH_2OCH_3$ |
| | | | $CH_2CH_2OCH_2Ph$ |
| | | $N(CH_3)R$ | $CH_3$ |
| | | | $CH_2CH_2OH$ |
| | | | $CH_2CH_2OCH_3$ |
| | | 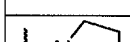 | |
| | | 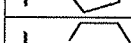 | |
| | | OH | |
| | | $C_1$-alkoxy | |
| | | $C_2$-alkoxy | |
| | | $C_3$-alkoxy | |

FIGURE 5N
| Structure | X | R^b | R |
|---|---|---|---|
| 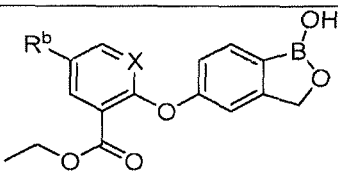 | CH | C₄-alkoxy | |
| | |  | |
| | | 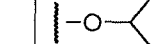 | |
| | | 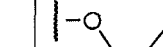 | |
| | | OCH₂CH₂R | F |
| | | | N(CH₃)₂ |
| | | | OH |
| | | | OCH₃ |
| | | | OC(O)CH₃ |
| | | | 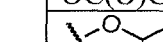 |
| | | OCH₂CF₃ | |
| | | 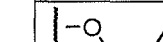 | |
| | | OC(O)CH₃ | |
| | | OCH₂C(O)R | OH |
| | | | OCH₂CH₃ |
| | | | OC(CH₃)₃ |
| | | | N(CH₂CH₃)₂ |
| | | | 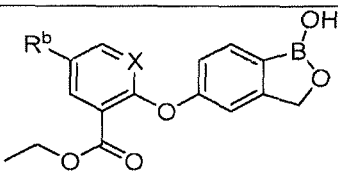 |
| | | | 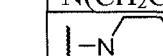 |
| | | | 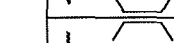 |
| | N | F | |
| | | Cl | |
| | | CH₃ | |
| | | CH₂CH₃ | |
| | | C₃-alkyl | |
| | | C₄-alkyl | |
| | | C₅-alkyl | |
| | | C₆-alkyl | |
| | | C₃-cycloalkyl | |
| | | C₄-cycloalkyl | |
| | | C₅-cycloalkyl | |
| | | C₆-cycloalkyl | |
| | | C₇-cycloalkyl | |
| | | C₈-cycloalkyl | |
| | | CH₂R | OH |
| | | | NH₂ |

FIGURE 5O

| Structure | X | R$^b$ | R |
|---|---|---|---|
| ethyl 2-((1-hydroxy-1,3-dihydrobenzo[c][1,2]oxaborol-5-yl)oxy)-5-R$^b$-pyridine-3-carboxylate | N | CH$_2$R | N(CH$_3$)$_2$ |
| | | | -N(morpholine) |
| | | | -N(N-methylpiperazine) |
| | | | NHCHO |
| | | CHO | |
| | | CH=N-OH | |
| | | COOR | H |
| | | | CH$_3$ |
| | | | CH$_2$CH$_3$ |
| | | CF$_3$ | |
| | | NHR | H |
| | | | CH$_3$ |
| | | | C(CH$_3$)$_3$ |
| | | | CH$_2$Ph |
| | | | CH$_2$CH$_2$OH |
| | | | CH$_2$CH$_2$OCH$_3$ |
| | | | CH$_2$CH$_2$OCH$_2$Ph |
| | | N(CH$_3$)R | CH$_3$ |
| | | | CH$_2$CH$_2$OH |
| | | | CH$_2$CH$_2$OCH$_3$ |
| | | -N(pyrrolidine) | |
| | | -N(morpholine) | |
| | | OH | |
| | | C$_1$-alkoxy | |
| | | C$_2$-alkoxy | |
| | | C$_3$-alkoxy | |
| | | C$_4$-alkoxy | |
| | | -O-CH$_2$-cyclopropyl | |
| | | -O-cyclopentyl | |
| | | -O-CH$_2$-cyclopentyl | |
| | | OCH$_2$CH$_2$R | F |
| | | | N(CH$_3$)$_2$ |
| | | | OH |
| | | | OCH$_3$ |
| | | | OC(O)CH$_3$ |
| | | | -O-tetrahydropyranyl |
| | | OCH$_2$CF$_3$ | |

FIGURE 5P
| Structure | X | R$^b$ | R |
|---|---|---|---|
| 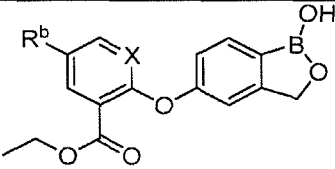 | N | 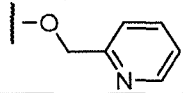 | |
| | | OC(O)CH$_3$ | |
| | | OCH$_2$C(O)R | OH |
| | | | OCH$_2$CH$_3$ |
| | | | OC(CH$_3$)$_3$ |
| | | | N(CH$_2$CH$_3$)$_2$ |
| | | |  |
| | | | 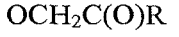 |
| | | |  |
| 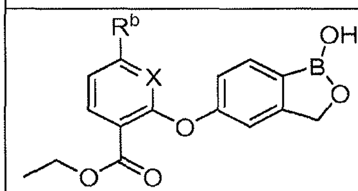 | CH | F | |
| | | Cl | |
| | | CH$_3$ | |
| | | CH$_2$CH$_3$ | |
| | | C$_3$-alkyl | |
| | | C$_4$-alkyl | |
| | | C$_5$-alkyl | |
| | | C$_6$-alkyl | |
| | | C$_3$-cycloalkyl | |
| | | C$_4$-cycloalkyl | |
| | | C$_5$-cycloalkyl | |
| | | C$_6$-cycloalkyl | |
| | | C$_7$-cycloalkyl | |
| | | C$_8$-cycloalkyl | |
| | | CH$_2$R | OH |
| | | | NH$_2$ |
| | | | N(CH$_3$)$_2$ |
| | | |  |
| | | |  |
| | | | NHCHO |
| | | CHO | |
| | | CH=N-OH | |
| | | COOR | H |
| | | | CH$_3$ |
| | | | CH$_2$CH$_3$ |
| | | CF$_3$ | |
| | | NHR | H |
| | | | CH$_3$ |
| | | | C(CH$_3$)$_3$ |
| | | | CH$_2$Ph |

FIGURE 5Q
| Structure | X | R$^b$ | R |
|---|---|---|---|
| 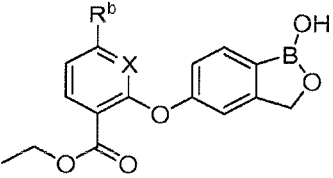 | CH | NHR | CH$_2$CH$_2$OH |
| | | | CH$_2$CH$_2$OCH$_3$ |
| | | | CH$_2$CH$_2$OCH$_2$Ph |
| | | N(CH$_3$)R | CH$_3$ |
| | | | CH$_2$CH$_2$OH |
| | | | CH$_2$CH$_2$OCH$_3$ |
| | | 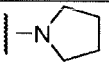 | |
| | | 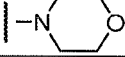 | |
| | | OH | |
| | | C$_1$-alkoxy | |
| | | C$_2$-alkoxy | |
| | | C$_3$-alkoxy | |
| | | C$_4$-alkoxy | |
| | | 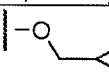 | |
| | | 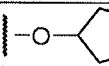 | |
| | | 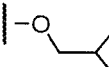 | |
| | | OCH$_2$CH$_2$R | F |
| | | | N(CH$_3$)$_2$ |
| | | | OH |
| | | | OCH$_3$ |
| | | | OC(O)CH$_3$ |
| | | | 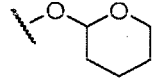 |
| | | OCH$_2$CF$_3$ | |
| | | 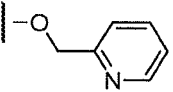 | |
| | | OC(O)CH$_3$ | |
| | | OCH$_2$C(O)R | OH |
| | | | OCH$_2$CH$_3$ |
| | | | OC(CH$_3$)$_3$ |
| | | | N(CH$_2$CH$_3$)$_2$ |
| | | |  |
| | | | 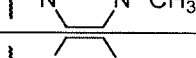 |
| | | | 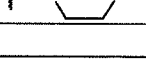 |
| | N | F | |
| | | Cl | |

FIGURE 5R

| Structure | X | R^b | R |
|---|---|---|---|
| (structure shown with R^b, X, ethyl ester, O linker, benzoxaborole with OH) | N | CH₃ | |
| | | CH₂CH₃ | |
| | | C₃-alkyl | |
| | | C₄-alkyl | |
| | | C₅-alkyl | |
| | | C₆-alkyl | |
| | | C₃-cycloalkyl | |
| | | C₄-cycloalkyl | |
| | | C₅-cycloalkyl | |
| | | C₆-cycloalkyl | |
| | | C₇-cycloalkyl | |
| | | C₈-cycloalkyl | |
| | | CH₂R | OH |
| | | | NH₂ |
| | | | N(CH₃)₂ |
| | | | -N(morpholine) |
| | | | -N(N-methylpiperazine)-CH₃ |
| | | | NHCHO |
| | | CHO | |
| | | CH=N-OH | |
| | | COOR | H |
| | | | CH₃ |
| | | | CH₂CH₃ |
| | | CF₃ | |
| | | NHR | H |
| | | | CH₃ |
| | | | C(CH₃)₃ |
| | | | CH₂Ph |
| | | | CH₂CH₂OH |
| | | | CH₂CH₂OCH₃ |
| | | | CH₂CH₂OCH₂Ph |
| | | N(CH₃)R | CH₃ |
| | | | CH₂CH₂OH |
| | | | CH₂CH₂OCH₃ |
| | | -N(pyrrolidine) | |
| | | -N(morpholine) | |
| | | OH | |
| | | C₁-alkoxy | |
| | | C₂-alkoxy | |
| | | C₃-alkoxy | |
| | | C₄-alkoxy | |

FIGURE 5S

| Structure | X | R^b | R |
|---|---|---|---|
| (structure 1) | N | -O-cyclopropylmethyl | |
| | | -O-cyclopentyl | |
| | | -O-CH2-cyclopentyl | |
| | | OCH$_2$CH$_2$R | F |
| | | | N(CH$_3$)$_2$ |
| | | | OH |
| | | | OCH$_3$ |
| | | | OC(O)CH$_3$ |
| | | | -O-tetrahydropyranyl |
| | | OCH$_2$CF$_3$ | |
| | | -O-CH2-pyridyl | |
| | | OC(O)CH$_3$ | |
| | | OCH$_2$C(O)R | OH |
| | | | OCH$_2$CH$_3$ |
| | | | OC(CH$_3$)$_3$ |
| | | | N(CH$_2$CH$_3$)$_2$ |
| | | | -N(4-methylpiperidinyl) |
| | | | -N(4-methylpiperazinyl) |
| | | | -N(morpholinyl) |
| (structure 2) | [n/a] | F | |
| | | Cl | |
| | | CH$_3$ | |
| | | CH$_2$CH$_3$ | |
| | | C$_3$-alkyl | |
| | | C$_4$-alkyl | |
| | | C$_5$-alkyl | |
| | | C$_6$-alkyl | |
| | | C$_3$-cycloalkyl | |
| | | C$_4$-cycloalkyl | |
| | | C$_5$-cycloalkyl | |
| | | C$_6$-cycloalkyl | |
| | | C$_7$-cycloalkyl | |
| | | C$_8$-cycloalkyl | |
| | | CH$_2$R | OH |
| | | | NH$_2$ |
| | | | N(CH$_3$)$_2$ |

FIGURE 5T

| Structure | X | R^b | R |
|---|---|---|---|
| ![structure with ethyl ester, phenoxy, benzoxaborole, R^b, OH] | [n/a] | CH$_2$R | -N(morpholine) |
| | | | -N(N-methylpiperazine)N-CH$_3$ |
| | | | NHCHO |
| | | CHO | |
| | | CH=N-OH | |
| | | COOR | H |
| | | | CH$_3$ |
| | | | CH$_2$CH$_3$ |
| | | CF$_3$ | |
| | | NHR | H |
| | | | CH$_3$ |
| | | | C(CH$_3$)$_3$ |
| | | | CH$_2$Ph |
| | | | CH$_2$CH$_2$OH |
| | | | CH$_2$CH$_2$OCH$_3$ |
| | | | CH$_2$CH$_2$OCH$_2$Ph |
| | | N(CH$_3$)R | CH$_3$ |
| | | | CH$_2$CH$_2$OH |
| | | | CH$_2$CH$_2$OCH$_3$ |
| | | -N(pyrrolidine) | |
| | | -N(morpholine) | |
| | | OH | |
| | | C$_1$-alkoxy | |
| | | C$_2$-alkoxy | |
| | | C$_3$-alkoxy | |
| | | C$_4$-alkoxy | |
| | | -O-CH$_2$-cyclopropyl | |
| | | -O-cyclopentyl | |
| | | -O-CH$_2$-cyclopentyl | |
| | | OCH$_2$CH$_2$R | F |
| | | | N(CH$_3$)$_2$ |
| | | | OH |
| | | | OCH$_3$ |
| | | | OC(O)CH$_3$ |
| | | | -O-tetrahydropyran |
| | | OCH$_2$CF$_3$ | |

FIGURE 5U

| Structure | X | R^b | R |
|---|---|---|---|
| ethyl 2-(1-hydroxy-1,3-dihydrobenzo[c][1,2]oxaborol-5-yloxy)-3-R^b-benzoate | [n/a] | -O-CH2-(2-pyridyl) | |
| | | OC(O)CH3 | |
| | | OCH2C(O)R | OH |
| | | | OCH2CH3 |
| | | | OC(CH3)3 |
| | | | N(CH2CH3)2 |
| | | | -N(4-methylpiperidinyl) |
| | | | -N(4-methylpiperazinyl) |
| | | | -N(morpholinyl) |
| ethyl 2-(1-hydroxy-1,3-dihydrobenzo[c][1,2]oxaborol-5-yloxy)-3-R^b-pyridine-4-carboxylate | CH | F | |
| | | Cl | |
| | | CH3 | |
| | | CH2CH3 | |
| | | C3-alkyl | |
| | | C4-alkyl | |
| | | C5-alkyl | |
| | | C6-alkyl | |
| | | C3-cycloalkyl | |
| | | C4-cycloalkyl | |
| | | C5-cycloalkyl | |
| | | C6-cycloalkyl | |
| | | C7-cycloalkyl | |
| | | C8-cycloalkyl | |
| | | CH2R | OH |
| | | | NH2 |
| | | | N(CH3)2 |
| | | | -N(morpholinyl) |
| | | | -N(4-methylpiperazinyl) |
| | | | NHCHO |
| | | CHO | |
| | | CH=N-OH | |
| | | COOR | H |
| | | | CH3 |
| | | | CH2CH3 |
| | | CF3 | |
| | | NHR | H |
| | | | CH3 |
| | | | C(CH3)3 |
| | | | CH2Ph |

FIGURE 5V

| Structure | X | R^b | R |
|---|---|---|---|
| (ethyl benzoate linked via O to benzoxaborole with OH, bearing R^b) | CH | NHR | CH$_2$CH$_2$OH |
| | | | CH$_2$CH$_2$OCH$_3$ |
| | | | CH$_2$CH$_2$OCH$_2$Ph |
| | | N(CH$_3$)R | CH$_3$ |
| | | | CH$_2$CH$_2$OH |
| | | | CH$_2$CH$_2$OCH$_3$ |
| | | -N(pyrrolidine) | |
| | | -N(morpholine) | |
| | | OH | |
| | | C$_1$-alkoxy | |
| | | C$_2$-alkoxy | |
| | | C$_3$-alkoxy | |
| | | C$_4$-alkoxy | |
| | | -O-CH$_2$-cyclopropyl | |
| | | -O-cyclopentyl | |
| | | -O-CH$_2$-cyclopentyl | |
| | | OCH$_2$CH$_2$R | F |
| | | | N(CH$_3$)$_2$ |
| | | | OH |
| | | | OCH$_3$ |
| | | | OC(O)CH$_3$ |
| | | | -O-(tetrahydropyran) |
| | | OCH$_2$CF$_3$ | |
| | | -O-CH$_2$-(2-pyridyl) | |
| | | OC(O)CH$_3$ | |
| | | OCH$_2$C(O)R | OH |
| | | | OCH$_2$CH$_3$ |
| | | | OC(CH$_3$)$_3$ |
| | | | N(CH$_2$CH$_3$)$_2$ |
| | | | -N(4-methylpiperidine)-CH$_3$ |
| | | | -N(piperazine)N-CH$_3$ |
| | | | -N(morpholine) |
| | N | F | |
| | | Cl | |

FIGURE 5W

| Structure | X | R$^b$ | R |
|---|---|---|---|
| 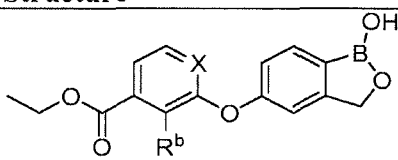 | N | CH$_3$ | |
| | | CH$_2$CH$_3$ | |
| | | C$_3$-alkyl | |
| | | C$_4$-alkyl | |
| | | C$_5$-alkyl | |
| | | C$_6$-alkyl | |
| | | C$_3$-cycloalkyl | |
| | | C$_4$-cycloalkyl | |
| | | C$_5$-cycloalkyl | |
| | | C$_6$-cycloalkyl | |
| | | C$_7$-cycloalkyl | |
| | | C$_8$-cycloalkyl | |
| | | CH$_2$R | OH |
| | | | NH$_2$ |
| | | | N(CH$_3$)$_2$ |
| | | | 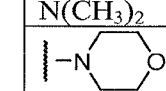 |
| | | | 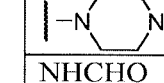 |
| | | | NHCHO |
| | | CHO | |
| | | CH=N-OH | |
| | | COOR | H |
| | | | CH$_3$ |
| | | | CH$_2$CH$_3$ |
| | | CF$_3$ | |
| | | NHR | H |
| | | | CH$_3$ |
| | | | C(CH$_3$)$_3$ |
| | | | CH$_2$Ph |
| | | | CH$_2$CH$_2$OH |
| | | | CH$_2$CH$_2$OCH$_3$ |
| | | | CH$_2$CH$_2$OCH$_2$Ph |
| | | N(CH$_3$)R | CH$_3$ |
| | | | CH$_2$CH$_2$OH |
| | | | CH$_2$CH$_2$OCH$_3$ |
| | | 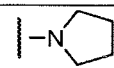 | |
| | | 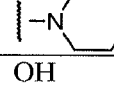 | |
| | | OH | |
| | | C$_1$-alkoxy | |
| | | C$_2$-alkoxy | |
| | | C$_3$-alkoxy | |
| | | C$_4$-alkoxy | |

FIGURE 5X

| Structure | X | R^b | R |
|---|---|---|---|
| ethyl 3-((1-hydroxy-1,3-dihydrobenzo[c][1,2]oxaborol-5-yl)oxy)-R^b-substituted pyridine-4-carboxylate | N | −O−CH₂−cyclopropyl | |
| | | −O−cyclopentyl | |
| | | −O−CH₂−cyclopentyl | |
| | | OCH₂CH₂R | F |
| | | | N(CH₃)₂ |
| | | | OH |
| | | | OCH₃ |
| | | | OC(O)CH₃ |
| | | | −O−tetrahydropyran-2-yl |
| | | OCH₂CF₃ | |
| | | −O−CH₂−(pyridin-2-yl) | |
| | | OC(O)CH₃ | |
| | | OCH₂C(O)R | OH |
| | | | OCH₂CH₃ |
| | | | OC(CH₃)₃ |
| | | | N(CH₂CH₃)₂ |
| | | | −N(4-methylpiperidin-1-yl) |
| | | | −N(4-methylpiperazin-1-yl) |
| | | | −N(morpholin-4-yl) |
| ethyl 5-((1-hydroxy-1,3-dihydrobenzo[c][1,2]oxaborol-5-yl)oxy)-R^b-substituted benzoate | CH | F | |
| | | Cl | |
| | | CH₃ | |
| | | CH₂CH₃ | |
| | | C₃-alkyl | |
| | | C₄-alkyl | |
| | | C₅-alkyl | |
| | | C₆-alkyl | |
| | | C₃-cycloalkyl | |
| | | C₄-cycloalkyl | |
| | | C₅-cycloalkyl | |
| | | C₆-cycloalkyl | |
| | | C₇-cycloalkyl | |
| | | C₈-cycloalkyl | |
| | | CH₂R | OH |
| | | | NH₂ |
| | | | N(CH₃)₂ |

FIGURE 5Y
| Structure | X | R$^b$ | R |
|---|---|---|---|
| 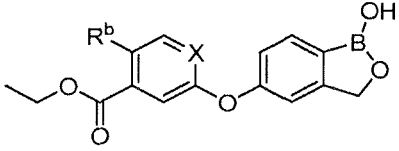 | CH | CH$_2$R |  |
| | | | 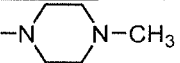 |
| | | | NHCHO |
| | | CHO | |
| | | CH=N-OH | |
| | | COOR | H |
| | | | CH$_3$ |
| | | | CH$_2$CH$_3$ |
| | | CF$_3$ | |
| | | NHR | H |
| | | | CH$_3$ |
| | | | C(CH$_3$)$_3$ |
| | | | CH$_2$Ph |
| | | | CH$_2$CH$_2$OH |
| | | | CH$_2$CH$_2$OCH$_3$ |
| | | | CH$_2$CH$_2$OCH$_2$Ph |
| | | N(CH$_3$)R | CH$_3$ |
| | | | CH$_2$CH$_2$OH |
| | | | CH$_2$CH$_2$OCH$_3$ |
| | |  | |
| | |  | |
| | | OH | |
| | | C$_1$-alkoxy | |
| | | C$_2$-alkoxy | |
| | | C$_3$-alkoxy | |
| | | C$_4$-alkoxy | |
| | |  | |
| | |  | |
| | |  | |
| | | OCH$_2$CH$_2$R | F |
| | | | N(CH$_3$)$_2$ |
| | | | OH |
| | | | OCH$_3$ |
| | | | OC(O)CH$_3$ |
| | | |  |
| | | OCH$_2$CF$_3$ | |

FIGURE 5Z
| Structure | X | R[b] | R |
|---|---|---|---|
| 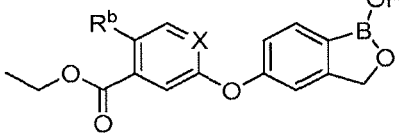 | CH | 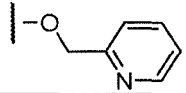 | |
| | | OC(O)CH₃ | |
| | | OCH₂C(O)R | OH |
| | | | OCH₂CH₃ |
| | | | OC(CH₃)₃ |
| | | | N(CH₂CH₃)₂ |
| | | |  |
| | | |  |
| | | | 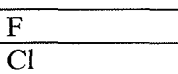 |
| | N | F | |
| | | Cl | |
| | | CH₃ | |
| | | CH₂CH₃ | |
| | | C₃-alkyl | |
| | | C₄-alkyl | |
| | | C₅-alkyl | |
| | | C₆-alkyl | |
| | | C₃-cycloalkyl | |
| | | C₄-cycloalkyl | |
| | | C₅-cycloalkyl | |
| | | C₆-cycloalkyl | |
| | | C₇-cycloalkyl | |
| | | C₈-cycloalkyl | |
| | | CH₂R | OH |
| | | | NH₂ |
| | | | N(CH₃)₂ |
| | | |  |
| | | |  |
| | | | NHCHO |
| | | CHO | |
| | | CH=N-OH | |
| | | COOR | H |
| | | | CH₃ |
| | | | CH₂CH₃ |
| | | CF₃ | |
| | | NHR | H |
| | | | CH₃ |
| | | | C(CH₃)₃ |
| | | | CH₂Ph |

FIGURE 5AA
| Structure | X | R<sup>b</sup> | R |
|---|---|---|---|
| 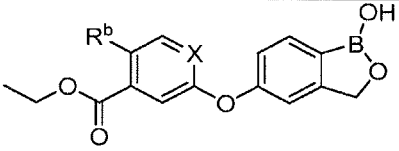 | N | NHR | CH₂CH₂OH |
| | | | CH₂CH₂OCH₃ |
| | | | CH₂CH₂OCH₂Ph |
| | | N(CH₃)R | CH₃ |
| | | | CH₂CH₂OH |
| | | | CH₂CH₂OCH₃ |
| | | 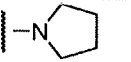 | |
| | | 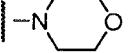 | |
| | | OH | |
| | | C₁-alkoxy | |
| | | C₂-alkoxy | |
| | | C₃-alkoxy | |
| | | C₄-alkoxy | |
| | |  | |
| | |  | |
| | | 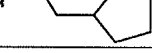 | |
| | | OCH₂CH₂R | F |
| | | | N(CH₃)₂ |
| | | | OH |
| | | | OCH₃ |
| | | | OC(O)CH₃ |
| | | | 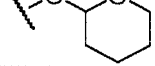 |
| | | OCH₂CF₃ | |
| | | 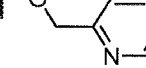 | |
| | | OC(O)CH₃ | |
| | | OCH₂C(O)R | OH |
| | | | OCH₂CH₃ |
| | | | OC(CH₃)₃ |
| | | | N(CH₂CH₃)₂ |
| | | | 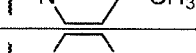 |
| | | | 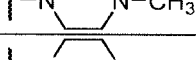 |
| | | | 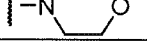 |

FIGURE 5BB

| Structure | X | R^b | R |
|---|---|---|---|
| 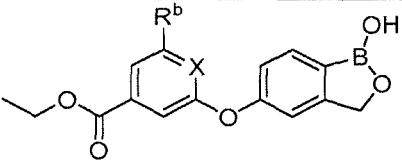 | CH | F | |
| | | Cl | |
| | | CH$_3$ | |
| | | CH$_2$CH$_3$ | |
| | | C$_3$-alkyl | |
| | | C$_4$-alkyl | |
| | | C$_5$-alkyl | |
| | | C$_6$-alkyl | |
| | | C$_3$-cycloalkyl | |
| | | C$_4$-cycloalkyl | |
| | | C$_5$-cycloalkyl | |
| | | C$_6$-cycloalkyl | |
| | | C$_7$-cycloalkyl | |
| | | C$_8$-cycloalkyl | |
| | | CH$_2$R | OH |
| | | | NH$_2$ |
| | | | N(CH$_3$)$_2$ |
| | | | 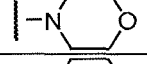 |
| | | | 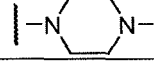 |
| | | | NHCHO |
| | | CHO | |
| | | CH=N-OH | |
| | | COOR | H |
| | | | CH$_3$ |
| | | | CH$_2$CH$_3$ |
| | | CF$_3$ | |
| | | NHR | H |
| | | | CH$_3$ |
| | | | C(CH$_3$)$_3$ |
| | | | CH$_2$Ph |
| | | | CH$_2$CH$_2$OH |
| | | | CH$_2$CH$_2$OCH$_3$ |
| | | | CH$_2$CH$_2$OCH$_2$Ph |
| | | N(CH$_3$)R | CH$_3$ |
| | | | CH$_2$CH$_2$OH |
| | | | CH$_2$CH$_2$OCH$_3$ |
| | | 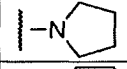 | |
| | | 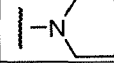 | |
| | | OH | |
| | | C$_1$-alkoxy | |
| | | C$_2$-alkoxy | |
| | | C$_3$-alkoxy | |

FIGURE 5CC
| Structure | X | R$^b$ | R |
|---|---|---|---|
| 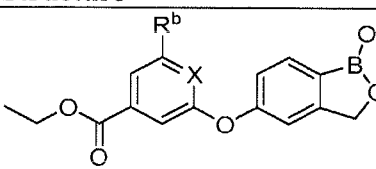 | CH | C$_4$-alkoxy | |
| | | 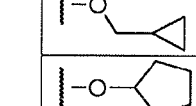 | |
| | | 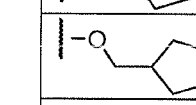 | |
| | | 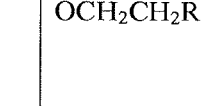 | |
| | | OCH$_2$CH$_2$R | F |
| | | | N(CH$_3$)$_2$ |
| | | | OH |
| | | | OCH$_3$ |
| | | | OC(O)CH$_3$ |
| | | | 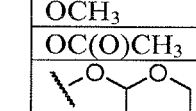 |
| | | OCH$_2$CF$_3$ | |
| | | 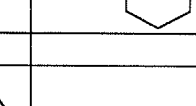 | |
| | | OC(O)CH$_3$ | |
| | | OCH$_2$C(O)R | OH |
| | | | OCH$_2$CH$_3$ |
| | | | OC(CH$_3$)$_3$ |
| | | | N(CH$_2$CH$_3$)$_2$ |
| | | |  |
| | | | 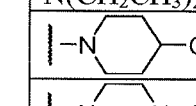 |
| | | | 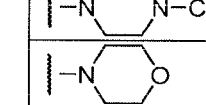 |
| | N | F | |
| | | Cl | |
| | | CH$_3$ | |
| | | CH$_2$CH$_3$ | |
| | | C$_3$-alkyl | |
| | | C$_4$-alkyl | |
| | | C$_5$-alkyl | |
| | | C$_6$-alkyl | |
| | | C$_3$-cycloalkyl | |
| | | C$_4$-cycloalkyl | |
| | | C$_5$-cycloalkyl | |
| | | C$_6$-cycloalkyl | |
| | | C$_7$-cycloalkyl | |
| | | C$_8$-cycloalkyl | |
| | | CH$_2$R | OH |
| | | | NH$_2$ |

FIGURE 5DD

| Structure | X | R^b | R |
|---|---|---|---|
| (ethyl benzoate-pyridine-O-benzoxaborole structure) | N | CH₂R | N(CH₃)₂ |
| | | | -N(morpholine) |
| | | | -N(N-methylpiperazine) |
| | | | NHCHO |
| | | CHO | |
| | | CH=N-OH | |
| | | COOR | H |
| | | | CH₃ |
| | | | CH₂CH₃ |
| | | CF₃ | |
| | | NHR | H |
| | | | CH₃ |
| | | | C(CH₃)₃ |
| | | | CH₂Ph |
| | | | CH₂CH₂OH |
| | | | CH₂CH₂OCH₃ |
| | | | CH₂CH₂OCH₂Ph |
| | | N(CH₃)R | CH₃ |
| | | | CH₂CH₂OH |
| | | | CH₂CH₂OCH₃ |
| | | -N(pyrrolidine) | |
| | | -N(morpholine) | |
| | | OH | |
| | | C₁-alkoxy | |
| | | C₂-alkoxy | |
| | | C₃-alkoxy | |
| | | C₄-alkoxy | |
| | | -O-cyclopropylmethyl | |
| | | -O-cyclopentyl | |
| | | -O-cyclopentylmethyl | |
| | | OCH₂CH₂R | F |
| | | | N(CH₃)₂ |
| | | | OH |
| | | | OCH₃ |
| | | | OC(O)CH₃ |
| | | | -O-tetrahydropyranyl |
| | | OCH₂CF₃ | |

FIGURE 5EE

| Structure | X | R$^b$ | R |
|---|---|---|---|
| 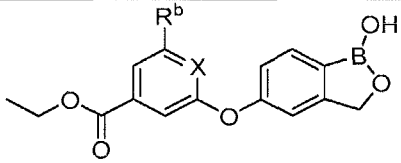 | N | -O-CH$_2$-(2-pyridyl) | |
| | | OC(O)CH$_3$ | |
| | | OCH$_2$C(O)R | OH |
| | | | OCH$_2$CH$_3$ |
| | | | OC(CH$_3$)$_3$ |
| | | | N(CH$_2$CH$_3$)$_2$ |
| | | | -N(4-methylpiperidinyl) |
| | | | -N(4-methylpiperazinyl) |
| | | | -N(morpholinyl) |
| 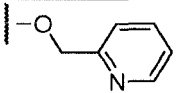 | [n/a] | F | |
| | | Cl | |
| | | CH$_3$ | |
| | | CH$_2$CH$_3$ | |
| | | C$_3$-alkyl | |
| | | C$_4$-alkyl | |
| | | C$_5$-alkyl | |
| | | C$_6$-alkyl | |
| | | C$_3$-cycloalkyl | |
| | | C$_4$-cycloalkyl | |
| | | C$_5$-cycloalkyl | |
| | | C$_6$-cycloalkyl | |
| | | C$_7$-cycloalkyl | |
| | | C$_8$-cycloalkyl | |
| | | CH$_2$R | OH |
| | | | NH$_2$ |
| | | | N(CH$_3$)$_2$ |
| | | | -N(morpholinyl) |
| | | | -N(4-methylpiperazinyl) |
| | | | NHCHO |
| | | CHO | |
| | | CH=N-OH | |
| | | COOR | H |
| | | | CH$_3$ |
| | | | CH$_2$CH$_3$ |
| | | CF$_3$ | |
| | | NHR | H |
| | | | CH$_3$ |
| | | | C(CH$_3$)$_3$ |
| | | | CH$_2$Ph |

FIGURE 5FF

| Structure | X | R$^b$ | R |
|---|---|---|---|
| ethyl 4-R$^b$-3-[(1-hydroxy-1,3-dihydro-2,1-benzoxaborol-5-yl)oxy]benzoate | [n/a] | NHR | CH$_2$CH$_2$OH |
| | | | CH$_2$CH$_2$OCH$_3$ |
| | | | CH$_2$CH$_2$OCH$_2$Ph |
| | | N(CH$_3$)R | CH$_3$ |
| | | | CH$_2$CH$_2$OH |
| | | | CH$_2$CH$_2$OCH$_3$ |
| | | -N(pyrrolidinyl) | |
| | | -N(morpholinyl) | |
| | | OH | |
| | | C$_1$-alkoxy | |
| | | C$_2$-alkoxy | |
| | | C$_3$-alkoxy | |
| | | C$_4$-alkoxy | |
| | | -O-CH$_2$-cyclopropyl | |
| | | -O-cyclopentyl | |
| | | -O-CH$_2$-cyclopentyl | |
| | | OCH$_2$CH$_2$R | F |
| | | | N(CH$_3$)$_2$ |
| | | | OH |
| | | | OCH$_3$ |
| | | | OC(O)CH$_3$ |
| | | | -O-tetrahydropyranyl |
| | | OCH$_2$CF$_3$ | |
| | | -O-CH$_2$-(2-pyridyl) | |
| | | OC(O)CH$_3$ | |
| | | OCH$_2$C(O)R | OH |
| | | | OCH$_2$CH$_3$ |
| | | | OC(CH$_3$)$_3$ |
| | | | N(CH$_2$CH$_3$)$_2$ |
| | | | -N(4-methylpiperidinyl) |
| | | | -N(4-methylpiperazinyl) |
| | | | -N(morpholinyl) |

FIGURE 6A

| Structure | n | R$^s$ |
|---|---|---|
| 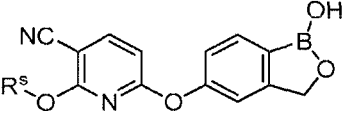 |  | H |
|  |  | Methyl |
|  |  | Ethyl |
|  |  | n-Propyl |
|  |  | iso-Propyl |
|  |  | n-Butyl |
|  |  | iso-Butyl |
|  |  | sec-Butyl |
|  |  | tert-Butyl |
|  |  | n-Pentyl |
|  |  | iso-Pentyl |
|  |  | neo-Pentyl |
|  |  | sec-Pentyl |
|  |  |  |
|  |  | n-Hexyl |
|  |  | iso-Hexyl |
|  |  |  |
|  |  | sec-Hexyl |
|  |  |  |
| 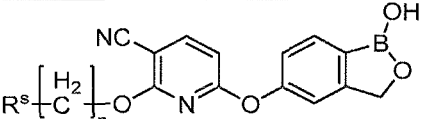 | 0 | cyclo-Propyl |
|  |  | cyclo-Butyl |
|  |  | cyclo-Pentyl |
|  |  | cyclo-Hexyl |
|  |  | cyclo-Heptyl |
|  |  | cyclo-Octyl |
|  | 1 | cyclo-Propyl |
|  |  | cyclo-Butyl |
|  |  | cyclo-Pentyl |
|  |  | cyclo-Hexyl |
|  |  | cyclo-Heptyl |
|  |  | cyclo-Octyl |
|  | 2 | cyclo-Propyl |
|  |  | cyclo-Butyl |
|  |  | cyclo-Pentyl |
|  |  | cyclo-Hexyl |
|  |  | cyclo-Heptyl |
|  |  | cyclo-Octyl |
|  | 3 | cyclo-Propyl |
|  |  | cyclo-Butyl |
|  |  | cyclo-Pentyl |
|  |  | cyclo-Hexyl |
|  |  | cyclo-Heptyl |
|  |  | cyclo-Octyl |
|  | 0 | CH$_2$F |
|  |  | CHF$_2$ |
|  |  | CF$_3$ |

FIGURE 6B
| Structure | n | R$^s$ |
|---|---|---|
| 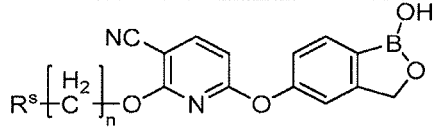 | 1 | CH$_2$F |
| | | CHF$_2$ |
| | | CF$_3$ |
| | 2 | CH$_2$F |
| | | CHF$_2$ |
| | | CF$_3$ |
| | 3 | CH$_2$F |
| | | CHF$_2$ |
| | | CF$_3$ |
| | 4 | CH$_2$F |
| | | CHF$_2$ |
| | | CF$_3$ |
| | 5 | CH$_2$F |
| | | CHF$_2$ |
| | | CF$_3$ |
| 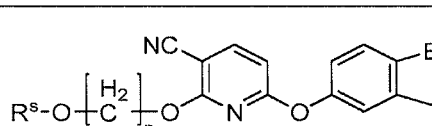 | 2 | H |
| | | Methyl |
| | | Ethyl |
| | | n-Propyl |
| | | iso-Propyl |
| | | n-Butyl |
| | | iso-Butyl |
| | | sec-Butyl |
| | | tert-Butyl |
| | | n-Pentyl |
| | | iso-Pentyl |
| | | neo-Pentyl |

FIGURE 6C

| Structure | n | R^s |
|---|---|---|
| (structure shown: R^s-O-[CH₂]_n-O-pyridine(CN)-O-benzoxaborole-OH) | 2 | sec-Pentyl |
| | | |
| | | n-Hexyl |
| | | iso-Hexyl |
| | | |
| | | sec-Hexyl |
| | | |
| | 3 | H |
| | | Methyl |
| | | Ethyl |
| | | n-Propyl |
| | | iso-Propyl |
| | | n-Butyl |
| | | iso-Butyl |
| | | sec-Butyl |
| | | tert-Butyl |
| | | n-Pentyl |
| | | iso-Pentyl |
| | | neo-Pentyl |
| | | sec-Pentyl |
| | | |
| | | n-Hexyl |
| | | iso-Hexyl |
| | | |
| | | sec-Hexyl |
| | | |
| | 4 | H |
| | | Methyl |
| | | Ethyl |
| | | n-Propyl |
| | | iso-Propyl |
| | | n-Butyl |
| | | iso-Butyl |
| | | sec-Butyl |
| | | tert-Butyl |
| | | n-Pentyl |
| | | iso-Pentyl |
| | | neo-Pentyl |
| | | sec-Pentyl |
| | | |
| | | n-Hexyl |
| | | iso-Hexyl |
| | | |
| | | sec-Hexyl |
| | | |
| | 5 | H |

FIGURE 6D

| Structure | n | R$^s$ |
|---|---|---|
| [structure: R$^s$-O-(CH$_2$)$_n$-O-pyridine(CN)-O-benzoxaborole-OH] | 5 | Methyl |
| | | Ethyl |
| | | n-Propyl |
| | | iso-Propyl |
| | | n-Butyl |
| | | iso-Butyl |
| | | sec-Butyl |
| | | tert-Butyl |
| | | n-Pentyl |
| | | iso-Pentyl |
| | | neo-Pentyl |
| | | sec-Pentyl |
| | | |
| | | n-Hexyl |
| | | iso-Hexyl |
| | | |
| | | sec-Hexyl |
| | | |
| | 6 | H |
| | | Methyl |
| | | Ethyl |
| | | n-Propyl |
| | | iso-Propyl |
| | | n-Butyl |
| | | iso-Butyl |
| | | sec-Butyl |
| | | tert-Butyl |
| | | n-Pentyl |
| | | iso-Pentyl |
| | | neo-Pentyl |
| | | sec-Pentyl |
| | | |
| | | n-Hexyl |
| | | iso-Hexyl |
| | | |
| | | sec-Hexyl |
| | | |
| [structure: R$^s$-C(=O)-O-(CH$_2$)$_n$-O-pyridine(CN)-O-benzoxaborole-OH] | | |

| Structure | n | R<sup>s</sup> |
|---|---|---|
| | 2 | Methyl |
| | | Ethyl |
| | | n-Propyl |
| | | iso-Propyl |
| | | n-Butyl |
| | | iso-Butyl |
| | | sec-Butyl |
| | | tert-Butyl |
| | | n-Pentyl |
| | | iso-Pentyl |
| | | neo-Pentyl |
| | | sec-Pentyl |
| | | |
| | | n-Hexyl |
| | | iso-Hexyl |
| | | |
| | | sec-Hexyl |
| | | |
| | 3 | Methyl |
| | | Ethyl |
| | | n-Propyl |
| | | iso-Propyl |
| | | n-Butyl |
| | | iso-Butyl |
| | | sec-Butyl |
| | | tert-Butyl |
| | | n-Pentyl |
| | | iso-Pentyl |
| | | neo-Pentyl |
| | | sec-Pentyl |
| | | |
| | | n-Hexyl |
| | | iso-Hexyl |
| | | |
| | | sec-Hexyl |

FIGURE 6F

| Structure | n | R$^s$ |
|---|---|---|
| ![structure] | 3 | |
| | 4 | Methyl |
| | | Ethyl |
| | | n-Propyl |
| | | iso-Propyl |
| | | n-Butyl |
| | | iso-Butyl |
| | | sec-Butyl |
| | | tert-Butyl |
| | | n-Pentyl |
| | | iso-Pentyl |
| | | neo-Pentyl |
| | | sec-Pentyl |
| | | |
| | | n-Hexyl |
| | | iso-Hexyl |
| | | |
| | | sec-Hexyl |
| | | |
| | 5 | Methyl |
| | | Ethyl |
| | | n-Propyl |
| | | iso-Propyl |
| | | n-Butyl |
| | | iso-Butyl |
| | | sec-Butyl |
| | | tert-Butyl |
| | | n-Pentyl |
| | | iso-Pentyl |
| | | neo-Pentyl |
| | | sec-Pentyl |
| | | |
| | | n-Hexyl |
| | | iso-Hexyl |
| | | |
| | | sec-Hexyl |
| | | |
| | 6 | Methyl |
| | | Ethyl |
| | | n-Propyl |
| | | iso-Propyl |
| | | n-Butyl |
| | | iso-Butyl |

FIGURE 6G

| Structure | n | R$^s$ |
|---|---|---|
| 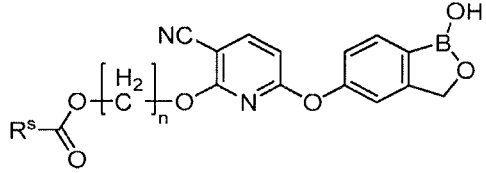 | 6 | sec-Butyl |
| | | tert-Butyl |
| | | n-Pentyl |
| | | iso-Pentyl |
| | | neo-Pentyl |
| | | sec-Pentyl |
| | | |
| | | n-Hexyl |
| | | iso-Hexyl |
| | | |
| | | sec-Hexyl |
| | | |
| 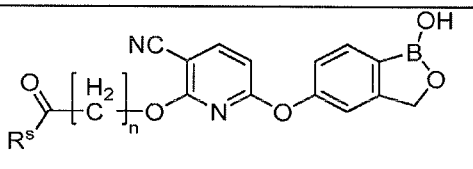 | 1 | Methyl |
| | | Ethyl |
| | | n-Propyl |
| | | iso-Propyl |
| | | n-Butyl |
| | | iso-Butyl |
| | | sec-Butyl |
| | | tert-Butyl |
| | | n-Pentyl |
| | | iso-Pentyl |
| | | neo-Pentyl |
| | | sec-Pentyl |
| | | |
| | | n-Hexyl |
| | | iso-Hexyl |
| | | |
| | | sec-Hexyl |
| | | |
| | 2 | Methyl |
| | | Ethyl |
| | | n-Propyl |
| | | iso-Propyl |
| | | n-Butyl |
| | | iso-Butyl |
| | | sec-Butyl |
| | | tert-Butyl |
| | | n-Pentyl |
| | | iso-Pentyl |
| | | neo-Pentyl |
| | | sec-Pentyl |
| | | |
| | | n-Hexyl |

FIGURE 6H

| Structure | n | R^s |
|---|---|---|
| (structure shown) | 2 | iso-Hexyl |
| | | sec-Hexyl |
| | 3 | Methyl |
| | | Ethyl |
| | | n-Propyl |
| | | iso-Propyl |
| | | n-Butyl |
| | | iso-Butyl |
| | | sec-Butyl |
| | | tert-Butyl |
| | | n-Pentyl |
| | | iso-Pentyl |
| | | neo-Pentyl |
| | | sec-Pentyl |
| | | n-Hexyl |
| | | iso-Hexyl |
| | | sec-Hexyl |
| | 4 | Methyl |
| | | Ethyl |
| | | n-Propyl |
| | | iso-Propyl |
| | | n-Butyl |
| | | iso-Butyl |
| | | sec-Butyl |
| | | tert-Butyl |
| | | n-Pentyl |
| | | iso-Pentyl |
| | | neo-Pentyl |
| | | sec-Pentyl |
| | | n-Hexyl |
| | | iso-Hexyl |
| | | sec-Hexyl |
| | 5 | Methyl |
| | | Ethyl |
| | | n-Propyl |

FIGURE 6I

| Structure | n | R$^s$ |
|---|---|---|
| (structure with NC-pyridine-O-benzoxaborole, R$^s$-C(O)-[CH$_2$]$_n$-O-) | 5 | iso-Propyl |
| | | n-Butyl |
| | | iso-Butyl |
| | | sec-Butyl |
| | | tert-Butyl |
| | | n-Pentyl |
| | | iso-Pentyl |
| | | neo-Pentyl |
| | | sec-Pentyl |
| | | |
| | | n-Hexyl |
| | | iso-Hexyl |
| | | |
| | | sec-Hexyl |
| | | |
| | 6 | Methyl |
| | | Ethyl |
| | | n-Propyl |
| | | iso-Propyl |
| | | n-Butyl |
| | | iso-Butyl |
| | | sec-Butyl |
| | | tert-Butyl |
| | | n-Pentyl |
| | | iso-Pentyl |
| | | neo-Pentyl |
| | | sec-Pentyl |
| | | |
| | | n-Hexyl |
| | | iso-Hexyl |
| | | |
| | | sec-Hexyl |
| | | |
| (structure with NC-pyridine-O-benzoxaborole, R$^s$-O-C(O)-[CH$_2$]$_n$-O-) | 1 | Methyl |
| | | Ethyl |
| | | n-Propyl |
| | | iso-Propyl |
| | | n-Butyl |
| | | iso-Butyl |
| | | sec-Butyl |
| | | tert-Butyl |
| | | n-Pentyl |
| | | iso-Pentyl |
| | | neo-Pentyl |

FIGURE 6J

| Structure | n | R^s |
|---|---|---|
| [chemical structure: R^s-O-C(=O)-(CH2)n-O-pyridine(CN)-O-benzoxaborole-OH] | 1 | sec-Pentyl |
| | | n-Hexyl |
| | | iso-Hexyl |
| | | sec-Hexyl |
| | 2 | Methyl |
| | | Ethyl |
| | | n-Propyl |
| | | iso-Propyl |
| | | n-Butyl |
| | | iso-Butyl |
| | | sec-Butyl |
| | | tert-Butyl |
| | | n-Pentyl |
| | | iso-Pentyl |
| | | neo-Pentyl |
| | | sec-Pentyl |
| | | n-Hexyl |
| | | iso-Hexyl |
| | | sec-Hexyl |
| | 3 | Methyl |
| | | Ethyl |
| | | n-Propyl |
| | | iso-Propyl |
| | | n-Butyl |
| | | iso-Butyl |
| | | sec-Butyl |
| | | tert-Butyl |
| | | n-Pentyl |
| | | iso-Pentyl |
| | | neo-Pentyl |
| | | sec-Pentyl |
| | | n-Hexyl |
| | | iso-Hexyl |
| | | sec-Hexyl |

FIGURE 6K

| Structure | n | R$^s$ |
|---|---|---|
| [structure: R$^s$-O-C(=O)-(CH$_2$)$_n$-O-pyridine(CN)-O-benzoxaborole-OH] | 4 | Methyl |
| | | Ethyl |
| | | n-Propyl |
| | | iso-Propyl |
| | | n-Butyl |
| | | iso-Butyl |
| | | sec-Butyl |
| | | tert-Butyl |
| | | n-Pentyl |
| | | iso-Pentyl |
| | | neo-Pentyl |
| | | sec-Pentyl |
| | | |
| | | n-Hexyl |
| | | iso-Hexyl |
| | | |
| | | sec-Hexyl |
| | | |
| | 5 | Methyl |
| | | Ethyl |
| | | n-Propyl |
| | | iso-Propyl |
| | | n-Butyl |
| | | iso-Butyl |
| | | sec-Butyl |
| | | tert-Butyl |
| | | n-Pentyl |
| | | iso-Pentyl |
| | | neo-Pentyl |
| | | sec-Pentyl |
| | | |
| | | n-Hexyl |
| | | iso-Hexyl |
| | | |
| | | sec-Hexyl |
| | | |
| | 6 | Methyl |
| | | Ethyl |
| | | n-Propyl |
| | | iso-Propyl |
| | | n-Butyl |
| | | iso-Butyl |
| | | sec-Butyl |
| | | tert-Butyl |

| Structure | n | R$^s$ |
|---|---|---|
| (see figure) | 6 | n-Pentyl |
| | | iso-Pentyl |
| | | neo-Pentyl |
| | | sec-Pentyl |
| | | n-Hexyl |
| | | iso-Hexyl |
| | | sec-Hexyl |

FIGURE 7A

| Structure | n | R$^s$ | m | R$^t$ |
|---|---|---|---|---|
| 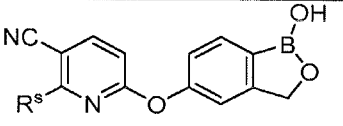 | | 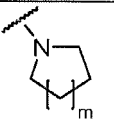 | 1 | |
| | | | 2 | |
| | | | 3 | |
| | | | 4 | |
| | | 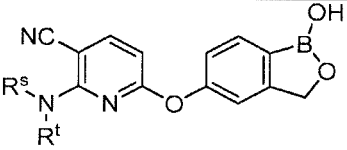 | | |
| 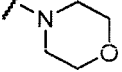 | | H | | H |
| | | | | C$_1$-alkyl |
| | | | | C$_2$-alkyl |
| | | | | C$_3$-alkyl |
| | | Methyl | | H |
| | | | | C$_1$-alkyl |
| | | | | C$_2$-alkyl |
| | | | | C$_3$-alkyl |
| | | Ethyl | | H |
| | | | | C$_1$-alkyl |
| | | | | C$_2$-alkyl |
| | | | | C$_3$-alkyl |
| | | n-Propyl | | H |
| | | | | C$_1$-alkyl |
| | | | | C$_2$-alkyl |
| | | | | C$_3$-alkyl |
| | | iso-Propyl | | H |
| | | | | C$_1$-alkyl |
| | | | | C$_2$-alkyl |
| | | | | C$_3$-alkyl |
| | | n-Butyl | | H |
| | | | | C$_1$-alkyl |
| | | | | C$_2$-alkyl |
| | | | | C$_3$-alkyl |
| | | iso-Butyl | | H |
| | | | | C$_1$-alkyl |
| | | | | C$_2$-alkyl |
| | | | | C$_3$-alkyl |
| | | sec-Butyl | | H |
| | | | | C$_1$-alkyl |
| | | | | C$_2$-alkyl |
| | | | | C$_3$-alkyl |
| | | tert-Butyl | | H |
| | | | | C$_1$-alkyl |
| | | | | C$_2$-alkyl |
| | | | | C$_3$-alkyl |
| | | n-Pentyl | | H |
| | | | | C$_1$-alkyl |
| | | | | C$_2$-alkyl |

FIGURE 7B

| Structure | n | R^s | m | R^t |
|---|---|---|---|---|
| ![structure with NC, R^s, R^t, N, pyridine-O-benzoxaborole-OH] | | n-Pentyl | | C_3-alkyl |
| | | iso-Pentyl | | H |
| | | | | C_1-alkyl |
| | | | | C_2-alkyl |
| | | | | C_3-alkyl |
| | | neo-Pentyl | | H |
| | | | | C_1-alkyl |
| | | | | C_2-alkyl |
| | | | | C_3-alkyl |
| | | sec-Pentyl | | H |
| | | | | C_1-alkyl |
| | | | | C_2-alkyl |
| | | | | C_3-alkyl |
| | | | | |
| | | | | |
| | | | | |
| | | | | |
| | | n-Hexyl | | H |
| | | | | C_1-alkyl |
| | | | | C_2-alkyl |
| | | | | C_3-alkyl |
| | | iso-Hexyl | | H |
| | | | | C_1-alkyl |
| | | | | C_2-alkyl |
| | | | | C_3-alkyl |
| | | | | |
| | | | | |
| | | | | |
| | | | | |
| | | sec-Hexyl | | H |
| | | | | C_1-alkyl |
| | | | | C_2-alkyl |
| | | | | C_3-alkyl |
| | | | | |
| | | | | |
| | | | | |
| | | -(CH_2)_m-phenyl | 1 | H |
| | | | 2 | |
| | | | 3 | |
| | | | 1 | C_1-alkyl |
| | | | 2 | |
| | | | 3 | |
| | | | 1 | C_2-alkyl |
| | | | 2 | |
| | | | 3 | |

FIGURE 7C

| Structure | n | R^s | m | R^t |
|---|---|---|---|---|
| ![structure1] | | $\dashv\!\!\left[\text{CH}_2\right]_m\!\!-\!\text{Ph}$ | 1 | C$_3$-alkyl |
| | | | 2 | |
| | | | 3 | |
| ![structure2] | 1 | H | | H |
| | | | | C$_1$-alkyl |
| | | | | C$_2$-alkyl |
| | | | | C$_3$-alkyl |
| | | Methyl | | H |
| | | | | C$_1$-alkyl |
| | | | | C$_2$-alkyl |
| | | | | C$_3$-alkyl |
| | | Ethyl | | H |
| | | | | C$_1$-alkyl |
| | | | | C$_2$-alkyl |
| | | | | C$_3$-alkyl |
| | | n-Propyl | | H |
| | | | | C$_1$-alkyl |
| | | | | C$_2$-alkyl |
| | | | | C$_3$-alkyl |
| | | iso-Propyl | | H |
| | | | | C$_1$-alkyl |
| | | | | C$_2$-alkyl |
| | | | | C$_3$-alkyl |
| | | n-Butyl | | H |
| | | | | C$_1$-alkyl |
| | | | | C$_2$-alkyl |
| | | | | C$_3$-alkyl |
| | | iso-Butyl | | H |
| | | | | C$_1$-alkyl |
| | | | | C$_2$-alkyl |
| | | | | C$_3$-alkyl |
| | | sec-Butyl | | H |
| | | | | C$_1$-alkyl |
| | | | | C$_2$-alkyl |
| | | | | C$_3$-alkyl |
| | | tert-Butyl | | H |
| | | | | C$_1$-alkyl |
| | | | | C$_2$-alkyl |
| | | | | C$_3$-alkyl |
| | | n-Pentyl | | H |
| | | | | C$_1$-alkyl |
| | | | | C$_2$-alkyl |
| | | | | C$_3$-alkyl |
| | | iso-Pentyl | | H |
| | | | | C$_1$-alkyl |

FIGURE 7D

| Structure | n | R$^s$ | m | R$^t$ |
|---|---|---|---|---|
| [structure: R$^s$-O-[CH$_2$]$_n$-N(R$^t$)- attached to pyridine with NC and O-benzoxaborole-OH] | 1 | iso-Pentyl | | C$_2$-alkyl |
| | | | | C$_3$-alkyl |
| | | neo-Pentyl | | H |
| | | | | C$_1$-alkyl |
| | | | | C$_2$-alkyl |
| | | | | C$_3$-alkyl |
| | | sec-Pentyl | | H |
| | | | | C$_1$-alkyl |
| | | | | C$_2$-alkyl |
| | | | | C$_3$-alkyl |
| | | | | |
| | | | | |
| | | | | |
| | | n-Hexyl | | H |
| | | | | C$_1$-alkyl |
| | | | | C$_2$-alkyl |
| | | | | C$_3$-alkyl |
| | | iso-Hexyl | | H |
| | | | | C$_1$-alkyl |
| | | | | C$_2$-alkyl |
| | | | | C$_3$-alkyl |
| | | | | |
| | | | | |
| | | | | |
| | | sec-Hexyl | | H |
| | | | | C$_1$-alkyl |
| | | | | C$_2$-alkyl |
| | | | | C$_3$-alkyl |
| | | | | |
| | | | | |
| | | | | |
| | | -[CH$_2$]$_m$-phenyl | 1 | H |
| | | | 2 | |
| | | | 3 | |
| | | | 1 | C$_1$-alkyl |
| | | | 2 | |
| | | | 3 | |
| | | | 1 | C$_2$-alkyl |
| | | | 2 | |
| | | | 3 | |
| | | | 1 | C$_3$-alkyl |
| | | | 2 | |
| | | | 3 | |

FIGURE 7E

| Structure | n | R$^s$ | m | R$^t$ |
|---|---|---|---|---|
| 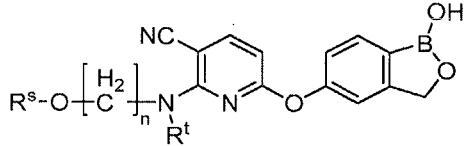 | 2 | H | | H |
| | | | | C$_1$-alkyl |
| | | | | C$_2$-alkyl |
| | | | | C$_3$-alkyl |
| | | Methyl | | H |
| | | | | C$_1$-alkyl |
| | | | | C$_2$-alkyl |
| | | | | C$_3$-alkyl |
| | | Ethyl | | H |
| | | | | C$_1$-alkyl |
| | | | | C$_2$-alkyl |
| | | | | C$_3$-alkyl |
| | | n-Propyl | | H |
| | | | | C$_1$-alkyl |
| | | | | C$_2$-alkyl |
| | | | | C$_3$-alkyl |
| | | iso-Propyl | | H |
| | | | | C$_1$-alkyl |
| | | | | C$_2$-alkyl |
| | | | | C$_3$-alkyl |
| | | n-Butyl | | H |
| | | | | C$_1$-alkyl |
| | | | | C$_2$-alkyl |
| | | | | C$_3$-alkyl |
| | | iso-Butyl | | H |
| | | | | C$_1$-alkyl |
| | | | | C$_2$-alkyl |
| | | | | C$_3$-alkyl |
| | | sec-Butyl | | H |
| | | | | C$_1$-alkyl |
| | | | | C$_2$-alkyl |
| | | | | C$_3$-alkyl |
| | | tert-Butyl | | H |
| | | | | C$_1$-alkyl |
| | | | | C$_2$-alkyl |
| | | | | C$_3$-alkyl |
| | | n-Pentyl | | H |
| | | | | C$_1$-alkyl |
| | | | | C$_2$-alkyl |
| | | | | C$_3$-alkyl |
| | | iso-Pentyl | | H |
| | | | | C$_1$-alkyl |
| | | | | C$_2$-alkyl |
| | | | | C$_3$-alkyl |
| | | neo-Pentyl | | H |
| | | | | C$_1$-alkyl |

FIGURE 7F

| Structure | n | R$^s$ | m | R$^t$ |
|---|---|---|---|---|
| [structure: R$^s$-O-[CH$_2$]$_n$-N(R$^t$)- linked to pyridine bearing NC and O-benzoxaborole-OH] | 2 | neo-Pentyl | | C$_2$-alkyl |
| | | | | C$_3$-alkyl |
| | | sec-Pentyl | | H |
| | | | | C$_1$-alkyl |
| | | | | C$_2$-alkyl |
| | | | | C$_3$-alkyl |
| | | | | |
| | | | | |
| | | | | |
| | | | | |
| | | n-Hexyl | | H |
| | | | | C$_1$-alkyl |
| | | | | C$_2$-alkyl |
| | | | | C$_3$-alkyl |
| | | iso-Hexyl | | H |
| | | | | C$_1$-alkyl |
| | | | | C$_2$-alkyl |
| | | | | C$_3$-alkyl |
| | | | | |
| | | | | |
| | | | | |
| | | sec-Hexyl | | H |
| | | | | C$_1$-alkyl |
| | | | | C$_2$-alkyl |
| | | | | C$_3$-alkyl |
| | | | | |
| | | | | |
| | | | | |
| | | -[CH$_2$]$_m$-Ph | 1 | H |
| | | | 2 | |
| | | | 3 | |
| | | | 1 | C$_1$-alkyl |
| | | | 2 | |
| | | | 3 | |
| | | | 1 | C$_2$-alkyl |
| | | | 2 | |
| | | | 3 | |
| | | | 1 | C$_3$-alkyl |
| | | | 2 | |
| | | | 3 | |
| | 3 | H | | H |
| | | | | C$_1$-alkyl |
| | | | | C$_2$-alkyl |
| | | | | C$_3$-alkyl |

FIGURE 7G

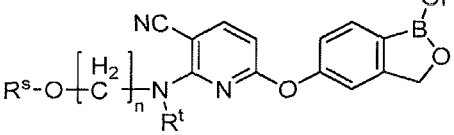

| Structure | n | R$^s$ | m | R$^t$ |
|---|---|---|---|---|
| 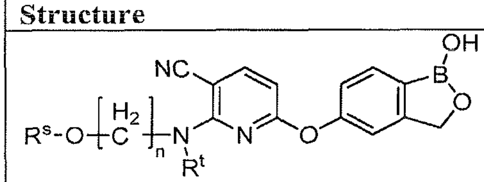 | 3 | Methyl | | H |
| | | | | C$_1$-alkyl |
| | | | | C$_2$-alkyl |
| | | | | C$_3$-alkyl |
| | | Ethyl | | H |
| | | | | C$_1$-alkyl |
| | | | | C$_2$-alkyl |
| | | | | C$_3$-alkyl |
| | | n-Propyl | | H |
| | | | | C$_1$-alkyl |
| | | | | C$_2$-alkyl |
| | | | | C$_3$-alkyl |
| | | iso-Propyl | | H |
| | | | | C$_1$-alkyl |
| | | | | C$_2$-alkyl |
| | | | | C$_3$-alkyl |
| | | n-Butyl | | H |
| | | | | C$_1$-alkyl |
| | | | | C$_2$-alkyl |
| | | | | C$_3$-alkyl |
| | | iso-Butyl | | H |
| | | | | C$_1$-alkyl |
| | | | | C$_2$-alkyl |
| | | | | C$_3$-alkyl |
| | | sec-Butyl | | H |
| | | | | C$_1$-alkyl |
| | | | | C$_2$-alkyl |
| | | | | C$_3$-alkyl |
| | | tert-Butyl | | H |
| | | | | C$_1$-alkyl |
| | | | | C$_2$-alkyl |
| | | | | C$_3$-alkyl |
| | | n-Pentyl | | H |
| | | | | C$_1$-alkyl |
| | | | | C$_2$-alkyl |
| | | | | C$_3$-alkyl |
| | | iso-Pentyl | | H |
| | | | | C$_1$-alkyl |
| | | | | C$_2$-alkyl |
| | | | | C$_3$-alkyl |
| | | neo-Pentyl | | H |
| | | | | C$_1$-alkyl |
| | | | | C$_2$-alkyl |
| | | | | C$_3$-alkyl |
| | | sec-Pentyl | | H |
| | | | | C$_1$-alkyl |

FIGURE 7H

| Structure | n | R$^s$ | m | R$^t$ |
|---|---|---|---|---|
| ![structure: R$^s$-O-[CH$_2$]$_n$-N(R$^t$)-pyridine(CN)-O-benzoxaborole-OH] | 3 | sec-Pentyl | | C$_2$-alkyl |
| | | | | C$_3$-alkyl |
| | | n-Hexyl | | H |
| | | | | C$_1$-alkyl |
| | | | | C$_2$-alkyl |
| | | | | C$_3$-alkyl |
| | | iso-Hexyl | | H |
| | | | | C$_1$-alkyl |
| | | | | C$_2$-alkyl |
| | | | | C$_3$-alkyl |
| | | sec-Hexyl | | H |
| | | | | C$_1$-alkyl |
| | | | | C$_2$-alkyl |
| | | | | C$_3$-alkyl |
| | | -[CH$_2$]$_m$-phenyl | 1 | H |
| | | | 2 | |
| | | | 3 | |
| | | | 1 | C$_1$-alkyl |
| | | | 2 | |
| | | | 3 | |
| | | | 1 | C$_2$-alkyl |
| | | | 2 | |
| | | | 3 | |
| | | | 1 | C$_3$-alkyl |
| | | | 2 | |
| | | | 3 | |
| | 4 | H | | H |
| | | | | C$_1$-alkyl |
| | | | | C$_2$-alkyl |
| | | | | C$_3$-alkyl |
| | | Methyl | | H |
| | | | | C$_1$-alkyl |
| | | | | C$_2$-alkyl |
| | | | | C$_3$-alkyl |

FIGURE 7I

| Structure | n | R$^s$ | m | R$^t$ |
|---|---|---|---|---|
| R$^s$-O-[CH$_2$]$_n$-N(R$^t$)-pyridine(CN)-O-benzoxaborole-OH | 4 | Ethyl | | H |
| | | | | C$_1$-alkyl |
| | | | | C$_2$-alkyl |
| | | | | C$_3$-alkyl |
| | | n-Propyl | | H |
| | | | | C$_1$-alkyl |
| | | | | C$_2$-alkyl |
| | | | | C$_3$-alkyl |
| | | iso-Propyl | | H |
| | | | | C$_1$-alkyl |
| | | | | C$_2$-alkyl |
| | | | | C$_3$-alkyl |
| | | n-Butyl | | H |
| | | | | C$_1$-alkyl |
| | | | | C$_2$-alkyl |
| | | | | C$_3$-alkyl |
| | | iso-Butyl | | H |
| | | | | C$_1$-alkyl |
| | | | | C$_2$-alkyl |
| | | | | C$_3$-alkyl |
| | | sec-Butyl | | H |
| | | | | C$_1$-alkyl |
| | | | | C$_2$-alkyl |
| | | | | C$_3$-alkyl |
| | | tert-Butyl | | H |
| | | | | C$_1$-alkyl |
| | | | | C$_2$-alkyl |
| | | | | C$_3$-alkyl |
| | | n-Pentyl | | H |
| | | | | C$_1$-alkyl |
| | | | | C$_2$-alkyl |
| | | | | C$_3$-alkyl |
| | | iso-Pentyl | | H |
| | | | | C$_1$-alkyl |
| | | | | C$_2$-alkyl |
| | | | | C$_3$-alkyl |
| | | neo-Pentyl | | H |
| | | | | C$_1$-alkyl |
| | | | | C$_2$-alkyl |
| | | | | C$_3$-alkyl |
| | | sec-Pentyl | | H |
| | | | | C$_1$-alkyl |
| | | | | C$_2$-alkyl |
| | | | | C$_3$-alkyl |

FIGURE 7J
| Structure | n | R^s | m | R^t |
|---|---|---|---|---|
| 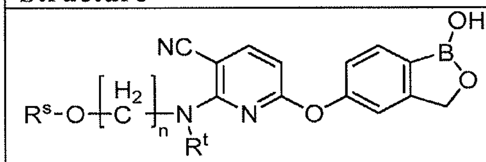 | 4 | | | |
| | | | | |
| | | n-Hexyl | | H |
| | | | | $C_1$-alkyl |
| | | | | $C_2$-alkyl |
| | | | | $C_3$-alkyl |
| | | iso-Hexyl | | H |
| | | | | $C_1$-alkyl |
| | | | | $C_2$-alkyl |
| | | | | $C_3$-alkyl |
| | | | | |
| | | | | |
| | | | | |
| | | | | |
| | | sec-Hexyl | | H |
| | | | | $C_1$-alkyl |
| | | | | $C_2$-alkyl |
| | | | | $C_3$-alkyl |
| | | | | |
| | | | | |
| | | | | |
| | | 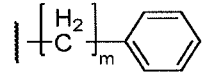 | 1 | H |
| | | | 2 | |
| | | | 3 | |
| | | | 1 | $C_1$-alkyl |
| | | | 2 | |
| | | | 3 | |
| | | | 1 | $C_2$-alkyl |
| | | | 2 | |
| | | | 3 | |
| | | | 1 | $C_3$-alkyl |
| | | | 2 | |
| | | | 3 | |
| | 5 | H | | H |
| | | | | $C_1$-alkyl |
| | | | | $C_2$-alkyl |
| | | | | $C_3$-alkyl |
| | | Methyl | | H |
| | | | | $C_1$-alkyl |
| | | | | $C_2$-alkyl |
| | | | | $C_3$-alkyl |
| | | Ethyl | | H |
| | | | | $C_1$-alkyl |
| | | | | $C_2$-alkyl |
| | | | | $C_3$-alkyl |

FIGURE 7K

| Structure | n | R$^s$ | m | R$^t$ |
|---|---|---|---|---|
| R$^s$-O-[CH$_2$]$_n$-N(R$^t$)-pyridine(CN)-O-benzoxaborole-OH | 5 | n-Propyl | | H |
| | | | | C$_1$-alkyl |
| | | | | C$_2$-alkyl |
| | | | | C$_3$-alkyl |
| | | iso-Propyl | | H |
| | | | | C$_1$-alkyl |
| | | | | C$_2$-alkyl |
| | | | | C$_3$-alkyl |
| | | n-Butyl | | H |
| | | | | C$_1$-alkyl |
| | | | | C$_2$-alkyl |
| | | | | C$_3$-alkyl |
| | | iso-Butyl | | H |
| | | | | C$_1$-alkyl |
| | | | | C$_2$-alkyl |
| | | | | C$_3$-alkyl |
| | | sec-Butyl | | H |
| | | | | C$_1$-alkyl |
| | | | | C$_2$-alkyl |
| | | | | C$_3$-alkyl |
| | | tert-Butyl | | H |
| | | | | C$_1$-alkyl |
| | | | | C$_2$-alkyl |
| | | | | C$_3$-alkyl |
| | | n-Pentyl | | H |
| | | | | C$_1$-alkyl |
| | | | | C$_2$-alkyl |
| | | | | C$_3$-alkyl |
| | | iso-Pentyl | | H |
| | | | | C$_1$-alkyl |
| | | | | C$_2$-alkyl |
| | | | | C$_3$-alkyl |
| | | neo-Pentyl | | H |
| | | | | C$_1$-alkyl |
| | | | | C$_2$-alkyl |
| | | | | C$_3$-alkyl |
| | | sec-Pentyl | | H |
| | | | | C$_1$-alkyl |
| | | | | C$_2$-alkyl |
| | | | | C$_3$-alkyl |
| | | | | |
| | | | | |
| | | | | |
| | | | | |
| | | n-Hexyl | | H |
| | | | | C$_1$-alkyl |

FIGURE 7L
| Structure | n | R$^s$ | m | R$^t$ |
|---|---|---|---|---|
| 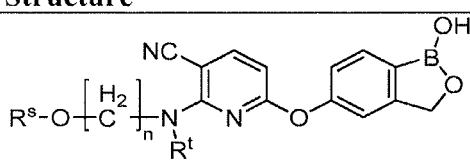 | 5 | n-Hexyl | | C$_2$-alkyl |
| | | | | C$_3$-alkyl |
| | | iso-Hexyl | | H |
| | | | | C$_1$-alkyl |
| | | | | C$_2$-alkyl |
| | | | | C$_3$-alkyl |
| | | | | |
| | | | | |
| | | | | |
| | | sec-Hexyl | | H |
| | | | | C$_1$-alkyl |
| | | | | C$_2$-alkyl |
| | | | | C$_3$-alkyl |
| | | | | |
| | | | | |
| | | | | |
| | | 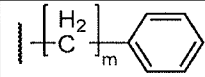 | 1 | H |
| | | | 2 | |
| | | | 3 | |
| | | | 1 | C$_1$-alkyl |
| | | | 2 | |
| | | | 3 | |
| | | | 1 | C$_2$-alkyl |
| | | | 2 | |
| | | | 3 | |
| | | | 1 | C$_3$-alkyl |
| | | | 2 | |
| | | | 3 | |
| | 6 | H | | H |
| | | | | C$_1$-alkyl |
| | | | | C$_2$-alkyl |
| | | | | C$_3$-alkyl |
| | | Methyl | | H |
| | | | | C$_1$-alkyl |
| | | | | C$_2$-alkyl |
| | | | | C$_3$-alkyl |
| | | Ethyl | | H |
| | | | | C$_1$-alkyl |
| | | | | C$_2$-alkyl |
| | | | | C$_3$-alkyl |
| | | n-Propyl | | H |
| | | | | C$_1$-alkyl |
| | | | | C$_2$-alkyl |
| | | | | C$_3$-alkyl |

FIGURE 7M

| Structure | n | R$^s$ | m | R$^t$ |
|---|---|---|---|---|
| (structure shown) | 6 | iso-Propyl | | H |
| | | | | C$_1$-alkyl |
| | | | | C$_2$-alkyl |
| | | | | C$_3$-alkyl |
| | | n-Butyl | | H |
| | | | | C$_1$-alkyl |
| | | | | C$_2$-alkyl |
| | | | | C$_3$-alkyl |
| | | iso-Butyl | | H |
| | | | | C$_1$-alkyl |
| | | | | C$_2$-alkyl |
| | | | | C$_3$-alkyl |
| | | sec-Butyl | | H |
| | | | | C$_1$-alkyl |
| | | | | C$_2$-alkyl |
| | | | | C$_3$-alkyl |
| | | tert-Butyl | | H |
| | | | | C$_1$-alkyl |
| | | | | C$_2$-alkyl |
| | | | | C$_3$-alkyl |
| | | n-Pentyl | | H |
| | | | | C$_1$-alkyl |
| | | | | C$_2$-alkyl |
| | | | | C$_3$-alkyl |
| | | iso-Pentyl | | H |
| | | | | C$_1$-alkyl |
| | | | | C$_2$-alkyl |
| | | | | C$_3$-alkyl |
| | | neo-Pentyl | | H |
| | | | | C$_1$-alkyl |
| | | | | C$_2$-alkyl |
| | | | | C$_3$-alkyl |
| | | sec-Pentyl | | H |
| | | | | C$_1$-alkyl |
| | | | | C$_2$-alkyl |
| | | | | C$_3$-alkyl |
| | | | | |
| | | | | |
| | | | | |
| | | | | |
| | | n-Hexyl | | H |
| | | | | C$_1$-alkyl |
| | | | | C$_2$-alkyl |
| | | | | C$_3$-alkyl |
| | | iso-Hexyl | | H |
| | | | | C$_1$-alkyl |

FIGURE 7N

| Structure | n | R$^s$ | m | R$^t$ |
|---|---|---|---|---|
| [structure: R$^s$-O-(CH$_2$)$_n$-N(R$^t$)-pyridine(CN)-O-benzoxaborole-OH] | 6 | iso-Hexyl | | C$_2$-alkyl |
| | | | | C$_3$-alkyl |
| | | | | |
| | | | | |
| | | | | |
| | | | | |
| | | sec-Hexyl | | H |
| | | | | C$_1$-alkyl |
| | | | | C$_2$-alkyl |
| | | | | C$_3$-alkyl |
| | | | | |
| | | | | |
| | | | | |
| | | -(CH$_2$)$_m$-phenyl | 1 | H |
| | | | 2 | |
| | | | 3 | |
| | | | 1 | C$_1$-alkyl |
| | | | 2 | |
| | | | 3 | |
| | | | 1 | C$_2$-alkyl |
| | | | 2 | |
| | | | 3 | |
| | | | 1 | C$_3$-alkyl |
| | | | 2 | |
| | | | 3 | |

BORON-CONTAINING SMALL MOLECULES AS ANTI-INFLAMMATORY AGENTS

CROSS-REFERENCE TO RELATED APPLICATIONS

This application is a continuation of U.S. patent application Ser. No. 13/915,494, filed Jun. 11, 2013, now U.S. Pat. No. 9,012,431, which is a continuation of U.S. patent application Ser. No. 13/236,543, filed Sep. 19, 2011, now U.S. Pat. No. 8,461,135, which is a continuation of U.S. patent application Ser. No. 12/399,015, filed Mar. 5, 2009, now U.S. Pat. No. 8,039,450, which claims the benefit of U.S. Provisional Patent Application No. 61/034,371, filed Mar. 6, 2008, U.S. Provisional Patent Application No. 61/052,637, filed May 12, 2008, U.S. Provisional Patent Application No. 61/094,406, filed Sep. 4, 2008, U.S. Provisional Patent Application No. 61/105,990, filed Oct. 16, 2008, U.S. Provisional Patent Application No. 61/110,903, filed Nov. 3, 2008, U.S. Provisional Patent Application No. 61/143,700, filed Jan. 9, 2009, and U.S. Provisional Patent Application No. 61/148,731, filed Jan. 30, 2009, each of which is incorporated by reference in its entirety for all purposes.

BACKGROUND FOR THE INVENTION

Irregular inflammation is a major component of a wide range of human diseases. People suffering from degenerative disorders often exhibit excess levels of pro-inflammatory regulators in their blood. One type of such pro-inflammatory regulators are cytokines including IL-1α, β, IL-2, IL-3, IL-6, IL-7, IL-9, IL-12, IL-17, IL-18, IL-23, TNF-α, LT, LIF, Oncostatin, and IFNc1α, β, γ.

A non-limiting list of common medical problems that are directly caused by inflammatory cytokines include: arthritis where inflammatory cytokines can lead to lesions in the synovial membrane and destruction of joint cartilage and bone; kidney failure where inflammatory cytokines restrict circulation and damage nephrons; lupus where inflammatory cytokines exacerbate immune complex deposition and damage; asthma where inflammatory cytokines close the airway; psoriasis where inflammatory cytokines induce dermatitis; pancreatitis where inflammatory cytokines induce pancreatic cell injury; allergy where inflammatory cytokines induce vasopermeability and congestion; fibrosis where inflammatory cytokines attack traumatized tissue; surgical complications where inflammatory cytokines prevent healing; anemia where inflammatory cytokines attack erythropoietin production; and fibromyalgia where inflammatory cytokines are elevated in fibromyalgia patients.

Other diseases associated with chronic inflammation include cancer; heart attack where chronic inflammation contributes to coronary atherosclerosis; Alzheimer's disease where chronic inflammation destroys brain cells; congestive heart failure where chronic inflammation causes heart muscle wasting; stroke where chronic inflammation promotes thrombo-embolic events; and aortic valve stenosis where chronic inflammation damages heart valves. Arteriosclerosis, osteoporosis, Parkinson's disease, infection, inflammatory bowel disease including Crohn's disease and ulcerative colitis as well as multiple sclerosis (a typical autoimmune inflammatory-related disease) are also related to inflammation (Bebo, B. F., Jr., *J Neurosci Res,* 45: 340-348, (1996); Mennicken, F., *Trends Pharmacol Sci,* 20: 73-78, (1999); Watanabe, T, *Int J Cardiol,* 66 Suppl 1: S45-53; discussion S55, (1998); Sullivan, G. W., *J Leukoc Biol,* 67: 591-602, (2000); Franceschi, C, Ann NY Acad Sci, 908: 244-254, (2000); Rogers, J, Ann NY Acad Sci, 924: 132-135, (2000); Li, Y. J., Hum Mol Genet, 12: 3259-3267, (2003); Maccarrone, M., *Curr Drug Targets Inflamm Allergy,* 1: 53-63, (2002); Lindsberg, P. J., *Stroke,* 34: 2518-2532, (2003); DeGraba, T. J., *Adv Neurol,* 92: 29-42, (2003); Ito, H., *Curr Drug Targets Inflamm Allergy,* 2: 125-130, (2003); von der Thusen, J. H., *Pharmacol Rev,* 55: 133-166, (2003); Schmidt, M. I., *Clin Chem Lab Med,* 41: 1120-1130, (2003); Virdis, A., *Curr Opin Nephrol Hypertens,* 12: 181-187, (2003); Tracy, R. P., *Int J Clin Pract, Suppl* 10-17, (2003); Haugeberg, G., *Curr Opin Rheumatol,* 15: 469-475, (2003); Tanaka, Y., *J Bone Miner Metab,* 21: 61-66, (2003); Williams, J. D., *Clin Exp Dermatol,* 27: 585-590, (2002)). Some diseases in advanced stages can be life threatening. Several methodologies are available for the treatment of such inflammatory diseases; the results, however, are generally unsatisfactory as evidenced by a lack of efficacy and drug related side effects associated therewith.

Inflammatory Bowel Disease

Inflammatory bowel disease (IBD) comprises Crohn's disease (CD) and ulcerative colitis (UC), both of which are idiopathic chronic diseases occurring with an increasing frequency in many parts of the world. In the United States, more than 600,000 are affected every year. IBD can involve either small bowel, large bowel, or both. CD can involve any part of the gastrointestinal tract, but most frequently involves the distal small bowel and colon. It either spares the rectum, or causes inflammation or infection with drainage around the rectum. UC usually causes ulcers in the lower part of the large intestine, often starting at the rectum. Patients with IBD have defective intestinal epithelial barrier function, which allows bacterial colonization of the epithelia. As a result, bacterial products and pro-inflammatory cytokines (TNF-α, IL-1 and IL-6) cause persistent inflammatory stimulation. Bacterial antigens are introduced into the immune system by mucosal dendritic cells and macrophases. In response, intestinal phagocytes (mainly monocytes and neutrophils) proliferate and increase expression and secretion of pro-inflammatory cytokines Symptoms vary but may include diarrhea, fever, and pain. Patients with prolonged UC are at an increased risk of developing colon cancer. There is currently no satisfactory treatment, as the cause for IBD remains unclear although infectious and immunologic mechanisms have been proposed. IBD treatments aim at controlling inflammatory symptoms, conventionally using corticosteroids, aminosalicylates and standard immunosuppressive agents such as azathioprine (6-mercaptopurine), methotrexate and ciclosporine. Of these, the only disease-modifying therapies are the immunosuppressive agents azathioprine and methotrexate, both of which have a slow onset of action and only a moderate efficacy. Long-term therapy may cause liver damage (fibrosis or cirrhosis) and bone marrow suppression. Also patients often become refractory to such treatment. Other therapeutic regimes merely address symptoms (Rutgeerts, P. A, *J Gastroenterol Hepatol,* 17 Suppl: S176-185 (2002); Rutgeerts, P., *Aliment Pharmacol Ther,* 17: 185-192 (2003)).

Psoriasis

Psoriasis is one of the most common immune-mediated chronic skin diseases that comes in different forms and varied levels of severity, affecting approximately 2% of the population or more than 4.5 million people in the United States of which 1.5 million are considered to have a moderate to severe form of the disease. Ten to thirty percent of patients with psoriasis also develop a form of arthritis—psoriatic arthritis, which damages the bone and connective tissue around the joints. Psoriasis appears as patches of raised red skin covered by a flaky white buildup. It may also have a pimple-ish (pustular psoriasis) or burned (erythrodermic) appearance. Psoriasis may also cause intense itching and burning. Patients suffer psychologically as well as physically. Several modalities are currently available for treatment of psoriasis, including topical treatment, phototherapy, and systemic applications. However, they are generally considered to be only disease suppressive and disease modifying; none of them are curative. Moreover, many treatments are either cosmetically undesirable, inconvenient for long-term use, or associated with significant toxicity.

There are several types of psoriasis. Plaque psoriasis (psoriasis vulgaris) is the most common form of psoriasis. It affects 80 to 90% of people with psoriasis. Plaque psoriasis typically appears as raised areas of inflamed skin covered with silvery white scaly skin. These areas are called plaques. Flexural psoriasis (inverse psoriasis) appears as smooth inflamed patches of skin. It occurs in skin folds, particularly around the genitals (between the thigh and groin), the armpits, under an overweight stomach (pannus), and under the breasts (intramammary fold). It is aggravated by friction and sweat, and is vulnerable to fungal infections. Guttate psoriasis is characterized by numerous small oval (teardrop-shaped) spots. These numerous spots of psoriasis appear over large areas of the body, such as the trunk, limbs, and scalp. Guttate psoriasis is associated with streptococcal throat infection. Pustular psoriasis appears as raised bumps that are filled with non-infectious pus (pustules). The skin under and surrounding pustules is red and tender. Pustular psoriasis can be localised, commonly to the hands and feet (palmoplantar pustulosis), or generalised with widespread patches occurring randomly on any part of the body. Nail psoriasis produces a variety of changes in the appearance of finger and toe nails. These changes include discoloring under the nail plate, pitting of the nails, lines going across the nails, thickening of the skin under the nail, and the loosening (onycholysis) and crumbling of the nail. Psoriatic arthritis involves joint and connective tissue inflammation. Psoriatic arthritis can affect any joint but is most common in the joints of the fingers and toes. This can result in a sausage-shaped swelling of the fingers and toes known as dactylitis. Psoriatic arthritis can also affect the hips, knees and spine (spondylitis). About 10-15% of people who have psoriasis also have psoriatic arthritis. Erythrodermic psoriasis involves the widespread inflammation and exfoliation of the skin over most of the body surface. It may be accompanied by severe itching, swelling and pain. It is often the result of an exacerbation of unstable plaque psoriasis, particularly following the abrupt withdrawal of systemic treatment. This form of psoriasis can be fatal, as the extreme inflammation and exfoliation disrupt the body's ability to regulate temperature and for the skin to perform barrier functions.

With increased understanding of the biological properties of psoriasis over the past two decades, biologic therapies targeting the activity of T lymphocytes and cytokines responsible for the inflammatory nature of this disease have become available. Currently, drugs prescribed for psoriasis include TNF-α inhibitors initially used for rheumatoid arthritis (RA) treatment, ENBREL® (etanercept), REMICADE® (infliximab) and HUMIRA® (adalimumab), and T-cell inhibitor AMEVIVE® (alefacept) from Biogen approved in 2002 and RAPTIVA® (efalizumab) from Genentech/Xoma approved in 2003 (Weinberg, J. M., *J Drugs Dermatol*, 1: 303-310, (2002)). AMEVIVE® (alefacept) is an immunoglobulin fusion protein composed of the first extracellular domain of human LFA-3 fused to the hinge, C(H)2 and C(H)3 domains of human IgG(1). It inhibits T cell proliferation through NK cells (Cooper, J. C., *Eur J Immunol*, 33: 666-675, (2003)).

RAPTIVA® is also known as anti-CD 11a, a humanized monoclonal antibody which targets the T cell adhesion molecule, leukocyte function-associated antigen-1 (LFA-1). Prevention of LFA-1 binding to its ligand (ICAM-1, intercellular adhesion molecule-1) inhibits lymphocyte activation and migration, resulting in a decreased lymphocyte infiltration, thereby limiting the cascade of events eventually leading to the signs and symptoms of psoriasis (Cather, J. C., *Expert Opin Biol Ther*, 3: 361-370, (2003)). Potential side effects for current TNF-α inhibitors of the prior art, however, are severe, including development of lymphoma (Brown, S. L., *Arthritis Rheum*, 46: 3151-3158, (2002)), worsening congestive heart failure, resulting in a serious infection and sepsis, and exacerbations of multiple sclerosis and central nervous system problems (Weisman, M. H., *J Rheumatol Suppl*, 65: 33-38, (2002); Antoni, C., *Clin Exp Rheumatol*, 20: S152-157, (2002)). While side effects of the T-cell inhibitor of AMEVIVE®/RAPTIVA® may be more tolerable in psoriasis treatment, RAPTIVA® is an immunosuppressive agent. Immunosuppressive agents have the potential to increase the risk of infection, reactivate latent, chronic infections or increase the risk of cancer development.

Although many advances have been made in the understanding of the biological properties of psoriasis over the past two decades and an unconventional treatment for psoriasis has become available as described above, much of the suffering it produces is still not adequately addressed. A survey of over 40,000 American patients with psoriasis performed by the National Psoriasis Foundation in 1998 showed 79% of the younger patients felt frustrated by the ineffectiveness of their treatment. Of those with severe disease, 32% felt their treatment was not aggressive enough (Mendonca, C. O., *Pharmacol Ther*, 99: 133-147, (2003); Schon, M. P., *J Invest Dermatol*, 112: 405-410, (1999)).

Rheumatoid Arthritis

Rheumatoid arthritis (RA) represents another example of troublesome inflammatory disorders. It is a common chronic inflammatory-related disease characterized by chronic inflammation in the membrane lining (the synovium) of the joints and/or other internal organs. The inflammatory cells can also invade and damage bone and cartilage. The joint involved can lose its shape and alignment, resulting in loss of movement. Patients with RA have pain, stiffness, warmth, redness and swelling in the joint, and other systemic symptoms like fever, fatigue, and anemia. Approximately 1% of the population or 2.1 million in the U.S. are currently affected, of which more are women (1.5 million) than men (0.6 million). The pathology of RA is not fully understood although the cascade of improper immunological reactions has been postulated as a mechanism. Conventional treatment is unfortunately inefficient in RA (Bessis, N., *J Gene Med*, 4: 581-591, (2002)) (29). The disease does not respond completely to symptomatic medications including corticosteroids and non-steroidal anti-inflammatory drugs (NSAIDs) used since the 1950s. Also, these medications carry a risk of serious adverse effects. The therapeutic effects of the disease-modifying anti-rheumatic drugs (DMARDs) such as Methotrexate (MTX) are often inconsistent and short-lived.

The role of the cytokine network in mediating inflammation and joint destruction in RA has been extensively investigated in recent years. In addition to TNF-α, IL-1 plays a pivotal role in the pathogenesis and the clinical manifestations of RA (54). The ability of IL-1 to drive inflammation and joint erosion and to inhibit tissue repair processes has been clearly established in in vitro systems and in animal models, and alleviation of inflammatory symptoms in RA patients has been achieved by blockage of IL-1 (Bresnihan, B., *Arthritis*

*Rheum*, 41: 2196-2204, (1998)). IL-6 is a multifunctional cytokine that regulates the immune response, hematopoiesis, the acute phase response, and inflammation. Deregulation of IL-6 production is implicated in the pathology of several diseases including RA. A therapeutic approach to block the IL-6 signal has been carried out by using humanized anti-IL-6R antibody for RA among other diseases (Ito, H., *Curr Drug Targets Inflamm Allergy*, 2: 125-130, (2003); Ishihara, *K Cytokine Growth Factor Rev*, 13: 357-368, (2002)). IL-10 is an anti-inflammatory cytokine Expressing IL-10 has been shown to prevent arthritis or ameliorate the disease in animal models (57, 58). While it is obvious that cytokines such as TNF-α, IL-1, IL-6 and IL-10 have independent roles, they act in concert in mediating certain pathophysiological processes in RA. The finding of a class of molecules described in this invention, which are able to modulate these different cytokines, will result in dramatic therapeutic progress in the treatment of RA.

A new class of biologic DMARDs (disease-modifying antirheumatic drugs) for the treatment of RA has recently been developed based on an understanding of the role of cytokines, TNF-α and IL-1, in the inflammatory process. The FDA has approved several such DMARDs including ENBREL® (etanercept) from Immunex/Amgen Inc. in 1998, REMICADE® (infliximab) from Centocor/Johnson & Johnson, HUMIRA® (adalimumab) from Abbott Laboratories Inc. in 2002, and KINERET® (anakinra) from Amgen in 2001. ENBREL® is a soluble TNF receptor (TNFR) recombinant protein. REMICADE® is a humanized mouse (chimeric) anti-TNF-α monoclonal antibody. HUMIRA® is a fully human anti-TNF monoclonal antibody created using phage display technology resulting in an antibody with human-derived heavy and light chain variable regions and human IgG1:k constant regions. All these 3 protein-based drugs target and bind to TNF-α to block the effects of TNF-α. KINERET® is a recombinant IL-1 receptor antagonist, which is similar to native human IL-1Ra, except for the addition of a single methionine residue at its amino terminus. KINERET® blocks the biologic activity of IL-1 by competitively inhibiting IL-1 binding to the IL-1 type I receptor (IL-1RI) and consequently reducing the pro-inflammatory effects of IL-1.

Multiple Sclerosis

Multiple Sclerosis (MS) is an autoimmune disease diagnosed in 350,000 to 500,000 people in the United States. Multiple areas of inflammation and loss of myelin in the brain and spinal cord signify the disease. Patients with MS exhibit varied degrees of neurological impairment depending on the location and extent of the loss of the myelin. There is evidence that the expression of chemokines (IL-8 family members) during CNS autoimmune inflammation is regulated by some pro-inflammatory cytokines, such as TNF (Glabinski, A. R., *Scand J Immunol*, 58: 81-88, (2003)). The roles of other pro-/anti-inflammatory cytokines such as IL-1.beta., IL-6 and IL-10 were also confirmed in EAE animal models (Diab, A., *J Neuropathol Exp Neurol*, 56: 641-650, (1997); Samoilova, E. B., *J Immunol*, 161: 6480-6486, (1998); Robertson, J., *J Cell Biol*, 155: 217-226, (2001)) as well as in humans (de Jong, B. A., *J Neuroimmunol*, 126: 172-179, (2002)). IL-10 is present in MS lesions. IL-1 receptor antagonist (IL-1Ra) moderates the induction of experimental autoimmune encephalomyelitis (EAE). Increased risk of MS has been seen in individuals with High IL-1 (3 over IL-1Ra production ratio and high TNF over IL-10 production ratio (de Jong, B. A., *J Neuroimmunol*, 126: 172-179, (2002)). Common symptoms of MS include fatigue, weakness, spasticity, balance problems, bladder and bowel problems, numbness, vision loss, tremors and depression. Current treatment of MS only alleviates symptoms or delays the progression of disability, and several new treatments for MS including stem cell transplantation and gene therapy are conservatory (Fassas, A., *Blood Rev*, 17: 233-240, (2003); Furlan, R., *Curr Pharm Des*, 9: 2002-2008, (2003)). While anti-TNF antibodies have shown protective effects in experimental autoimmune encephalomyelitis (EAE), they aggravate the disease in MS patients, suggesting that inhibition of TNF-α alone is not sufficient (Ghezzi, P., *Neuroimmunomodulation*, 9: 178-182, (2001)).

Neurodegenerative Disorders

Alzheimer's disease (AD) and Parkinson's disease (PK) are the two most common neurodegenerative disorders. AD seriously affects a person's ability to carry out daily activities. It involves the parts of the brain that control thought, memory, and language. About 4 million Americans, usually after age 60, are estimated to suffer from AD.

PK is a progressive disorder of the central nervous system affecting over 1.5 million people in the United States. Clinically, the disease is characterized by a decrease in spontaneous movements, gait difficulty, postural instability, rigidity and tremor. PK is caused by the degeneration of the pigmented neurons in the substantia nigra of the brain, resulting in decreased dopamine availability. The causes of these neurodegenerative disorders are unknown and there is currently no cure for the disease.

Thus, novel approaches for the treatment of the above and other inflammatory-related diseases are needed. Although inflammatory-related disease mechanisms remain unclear and often vary from each other, dysfunction of the immune system caused by deregulation of cytokines has been demonstrated to play an important role in the initiation and progression of inflammation (Schon, M. P., *J Invest Dermatol*, 112: 405-410, (1999); Andreakos, E. T., *Cytokine Growth Factor Rev*, 13: 299-313, (2002); Najarian, D. J., *J Am Acad Dermatol*, 48: 805-821, (2003)).

Post-Radiotherapy Related Inflammation:

Radiation damage related inflammatory diseases to the rectum and sigmoid colon are most common complications with radiation therapy for cancers in the pelvic region, which include cancers of the cervix, uterus, prostate, bladder, and testes. Radiation proctosigmoiditis is the most common clinically apparent form of colonic damage after pelvic irradiation with an incidence of 5% to 20%. Patients typically exhibit symptoms of tenesmus, bleeding, low-volume diarrhea, and rectal pain. Rarely, low-grade obstruction or fistulous tracts into adjacent organs may develop.

Cytokines can be generally classified into 3 types: pro-inflammatory (IL-1α, β, IL-2, IL-3, IL-6, IL-7, IL-9, IL-12, IL-17, IL-18, IL-23, TNF-α, LT, LIF, Oncostatin, and IFNc1α, β, γ); anti-inflammatory (IL-4, IL-1β, IL-11, W-13 and TGF-β); and chemokines (IL-8, Gro-α, MIP-1, MCP-1, ENA-78, and RANTES).

Tumor necrosis factor-α (TNF-α) and interleukin-1 (IL-1) are proinflammatory cytokines that mediate inflammatory responses associated with infectious agents and other cellular stresses. Overproduction of cytokines such as IL-1 and TNF-α is believed to underlie the progression of many inflammatory diseases including rheumatoid arthritis (RA), Crohn's disease, inflammatory bowel disease, multiple sclerosis, endotoxin shock, osteoporosis, Alzheimer's disease, congestive heart failure, and psoriasis among others (Dinarello, C. A. et al., *Rev. Infect. Diseases* 1984, 6:51; Salituro et al., *Curr. Med. Chem.* 1999, 6:807-823; Henry et al., *Drugs Fut.* 1999, 24:1345-1354). An accepted therapeutic approach for potential drug intervention in these conditions is the reduction of proinflammatory cytokines such as TNF-α (also referred to as TNFa) and interleukin-1β (IL-1b).
Phosphodiesterase4

The cyclic nucleotide specific phosphodiesterases (PDEs) represent a family of enzymes that catalyze the hydrolysis of various cyclic nucleoside monophosphates (including cAMP and cGMP). These cyclic nucleotides act as second messengers within cells, and as messengers, carry impulses from cell surface receptors having bound various hormones and neurotransmitters. PDEs act to regulate the level of cyclic nucleotides within cells and maintain cyclic nucleotide homeostasis by degrading such cyclic mononucleotides resulting in termination of their messenger role.

PDE enzymes can be grouped into eleven families according to their specificity toward hydrolysis of cAMP or cGMP, their sensitivity to regulation by calcium, calmodulin or cGMP, and their selective inhibition by various compounds. For example, PDE 1 is stimulated by $Ca^{2+}$/calmodulin. PDE 2 is cGMP-dependent, and is found in the heart and adrenals. PDE 3 is cGMP-dependent, and inhibition of this enzyme creates positive inotropic activity. PDE 4 is cAMP specific, and its inhibition causes airway relaxation, antiinflammatory and antidepressant activity. PDE 5 appears to be important in regulating cGMP content in vascular smooth muscle, and therefore PDE 5 inhibitors may have cardiovascular activity. Since the PDEs possess distinct biochemical properties, it is likely that they are subject to a variety of different forms of regulation.

PDE4 is distinguished by various kinetic properties including low Michaelis constant for cAMP and sensitivity to certain drugs. The PDE4 enzyme family consists of four genes, which produce 4 isoforms of the PDE4 enzyme designated PDE4A, PDE4B, PDE4C, and PDE4D [See: Wang et al., Expression, Purification, and Characterization of human cAMP-Specific Phosphodiesterase (PDE4) Subtypes A, B, C, and D, Biochem. Biophys. Res. Comm., 234, 320 324 (1997)] In addition, various splice variants of each PDE4 isoform have been identified.

PDE4 isoenzymes are localized in the cytosol of cells and are unassociated with any known membranous structures. PDE4 isoenzymes specifically inactivate cAMP by catalyzing its hydrolysis to adenosine 5'-monophosphate (AMP). Regulation of cAMP activity is important in many biological processes, including inflammation and memory Inhibitors of PDE4 isoenzymes such as rolipram, piclamilast, CDP-840 and ariflo are powerful antiinflammatory agents and therefore may be useful in treating diseases where inflammation is problematic such as asthma or arthritis. Further, rolipram improves the cognitive performance of rats and mice in learning paradigms.

Compounds which can inhibit the biological moieties described above, or treat diseases involving those biological moieties, would be a significant advance in the art.

SUMMARY OF THE INVENTION

In a first aspect, the invention provides a compound of the invention. In an exemplary embodiment, the compound is described herein or a pharmaceutically acceptable salt thereof. In an exemplary embodiment, the compound is according to a formula described herein. In an exemplary embodiment, the compound is a member selected from D1, D2, D3, D4, D5, D6, D7, D8, D9, D10, D11, D12, D13, D14, D15, D16, D17, D18, D19, D20, D21, D22, D23, D24, D25, D26, D27, D28, D29, D30, D31, D32, D33, D34, D35, D36, D37, D38, D39, D40, D41, D42, D43, D44, D45, D46, D47, D48, D49, D50, D51, D52, D53, D54, D55, D56, D57, D58, D59, D60, D61, D62, D63, D64, D65, D66, D67, D68, D69, D70, D71, D72, D73, D74, D75, D76, D77, D78, D79, D80, D81, D82, D83, D84, D85, D86, D87, D88, D89, D90, D91, D92, D93, D94, D95, D96, D97, D98, D99, D100, D101, D102, D103, D104, D105, D106, D107, D108, D109, D110, D111, D112, D113, D114, D115, D116, D117, D118, D119, D120, D121, D122, D123, D124, D125, D126, D127, D128, D129, D130, D131, D132, D133, D134, D135, D136, D137, D138, D139, D140, D141, D142, D143, D144, D145, D146, D147, D148, D149, D150, D151, D152, D153, D154, D155, D156, D157, D158, D159, D160, D161, D162, D163, D164, D165, D166, D167, D168, D169, D170, D171, D172, D173, D174, D175, D176, D177, D178, D179, D180, D181, D182, D183, D184, D185, D186, D187, D188, D189, D190, D191, D192, D193, D194, D195, D196, D197, D198, D199, D200, D201, D202, D203, D204, D205, D206, D207, D208, D209, D210, D211, D212, D213, D214, D215, D216, D217, D218, D219, D220, D221, D222, D223, D224, D225, D226, D227, D228 and D229.

In a second aspect, the invention provides a compound, and salts thereof, having a structure according to the formula:

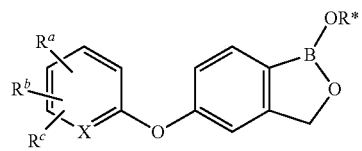

wherein R* is a member selected from H, a negative charge and a positively charged counterion. X is a member selected from $CR^a$, $CR^b$ and N. $R^a$ is a member selected from CN, —C(O)NR$^1$R$^2$, and —C(O)OR$^3$. $R^b$ and $R^c$ are members independently selected from H, OR$^4$, NR$^4$R$^5$, SR$^4$, —S(O)R$^4$, —S(O)$_2$R$^4$, —S(O)$_2$NR$^4$R$^5$, —C(O)R$^4$, —C(O)OR$^4$, —C(O)NR$^4$R$^5$, nitro, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, wherein each R$^1$, R$^2$, R$^4$ and R$^5$ are members independently selected from H, nitro, halogen, cyano, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. R$^3$ is a member selected from H and substituted or unsubstituted alkyl. There is a proviso that R$^1$ and R$^2$, together with the atoms to which they are attached, are optionally combined to form a 5- to 7-membered substituted or unsubstituted heterocycloalkyl ring. There is a proviso that R$^4$ and R$^5$, together with the atoms to which they are attached, are optionally combined to form a 5- to 7-membered substituted or unsubstituted heterocycloalkyl ring. There is a proviso R$^b$ and R$^c$ cannot both be H. There is a proviso that R$^a$ and R$^b$ are optionally joined to form a 5- to 8-membered ring comprising two oxo moieties.

The invention also provides pharmaceutical formulations, and methods of making and using the compounds described herein.

BRIEF DESCRIPTION OF THE DRAWINGS

FIGS. 1A-1K display exemplary compounds of the invention.

FIGS. 2A-2H display exemplary compounds of the invention.

FIGS. 3A-3FF display exemplary compounds of the invention.

FIGS. 4A-4FF display exemplary compounds of the invention.

FIGS. 5A-5FF display exemplary compounds of the invention.

FIGS. 6A-6L display exemplary compounds of the invention.

FIGS. 7A-7N display exemplary compounds of the invention.

DETAILED DESCRIPTION OF THE INVENTION

I. Definitions and Abbreviations

Figure 1A:
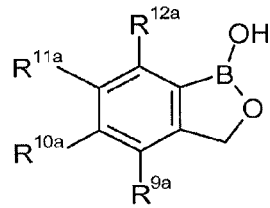

As used herein, the singular forms "a," "an", and "the" include plural references unless the context clearly dictates otherwise. For example, reference to "an active agent" includes a single active agent as well as two or more different active agents in combination. It is to be understood that present teaching is not limited to the specific dosage forms, carriers, or the like, disclosed herein and as such may vary.

The abbreviations used herein generally have their conventional meaning within the chemical and biological arts.

The following abbreviations have been used: aq.-aqueous; HATU-O-(7-azabenzotriazol-1-yl)-N,N,N',N'-tetramethyluronium hexafluorophosphate; EDCI-N-(3-dimethylaminopropyl)-N'-ethylcarbodiimide hydrochloride; m-CPBA-3-chloroperoxybenzoic acid; equiv-equivalent; DIAD-diisopropyl azodicarboxylate; DMF-N,N-dimethylformamide; DMSO-dimethylsulfoxide; AcOH-acetic acid; NaCNBH$_3$-sodium cyanoborohydride; Rt-room temperature; THF-tetrahydrofuran; Boc$_2$O-di-tert-butyl dicarbonate; MeOH-methanol; EtOH-ethanol; TFA-trifluoroacetic acid; DIPEA-N,N-diisopropylethylamine; PrOH-1-propanol; i-PrOH-2-propanol; mp-melting point; NMM-N-methylmorpholine; B$_2$pin$_2$-bis(pinacolato)diboron; O/N-overnight; BzOOH-benzoyl peroxide; THP-tetrahydopyranyl; Ac-acetyl; PTSA-para-toluene sulfonic acid; Pyr.-Pyridine; Cbz-benzyloxycarbonyl; MPM-p-methoxybenzyl; DHP-dihydropyran; CSA-camphor sulfonic acid; CTAB-cetyltrimethylammonium bromide; sat.-saturated; Cy-cyclohexyl; Ph-phenyl; Ar-aryl.

"Compound of the invention," as used herein refers to the compounds discussed herein, salts (such as pharmaceutically acceptable salts), prodrugs, solvates and hydrates of these compounds.

"Inhibiting" and "blocking," are used interchangeably herein to refer to the partial or full blockade of the expression of a pro-inflammatory cytokine by a method of the invention, which leads to a decrease in the amount of the cytokine in the animal.

Where substituent groups are specified by their conventional chemical formulae, written from left to right, they equally encompass the chemically identical substituents, which would result from writing the structure from right to left, e.g., —CH$_2$O— is intended to also recite —OCH$_2$—.

The term "poly" as used herein means at least 2. For example, a polyvalent metal ion is a metal ion having a valency of at least 2.

"Moiety" refers to the radical of a molecule that is attached to another moiety.

The symbols , whether utilized as a bond or displayed perpendicular to a bond, indicates the point at which the displayed moiety is attached to the remainder of the molecule.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. C$_1$-C$_{10}$ means one to ten carbons). In some embodiments, the term "alkyl" means a straight or branched chain, or combinations thereof, which may be fully saturated, mono- or polyunsaturated and can include di- and multivalent radicals. Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "unsubstituted alkyl" encompasses straight or branched chain saturated hydrocarbon radicals. Examples of saturated hydrocarbon radicals include, but are not limited to, groups such as methyl, ethyl, n-propyl, isopropyl, n-butyl, t-butyl, isobutyl, sec-butyl, n-pentyl.

The term "alkylene" by itself or as part of another substituent means a divalent radical derived from an alkane, as exemplified, but not limited, by —CH$_2$CH$_2$CH$_2$CH$_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom. In some embodiments, the term "heteroalkyl," by itself or in combination with another term, means a stable straight or branched chain, or combinations thereof, consisting of the stated number of carbon atoms and at least one heteroatom. In an exemplary embodiment, the heteroatoms can be selected from the group consisting of B, O, N and S, and wherein the nitrogen and sulfur atoms may optionally be oxidized and the nitrogen heteroatom may optionally be quaternized. The heteroatom(s) B, O, N and S may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'-represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo(C$_1$-C$_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl groups (or rings) that contain from one to four heteroatoms. In an exemplary embodiment, the heteroatom is selected from B, N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, 6-quinolyl, dioxaborolane, dioxaborinane and dioxaborepane. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes those radicals in which an aryl group is attached through the next moiety to the rest of the molecule. Thus, the term "arylalkyl" is meant to include those radicals in which an aryl group is attached to an alkyl group (e.g., benzyl, 1-(3-nitrophenyl)ethyl and the like). A substituent such as benzyl or 1-(3-nitrophenyl)ethyl can also be represented by 'substituted alkyl' wherein the ethyl radical is substituted with a 3-nitrophenyl moiety. The term "aryloxy" is meant to include those radicals in which an aryl group is attached to an oxygen atom. The term "aryloxyalkyl" is meant to include those radicals in which an aryl group is attached to an oxygen atom which is then attached to an alkyl group (e.g., phenoxymethyl, 3-(1-naphthyloxy)propyl, and the like).

For brevity, the term "heteroaryl" when used in combination with other terms (e.g., heteroaryloxy, heteroarylthioxy, heteroarylalkyl) includes those radicals in which a heteroaryl group is attached through the next moiety to the rest of the molecule. Thus, the term "heteroarylalkyl" is meant to include those radicals in which a heteroaryl group is attached to an alkyl group (e.g., pyridylmethyl and the like). The term "heteroaryloxy" is meant to include those radicals in which a heteroaryl group is attached to an oxygen atom. The term "heteroaryloxyalkyl" is meant to include those radicals in which an aryl group is attached to an oxygen atom which is then attached to an alkyl group. (e.g., 2-pyridyloxymethyl and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —R', —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR'—C(NR'R"R"')=NR"", —NR""—C(NR'R")=NR"', —S(O)R', —S(O)$_2$R', —S(O)$_2$NR'R", —NR"SO$_2$R', —CN, —NO$_2$, —N$_3$, —CH(Ph)$_2$, fluoro(C$_1$-C$_4$)alkoxy, and fluoro(C$_1$-C$_4$)alkyl, in a number ranging from zero to (2m'+1), where m' is the total number of carbon atoms in such radical. R', R", R"', R"" and R""' each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R"', R"" and R""' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: —R', —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR""—C(NR'R"R"')=NR"", —NR""—C(NR'R")=NR"', —S(O)R', —S(O)$_2$R', —S(O)$_2$NR'R", —NR"SO$_2$R', —CN, —NO$_2$, —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R"', R"" and R""' are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R"', R"" and R""' groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$),—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_d$—, where s and d are independently integers of from 0 to 3, and X is —O—, —NR'—, —S—, —S(O)—, —S(O)$_2$—, or —S(O)$_2$NR'—. The substituents R, R', R" and R'" are preferably independently selected from hydrogen or substituted or unsubstituted (C$_1$-C$_6$)alkyl.

"Ring" as used herein, means a substituted or unsubstituted cycloalkyl, substituted or unsubstituted heterocycloalkyl, substituted or unsubstituted aryl, or substituted or unsubstituted heteroaryl. A ring includes fused ring moieties. The number of atoms in a ring is typically defined by the number of members in the ring. For example, a "5- to 7-membered ring" means there are 5 to 7 atoms in the encircling arrangement. Unless otherwise specified, the ring optionally includes a heteroatom. Thus, the term "5- to 7-membered ring" includes, for example phenyl, pyridinyl and piperidinyl. The term "5- to 7-membered heterocycloalkyl ring", on the other hand, would include pyridinyl and piperidinyl, but not phenyl. The term "ring" further includes a ring system comprising more than one "ring", wherein each "ring" is independently defined as above.

As used herein, the term "heteroatom" includes atoms other than carbon (C) and hydrogen (H). Examples include oxygen (O), nitrogen (N) sulfur (S), silicon (Si), germanium (Ge), aluminum (Al) and boron (B).

The symbol "R" is a general abbreviation that represents a substituent group that is selected from substituted or unsubstituted alkyl, substituted or unsubstituted heteroalkyl, substituted or unsubstituted aryl, substituted or unsubstituted heteroaryl, substituted or unsubstituted cycloalkyl and substituted or unsubstituted heterocycloalkyl groups.

By "effective" amount of a drug, formulation, or permeant is meant a sufficient amount of a active agent to provide the desired local or systemic effect. A "Topically effective," "Cosmetically effective," "pharmaceutically effective," or "therapeutically effective" amount refers to the amount of drug needed to effect the desired therapeutic result.

"Topically effective" refers to a material that, when applied to the skin, nail, hair, claw or hoof produces a desired pharmacological result either locally at the place of application or systemically as a result of transdermal passage of an active ingredient in the material.

"Cosmetically effective" refers to a material that, when applied to the skin, nail, hair, claw or hoof, produces a desired cosmetic result locally at the place of application of an active ingredient in the material.

The terms "pharmaceutically acceptable salts" or "a salt thereof" are meant to include salts of the compounds of the invention which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science 66: 1-19 (1977)). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compounds in the conventional manner. The parent form of the compound differs from the various salt forms in certain physical properties, such as solubility in polar solvents.

In addition to salt forms, the present invention provides compounds which are in a prodrug form. Prodrugs of the compounds or complexes described herein readily undergo chemical changes under physiological conditions to provide the compounds of the present invention. Additionally, prodrugs can be converted to the compounds of the present invention by chemical or biochemical methods in an ex vivo environment.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention. The graphic representations of racemic, ambiscalemic and scalemic or enantiomerically pure compounds used herein are taken from Maehr, J. Chem. Ed. 1985, 62: 114-120. Solid and broken wedges are used to denote the absolute configuration of a stereocenter unless otherwise noted. When the compounds described herein contain olefinic double bonds or other centers of geometric asymmetry, and unless specified otherwise, it is intended that the compounds include both E and Z geometric isomers. Likewise, all tautomeric forms are included.

Compounds of the invention can exist in particular geometric or stereoisomeric forms. The invention contemplates all such compounds, including cis- and trans-isomers, (−)- and (+)-enantiomers, (R)- and (S)-enantiomers, diastereomers, (D)-isomers, (L)-isomers, the racemic mixtures thereof, and other mixtures thereof, such as enantiomerically or diastereomerically enriched mixtures, as falling within the scope of the invention. Additional asymmetric carbon atoms can be present in a substituent such as an alkyl group. All such isomers, as well as mixtures thereof, are intended to be included in this invention.

Optically active (R)- and (S)-isomers and d and l isomers can be prepared using chiral synthons or chiral reagents, or resolved using conventional techniques. If, for instance, a particular enantiomer of a compound of the present invention is desired, it can be prepared by asymmetric synthesis, or by derivatization with a chiral auxiliary, where the resulting diastereomeric mixture is separated and the auxiliary group cleaved to provide the pure desired enantiomers. Alternatively, where the molecule contains a basic functional group, such as an amino group, or an acidic functional group, such as a carboxyl group, diastereomeric salts can be formed with an appropriate optically active acid or base, followed by resolution of the diastereomers thus formed by fractional crystallization or chromatographic means known in the art, and subsequent recovery of the pure enantiomers. In addition, separation of enantiomers and diastereomers is frequently accomplished using chromatography employing chiral, stationary phases, optionally in combination with chemical derivatization (e.g., formation of carbamates from amines).

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

The term "pharmaceutically acceptable carrier" or "pharmaceutically acceptable vehicle" refers to any formulation or carrier medium that provides the appropriate delivery of an effective amount of an active agent as defined herein, does not interfere with the effectiveness of the biological activity of the active agent, and that is sufficiently non-toxic to the host or patient. Representative carriers include water, oils, both vegetable and mineral, cream bases, lotion bases, ointment bases and the like. These bases include suspending agents, thickeners, penetration enhancers, and the like. Their formulation is well known to those in the art of cosmetics and topical pharmaceuticals. Additional information concerning carriers can be found in *Remington: The Science and Practice of Pharmacy*, 21st Ed., Lippincott, Williams & Wilkins (2005) which is incorporated herein by reference.

The term "pharmaceutically acceptable carrier" or "pharmaceutically acceptable vehicle" refers to any formulation or carrier medium that provides the appropriate delivery of an effective amount of a active agent as defined herein, does not interfere with the effectiveness of the biological activity of the active agent, and that is sufficiently non-toxic to the host or patient. Representative carriers include water, oils, both vegetable and mineral, cream bases, lotion bases, ointment bases and the like. These bases include suspending agents, thickeners, penetration enhancers, and the like. Their formulation is well known to those in the art of cosmetics and topical pharmaceuticals. Additional information concerning carriers can be found in *Remington: The Science and Practice of Pharmacy*, 21st Ed., Lippincott, Williams & Wilkins (2005) which is incorporated herein by reference.

"Pharmaceutically acceptable topical carrier" and equivalent terms refer to pharmaceutically acceptable carriers, as described herein above, suitable for topical application. An inactive liquid or cream vehicle capable of suspending or dissolving the active agent(s), and having the properties of being nontoxic and non-inflammatory when applied to the skin, nail, hair, claw or hoof is an example of a pharmaceutically-acceptable topical carrier. This term is specifically intended to encompass carrier materials approved for use in topical cosmetics as well.

The term "pharmaceutically acceptable additive" refers to preservatives, antioxidants, fragrances, emulsifiers, dyes and excipients known or used in the field of drug formulation and that do not unduly interfere with the effectiveness of the biological activity of the active agent, and that is sufficiently non-toxic to the host or patient. Additives for topical formulations are well-known in the art, and may be added to the topical composition, as long as they are pharmaceutically acceptable and not deleterious to the epithelial cells or their function. Further, they should not cause deterioration in the stability of the composition. For example, inert fillers, anti-irritants, tackifiers, excipients, fragrances, opacifiers, antioxidants, gelling agents, stabilizers, surfactant, emollients, coloring agents, preservatives, buffering agents, other permeation enhancers, and other conventional components of topical or transdermal delivery formulations as are known in the art.

The terms "enhancement," "penetration enhancement" or "permeation enhancement" relate to an increase in the permeability of the skin, nail, hair, claw or hoof to a drug, so as to increase the rate at which the drug permeates through the skin, nail, hair, claw or hoof. The enhanced permeation effected through the use of such enhancers can be observed, for example, by measuring the rate of diffusion of the drug through animal skin, nail, hair, claw or hoof using a diffusion cell apparatus. A diffusion cell is described by Merritt et al. Diffusion Apparatus for Skin Penetration, *J of Controlled Release*, 1 (1984) pp. 161-162. The term "permeation enhancer" or "penetration enhancer" intends an agent or a mixture of agents, which, alone or in combination, act to increase the permeability of the skin, nail, hair or hoof to a drug.

The term "excipients" is conventionally known to mean carriers, diluents and/or vehicles used in formulating drug compositions effective for the desired use.

The terms "effective amount" or a "therapeutically effective amount" of a drug or pharmacologically active agent refers to a nontoxic but sufficient amount of the drug or agent to provide the desired effect. In the oral dosage forms of the present disclosure, an "effective amount" of one active of the combination is the amount of that active that is effective to provide the desired effect when used in combination with the other active of the combination. The amount that is "effective" will vary from subject to subject, depending on the age and general condition of the individual, the particular active agent or agents, and the appropriate "effective" amount in any individual case may be determined by one of ordinary skill in the art using routine experimentation.

The phrases "active ingredient", "therapeutic agent", "active", or "active agent" mean a chemical entity which can be effective in treating a targeted disorder, disease or condition.

The phrase "pharmaceutically acceptable" means moieties or compounds that are, within the scope of medical judgment, suitable for use in humans without causing undesirable biological effects such as undue toxicity, irritation, allergic response, and the like, for example.

The phrase "oral dosage form" means any pharmaceutical composition administered to a subject via the oral cavity, in which one or more antiplatelet agents and one or more acid inhibitors are administered concurrently in combination, optionally with one or more additional drugs. Exemplary oral dosage forms include tablets, capsules, films, powders, sachets, granules, solutions, solids, suspensions or as more than one distinct unit (e.g., granules, tablets, and/or capsules containing different actives) packaged together for co-administration, and other formulations known in the art. An oral dosage form can be one, two, three, four, five or six units. When the oral dosage form has multiple units, all of the units are contained within a single package, (e.g. a bottle or other form of packaging such as a blister pack). When the oral dosage form is a single unit, it may or may not be in a single package.

In a preferred embodiment, the oral dosage form is one, two or three units. In a particularly preferred embodiment, the oral dosage form is one unit.

The phrase "unit", as used herein, refers to the number of discrete objects to be administered which comprise the dosage form. In some embodiments, the dosage form includes a compound of the invention in one capsule. This is a single unit. In some embodiments, the dosage form includes a compound of the invention as part of a therapeutically effective dosage of a cream or ointment. This is also a single unit. In some embodiments, the dosage form includes a compound of the invention and another active ingredient contained within one capsule, or as part of a therapeutically effective dosage of a cream or ointment or lotion. This is a single unit, whether or not the interior of the capsule includes multiple discrete granules of the active ingredient. In some embodiments, the dosage form includes a compound of the invention in one capsule, and the active ingredient in a second capsule. This is a two unit dosage form, such as two capsules or tablets, and so such units are contained in a single package. Thus the term 'unit' refers to the object which is administered to the animal, not to the interior components of the object.

The term, "prodrug", as defined herein, is a biologically inactive derivative of a parent drug molecule that exerts its pharmacological effect only after chemical and/or enzymatic conversion to its active form in vivo. Prodrugs include those designed to circumvent problems associated with delivery of the parent drug. This may be due to poor physicochemical properties, such as poor chemical stability or low aqueous solubility, and may also be due to poor pharmacokinetic properties, such as poor bioavailability or poor half-life. Thus, certain advantages of prodrugs may include improved chemical stability, absorption, and/or PK properties of the parent carboxylic acids. Prodrugs may also be used to make drugs more "patient friendly," by minim/zing the frequency (e.g., once daily) or route of dosing (e.g., oral), or to improve the taste or odor if given orally, or to minim/ze pain if given parenterally.

In some embodiments, the prodrugs effect a "slow-release" of the active drug, thereby changing the time-course of D-serine increase in a manner that improves the efficacy of the parent compound. For example, compounds of the invention that extend D-serine level increases demonstrate improved efficacy in animal models of cognition (e.g., Contextual Fear Conditioning or Novel Object Recognition).

In some embodiments, the prodrugs are chemically more stable than the active drug, thereby improving formulation and delivery of the parent drug, compared to the drug alone.

Prodrugs for carboxylic acid analogs of the invention may include a variety of esters. In an exemplary embodiment, the pharmaceutical compositions of the invention include a carboxylic acid ester. In an exemplary embodiment, the prodrug is suitable for treatment/prevention of those diseases and conditions that require the drug molecule to cross the blood brain barrier. In an exemplary embodiment, the prodrug enters the brain, where it is converted into the active form of the drug molecule. In one embodiment, a prodrug is used to enable an active drug molecule to reach the inside of the eye after topical application of the prodrug to the eye.

Additionally, a prodrug can be converted to its parent compound by chemical or biochemical methods in an ex vivo environment. For example, a prodrug can be slowly converted to its parent compound when placed in a transdermal patch reservoir with a suitable enzyme or chemical reagent.

The term "substrates" means pharmaceutically acceptable particulate materials such as beads, particles, granules, pellets, and the like, in an oral dosage form.

The term, "substantially free", as used herein, refers to a composition which contains none of the substance or less than a therapeutically effective amount of the substance for any known purpose for which the composition is intended.

The term "topical administration" refers to the application of a pharmaceutical agent to the external surface of the skin, nail, hair, claw or hoof, such that the agent crosses the external surface of the skin, nail, hair, claw or hoof and enters the underlying tissues. Topical administration includes application of the composition to intact skin, nail, hair, claw or hoof, or to an broken, raw or open wound of skin, nail, hair, claw or hoof. Topical administration of a pharmaceutical agent can result in a limited distribution of the agent to the skin and surrounding tissues or, when the agent is removed from the treatment area by the bloodstream, can result in systemic distribution of the agent.

The term "transdermal delivery" refers to the diffusion of an agent across the barrier of the skin, nail, hair, claw or hoof resulting from topical administration or other application of a composition. The stratum corneum acts as a barrier and few pharmaceutical agents are able to penetrate intact skin. In contrast, the epidermis and dermis are permeable to many solutes and absorption of drugs therefore occurs more readily through skin, nail, hair, claw or hoof that is abraded or otherwise stripped of the stratum corneum to expose the epidermis. Transdermal delivery includes injection or other delivery through any portion of the skin, nail, hair, claw or hoof or mucous membrane and absorption or permeation through the remaining portion. Absorption through intact skin, nail, hair, claw or hoof can be enhanced by placing the active agent in an appropriate pharmaceutically acceptable vehicle before application to the skin, nail, hair, claw or hoof. Passive topical administration may consist of applying the active agent directly to the treatment site in combination with emollients or penetration enhancers. As used herein, transdermal delivery is intended to include delivery by permeation through or past the integument, i.e. skin, nail, hair, claw or hoof.

The term "substrates" means pharmaceutically acceptable particulate materials such as beads, particles, granules, pellets, and the like, in an oral dosage form.

The term, "substantially free", as used herein, refers to a composition which contains none of the substance or less than a therapeutically effective amount of the substance for any known purpose for which the composition is intended.

The term "microbial infection" refers to any infection of a host tissue by an infectious agent including, but not limited to, viruses, bacteria, mycobacteria, fungus and parasites (see, e.g., Harrison's Principles of Internal Medicine, pp. 93-98 (Wilson et al., eds., 12th ed. 1991); Williams et al., *J. of Medicinal Chem.* 42:1481-1485 (1999), herein each incorporated by reference in their entirety).

"Biological medium," as used herein refers to both in vitro and in vivo biological milieus. Exemplary in vitro "biological media" include, but are not limited to, cell culture, tissue culture, homogenates, plasma and blood. In vivo applications are generally performed in mammals, preferably humans.

A "human nail unit", as defined herein, can be the nail plate, the nail bed, proximal nail fold, lateral nail fold and combinations thereof.

The term "leaving group" means a functional group or atom which can be displaced by another functional group or atom in a substitution reaction, such as a nucleophilic substitution reaction. By way of example, representative leaving groups include triflate, chloro, bromo and iodo groups; sulfonic ester groups, such as mesylate, tosylate, brosylate, nosylate and the like; and acyloxy groups, such as acetoxy, trifluoroacetoxy and the like.

The term "amino-protecting group" means a protecting group suitable for preventing undesired reactions at an amino nitrogen. Representative amino-protecting groups include, but are not limited to, formyl; acyl groups, for example alkanoyl groups, such as acetyl, trichloroacetyl or trifluoroacetyl; alkoxycarbonyl groups, such as tert-butoxycarbonyl (Boc); arylmethoxycarbonyl groups, such as benzyloxycarbonyl (Cbz) and 9-fluorenylmethoxycarbonyl (Fmoc); arylmethyl groups, such as benzyl (Bn), trityl (Tr), and 1,1-di-(4'-methoxyphenyl)methyl; silyl groups, such as trimethylsilyl (TMS) and tert-butyldimethylsilyl (TBS); and the like.

The term "hydroxy-protecting group" means a protecting group suitable for preventing undesired reactions at a hydroxy group. Representative hydroxy-protecting groups include, but are not limited to, alkyl groups, such as methyl, ethyl, and tert-butyl; acyl groups, for example alkanoyl groups, such as acetyl; arylmethyl groups, such as benzyl (Bn), p-methoxybenzyl (PMB), 9-fluorenylmethyl (Fm), and diphenylmethyl (benzhydryl, DPM); silyl groups, such as trimethylsilyl (TMS) and tert-butyldimethylsilyl (TBS); and the like.

Boron is able to form dative bonds (or coordination bonds) with oxygen, sulfur or nitrogen under some circumstances in this invention. Dative bonds are usually weaker than covalent bonds. In situations where a boron atom is covalently bonded to at least one oxygen, sulfur or nitrogen, and is at the same time datively bonded to an oxygen, sulfur or nitrogen, respectively, the dative bond and covalent bond between the boron and the two identical heteroatoms can interconvert or be in the form of a resonance hybrid. There is potential uncertainty surrounding the exact nature and extent of electron sharing in these situations. The structures supplied are not intended to include any and all possible bonding scenarios between boron and the atom to which it is bound. Non limiting examples of these bonds are as follows:

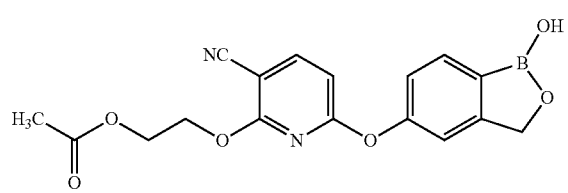

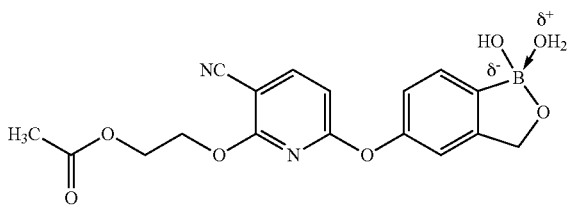

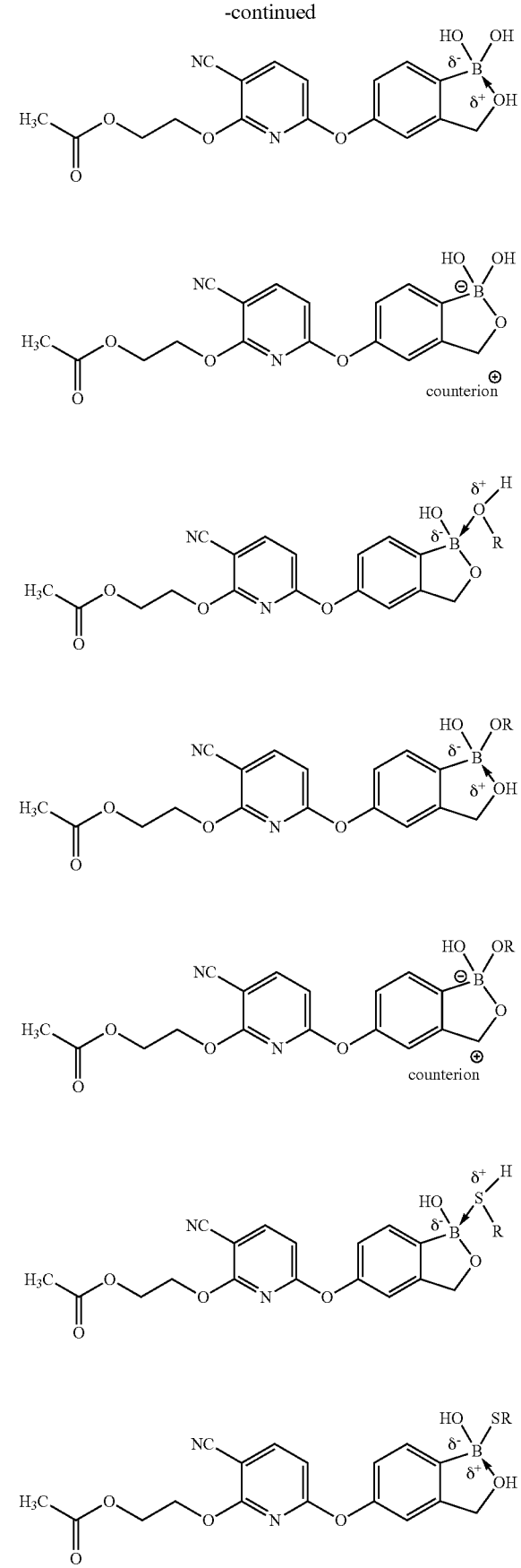

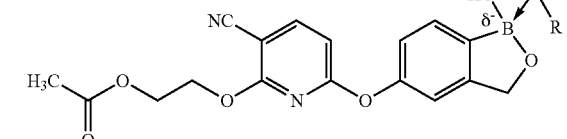

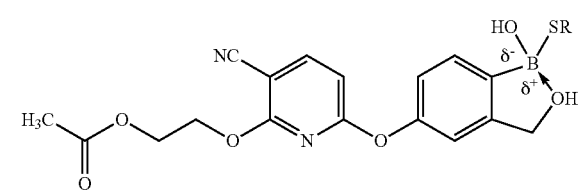

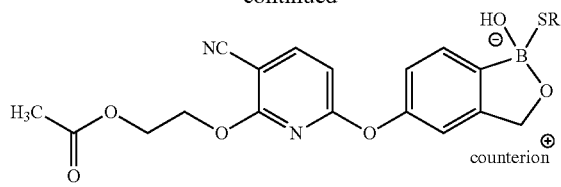

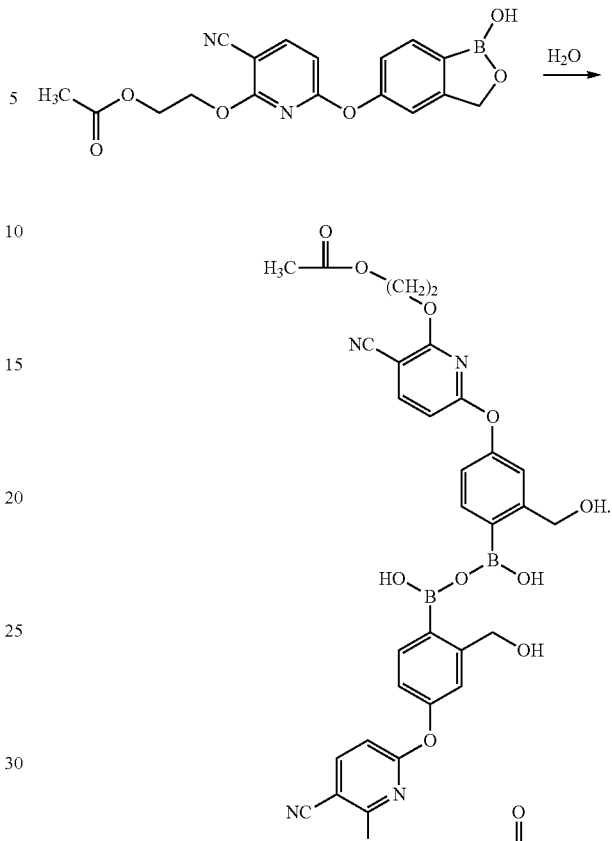

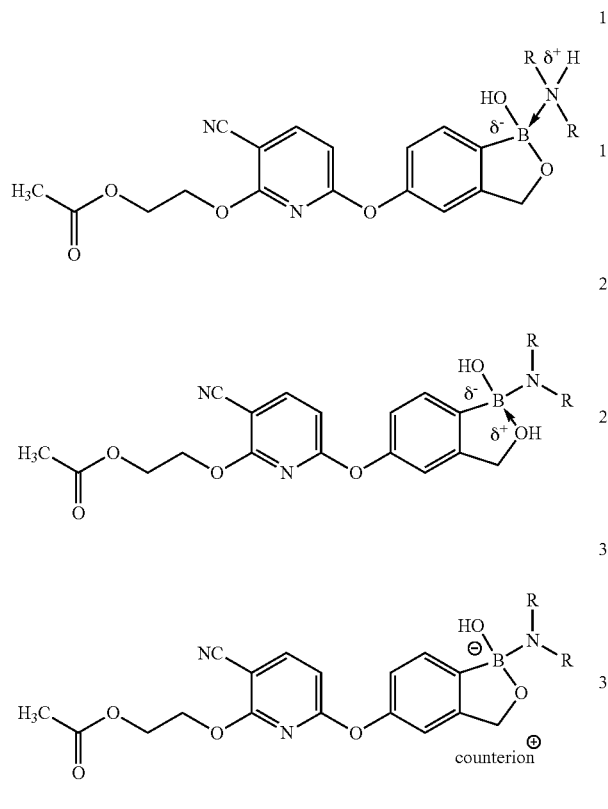

"Salt counterion", as used herein, refers to positively charged ions that associate with a compound of the invention when the boron is fully negatively or partially negatively charged. Examples of salt counterions include H', $H_3O^+$, ammonium, potassium, calcium, magnesium and sodium.

The compounds comprising a boron bonded to a carbon and three heteroatoms (such as three oxygens described in this section) can optionally contain a fully negatively charged boron or partially negatively charged boron, due to the nature of the dative bond between the boron and one of the oxygens. Due to the negative charge, a positively charged counterion may associate with this compound, thus forming a salt. Examples of positively charged counterions include $H^+$, $H_3O^+$, calcium, sodium, ammonium, potassium. The salts of these compounds are implicitly contained in descriptions of these compounds.

The present invention also encompasses compounds that are poly- or multi-valent species, including, for example, species such as dimers, trimers, tetramers and higher homologs of the compounds of use in the invention or reactive analogues thereof. For example, dimers of oxaboroles can form under the following conditions:

The present invention also encompasses compounds that are anhydrides of the cyclic boronic esters are synthesized by subjecting these compounds to dehydrating conditions. Examples of these anhydrides are provided below:

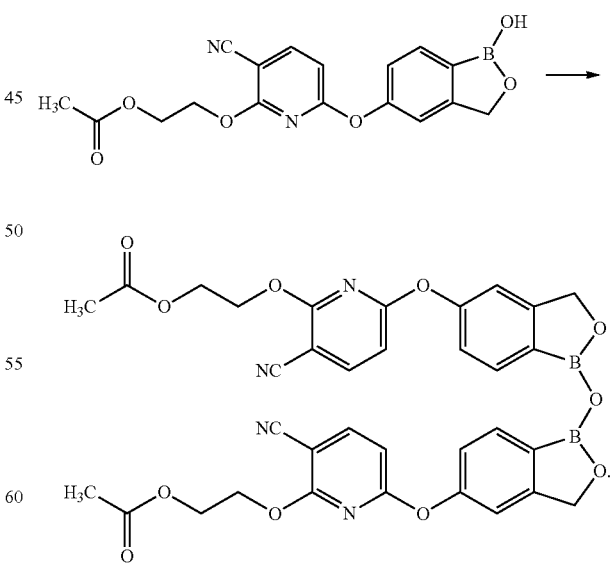

Trimers of the compounds of the invention are also produced. For example, trimers of acyclic boronic esters can be formed as follows:

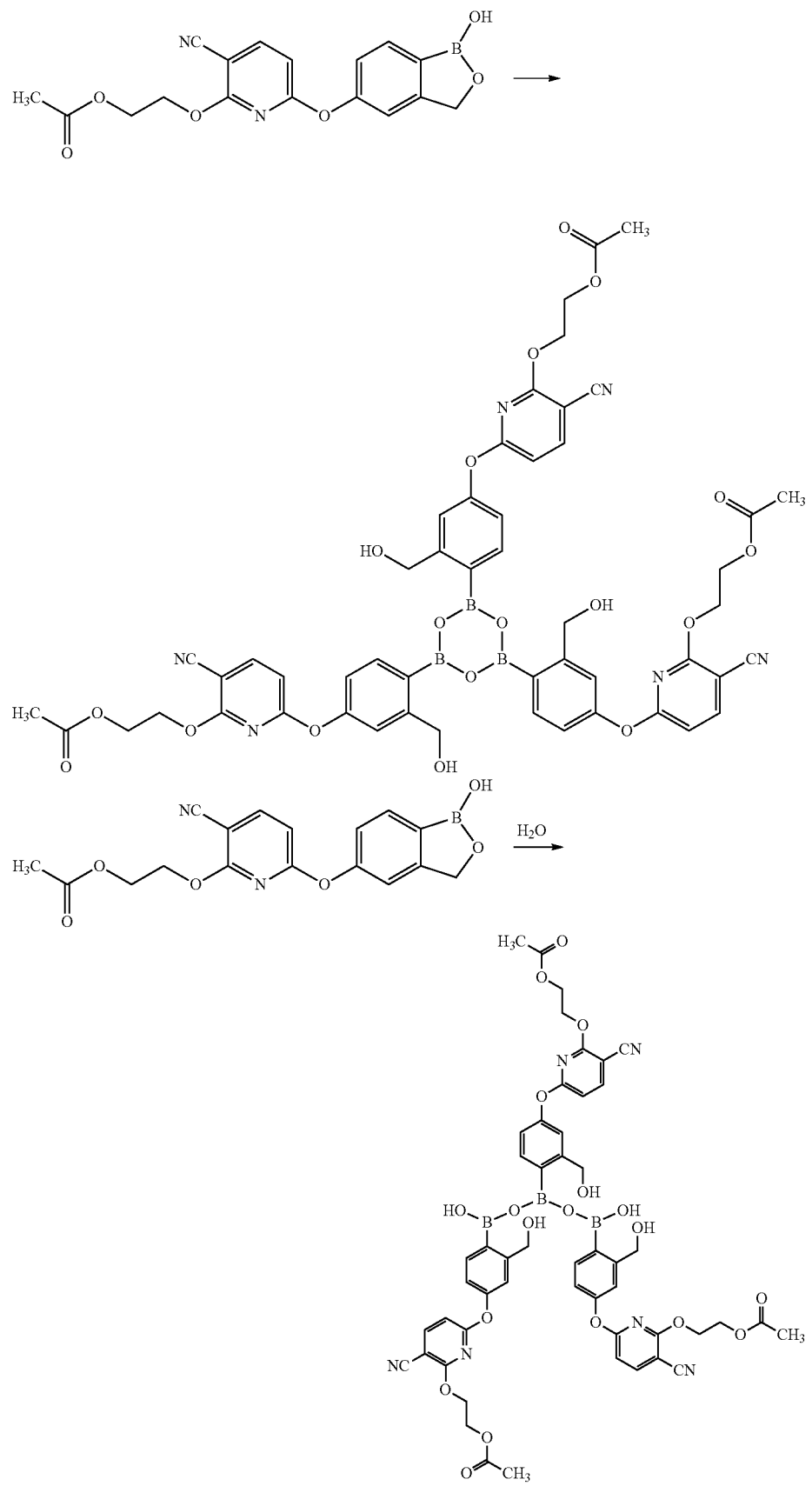

Polymers of the compounds of the invention are also produced through the removal of certain protecting groups in strong acid. For example, trimers of acyclic boronic esters can be formed as follows:

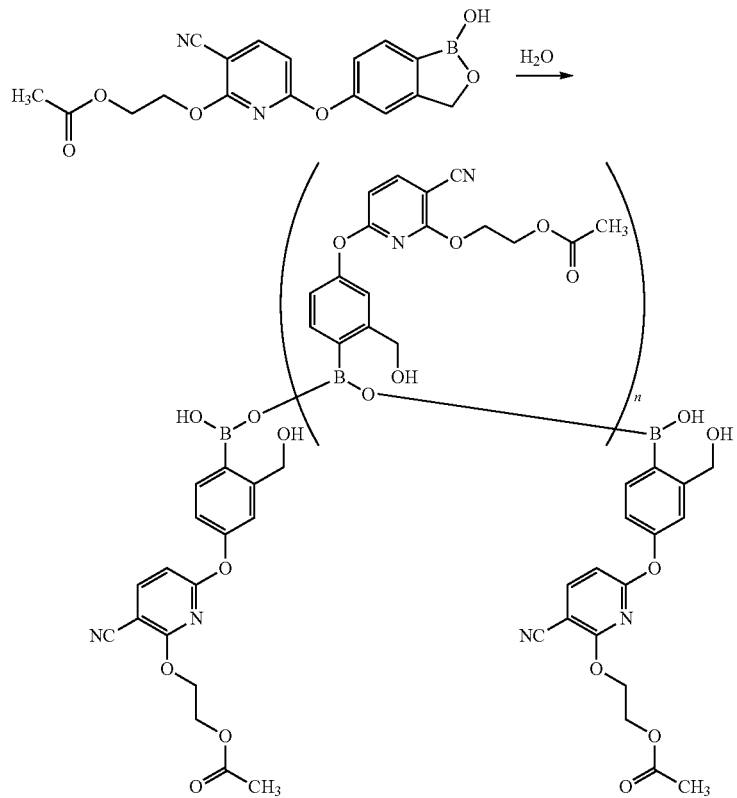

Also of use in the present invention are compounds that are poly- or multi-valent species, including, for example, species such as dimers, trimers, tetramers and higher homologs of the compounds of use in the invention or reactive analogues thereof. The poly- and multi-valent species can be assembled from a single species or more than one species of the invention. For example, a dimeric construct can be "homodimeric" or "heterodimeric." Moreover, poly- and multi-valent constructs in which a compound of the invention or a reactive analogue thereof, is attached to an oligomeric or polymeric framework (e.g., polylysine, dextran, hydroxyethyl starch and the like) are within the scope of the present invention. The framework is preferably polyfunctional (i.e. having an array of reactive sites for attaching compounds of use in the invention). Moreover, the framework can be derivatized with a single species of the invention or more than one species of the invention.

Moreover, the present invention includes the use of compounds within the motif set forth in the formulae contained herein, which are functionalized to afford compounds having water-solubility that is enhanced relative to analogous compounds that are not similarly functionalized. Thus, any of the substituents set forth herein can be replaced with analogous radicals that have enhanced water solubility. For example, it is within the scope of the invention to replace a hydroxyl group with a diol, or an amine with a quaternary amine, hydroxy amine or similar more water-soluble moiety. In a preferred embodiment, additional water solubility is imparted by substitution at a site not essential for the activity towards the editing domain of the compounds set forth herein with a moiety that enhances the water solubility of the parent compounds. Methods of enhancing the water-solubility of organic compounds are known in the art. Such methods include, but are not limited to, functionalizing an organic nucleus with a permanently charged moiety, e.g., quaternary ammonium, or a group that is charged at a physiologically relevant pH, e.g. carboxylic acid, amine. Other methods include, appending to the organic nucleus hydroxyl- or amine-containing groups, e.g. alcohols, polyols, polyethers, and the like. Representative examples include, but are not limited to, polylysine, polyethyleneimine, poly(ethyleneglycol) and poly(propyleneglycol). Suitable functionalization chemistries and strategies for these compounds are known in the art. See, for example, Dunn, R. L., et al., Eds. POLYMERIC DRUGS AND DRUG DELIVERY SYSTEMS, ACS Symposium Series Vol. 469, American Chemical Society, Washington, D.C. 1991.

II. Introduction

The present invention has multiple aspects. These aspects include inventions directed to compounds, pharmaceutical formulations, methods of treating a condition, enhancing an effect, increasing the production of a cytokine and/or chemokine, decreasing the production of a cytokine and/or chemokine, increasing the release of a cytokine and/or chemokine, decreasing the release of a cytokine and/or chemokine, or inhibiting a phosphodiesterase.

III. Compounds

IIIa.

In a first aspect, the invention is a compound of the invention. In an exemplary embodiment, the invention is a compound described herein. In an exemplary embodiment, the compound is according to a formula described herein. In an exemplary embodiment, the compound is a member selected from D2, D3, D4, D5, D6, D7, D8, D9, D10, D11, D12, D13, D14, D15, D16, D17, D18, D19, D20, D21, D22, D23, D24, D25, D26, D27, D28, D29, D30, D31, D32, D33, D34, D35, D36, D37, D38, D39, D40, D41, D42, D43, D44, D45, D46, D47, D48, D49, D50, D51, D52, D53, D54, D55, D56, D57, D58, D59, D60, D61, D62, D63, D64, D65, D66, D67, D68, D69, D70, D71, D72, D73, D74, D75, D76, D77, D78, D79, D80, D81, D83, D84, D85, D86, D87, D88, D89, D90, D91, D92, D93, D94, D95, D96, D97, D98, D99, D100, D101, D102, D103, D104, D105, D106, D107, D108, D109, D110, D111, D112, D113, D114, D115, D116, D117, D118, D119, D120, D121, D122, D123, D124, D125, D126, D127, D128, D129, D130, D131, D132, D133, D134, D135, D136, D137, D138, D139, D140, D141, D142, D143, D144, D145, D146, D147, D148, D149, D150, D151, D152, D153, D154, D155, D156, D157, D158, D159, D160, D161, D162, D163, D164, D165, D166, D167, D168, D169, D170, D171, D172, D173, D174, D175, D176, D177, D178, D179, D180, D181, D182, D183, D184, D185, D186, D187, D188, D189, D190, D191, D192, D193, D194, D195, D196, D197, D198, D199, D200, D201, D202, D203, D204, D205, D206, D207, D208, D209, D210, D211, D212, D213, D214, D215, D216, D217, D218, D219, D220, D221, D222, D223, D224, D225, D228 and D229. In an exemplary embodiment, the compound is a member selected from In a second aspect, the invention provides a compound having a structure according to the formula:

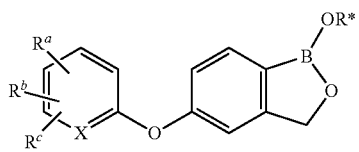

wherein R* is a member selected from H, a negative charge and a positively charged counterion. X is a member selected from $CR^a$, $CR^b$ and N. $R^a$ is a member selected from CN, —C(O)NR$^1$R$^2$, and —C(O)OR$^3$. $R^b$ and $R^c$ are members independently selected from H, OR$^4$, NR$^4$R$^5$, SR$^4$, —S(O) R$^4$, —S(O)$_2$R$^4$, —S(O)$_2$NR$^4$R$^5$, —C(O)R$^4$, —C(O)OR$^4$, —C(O)NR$^4$R$^5$, nitro, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, wherein each R', R$^2$, R$^4$ and R$^5$ are members independently selected from H, nitro, halogen, cyano, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. R$^3$ is a member selected from H and substituted or unsubstituted alkyl. There is a proviso that R$^1$ and R$^2$, together with the atoms to which they are attached, are optionally combined to form a 5- to 7-membered substituted or unsubstituted heterocycloalkyl ring. There is a proviso that R$^4$ and R$^5$, together with the atoms to which they are attached, are optionally combined to form a 5- to 7-membered substituted or unsubstituted heterocycloalkyl ring. There is a proviso $R^b$ and $R^c$ cannot both be H. There is a proviso that $R^a$ and $R^b$ are optionally joined to form a 5- to 8-membered ring comprising two oxo moieties.

In an exemplary embodiment, X is N. In an exemplary embodiment, X is CH. In an exemplary embodiment, X is $CR^b$.

In an exemplary embodiment, R* is H.

In an exemplary embodiment, at least one of $R^b$ and $R^c$ is a member selected from F and Cl. In an exemplary embodiment, at least one of $R^b$ and $R^c$ is substituted or unsubstituted alkyl, which is a member selected from unsubstituted alkyl, hydroxyalkyl, haloalkyl, trihaloalkyl, substituted or unsubstituted aminoalkyl, —CH$_2$C(O)OR$^6$, —CH$_2$NHC(O)R$^6$, —CH$_2$NR$^6$R$^7$, wherein each R$^6$ and R$^7$ are members independently selected from H, substituted or unsubstituted alkyl, substituted or unsubstituted cycloalkyl and substituted or unsubstituted heteroaryl, with the proviso that R$^6$ and R$^7$, together with the atoms to which they are attached, are optionally combined to form a 5- to 7-membered substituted or unsubstituted heterocycloalkyl ring.

In an exemplary embodiment, $R^b$ is H. In an exemplary embodiment, $R^c$ is H. In an exemplary embodiment, $R^c$ is H, and $R^b$ is a member selected from halogen, unsubstituted alkyl, halogen substituted alkyl, unsubstituted alkoxy. In an exemplary embodiment, $R^c$ is H, and $R^b$ is a member selected from methyl and ethyl. In an exemplary embodiment, $R^c$ is H, and $R^b$ is a member selected from unsubstituted C$_3$ alkyl, unsubstituted C$_4$ alkyl, unsubstituted C$_5$ alkyl and unsubstituted C$_6$ alkyl. In an exemplary embodiment, $R^b$ is H, and $R^c$ is trifluoromethyl. In an exemplary embodiment, $R^c$ is H, and $R^b$ is a member selected from methoxy, ethoxy, unsubstituted C$_3$ alkoxy, unsubstituted C$_4$ alkoxy, unsubstituted C$_5$ alkoxy and unsubstituted C$_6$ alkoxy.

In an exemplary embodiment, at least one of $R^b$ and $R^c$ is a member selected from —CH$_2$C(O)OR$^6$, —CH$_2$NHC(O)R$^6$, —CH$_2$NR$^6$R$^7$, wherein each R$^6$ and R$^7$ are members independently selected from H, methyl, trifluoromethyl, ethyl, propyl, butyl, t-butyl, —C(O)H, wherein R$^6$ and R$^7$, together with the together with nitrogen to which they are attached, are optionally combined to form a member selected from 4-methylpiperazinyl, piperidinyl, morpholino and pyrrolidinyl.

In an exemplary embodiment, at least one of $R^b$ and $R^c$ is methyl, trifluoromethyl,

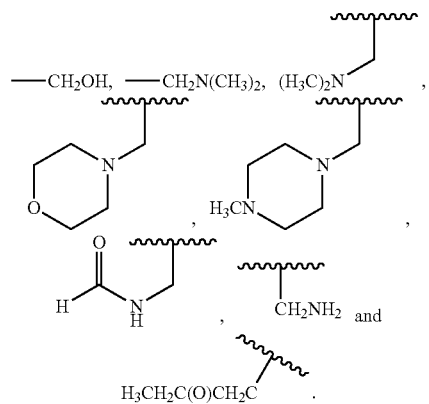

In an exemplary embodiment, at least one of $R^b$ and $R^c$ is a member selected from —OR$^4$, —C(O)R$^4$, —C(O)OR$^4$ and —C(O)NR$^4$R$^5$, wherein each R$^4$ and R$^5$ are members independently selected from H, methyl, ethyl, methoxyethyl, cyclopropyl, —CH$_2$C(O)OR$^8$, —CH$_2$C(O)NR$^8$R$^9$, 2-(dimethylamino)ethyl, 2-pyridinylmethyl, 2-(4-cyano)pyridinyl, with the proviso that R$^8$ and R$^9$, together with the atoms to which they are attached, are optionally combined to form a 5- to 7-membered substituted or unsubstituted heterocycloalkyl ring.

In an exemplary embodiment, at least one of $R^b$ and $R^c$ is a member selected from —OH, —OCH$_3$, —OCH$_2$CH$_3$, —OCH$_2$CH$_2$OCH$_3$, —OCH$_2$C(O)OH, —OCH$_2$C(O)OCH$_2$CH$_3$, —OCH$_2$C(O)OC(CH$_3$)$_3$, —C(O)OCH$_3$, —C(O)OH, —C(O)H,

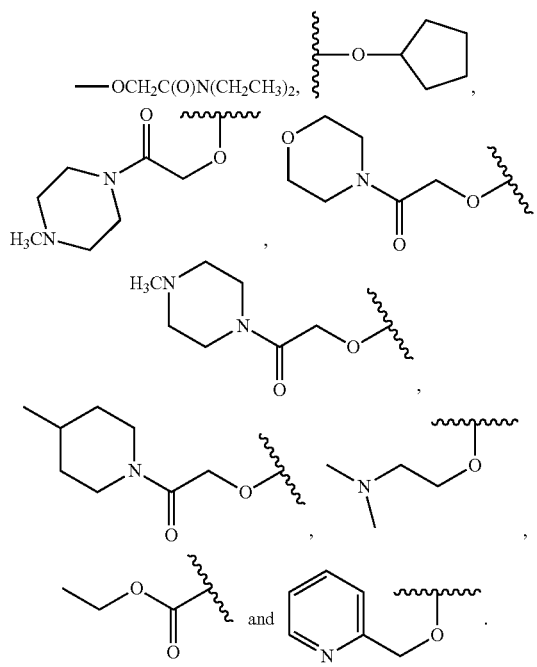

In an exemplary embodiment, at least one of $R^b$ and $R^c$ is a member selected from F, Cl, methyl, trifluoromethyl, —CH$_2$OH, —CH$_2$N(CH$_3$)$_2$, —OH, —OCH$_3$, —OCH$_2$CH$_3$, —OCH$_2$CH$_2$OCH$_3$, —OCH$_2$C(O)OH, —OCH$_2$C(O)OCH$_2$CH$_3$, —OCH$_2$C(O)OC(CH$_3$)$_3$, —C(O)OCH$_3$, —C(O)OH, —C(O)H, —OCH$_2$C(O)N(CH$_2$CH$_3$)$_2$,

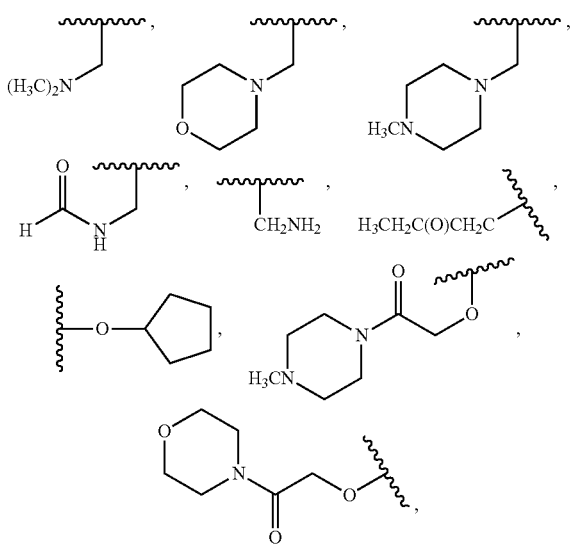

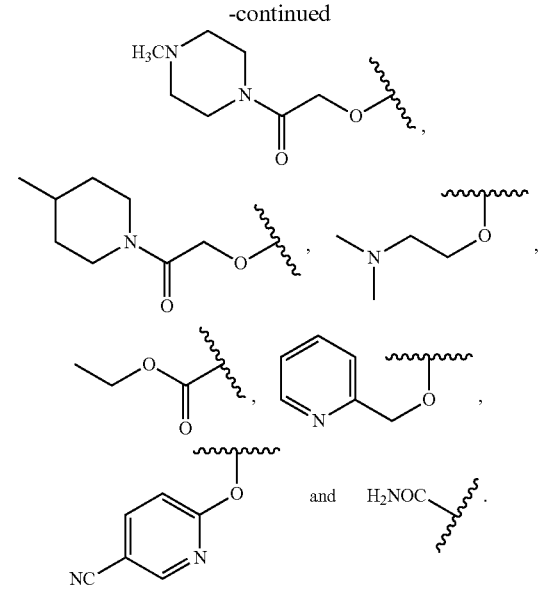

In an exemplary embodiment, the compound has a structure according to the formula

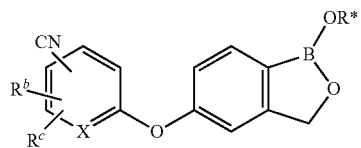

wherein X, R*, $R^b$ and $R^c$ are as described herein.

In an exemplary embodiment, at least one of $R^b$ and $R^c$ is a member selected from halogen, haloalkyl, —C(O)R$^4$, —C(O)OR$^4$, —C(O)NR$^4$R$^5$, —CH$_2$C(O)OR$^4$, —CH$_2$NHC(O)R$^4$ and OR$^4$, wherein R$^4$ and R$^5$ are members independently selected from H and substituted or unsubstituted alkyl In an exemplary embodiment, at least one of $R^b$ and $R^c$ is a member selected from F, Cl, methyl, trifluoromethyl, —CH$_2$OH, —CH$_2$N(CH$_3$)$_2$, —OH, —OCH$_3$, —OCH$_2$CH$_3$, —OCH$_2$CH$_2$OCH$_3$, —OCH$_2$C(O)OH, —OCH$_2$C(O)OCH$_2$CH$_3$, —OCH$_2$C(O)OC(CH$_3$)$_3$, —C(O)OCH$_3$, —C(O)OH, —C(O)H, —OCH$_2$C(O)N(CH$_2$CH$_3$)$_2$,

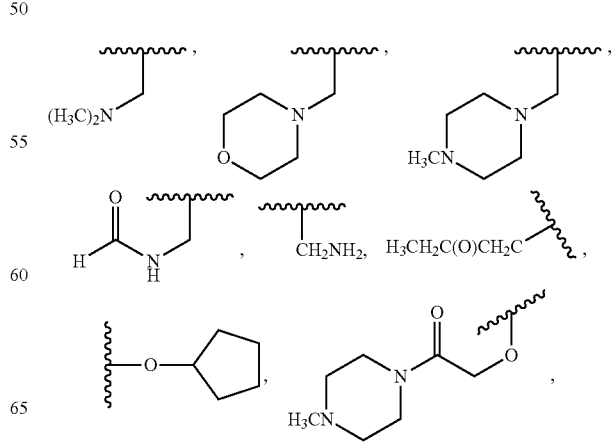

-continued

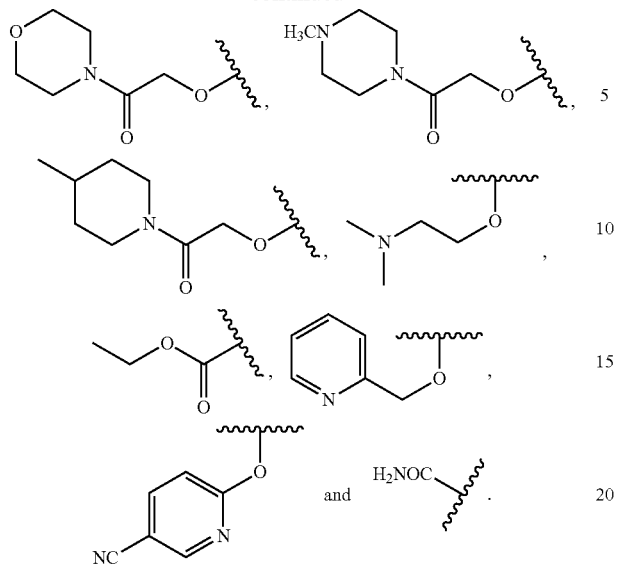

In an exemplary embodiment, the compound has a structure according to the formula:

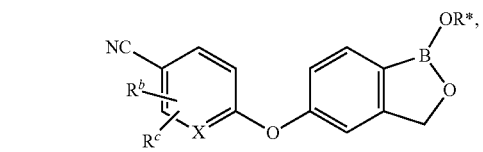

wherein X, R*, R$^b$ and R$^c$ are as described herein.

In an exemplary embodiment, at least one of R$^b$ and R$^c$ is a member selected from F, Cl, methyl, trifluoromethyl, —CH$_2$OH, —CH$_2$N(CH$_3$)$_2$, —OH, —OCH$_3$, —OCH$_2$CH$_3$, —OCH$_2$C(O)OH, —OCH$_2$CH$_2$OCH$_3$, —OCH$_2$C(O)OCH$_2$CH$_3$, —OCH$_2$C(O)OC(CH$_3$)$_3$, —C(O)OCH$_3$, —C(O)OH, —C(O)H, —OCH$_2$C(O)N(CH$_2$CH$_3$)$_2$,

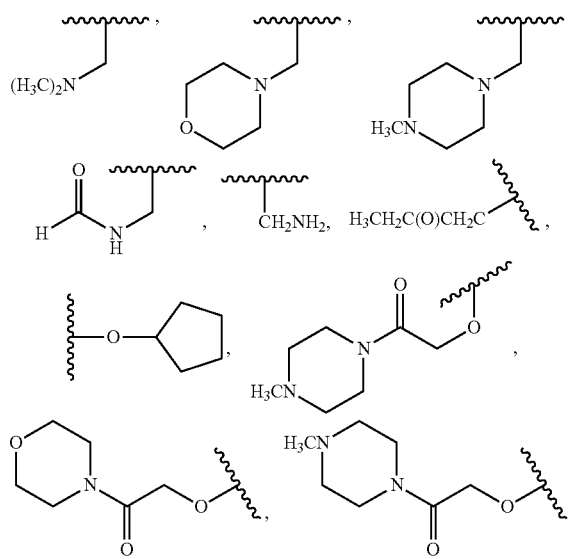

-continued

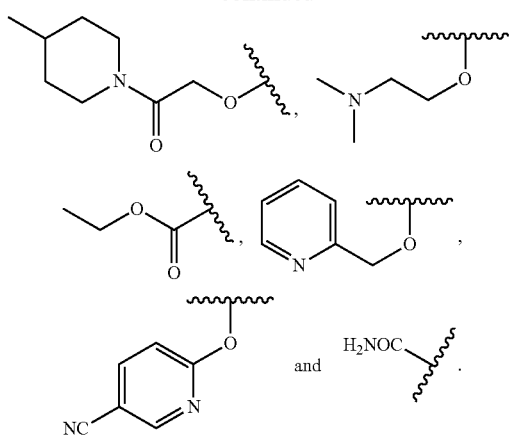

In an exemplary embodiment, R$^c$ is H, and R$^b$ is a member selected from F, Cl, methyl, trifluoromethyl, —CH$_2$OH, —CH$_2$N(CH$_3$)$_2$, —OH, —OCH$_3$, —OCH$_2$CH$_3$, —OCH$_2$C(O)OH, —OCH$_2$CH$_2$OCH$_3$, —OCH$_2$C(O)OCH$_2$CH$_3$, —OCH$_2$C(O)OC(CH$_3$)$_3$, —C(O)OCH$_3$, —C(O)OH, —C(O)H, —OCH$_2$C(O)N(CH$_2$CH$_3$)$_2$,

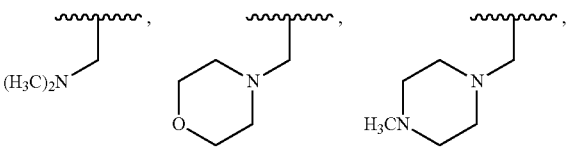

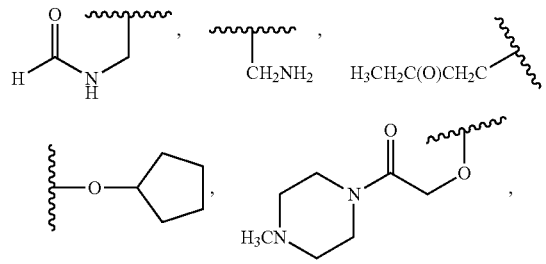

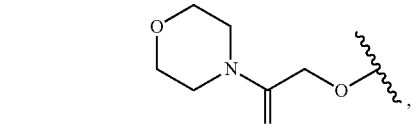

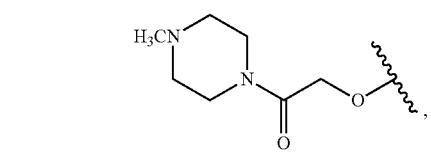

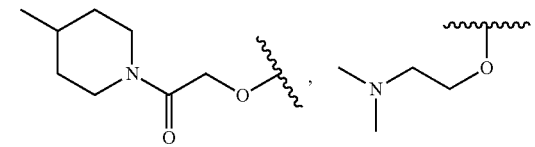

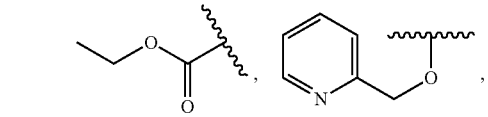

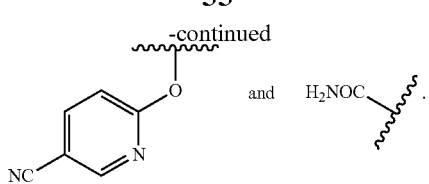

In an exemplary embodiment, the compound has a structure according to the formula:

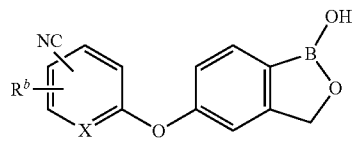

wherein X is N or CH or $CR^b$, $R^b$ is a member selected from halogen and substituted or unsubstituted alkyl, $C(O)R^4$, $C(O)OR^4$, $OR^4$, $NR^4R^5$, wherein $R^4$ and $R^5$ are members independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, with the proviso that $R^4$ and $R^5$, together with the atoms to which they are attached, are optionally combined to form a 5- to 7-membered substituted or unsubstituted heterocycloalkyl ring, and salts thereof. In an exemplary embodiment, $R^b$ is a member selected from $OR^4$ and $NR^4R^5$, wherein $R^4$ and $R^5$ are members independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, with the proviso that $R^4$ and $R^5$, together with the atoms to which they are attached, are optionally combined to form a 5- to 7-membered substituted or unsubstituted heterocycloalkyl ring.

In an exemplary embodiment, $R^b$ is alkyl, optionally substituted with a member selected from halogen, $OR^{4a}$, $C(O)OR^{4a}$, $NR^{4a}R^{4b}$, substituted or unsubstituted heterocycloalkyl or unsubstituted heteroaryl, wherein $R^{4a}$ and $R^{4b}$ are independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{4a}$ is H or unsubstituted alkyl. In an exemplary embodiment, $R^{4b}$ is H or unsubstituted alkyl or $C(O)H$. In an exemplary embodiment, $R^b$ is fluoro. In an exemplary embodiment, $R^b$ is chloro.

In an exemplary embodiment, $R^b$ is OH. In an exemplary embodiment, $R^b$ is $OR^4$, wherein $R^4$ is alkyl is optionally substituted with at least one halogen, hydroxyl, ether, carboxy or ester moiety.

In an exemplary embodiment, $R^b$ is $OR^4$, wherein $R^4$ is unsubstituted alkyl. In an exemplary embodiment, $R^b$ is $OR^4$, wherein $R^4$ is unsubstituted $C_1$ or $C_2$ or $C_3$ alkyl. In an exemplary embodiment, $R^b$ is $OR^4$, wherein $R^4$ is unsubstituted $C_4$ or $C_5$ or $C_6$ alkyl. In an exemplary embodiment, $R^b$ is $OR^4$, wherein $R^4$ is methyl or ethyl or propyl or isopropyl or isobutyl.

In an exemplary embodiment, $R^b$ is $OR^4$, wherein $R^4$ is alkyl substituted with at least one halogen. In an exemplary embodiment, $R^b$ is $OR^4$, wherein $R^4$ is alkyl substituted with one or two or three halogen(s). In an exemplary embodiment, $R^b$ is $O(CH_2)_{m1}R^{31}$, wherein m1 is 1 or 2 or 3 or 4 or 5 or 6 and $R^{31}$ is a methyl moiety wherein at least one of the methyl hydrogens is substituted with a halogen. In an exemplary embodiment, the halogen is chloro. In an exemplary embodiment, the halogen is fluoro. In an exemplary embodiment, $R^{31}$ is $—CF_3$. In an exemplary embodiment, $R^{31}$ is $—CHF_2$. In an exemplary embodiment, m1 is 1 or 2 or 3. In an exemplary embodiment, $R^b$ is $—OCH_2CF_3$. In an exemplary embodiment, $R^b$ is $—OCH_2CHF_2$.

In an exemplary embodiment, $R^b$ is $—O(CH_2)_{m1}OC(O)R^{4d}$, wherein m1 is a number selected from 1 or 2 or 3 or 4 or 5 or 6 and $R^{4d}$ is unsubstituted alkyl. In an exemplary embodiment, m1 is 1 or 2 or 3. In an exemplary embodiment, m1 is 2. In an exemplary embodiment, $R^{4d}$ is unsubstituted $C_1$ or $C_2$ or $C_3$ alkyl. In an exemplary embodiment, $R^{4d}$ is unsubstituted $C_4$ or $C_5$ or $C_6$ alkyl. In an exemplary embodiment, $R^{4d}$ is methyl. In an exemplary embodiment, $R^b$ is $—O(CH_2)_2OC(O)CH_3$.

In an exemplary embodiment, $R^b$ is $—O(CH_2)_{m1}C(O)R^{4d}$, wherein m1 is a number selected from 1 or 2 or 3 or 4 or 5 or 6 and $R^{4d}$ is unsubstituted alkyl. In an exemplary embodiment, m1 is 2 or 3 or 4. In an exemplary embodiment, m1 is 3. In an exemplary embodiment, $R^{4d}$ is unsubstituted $C_1$ or $C_2$ or $C_3$ alkyl. In an exemplary embodiment, $R^{4d}$ is unsubstituted $C_4$ or $C_5$ or $C_6$ alkyl. In an exemplary embodiment, $R^{4d}$ is methyl. In an exemplary embodiment, $R^b$ is $—O(CH_2)_3C(O)CH_3$.

In an exemplary embodiment, $R^b$ is $—O(CH_2)_{m1}C(O)OR^{4d}$, wherein m1 is a number selected from 1 or 2 or 3 or 4 or 5 or 6 and $R^{4d}$ is H or unsubstituted alkyl. In an exemplary embodiment, $R^b$ is $—OCH_2C(O)OR^{4d}$, wherein $R^{4d}$ is as described herein. In an exemplary embodiment, $R^{4d}$ is H or methyl or ethyl or t-butyl. In an exemplary embodiment, $R^b$ is $—O(CH_2)C(O)OCH_2CH_3$ or $—O(CH_2)C(O)OH$ or $—O(CH_2)C(O)OC(CH_3)_3$.

In an exemplary embodiment, $R^b$ is $OR^4$, wherein $R^4$ is alkyl substituted with a substituted or unsubstituted amino. In an exemplary embodiment, $R^b$ is $—O(CH_2)_{m2}C(O)NR^{4e}R^{4f}$, wherein m2 is a number selected from 1 or 2 or 3 or 4 or 5 or 6, and $R^{4e}$ and $R^{4f}$ are independently selected from H or unsubstituted alkyl, or $R^{4e}$ and $R^{4f}$, together with the nitrogen to which they are attached, are optionally joined to form a substituted or unsubstituted 4 to 8 membered ring.

In an exemplary embodiment, $R^b$ is $—OCH_2C(O)NR^{4e}R^{4f}$, wherein $R^{4e}$ and $R^{4f}$ are as described herein. In an exemplary embodiment, $R^{4e}$ and $R^{4f}$ are the same and are independently selected unsubstituted alkyl. In an exemplary embodiment, $R^{4e}$ and $R^{4f}$ are different and are independently selected unsubstituted alkyl. In an exemplary embodiment, $R^{4e}$ is H. In an exemplary embodiment, $R^{4f}$ is H. In an exemplary embodiment, $R^{4e}$ and $R^{4f}$ are ethyl. In an exemplary embodiment, $R^{4e}$ and $R^{4f}$, together with the nitrogen to which they are attached, are joined to form piperazinyl, either unsubstituted or substituted with unsubstituted alkyl on the nitrogen at the 4-position. In an exemplary embodiment, $R^{4e}$ and $R^{4f}$, together with the nitrogen to which they are attached, are joined to form N-methyl piperazinyl. In an exemplary embodiment, $R^{4e}$ and $R^{4f}$, together with the nitrogen to which they are attached, are joined to form piperidinyl, either unsubstituted or substituted with unsubstituted alkyl. In an exemplary embodiment, $R^{4e}$ and $R^{4f}$, together with the nitrogen to which they are attached, are joined to form 4-methyl piperidinyl. In an exemplary embodiment, $R^{4e}$ and $R^{4f}$, together with the nitrogen to which they are attached, are joined to form unsubstituted morpholinyl.

In an exemplary embodiment, $R^b$ is $OR^4$, wherein $R^4$ is unsubstituted alkyl. In an exemplary embodiment, $R^4$ is $C_1$ or $C_2$ or $C_3$ or $C_4$ or $C_5$ or $C_6$ alkyl. In an exemplary embodiment, $R^4$ is $C_1$ alkyl. In an exemplary embodiment, $R^b$ is $OR^4$, wherein $R^4$ is alkyl substituted with unsubstituted pyridinyl. In an exemplary embodiment, $R^b$ is

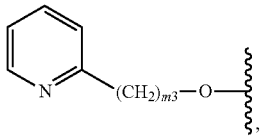

wherein m3 is 1 or 2 or 3 or 4 or 5 or 6. In an exemplary embodiment, m3 is 1.

In an exemplary embodiment, $R^b$ is $OR^4$, wherein $R^4$ is substituted or unsubstituted cycloalkyl. In an exemplary embodiment, $R^b$ is $OR^4$, wherein $R^4$ is unsubstituted cycloalkyl. In an exemplary embodiment, $R^b$ is $OR^4$, wherein $R^4$ is cyclopenyl. In an exemplary embodiment, $R^4$ is unsubstituted cyclohexyl.

In an exemplary embodiment, $R^b$ is $OR^4$, wherein $R^4$ is alkyl substituted with unsubstituted alkoxy. In an exemplary embodiment, $R^b$ is —O(CH$_2$)$_{m5}$OR$^{30}$, wherein m5 is 1 or 2 or 3 or 4 or 5 or 6 and $R^{30}$ is H or unsubstituted alkyl or unsubstituted tetrahydropyran. In an exemplary embodiment, $R^{30}$ is $C_1$ or $C_2$ or $C_3$ or $C_4$ or $C_5$ or $C_6$ alkyl. In an exemplary embodiment, m5 is 1 or 2 or 3. In an exemplary embodiment, m5 is 2. In an exemplary embodiment, $R^{30}$ is $C_1$ or $C_2$ or $C_3$ alkyl. In an exemplary embodiment, $R^{30}$ is $C_4$ or $C_5$ or $C_6$ alkyl. In an exemplary embodiment, $R^{30}$ is H. In an exemplary embodiment, $R^{30}$ is methyl or isopropyl. In an exemplary embodiment, $R^{30}$ is 2-tetrahydropyran. In an exemplary embodiment, $R^b$ is —O(CH$_2$)$_2$OC(CH$_3$)$_2$ or —O(CH$_2$)$_2$OH or —O(CH$_2$)$_2$O-THP (TetraHydroPyran).

In an exemplary embodiment, $R^b$ is $OR^4$, wherein $R^4$ is alkyl substituted with unsubstituted cycloalkyl. In an exemplary embodiment, $R^b$ is —O(CH$_2$)$_{m5}$OR$^{30}$, wherein m5 is 1 or 2 or 3 or 4 or 5 or 6 and $R^{30}$ is a 3-8 membered cycloalkyl. In an exemplary embodiment, $R^{30}$ is a 3-6 membered cycloalkyl. In an exemplary embodiment, $R^{30}$ is a member selected from cyclopropyl and cyclopentyl. In an exemplary embodiment, m5 is 1 or 2 or 3. In an exemplary embodiment, m5 is 1.

In an exemplary embodiment, $R^b$ is $C(O)R^4$, wherein $R^4$ is unsubstituted alkyl. In an exemplary embodiment, $R^4$ is $C_1$ or $C_2$ or $C_3$ or $C_4$ or $C_5$ or $C_6$ alkyl. In an exemplary embodiment, $R^4$ is $C_1$ alkyl. In an exemplary embodiment, $R^b$ is $C(O)H$. In an exemplary embodiment, $R^b$ is $C_1$ or $C_2$ or $C_3$ or $C_4$ or $C_5$ or $C_6$ alkyl. In an exemplary embodiment, $R^b$ is $C_1$ alkyl. In an exemplary embodiment, $R^b$ is alkyl substituted with halogen. In an exemplary embodiment, $R^b$ is alkyl substituted with at least one halogen. In an exemplary embodiment, $R^b$ is alkyl substituted with at least one fluoro. In an exemplary embodiment, $R^b$ is $CF_3$.

In an exemplary embodiment, $R^b$ is alkyl substituted with hydroxy. In an exemplary embodiment, $R^b$ is —(CH$_2$)$_{m4}$OH, wherein m4 is a number selected from 1 or 2 or 3 or 4 or 5 or 6. In an exemplary embodiment, m4 is 1.

In an exemplary embodiment, $R^b$ is alkyl substituted with carboxy or ester. In an exemplary embodiment, $R^b$ is —(CH$_2$)$_{m1}$C(O)OR$^{4a}$, wherein m1 is a number selected from 1 or 2 or 3 or 4 or 5 or 6 and $R^{4a}$ is H or unsubstituted alkyl.

In an exemplary embodiment, $R^b$ is —CH$_2$C(O)OR$^{4a}$, wherein $R^{4a}$ is as described herein. In an exemplary embodiment, $R^{4a}$ is H or methyl or ethyl or t-butyl.

In an exemplary embodiment, $R^b$ is alkyl substituted with amino. In an exemplary embodiment, $R^b$ is —(CH$_2$)$_{m7}$NR$^{4a}$R$^{4b}$, wherein m7 is a number selected from 1 or 2 or 3 or 4 or 5 or 6 and R$^{4a}$ and R$^{4b}$ are members independently selected from H and unsubstituted alkyl and formyl, or R$^{4a}$ and R$^{4b}$, together with the nitrogen to which they are attached, are optionally joined to form a substituted or unsubstituted 4 to 8 membered ring. In an exemplary embodiment, R$^{4b}$ is as described herein, R$^{4a}$ is H. In an exemplary embodiment, R$^{4a}$ is as described herein, R$^{4b}$ is H. In an exemplary embodiment, R$^{4b}$ is as described herein, R$^{4a}$ is methyl. In an exemplary embodiment, R$^{4a}$ is as described herein, R$^{4b}$ is methyl. In an exemplary embodiment, m7 is 1. In an exemplary embodiment, R$^{4a}$ and R$^{4b}$, together with the nitrogen to which they are attached, are joined to form piperazinyl, either unsubstituted or substituted with unsubstituted alkyl on the nitrogen at the 4-position. In an exemplary embodiment, R$^{4a}$ and R$^{4b}$, together with the nitrogen to which they are attached, are joined to form N-methyl piperazinyl. In an exemplary embodiment, R$^{4a}$ and R$^{4b}$, together with the nitrogen to which they are attached, are joined to form piperidinyl, either unsubstituted or substituted with unsubstituted alkyl. In an exemplary embodiment, R$^{4a}$ and R$^{4b}$, together with the nitrogen to which they are attached, are joined to form 4-methyl piperidinyl. In an exemplary embodiment, R$^{4a}$ and R$^{4b}$, together with the nitrogen to which they are attached, are joined to form unsubstituted morpholinyl.

In an exemplary embodiment, $R^b$ is NH$_2$. In an exemplary embodiment, $R^b$ is NR$^4$R$^5$ wherein R$^4$ is a member selected from H and unsubstituted alkyl, and R$^5$ is a member selected from substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, R$^b$ is NR$^4$R$^5$, R$^4$ is as described herein, R$^5$ is unsubstituted alkyl. In an exemplary embodiment, R$^b$ is NR$^4$R$^5$, wherein R$^4$ is H, R$^5$ is as described herein. In an exemplary embodiment, R$^b$ is NR$^4$R$^5$, wherein R$^4$ is unsubstituted alkyl, R$^5$ is as described herein. In an exemplary embodiment, R$^b$ is NR$^4$R$^5$, wherein R$^5$ is as described herein, R$^4$ is unsubstituted $C_1$ or $C_2$ or $C_3$ or $C_4$ or $C_5$ or $C_6$ alkyl. In an exemplary embodiment, R$^b$ is NR$^4$R$^5$, wherein R$^4$ is unsubstituted $C_1$ or $C_2$ or $C_3$ alkyl and R$^5$ is as described herein. In an exemplary embodiment, R$^b$ is NR$^4$R$^5$, wherein R$^4$ is methyl and R$^5$ is as described herein. In an exemplary embodiment, R$^b$ is NR$^4$R$^5$, wherein R$^4$ is as described herein R$^5$ is unsubstituted $C_1$ or $C_2$ or $C_3$ or $C_4$ or $C_5$ or $C_6$ alkyl. In an exemplary embodiment, R$^b$ is NR$^4$R$^5$, wherein R$^5$ is a member selected from methyl and tert-butyl, and R$^4$ is as described herein.

In an exemplary embodiment, R$^b$ is NR$^4$R$^5$, wherein R$^4$ is as described herein, R$^5$ is alkyl, substituted with a member selected from OH, unsubstituted arylalkoxy, unsubstituted alkoxy, and unsubstituted aryl. In an exemplary embodiment, R$^b$ is NR$^4$R$^5$, wherein R$^5$ is —(CH$_2$)$_{m8}$Ph.

In an exemplary embodiment, R$^b$ is NR$^4$R$^5$, wherein R$^5$ is —(CH$_2$)$_{m8}$OR$^{26}$, wherein m8 is a number selected from 1 or 2 or 3 or 4 or 5 or 6 and R$^{26}$ is a member selected from H, unsubstituted or arylsubstituted $C_1$ or $C_2$ or $C_3$ or $C_4$ or $C_5$ or $C_6$ alkyl. In an exemplary embodiment, m8 is 1 or 2 or 3. In an exemplary embodiment, m8 is 2. In an exemplary embodiment, R$^{26}$ is unsubstituted $C_1$ or $C_2$ or $C_3$ or $C_4$ or $C_5$ or $C_6$ alkyl. In an exemplary embodiment, R$^{26}$ is methyl. In an exemplary embodiment, R$^{26}$ is benzyl. In an exemplary embodiment, $R^b$ is $NR^4R^5$, wherein $R^4$ is as described herein, $R^5$ is —$(CH_2)_{m8}O(CH_2)_{m9}Ph$, wherein m8 and m9 are each independently selected from 1 or 2 or 3 or 4 or 5 or 6. In an exemplary embodiment, $R^b$ is $NR^4R^5$, wherein $R^4$ is as described herein $R^5$ is —$(CH_2)_{m8}O(CH_2)_{m9}Ph$, wherein m8 and m9 are each independently selected from 1 or 2 or 3. In an exemplary embodiment, $R^b$ is $NR^4R^5$, wherein $R^4$ is as described herein, $R^5$ is —$(CH_2)_{m8}O(CH_2)Ph$. In an exemplary embodiment, $R^b$ is $NR^4R^5$, wherein $R^4$ is as described herein $R^5$ is —$(CH_2)_2O(CH_2)_{m9}Ph$. In an exemplary embodiment, $R^b$ is $NR^4R^5$, wherein $R^4$ is as described herein $R^5$ is —$(CH_2)_2O(CH_2)Ph$.

In an exemplary embodiment, $R^b$ is a member selected from —$NH(CH_2)_2OH$, —$NH(CH_2)_2OCH_3$, —$NHCH_3$, —$NHC(CH_3)_3$, —$NH(CH_2)Ph$, —$NH(CH_2)_2O(CH_2)Ph$.

In an exemplary embodiment, $R^b$ is a member selected from —$N(CH_3)_2$, —$N(CH_3)(CH_2)_2OH$, —$N(CH_3)(CH_2)_2OCH_3$, —$NHCH_3$, —$NHC(CH_3)_3$, —$NH(CH_2)Ph$, —$NH(CH_2)_2O(CH_2)Ph$.

In an exemplary embodiment, $R^b$ is —$NR^4R^5$, wherein $R^4$ and $R^5$, together with the nitrogen to which they are attached, are joined to form a substituted or unsubstituted 4 to 8 membered ring. In an exemplary embodiment, the only non-carbon atom which forms the ring is the nitrogen to which $R^4$ and $R^5$ are attached. In an exemplary embodiment, $R^b$ is —$NR^4R^5$, wherein $R^4$ and $R^5$, together with the nitrogen to which they are attached, are joined to form a member selected from substituted or unsubstituted pyrrolidinyl and substituted or unsubstituted piperidinyl. In an exemplary embodiment, $R^b$ is —$NR^4R^5$, wherein $R^4$ and $R^5$, together with the nitrogen to which they are attached, are joined to form a member selected from unsubstituted pyrrolidinyl and unsubstituted piperidinyl. In an exemplary embodiment, the only non-carbon atom which forms the ring is nitrogen. In an exemplary embodiment, the ring contains one nitrogen atom and one oxygen atom. In an exemplary embodiment, the ring contains one nitrogen atom and one oxygen atom. In an exemplary embodiment, $R^b$ is —$NR^4R^5$, wherein $R^4$ and $R^5$, together with the nitrogen to which they are attached, are joined to form substituted or unsubstituted morpholinyl. In an exemplary embodiment, $R^b$ is —$NR^4R^5$, wherein $R^4$ and $R^5$, together with the nitrogen to which they are attached, are joined to form unsubstituted morpholinyl.

In an exemplary embodiment, the compound has a structure according to the following formula:

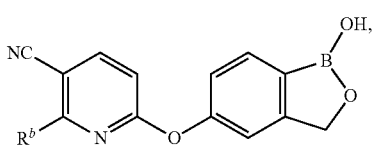

and salts thereof, wherein $R^b$ is as described herein.

In an exemplary embodiment, the compound has a structure according to the following formula:

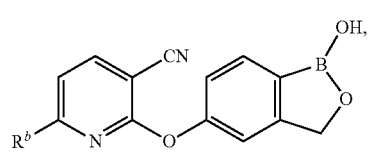

and salts thereof, wherein $R^b$ is as described herein.

In an exemplary embodiment, the compound has a structure according to the following formula:

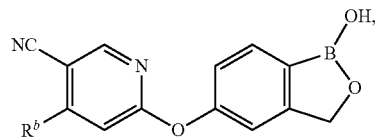

and salts thereof, wherein $R^b$ is as described herein.

In an exemplary embodiment, the compound has a structure according to the following formula:

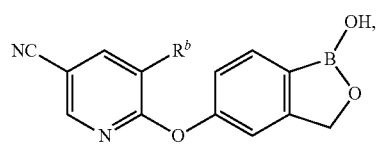

and salts thereof, wherein $R^b$ is as described herein.

In an exemplary embodiment, the compound has a structure according to the following formula:

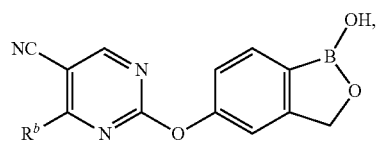

and salts thereof, wherein $R^b$ is as described herein.

In an exemplary embodiment, the compound has a structure according to the following formula:

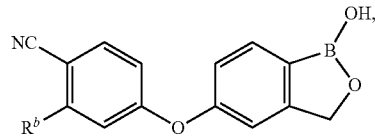

and salts thereof, wherein $R^b$ is as described herein.

In an exemplary embodiment, the compound has a structure according to the following formula:

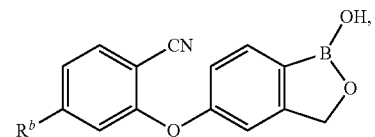

and salts thereof, wherein $R^b$ is as described herein.

In an exemplary embodiment, the compound has a structure according to the following formula:

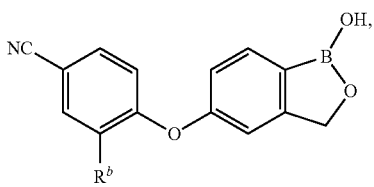

and salts thereof, wherein $R^b$ is as described herein.

In an exemplary embodiment, the compound is a member selected from D46, D86, D99, D100, D107, D108, D114, D122, D125, D126, D127, D128, D131, D140 and D141, and salts thereof. In an exemplary embodiment, the compound is a member selected from D95, D96, D97, D102, D110, D111, D113, D115, D121, D129, D130, D132, and salts thereof. In an exemplary embodiment, the compound is a member selected from D47, D109, D116, D118, D119, D120, D123, and salts thereof. In an exemplary embodiment, the compound is a member selected from D98, D101, D106, and salts thereof. In an exemplary embodiment, the compound is a member selected from D11, D12, D37, D38, D39, D40, D41, D42, D43, D124, D142, D143, D146, and salts thereof. In an exemplary embodiment, the compound is a member selected from D14, D15, D16, D17, D28, D29, D30, D31, D133, D134, D135, D144, D145, D147, and salts thereof.

In an exemplary embodiment, the compound has a structure which is a member selected from

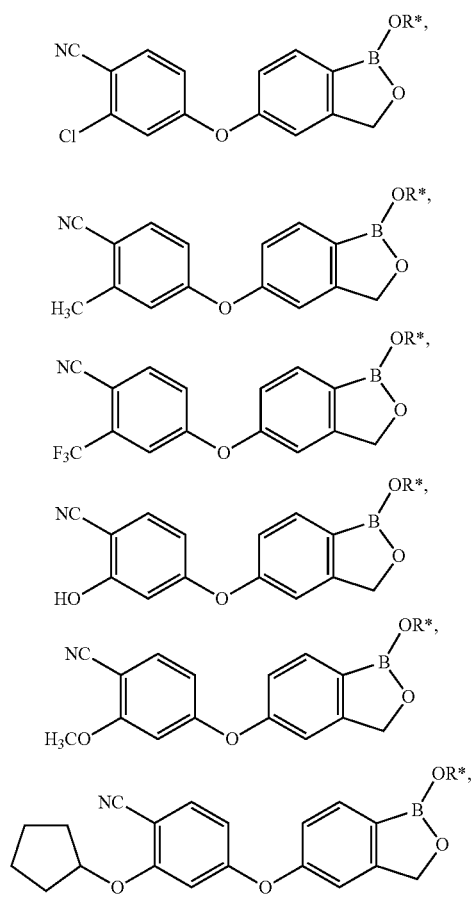

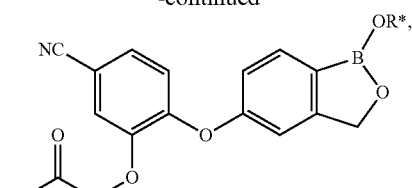
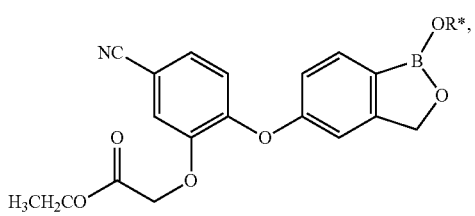
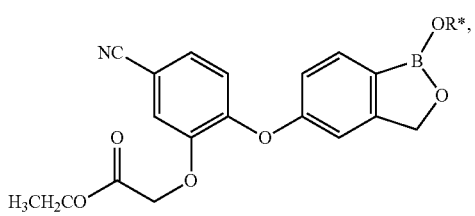
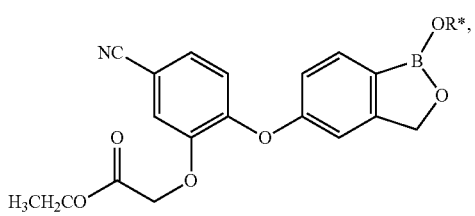
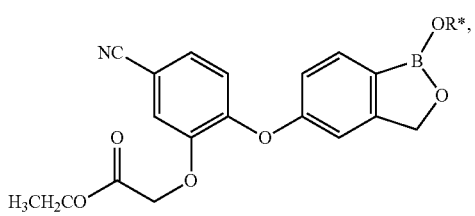
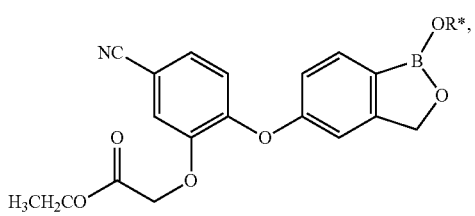
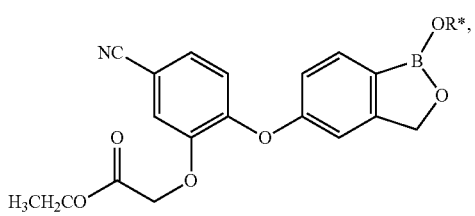
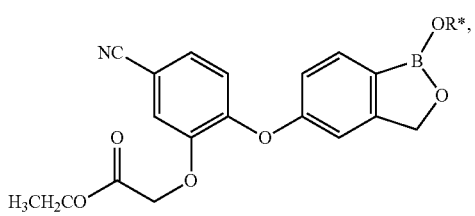
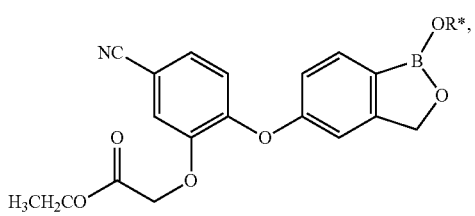
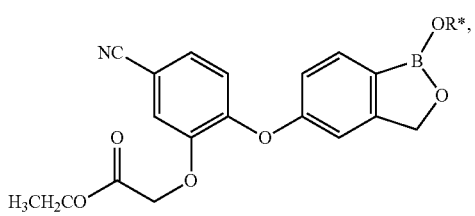
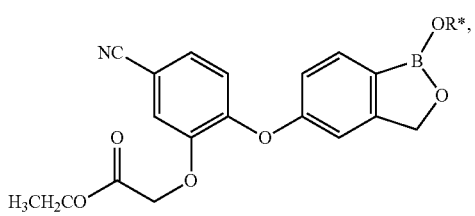
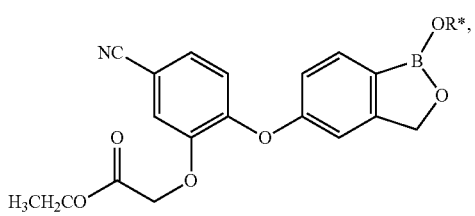
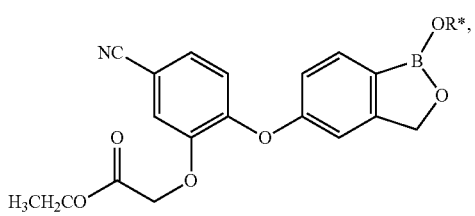

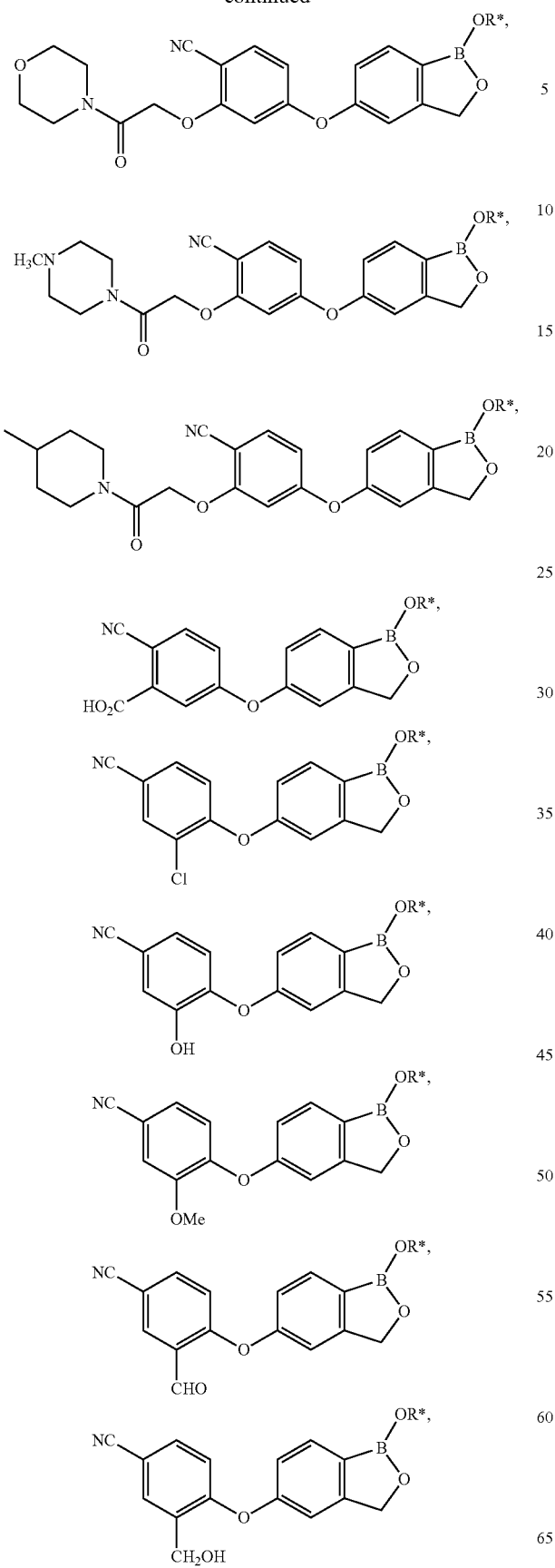
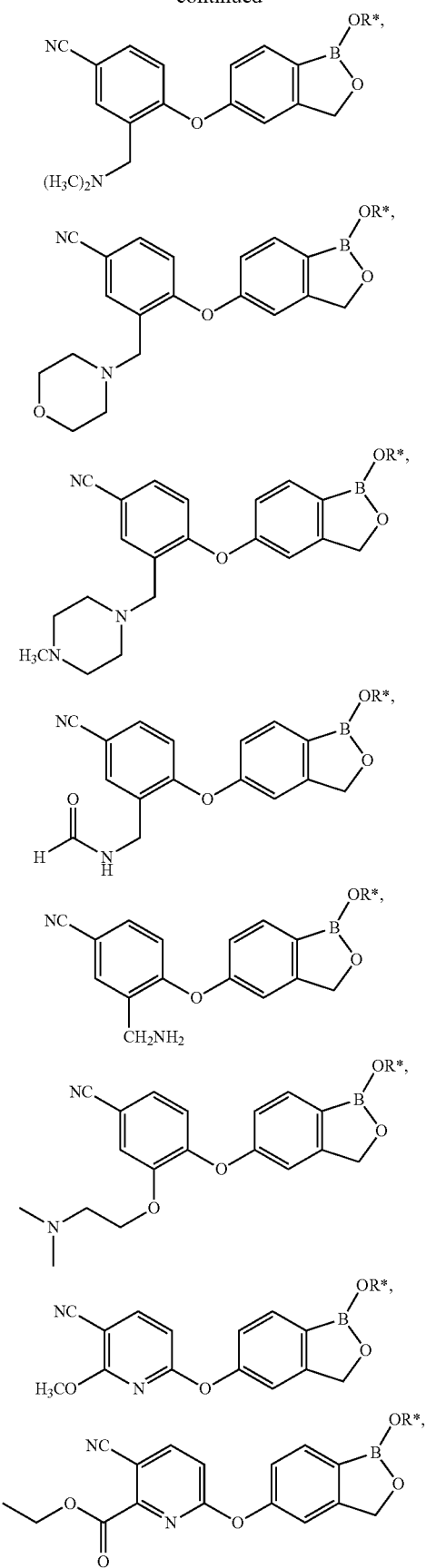

-continued

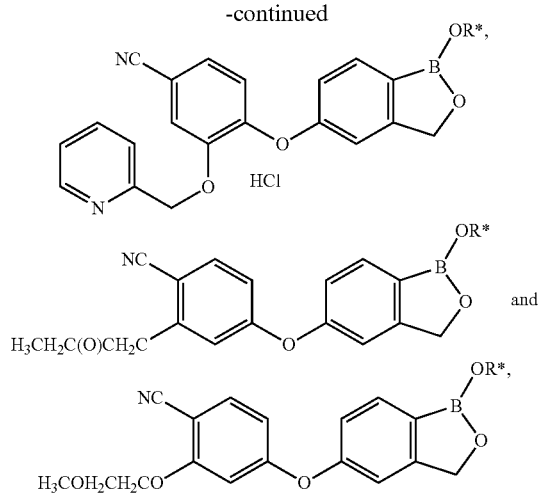

wherein R* is as defined herein.

In an exemplary embodiment, the compound has a structure according to the formula:

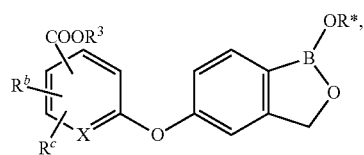

wherein $R^3$, X, R*, $R^b$ and $R^c$ are as described herein.

In an exemplary embodiment, $R^3$ is H. In an exemplary embodiment, $R^3$ is unsubstituted alkyl. In an exemplary embodiment, $R^3$ is methyl. In an exemplary embodiment, $R^3$ is $C_2$ alkyl. In an exemplary embodiment, $R^3$ is $C_3$ alkyl. In an exemplary embodiment, $R^3$ is $C_4$ alkyl. In an exemplary embodiment, $R^3$ is $C_5$ alkyl. In an exemplary embodiment, $R^3$ is $C_6$ alkyl.

In an exemplary embodiment, at least one of $R^b$ and $R^c$ is a member selected from —C(O)NR$^4$R$^5$, —C(O)OR$^4$, —CH$_2$C(O)OR$^4$, —CH$_2$NHC(O)R$^4$ and OR$^4$, wherein each $R^4$ and $R^5$ is a member independently selected from H, substituted or unsubstituted alkyl, substituted or unsubstituted cycloalkyl and substituted or unsubstituted heteroaryl.

In an exemplary embodiment, at least one of $R^b$ and $R^c$ is a member selected from F, Cl, methyl, trifluoromethyl, —CH$_2$OH, —CH$_2$N(CH$_3$)$_2$, —OH, —OCH$_3$, —OCH$_2$CH$_3$, —OCH$_2$C(O)OH, —OCH$_2$C(O)OCH$_2$CH$_3$, —OCH$_2$C(O)OC(CH$_3$)$_3$, —C(O)OCH$_3$, —C(O)OH, —C(O)H, —OCH$_2$C(O)N(CH$_2$CH$_3$)$_2$,

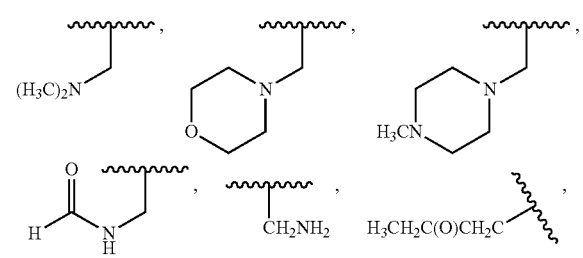

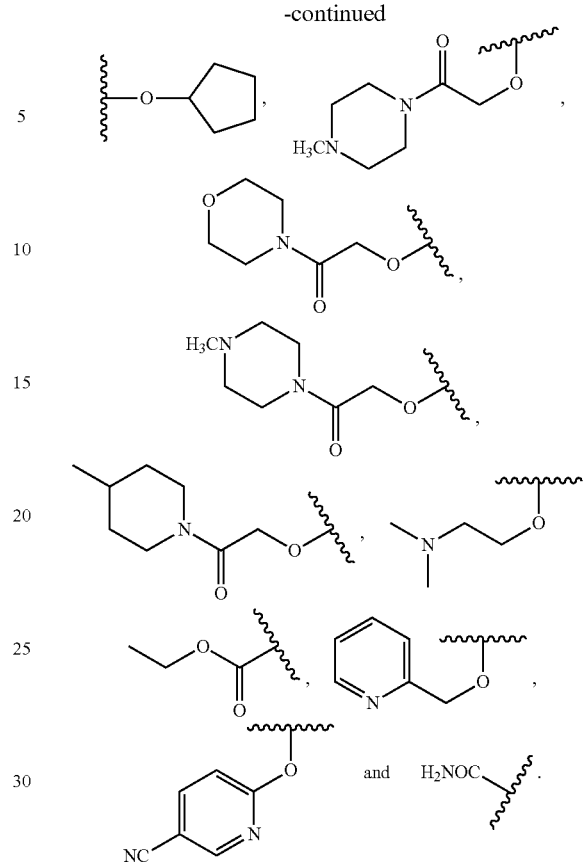

In an exemplary embodiment, the compound has a structure according to the formula:

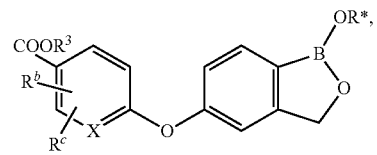

wherein $R^3$, X, R*, $R^b$ and $R^c$ are as described herein.

In an exemplary embodiment, at least one of $R^b$ and $R^c$ is a member selected from —C(O)NH$_2$, —OH, —OCH$_3$, cyclopropyloxy and 4-cyanopyridin-2-yloxy.

In an exemplary embodiment, the compound has a structure according to the formula:

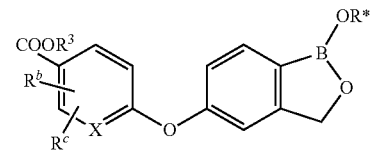

wherein $R^3$, X, R* are as described herein, and at least one of $R^b$ and $R^c$ is a member selected from F, Cl, methyl, trifluoromethyl, —CH$_2$OH, —CH$_2$N(CH$_3$)$_2$, —OH, —OCH$_3$, —OCH$_2$CH$_3$, —OCH$_2$C(O)OH, —OCH$_2$C(O)OCH$_2$CH$_3$, —OCH$_2$C(O)OC(CH$_3$)$_3$, —C(O)OCH$_3$, —C(O)OH, —C(O)H, —OCH$_2$C(O)N(CH$_2$CH$_3$)$_2$,

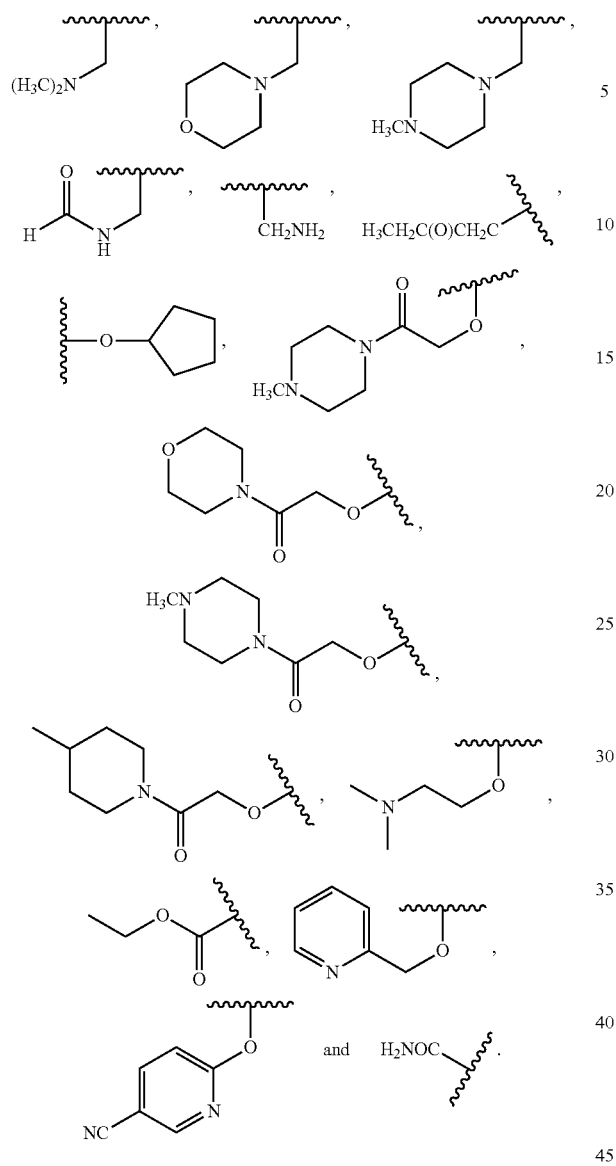

In an exemplary embodiment, the compound has a structure according to the formula:

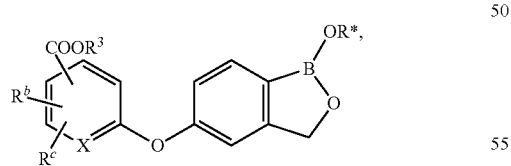

wherein $R^3$, X and R* are as described herein, and at least one of $R^b$ and $R^c$ is a member selected from —C(O)NR$^4$R$^5$, —C(O)OR$^4$, —CH$_2$C(O)OR$^4$, —CH$_2$NHC(O)R$^4$ and OR$^4$, wherein each $R^4$ and $R^5$ is a member independently selected from H, substituted or unsubstituted alkyl, substituted or unsubstituted cycloalkyl and substituted or unsubstituted heteroaryl.

In an exemplary embodiment, the compound has a formula which is a member selected from

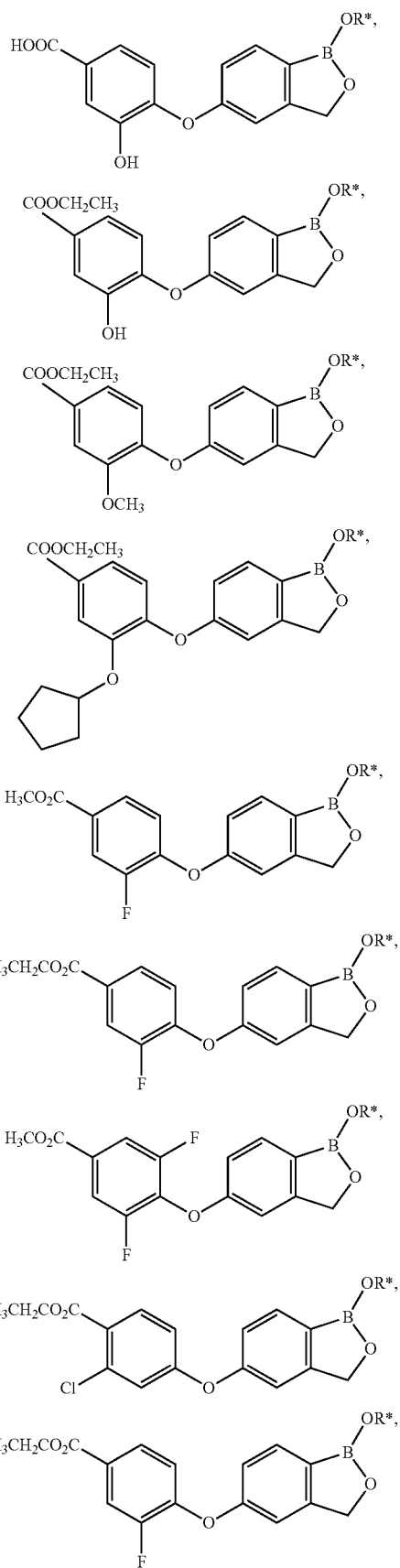

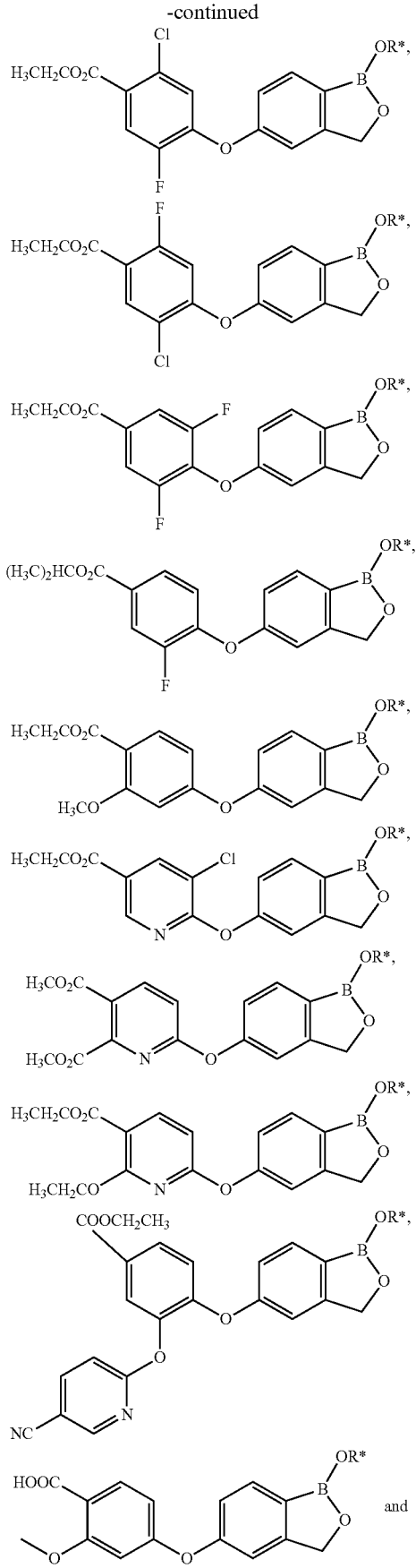

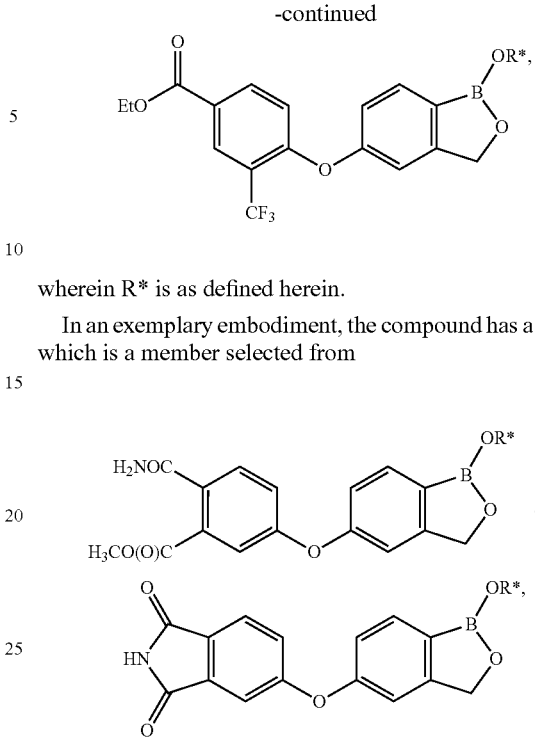

wherein R* is as defined herein.

In an exemplary embodiment, the compound has a formula which is a member selected from wherein R* is as described herein.

IIIb. Soft Drugs

Soft drugs (or ante-drugs) are therapeutic agents that undergo predictable metabolism to inactive metabolites after exerting their therapeutic effect. Hence, they are obtained by building into the molecule, in addition to the activity, the most desired way in which the molecule is to be deactivated and detoxified.

In a third aspect, the invention provides an oxaborole which comprises an ester attached to its 5-position moiety. These 5-position oxaborole esters are metabolically stable in topical applications (such as the skin or nail) and exert their therapeutic action. The 5-position oxaborole ester is then hydrolyzed by an esterase. Esterases are classified broadly as cholinesterases (including acetylcholinesterases), carboxylesterases and arylesterases. The mechanism involved follows the general formula:

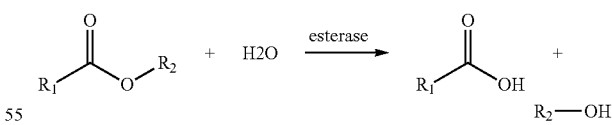

Highly variable esterase activity is present in a wide variety of organs, tissues and body fluids. After hydrolysis, the 5-position oxaborole ester is converted into a 5-position oxaborole acid, which is largely inactive and non-toxic if any drug penetrates the skin and reaches systemic circulation. This so-called soft-drug approach improves the therapeutic index of 5-position oxaborole bioactive compounds.

In a third aspect, the invention provides a compound having a structure according to the formula:

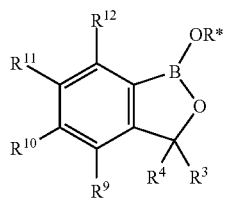

wherein R* is a member selected from H, a negative charge and a positively charged counterion. $R^3$ and $R^4$ are members independently selected from H, cyano, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. $R^9$, $R^{10}$, $R^{11}$ and $R^{12}$ are members independently selected from H, $OR^{20}$, $NR^{20}R^{21}$, $SR^{20}$, —$S(O)R^{20}$, —$S(O)_2R^{20}$, —$S(O)_2NR^{20}R^{21}$, nitro, halogen, cyano, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. Each $R^{20}$ and $R^{21}$ are members independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. $R^3$ and $R^4$, together with the atoms to which they are attached, are optionally joined to form a 4 to 7 membered ring. $R^9$ and $R^{10}$, together with the atoms to which they are attached, are optionally joined to form a 4 to 7 membered ring. $R^{10}$ and $R^{11}$, together with the atoms to which they are attached, are optionally joined to form a 4 to 7 membered ring. $R^{11}$ and $R^{12}$, together with the atoms to which they are attached, are optionally joined to form a 4 to 7 membered ring. $R^{20}$ and $R^{21}$, together with the atoms to which they are attached, are optionally joined to form a 4 to 7 membered ring. There is a proviso that $R^{10}$ comprises a moiety having the structure according to the formula:

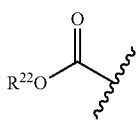

wherein $R^{22}$ is a member selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In an exemplary embodiment, there is the proviso that the compound is not

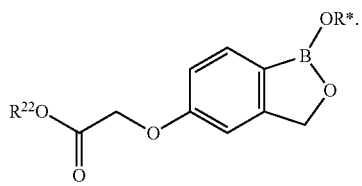

In an exemplary embodiment, there is the proviso that the compound is not

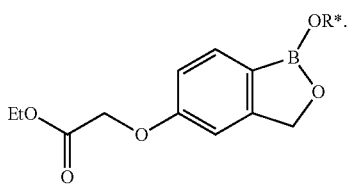

In an exemplary embodiment, $R^{22}$ is H. In an exemplary embodiment, $R^{22}$ is a member selected from substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{22}$ is a member selected from substituted or unsubstituted alkyl, substituted or unsubstituted cycloalkyl, substituted or unsubstituted aryl, and substituted or unsubstituted heteroaryl.

In an exemplary embodiment, there is the proviso that at least one member selected from $R^{10}$ and $R^{11}$ must comprise a moiety having the structure according to the formula:

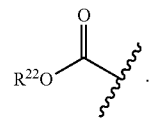

In an exemplary embodiment, $R^{22}$ is a member selected from substituted or unsubstituted methyl, substituted or unsubstituted ethyl, substituted or unsubstituted propyl, substituted or unsubstituted isopropyl, substituted or unsubstituted butyl.

In an exemplary embodiment, the compound has a structure which is a member selected from:

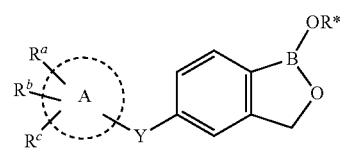

wherein Y is a member selected from S and O; A is a member selected from substituted or unsubstituted aryl and substituted or unsubstituted heteroaryl; $R^a$, $R^b$ and $R^c$ are members independently selected from H, $OR^{20}$, $NR^{20}R^{21}$, $SR^{20}$, —$S(O)R^{20}$, —$S(O)_2R^{20}$, —$S(O)_2NR^{20}R^{21}$, —$C(O)R^{20}$, —$C(O)NR^{20}R^{21}$, —$C(O)OR^{22}$, nitro, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, wherein each $R^{20}$ and $R^{21}$ are members independently selected from H, nitro, halogen, cyano, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, with the proviso that $R^{20}$ and $R^{21}$, together with the atoms to which they are attached, are optionally combined to form a 5- to 7-membered substituted or unsubstituted heterocycloalkyl ring, with the proviso that at least one member selected from $R^a$, $R^b$, $R^c$ comprises —C(O)OR$^{22}$.

In an exemplary embodiment, the compound has a structure which is a member selected from:

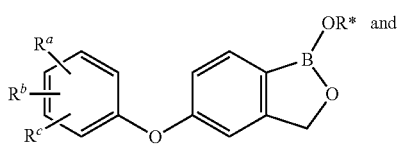
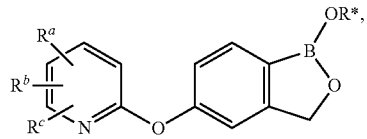

wherein R*, $R^a$, $R^b$, and $R^c$ are as described herein.

In an exemplary embodiment, the compound has a structure which is a member selected from:

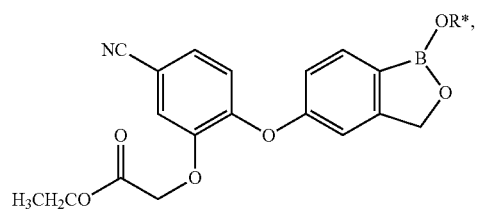
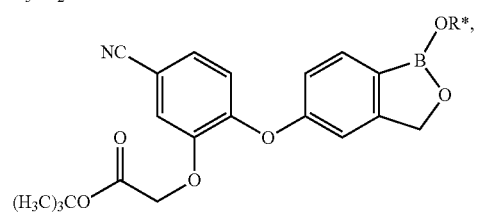
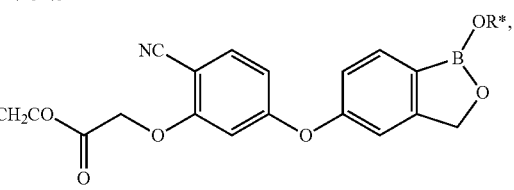
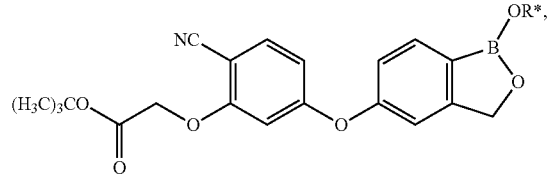
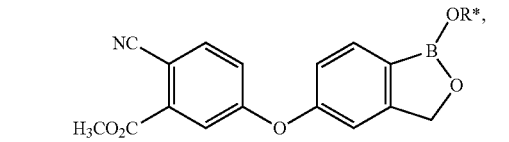
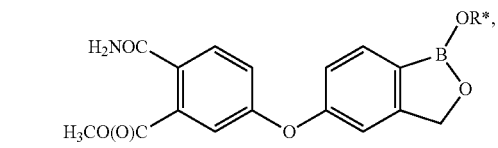

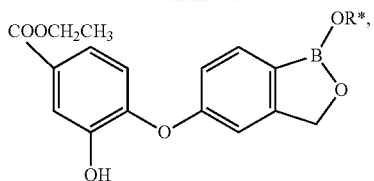
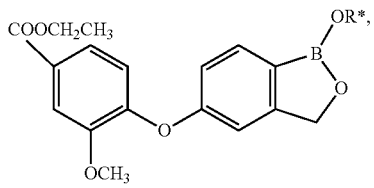
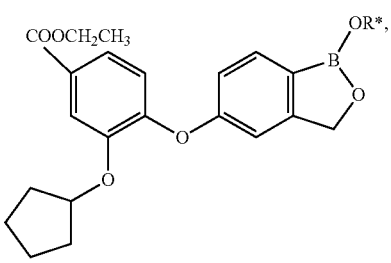
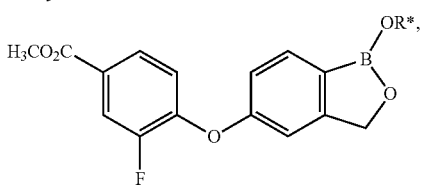
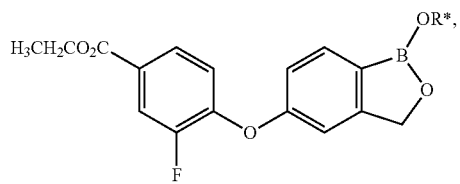
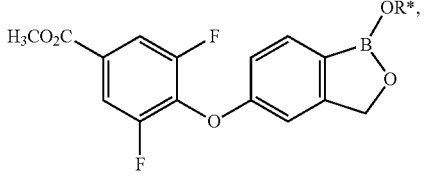
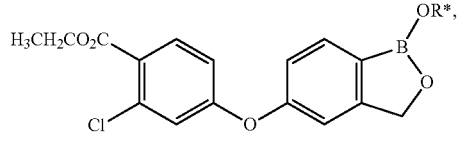
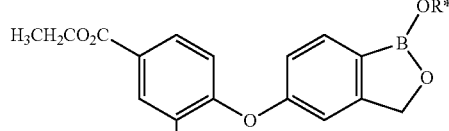
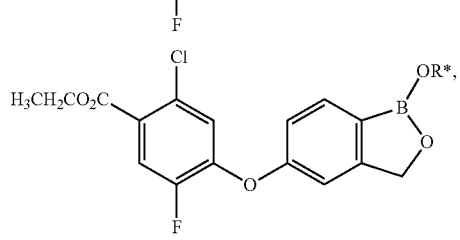

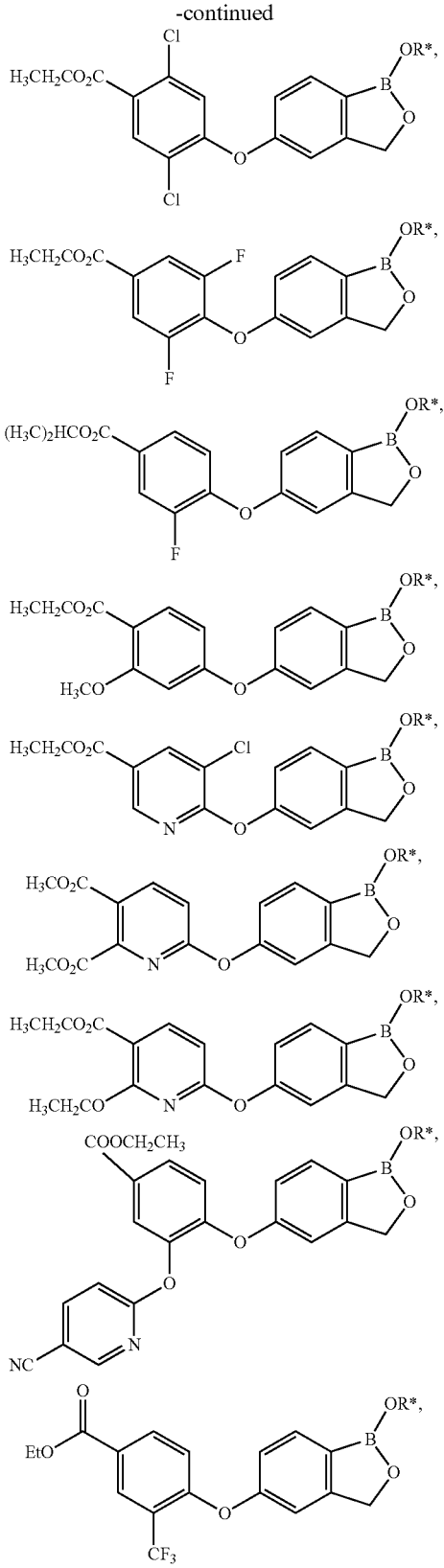

wherein R* is as defined herein.

In an exemplary embodiment, the compound has a structure according to the formula

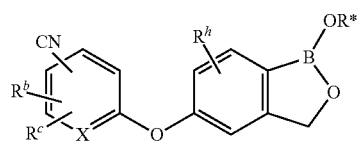

wherein X, R*, $R^b$ and $R^c$ are as described herein, and wherein $R^h$ is a halogen. In another exemplary embodiment, $R^h$ is fluoro. In another exemplary embodiment, $R^h$ is chloro. In another exemplary embodiment, the compound has a structure which is a member selected from:

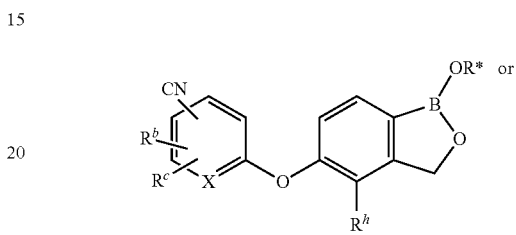

wherein X, R*, $R^b$, $R^c$ and $R^h$ are as described herein. In another exemplary embodiment, the compound has a structure which is a member selected from:

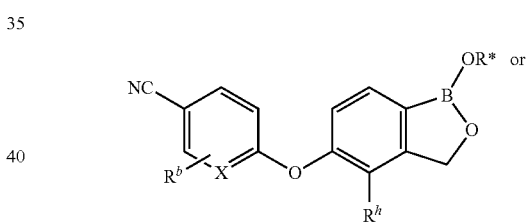

wherein X, R*, $R^b$, $R^c$ and $R^h$ are as described herein.

In an exemplary embodiment, the compound has a structure which is a member selected from:

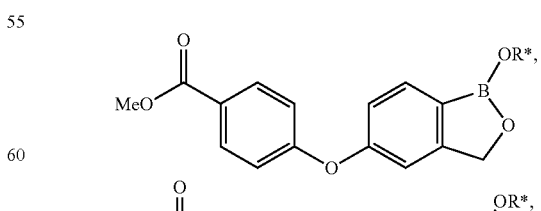

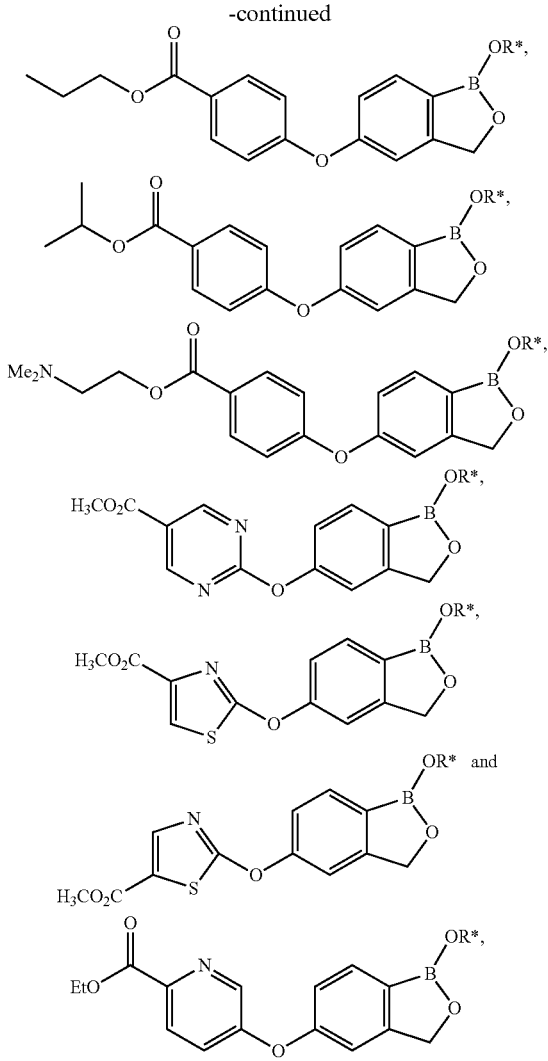

wherein R* is as defined herein.

IIIc.

In a fourth aspect, the invention provides a compound having a structure according to the formula:

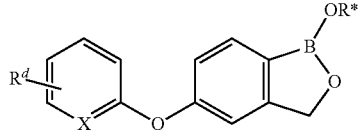

wherein R* is a member selected from H, a negative charge and a positively charged counterion, X is CH or N, and $R^d$ is aminosubstituted alkyl.

In an exemplary embodiment, $R^d$ is —($CR^{10}R^{11}$)$_n$$NR^{12}R^{13}$ in which n is a member selected from 1-10, and $R^{10}$, $R^{11}$, $R^{12}$ and $R^{13}$ are members independently selected from H, $OR^{14}$, $NR^{14}R^{15}$, $SR^{14}$, —$S(O)R^{14}$, —$S(O)_2R^{14}$, —$S(O)_2NR^{14}R^{15}$, —$C(O)R^{14}$, —$C(O)OR^{14}$, —$C(O)NR^{14}R^{15}$, nitro, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl wherein each $R^{14}$ and $R^{15}$ are members independently selected from H, nitro, halogen, cyano, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In an exemplary embodiment, $R^{10}$ and $R^{11}$ are H. In an exemplary embodiment, $R^{12}$ and $R^{13}$ are H. In an exemplary embodiment, n is a member selected from 1 to 5. In another exemplary embodiment, n is a member selected from 1 to 3. In an exemplary embodiment, n is 1.

In an exemplary embodiment, $R^d$ is —($CH_2$)—$NHR^{13}$ in which n is a member selected from 1-10, and $R^{13}$ is a member selected from H, $OR^{14}$, $NR^{14}R^{15}$, $SR^{14}$, —$S(O)R^{14}$, —$S(O)_2R^{14}$, —$S(O)_2NR^{14}R^{15}$, —$C(O)R^{14}$, —$C(O)OR^{14}$, —$C(O)NR^{14}R^{15}$, wherein each $R^{14}$ and $R^{15}$ are members independently selected from H, nitro, halogen, cyano, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In an exemplary embodiment, $R^d$ is —($CH_2$)—$NHR^{13}$ in which n is a member selected from 1-10, and $R^{13}$ is —$S(O)_2R^{14}$, wherein $R^{14}$ is a member selected from H, unsubstituted alkyl and substituted or unsubstituted aryl.

In an exemplary embodiment, $R^d$ is —($CH_2$)—$NHR^{13}$ in which n is a member selected from 1-10, and $R^{13}$ is —$S(O)_2R^{14}$, wherein $R^{14}$ is unsubstituted alkyl or substituted or unsubstituted aryl. In an exemplary embodiment, $R^{14}$ is unsubstituted $C_1$ or $C_2$ or $C_3$ alkyl. In an exemplary embodiment, $R^{14}$ is unsubstituted $C_4$ or $C_5$ or $C_6$ alkyl. In an exemplary embodiment, $R^{14}$ is $C_1$ alkyl.

In an exemplary embodiment, $R^d$ is —($CH_2$)—$NHR^{13}$ in which n is a member selected from 1-10, and $R^{13}$ is —$S(O)_2R^{14}$, wherein $R^{14}$ is substituted or unsubstituted aryl. In an exemplary embodiment, $R^{14}$ is substituted or unsubstituted phenyl. In an exemplary embodiment, $R^{14}$ is unsubstituted phenyl. In an exemplary embodiment, $R^{14}$ is phenyl substituted with at least one halogen and/or at least one unsubstituted alkyl. In an exemplary embodiment, $R^d$ has a structure which is a member selected from

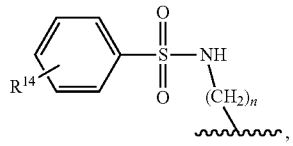

wherein $R^{14}$ is chloro or fluoro or unsubstituted $C_1$ or $C_2$ or $C_3$ or $C_4$ alkyl. In an exemplary embodiment, $R^{14}$ is chloro or methyl. In an exemplary embodiment, n is 1 or 2 or 3. In an exemplary embodiment, n is 1.

In an exemplary embodiment, $R^d$ has a structure which is a member selected from

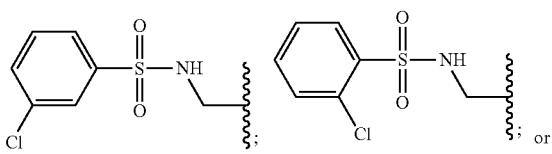

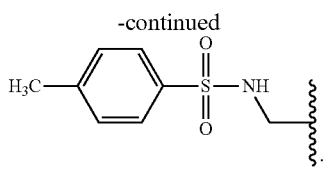

In an exemplary embodiment, $R^d$ is —($CH_2$)—$NH_2$ in which n is a member selected from 1-10. In an exemplary embodiment, n is 1 or 2 or 3 or 4 or 5. In an exemplary embodiment, n is 1 or 2 or 3. In an exemplary embodiment, $R^d$ is —$CH_2NH_2$.

In an exemplary embodiment, $R^d$ is —($CH_2$)—$NHR^{13}$ in which n is a member selected from 1-10, and $R^{13}$ is unsubstituted cycloalkyl. In an exemplary embodiment, $R^{13}$ is unsubstituted $C_3$-$C_8$ cycloalkyl. In an exemplary embodiment, $R^{13}$ is cyclopentyl or cyclohexyl or cycloheptyl. In an exemplary embodiment, n is 1 or 2 or 3. In an exemplary embodiment, n is 1. In an exemplary embodiment, n is 1 and $R^{13}$ is cyclohexyl.

In an exemplary embodiment, $R^d$ is —($CH_2$)—$NHR^{13}$ in which n is a member selected from 1-10, and $R^{13}$ is unsubstituted alkyl. In an exemplary embodiment, $R^{13}$ is $C_1$ or $C_2$ or $C_3$ alkyl. In an exemplary embodiment, $R^{13}$ is $C_4$ or $C_5$ or $C_6$ alkyl. In an exemplary embodiment, n is 1 or 2 or 3. In an exemplary embodiment, n is 1. In an exemplary embodiment, $R^d$ is —($CH_2$)$_n$—$NHCH_3$. In an exemplary embodiment, $R^d$ is —($CH_2$)$NHCH_3$.

In an exemplary embodiment, $R^d$ is —($CH_2$)—$NR^{13a}R^{13}$ in which n is a member selected from 1-10, and $R^{13}$ and $R^{13a}$ are each members independently selected unsubstituted alkyl. In an exemplary embodiment, $R^{13}$ and $R^{13a}$ are each members independently selected from unsubstituted alkyl. In an exemplary embodiment, $R^{13}$ and $R^{13a}$ are each members independently selected from $C_1$ or $C_2$ or $C_3$ or $C_4$ or $C_5$ or $C_6$ alkyl. In an exemplary embodiment, $R^{13}$ and $R^{13a}$ are each members independently selected from $C_1$ or $C_2$ or $C_3$ alkyl. In an exemplary embodiment, $R^d$ is —($CH_2$)$NR^{13a}R^{13}$, wherein $R^{13}$ and $R^{13a}$ are each members independently selected from $C_1$ or $C_2$ or $C_3$ alkyl. In an exemplary embodiment, $R^d$ is —($CH_2$)$N(CH_3)_2$.

In an exemplary embodiment, $R^d$ is —($CH_2$)—$NH(CH_2)_{n1}R^{16}$ in which n is a member selected from 1-10, n1 is a member selected from 1-10, and $R^{16}$ is substituted or unsubstituted aryl. In an exemplary embodiment, n1 is 1 or 2 or 3 or 4 or 5. In an exemplary embodiment, n1 is 1. In an exemplary embodiment, $R^{16}$ is unsubstituted phenyl. In an exemplary embodiment, $R^{16}$ is phenyl optionally substituted with at least one halogen. In an exemplary embodiment, $R^{16}$ is phenyl optionally substituted with at least one halogen. In an exemplary embodiment, $R^{16}$ is phenyl optionally substituted with at least one chloro or fluoro or bromo. In an exemplary embodiment, $R^{16}$ is ortho-bromophenyl or meta-bromophenyl or para-bromophenyl. In an exemplary embodiment, $R^d$ is —$CH_2NHCH_2R^{16}$, wherein $R^{16}$ is phenyl or ortho-bromophenyl or meta-bromophenyl.

In an exemplary embodiment, $R^{16}$ is phenyl substituted with nitro or cyano or unsubstituted alkoxy or unsubstituted alkyl. In an exemplary embodiment, $R^{16}$ is ortho-cyanophenyl or meta-cyanophenyl or para-cyanophenyl. In an exemplary embodiment, $R^{16}$ is ortho-nitrophenyl or meta-nitrophenyl or para-nitrophenyl. In an exemplary embodiment, $R^d$ is —$CH_2NHCH_2R^{16}$, wherein $R^{16}$ is ortho-cyanophenyl or meta-cyanophenyl or para-cyanophenyl or ortho-nitrophenyl or meta-nitrophenyl or para-nitrophenyl.

In an exemplary embodiment, $R^{16}$ is phenyl substituted with unsubstituted $C_1$ or $C_2$ or $C_3$ or $C_4$ or $C_5$ or $C_6$ alkyl. In an exemplary embodiment, $R^{16}$ is ortho-methylphenyl or meta-methylphenyl or para-methylphenyl. In an exemplary embodiment, $R^d$ is —$CH_2NHCH_2R^{16}$, wherein $R^{16}$ is ortho-methylphenyl or meta-methylphenyl or para-methylphenyl.

In an exemplary embodiment, $R^{16}$ is phenyl substituted with unsubstituted $C_1$ or $C_2$ or $C_3$ or $C_4$ or $C_5$ or $C_6$ alkyloxy. In an exemplary embodiment, $R^{16}$ is ortho-methoxyphenyl or meta-methyloxyphenyl or para-methoxyphenyl. In an exemplary embodiment, $R^d$ is —$CH_2NHCH_2R^{16}$, wherein $R^{16}$ is ortho-methoxyphenyl or meta-methoxyphenyl or para-methoxyphenyl.

In an exemplary embodiment, $R^{16}$ is unsubstituted $C_3$ or $C_4$ or $C_5$ or $C_6$ or $C_7$ or $C_8$ cycloalkyl. In an exemplary embodiment, $R^{16}$ is unsubstituted cyclohexyl. In an exemplary embodiment, $R^d$ is —$CH_2NHCH_2R^{16}$, wherein $R^{16}$ is cyclohexyl.

In an exemplary embodiment, $R^{16}$ is unsubstituted heteroaryl. In an exemplary embodiment, $R^{16}$ is unsubstituted pyrrole. In an exemplary embodiment, $R^{16}$ is unsubstituted 2-pyrrole. In an exemplary embodiment, $R^d$ is —$CH_2NHCH_2R^{16}$, wherein $R^{16}$ is 2-pyrrole.

In an exemplary embodiment, $R^{16}$ is unsubstituted $C_1$ or $C_2$ or $C_3$ alkyl. In an exemplary embodiment, $R^{16}$ is unsubstituted $C_4$ or $C_5$ or $C_6$ alkyl. In an exemplary embodiment, $R^d$ is —$CH_2NHC(CH_3)_2$.

In an exemplary embodiment, $R^{16}$ is phenyl substituted with —NHC(O)—$R^{34}$, wherein $R^{34}$ is unsubstituted $C_1$ or $C_2$ or $C_3$ or $C_4$ or $C_5$ or $C_6$ alkyl. In an exemplary embodiment, $R^{16}$ is phenyl substituted with —NHC(O)$CH_3$. In an exemplary embodiment, $R^d$ is —$CH_2NHCH_2R^{16}$, wherein $R^{16}$ is ortho-($CH_3C(O)NH$-)phenyl or meta-($CH_3C(O)NH$-)phenyl or para-($CH_3C(O)NH$-)phenyl.

In an exemplary embodiment, $R^d$ is —($CH_2$)$_n$—NHC(O)$R^{14}$ in which n is a member selected from 1-10, wherein $R^{14}$ is unsubstituted alkyl. In an exemplary embodiment, $R^{14}$ is unsubstituted $C_1$ or $C_2$ or $C_3$ alkyl. In an exemplary embodiment, $R^{14}$ is unsubstituted $C_4$ or $C_5$ or $C_6$ alkyl. In an exemplary embodiment, $R^{14}$ is methyl or ethyl or isopropyl or t-butyl or. In an exemplary embodiment, $R^{14}$ is $C_1$ alkyl. In an exemplary embodiment, $R^d$ is —($CH_2$)$NHC(O)CH_3$ or —($CH_2$)$NHC(O)CH_2CH_3$ or —($CH_2$)$NHC(O)CH(CH_3)_2$ or —($CH_2$)$NHC(O)C(CH_3)_3$.

In an exemplary embodiment, $R^d$ is —($CH_2$)$_n$—NHC(O)$R^{14}$ in which n is a member selected from 1-10, wherein $R^{14}$ is substituted or unsubstituted aryl. In an exemplary embodiment, $R^{14}$ is unsubstituted phenyl. In an exemplary embodiment, $R^{14}$ is phenyl, substituted with nitro or cyano or unsubstituted alkoxy or unsubstituted alkyl. In an exemplary embodiment, $R^{14}$ is ortho-cyanophenyl or meta-cyanophenyl or para-cyanophenyl. In an exemplary embodiment, $R^{14}$ is ortho-nitrophenyl or meta-nitrophenyl or para-nitrophenyl. In an exemplary embodiment, $R^d$ is $CH_2NHC(O)R^{14}$, wherein $R^{14}$ is ortho-cyanophenyl or meta-cyanophenyl or para-cyanophenyl or ortho-nitrophenyl or meta-nitrophenyl or para-nitrophenyl.

In an exemplary embodiment, $R^{14}$ is phenyl substituted with unsubstituted $C_1$ or $C_2$ or $C_3$ or $C_4$ or $C_5$ or $C_6$ alkyl. In an exemplary embodiment, $R^{14}$ is ortho-methylphenyl or meta-methylphenyl or para-methylphenyl. In an exemplary embodiment, $R^d$ is —$CH_2NHC(O)R^{14}$, wherein $R^{14}$ is ortho-methylphenyl or meta-methylphenyl or para-methylphenyl.

In an exemplary embodiment, $R^{14}$ is phenyl substituted with unsubstituted $C_1$ or $C_2$ or $C_3$ or $C_4$ or $C_5$ or $C_6$ alkyloxy. In an exemplary embodiment, $R^{14}$ is ortho-methoxyphenyl or meta-methyloxyphenyl or para-methoxyphenyl. In an exemplary embodiment, $R^d$ is —CH$_2$NHC(O)R$^{14}$, wherein R$^{14}$ is ortho-methoxyphenyl or meta-methoxyphenyl or para-methoxyphenyl.

In an exemplary embodiment, R$^{14}$ is phenyl substituted with a halogen. In an exemplary embodiment, R$^{14}$ is chloro or fluoro. In an exemplary embodiment, $R^d$ is —CH$_2$NHC(O)R$^{14}$, wherein R$^{14}$ is ortho-fluorophenyl or meta-fluorophenyl or para-fluorophenyl.

In an exemplary embodiment, R$^{14}$ is phenyl substituted with haloalkyl. In an exemplary embodiment, the halogen is chloro or fluoro. In an exemplary embodiment, R$^{14}$ is phenyl substituted with alkyl substituted with three fluorines. In an exemplary embodiment, R$^{14}$ is phenyl substituted with alkyl substituted with two fluorines. In an exemplary embodiment, R$^{14}$ is ortho(trifluoromethyl)phenyl or meta(trifluoromethyl)phenyl or para(trifluoromethyl)phenyl. In an exemplary embodiment, $R^d$ is —CH$_2$NHC(O)R$^{14}$, wherein R$^{14}$ is R$^{14}$ is ortho(trifluoromethyl)phenyl or meta(trifluoromethyl)phenyl or para(trifluoromethyl)phenyl.

In an exemplary embodiment, $R^d$ is —(CH$_2$)$_n$—NHC(O)(CR$^{40}$R$^{41}$)$_{n9}$OC(O)R$^{42}$ in which n is a member selected from 1-10, wherein R$^{40}$ is unsubstituted alkyl, R$^{41}$ is unsubstituted alkyl, R$^{42}$ is unsubstituted alkyl. In an exemplary embodiment, R$^{40}$ or R$^{41}$ or R$^{42}$ are each independently selected C$_1$ or C$_2$ or C$_3$ or C$_4$ or C$_5$ or C$_6$ alkyl. In an exemplary embodiment, R$^{40}$ or R$^{41}$ or R$^{42}$ are each methyl. In an exemplary embodiment, n9 is 1. In an exemplary embodiment, $R^d$ is —(CH$_2$)$_n$—NHC(O)(C(CH$_3$)(CH$_3$))OC(O)R$^{42}$, wherein R$^{42}$ is C$_1$ or C$_2$ or C$_3$ or C$_4$ or C$_5$ or C$_6$ alkyl. In an exemplary embodiment, $R^d$ is —(CH$_2$)$_n$—NHC(O)(C(CH$_3$)(CH$_3$))OC(O)CH$_3$.

In an exemplary embodiment, $R^d$ is —(CH$_2$)$_n$—NHC(O)R$^{14}$ in which n is a member selected from 1-10, wherein R$^{14}$ is unsubstituted cycloalkyl. In an exemplary embodiment, R$^{14}$ is unsubstituted C3 or C4 or C5 or C6 or C7 or C8 cycloalkyl. In an exemplary embodiment, R$^{14}$ is unsubstituted cyclopentyl or cyclohexyl.

In an exemplary embodiment, $R^d$ is —(CH$_2$)$_n$—NHC(O)R$^{14}$ in which n is a member selected from 1-10, wherein R$^{14}$ is unsubstituted heteroaryl. In an exemplary embodiment, R$^{14}$ is unsubstituted furan. In an exemplary embodiment, R$^{14}$ is unsubstituted 2-furan.

In an exemplary embodiment, $R^d$ is —(CH$_2$)$_n$—NHC(O)OR$^{14}$ in which n is a member selected from 1-10, wherein R$^{14}$ is unsubstituted alkyl. In an exemplary embodiment, R$^{14}$ is C$_1$ or C$_2$ or C$_3$ or C$_4$ or C$_5$ or C$_6$ alkyl. In an exemplary embodiment, R$^{14}$ is C$_4$ alkyl. In an exemplary embodiment, R$^{14}$ is a member selected from n-butyl, isobutyl, sec-butyl and tert-butyl. In an exemplary embodiment, $R^d$ is —(CH$_2$)NHC(O)OR$^{14}$, wherein R$^{14}$ is C$_1$ or C$_2$ or C$_3$ or C$_4$ or C$_5$ or C$_6$ alkyl. In an exemplary embodiment, $R^d$ is —(CH$_2$)NHC(O)OC(CH$_3$)$_3$.

In an exemplary embodiment, $R^d$ is —(CH$_2$)$_n$—NHC(O)NR$^{43}$R$^{44}$ in which n is an integer selected from 1-10, wherein R$^{43}$ and R$^{44}$ are independently selected from H, substituted or unsubstituted alkyl, substituted or unsubstituted cycloalkyl and substituted or unsubstituted aryl. In an exemplary embodiment, R$^{43}$ and R$^{44}$, together with the nitrogen to which they are attached, are joined to form a 3 to 8 membered ring. In an exemplary embodiment, R$^{43}$ and R$^{44}$, together with the nitrogen to which they are attached, are joined to form a 4 to 7 membered ring. In an exemplary embodiment, R$^{43}$ and R$^{44}$, together with the nitrogen to which they are attached, are joined to form a 5 to 6 membered ring. In an exemplary embodiment, n is 1 or 2 or 3. In an exemplary embodiment, $R^d$ is

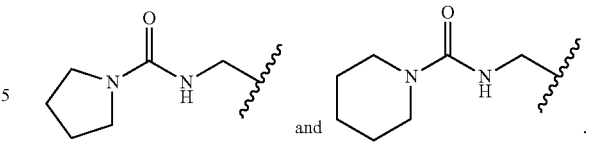

In an exemplary embodiment, $R^d$ is —(CH$_2$)$_n$—NHC(O)NHR$^{44}$ in which n is an integer selected from 1-10, wherein R$^{44}$ is substituted or unsubstituted alkyl, substituted or unsubstituted cycloalkyl and substituted or unsubstituted aryl. In an exemplary embodiment, R$^{44}$ is unsubstituted aryl. In an exemplary embodiment, R$^{44}$ is unsubstituted phenyl. In an exemplary embodiment, R$^{44}$ is aryl, substituted with unsubstituted alkyl. In an exemplary embodiment, R$^{44}$ is aryl, substituted with unsubstituted C$_1$ or C$_2$ or C$_3$ alkyl. In an exemplary embodiment, R$^{44}$ is aryl, substituted with unsubstituted C$_4$ or C$_5$ or C$_6$ alkyl. In an exemplary embodiment, R$^{44}$ is phenyl, substituted with unsubstituted C$_1$ or C$_2$ or C$_3$ alkyl. In an exemplary embodiment, R$^{44}$ is ortho methylphenyl or meta methylphenyl or para methylphenyl. In an exemplary embodiment, $R^d$ is —(CH$_2$)NHC(O)NHR$^{44}$, wherein R$^{44}$ is para methylphenyl.

In an exemplary embodiment, $R^d$ is —(CH$_2$)$_n$—NHC(O)NHR$^{44}$ in which n is an integer selected from 1-10, wherein R$^{44}$ is aryl, substituted with unsubstituted alkylamino. In an exemplary embodiment, R$^{44}$ is aryl, substituted with NR$^{50}$R$^{51}$, wherein R$^{50}$ and R$^{51}$ are each independently selected from H and unsubstituted alkyl. In an exemplary embodiment, R$^{44}$ is phenyl, substituted with NR$^{50}$R$^{51}$, wherein R$^{50}$ and R$^{51}$ are each independently selected from C$_1$ or C$_2$ or C$_3$ or C$_4$ or C$_5$ or C$_6$ alkyl. In an exemplary embodiment, R$^{44}$ is phenyl, substituted with NR$^{50}$R$^{51}$, wherein R$^{50}$ and R$^{51}$ are each independently selected from C$_1$ or C$_2$ or C$_3$ alkyl. In an exemplary embodiment, R$^{44}$ is ortho (NR$^{50}$R$^{51}$)phenyl or meta (NR$^{50}$R$^{51}$)phenyl or para (NR$^{50}$R$^{51}$)phenyl. In an exemplary embodiment, R$^{50}$ is C$_1$ or C$_2$ or C$_3$ alkyl. In an exemplary embodiment, R$^{51}$ is C$_1$ or C$_2$ or C$_3$ alkyl. In an exemplary embodiment, R$^{50}$ is C$_1$ or C$_2$ or C$_3$ alkyl. In an exemplary embodiment, R$^{44}$ is phenyl, substituted with N(CH$_3$)$_2$. In an exemplary embodiment, $R^d$ is —(CH$_2$)NHC(O)NHR$^{44}$, wherein R$^{44}$ is para(N(CH$_3$)$_2$)phenyl.

In an exemplary embodiment, $R^d$ is —(CH$_2$)$_n$—NHC(O)(CH$_2$)$_{n10}$NR$^{43}$R$^{44}$ in which n is an integer selected from 1-10, n10 is an integer selected from 1-10, wherein R$^{43}$ and R$^{44}$ are independently selected from H, substituted or unsubstituted alkyl, substituted or unsubstituted cycloalkyl and substituted or unsubstituted aryl. In an exemplary embodiment, R$^{43}$ and R$^{44}$, together with the nitrogen to which they are attached, are joined to form a 3 to 8 membered ring. In an exemplary embodiment, R$^{43}$ and R$^{44}$, together with the nitrogen to which they are attached, are joined to form a 4 to 7 membered ring. In an exemplary embodiment, R$^{43}$ and R$^{44}$, together with the nitrogen to which they are attached, are joined to form a 5 to 6 membered ring. In an exemplary embodiment, n is 1 or 2 or 3. In an exemplary embodiment, n10 is 1 or 2 or 3. In an exemplary embodiment, $R^d$ is —(CH$_2$NHC(O)(CH$_2$)$_{n10}$NR$^{43}$R$^{44}$ In an exemplary embodiment, $R^d$ is —(CH$_2$)$_n$—NHC(O)NHR$^{44}$ in which n is an integer selected from 1-10, wherein R$^{44}$ is aryl, substituted with halogen. In an exemplary embodiment, R$^{44}$ is phenyl, substituted with halogen. In an exemplary embodiment, R$^{44}$ is ortho (halogen)phenyl or meta (halogen)phenyl or para (halogen)phenyl. In an exemplary embodiment, R$^{44}$ is ortho (chloro)phenyl or meta (chloro)phenyl or para(chloro)phenyl. In an exemplary embodiment, $R^{44}$ is ortho (fluoro)phenyl or meta (fluoro)phenyl or para (fluoro)phenyl. In an exemplary embodiment, $R^d$ is —(CH$_2$)NHC(O)NHR$^{44}$, wherein $R^{44}$ is para(chloro)phenyl.

In an exemplary embodiment, $R^d$ is —(CH$_2$)$_n$—NHC(O)NHR$^{44}$ in which n is an integer selected from 1-10, wherein $R^{44}$ is unsubstituted aryl. In an exemplary embodiment, $R^{44}$ is unsubstituted phenyl. In an exemplary embodiment, $R^d$ is —(CH$_2$)NHC(O)NHR$^{44}$, wherein $R^{44}$ is unsubstituted phenyl.

In an exemplary embodiment, $R^d$ is —(CH$_2$)$_n$—NHC(O)NHR$^{44}$ in which n is an integer selected from 1-10, wherein $R^{44}$ is unsubstituted alkyl. In an exemplary embodiment, $R^{44}$ is $C_1$ or $C_2$ or $C_3$ alkyl. In an exemplary embodiment, $R^d$ is —(CH$_2$)NHC(O)NHR$^{44}$, wherein $R^{44}$ is $C_4$ or $C_5$ or $C_6$ alkyl. In an exemplary embodiment, $R^d$ is —(CH$_2$)NHC(O)NHR$^{44}$, wherein $R^{44}$ is ethyl.

In an exemplary embodiment, $R^d$ is —(CH$_2$)$_n$—NHC(O)(CR$^{52}$R$^{53}$)$_{n11}$NR$^{54}$R$^{55}$ in which n is an integer selected from 1-10, n11 is an integer selected from 1-10, wherein $R^{52}$ and $R^{53}$ are independently selected from H and alkyl optionally substituted with aryl, and wherein $R^{54}$ and $R^{55}$ are independently selected from H, unsubstituted alkyl, and —C(O)OR$^{56}$, wherein $R^{56}$ is unsubstituted alkyl.

In an exemplary embodiment, $R^d$ is —(CH$_2$)NHC(O)(CH$_2$)$_{n11}$NR$^{54}$R$^{55}$ in which n11 is an integer selected from 1-10, and wherein $R^{54}$ and $R^{55}$ are independently selected from H, unsubstituted alkyl, and —C(O)OR$^{56}$, wherein $R^{56}$ is unsubstituted alkyl. In an exemplary embodiment, $R^d$ is —(CH$_2$)NHC(O)(CH$_2$)NHR$^{55}$ and wherein $R^{55}$ is —C(O)OR$^{56}$, wherein $R^{56}$ is unsubstituted alkyl. In an exemplary embodiment, $R^d$ is —(CH$_2$)NHC(O)(CH$_2$)NHR$^{55}$ and wherein $R^{55}$ is —C(O)OR$^{56}$, wherein $R^{56}$ is $C_1$ or $C_2$ or $C_3$ alkyl. In an exemplary embodiment, $R^d$ is —(CH$_2$)NHC(O)(CH$_2$)NHR$^{55}$ and wherein $R^{55}$ is —C(O)OR$^{56}$, wherein $R^{56}$ is $C_4$ or $C_5$ or $C_6$ alkyl.

In an exemplary embodiment, $R^d$ is —(CH$_2$)NHC(O)(CH$_2$)NR$^{54}$R$^{55}$ and wherein $R^{54}$ is unsubstituted alkyl, and $R^{55}$ is —C(O)OR$^{56}$, wherein $R^{56}$ is unsubstituted alkyl. In an exemplary embodiment, $R^d$ is —(CH$_2$)NHC(O)(CH$_2$)NR$^{54}$R$^{55}$ and wherein $R^{54}$ is $C_1$ or $C_2$ or $C_3$ or $C_4$ or $C_5$ or $C_6$ alkyl, $R^{55}$ is —C(O)OR$^{56}$, wherein $R^{56}$ is $C_1$ or $C_2$ or $C_3$ or $C_4$ or $C_5$ or $C_6$ alkyl. In an exemplary embodiment, $R^d$ is —(CH$_2$)NHC(O)(CH$_2$)NR$^{54}$R$^{55}$ and wherein $R^{54}$ is $C_1$ alkyl, $R^{55}$ is —C(O)OR$^{56}$, wherein $R^{56}$ is $C_1$ or $C_2$ or $C_3$ or $C_4$ or $C_5$ or $C_6$ alkyl. In an exemplary embodiment, $R^d$ is —(CH$_2$)NHC(O)(CH$_2$)NR$^{54}$R$^{55}$ and wherein $R^{54}$ is $C_1$ or $C_2$ or $C_3$ alkyl, $R^{55}$ is —C(O)OR$^{56}$, wherein $R^{56}$ is $C_3$ or $C_4$ or $C_5$ alkyl. In an exemplary embodiment, $R^d$ is —(CH$_2$)NHC(O)(CH$_2$)NR$^{54}$R$^{55}$ and wherein $R^{54}$ is $C_1$ alkyl, $R^{55}$ is —C(O)OR$^{56}$, wherein $R^{56}$ is $C_4$ alkyl.

In an exemplary embodiment, $R^d$ is —(CH$_2$)$_n$—NHC(O)(CH$_2$)$_{n11}$NR$^{54}$R$^{55}$ in which n is an integer selected from 1-10, n11 is an integer selected from 1-10, and wherein $R^{54}$ and $R^{55}$ are independently selected from H and unsubstituted alkyl. In an exemplary embodiment, $R^d$ is —(CH$_2$)$_n$NHC(O)(CH$_2$)$_{n11}$NH$_2$. In an exemplary embodiment, n is 1 or 2 or 3. In an exemplary embodiment, n11 is 1 or 2 or 3. In an exemplary embodiment, $R^d$ is —(CH$_2$)NHC(O)(CH$_2$)NH$_2$. In an exemplary embodiment, $R^d$ is —(CH$_2$)$_n$—NHC(O)(CH$_2$)$_{n11}$NHR$^{55}$ in which n is an integer selected from 1-10, n11 is an integer selected from 1-10, and wherein $R^{55}$ is unsubstituted alkyl. In an exemplary embodiment, $R^d$ is —(CH$_2$)NHC(O)(CH$_2$)NHR$^{55}$ in which $R^{55}$ is unsubstituted alkyl. In an exemplary embodiment, $R^d$ is —(CH$_2$)NHC(O)(CH$_2$)NHR$^{55}$ in which $R^{55}$ is $C_1$ or $C_2$ or $C_3$ alkyl. In an exemplary embodiment, $R^d$ is —(CH$_2$)NHC(O)(CH$_2$)NHR$^{55}$ in which $R^{55}$ is $C_4$ or $C_5$ or $C_6$ alkyl. In an exemplary embodiment, $R^d$ is —(CH$_2$)NHC(O)(CH$_2$)NHCH$_3$.

In an exemplary embodiment, $R^d$ is —(CH$_2$)$_n$—NHC(O)(CH$_2$)$_{n11}$NR$^{54}$R$^{55}$ in which n is an integer selected from 1-10, n11 is an integer selected from 1-10, and wherein $R^{54}$ and $R^{55}$ are independently selected unsubstituted alkyl. In an exemplary embodiment, $R^{54}$ and $R^{55}$ are each members independently selected from $C_1$ or $C_2$ or $C_3$ or $C_4$ or $C_5$ or $C_6$ alkyl. In an exemplary embodiment, $R^{54}$ and $R^{55}$ are each members independently selected from $C_1$ or $C_2$ or $C_3$ alkyl. In an exemplary embodiment, $R^d$ is —(CH$_2$)NHC(O)(CH$_2$)NR$^{54}$R$^{55}$, wherein $R^{54}$ and $R^{55}$ are each members independently selected from $C_1$ or $C_2$ or $C_3$ alkyl. In an exemplary embodiment, $R^d$ is —(CH$_2$)NHC(O)(CH$_2$)N(CH$_3$)$_2$.

In an exemplary embodiment, $R^d$ is —(CH$_2$)$_n$—NHC(O)(CHR$^{53}$)$_{n11}$NR$^{54}$R$^{55}$ in which n is an integer selected from 1-10, n11 is an integer selected from 1-10, wherein $R^{53}$ is alkyl, and wherein $R^{54}$ and $R^{55}$ are independently selected from H, unsubstituted alkyl, and —C(O)OR$^{56}$, wherein $R^{56}$ is unsubstituted alkyl. In an exemplary embodiment, n is 1 or 2 or 3 and n11 is 1 or 2 or 3. In an exemplary embodiment, n is 1 and n11 is 1. In an exemplary embodiment, $R^d$ is —(CH$_2$)$_n$NHC(O)(CHR$^{53}$)$_{n11}$NH$_2$ in which n is an integer selected from 1-10, n11 is an integer selected from 1-10, wherein $R^{53}$ is alkyl. In an exemplary embodiment, $R^d$ is —(CH$_2$)NHC(O)CH(R$^{53}$)(NH$_2$) in which $R^{53}$ is alkyl. In an exemplary embodiment, $R^{53}$ is $C_1$ or $C_2$ or $C_3$ or $C_4$ or $C_5$ or $C_6$ alkyl. In an exemplary embodiment, $R^{53}$ is $C_1$ or $C_2$ or $C_3$ alkyl. In an exemplary embodiment, $R^d$ is —(CH$_2$)NHC(O)CH(R$^{53}$)(NH$_2$) in which $R^{53}$ is $C_1$ or $C_2$ or $C_3$ or $C_4$ alkyl. In an exemplary embodiment, $R^d$ is —(CH$_2$)NHC(O)CH(R$^{53}$)(NH$_2$) in which $R^{53}$ is $C_4$ alkyl. In an exemplary embodiment, $R^d$ is —(CH$_2$)NHC(O)CH(CH$_3$)(NH$_2$). In an exemplary embodiment, $R^d$ is —(CH$_2$)NHC(O)CH(NH$_2$)(CH$_2$CH(CH$_3$)$_2$).

In an exemplary embodiment, $R^d$ is —(CH$_2$)$_n$—NHC(O)(CHR$^{53}$)$_{n11}$NR$^{54}$R$^{55}$ in which n is an integer selected from 1-10, n11 is an integer selected from 1-10, wherein $R^{53}$ is alkyl substituted with aryl, and wherein $R^{54}$ and $R^{55}$ are independently selected unsubstituted alkyl. In an exemplary embodiment, n is 1 or 2 or 3 and n11 is 1 or 2 or 3. In an exemplary embodiment, n is 1 and n11 is 1. In an exemplary embodiment, $R^d$ is —(CH$_2$)$_n$—NHC(O)(CHR$^{53}$)$_{n11}$NR$^{54}$R$^{55}$ in which n is an integer selected from 1-10, n11 is an integer selected from 1-10, wherein $R^{53}$ is alkyl substituted with aryl. In an exemplary embodiment, $R^d$ is —(CH$_2$)NHC(O)CH(R$^{53}$)(NR$^{54}$R$^{55}$) in which $R^{53}$ is alkyl substituted with aryl. In an exemplary embodiment, $R^{53}$ is (CH$_2$)$_{n12}$-Ph, wherein n12 is an integer selected from 1-10. In an exemplary embodiment, n is 1 or 2 or 3, n11 is 1 or 2 or 3 and n12 is 1 or 2 or 3. In an exemplary embodiment, n is 1, n11 is 1 and n12 is 1. In an exemplary embodiment, $R^d$ is —(CH$_2$)NHC(O)CH(CH$_2$-Ph)(NR$^{54}$R$^{55}$) in which $R^{54}$ or $R^{55}$ is $C_1$ or $C_2$ or $C_3$ or $C_4$ alkyl. In an exemplary embodiment, $R^d$ is —(CH$_2$)NHC(O)CH((CH$_2$)$_{n12}$-Ph)(N(CH$_3$)$_2$). In an exemplary embodiment, $R^d$ is —(CH$_2$)NHC(O)CH(CH$_2$-Ph)(N(CH$_3$)$_2$).

In an exemplary embodiment, $R^d$ is —(CH$_2$)$_n$—NHC(O)R$^{58}$ in which n is an integer selected from 1-10, and $R^{58}$ is a member selected from

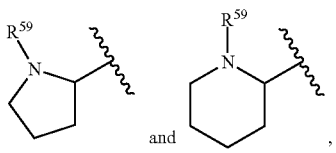

wherein R⁵⁹ is H or unsubstituted alkyl or C(O)OR⁵⁶, wherein R⁵⁶ is unsubstituted alkyl. In an exemplary embodiment, R$^d$ is —(CH₂)NHC(O)R⁵⁸ in which R⁵⁸ is

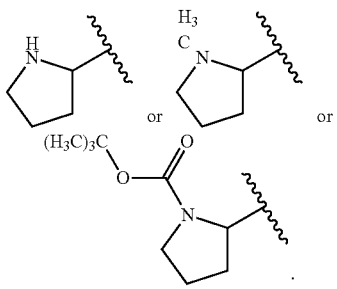

In an exemplary embodiment, R$^d$ is —(CH₂)NHC(O)R⁵⁸ in which R⁵⁸ is

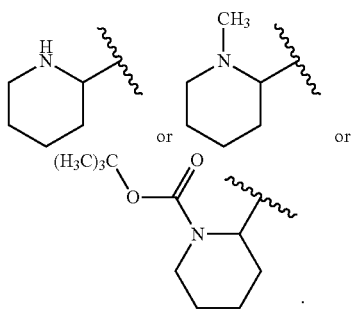

In an exemplary embodiment, R$^d$ is —(CH₂)$_n$—NHC(O)(CHR⁵³)$_{n11}$NHR⁵⁵ in which n is an integer selected from 1-10, n11 is an integer selected from 1-10, wherein R⁵³ is alkyl, and wherein R⁵⁵ is —C(O)OR⁵⁶, wherein R⁵⁶ is unsubstituted alkyl. In an exemplary embodiment, n is 1 or 2 or 3 and n11 is 1 or 2 or 3. In an exemplary embodiment, n is 1 and n11 is 1. In an exemplary embodiment, R$^d$ is —(CH₂)NHC(O)CH(R⁵³)(NHC(O)OR⁵⁶) in which R⁵³ is C₁ or C₂ or C₃ or C₄ or C₅ or C₆ alkyl and R⁵⁶ is C₁ or C₂ or C₃ or C₄ or C₅ or C₆ alkyl. In an exemplary embodiment, R⁵³ is C₁ or C₂ or C₃ alkyl. In an exemplary embodiment, R⁵⁶ is C₄ or C₅ or C₆ alkyl. In an exemplary embodiment, R$^d$ is —(CH₂)NHC(O)CH(CH₂CH(CH₃)₂)(NHC(O)OR⁵⁶). In an exemplary embodiment, R$^d$ is —(CH₂)NHC(O)CH(R⁵³)(NHC(O)OC(CH₃)₃). In an exemplary embodiment, R$^d$ is —(CH₂)NHC(O)CH(CH₂CH(CH₃)₂)(NHC(O)OC(CH₃)₃).

In an exemplary embodiment, R$^d$ is —(CH₂)$_n$—NHC(O)(CHR⁵³)$_{n11}$NH₂ in which n is an integer selected from 1-10, n11 is an integer selected from 1-10, wherein R⁵³ is unsubstituted alkyl, optionally substituted with aryl. In an exemplary embodiment, n is 1 or 2 or 3 and n11 is 1 or 2 or 3. In an exemplary embodiment, n is 1 and n11 is 1. In an exemplary embodiment, R$^d$ is —(CH₂)$_n$—NHC(O)(CHR⁵³)$_{n11}$NH₂ in which n is an integer selected from 1-10, n11 is an integer selected from 1-10, wherein R⁵³ is (CH₂)$_{n12}$-Ph, wherein n12 is an integer selected from 1-10. In an exemplary embodiment, n is 1 or 2 or 3, n11 is 1 or 2 or 3 and n12 is 1 or 2 or 3. In an exemplary embodiment, n is 1, n11 is 1 and n12 is 1. In an exemplary embodiment, R$^d$ is —(CH₂)NHC(O)CH[(CH₂)-Ph])(NH₂).

In an exemplary embodiment, R$^d$ is —(CH₂)$_n$—NHC(O)(CHR⁵³)$_{n11}$NH(C(O)OR⁵⁶) in which n is an integer selected from 1-10, n11 is an integer selected from 1-10, wherein R⁵⁶ is C₁ or C₂ or C₃ or C₄ or C₅ or C₆ alkyl, and R⁵³ is unsubstituted alkyl. In an exemplary embodiment, n is 1 or 2 or 3 and n11 is 1 or 2 or 3. In an exemplary embodiment, n is 1 and n11 is 1. In an exemplary embodiment, R$^d$ is —(CH₂)NHC(O)(CHR⁵³)NH(C(O)OR⁵⁶), wherein R⁵⁶ is C₄ alkyl, and R⁵³ is C₁ or C₂ or C₃ or C₄ alkyl. In an exemplary embodiment, R$^d$ is —(CH₂)NHC(O)CH(CH₃)(NH(C(O)OR⁵⁶)). In an exemplary embodiment, R$^d$ is —(CH₂)NHC(O)CH(R⁵³)(NH(C(O)OC(CH₃)₃)). In an exemplary embodiment, R$^d$ is —(CH₂)NHC(O)CH(CH₃))NH(C(O)OC(CH₃)₃).

In an exemplary embodiment, R$^d$ is —(CH₂)$_n$—NHC(O)(CHR⁵³)$_{n11}$NH(C(O)OR⁵⁶) in which n is an integer selected from 1-10, n11 is an integer selected from 1-10, wherein R⁵⁶ is C₁ or C₂ or C₃ or C₄ or C₅ or C₆ alkyl, and R⁵³ is alkyl substituted with aryl. In an exemplary embodiment, n is 1 or 2 or 3 and n11 is 1 or 2 or 3. In an exemplary embodiment, n is 1 and n11 is 1. In an exemplary embodiment, R$^d$ is —(CH₂)NHC(O)(CHR⁵³)NH(C(O)OR⁵⁶), wherein R⁵⁶ is C₄ alkyl, and R⁵³ is (CH₂)$_{n12}$-Ph, wherein n₁₂ is an integer selected from 1-10. In an exemplary embodiment, R$^d$ is —(CH₂)NHC(O)CH((CH₂)-Ph)(NH(C(O)OR⁵⁶)). In an exemplary embodiment, R$^d$ is —(CH₂)NHC(O)CH(R⁵³)(NH(C(O)OC(CH₃)₃)). In an exemplary embodiment, R$^d$ is —(CH₂)NHC(O)CH((CH₂)-Ph))(NH(C(O)OC(CH₃)₃)).

In an exemplary embodiment, the compound has a structure according to the formula:

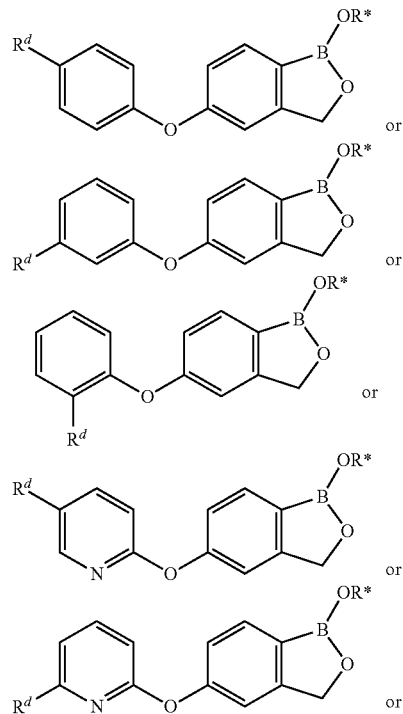

-continued

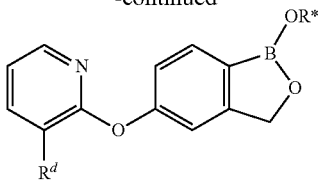

wherein $R^d$ is as defined herein.

In an exemplary embodiment, compound has a structure according to the formula:

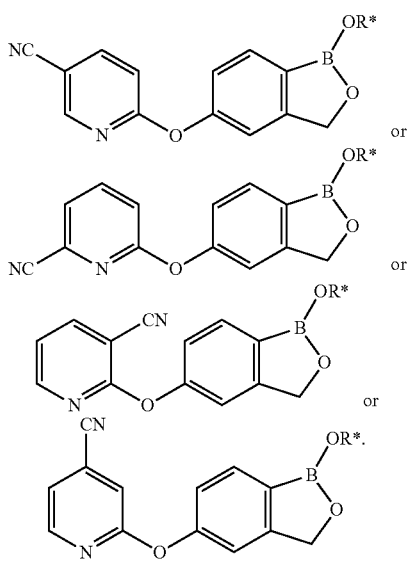

In an exemplary embodiment, the compound has a structure according to the formula:

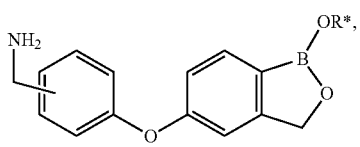

wherein R* is as defined herein.

In an exemplary embodiment, the compound has a structure which is a member selected from:

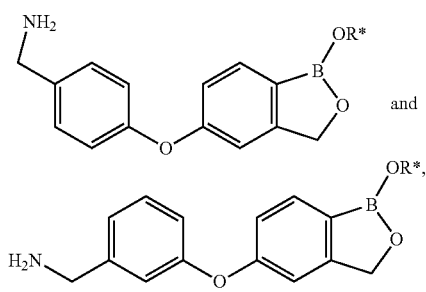

wherein R* is as defined herein.

In an exemplary embodiment, the compound has a structure according to the formula:

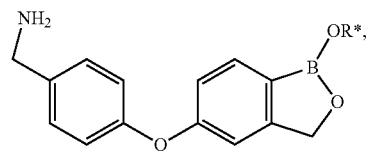

wherein R* is as defined herein.

IIId.

In a fifth aspect, the invention provides a compound having a structure according to the formula:

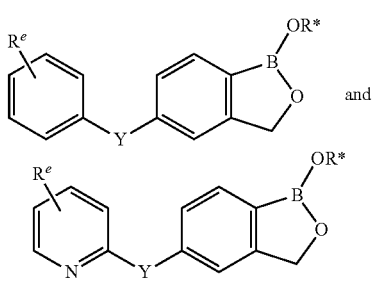

wherein Y is a member selected from S and O; R* is a member selected from H, a negative charge and a positively charged counterion; $R^e$ is a member selected from substituted or unsubstituted hydroxyalkyl, —C(O)H and —C(O)NR$^{20}$R$^{21}$. Each R$^{20}$ and R$^{21}$ are members independently selected from H, nitro, halogen, cyano, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. There is a proviso that R$^{20}$ and R$^{21}$, together with the atoms to which they are attached, are optionally combined to form a 5- to 7-membered substituted or unsubstituted heterocycloalkyl ring.

In an exemplary embodiment, compound has a structure according to the formula:

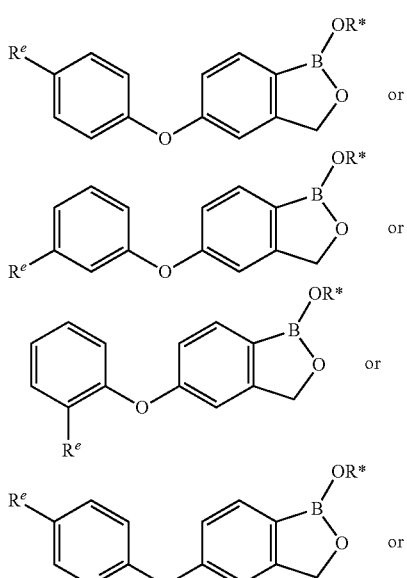

-continued

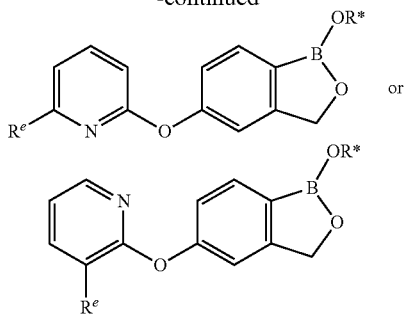

or wherein $R^e$ is as defined herein.

In an exemplary embodiment, the compound has a structure according to the formula:

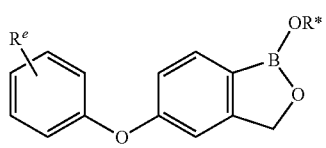

wherein R* is as defined herein, and $R^e$ is substituted or unsubstituted hydroxyalkyl. In an exemplary embodiment, $R^e$ is unsubstituted hydroxyalkyl. In an exemplary embodiment, $R^e$ is unsubstituted $C_1$-$C_6$ hydroxyalkyl. In an exemplary embodiment, $R^e$ is unsubstituted $C_1$ or $C_2$ or $C_3$ or $C_4$ or $C_5$ or $C_6$ hydroxyalkyl. In an exemplary embodiment, the compound has a structure which is

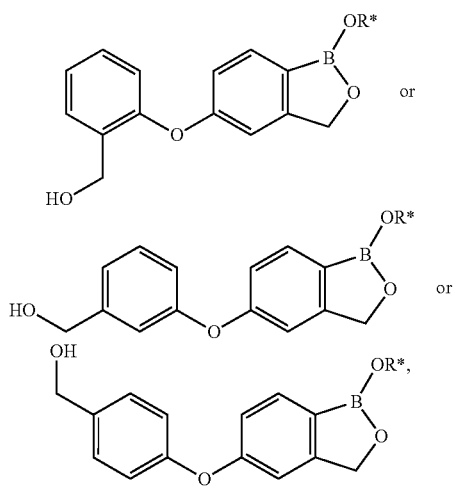

wherein R* is as defined herein.

In an exemplary embodiment, the compound has a structure according to the formula:

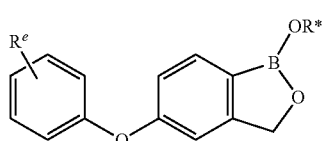

wherein R* is as defined herein, and $R^e$ is C(O)H. In an exemplary embodiment, the compound has a structure which is

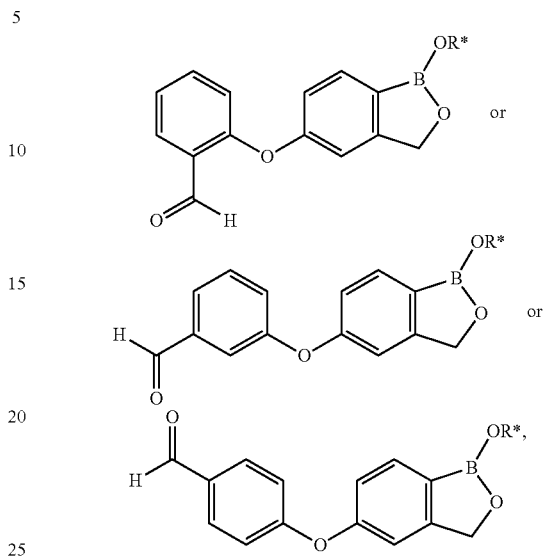

wherein R* is as described herein.

In an exemplary embodiment, the compound has a structure having the following formula:

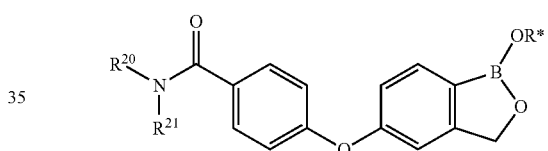

wherein R* is as defined herein, and with the proviso that both $R^{20}$ and $R^{21}$ are not both members selected from substituted or unsubstituted alkyl, and with the proviso that $R^{20}$ and $R^{21}$, together with the atoms to which they are attached, are not optionally combined to form a substituted or unsubstituted morpholino ring. In an exemplary embodiment, there is the proviso that both $R^{20}$ and $R^{21}$ are not both members selected from unsubstituted alkyl. In an exemplary embodiment, there is the proviso that both $R^{20}$ and $R^{21}$ are not both ethyl.

In an exemplary embodiment, the compound has a structure according to the following formula:

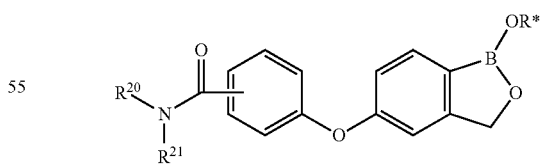

wherein R* is as defined herein, $R^{20}$ and $R^{21}$ are independently selected unsubstituted alkyl. In an exemplary embodiment, there is a proviso that each $R^{20}$ and $R^{21}$ is not unsubstituted $C_4$-$C_6$ alkyl. In an exemplary embodiment, there is a proviso that each $R^{20}$ and $R^{21}$ is not unsubstituted $C_1$-$C_3$ alkyl. In an exemplary embodiment, there is a proviso that both $R^{20}$ and $R^{21}$ are not methyl. In an exemplary embodiment, there is a proviso that both $R^{20}$ and $R^{21}$ are not ethyl. In an exemplary embodiment, there is a proviso that both $R^{20}$ and $R^{21}$ are not n-propyl. In an exemplary embodiment, the compound is

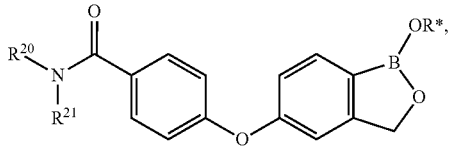

wherein each $R^{20}$ and $R^{21}$ is unsubstituted $C_4$-$C_6$ alkyl. In an exemplary embodiment, there is a proviso that the compound is not

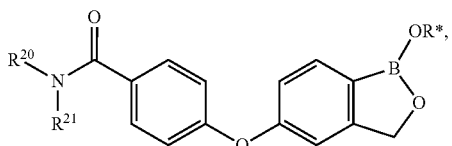

wherein each $R^{20}$ and $R^{21}$ is unsubstituted $C_1$-$C_3$ alkyl. In an exemplary embodiment, there is a proviso that the compound is not

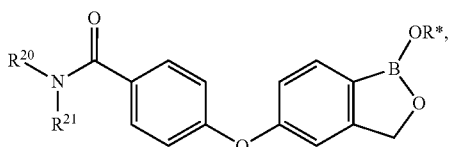

wherein both $R^{20}$ and $R^{21}$ are methyl. In an exemplary embodiment, there is a proviso that the compound is not

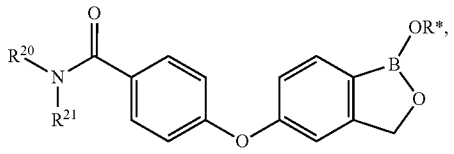

wherein both $R^{20}$ and $R^{21}$ are ethyl. In an exemplary embodiment, there is a proviso that the compound is not

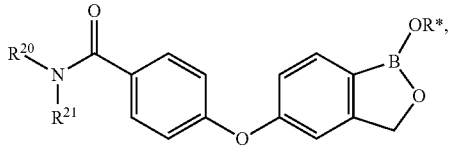

wherein both $R^{20}$ and $R^{21}$ are n-propyl.

In an exemplary embodiment, the compound has a structure according to:

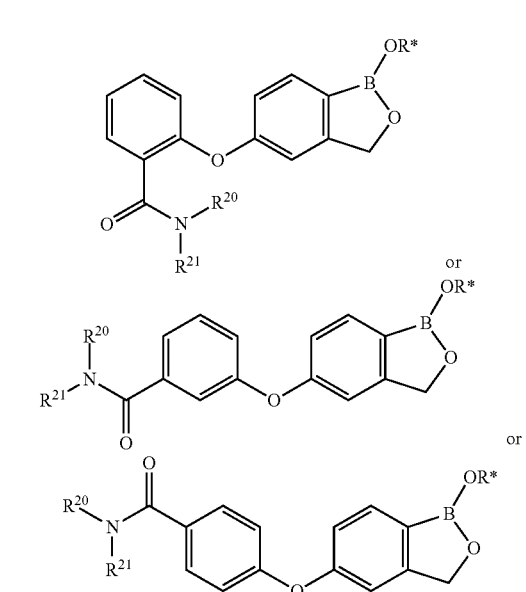

wherein $R^*$, $R^{20}$ and $R^{21}$ are as described herein.

In an exemplary embodiment, the compound is:

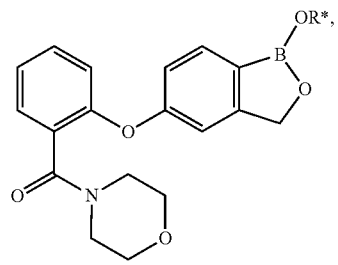

wherein $R^*$ is as described herein. In an exemplary embodiment, the compound is:

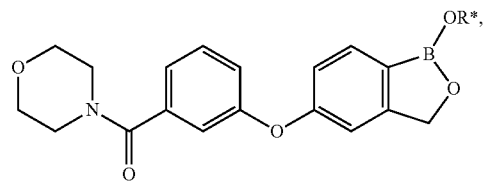

wherein $R^*$ is as described herein. In an exemplary embodiment, the compound is:

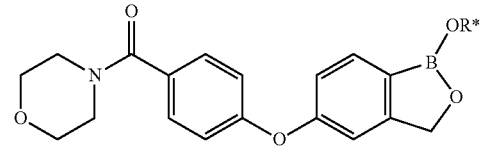

wherein $R^*$ is as described herein.

In an exemplary embodiment, the compound does not have a structure according to the following formula:

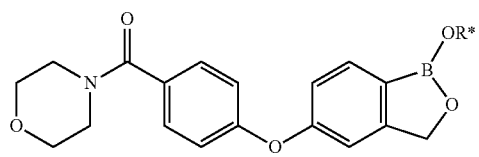

wherein R* is as described herein.

In an exemplary embodiment, the compound has a structure according to the following formula:

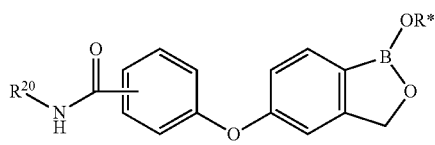

wherein R* is as defined herein, $R^{20}$ is $NH_2$. In an exemplary embodiment, the compound has a structure according to the following formula:

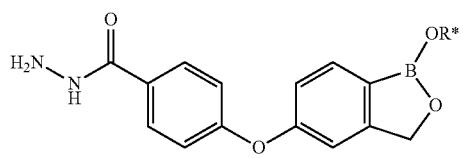

wherein R* is as defined herein.

In an exemplary embodiment, the compound has a structure according to the following formula:

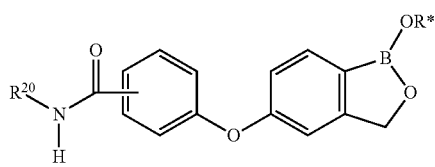

wherein R* is as defined herein, $R^{20}$ is tetrahydro-furan-2-ylmethyl. In an exemplary embodiment, the compound has a structure according to:

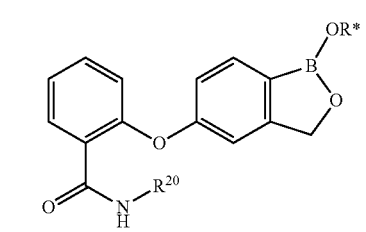

or

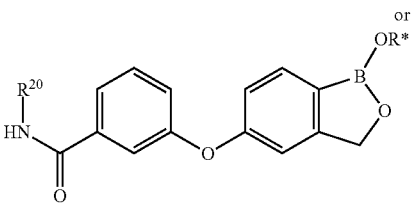

or

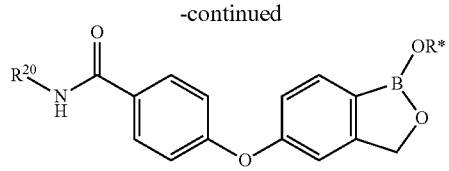

wherein $R^{20}$ is tetrahydro-furan-2-ylmethyl.

In an exemplary embodiment, the compound has a structure according to the following formula:

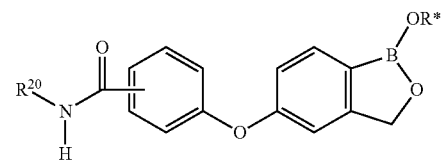

wherein R* is as defined herein, $R^{20}$ is $-NC(O)OR^{56}$, wherein $R^{56}$ is unsubstituted alkyl. In an exemplary embodiment, $R^{56}$ is a member selected from $C_1$ or $C_2$ or $C_3$ or $C_4$ or $C_5$ or $C_6$ alkyl. In an exemplary embodiment, the compound has a structure according to:

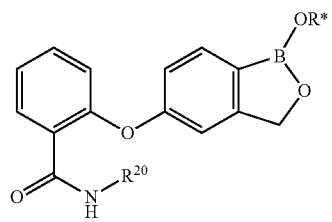

or

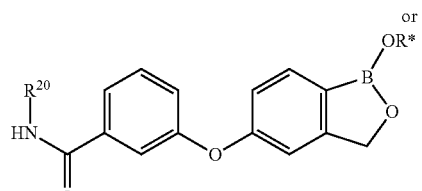

or

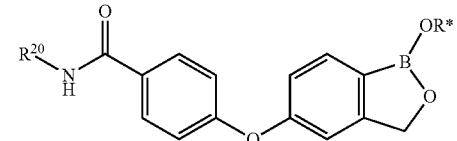

wherein $R^{20}$ is $NC(O)OR^{56}$. In an exemplary embodiment, $R^{56}$ is tert-butyl.

In an exemplary embodiment, the compound has a structure according to the following formula:

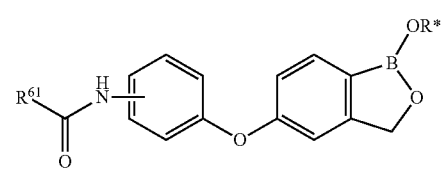

wherein R* is as defined herein, $R^{61}$ is unsubstituted alkyl. In an exemplary embodiment, $R^{61}$ is $C_1$ or $C_2$ or $C_3$ alkyl. In an exemplary embodiment, the compound has a structure according to:

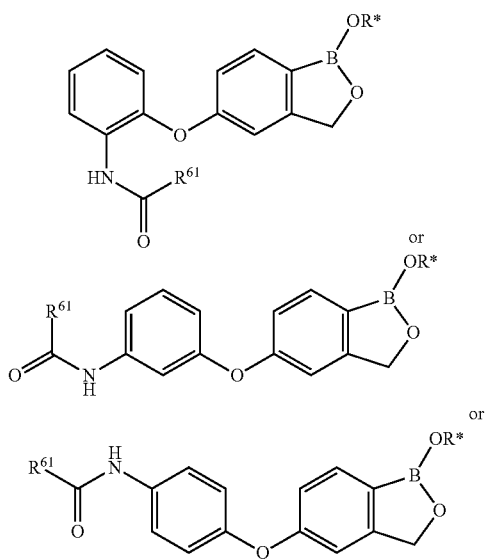

wherein $R^{61}$ is as described herein. In an exemplary embodiment, $R^{61}$ is methyl.

In an exemplary embodiment, the compound has a structure according to the formula:

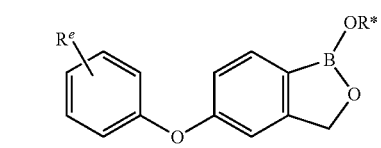

wherein R* is as defined herein, and $R^e$ is substituted or unsubstituted alkyloxy. In an exemplary embodiment, $R^e$ is unsubstituted alkyloxy. In an exemplary embodiment, $R^e$ is unsubstituted $C_1$-$C_6$ alkyloxy. In an exemplary embodiment, $R^e$ is unsubstituted $C_1$ or $C_2$ or $C_3$ or $C_4$ or $C_5$ or $C_6$ alkyloxy. In an exemplary embodiment, the compound has a structure which is

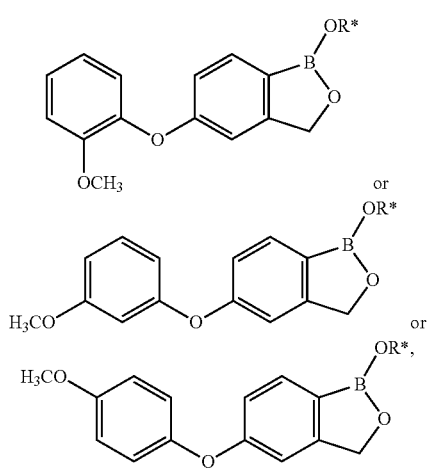

wherein R* is as defined herein.

In an exemplary embodiment, the compound has a structure according to the formula:

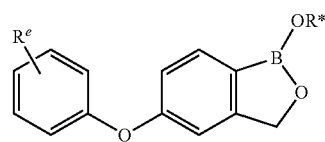

wherein R* is as defined herein, and $R^e$ is $NO_2$. In an exemplary embodiment, the compound has a structure which is

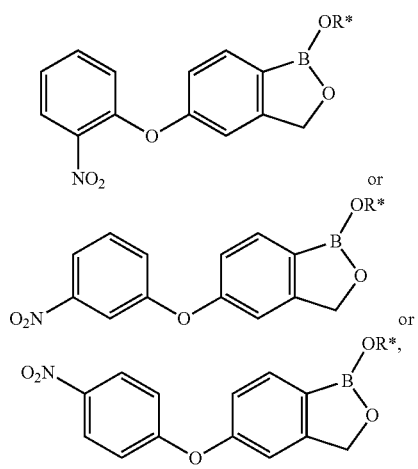

wherein R* is as defined herein.

In an exemplary embodiment, the compound has a structure according to the formula:

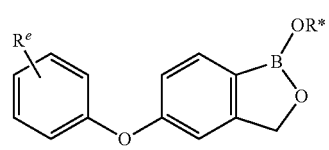

wherein R* is as defined herein, and $R^e$ is $NH_2$. In an exemplary embodiment, the compound has a structure which is

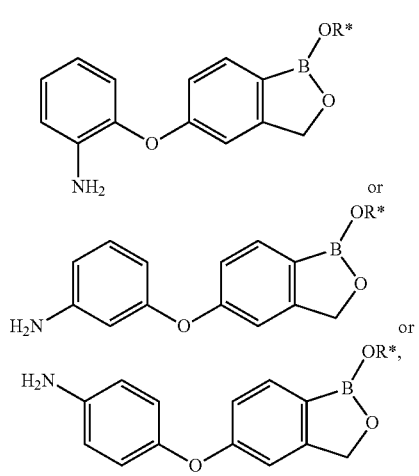

wherein R* is as defined herein.

In an exemplary embodiment, the compound has a structure according to the formula:

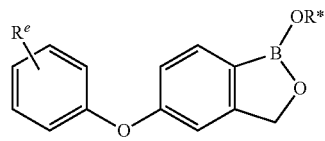

wherein R* is as defined herein, and $R^e$ is $R^{60}S(O)_2NH—$, wherein $R^{60}$ is unsubstituted alkyl. In an exemplary embodiment, $R^{60}$ is methyl. In an exemplary embodiment, the compound has a structure which is

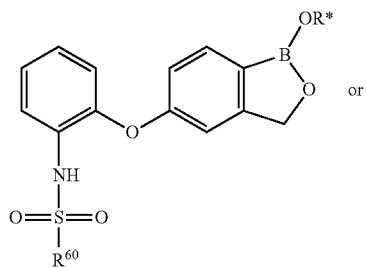

or

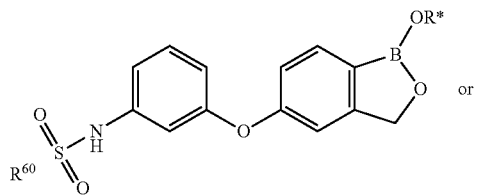

or

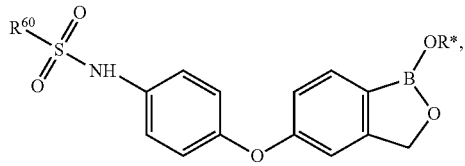

wherein R* is as defined herein.

In an exemplary embodiment, the compound has a structure according to the formula:

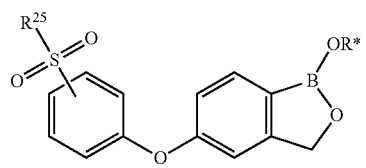

wherein R* is as defined herein, and $R^f$ is substituted or unsubstituted alkyl. In an exemplary embodiment, $R^f$ is unsubstituted alkyl. In an exemplary embodiment, $R^f$ is unsubstituted $C_1$-$C_6$ alkyl. In an exemplary embodiment, $R^f$ is unsubstituted $C_1$ or $C_2$ or $C_3$ or $C_4$ or $C_5$ or $C_6$ alkyl. In an exemplary embodiment, $R^f$ is unsubstituted $C_1$ or $C_2$ or $C_3$ alkyl. In an exemplary embodiment, $R^f$ is methyl or ethyl or isopropyl. In an exemplary embodiment, the compound has a structure which is

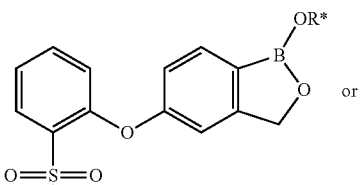

or

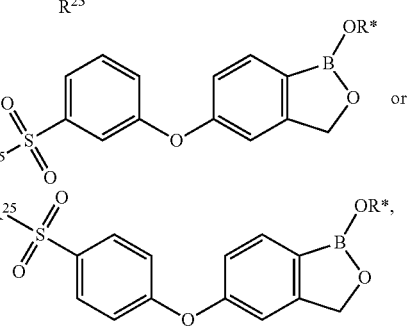

wherein R* is as defined herein.

In an exemplary embodiment, the compound has a structure which is a member selected from:

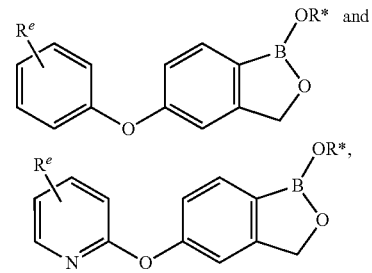

wherein R* and R' are as described herein.

In an exemplary embodiment, the compound has a structure which is a member selected from:

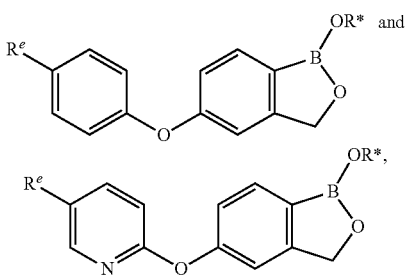

wherein R* and $R^e$ are as described herein.

In an exemplary embodiment, $R^e$ is —C(O)NR$^{20}$R$^{21}$, wherein each $R^{20}$ and $R^{21}$ is a member selected from H, hydroxyalkyl, substituted or unsubstituted aminoalkyl, substituted or unsubstituted arylalkyl, substituted or unsubstituted heteroarylalkyl, or $R^{20}$ and $R^{21}$, along with the nitrogen to which they are attached, are optionally joined to form a substituted or unsubstituted piperazinyl ring. In an exemplary embodiment, $R^{20}$ is H. In an exemplary embodiment, $R^{21}$ is a member selected from unsubstituted hydroxyalkyl, substituted or unsubstituted aminoalkyl, unsubstituted phenylalkyl, N-substituted aminoalkyl. In an exemplary embodiment, $R^{20}$ is H, and $R^{21}$ is unsubstituted alkyl. In an exemplary embodiment, $R^{20}$ is H, and $R^{21}$ is unsubstituted $C_1$-$C_6$ alkyl. In an exemplary embodiment, $R^{20}$ is H, and $R^{21}$ is $C_1$ or $C_2$ or $C_3$ or $C_4$ or $C_5$ or $C_6$ alkyl. In an exemplary embodiment, $R^{20}$ and $R^{21}$, along with the nitrogen to which they are attached, are joined to form an unsubstituted piperazinyl ring. In an exemplary embodiment, $R^{20}$ and $R^{21}$, along with the nitrogen to which they are attached, are joined to form a N-substituted piperazinyl ring. In an exemplary embodiment, the N-substituted piperazinyl ring is substituted with unsubstituted $C_1$-$C_6$ alkyl and unsubstituted $C_1$-$C_6$ alkylcarbonyl. In an exemplary embodiment, $R^{20}$ is H, and $R^{21}$ is a member selected from ortho-unsubstituted alkylbenzyl or meta-unsubstitutedalkylbenzyl or para-unsubstituted alkylbenzyl. In an exemplary embodiment, $R^{20}$ is H, and $R^{21}$ is paramethylbenzyl. In an exemplary embodiment, $R^{20}$ is H, and $R^{21}$ is a member selected from ortho-alkoxybenzyl or meta-alkoxybenzyl or para-alkoxybenzyl. In an exemplary embodiment, $R^{20}$ is H, and $R^{21}$ is a member selected from ortho-methoxybenzyl or meta-methoxybenzyl or para-methoxybenzyl. In an exemplary embodiment, $R^{20}$ is H, and $R^{21}$ is para-methoxybenzyl. In an exemplary embodiment, $R^{20}$ is H, and $R^{21}$ is phenyl. In an exemplary embodiment, $R^{20}$ is H, and $R^{21}$ is cycloalkyl. In an exemplary embodiment, $R^{20}$ is H, and $R^{21}$ is cyclopropyl. In an exemplary embodiment, $R^{20}$ is H, and $R^{21}$ is cyclobutyl. In an exemplary embodiment, $R^{20}$ is H, and $R^{21}$ is cyclopentyl. In an exemplary embodiment, $R^{20}$ is H, and $R^{21}$ is cyclohexyl. In an exemplary embodiment, $R^{20}$ is H, and $R^{21}$ is $CH_3$. In an exemplary embodiment, $R^{20}$ is $CH_3$, and $R^{21}$ is $CH_3$.

In an exemplary embodiment, $R^e$ is a member selected from

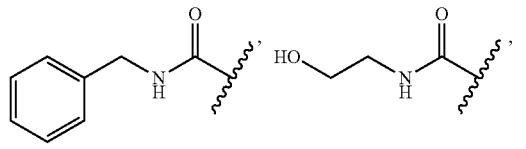

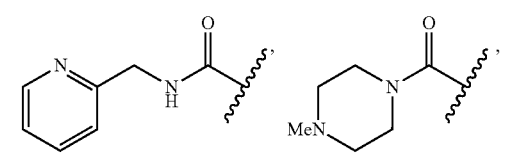

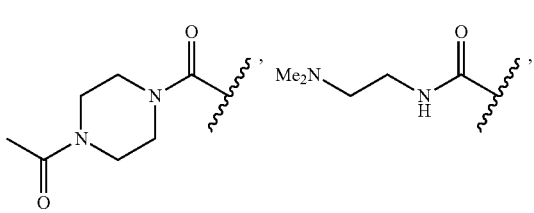

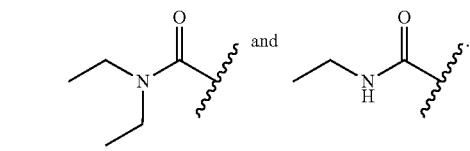

In an exemplary embodiment, the compound is a member selected from N-Benzyl-4-(1-hydroxy-1,3-dihydro-benzo[c][1,2]oxaborol-5-yloxy)-benzamide,

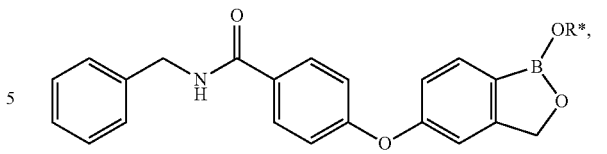

4-(1-Hydroxy-1,3-dihydro-benzo[c][1,2]oxaborol-5-yloxy)-N-(2-hydroxy-ethyl)-benzamide

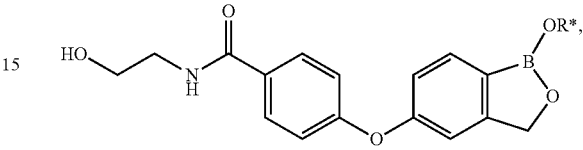

4-(1-Hydroxy-1,3-dihydro-benzo[c][1,2]oxaborol-5-yloxy)-N-pyridin-2-ylmethyl-benzamide

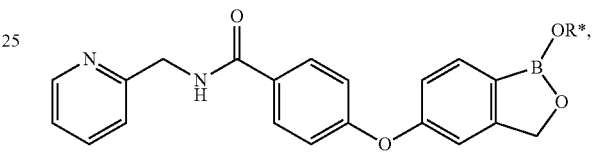

[4-(1-Hydroxy-1,3-dihydro-benzo[c][1,2]oxaborol-5-yloxy)-phenyl]-(4-methyl-piperazin-1-yl)-methanone

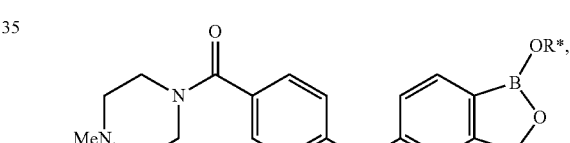

1-{4-[4-(1-Hydroxy-1,3-dihydro-benzo[c][1,2]oxaborol-5-yloxy)-benzoyl]-piperazin-1-yl}-ethanone

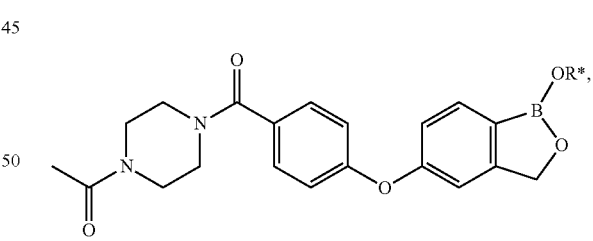

N-(2-Dimethylamino-ethyl)-4-(1-hydroxy-1,3-dihydro-benzo[c][1,2]oxaborol-5-yloxy)-benzamide

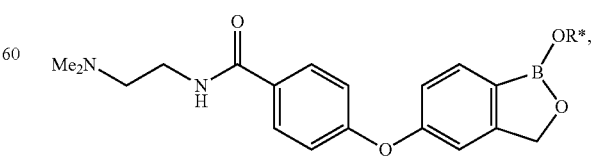

N,N-diethyl-6-(1-hydroxy-1,3-dihydrobenzo[c][1,2]oxaborol-5-yloxy)nicotinamide

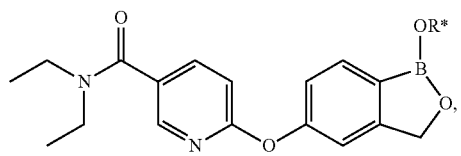

N-Ethyl-6-(1-hydroxy-1,3-dihydrobenzo[c][1,2]oxaborol-5-yloxy)nicotinamide

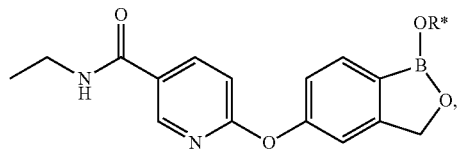

5-(5-(Hydroxymethyl)pyridin-2-yloxy)benzo[c][1,2]oxaborol-1(3H)-ol

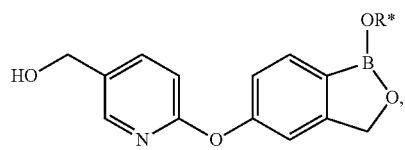

6-(1-hydroxy-1,3-dihydrobenzo[c][1,2]oxaborol-5-yloxy)nicotinaldehyde

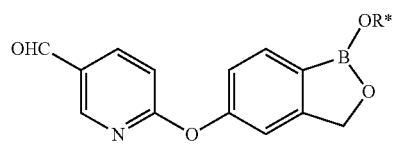

and (Z)—N-((6-(1-hydroxy-1,3-dihydrobenzo[c][1,2]oxaborol-5-yloxy)pyridin-3-yl)methylene)-2-methylpropan-2-amine oxide

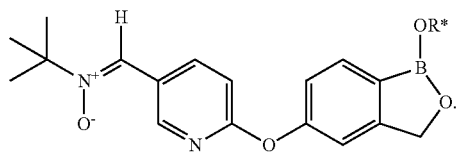

In an exemplary embodiment, the compound has a structure according to the following formula:

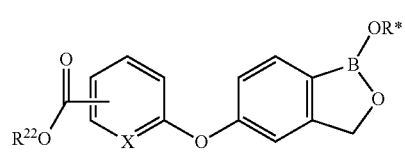

wherein X is a member selected from N, CH or C(O)R$^{22}$, R$^{22}$ is a member selected from alkyl, optionally substituted with dialkylamino, and R* is as described herein. In an exemplary embodiment, the compound has a structure according to:

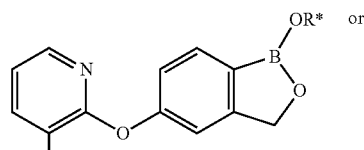

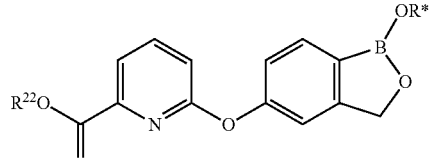

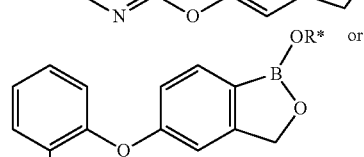

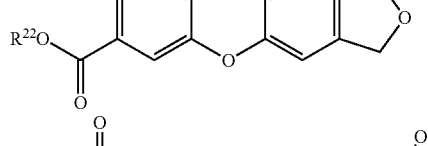

wherein R$^{22}$ is unsubstituted alkyl, and R* is as described herein. In an exemplary embodiment, R$^{22}$ is unsubstituted $C_1$-$C_6$ alkyl. In an exemplary embodiment, R$^{22}$ is unsubstituted $C_1$ or $C_2$ or $C_3$ or $C_4$ or $C_5$ or $C_6$ alkyl. In an exemplary embodiment, R$^{22}$ is unsubstituted $C_1$ alkyl. In an exemplary embodiment, R$^{22}$ is unsubstituted $C_2$ alkyl. In an exemplary embodiment, R$^{22}$ is unsubstituted $C_3$ alkyl. In an exemplary embodiment, R$^{22}$ is isopropyl. In an exemplary embodiment, R$^{22}$ is dialkylaminoalkyl. In an exemplary embodiment, R$^{22}$ is dialkylaminoethyl. In an exemplary embodiment, R$^{22}$ is dimethylaminoalkyl. In an exemplary embodiment, R$^{22}$ is dimethylaminoethyl.

In an exemplary embodiment, the compound has a structure according to the following formula:

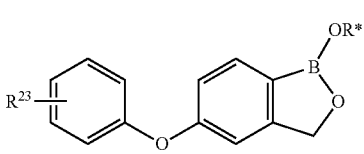

wherein R$^{23}$ is halogen, and R* is as described herein. In an exemplary embodiment, the compound has a structure according to:

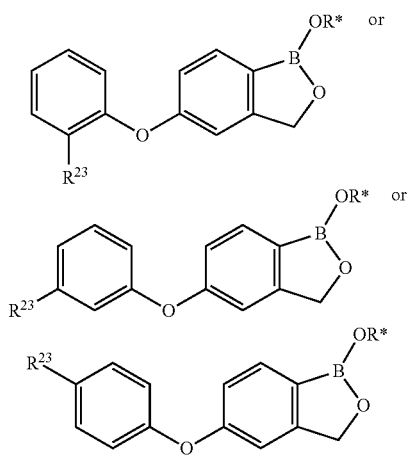

wherein R²³ is halogen, and R* is as described herein. In an exemplary embodiment, R²³ is fluoro or chloro.

In an exemplary embodiment, the compound has a structure according to the following formula:

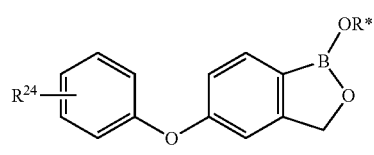

wherein R²⁴ is unsubstituted alkyl or halosubstituted alkyl, and R* is as described herein. In an exemplary embodiment, the compound has a structure according to:

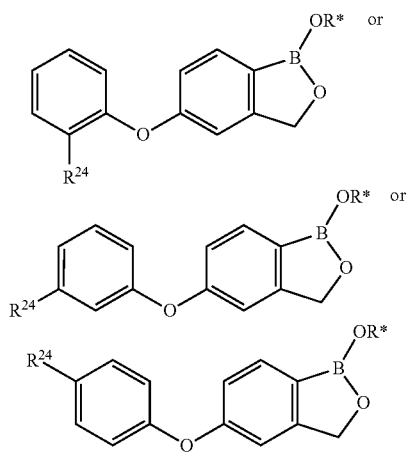

wherein R²⁴ is unsubstituted alkyl or halosubstituted alkyl, and R* is as described herein. In an exemplary embodiment, R²⁴ is unsubstituted $C_1$-$C_6$ alkyl or halosubstituted $C_1$-$C_6$ alkyl. In an exemplary embodiment, R²⁴ is unsubstituted $C_1$ or $C_2$ or $C_3$ or $C_4$ or $C_5$ or $C_6$ alkyl. In an exemplary embodiment, R²⁴ is halosubstituted $C_1$ or $C_2$ or $C_3$ or $C_4$ or $C_5$ or $C_6$ alkyl. In an exemplary embodiment, R²⁴ is fluorosubstituted $C_1$ or $C_2$ or $C_3$ or $C_4$ or $C_5$ or $C_6$ alkyl. In an exemplary embodiment, R²⁴ is trifluoromethyl. In an exemplary embodiment, R²⁴ is methyl.

In an exemplary embodiment, the compound is

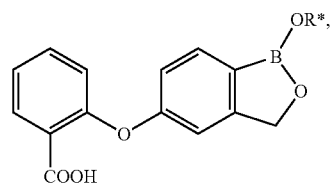

wherein R* is as described herein.
In an exemplary embodiment, the compound is

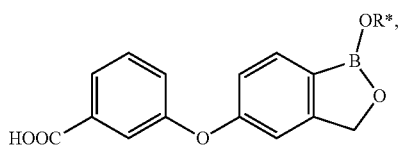

wherein R* is as described herein.
In an exemplary embodiment, the compound has a structure according to the following formula:

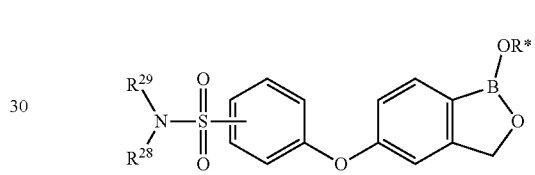

wherein R²⁸ or R²⁹ are independently selected unsubstituted alkyl, and R* is as described herein. In an exemplary embodiment, the compound has a structure which is a member selected from:

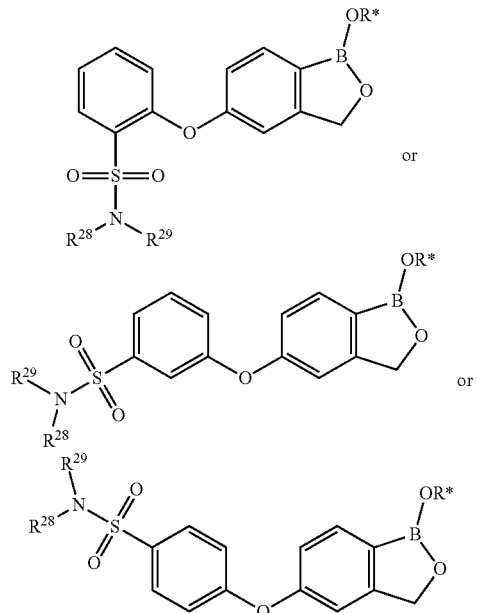

In an exemplary embodiment, R²⁸ is ethyl. In an exemplary embodiment, R²⁹ is ethyl.

In an exemplary embodiment, the compound has a structure according to the following formula:

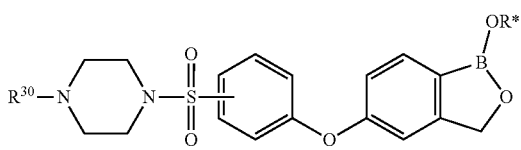

wherein R³⁰ is H and unsubstituted alkyl, and R* is as described herein. In an exemplary embodiment, the compound has a structure according to:

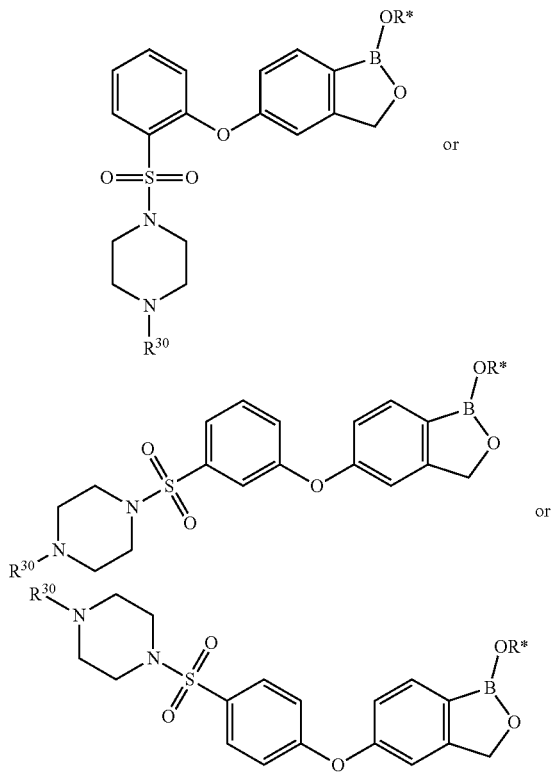

wherein R³⁰ is unsubstituted alkyl, and R* is as described herein. In an exemplary embodiment, R³⁰ is methyl.

In an exemplary embodiment, the compound has a structure according to the following formula:

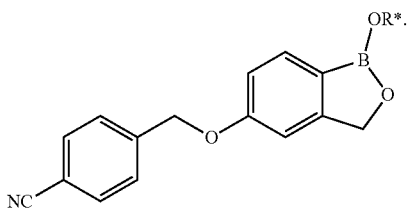

Figure 6E:
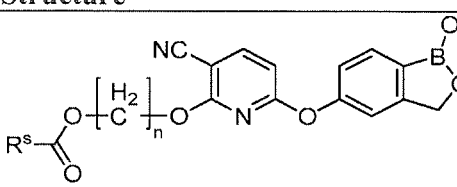
Figure 6L:
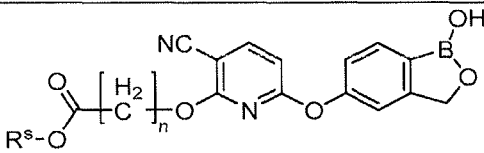

In an exemplary embodiment, the compound has a structure which is listed in FIGS. 1A-1K, or a salt thereof. In an exemplary embodiment, the compound has a structure which is listed in FIGS. 2A-2H, or a salt thereof. In an exemplary embodiment, the compound has a structure which is listed in FIGS. 3A-3FF, or a salt thereof. In an exemplary embodiment, the compound has a structure which is listed in FIGS. 4A-4FF, or a salt thereof. In an exemplary embodiment, the compound has a structure which is listed in FIGS. 5A-5FF, or a salt thereof. In an exemplary embodiment, the compound has a structure which is listed in FIGS. 6A-6L, or a salt thereof. In an exemplary embodiment, the compound has a structure which is listed in FIGS. 7A-7N, or a salt thereof.

In an exemplary embodiment, for the compound of any formula described herein, R* is H.

In another exemplary embodiment, the invention provides poly- or mutli-valent species of the compounds of the invention. In an exemplary embodiment, the invention provides a dimer of the compounds described herein. In an exemplary embodiment, the invention provides a dimer of the compounds described herein. In an exemplary embodiment, the invention provides a dimer of a compound which is a member selected from D1, D2, D3, D4, D5, D6, D7, D8, D9, D10, D11, D12, D13, D14, D15, D16, D17, D18, D19, D20, D21, D22, D23, D24, D25, D26, D27, D28, D29, D30, D31, D32, D33, D34, D35, D36, D37, D38, D39, D40, D41, D42, D43, D44, D45, D46, D47, D48, D49, D50, D51, D52, D53, D54, D55, D56, D57, D58, D59, D60, D61, D62, D63, D64, D65, D66, D67, D68, D69, D70, D71, D72, D73, D74, D75, D76, D77, D78, D79, D80, D81, D82, D83, D84, D85, D86, D87, D88, D89, D90, D91, D92, D93, D94, D95, D96, D97, D98, D99, D100, D101, D102, D103, D104, D105, D106, D107, D108, D109, D110, D111, D112, D113, D114, D115, D116, D117, D118, D119, D120, D121, D122, D123, D124, D125, D126, D127, D128, D129, D130, D131, D132, D133, D134, D135, D136, D137, D138, D139, D140, D141, D142, D143, D144, D145, D146, D147, D148, D149, D150, D151, D152, D153, D154, D155, D156, D157, D158, D159, D160, D161, D162, D163, D164, D165, D166, D167, D168, D169, D170, D171, D172, D173, D174, D175, D176, D177, D178, D179, D180, D181, D182, D183, D184, D185, D186, D187, D188, D189, D190, D191, D192, D193, D194, D195, D196, D197, D198, D199, D200, D201, D202, D203, D204, D205, D206, D207, D208, D209, D210, D211, D212, D213, D214, D215, D216, D217, D218, D219, D220, D221, D222, D223, D224, D225, D226, D227, D228 and D229.

In an exemplary embodiment, the invention provides an anhydride of the compounds described herein. In an exemplary embodiment, the invention provides an anhydride of the compounds described herein. In an exemplary embodiment, the invention provides an anhydride of a compound which is a member selected from D1, D2, D3, D4, D5, D6, D7, D8, D9, D10, D11, D12, D13, D14, D15, D16, D17, D18, D19, D20, D21, D22, D23, D24, D25, D26, D27, D28, D29, D30, D31, D32, D33, D34, D35, D36, D37, D38, D39, D40, D41, D42, D43, D44, D45, D46, D47, D48, D49, D50, D51, D52, D53, D54, D55, D56, D57, D58, D59, D60, D61, D62, D63, D64, D65, D66, D67, D68, D69, D70, D71, D72, D73, D74, D75, D76, D77, D78, D79, D80, D81, D82, D83, D84, D85, D86, D87, D88, D89, D90, D91, D92, D93, D94, D95, D96, D97, D98, D99, D100, D101, D102, D103, D104, D105, D106, D107, D108, D109, D110, D111, D112, D113, D114, D115, D116, D117, D118, D119, D120, D121, D122, D123, D124, D125, D126, D127, D128, D129, D130, D131, D132, D133, D134, D135, D136, D137, D138, D139, D140, D141, D142, D143, D144, D145, D146, D147, D148, D149, D150, D151, D152, D153, D154, D155, D156, D157, D158, D159, D160, D161, D162, D163, D164, D165, D166, D167, D168, D169, D170, D171, D172, D173, D174, D175, D176, D177, D178, D179, D180, D181, D182, D183, D184, D185, D186, D187, D188, D189, D190, D191, D192, D193, D194, D195, D196, D197, D198, D199, D200, D201, D202, D203, D204, D205, D206, D207, D208, D209, D210, D211, D212, D213, D214, D215, D216, D217, D218, D219, D220, D221, D222, D223, D224, D225, D226, D227, D228 and D229.

In an exemplary embodiment, the invention provides a trimer of the compounds described herein. In an exemplary embodiment, the invention provides a trimer of the compounds described herein. In an exemplary embodiment, the invention provides a trimer of a compound which is a member selected from D1, D2, D3, D4, D5, D6, D7, D8, D9, D10, D11, D12, D13, D14, D15, D16, D17, D18, D19, D20, D21, D22, D23, D24, D25, D26, D27, D28, D29, D30, D31, D32, D33, D34, D35, D36, D37, D38, D39, D40, D41, D42, D43, D44, D45, D46, D47, D48, D49, D50, D51, D52, D53, D54, D55, D56, D57, D58, D59, D60, D61, D62, D63, D64, D65, D66, D67, D68, D69, D70, D71, D72, D73, D74, D75, D76, D77, D78, D79, D80, D81, D82, D83, D84, D85, D86, D87, D88, D89, D90, D91, D92, D93, D94, D95, D96, D97, D98, D99, D100, D101, D102, D103, D104, D105, D106, D107, D108, D109, D110, D111, D112, D113, D114, D115, D116, D117, D118, D119, D120, D121, D122, D123, D124, D125, D126, D127, D128, D129, D130, D131, D132, D133, D134, D135, D136, D137, D138, D139, D140, D141, D142, D143, D144, D145, D146, D147, D148, D149, D150, D151, D152, D153, D154, D155, D156, D157, D158, D159, D160, D161, D162, D163, D164, D165, D166, D167, D168, D169, D170, D171, D172, D173, D174, D175, D176, D177, D178, D179, D180, D181, D182, D183, D184, D185, D186, D187, D188, D189, D190, D191, D192, D193, D194, D195, D196, D197, D198, D199, D200, D201, D202, D203, D204, D205, D206, D207, D208, D209, D210, D211, D212, D213, D214, D215, D216, D217, D218, D219, D220, D221, D222, D223, D224, D225, D226, D227, D228 and D229.

In an exemplary embodiment, the invention provides a compound described herein, or a salt, hydrate or solvate thereof, or a combination thereof. In an exemplary embodiment, the invention provides a compound described herein, or a salt, hydrate or solvate thereof. In an exemplary embodiment, the invention provides a compound described herein, or a salt thereof. In an exemplary embodiment, the salt is a pharmaceutically acceptable salt. In an exemplary embodiment, the invention provides a compound described herein, or a hydrate thereof. In an exemplary embodiment, the invention provides a compound described herein, or a solvate thereof. In an exemplary embodiment, the invention provides a compound described herein, or a prodrug thereof. In an exemplary embodiment, the invention provides a salt of a compound described herein. In an exemplary embodiment, the invention provides a pharmaceutically acceptable salt of a compound described herein. In an exemplary embodiment, the invention provides a hydrate of a compound described herein. In an exemplary embodiment, the invention provides a solvate of a compound described herein. In an exemplary embodiment, the invention provides a prodrug of a compound described herein.

In an exemplary embodiment, alkyl is a member selected from linear alkyl and branched alkyl. In another exemplary embodiment, heteroalkyl is a member selected from linear heteroalkyl and branched heteroalkyl.

Additional compounds which are useful in the methods of the invention are disclosed in U.S. Prov. Pat. App. 60/654,060; Filed Feb. 16, 2005; U.S. patent application Ser. No. 11/357,687, Filed Feb. 16, 2006; U.S. patent application Ser. No. 11/505,591, Filed Aug. 16, 2006, U.S. Prov. Pat. App. 60/823,888 filed on Aug. 29, 2006 and 60/774,532 filed on Feb. 16, 2006; U.S. patent application Ser. No. 11/676,120, Filed Feb. 16, 2007, which are herein incorporated by reference in their entirety for all purposes. Methods of producing the compounds of the invention are also described in these patent applications.

IIIe. Methods of Making the Compounds

The following exemplary schemes illustrate methods of preparing boron-containing molecules of the present invention. These methods are not limited to producing the compounds shown, but can be used to prepare a variety of molecules such as the compounds and complexes described herein. The compounds of the present invention can also be synthesized by methods not explicitly illustrated in the schemes but are well within the skill of one in the art. The compounds can be prepared using readily available materials of known intermediates.

The compounds of the invention can be produced according to the strategies described herein. Strategy A is described below for the production of 5-disubstituted phenoxy(halo-substituted)benzoxaborole derivatives:

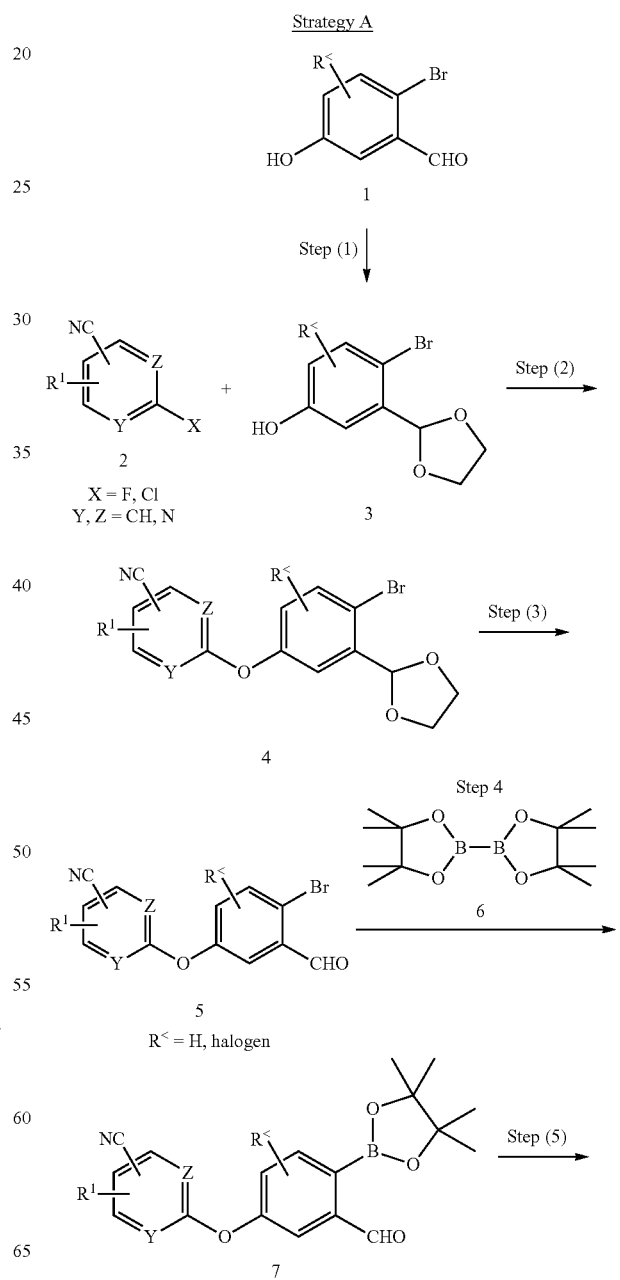

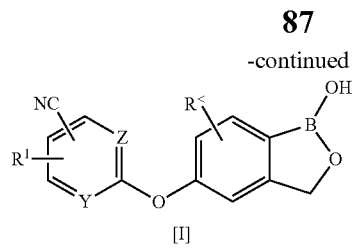

Step 1: The formyl group of compound 1 was protected as ethylene acetal with ethylene glycol in the presence of acid catalyst. Ethylene glycol was used in excess, typically from about 2 to about 10 equivalents to compound 1. As for the acid catalysts, sulfonic acids, such as para-toluene sulfonic acid or methanesulfonic acid, hydrogen chloride, hydrogen bromide, and the like are used at from about 1 to about 10 mol %. As for the solvent, toluene, benzene, xylene are used. The reaction is carried out under azetropic condition with a Dean-Stark head at reflux. The reaction is typically complete in from about 1 to about 24 hours. This step may not be needed depending the reactivity of compound 2.

Step 2: Compounds 2 and 3 are coupled in the presence of a base to give 4. As for the base, carbonates, such as potassium carbonate, cesium carbonate, and sodium carbonate, sodium hydride, potassium tert-butoxide, and the like are used. The amount is between from about 1 to about 5 equivalent. Useful solvents include N,N-dimethylformamide, N,N-dimethylacetamide, dimethylsulfoxide, acetonitrile, and the like. The reaction is carried out at from about 70 to about 150° C. and completed in from about 1 to about 24 hours.

Step 3: Compound 4 is treated with acid to hydrolyze the acetal. Useful acids include hydrochloric acid, hydrobromic acid, para-toluenesulfonic acid, methansulfonic acid, acetic acid, and the like in amounts of from about 1 to about 50 equivalents. Useful solvents include methanol, ethanol, tetrahydrofuran, 1,4-dioxane, 1,2-dimethoxyethane, and the like. The reaction is carried out at room temperature to reflux. The reaction is complete in from about 1 to about 24 hours.

Step 4: Compound 5 is subjected to Miyaura coupling to introduce boron atom. A mixture of compounds 5, 6, [1,1'-bis(diphenylphosphino)ferrocene]dichloropalladium(II) complex with dichloromethane, and potassium carbonate in a solvent is stirred at about 50° C. to reflux. The solvent is chosen from 1,4-dioxane, 1,2-dimethoxyethane, tetrahydrofuran, dimethylsulfoxide, dimethylformamide, toluene, and the like. The palladium catalyst is used at from about 1 to about 5 mol %, and the base is used from about 2 to about 5 equivalent. The reaction is completed in from about 1 to about 24 hours.

Step 5: Compound 7 is treated with a reducing agent, such as sodium borohydride and lithium aluminum hydride, in an inert solvent. Reducing agent is used from about 0.5 to about 2 equivalent. Inert solvent is methanol, ethanol, tetrahydrofuran, ether, and the like. The reaction is carried out at about 0° C. to room temperature, and complete in from about 1 to about 12 hours. Pinacol is removed by washing with aqueous boric acid during the extraction, treating crude product with water, or by freezedrying after purification.

Some 2-alkoxy-6-chloronicotinonitriles (2a) are prepared as follows:

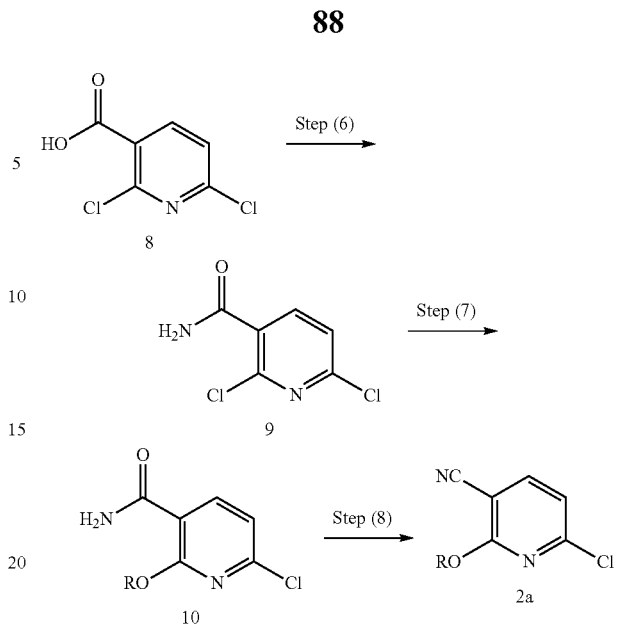

Step 6: 2,6-Dichloronicotinic acid (8) is converted into corresponding acid chloride using oxalyl chloride or thionyl chloride in inert solvent. As for the solvent, dichloromethane, 1,2-dichloroethane, tetrahydrofuran, are used. The reaction is carried out at about 0° C. to reflux, and completes in from about 1 to about 24 hours. Small amount of N,N-dimethylformamide can be added to accelerate the reaction. The acid chloride formed is treated with ammonia to give compound 8.

Step 7: Compound 10 is obtained by treating 8 with corresponding alkoxide. As for the alkoxide, commercially available sodium methoxide or sodium ethoxide can be used. Otherwise, it is prepared in situ from alcohol (ROH) and a base, such as sodium, sodium hydride, potassium hydride, butyllithium, and the like. As for the solvent, tetrahydrofuran, 1,4-dioxane, N, N-dimethylformamide, 1,2-dimethoxyethane, toluene, and the like are used. The reaction is carried out at about 0° C. to room temperature for from about 1 to about 24 hours.

Step 8: Compound 10 is treated with phosphorous oxychloride and pyridine to give 2a. Phosphorous oxychloride and pyridine are used in about 3 to about 6 equivalent. The solvent is chosen from acetonitrile, tetrahydrofuran, toluene, and the like. The reaction is carried out at room temperature to reflux and complete in from about 1 to about 24 hours.

Some 2-alkoxy-6-chloronicotinonitriles (2a) and 6-alkoxy-2-chloronicotinonitriles (2b) are alternatively prepared as follows:

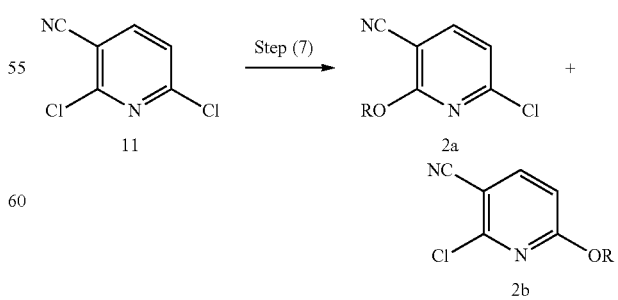

Compounds 2a and 2b are obtained in the same condition as described above for step 7 from 2,6-dichloronicotinonitrile (11). The mixture can be separated by silica gel column chromatography, preparative thin layer chromatography or high performance liquid chromatography.

Some 2-amino-6-chloronicotinonitrile derivatives (2c) and 6-amino-2-chloronicotinonitrile derivatives (2d) are alternatively prepared as follows:

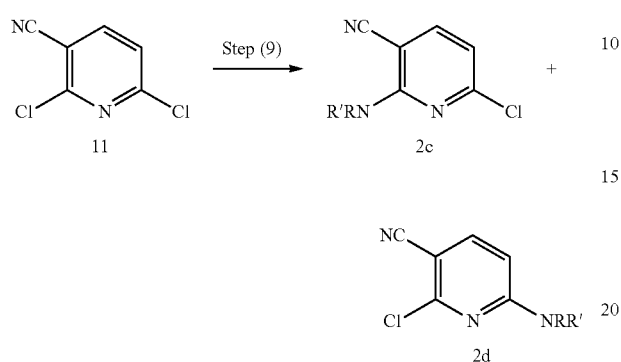

Step 9: Compounds 2c and 2d are obtained by treating 11 with corresponding amines with or without a base. Amine is used from about 1 to about 10 equivalent. The base includes potassium carbonate, sodium carbonate, cesium carbonate, sodium hydride, potassium hydride, butyllithium, and the like. As for the solvent, tetrahydrofuran, 1,4-dioxane, N,N-dimethylformamide, 1,2-dimethoxyethane, toluene, and the like are used. The reaction is carried out at about 0° C. to reflux for from about 1 to about 24 hours. The mixture can be separated by silica gel column chromatography, preparative thin layer chromatography or high performance liquid chromatography.

Compounds 1a and 1b are prepared as follows.

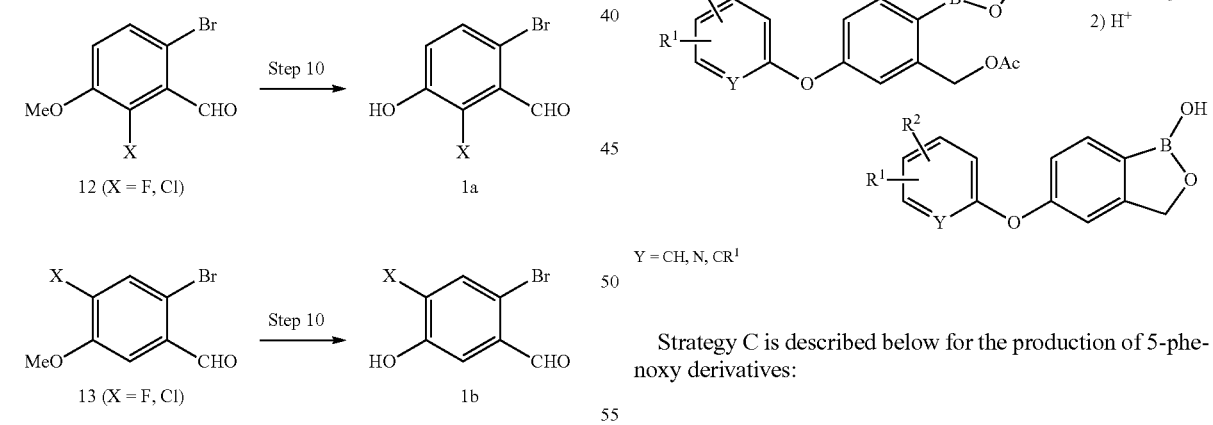

Step 10: (a) Compound 12 or 13 are treated with boron tribromide in dichloromethane. Boron tribromide is used from about 1 to about 3 equivalents. The reaction is carried out at about −78° C. to room temperature and complete in from about 1 to about 24 hours. (b) Alternatively, compound 12 or 13 are treated with 48% hydrobromic acid in acetic acid at from about 30 to about 100° C. for from about 6 to about 72 hours.

Strategy B is described below for the production of mono- or disubstituted 5-phenoxy derivatives:

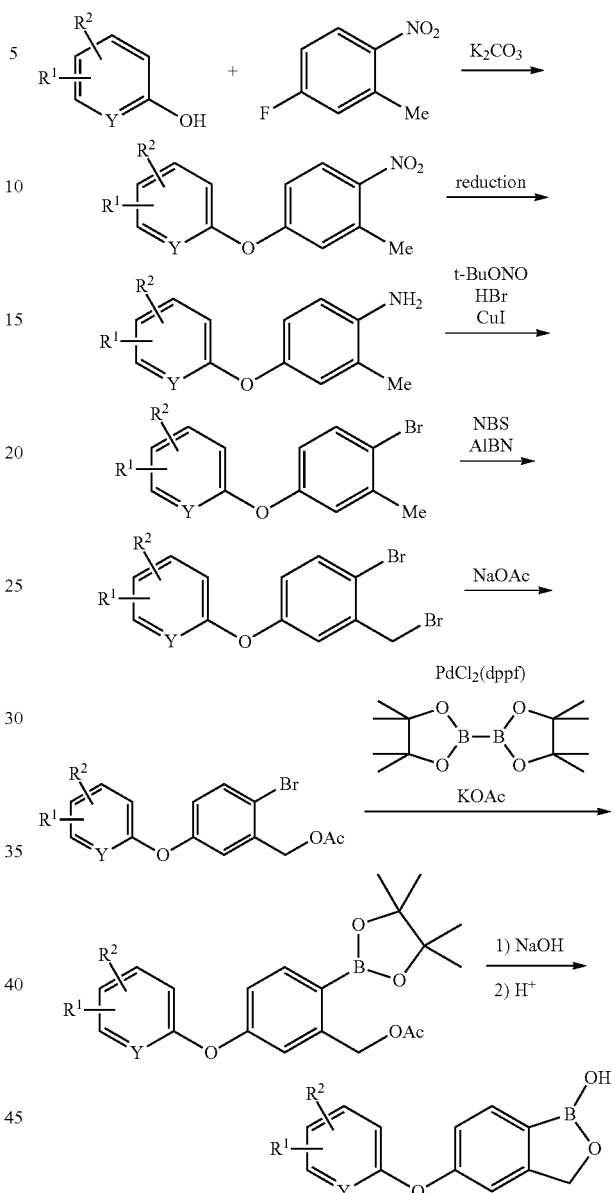

Strategy C is described below for the production of 5-phenoxy derivatives:

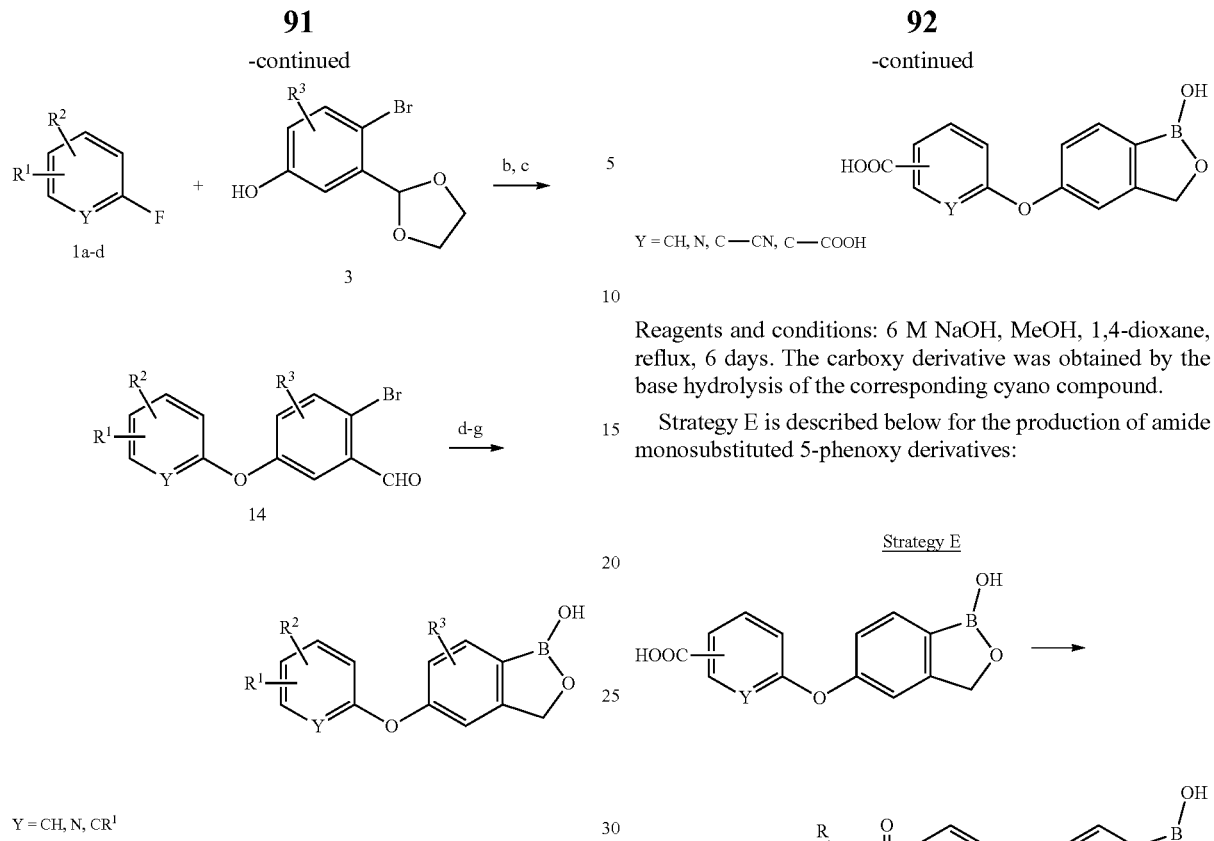

Y = CH, N, C—CN, C—COOH

Reagents and conditions: 6 M NaOH, MeOH, 1,4-dioxane, reflux, 6 days. The carboxy derivative was obtained by the base hydrolysis of the corresponding cyano compound.

Strategy E is described below for the production of amide monosubstituted 5-phenoxy derivatives:

Y = CH, N, CR¹

Reagents and conditions: (a) ethylene glycol, p-TsOH, toluene, reflux, 6 h; (b) $K_2CO_3$, DMF, 100° C., overnight; (c) 3 M HCl, THF, reflux, 2 h; (d) $NaBH_4$, MeOH, rt, 1 h; (e) 3,4-dihydro-2H-pyran, camphorsulfonic acid, $CH_2Cl_2$, rt, 2 h; (f) (i-PrO)$_3$B, n-BuLi, THF, −78° C. to rt, 3 h; (g) 6 M HCl, THF, rt, 3 h; (h) 6 M NaOH, MeOH, 1,4-dioxane, reflux, 6 days; (i) EDCI, HOBt, DMAP, DMF, rt, overnight.

5-Phenoxybenzoxaborole derivatives were synthesized as shown above. Diaryl ether scaffold was made by nucleophilic aromatic substitution reaction. The formyl group of compound 2 was protected as an acetal to avoid self condensation of 2. The formyl group of 4 was reduced to alcohol and protected as THP ether. The boron atom was then introduced by halogen-metal exchange with n-BuLi in the presence of triisopropyl borate, which is known as the in-situ quench protocol (Li, W., et al. *J. Org. Chem.* 2002, 67, 5394-5397. Upon deprotection of THP group by HCl, the resulting hydroxymethyl group spontaneously cyclized to afford the desired oxaborole.

Strategy D is described below for the production of carboxy monosubstituted 5-phenoxy derivatives:

Strategy D

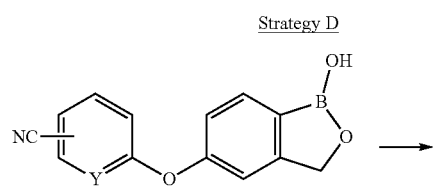

Y = CH, N, C—COOH, CC(O)NR₂

Reagents and conditions: EDCI, HOBt, DMAP, DMF, rt, overnight. Amide derivatives were synthesized from the carboxy derivative using regular EDC/HOBt conditions.

Strategy F is described below for the production of ester monosubstituted 5-phenoxy derivatives:

Y = CH, N, C—COOH, CC(O)OR

Step 11: Reagents and conditions: (a) ROH, sulfuric acid (1 to 10 mol %), reflux 1 to 24 hours or (b) RX (X=Cl, Br, I), base (potassium carbonate, sodium carbonate, sodium hydride, and the like), solvent (acetone, tetrahydrofuran, N,N-dimethylformamide, and the like), 0° C. to reflux, 1 to 24 hours.

Various 4-cyanophenoxy derivatives are synthesized as shown in Strategy G in similar ways to make compounds [I].

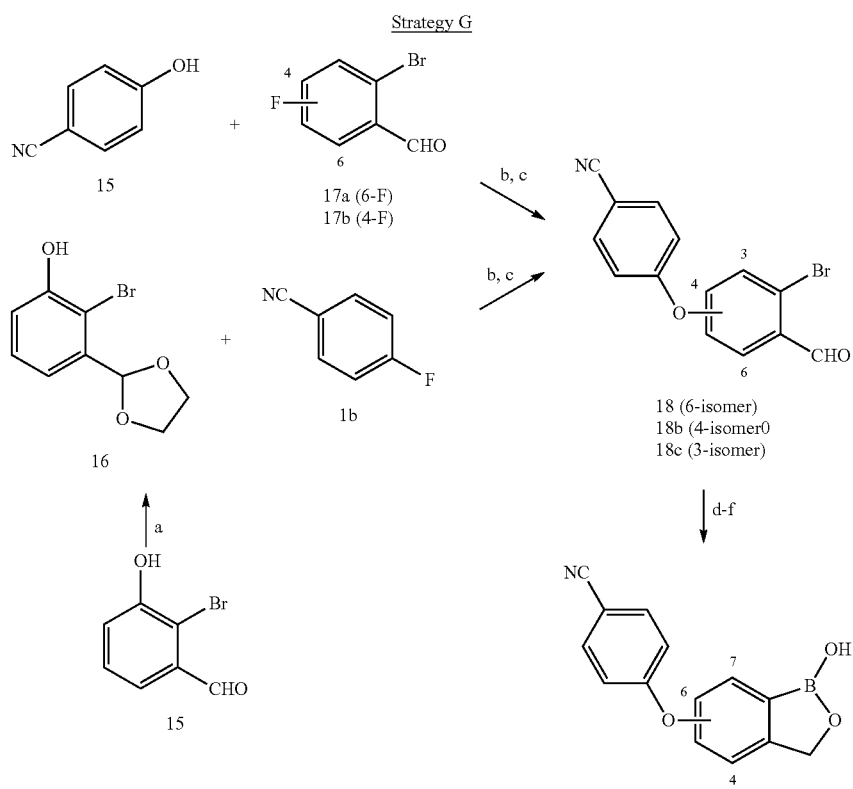

Reagents and conditions: (a) ethylene glycol, p-TsOH, toluene, reflux, 6 h; (b) K₂CO₃, DMF, 100° C., overnight; (c) 3 M HCl, THF, reflux, 2 h; (d) NaBH₄, MeOH, rt, 1 h; (e) 3,4-dihydro-2H-pyran, camphorsulfonic acid, CH₂Cl₂, rt, 2 h; (f) (i-PrO)₃B, n-BuLi, THF, −78° C. to rt, 3 h.

Carbamoyl substituted derivatives are prepared as follows:

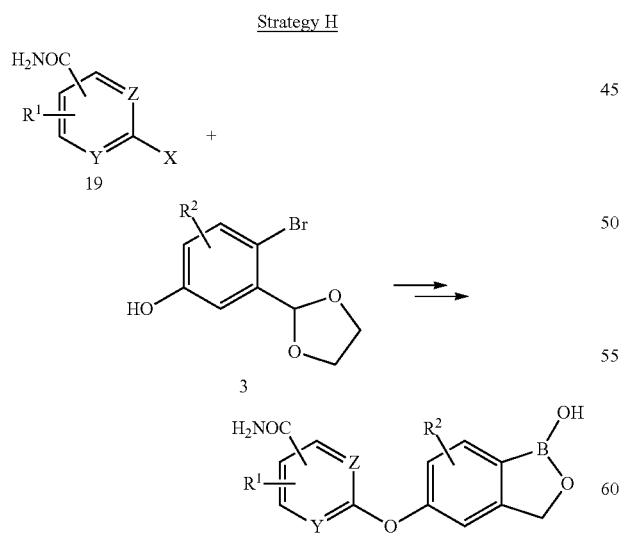

These compounds are prepared from compounds 19 and 3 in a similar manner to Strategy A.

Aminomethyl substituted derivatives are prepared as follows:

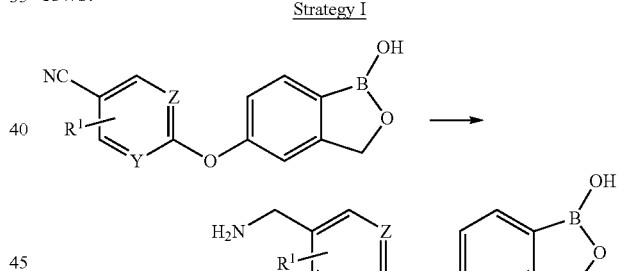

These compounds are prepared by hydrogenation of corresponding cyano derivatives. Typical condition is using palladium on charcoal (5 to 10%) in ethanol, methanol, ethyl acetate, and the like, at room temperature to reflux at atmosphere pressure to about 50 psi for from about 1 to about 72 hours. Alternatively, these compounds are prepared by lithium aluminum hydride reduction in ether or tetrahydrofuran at about 0° C. to reflux for from about 1 to about 24 hours.

Alkylaminomethyl derivatives are prepared as follows:

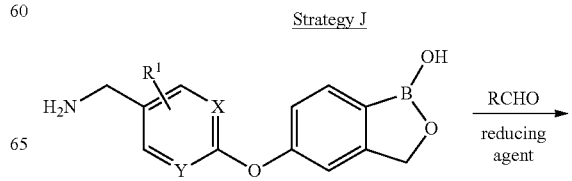

-continued

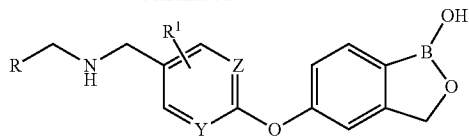

Those compounds are prepared by regular reductive alkylration. As for the reducing agent, sodium borohydride or sodium cyanoborohydride is typically used. As for the solvent, methanol, ethanol, tetrahydrofuran, 1,4-dioxane, and the like are used. The reaction is carried out at from about 0 to about 50° C. and complete in from about 1 to about 24 hours.

Sulfonylaminomethyl derivatives are prepared as follows:

Strategy K

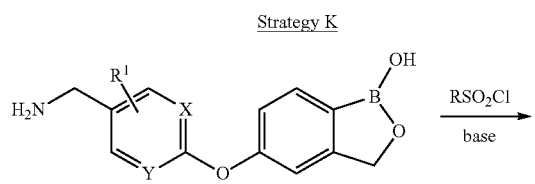

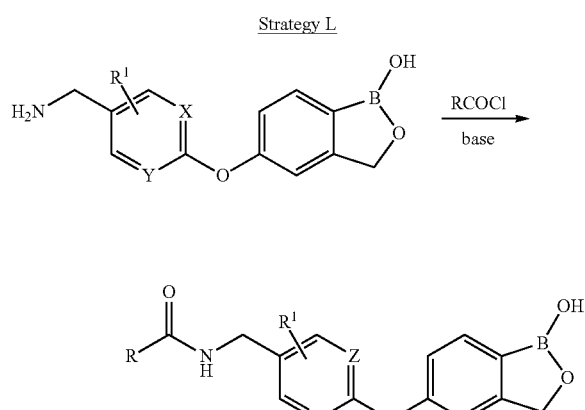

These compounds are prepared by regular sulfonylation. The amine is treated with 1 to 10 equivalent of sulfonyl chloride. As for the base, triethylamine, diisopropylethylamine, DBU, pyridine, 4-N,N-dimethylaminopyridine, sodium hydride, butyllithium, and the like are used. As for the solvents, dichloromethane, 1,2-dichloroethane, tetrahydrofuran, acetonitrile, N,N-dimethylformamide, and the like are used. The reaction is carried out at from about 0 to about 50° C. and complete in from about 1 to about 24 hours.

Alkanoylaminomethyl derivatives are prepared as follows:

Strategy L

These compounds are prepared in a similar manner to Strategy K using acid chloride instead of sulfonyl chloride.

Urea derivatives are prepared as follows:

Strategy M

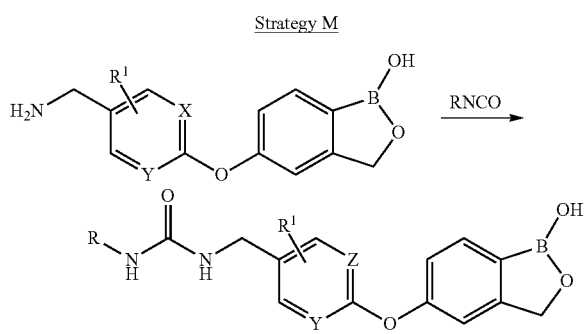

These compounds are prepared by treating the amine with 1 to 10 equivalent of corresponding isocyanate. As for the solvent, dichloromethane, 1,2-dichloroethane, tetrahydrofuran, acetonitrile, N,N-dimethylformamide, and the like are used. The reaction is carried out at from about 0 to about 80° C. and complete in from about 1 to about 24 hours.

Alternatively, urea derivatives are prepared as follows:

Strategy N

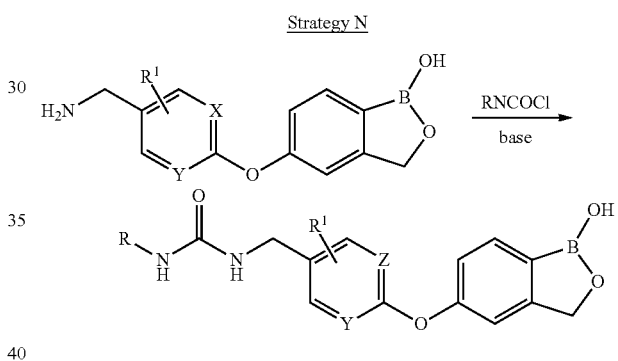

These compounds are prepared in a similar manner to Strategy K using carbamoyl chloride instead of sulfonyl chloride.

5-Alkoxy derivatives are prepared as follows:

Strategy P

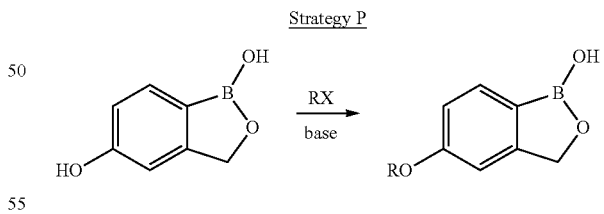

These compounds are prepared from 5-hydroxy derivative by regular alkylation with from about 1 to about 10 equivalent of alkyl halide (RX) and a base. As for the base, potassium carbonate, sodium carbonate, cesium carbonate, sodium hydride, potassium tert-butoxide, and the like are used. As for the solvent, acetone, acetonitrile, tetrahydrofuran, dichloromethane, N,N-dimethylformamide, and the like are used. The reaction is carried out at from about 0 to about 100° C. and complete in from about 1 to about 24 hours.

5-alkanoyloxy and 5-aryloyloxy derivatives are prepared as follows:

Strategy Q

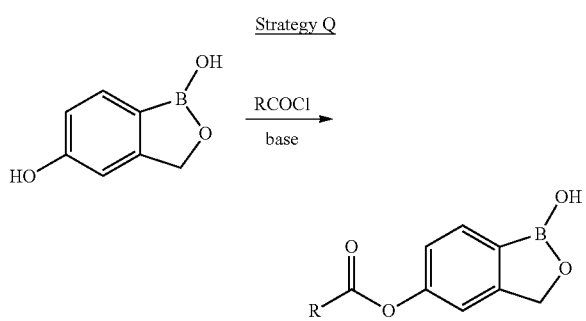

These compounds are prepared in a similar manner to Strategy L.

The compounds of the invention can be converted into hydrates and solvates by methods similar to those described herein.

III.f) Combinations Comprising Additional Therapeutic Agents

The compounds of the invention may also be used in combination with additional therapeutic agents. The invention thus provides, in a further aspect, a combination comprising a compound described herein or a pharmaceutically acceptable salt thereof together with at least one additional therapeutic agent. In an exemplary embodiment, the additional therapeutic agent is a compound of the invention. In an exemplary embodiment, the additional therapeutic agent includes a boron atom. In an exemplary embodiment, the additional therapeutic agent does not contain a boron atom. In an exemplary embodiment, the additional therapeutic agent is a compound described in sections III a)-e).

When a compound of the invention is used in combination with a second therapeutic agent active against the same disease state, the dose of each compound may differ from that when the compound is used alone. Appropriate doses will be readily appreciated by those skilled in the art. It will be appreciated that the amount of a compound of the invention required for use in treatment will vary with the nature of the condition being treated and the age and the condition of the patient and will be ultimately at the discretion of the attendant physician or veterinarian. In an exemplary embodiment, the additional therapeutic agent is an antiflammatory. In an exemplary embodiment, the additional therapeutic agent is a steroid or cyclosporineor psoralen or UVA or retinoid or methotrexete or vitamin $D_3$ analog. In an exemplary embodiment, the steroid is a systemic steroid or a topical steroid. In an exemplary embodiment, the additional therapeutic agent is topical steroid or antihistamine or calcineurin inhibitor. In an exemplary embodiment, the additional therapeutic agent is CC-10004 or AWD-12-281. In an exemplary embodiment, the additional therapeutic agent is a corticosteroid or a NSAIDs. In an exemplary embodiment, the additional therapeutic agent is a PDE4 inhibitor. In an exemplary embodiment, the additional therapeutic agent is rolipram or roflumilast.

The individual components of such combinations may be administered either simultaneously or sequentially in a unit dosage form. The unit dosage form may be a single or multiple unit dosage forms. In an exemplary embodiment, the invention provides a combination in a single unit dosage form. An example of a single unit dosage form is a capsule wherein both the compound of the invention and the additional therapeutic agent are contained within the same capsule. In an exemplary embodiment, the invention provides a combination in a two unit dosage form. An example of a two unit dosage form is a first capsule which contains the compound of the invention and a second capsule which contains the additional therapeutic agent. Thus the term 'single unit' or 'two unit' or 'multiple unit' refers to the object which the patient ingests, not to the interior components of the object. Appropriate doses of known therapeutic agents will be readily appreciated by those skilled in the art.

The combinations referred to herein may conveniently be presented for use in the form of a pharmaceutical formulation. Thus, an exemplary embodiment of the invention is a pharmaceutical formulation comprising a) a compound of the invention; b) an additional therapeutic agent and c) a pharmaceutically acceptable excipient. In an exemplary embodiment, the pharmaceutical formulation is a unit dosage form. In an exemplary embodiment, the pharmaceutical formulation is a single unit dosage form. In an exemplary embodiment, the pharmaceutical formulation is a two unit dosage form. In an exemplary embodiment, the pharmaceutical formulation is a two unit dosage form comprising a first unit dosage form and a second unit dosage form, wherein the first unit dosage form includes a) a compound of the invention and b) a first pharmaceutically acceptable excipient; and the second unit dosage form includes c) an additional therapeutic agent and d) a second pharmaceutically acceptable excipient.

IV. The Methods a) Decreasing the Production of a Cytokine and/or Chemokine

In another aspect, the invention provides a method for decreasing the production of a cytokine and/or a chemokine, the method comprising: contacting a cell with a compound of the invention, wherein production of the cytokine and/or chemokine by the cell is decreased. In another aspect, the invention provides a method for decreasing the production of a cytokine and/or a chemokine, the method comprising: contacting a cell with a compound described herein or a pharmaceutically acceptable salt thereof, wherein production of the cytokine and/or chemokine by the cell is decreased. In an exemplary embodiment, the compound of the invention is a compound described herein, or a pharmaceutically acceptable salt thereof. In an exemplary embodiment, the compound of the invention is a compound described herein. In an exemplary embodiment, the cell is contacted with a therapeutically effective amount of the compound. In an exemplary embodiment, the compound is according to a formula described herein. In an exemplary embodiment, the compound is a member selected from C1, C2, C3, C4, C5, C6, C7, C8, C9, C10, C11, C12, C13, C14, C15, C16, C17, C18, C19, C20, C21, C22, C23, C24, C25, C26, C27, C28, C29, C30, C31, C32, C33, C34, C35, C36, C37, C38, C39, C40, C41, C42, C43, C44, C45, C46, C47, C48, C49, C50, C51, C52, C53, CM, C55, C56, C57, C58, C59, C60, C61, C62, C63, C64, C65, C66, C67, C68, C69, C70, C71, C72, C73, C74, C75, C76, C77, C78, C79, C80, C81, C82, C83, C84, C85, C86, C87, C88, C89, C90, C91, C92, C93, C94, C95, C96, C97, C98, C99 and C100. In an exemplary embodiment, the compound is a member selected from D1, D2, D3, D4, D5, D6, D7, D8, D9, D10, D11, D12, D13, D14, D15, D16, D17, D18, D19, D20, D21, D22, D23, D24, D25, D26, D27, D28, D29, D30, D31, D32, D33, D34, D35, D36, D37, D38, D39, D40, D41, D42, D43, D44, D45, D46, D47, D48, D49, D50, D51, D52, D53, D54, D55, D56, D57, D58, D59, D60, D61, D62, D63, D64, D65, D66, D67, D68, D69, D70, D71, D72, D73, D74, D75, D76, D77, D78, D79, D80, D81, D82, D83, D84, D85, D86, D87, D88, D89, D90, D91, D92, D93, D94, D95, D96, D97, D98, D99, D100, D101, D102, D103, D104, D105, D106, D107, D108, D109, D110, D111, D112, D113, D114, D115, D116, D117, D118, D119, D120, D121, D122, D123, D124, D125, D126, D127, D128, D129, D130, D131, D132, D133, D134, D135, D136, D137, D138, D139, D140, D141, D142, D143, D144, D145, D146, D147, D148, D149, D150, D151, D152, D153, D154, D155, D156, D157, D158, D159, D160, D161, D162, D163, D164, D165, D166, D167, D168, D169, D170, D171, D172, D173, D174, D175, D176, D177, D178, D179, D180, D181, D182, D183, D184, D185, D186, D187, D188, D189, D190, D191, D192, D193, D194, D195, D196, D197, D198, D199, D200, D201, D202, D203, D204, D205, D206, D207, D208, D209, D210, D211, D212, D213, D214, D215, D216, D217, D218, D219, D220, D221, D222, D223, D224, D225, D226, D227, D228 and D229. In an exemplary embodiment, the compound is C17. In another exemplary embodiment, the compound is C27. In another exemplary embodiment, the compound is C23 or C24. In another exemplary embodiment, the compound is C25. In another exemplary embodiment, the compound is C26. In another exemplary embodiment, the compound is C37. In an exemplary embodiment, the compound is a member selected from D46, D86, D99, D100, D107, D108, D114, D122, D125, D126, D127, D128, D131, D140 and D141, and salts thereof. In an exemplary embodiment, the compound is a member selected from D95, D96, D97, D102, D110, D111, D113, D115, D121, D129, D130, D132, and salts thereof. In an exemplary embodiment, the compound is a member selected from D47, D109, D116, D118, D119, D120, D123, and salts thereof. In an exemplary embodiment, the compound is a member selected from D98, D101, D106, and salts thereof. In an exemplary embodiment, the compound is a member selected from D11, D12, D37, D38, D39, D40, D41, D42, D43, D124, D142, D143, D146, and salts thereof. In an exemplary embodiment, the compound is a member selected from D14, D15, D16, D17, D28, D29, D30, D31, D133, D134, D135, D144, D145, D147, and salts thereof.

In an exemplary embodiment, the method is for decreasing the production of a cytokine, which is a TH1 cytokine. In an exemplary embodiment, the TH1 cytokine is a member selected from IFN-γ and IL-2.

In an exemplary embodiment, the method is for decreasing the production of a cytokine, which is a TH2 cytokine. In an exemplary embodiment, the TH2 cytokine is a member selected from IL-4, IL-5 and IL-10.

In an exemplary embodiment, the method is for decreasing the production of a cytokine, which is a member selected from IL-1α, IL-1β, IL-2, IL-3, IL-6, IL-7, IL-9, IL-12, IL-17, IL-18, IL-23, TNF-α, LT, LIF, Oncostatin, IFNα, IFNβ and IFN-γ. In another exemplary embodiment, the cytokine is a member selected from IL-1β, IL-2, IL-3, IL-6, IL-7, IL-9, IL-12, IL-23, TNF-α, LT, LIF, Oncostatin, and IFN-γ. In another exemplary embodiment, the cytokine is a member selected from IL-1β, IL-2, IL-23, TNF-α and IFN-γ. In another exemplary embodiment, the cytokine is TNF-α.

In an exemplary embodiment, the method is for decreasing the release of a cytokine, which is a member selected from IL-1β, IL-2, IL-4, IL-5, IL-6, IL-8, IL-1β, IL-12, IL-23, TNF-α and IFN-γ.

In an exemplary embodiment, the method is for decreasing the production of a cytokine, which is a member selected from IL-4, IL-1β, IL-11, W-13 and TGF-β.

In an exemplary embodiment, the method is for decreasing the production of a chemokine, which is a member selected from IL-8, Gro-α, MIP-1, MCP-1, PGE2, ENA-78, and RANTES. In an exemplary embodiment, the chemokine is a member selected from MCP-1 and PGE2.

In an exemplary embodiment, for any of the methods described herein, the compound of the invention is present in an amount which will inhibit the production of a cytokine and/or a chemokine by at least about 5 to about 100%, or at least about 30 to about 100%, 40 to about 100%, or at least about 50 to about 100%, or at least about 60 to about 100%, or at least about 70 to about 100%, or at least about 80 to about 100%, or at least about 90 to about 100%, or at least about 30 to about 70%, or at least about 40 to about 90%, or at least about 45 to about 80%, or at least about 55 to about 75%, or at least about 75 to about 98%, or at least about 55 to about 99%, or at least about 5% to about 20% or at least about 10% to about 25%. In an exemplary embodiment, the compound of the invention is a compound described herein.

b) Increasing the Production of a Cytokine and/or a Chemokine

In another aspect, the invention provides a method for increasing the production of a cytokine and/or a chemokine, the method comprising: contacting a cell with a compound of the invention, wherein production of the cytokine and/or chemokine by the cell is increased. In an exemplary embodiment, the compound is described herein or a pharmaceutically acceptable salt thereof. In an exemplary embodiment, the compound of the invention is a compound described herein. In an exemplary embodiment, the cell is contacted with a therapeutically effective amount of the compound. In an exemplary embodiment, the compound is according to a formula described herein. In an exemplary embodiment, the compound is a member selected from C1, C2, C3, C4, C5, C6, C7, C8, C9, C10, C11, C12, C13, C14, C15, C16, C17, C18, C19, C20, C21, C22, C23, C24, C25, C26, C27, C28, C29, C30, C31, C32, C33, C34, C35, C36, C37, C38, C39, C40, C41, C42, C43, C44, C45, C46, C47, C48, C49, C50, C51, C52, C53, CM, C55, C56, C57, C58, C59, C60, C61, C62, C63, C64, C65, C66, C67, C68, C69, C70, C71, C72, C73, C74, C75, C76, C77, C78, C79, C80, C81, C82, C83, C84, C85, C86, C87, C88, C89, C90, C91, C92, C93, C94, C95, C96, C97, C98, C99 and C100. In an exemplary embodiment, the compound is a member selected from D1, D2, D3, D4, D5, D6, D7, D8, D9, D10, D11, D12, D13, D14, D15, D16, D17, D18, D19, D20, D21, D22, D23, D24, D25, D26, D27, D28, D29, D30, D31, D32, D33, D34, D35, D36, D37, D38, D39, D40, D41, D42, D43, D44, D45, D46, D47, D48, D49, D50, D51, D52, D53, D54, D55, D56, D57, D58, D59, D60, D61, D62, D63, D64, D65, D66, D67, D68, D69, D70, D71, D72, D73, D74, D75, D76, D77, D78, D79, D80, D81, D82, D83, D84, D85, D86, D87, D88, D89, D90, D91, D92, D93, D94, D95, D96, D97, D98, D99, D100, D101, D102, D103, D104, D105, D106, D107, D108, D109, D110, D111, D112, D113, D114, D115, D116, D117, D118, D119, D120, D121, D122, D123, D124, D125, D126, D127, D128, D129, D130, D131, D132, D133, D134, D135, D136, D137, D138, D139, D140, D141, D142, D143, D144, D145, D146, D147, D148, D149, D150, D151, D152, D153, D154, D155, D156, D157, D158, D159, D160, D161, D162, D163, D164, D165, D166, D167, D168, D169, D170, D171, D172, D173, D174, D175, D176, D177, D178, D179, D180, D181, D182, D183, D184, D185, D186, D187, D188, D189, D190, D191, D192, D193, D194, D195, D196, D197, D198, D199, D200, D201, D202, D203, D204, D205, D206, D207, D208, D209, D210, D211, D212, D213, D214, D215, D216, D217, D218, D219, D220, D221, D222, D223, D224, D225, D226, D227, D228 and D229. In an exemplary embodiment, the compound is C17. In another exemplary embodiment, the compound is C27. In another exemplary embodiment, the compound is C23 or C24. In another exemplary embodiment, the compound is C26.

In an exemplary embodiment, the method is for increasing the production of a cytokine, which is a TH1 cytokine. In an exemplary embodiment, the TH1 cytokine is a member selected from IFN-γ and IL-2.

In an exemplary embodiment, the method is for increasing the production of a cytokine, which is a TH2 cytokine. In an exemplary embodiment, the TH2 cytokine is a member selected from IL-4, IL-5 and IL-10.

In an exemplary embodiment, the method is for increasing the production of a cytokine, which is a member selected from IL-4, IL-1β, IL-11, W-13 and TGF-β.

In an exemplary embodiment, the method is for increasing the production of a chemokine, which is a member selected from IL-8, Gro-α, MIP-1, MCP-1, PGE2, ENA-78, and RANTES. In an exemplary embodiment, the chemokine is a member selected from MCP-1 and PGE2.

In an exemplary embodiment, for any of the methods described herein, the compound of the invention is present in an amount which will increase the production of a cytokine and/or a chemokine by at least about 5 to about 100%, or at least about 30 to about 100%, 40 to about 100%, or at least about 50 to about 100%, or at least about 60 to about 100%, or at least about 70 to about 100%, or at least about 80 to about 100%, or at least about 90 to about 100%, or at least about 30 to about 70%, or at least about 40 to about 90%, or at least about 45 to about 80%, or at least about 55 to about 75%, or at least about 75 to about 98%, or at least about 55 to about 99%, or at least about 5% to about 20% or at least about 10% to about 25%. In an exemplary embodiment, the compound of the invention is a compound described herein.

c) Decreasing the Release of a Cytokine and/or Chemokine

In another aspect, the invention provides a method for decreasing the release of a cytokine and/or a chemokine, the method comprising: contacting a cell with a compound of the invention, wherein the release of the cytokine and/or chemokine by the cell is decreased. In an exemplary embodiment, the compound of the invention is a compound described herein or a pharmaceutically acceptable salt thereof. The compound of the invention is a compound described herein. In an exemplary embodiment, the cell is contacted with a therapeutically effective amount of the compound. In an exemplary embodiment, the compound is according to a formula described herein. In an exemplary embodiment, the compound is a member selected from C1, C2, C3, C4, C5, C6, C7, C8, C9, C10, C11, C12, C13, C14, C15, C16, C17, C18, C19, C20, C21, C22, C23, C24, C25, C26, C27, C28, C29, C30, C31, C32, C33, C34, C35, C36, C37, C38, C39, C40, C41, C42, C43, C44, C45, C46, C47, C48, C49, C50, C51, C52, C53, CM, C55, C56, C57, C58, C59, C60, C61, C62, C63, C64, C65, C66, C67, C68, C69, C70, C71, C72, C73, C74, C75, C76, C77, C78, C79, C80, C81, C82, C83, C84, C85, C86, C87, C88, C89, C90, C91, C92, C93, C94, C95, C96, C97, C98, C99 and C100. In an exemplary embodiment, the compound is a member selected from D1, D2, D3, D4, D5, D6, D7, D8, D9, D10, D11, D12, D13, D14, D15, D16, D17, D18, D19, D20, D21, D22, D23, D24, D25, D26, D27, D28, D29, D30, D31, D32, D33, D34, D35, D36, D37, D38, D39, D40, D41, D42, D43, D44, D45, D46, D47, D48, D49, D50, D51, D52, D53, D54, D55, D56, D57, D58, D59, D60, D61, D62, D63, D64, D65, D66, D67, D68, D69, D70, D71, D72, D73, D74, D75, D76, D77, D78, D79, D80, D81, D82, D83, D84, D85, D86, D87, D88, D89, D90, D91, D92, D93, D94, D95, D96, D97, D98, D99, D100, D101, D102, D103, D104, D105, D106, D107, D108, D109, D110, D111, D112, D113, D114, D115, D116, D117, D118, D119, D120, D121, D122, D123, D124, D125, D126, D127, D128, D129, D130, D131, D132, D133, D134, D135, D136, D137, D138, D139, D140, D141, D142, D143, D144, D145, D146, D147, D148, D149, D150, D151, D152, D153, D154, D155, D156, D157, D158, D159, D160, D161, D162, D163, D164, D165, D166, D167, D168, D169, D170, D171, D172, D173, D174, D175, D176, D177, D178, D179, D180, D181, D182, D183, D184, D185, D186, D187, D188, D189, D190, D191, D192, D193, D194, D195, D196, D197, D198, D199, D200, D201, D202, D203, D204, D205, D206, D207, D208, D209, D210, D211, D212, D213, D214, D215, D216, D217, D218, D219, D220, D221, D222, D223, D224, D225, D226, D227, D228 and D229. In an exemplary embodiment, the compound is C17. In another exemplary embodiment, the compound is C27. In another exemplary embodiment, the compound is C23 or C24. In another exemplary embodiment, the compound is C25. In another exemplary embodiment, the compound is C26. In another exemplary embodiment, the compound is C37. In an exemplary embodiment, the compound is a member selected from D46, D86, D99, D100, D107, D108, D114, D122, D125, D126, D127, D128, D131, D140 and D141, and salts thereof. In an exemplary embodiment, the compound is a member selected from D95, D96, D97, D102, D110, D111, D113, D115, D121, D129, D130, D132, and salts thereof. In an exemplary embodiment, the compound is a member selected from D47, D109, D116, D118, D119, D120, D123, and salts thereof. In an exemplary embodiment, the compound is a member selected from D98, D101, D106, and salts thereof. In an exemplary embodiment, the compound is a member selected from D11, D12, D37, D38, D39, D40, D41, D42, D43, D124, D142, D143, D146, and salts thereof. In an exemplary embodiment, the compound is a member selected from D14, D15, D16, D17, D28, D29, D30, D31, D133, D134, D135, D144, D145, D147, and salts thereof.

In an exemplary embodiment, the method is for decreasing the release of a cytokine, which is a TH1 cytokine. In an exemplary embodiment, the TH1 cytokine is a member selected from IFN-γ and IL-2.

In an exemplary embodiment, the method is for decreasing the release of a cytokine, which is a TH2 cytokine. In an exemplary embodiment, the TH2 cytokine is a member selected from IL-4, IL-5 and IL-10.

In an exemplary embodiment, the method is for decreasing the release of a cytokine, which is a member selected from IL-1α, IL-1β, IL-2, IL-3, IL-6, IL-7, IL-9, IL-12, IL-17, IL-18, IL-23, TNF-α, LT, LIF, Oncostatin, IFNα, IFNβ and IFN-γ. In another exemplary embodiment, the cytokine is a member selected from IL-1β, IL-2, IL-3, IL-6, IL-7, IL-9, IL-12, IL-23, TNF-α, LT, LIF, Oncostatin, and IFN-γ. In another exemplary embodiment, the cytokine is a member selected from IL-1β, IL-2, IL-23, TNF-α and IFN-γ. In another exemplary embodiment, the cytokine is TNF-α. In another exemplary embodiment, the cytokine is IFN-γ.

In an exemplary embodiment, the method is for decreasing the release of a cytokine, which is a member selected from IL-1β, IL-2, IL-4, IL-5, IL-6, IL-8, IL-1β, IL-12, IL-23, TNF-α and IFN-γ.

In an exemplary embodiment, the compound of the invention decreases the release of IL-1β, IL-2, IL-4, IL-5, IL-6, IL-8, IL-1β, IL-12, IL-23, TNF-α and IFN-γ. In an exemplary embodiment, the compound is C17.

In an exemplary embodiment, the method is for decreasing the release of a cytokine, which is a member selected from IL-4, IL-1β, IL-11, W-13 and TGF-β.

In an exemplary embodiment, the method is for decreasing the release of a chemokine, which is a member selected from IL-8, Gro-α, MIP-1, MCP-1, PGE2, ENA-78, and RANTES. In an exemplary embodiment, the chemokine is a member selected from MCP-1 and PGE2. In an exemplary embodiment, the compound is C17 and the chemokine is a member selected from MCP-1 and PGE2.

In an exemplary embodiment, the compound of the invention decreases the release of TNF-α, IL-2, IFNγ, IL-5, and IL-1β. In an exemplary embodiment, the compound of the invention does not substantially decrease the release of IL-1β, IL-6 and IL-8. In an exemplary embodiment, the compound of the invention does not substantially decrease the release of IL-1β. In an exemplary embodiment, the compound of the invention does not substantially decrease the release of IL-4. In an exemplary embodiment, the compound decreases the release of IL-12 and IL-23. In an exemplary embodiment, the compound is C27.

In an exemplary embodiment, for any of the methods described herein, the compound of the invention is present in an amount which will decrease the release of a cytokine and/or a chemokine by at least about 5 to about 100%, or at least about 30 to about 100%, 40 to about 100%, or at least about 50 to about 100%, or at least about 60 to about 100%, or at least about 70 to about 100%, or at least about 80 to about 100%, or at least about 90 to about 100%, or at least about 30 to about 70%, or at least about 40 to about 90%, or at least about 45 to about 80%, or at least about 55 to about 75%, or at least about 75 to about 98%, or at least about 55 to about 99%, or at least about 5% to about 20% or at least about 10% to about 25%. In another exemplary embodiment, the compound of the invention is a compound described herein or a pharmaceutically acceptable salt thereof.

d) Increasing the Release of a Cytokine and/or a Chemokine

In another aspect, the invention provides a method for increasing the production of a cytokine and/or a chemokine, the method comprising: contacting a cell with a compound of the invention, wherein release of the cytokine and/or chemokine by the cell is increased. In an exemplary embodiment, the compound of the invention is a compound described herein or a pharmaceutically acceptable salt thereof. In an exemplary embodiment, the compound is described herein. In an exemplary embodiment, the cell is contacted with a therapeutically effective amount of the compound. In an exemplary embodiment, the compound is according to a formula described herein. In an exemplary embodiment, the compound is a member selected from C1, C2, C3, C4, C5, C6, C7, C8, C9, C10, C11, C12, C13, C14, C15, C16, C17, C18, C19, C20, C21, C22, C23, C24, C25, C26, C27, C28, C29, C30, C31, C32, C33, C34, C35, C36, C37, C38, C39, C40, C41, C42, C43, C44, C45, C46, C47, C48, C49, C50, C51, C52, C53, C54, C55, C56, C57, C58, C59, C60, C61, C62, C63, C64, C65, C66, C67, C68, C69, C70, C71, C72, C73, C74, C75, C76, C77, C78, C79, C80, C81, C82, C83, C84, C85, C86, C87, C88, C89, C90, C91, C92, C93, C94, C95 and C96. In an exemplary embodiment, the compound is a member selected from D1, D2, D3, D4, D5, D6, D7, D8, D9, D10, D11, D12, D13, D14, D15, D16, D17, D18, D19, D20, D21, D22, D23, D24, D25, D26, D27, D28, D29, D30, D31, D32, D33, D34, D35, D36, D37, D38, D39, D40, D41, D42, D43, D44, D45, D46, D47, D48, D49, D50, D51, D52, D53, D54, D55, D56, D57, D58, D59, D60, D61, D62, D63, D64, D65, D66, D67, D68, D69, D70, D71, D72, D73, D74, D75, D76, D77, D78, D79, D80, D81, D82, D83, D84, D85, D86, D87, D88, D89, D90, D91, D92, D93, D94, D95, D96, D97, D98, D99, D100, D101, D102, D103, D104, D105, D106, D107, D108, D109, D110, D111, D112, D113, D114, D115, D116, D117, D118, D119, D120, D121, D122, D123, D124, D125, D126, D127, D128, D129, D130, D131, D132, D133, D134, D135, D136, D137, D138, D139, D140, D141, D142, D143, D144, D145, D146, D147, D148, D149, D150, D151, D152, D153, D154, D155, D156, D157, D158, D159, D160, D161, D162, D163, D164, D165, D166, D167, D168, D169, D170, D171, D172, D173, D174, D175, D176, D177, D178, D179, D180, D181, D182, D183, D184, D185, D186, D187, D188, D189, D190, D191, D192, D193, D194, D195, D196, D197, D198, D199, D200, D201, D202, D203, D204, D205, D206, D207, D208, D209, D210, D211, D212, D213, D214, D215, D216, D217, D218, D219, D220, D221, D222, D223, D224, D225, D226, D227, D228 and D229. In an exemplary embodiment, the compound is C17. In another exemplary embodiment, the compound is C27. In another exemplary embodiment, the compound is C23 or C24. In another exemplary embodiment, the compound is C26.

In an exemplary embodiment, the method is for increasing the release of a cytokine, which is a TH1 cytokine. In an exemplary embodiment, the TH1 cytokine is a member selected from IFN-γ and IL-2.

In an exemplary embodiment, the method is for increasing the release of a cytokine, which is a TH2 cytokine. In an exemplary embodiment, the TH2 cytokine is a member selected from IL-4, IL-5 and IL-10.

In an exemplary embodiment, the method is for increasing the release of a cytokine, which is a member selected from IL-4, IL-1β, IL-11, W-13 and TGF-β.

In an exemplary embodiment, the method is for increasing the release of a chemokine, which is a member selected from IL-8, Gro-α, MIP-1, MCP-1, PGE2, ENA-78, and RANTES. In an exemplary embodiment, the chemokine is a member selected from MCP-1 and PGE2.

In an exemplary embodiment, for any of the methods described herein, the compound of the invention is present in an amount which will increase release of a cytokine and/or a chemokine by at least about 5 to about 100%, or at least about 30 to about 100%, 40 to about 100%, or at least about 50 to about 100%, or at least about 60 to about 100%, or at least about 70 to about 100%, or at least about 80 to about 100%, or at least about 90 to about 100%, or at least about 30 to about 70%, or at least about 40 to about 90%, or at least about 45 to about 80%, or at least about 55 to about 75%, or at least about 75 to about 98%, or at least about 55 to about 99%, or at least about 5% to about 20% or at least about 10% to about 25%. In an exemplary embodiment, the compound of the invention is a compound described herein or a pharmaceutically acceptable salt thereof.

e) Inhibiting a Phosphodiesterase

In another aspect, the invention provides a method for inhibiting a phosphodiesterase (PDE), the method comprising: contacting the phosphodiesterase with a compound of the invention, wherein the phosphodiesterase is inhibited. In an exemplary embodiment, the compound of the invention is a compound described herein or a pharmaceutically acceptable salt thereof. In an exemplary embodiment, the compound of the invention is a compound described herein. In an exemplary embodiment, the amount of the compound is a therapeutically effective amount. In an exemplary embodiment, the compound is according to a formula described herein. In an exemplary embodiment, the compound is according to the following formula:

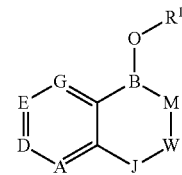

wherein B is boron. $R^1$ is a member selected from a negative charge, a salt counterion, H, cyano, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. M is a member selected from oxygen, sulfur and $NR^2$. $R^2$ is a member selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. J is a member selected from $(CR^3R^4)_{n1}$ and $CR^5$. $R^3$, $R^4$, and $R^5$ are members independently selected from H, cyano, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. n1 is an integer selected from 0 to 2. W is a member selected from C=O (carbonyl), $(CR^6R^7)_{m1}$ and $CR^8$. $R^6$, $R^7$, and $R^8$ are members independently selected from H, cyano, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. m1 is an integer selected from 0 and 1. A is a member selected from $CR^9$ and N. D is a member selected from $CR^{10}$ and N. E is a member selected from $CR^{11}$ and N. G is a member selected from $CR^{12}$ and N. $R^9$, $R^{10}$, $R^{11}$ and $R^{12}$ are members independently selected from H, OR*, NR*R**, SR*, —S(O)R*, —S(O)$_2$R*, —S(O)$_2$NR*R**, —C(O)R*, —C(O)OR*, —C(O)NR*R**, nitro, halogen, cyano, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, wherein each R* and R** are members independently selected from H, nitro, halogen, cyano, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. The combination of nitrogens (A+D+E+G) is an integer selected from 0 to 3. A member selected from $R^3$, $R^4$ and $R^5$ and a member selected from $R^6$, $R^7$ and $R^8$, together with the atoms to which they are attached, are optionally joined to form a 4 to 7 membered ring. $R^3$ and $R^4$, together with the atoms to which they are attached, are optionally joined to form a 4 to 7 membered ring. $R^6$ and $R^7$, together with the atoms to which they are attached, are optionally joined to form a 4 to 7 membered ring. $R^9$ and $R^{10}$, together with the atoms to which they are attached, are optionally joined to form a 4 to 7 membered ring. $R^{10}$ and $R^{11}$, together with the atoms to which they are attached, are optionally joined to form a 4 to 7 membered ring. $R^{11}$ and $R^{12}$, together with the atoms to which they are attached, are optionally joined to form a 4 to 7 membered ring.

In an exemplary embodiment, the compound is a member selected from Cl, C2, C3, C4, C5, C6, C7, C8, C9, C10, C11, C12, C13, C14, C15, C16, C17, C18, C19, C20, C21, C22, C23, C24, C25, C26, C27, C28, C29, C30, C31, C32, C33, C34, C35, C36, C37, C38, C39, C40, C41, C42, C43, C44, C45, C46, C47, C48, C49, C50, C51, C52, C53, CM, C55, C56, C57, C58, C59, C60, C61, C62, C63, C64, C65, C66, C67, C68, C69, C70, C71, C72, C73, C74, C75, C76, C77, C78, C79, C80, C81, C82, C83, C84, C85, C86, C87, C88, C89, C90, C91, C92, C93, C94, C95 and C96, or a pharmaceutically acceptable salt thereof. In an exemplary embodiment, the compound is a member selected from D1, D2, D3, D4, D5, D6, D7, D8, D9, D10, D11, D12, D13, D14, D15, D16, D17, D18, D19, D20, D21, D22, D23, D24, D25, D26, D27, D28, D29, D30, D31, D32, D33, D34, D35, D36, D37, D38, D39, D40, D41, D42, D43, D44, D45, D46, D47, D48, D49, D50, D51, D52, D53, D54, D55, D56, D57, D58, D59, D60, D61, D62, D63, D64, D65, D66, D67, D68, D69, D70, D71, D72, D73, D74, D75, D76, D77, D78, D79, D80, D81, D82, D83, D84, D85, D86, D87, D88, D89, D90, D91, D92, D93, D94, D95, D96, D97, D98, D99, D100, D101, D102, D103, D104, D105, D106, D107, D108, D109, D110, D111, D112, D113, D114, D115, D116, D117, D118, D119, D120, D121, D122, D123, D124, D125, D126, D127, D128, D129, D130, D131, D132, D133, D134, D135, D136, D137, D138, D139, D140, D141, D142, D143, D144, D145, D146, D147, D148, D149, D150, D151, D152, D153, D154, D155, D156, D157, D158, D159, D160, D161, D162, D163, D164, D165, D166, D167, D168, D169, D170, D171, D172, D173, D174, D175, D176, D177, D178, D179, D180, D181, D182, D183, D184, D185, D186, D187, D188, D189, D190, D191, D192, D193, D194, D195, D196, D197, D198, D199, D200, D201, D202, D203, D204, D205, D206, D207, D208, D209, D210, D211, D212, D213, D214, D215, D216, D217, D218, D219, D220, D221, D222, D223, D224, D225, D226, D227, D228 and D229. In an exemplary embodiment, the compound is C17. In another exemplary embodiment, the compound is C27. In another exemplary embodiment, the compound is C23. In another exemplary embodiment, the compound is C24. In another exemplary embodiment, the compound is C25. In another exemplary embodiment, the compound is C26. In an exemplary embodiment, the compound is a member selected from D46, D86, D99, D100, D107, D108, D114, D122, D125, D126, D127, D128, D131, D140 and D141, and salts thereof. In an exemplary embodiment, the compound is a member selected from D95, D96, D97, D102, D110, D111, D113, D115, D121, D129, D130, D132, and salts thereof. In an exemplary embodiment, the compound is a member selected from D47, D109, D116, D118, D119, D120, D123, and salts thereof. In an exemplary embodiment, the compound is a member selected from D98, D101, D106, and salts thereof. In an exemplary embodiment, the compound is a member selected from D11, D12, D37, D38, D39, D40, D41, D42, D43, D124, D142, D143, D146, and salts thereof. In an exemplary embodiment, the compound is a member selected from D14, D15, D16, D17, D28, D29, D30, D31, D133, D134, D135, D144, D145, D147, and salts thereof.

In an exemplary embodiment, the compound is a member selected from 5-(4-Cyanophenoxy)-1-hydroxy-2,1-benzoxaborole; 1,3-Dihydro-1-hydroxy-5-phenoxy-2,1-benzoxaborole

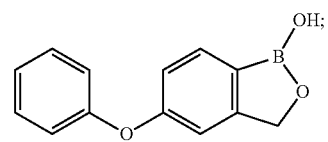 [SMILES: OB1OCc2cc(Oc3ccccc3)ccc21]

5-(2-Cyanophenoxy)-1,3-dihydro-1-hydroxy-2,1-benzoxaborole

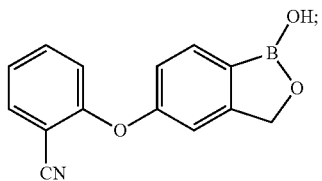 [SMILES: N#Cc1ccccc1Oc1ccc2c(c1)COB2O]

5-[4-(N,N-Diethylcarbamoyl)phenoxy]-1,3-dihydro-1-hydroxy-2,1-benzoxaborole

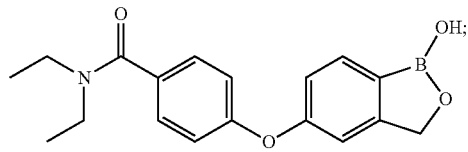 [SMILES: CCN(CC)C(=O)c1ccc(Oc2ccc3c(c2)COB3O)cc1]

1,3-Dihydro-1-hydroxy-5-[4-(morpholinocarbonyl)phenoxy]-2,1-benzoxaborole

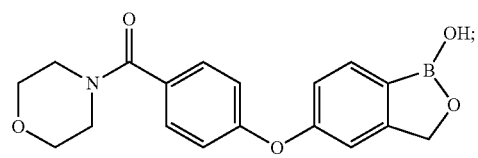 [SMILES: O=C(c1ccc(Oc2ccc3c(c2)COB3O)cc1)N1CCOCC1]

5-(3,4-Dicyanophenoxy)-1,3-dihydro-1-hydroxy-2,1-benzoxaborole

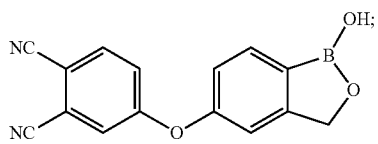 [SMILES: N#Cc1ccc(Oc2ccc3c(c2)COB3O)cc1C#N]

1,3-Dihydro-1-hydroxy-5-(3-cyanophenoxy)-2,1-benzoxaborole

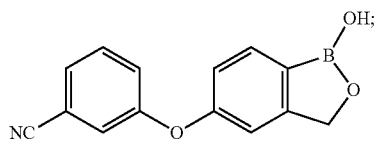 [SMILES: N#Cc1cccc(Oc2ccc3c(c2)COB3O)c1]

5-(4-Carboxyphenoxy)-1,3-dihydro-1-hydroxy-2,1-benzoxaborole

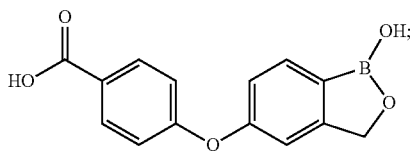 [SMILES: O=C(O)c1ccc(Oc2ccc3c(c2)COB3O)cc1]

5-(5-Cyanopyridin-2-yloxy)-1,3-dihydro-1-hydroxy-2,1-benzoxaborole

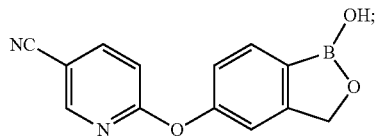 [SMILES: N#Cc1ccc(Oc2ccc3c(c2)COB3O)nc1]

5-(4-Cyanobenzyloxy)-1,3-dihydro-1-hydroxy-2,1-benzoxaborole

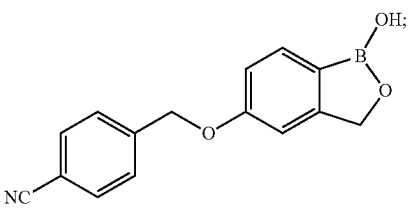 [SMILES: N#Cc1ccc(COc2ccc3c(c2)COB3O)cc1]

4-(1-Hydroxy-1,3-dihydro-benzo[c][1,2]oxaborol-5-yloxy)-benzoic acid methyl ester

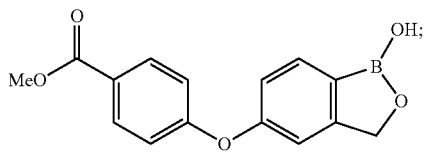 [SMILES: COC(=O)c1ccc(Oc2ccc3c(c2)COB3O)cc1]

4-(1-Hydroxy-1,3-dihydro-benzo[c][1,2]oxaborol-5-yloxy)-benzoic acid methyl ester

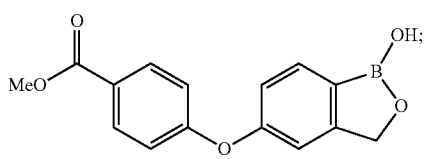 [SMILES: COC(=O)c1ccc(Oc2ccc3c(c2)COB3O)cc1]

4-(1-Hydroxy-1,3-dihydro-benzo[c][1,2]oxaborol-5-yloxy)-benzoic acid ethyl ester

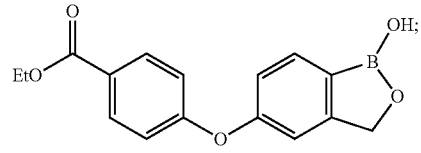 [SMILES: CCOC(=O)c1ccc(Oc2ccc3c(c2)COB3O)cc1]

4-(1-Hydroxy-1,3-dihydro-benzo[c][1,2]oxaborol-5-yloxy)-benzoic acid propyl ester

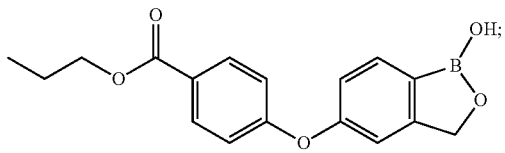 [SMILES: CCCOC(=O)c1ccc(Oc2ccc3c(c2)COB3O)cc1]

4-(1-Hydroxy-1,3-dihydro-benzo[c][1,2]oxaborol-5-yloxy)-benzoic acid isopropyl ester

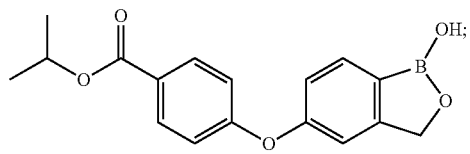 [SMILES: CC(C)OC(=O)c1ccc(Oc2ccc3c(c2)COB3O)cc1]

4-(1-Hydroxy-1,3-dihydro-benzo[c][1,2]oxaborol-5-yloxy)-benzoic acid 2-dimethylamino-ethyl ester

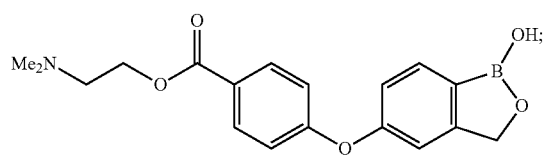 [SMILES: CN(C)CCOC(=O)c1ccc(Oc2ccc3c(c2)COB3O)cc1]

N-Benzyl-4-(1-hydroxy-1,3-dihydro-benzo[c][1,2]oxaborol-5-yloxy)-benzamide

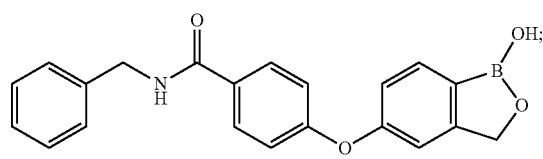 [SMILES: O=C(NCc1ccccc1)c1ccc(Oc2ccc3c(c2)COB3O)cc1]

4-(1-Hydroxy-1,3-dihydro-benzo[c][1,2]oxaborol-5-yloxy)-N-(2-hydroxy-ethyl)-benzamide

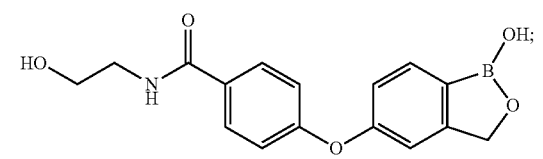 [SMILES: O=C(NCCO)c1ccc(Oc2ccc3c(c2)COB3O)cc1]

4-(1-Hydroxy-1,3-dihydro-benzo[c][1,2]oxaborol-5-yloxy)-N-pyridin-2-ylmethyl-benzamide

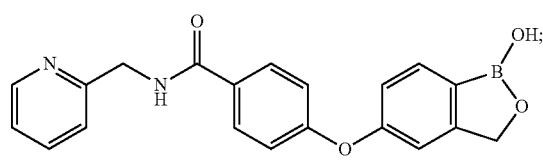 [SMILES: O=C(NCc1ccccn1)c1ccc(Oc2ccc3c(c2)COB3O)cc1]

[4-(1-Hydroxy-1,3-dihydro-benzo[c][1,2]oxaborol-5-yloxy)-phenyl]-(4-methyl-piperazin-1-yl)-methanone 1-{4-[4-(1-Hydroxy-1,3-dihydro-benzo[c][1,2]oxaborol-5-yloxy)-benzoyl]-piperazin-1-yl}-ethanone

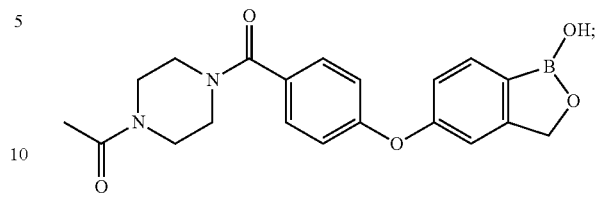

N-(2-Dimethylamino-ethyl)-4-(1-hydroxy-1,3-dihydro-benzo[c][1,2]oxaborol-5-yloxy)-benzamide

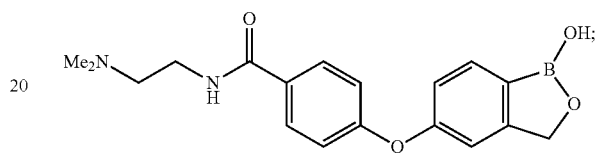

2-(1-Hydroxy-1,3-dihydro-benzo[c][1,2]oxaborol-5-yloxy)-pyrimidine-5-carboxylic acid methyl ester


2-(1-Hydroxy-1,3-dihydro-benzo[c][1,2]oxaborol-5-yloxy)-thiazole-4-carboxylic acid methyl ester

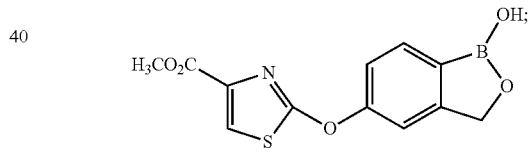

2-(1-Hydroxy-1,3-dihydro-benzo[c][1,2]oxaborol-5-yloxy)-thiazole-5-carboxylic acid methyl ester

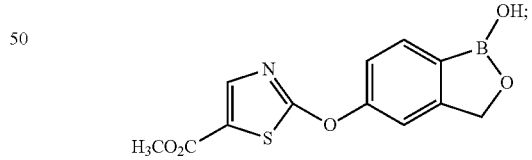

5-(1-Hydroxy-1,3-dihydro-benzo[c][1,2]oxaborol-5-yloxy)-pyridine-2-carboxylic acid ethyl ester

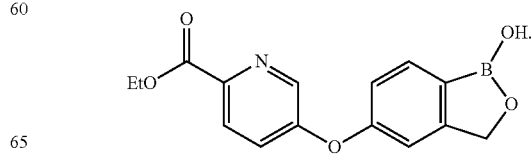

In an exemplary embodiment, the phosphodiesterase is a member selected from PDE1, PDE2, PDE3, PDE4, PDE5, PDE6, PDE7, PDE8, PDE9, PDE10 and PDE11. In an exemplary embodiment, the phosphodiesterase is PDE4. In an exemplary embodiment, the PDE4 is a member selected from PDE4A, PDE4B, PDE4C and PDE4D. In an exemplary embodiment, the PDE4 is PDE4B. In an exemplary embodiment, the phosphodiesterase is PDE7.

In an exemplary embodiment, the invention provides a method for inhibiting a phosphodiesterase4 (PDE4), but not significantly inhibiting at least one PDE which is a member selected from PDE1, PDE2, PDE3, PDE5 and PDE6, involving contacting a cell with a compound of the invention, thereby providing said inhibition. In an exemplary the compound is C27.

In another exemplary embodiment, the invention provides a method for inhibiting a phosphodiesterase4 (PDE4), the method comprising: contacting the phosphodiesterase with C17, or a pharmaceutically acceptable salt thereof, wherein the phosphodiesterase4 (PDE4) is inhibited. In another exemplary embodiment, the invention provides a method for inhibiting a phosphodiesterase7 (PDE7), the method comprising: contacting the phosphodiesterase with C17, or a pharmaceutically acceptable salt thereof, wherein the phosphodiesterase7 (PDE7) is inhibited. In another exemplary embodiment, the invention provides a method for inhibiting a phosphodiesterase4 (PDE4), the method comprising: contacting the phosphodiesterase with C27, or a pharmaceutically acceptable salt thereof, wherein the phosphodiesterase4 (PDE4) is inhibited. In another exemplary embodiment, the invention provides a method for inhibiting a phosphodiesterase7 (PDE7), the method comprising: contacting the phosphodiesterase with C27, or a pharmaceutically acceptable salt thereof, wherein the phosphodiesterase7 (PDE7) is inhibited. In an exemplary embodiment, the amount of the compound is a therapeutically effective amount.

In another exemplary embodiment, the invention provides a method for inhibiting a phosphodiesterase4 (PDE4), the method comprising: contacting the phosphodiesterase with C23 or C24 or C25, or a pharmaceutically acceptable salt thereof, wherein the phosphodiesterase4 (PDE4) is inhibited.

In another exemplary embodiment, the invention provides a method for inhibiting a phosphodiesterase4 (PDE4), the method comprising: contacting the phosphodiesterase with D46 or D86 or D99 or D100 or D107 or D108 or D114 or D122 or D125 or D126 or D127 or D128 or D131 or D140 and D141, or a pharmaceutically acceptable salt thereof, wherein the phosphodiesterase4 (PDE4) is inhibited.

In another exemplary embodiment, the invention provides a method for inhibiting a phosphodiesterase4 (PDE4), the method comprising: contacting the phosphodiesterase with D95 or D96 or D97 or D102 or D110 or D111 or D113 or D115 or D121 or D129 or D130 or D132, and, or a pharmaceutically acceptable salt thereof, wherein the phosphodiesterase4 (PDE4) is inhibited.

In another exemplary embodiment, the invention provides a method for inhibiting a phosphodiesterase4 (PDE4), the method comprising: contacting the phosphodiesterase with D47 or D109 or D116 or D118 or D119 or D120 or D123, and, or a pharmaceutically acceptable salt thereof, wherein the phosphodiesterase4 (PDE4) is inhibited.

In another exemplary embodiment, the invention provides a method for inhibiting a phosphodiesterase4 (PDE4), the method comprising: contacting the phosphodiesterase with D98 or D101 or D106, and, or a pharmaceutically acceptable salt thereof, wherein the phosphodiesterase4 (PDE4) is inhibited.

In another exemplary embodiment, the invention provides a method for inhibiting a phosphodiesterase4 (PDE4), the method comprising: contacting the phosphodiesterase with D11 or D12 or D37 or D38 or D39 or D40 or D41 or D42 or D43 or D124 or D142 or D143 or D146, and, or a pharmaceutically acceptable salt thereof, wherein the phosphodiesterase4 (PDE4) is inhibited.

In another exemplary embodiment, the invention provides a method for inhibiting a phosphodiesterase4 (PDE4), the method comprising: contacting the phosphodiesterase with D14 or D15 or D16 or D17 or D28 or D29 or D30 or D31 or D133 or D134 or D135 or D144 or D145 or D147, and, or a pharmaceutically acceptable salt thereof, wherein the phosphodiesterase4 (PDE4) is inhibited.

In an exemplary embodiment, for any of the methods described herein, the of the invention, or a compound described by a formula presented herein, is present in an amount which will inhibit a phosphodiesterase described herein by at least about 5 to about 100%, or at least about 30 to about 100%, 40 to about 100%, or at least about 50 to about 100%, or at least about 60 to about 100%, or at least about 70 to about 100%, or at least about 80 to about 100%, or at least about 90 to about 100%, or at least about 30 to about 70%, or at least about 40 to about 90%, or at least about 45 to about 80%, or at least about 55 to about 75%, or at least about 75 to about 98%, or at least about 55 to about 99%, or at least about 5% to about 20% or at least about 10% to about 25%. In an exemplary embodiment, the compound of the invention is a compound described herein or a pharmaceutically acceptable salt thereof.

f) Conditions and Effects

In another aspect, the invention provides a method of treating and/or preventing a condition, and/or enhancing an effect, in an animal, the method comprising administering to the animal an effective amount of a compound of the invention, thereby treating and/or preventing the condition. In an exemplary embodiment, the compound of the invention is a compound described herein. In an exemplary embodiment, the compound of the invention is a pharmaceutically acceptable salt of a compound described herein. In an exemplary embodiment, the effective amount is an amount effective to treat the condition. In an exemplary embodiment, the effective amount is an amount effective to prevent the condition. In an exemplary embodiment, the animal is not otherwise in need of treatment with the compound of the invention. In an exemplary embodiment, the compound is according to a formula described herein. In another aspect, the invention provides a method of treating a condition in an animal in need of the treatment, the method comprising administering to the animal an amount of a compound of the invention, thereby treating the condition. In another aspect, the invention provides a method of treating a condition in an animal in need of the treatment, the method comprising administering to the animal a therapeutically effective amount of a compound of the invention, thereby treating the condition. In another aspect, the invention provides a method of preventing a condition, in an animal, the method comprising administering to the animal an amount of a compound of the invention, thereby preventing the condition. In another aspect, the invention provides a method of enhancing an effect, in an animal, the method comprising administering to the animal an effective amount of a compound of the invention, thereby enhancing the effect. In an exemplary embodiment, the compound is according to a formula described in the section entitled "Inhibiting a phosphodiesterase". In an exemplary embodiment, the compound is a member selected from C1, C2, C3, C4, C5, C6, C7, C8, C9, C10, C11, C12, C13, C14, C15, C16, C17, C18, C19, C20, C21, C22, C23, C24, C25, C26, C27, C28, C29, C30, C31, C32, C33, C34, C35, C36, C37, C38, C39, C40, C41, C42, C43, C44, C45, C46, C47, C48, C49, C50, C51, C52, C53, C54, C55, C56, C57, C58, C59, C60, C61, C62, C63, C64, C65, C66, C67, C68, C69, C70, C71, C72, C73, C74, C75, C76, C77, C78, C79, C80, C81, C82, C83, C84, C85, C86, C87, C88, C89, C90, C91, C92, C93, C94, C95, C96, C97, C98, C99 and C100. In an exemplary embodiment, the compound is a member selected from D1, D2, D3, D4, D5, D6, D7, D8, D9, D10, D11, D12, D13, D14, D15, D16, D17, D18, D19, D20, D21, D22, D23, D24, D25, D26, D27, D28, D29, D30, D31, D32, D33, D34, D35, D36, D37, D38, D39, D40, D41, D42, D43, D44, D45, D46, D47, D48, D49, D50, D51, D52, D53, D54, D55, D56, D57, D58, D59, D60, D61, D62, D63, D64, D65, D66, D67, D68, D69, D70, D71, D72, D73, D74, D75, D76, D77, D78, D79, D80, D81, D82, D83, D84, D85, D86, D87, D88, D89, D90, D91, D92, D93, D94, D95, D96, D97, D98, D99, D100, D101, D102, D103, D104, D105, D106, D107, D108, D109, D110, D111, D112, D113, D114, D115, D116, D117, D118, D119, D120, D121, D122, D123, D124, D125, D126, D127, D128, D129, D130, D131, D132, D133, D134, D135, D136, D137, D138, D139, D140, D141, D142, D143, D144, D145, D146, D147, D148, D149, D150, D151, D152, D153, D154, D155, D156, D157, D158, D159, D160, D161, D162, D163, D164, D165, D166, D167, D168, D169, D170, D171, D172, D173, D174, D175, D176, D177, D178, D179, D180, D181, D182, D183, D184, D185, D186, D187, D188, D189, D190, D191, D192, D193, D194, D195, D196, D197, D198, D199, D200, D201, D202, D203, D204, D205, D206, D207, D208, D209, D210, D211, D212, D213, D214, D215, D216, D217, D218, D219, D220, D221, D222, D223, D224, D225, D226, D227, D228 and D229. In an exemplary embodiment, the compound is C17 or a pharmaceutically acceptable salt thereof. In an exemplary embodiment, the compound is C27 or a pharmaceutically acceptable salt thereof. In an exemplary embodiment, the compound is a member selected from D46, D86, D99, D100, D107, D108, D114, D122, D125, D126, D127, D128, D131, D140 and D141, and salts thereof. In an exemplary embodiment, the compound is a member selected from D95, D96, D97, D102, D110, D111, D113, D115, D121, D129, D130, D132, and salts thereof. In an exemplary embodiment, the compound is a member selected from D47, D109, D116, D118, D119, D120, D123, and salts thereof. In an exemplary embodiment, the compound is a member selected from D98, D101, D106, and salts thereof. In an exemplary embodiment, the compound is a member selected from D11, D12, D37, D38, D39, D40, D41, D42, D43, D124, D142, D143, D146, and salts thereof. In an exemplary embodiment, the compound is a member selected from D14, D15, D16, D17, D28, D29, D30, D31, D133, D134, D135, D144, D145, D147, and salts thereof.

In an exemplary embodiment, the condition is a disease. In an exemplary embodiment, the condition is an inflammatory-related condition. In an exemplary embodiment, the condition involves the increase of production of a cytokine and/or a chemokine. In an exemplary embodiment, the condition involves the decrease of production of a cytokine and/or a chemokine. In an exemplary embodiment, the condition involves the increase of release of a cytokine and/or a chemokine. In an exemplary embodiment, the condition involves the decrease of release of a cytokine and/or a chemokine. In an exemplary embodiment, the condition involves the inhibition of a phosphodiesterase. In an exemplary embodiment, the compound is in an amount sufficient to treat the inflammatory-related disease by inhibiting pro-inflammatory cytokine expression or by stimulating anti-inflammatory cytokine expression, but the amount is less than sufficient to substantially inhibit cyclin dependent kinases. In an exemplary embodiment, the condition is mediated by a cytokine. In an exemplary embodiment, the condition is mediated by a chemokine. In an exemplary embodiment, the condition is mediated by a neutrophil. In an exemplary embodiment, the condition is mediated by a phosphodiesterase. In an exemplary embodiment, the condition is mediated by a phosphodiesterase-4. In an exemplary embodiment, the condition is mediated by a phosphodiesterase-7.

In an exemplary embodiment, the condition is a member selected from periodontitis, keratoconjuncitivitis sicca, rheumatoid arthritis, osteoarthritis, Crohn's disease, ulcerative colitis, psoriatic arthritis, traumatic arthritis, rubella arthritis, inflammatory bowel disease, multiple sclerosis, psoriasis, graft versus host disease, systemic lupus erythematosus, cutaneous lupus erythematosus, toxic shock syndrome, irritable bowel syndrome, muscle degeneration, allograft rejections, pancreatitis, insulinitis, glomerulonephritis, diabetic nephropathy, renal fibrosis, chronic renal failure, gout, leprosy, acute synovitis, Reiter's syndrome, gouty arthritis, Behcet's disease, spondylitis, endometriosis, non-articular inflammatory conditions, such as intervertbral disk syndrome conditions, bursitis, tendonitis, tenosynovitis or fibromyalgic syndrome; and acute or chronic pain, including but not limited to neurological pain, neuropathies, polyneuropathies, diabetes-related polyneuropathies, trauma, migraine, tension and cluster headache, Horton's disease, varicose ulcers, neuralgias, musculo-skeletal pain, osteo-traumatic pain, fractures, algodystrophy, spondylarthritis, fibromyalgia, phantom limb pain, back pain, vertebral pain, post-surgery pain, herniated intervertebral disc-induced sciatica, cancer-related pain, vascular pain, visceral pain, childbirth, or HIV-related pain. Other cytokine mediated diseases are allergy, a metabolic disease, a chemotherapy/radiation related complication; diabetes type I; diabetes type II; a liver disease; a gastrointestinal disorder; an ophthamological disease; allergic conjunctivitis; diabetic retinopathy; Sjogren's syndrome; uvetitis; a pulmonary disorder, a renal disease; dermatitis; HIV-related cachexia; cerebral malaria; ankylosing spondolytis; leprosy; anemia; fibromyalgia, kidney failure, stroke, chronic heart failure, endotoxemia, reperfusion injury, ischemia reperfusion, myocardial ischemia, restenosis, thrombosis, angiogenesis, Coronary Heart Disease, Coronary Artery Disease, acute coronary syndrome, Takayasu arteritis, cardiac failure such as heart failure, aortic valve stenosis, cardiomyopathy, myocarditis, vasculitis, vascular restenosis, valvular disease or coronary artery bypass; hypercholesteremia, diseases or conditions related to blood coagulation or fibrinolysis, such as for example, acute venous thrombosis, pulmonary embolism, thrombosis during pregancy, hemorrhagic skin necrosis, acute or chronic disseminated intravascular coagulation (DIC), clot formation from surgery, long bed rest or long periods of immobilization, venous thrombosis, fulminant meningococcemia, acute thrombotic strokes, acute coronary occlusion, acute peripheral arterial occlusion, massive pulmonary embolism, axillary vein thrombosis, massive iliofemoral vein thrombosis, occluded arterial or venous cannulae, cardiomyopathy, venoocclusive disease of the liver, hypotension, decreased cardiac output, decreased vascular resistance, pulmonary hypertension, diminished lung compliance, leukopenia or thrombocytopenia; or atherosclerosis.

In an exemplary embodiment, the condition is a member selected from allergic conjunctivitis, uveitis, glaucoma, optic neuritis, retinal ischemia, diabetic retinopathy, laser induced optic damage, or surgery or trauma-induced proliferative vitreoretinopathy.

In an exemplary embodiment, the condition is a member selected from allergic rhinitis, asthma, adult respiratory distress syndrome, chronic pulmonary inflammation, chronic obstructive pulmonary disease, emphysema, bronchitis, mucus hypersecretion, silicosis, SARS infection and respiratory tract inflammation.

In an exemplary embodiment, the condition is a member selected from psoriasis, eczema, atopic dermatitis, contact dermatitis, inflammatory alopecia or acne.

In an exemplary embodiment, the condition is a member selected from Guillain-Barre syndrome, Parkinson's disease, Huntington's disease, Alzheimer's disease, amyotrophic lateral sclerosis, multiple sclerosis and other demyelinating diseases, viral and bacterial meningitis, CNS trauma, spinal cord injury, seizures, convulsions, olivopontocerebellar atrophy, AIDS dementia complex, MERRF and MELAS syndromes, Leber's disease, Wernicke's encephalophathy, Rett syndrome, homocysteinuria, hyperprolinemia, hyperhomocysteinemia, nonketotic hyperglycinemia, hydroxybutyric aminoaciduria, sulfite oxidase deficiency, combined systems disease, lead encephalopathy, Tourett's syndrome, hepatic encephalopathy, drug addiction, drug tolerance, drug dependency, depression, attention deficit disorder (ADD), anxiety and schizophrenia, aneurism, or epilepsy.

In an exemplary embodiment, the condition is a member selected from bone resorption diseases, osteopetrosis, osteoporosis, or osteoarthritis.

In an exemplary embodiment, the condition is a member selected from diabetes, systemic cachexia, cachexia secondary to infection or malignancy, cachexia secondary to acquired immune deficiency syndrome (AIDS), obesity, anorexia or bulimia nervosa. In an exemplary embodiment, the condition is a member selected from sepsis, HIV, HCV, malaria, infectious arthritis, leishmaniasis, Lyme disease, cancer, including but not limited to breast cancer, colon cancer, lung cancer, prostate cancer, multiple myeloma, acute myelogenous leukemia, myelodysplastic syndrome, non-Hodgkins lymphoma, or follicular lymphoma, Castleman's disease, or drug resistance.

In an exemplary embodiment, the condition is a member selected from is bronchial asthma, rhinitis, influenza, stroke, myocardial infarction, thermal injury, adult respiratory distress syndrome (ARDS), multiple organ injury secondary to trauma, acute glomerulonephritis, dermatoses with acute inflammatory components, acute purulent meningitis, hemodialysis, leukopheresis, granulocyte transfusion associated syndromes, or necrotizing enterocolitis.

In an exemplary embodiment, the condition is a member selected from inflammatory bowel disease (IBD), psoriasis, rheumatoid arthritis (RA), multiple sclerosis (MS), neurodegenerative disorder, cardiovascular disease (CVD) and atherosclerosis, and metabolic disease (the metabolic syndrome and diabetes) as well as infection-related inflammation. In an exemplary embodiment, the condition is a neurodegenerative disorder which is a member selected from Alzheimer's disease and Parkinson disease. In an exemplary embodiment, the condition is inflammatory bowel disease which is selected from the group consisting of: Crohn's disease or ulcerative colitis. In an exemplary embodiment, the condition is a gastrointestinal complication. In an exemplary embodiment, the condition is diarrhea. In an exemplary embodiment, the condition is a member selected from celiac disease and non-specific colitis. In an exemplary embodiment, the condition is a liver disease. In an exemplary embodiment, the condition is a member selected from an autoimmune hepatitis, hepatitis C, primary biliary cirrhosis, primary sclerosing cholangitis, or fulminant liver failure. In an exemplary embodiment, the condition is a bone disease. In an exemplary embodiment, the condition is osteoporosis. In an exemplary embodiment, the condition is a pulmonary disorder. In an exemplary embodiment, the condition is a member selected from: allergic rhinitis, asthma, chronic obstructive pulmonary disease, chronic granulomatous inflammation, cystic fibrosis, and sarcoidosis. In an exemplary embodiment, condition is cardiovascular disease. In an exemplary embodiment, the cardiovascular disease is a member selected from atheroscleotic cardiac disease, congestive heart failure and restenosis. In an exemplary embodiment, the condition is a renal disease. In an exemplary embodiment, the condition is a member selected from glomerulonephritis and vasculitis. In an exemplary embodiment, the condition is a member selected from post-radiotherapy related disease or atherosclerosis. In yet another embodiment the condition is atopic dermatitis. In yet another embodiment the condition is actinic keratosis.

In an exemplary embodiment, the condition is a member selected from psoriasis, inflammatory arthritis, rheumatoid arthritis, asthma, chronic bronchitis, inflammatory bowel disease (IBD), chronic obstructive pulmonary disease (COPD), atopic dermatitis, urticaria, allergic rhinitis, allergic conjunctivitis, vernal conjunctivitis, colitis, esoniophilic granuloma, septic shock, reperfusion injury of the myocardium, reperfusion injury of the brain, chronic glomerulonephritis, endotoxic shock, adult respiratory distress syndrome, cystic fibrosis, arterial restenosis, artherosclerosis, keratosis, rheumatoid spondylitis, osteoarthritis, pyresis, diabetes mellitus, pneumoconiosis, chronic obstructive airways disease, toxic contact eczema, allergic contact eczema, atopic eczema, seborrheic eczema, lichen simplex, sunburn, pruritis in the anogenital area, alopecia areata, hypertrophic scars, discoid lupus erythematosus, systemic lupus erythematosus, follicular pyodermias, wide-area pyodermias, endogenous acne, exogenous acne, acne rosacea, Behcet's disease, anaphylactoid purpura nephritis, leukemia, multiple sclerosis, gastrointestinal disease and autoimmune disease. In an exemplary embodiment, the colitis is a member selected from ulcerative colitis, Crohn's colitis, diversion colitis, ischemic colitis, infectious colitis, fulminant colitis, chemical colitis, microscopic colitis, lymphocytic colitis, and atypical colitis. In an exemplary embodiment, the colitis is a member selected from ulcerative colitis and Crohn's colitis. In an exemplary embodiment, the condition is sunburn. In an exemplary embodiment, the condition is inflammation caused by sunburn.

In an exemplary embodiment, the condition is psoriasis. In an exemplary embodiment, psoriasis is a member selected from plaque psoriasis, flexural psoriasis (inverse psoriasis), guttate psoriasis, pustular psoriasis, nail psoriasis, psoriatic arthritis and erythrodermic psoriasis. In an exemplary embodiment, the psoriasis is a member selected from plaque psoriasis and nail psoriasis. In an exemplary embodiment, the condition is psoriasis and the compound is C17. In an exemplary embodiment, the condition is psoriasis and the compound is C27. In an exemplary embodiment, the condition is plaque psoriasis or nail psoriasis and the compound is C17. In an exemplary embodiment, the condition is plaque psoriasis or nail psoriasis and the compound is C27.

In an exemplary embodiment, the disorder is a member selected from cognition impairment or decline and memory impairment. In an exemplary embodiment, the memory impairment is due to dementia. In an exemplary embodiment, the patient is suffering from memory impairment due to Alzheimer's disease, schizophrenia, Parkinson's disease, Huntington's disease, Pick's disease, Creutzfeld-Jakob disease, depression, aging, head trauma, stroke, CNS hypoxia, cerebral senility, multiinfarct dementia, an acute neuronal disease, age-related cognitive decline, HIV or a cardiovascular disease.

In an exemplary embodiment, the PDE4 inhibition is enhancing an effect, wherein the enhanced effect is cognition or memory.

In an exemplary embodiment, the invention provides a method for stimulating ovarian follicular growth in a female, comprising administering to a female a medicament comprising a compound of the invention, whereby ovarian follicular growth is stimulated in the female. In an exemplary embodiment, the compound of the invention is a compound described herein or a pharmaceutically acceptable salt thereof. In an exemplary embodiment, the female is undergoing ovulation induction. In an exemplary embodiment, the female is undergoing controlled ovarian hyperstimulation. In an exemplary embodiment, the medicament is administered simultaneously, separately or sequentially with follicle stimulating hormone (FSH), or an agent having FSH activity, or an agent that stimulates endogenous FSH release.

The invention also provides a method of treating an inflammatory-related disease associated with cytokine expression levels, which comprises administering to an animal in need of such treatment the compound of the invention. In an exemplary embodiment, the compound is according to a formula described herein. In an exemplary embodiment, the compound of the invention is a compound described herein or a pharmaceutically acceptable salt thereof.

In an exemplary embodiment, the invention provides a method of treating or preventing an inflammatory-related disease in an animal, the method comprising administering to the animal a therapeutically effective amount of a compound of the invention, wherein the compound is in an amount sufficient to treat the inflammatory-related disease by inhibiting pro-inflammatory cytokine expression or by stimulating anti-inflammatory cytokine expression, but the amount is less than sufficient to substantially inhibit cyclin dependent kinases. In an exemplary embodiment, the compound of the invention is a compound described herein or a pharmaceutically acceptable salt thereof.

In an exemplary embodiment, the invention provides a method for inhibiting the production of an inflammatory cytokine by cells capable of producing the inflammatory cytokine, the method comprises contacting a cell with a therapeutic amount of compound of the invention, wherein production of the inflammatory cytokine by the cells is inhibited. In an exemplary embodiment, the therapeutic amount is sufficient to inhibit the production of the inflammatory cytokine protein between about 50% and about 99%.

In an exemplary embodiment, the invention provides a method for inhibiting an inflammatory response in an animal, the method comprising: contacting the animal with a therapeutic amount of a compound of the invention, wherein the inflammatory response is inhibited.

In an exemplary embodiment, for any of the methods described herein, the animal is a member selected from human, cattle, deer, reindeer, goat, honey bee, pig, sheep, horse, cow, bull, dog, guinea pig, gerbil, rabbit, cat, camel, yak, elephant, ostrich, otter, chicken, duck, goose, guinea fowl, pigeon, swan, and turkey. In another exemplary embodiment, for any of the methods described herein, the animal is a member selected from a human, cattle, goat, pig, sheep, horse, cow, bull, dog, guinea pig, gerbil, rabbit, cat, chicken and turkey. In another exemplary embodiment, for any of the methods described herein, the animal is a human.

In an exemplary embodiment, for any of the methods described herein, a compound of the invention and/or a pharmaceutical formulation described herein can be used.

In another exemplary embodiment, in any of the methods of treating/preventing a condition or enhancing an effect described herein, the animal being administered the compound of the invention is not otherwise in need of treatment with the compound of the invention. In an exemplary embodiment, the compound is a member selected from C1, C2, C3, C4, C5, C6, C7, C8, C9, C10, C11, C12, C13, C14, C15, C16, C17, C18, C19, C20, C21, C22, C23, C24, C25, C26, C27, C28, C29, C30, C31, C32, C33, C34, C35, C36, C37, C38, C39, C40, C41, C42, C43, C44, C45, C46, C47, C48, C49, C50, C51, C52, C53, C54, C55, C56, C57, C58, C59, C60, C61, C62, C63, C64, C65, C66, C67, C68, C69, C70, C71, C72, C73, C74, C75, C76, C77, C78, C79, C80, C81, C82, C83, C84, C85, C86, C87, C88, C89, C90, C91, C92, C93, C94, C95, C96, C97, C98, C99 and C100. In an exemplary embodiment, the compound is C17. In an exemplary embodiment, the compound is C27. In an exemplary embodiment, the compound is D1. In an exemplary embodiment, the compound is D82. In an exemplary embodiment, the compound is D226. In an exemplary embodiment, the compound is D227.

In another exemplary embodiment, the method involves treating psoriasis by administering a compound of the invention to an animal not otherwise in need of treatment with the compounds of the invention.

In another exemplary embodiment, the method involves treating atopic dermatitis by administering a compound of the invention to an animal not otherwise in need of treatment with the compounds of the invention.

V. Pharmaceutical Formulations

In another aspect, the invention provides a pharmaceutical formulation comprising: (a) a compound of the invention and (b) a pharmaceutically acceptable excipient. In an exemplary embodiment, the compound of the invention is a compound described herein or a pharmaceutically acceptable salt thereof. In an exemplary embodiment, the compound of the invention is a compound described herein or a pharmaceutically acceptable salt thereof. In an exemplary embodiment, the compound is according to a formula described herein. In an exemplary embodiment, the compound is a member selected from C1, C2, C3, C4, C5, C6, C7, C8, C9, C10, C11, C12, C13, C14, C15, C16, C17, C18, C19, C20, C21, C22, C23, C24, C25, C26, C27, C28, C29, C30, C31, C32, C33, C34, C35, C36, C37, C38, C39, C40, C41, C42, C43, C44, C45, C46, C47, C48, C49, C50, C51, C52, C53, CM, C55, C56, C57, C58, C59, C60, C61, C62, C63, C64, C65, C66, C67, C68, C69, C70, C71, C72, C73, C74, C75, C76, C77, C78, C79, C80, C81, C82, C83, C84, C85, C86, C87, C88, C89, C90, C91, C92, C93, C94, C95, C96, C97, C98, C99 and C100. In an exemplary embodiment, the compound is a member selected from D1, D2, D3, D4, D5, D6, D7, D8, D9, D10, D11, D12, D13, D14, D15, D16, D17, D18, D19, D20, D21, D22, D23, D24, D25, D26, D27, D28, D29, D30, D31, D32, D33, D34, D35, D36, D37, D38, D39, D40, D41, D42, D43, D44, D45, D46, D47, D48, D49, D50, D51, D52, D53, D54, D55, D56, D57, D58, D59, D60, D61, D62, D63, D64, D65, D66, D67, D68, D69, D70, D71, D72, D73, D74, D75, D76, D77, D78, D79, D80, D81, D82, D83, D84, D85, D86, D87, D88, D89, D90, D91, D92, D93, D94, D95, D96, D97, D98, D99, D100, D101, D102, D103, D104, D105, D106, D107, D108, D109, D110, D111, D112, D113, D114, D115, D116, D117, D118, D119, D120, D121, D122, D123, D124, D125, D126, D127, D128, D129, D130, D131, D132, D133, D134, D135, D136, D137, D138, D139, D140, D141, D142, D143, D144, D145, D146, D147, D148, D149, D150, D151, D152, D153, D154, D155, D156, D157, D158, D159, D160, D161, D162, D163, D164, D165, D166, D167, D168, D169, D170, D171, D172, D173, D174, D175, D176, D177, D178, D179, D180, D181, D182, D183, D184, D185, D186, D187, D188, D189, D190, D191, D192, D193, D194, D195, D196, D197, D198, D199, D200, D201, D202, D203, D204, D205, D206, D207, D208, D209, D210, D211, D212, D213, D214, D215, D216, D217, D218, D219, D220, D221, D222, D223, D224, D225, D226, D227, D228 and D229. In an exemplary embodiment, the compound is C17. In an exemplary embodiment, the compound is C27. In an exemplary embodiment, the formulation is a unit dosage form. In an exemplary embodiment, the formulation is a member selected from an oral unit dosage form and a topical unit dosage form. In an exemplary embodiment, the topical unit dosage form is a member selected from a lotion, an ointment and a cream. In an exemplary embodiment, the formulation is for topical use.

In an exemplary embodiment, the compound of the invention is present in the pharmaceutical formulation in an amount of between about 0.0001% to about 60% (w/w). In an exemplary embodiment, the amount is between about 0.05% to about 0.2% (w/w). In an exemplary embodiment, the amount is between about 0.075% to about 0.15% (w/w). In an exemplary embodiment, the amount is between about 0.01% to about 10% (w/w). In an exemplary embodiment, the amount is between about 0.1% to about 10% (w/w). In an exemplary embodiment, the amount is between about 0.25% to about 6% (w/w). In an exemplary embodiment, the amount is between about 0.5% to about 5% (w/w). In an exemplary embodiment, the amount is between about 0.1% and about 1.0% (w/w). In an exemplary embodiment, the amount is between about 0.25% and about 0.75% (w/w). In an exemplary embodiment, the amount is between about 0.4% and about 0.6% (w/w). In an exemplary embodiment, the amount is between about 1.0% and about 2.0% (w/w). In an exemplary embodiment, the amount is between about 1.3% and about 1.7% (w/w). In an exemplary embodiment, the amount is between about 2.0% and about 3.0% (w/w). In an exemplary embodiment, the amount is between about 3.0% and about 4.0% (w/w). In an exemplary embodiment, the amount is between about 4.0% and about 5.0% (w/w). In an exemplary embodiment, the amount is between about 4.5% and about 5.5% (w/w). In an exemplary embodiment, the amount is between about 10% to about 20% (w/w). In an exemplary embodiment, the amount is between about 13% to about 17% (w/w). In an exemplary embodiment, the amount is between about 14% to about 16% (w/w). In an exemplary embodiment, the amount is a member selected from about 0.1%, 0.3, 0.5%, 1.0%, 1.5%, 2.0%, 5.0%, 10% and 15% (w/w).

The pharmaceutical formulations of the invention can take a variety of forms adapted to the chosen route of administration. Those skilled in the art will recognize various synthetic methodologies that may be employed to prepare non-toxic pharmaceutical formulations incorporating the compounds described herein. Those skilled in the art will recognize a wide variety of non-toxic pharmaceutically acceptable solvents that may be used to prepare solvates of the compounds of the invention, such as water, ethanol, propylene glycol, mineral oil, vegetable oil and dimethylsulfoxide (DMSO).

The pharmaceutical formulations of the invention may be administered orally, topically, ocularly, parenterally, by inhalation or spray or rectally in dosage unit formulations containing conventional non-toxic pharmaceutically acceptable carriers, adjuvants and vehicles. It is further understood that the best method of administration may be a combination of methods. Oral administration in the form of a pill, capsule, elixir, syrup, lozenge, troche, or the like is particularly preferred. The term parenteral as used herein includes subcutaneous injections, intradermal, intravascular (e.g., intravenous), intramuscular, spinal, intrathecal injection or like injection or infusion techniques.

The pharmaceutical formulations containing compounds of the invention are preferably in a form suitable for oral use, for example, as tablets, troches, lozenges, aqueous or oily suspensions, dispersible powders or granules, emulsion, hard or soft capsules, or syrups or elixirs.

Pharmaceutical formulations intended for oral use may be prepared according to any method known in the art for the manufacture of pharmaceutical formulations, and such compositions may contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; lubricating agents, for example magnesium stearate, stearic acid or talc; and extenders and bulking agents, such as microcrystalline cellulose. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; and dispersing or wetting agents, which may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Other dispersing agents include hydrophilic polymers, electrolytes, Tween® 60 or 80, PEG, polyvinylpyrrolidone (PVP; commercially known as Plasdone®), and the carbohydrate-based dispersing agents such as, for example, hydroxypropylcellulose and hydroxypropylcellulose ethers (e.g., HPC, HPC-SL, and HPC-L), hydroxypropylmethylcellulose and hydroxypropylmethylcellulose ethers (e.g. HPMC K100, HPMC K4M, HPMC K15M, and HPMC K100M), carboxymethylcellulose sodium, methylcellulose, hydroxyethylcellulose, hydroxypropylmethylcellulose phthalate, hydroxypropylmethylcellulose acetate stearate, noncrystalline cellulose, magnesium aluminum silicate, triethanolamine, polyvinyl alcohol (PVA), polyvinylpyrrolidone/vinyl acetate copolymer (Plasdone®, e.g., S-630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 9080, also known as Poloxamine 9080, which is a tetrafunctional block copolymer derived from sequential addition of propylene oxide and ethylene oxide to ethylenediamine (BASF Corporation, Parsippany, N.J.)). Additional excipients, for example sweetening, flavoring and coloring agents, may also be present.

Pharmaceutical formulations of the invention may also be in the form of oil-in-water emulsions and water-in-oil emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth; naturally-occurring phosphatides, for example soy bean, lecithin, and esters or partial esters derived from fatty acids and hexitol; anhydrides, for example sorbitan monooleate; and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical formulations may be in the form of a sterile injectable aqueous or oleaginous suspension. This suspension may be formulated according to the known art using those suitable dispersing or wetting agents and suspending agents, which have been mentioned above. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The pharmaceutical formulations may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials are cocoa butter and polyethylene glycols.

Alternatively, the pharmaceutical formulations can be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

In some embodiments, the pharmaceutical formulations may be administered ocularly. In some embodiments, the ophthalmic formulation contains a liquid vehicle. The compound, depending on the vehicle and concentration used, can either be suspended or dissolved in the vehicle. Such ophthalmic formulations can then be administered to the eye in the form of a droplet. Suitable vehicles, and optional tear substitute components, are known in the art.

For administration to non-human animals, the composition containing the therapeutic compound may be added to the animal's feed or drinking water. Also, it will be convenient to formulate animal feed and drinking water products so that the animal takes in an appropriate quantity of the compound in its diet. It will further be convenient to present the compound in a composition as a premix for addition to the feed or drinking water. The composition can also added as a food or drink supplement for humans.

Dosage levels of the order of from about 5 mg to about 250 mg per kilogram of body weight per day and more preferably from about 25 mg to about 150 mg per kilogram of body weight per day, are useful in the treatment of the above-indicated conditions. The amount of active ingredient that may be combined with the carrier materials to produce a single dosage form will vary depending upon the condition being treated and the particular mode of administration. Dosage unit forms will generally contain between from about 1 mg to about 500 mg of an active ingredient.

Frequency of dosage may also vary depending on the compound used and the particular disease treated. However, for treatment of most disorders, a dosage regimen of 4 times daily or less is preferred. It will be understood, however, that the specific dose level for any particular patient will depend upon a variety of factors including the activity of the specific compound employed, the age, body weight, general health, sex, diet, time of administration, route of administration and rate of excretion, drug combination and the severity of the particular disease undergoing therapy.

Preferred compounds of the invention will have desirable pharmacological properties that include, but are not limited to, oral bioavailability, low toxicity, low serum protein binding and desirable in vitro and in vivo half-lives. Penetration of the blood brain barrier for compounds used to treat CNS disorders is necessary, while low brain levels of compounds used to treat peripheral disorders are often preferred.

Assays may be used to predict these desirable pharmacological properties. Assays used to predict bioavailability include transport across human intestinal cell monolayers, including Caco-2 cell monolayers. Toxicity to cultured hepatocytes may be used to predict compound toxicity. Penetration of the blood brain barrier of a compound in humans may be predicted from the brain levels of laboratory animals that receive the compound intravenously.

Serum protein binding may be predicted from albumin binding assays. Such assays are described in a review by Oravcova, et al. (Journal of Chromatography B (1996) volume 677, pages 1-27).

Compound half-life is inversely proportional to the frequency of dosage of a compound. In vitro half-lives of compounds may be predicted from assays of microsomal half-life as described by Kuhnz and Gieschen (Drug Metabolism and Disposition, (1998) volume 26, pages 1120-1127).

The amount of the composition required for use in treatment will vary not only with the particular compound selected but also with the route of administration, the nature of the condition being treated and the age and condition of the patient and will ultimately be at the discretion of the attendant physician or clinician.

In an exemplary embodiment, the pharmaceutical composition described herein includes an additional active ingredient. In another exemplary embodiment, the additional active ingredient is an immunosuppressive agent. In still another exemplary embodiment, the additional active ingredient is a member selected from corticosteroids, aminosalicylates, azathioprine (6-mercaptopurine), methotrexate and ciclosporine, etanercept, infliximab, adalimumab, alefacept, efalizumab and anakinra.

In an exemplary embodiment, the additional active ingredient is a member selected from cilostazol, rolipram, roflumilast, piclamilast, CDP-840 and ariflo.

In still another exemplary embodiment, the additional active ingredient is a member selected from betamethasone, tacrolimus and pimecrolimus. In still another exemplary embodiment, the additional active ingredient is a member selected from an activated vitamin D analog and an arotinoid (an aromatic retinoic acid analog). In still another exemplary embodiment, the additional active ingredient is a member selected from carcipotriol, such as Tazorac (tazarotene).

V. a) Topical Formulations

In a preferred embodiment, the methods of the invention can be employed through the topical application of the compounds described herein. Topical administration includes for example, transmucosal, transdermal, ungual and transungual routes of administration.

The compositions of the present invention comprises fluid or semi-solid vehicles that may include but are not limited to polymers, thickeners, buffers, neutralizers, chelating agents, preservatives, surfactants or emulsifiers, antioxidants, waxes or oils, emollients, sunscreens, and a solvent or mixed solvent system. The solvent or mixed solvent system is important to the formation because it is primarily responsible for dissolving the drug. The best solvent or mixed solvent systems are also capable of maintaining clinically relevant levels of the drug in solution despite the addition of a poor solvent to the formulation. The topical compositions useful in the subject invention can be made into a wide variety of product types. These include, but are not limited to, lotions, creams, gels, sticks, sprays, ointments, pastes, foams, mousses, masks, eye ointments, eye or ear drops, impregnated dressings, wipes, cleansers including soaps, body washes and shampoos, and make-up products, such as bases, blushes, lipsticks, and eye shadows, among others. These product types can comprise several types of carrier systems including, but not limited to particles, nanoparticles, and liposomes. If desired, disintegrating agents can be added, such as the cross-linked polyvinyl pyrrolidone, agar or alginic acid or a salt thereof such as sodium alginate. Techniques for formulation and administration can be found in *Remington: The Science and Practice of Pharmacy*, supra. The formulation can be selected to maxim/ze delivery to a desired target site in the body. The formulations can also include various conventional colorants, fragrances, thickeners, preservatives, humectants, emollients, demulcents, solubilizing excipients, dispersants, penetration enhancers, plasticizing agents, preservatives, stabilizers, demulsifiers, wetting agents, sunscreens, emulsifiers, moisturizers, astringents, deodorants, and the like, which can be added to provide additional benefits such as, for example, improving the feel and/or appearance of the topical preparation.

Lotions, which are preparations that are to be applied to the skin, nail, hair, claw or hoof surface without friction, are typically liquid or semi-liquid preparations in which finely divided solid, waxy, or liquid are dispersed. Lotions will typically contain suspending agents to produce better dispersions as well as compounds useful for localizing and holding the active agent in contact with the skin, nail, hair, claw or hoof, e.g., methylcellulose, sodium carboxymethyl-cellulose, or the like.

Creams containing the active agent for delivery according to the present invention are viscous liquid or semisolid emulsions, either oil-in-water or water-in-oil. Cream bases are water-washable, and contain an oil phase, an emulsifier and an aqueous phase. The oil phase is generally comprised of petrolatum or a fatty alcohol, such as cetyl- or stearyl alcohol; the aqueous phase usually, although not necessarily, exceeds the oil phase in volume, and generally contains a humectant. The emulsifier in a cream formulation, as explained in *Remington: The Science and Practice of Pharmacy*, supra, is generally a nonionic, anionic, cationic or amphoteric surfactant.

A lotion or cream may include a relatively large aqueous phase and a relatively small oil phase. Furthermore, the lotions and creams of the invention may include the active compound "all-in-solution" in the oil phase so that substantially none of the active compound crystallizes out at room temperature. In one embodiment, the lotion or cream may comprise a biphasic system, that is, a system wherein a portion (from about 30 to about 75% by weight) of the active compound is in solution in the oil phase and the remainder is in suspension in the aqueous phase.

Gel formulations can also be used in connection with the present invention. As will be appreciated by those working in the field of topical drug formulation, gels are semisolid. Single-phase gels contain organic macromolecules distributed substantially uniformly throughout the carrier liquid, which is typically aqueous, but also may be a solvent or solvent blend. In various embodiments, conventional gelling agents can be used. In an exemplary embodiment, cellulose or its derivatives are used. In an exemplary embodiment, hydroxypropyl methyl cellulose, such as Methocel E4M, is used. Other gelling agents include methyl cellulose, hydroxypropyl cellulose, hydroxypropyl methyl cellulose, cellulose acetate, ethyl cellulose, methyl hydroxy ethyl cellulose, hydroxy ethyl cellulose, and cellulose gum. Cellulose based gelling agents, particularly hydroxymethylcellulose and hydroxypropyl methyl cellulose, are also useful in some embodiments. In some embodiments, cross-linked acrylic polymers including Carbopol may be used.

In one embodiment, the formulation of the invention is viscous enough to form a firm gel. In one embodiment, the viscosity is in the range of 25,000-300,000 cps (centipoise) or 75,000-200,000 cps, based on Brookfield (LV) analysis.

For ease of preparation, it may be convenient to prepare a first gel composition, named speed-gel herein, which can be used to add to other components in the formulation of a final composition for topical administration. There are several possible formulations of the speed-gel. For example, a speed-gel may be prepared by mixing lecithin organogel (L.O.), as a 1:1 (m/m) mixture of lecithin and isopropyl myristate, with LID oil (a 1:1 [m/m] mixture of L.O. and docusate sodium), dissolving additional docusate sodium powder into this mixture, and then adding aqueous urea.

Ointments, which are semisolid preparations, are typically based on petrolatum or other petroleum derivatives. As will be appreciated by the ordinarily skilled artisan, the specific ointment base to be used is one that provides for optimum delivery for the active agent chosen for a given formulation, and, preferably, provides for other desired characteristics as well, e.g., emolliency or the like. As with other carriers or vehicles, an ointment base should be inert, stable, nonirritating and non-sensitizing. As explained in Remington: The Science and Practice of Pharmacy, 19th Ed. (Easton, Pa.: Mack Publishing Co., 1995), at pages 1399-1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Examples of oleaginous ointment bases include White Ointment USP, Yellow Ointment NF, Oleic Acid USP, Olive Oil USP, Paraffin USP, Petrolatum NF, White Petrolatum USP, Spermaceti Wax USP, Synthetic Spermaceti NF, Starch Glycerite NF, White Wax USP, and Yellow Wax USP. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Preferred water-soluble ointment bases are prepared from polyethylene glycols of varying molecular weight; again, reference may be had to Remington: The Science and Practice of Pharmacy, supra, for further information.

Useful formulations of the invention also encompass sprays and aerosols. Sprays generally provide the active agent in an aqueous and/or alcoholic solution which can be misted onto the skin, nail, hair, claw or hoof for delivery. Such sprays include those formulated to provide for concentration of the active agent solution at the site of administration following delivery, e.g., the spray solution can be primarily composed of alcohol or other like volatile liquid in which the drug or active agent can be dissolved. Upon delivery to the skin, nail, hair, claw or hoof, the carrier evaporates, leaving concentrated active agent at the site of administration. Examples of aerosol technology are disclosed in U.S. Pat. Nos. 6,682,716; 6,716,415; 6,716,417; 6,783,753; 7,029,658; and 7,033,575.

The topical pharmaceutical compositions may also comprise suitable solid or gel phase carriers. Examples of such carriers include but are not limited to calcium carbonate, calcium phosphate, various sugars, starches, cellulose derivatives, gelatin, and polymers such as polyethylene glycols.

The topical pharmaceutical compositions may also comprise a suitable emulsifier which refers to an agent that enhances or facilitates mixing and suspending oil-in-water or water-in-oil. The emulsifying agent used herein may consist of a single emulsifying agent or may be a nonionic, anionic, cationic or amphoteric surfactant or blend of two or more such surfactants; preferred for use herein are nonionic or anionic emulsifiers. Such surface-active agents are described in "McCutcheon's Detergent and Emulsifiers," North American Edition, 1980 Annual published by the McCutcheon Division, MC Publishing Company, 175 Rock Road, Glen Rock, N.J. 07452, USA.

Examples of useful ionic surfactants include sodium caproate, sodium caprylate, sodium caprate, sodium laurate, sodium myristate, sodium myristolate, sodium palmitate, sodium palmitoleate, sodium oleate, sodium ricinoleate, sodium linoleate, sodium linolenate, sodium stearate, sodium lauryl sulfate (dodecyl), sodium tetradecyl sulfate, sodium lauryl sarcosinate, sodium dioctyl sulfosuccinate, sodium cholate, sodium taurocholate, sodium glycocholate, sodium deoxycholate, sodium taurodeoxycholate, sodium glycodeoxycholate, sodium ursodeoxycholate, sodium chenodeoxycholate, sodium taurochenodeoxycholate, sodium glyco cheno deoxycholate, sodium cholylsarcosinate, sodium N-methyl taurocholate, egg yolk phosphatides, hydrogenated soy lecithin, dimyristoyl lecithin, lecithin, hydroxylated lecithin, lysophosphatidylcholine, cardiolipin, sphingomyelin, phosphatidylcholine, phosphatidyl ethanolamine, phosphatidic acid, phosphatidyl glycerol, phosphatidyl serine, diethanolamine, phospholipids, polyoxyethylene-10 oleyl ether phosphate, esterification products of fatty alcohols or fatty alcohol ethoxylates, with phosphoric acid or anhydride, ether carboxylates (by oxidation of terminal OH group of, fatty alcohol ethoxylates), succinylated monoglycerides, sodium stearyl fumarate, stearoyl propylene glycol hydrogen succinate, mono/diacetylated tartaric acid esters of mono- and diglycerides, citric acid esters of mono-, diglycerides, glyceryl-lacto esters of fatty acids, acyl lactylates, lactylic esters of fatty acids, sodium stearoyl-2-lactylate, sodium stearoyl lactylate, alginate salts, propylene glycol alginate, ethoxylated alkyl sulfates, alkyl benzene sulfones, .alpha.-olefin sulfonates, acyl isethionates, acyl taurates, alkyl glyceryl ether sulfonates, sodium octyl sulfosuccinate, sodium undecylenamideo-MEA-sulfosuccinate, hexadecyl triammonium bromide, decyl trimethyl ammonium bromide, cetyl trimethyl ammonium bromide, dodecyl ammonium chloride, alkyl benzyldimethylammonium salts, diisobutyl phenoxyethoxydimethyl benzylammonium salts, alkylpyridinium salts, betaines (trialkylglycine), lauryl betaine (N-lauryl,N,N-dimethylglycine), and ethoxylated amines (polyoxyethylene-15 coconut amine). For simplicity, typical counterions are provided above. It will be appreciated by one skilled in the art, however, that any bioacceptable counterion may be used. For example, although the fatty acids are shown as sodium salts, other cation counterions can also be used, such as, for example, alkali metal cations or ammonium. Formulations of the invention may include one or more of the ionic surfactants above.

Preferred for use herein are high molecular weight alcohols such as cetearyl alcohol, cetyl alcohol, stearyl alcohol, emulsifying wax, glyceryl monostearate, and oleyl alcohol. Other examples are ethylene glycol distearate, sorbitan tristearate, propylene glycol monostearate, sorbitan monooleate, sorbitan monostearate (SPAN 60), diethylene glycol monolaurate, sorbitan monopalmitate, sucrose dioleate, sucrose stearate (CRODESTA F-160), polyoxyethylene lauryl ether (BRIJ 30), polyoxyethylene (2) stearyl ether (BRIJ 72), polyoxyethylene (21) stearyl ether (BRIJ 721), polyoxyethylene monostearate (Myrj 45), polyoxyethylene (20) sorbitan monolaurate (TWEEN 20, polysorbate 20), polyoxyethylene (20) sorbitan monopalmitate (TWEEN 40, polysorbate 40), polyoxyethylene (20) sorbitan monostearate (TWEEN 60, polysorbate 60), polyoxyethylene (20) sorbitan monooleate (TWEEN 80, polysorbate 80), other non-ionic polyoxyalkylene derivatives of hexitol anhydride partial long chain fatty acid esters, and sodium oleate. In an exemplary embodiment, the emulsifier is octyldodecanol. In an exemplary embodiment, xanthan gum or a xanthan gum blend is used. Cholesterol and cholesterol derivatives may also be employed in externally used emulsions and promote w/o emulsions.

Especially suitable nonionic emulsifying agents are those with hydrophile-lipophile balances (HLB) of about 3 to 6 for w/o system and 8 to 18 for o/w system as determined by the method described by Paul L. Lindner in "Emulsions and Emulsion", edited by Kenneth Lissant, published by Dekker, New York, N.Y., 1974, pages 188-190. More preferred for use herein are one or more nonionic surfactants that produce a system having HLB of about 8 to about 18.

Examples of such nonionic emulsifiers include but are not limited to "BRIJ 72", the trade name for a polyoxyethylene (2) stearyl ether having an HLB of 4.9; "BRIJ 721", the trade name for a polyoxyethylene (21) stearyl ether having an HLB of 15.5, "Brij 30", the trade name for polyoxyethylene lauryl ether having an HLB of 9.7; "Polawax", the trade name for emulsifying wax having an HLB of 8.0; "Span 60", the trade name for sorbitan monostearate having an HLB of 4.7; "Crodesta F-160", the trade name for sucrose stearate" having an HLB of 14.5. All of these materials are available from Ruger Chemicals Inc.; Croda; ICI Americas, Inc.; Spectrum Chemicals; and BASF. When the topical formulations of the present invention contain at least one emulsifying agent, each emulsifying agent is present in amount from about 0.5 to about 2.5 wt %, preferably 0.5 to 2.0%, more preferably 1.0% or 1.8%. Preferably the emulsifying agent comprises a mixture of steareth 21 (at about 1.8%) and steareth 2 (at about 1.0%).

The topical pharmaceutical compositions may also comprise suitable emollients. Emollients are materials used for the prevention or relief of dryness, as well as for the protection of the skin, nail, hair, claw or hoof. Useful emollients include, but are not limited to, hydrocarbon oils, waxes, silicone, cetyl alcohol, isopropyl myristate, stearyl alcohol, oleyl alcohol, octyl hydroxystearate, glycerin, other fatty alcohols including short or medium chain fatty alcohols having a carbon length of up to 18, medium or short chain fatty acid triglycerides, esters such as fatty acid esters, lecithins and related polar compounds such as phosphatidylcholine, phosphatidylethanolamine, phosphatidylserine, phosphatidylinositol, phosphatidic acid, lyso-phosphatidylcholine, lyso-phosphatidylethanolamine, and sphingomyelin and the like. Other suitable emollients include triglyceride oils like vegetable oils such as wheat germ, maize, sunflower, karite, castor, sweet almond, macadamia, apricot, soybean, cottonseed, alfalfa, poppy, pumpkinseed, sesame, cucumber, rapeseed, avocado, hazelnut, grape seed, blackcurrant seed, evening primrose, millet, barley, quinoa, olive, rye, safflower, candlenut, soya, palm, passion flower, or musk rose oil; triglycerides of caprylic/capric acid, such as those sold under the tradenames MIGLYOL® (Condea Chemie, Germany) and CRODAMOL (Croda, Inc., Edison, N.J.); fatty alcohols such as caprylic alcohol, lauryl alcohol, myristyl alcohol, cetyl alcohol, and stearyl alcohol; and fatty esters such as oleyl acetate, isotridecyl benzoate, diisooctyl sebacate, isopropyl myristate, cetyl octanoate, isopropyl palmitate, butyl stearate, hexyl laurate, myristyl myristate, decyl oleate, hexyldecyl dimethyloctanoate, cetyl lactate, myristyl lactate, lanoline acetate, isocetyl stearate, isocetyl isostearate, cholesteryl 12-hydroxystearate, dipentaerythritol fatty acid ester, and isostearyl malate. A wide variety of suitable emollients are known and can be used herein. See e.g., Sagarin, Cosmetics, Science and Technology, 2nd Edition, Vol. 1, pp. 32-43 (1972), and U.S. Pat. No. 4,919,934, to Deckner et al., issued Apr. 24, 1990, both of which are incorporated herein by reference in their entirety. These materials are available from Ruger Chemical Co, (Irvington, N.J.).

When the topical formulations of the present invention contain at least one emollient, each emollient is present in an amount from about 0.1 to 15%, preferably 0.1 to about 3.0, more preferably 0.5, 1.0, or 2.5 wt %. Preferably the emollient is a mixture of cetyl alcohol, isopropyl myristate and stearyl alcohol in a 1/5/2 ratio. The emollient may also be a mixture of cetyl alcohol and stearyl alcohol in a 1/2 ratio.

The topical pharmaceutical compositions may also comprise suitable antioxidants, substances known to inhibit oxidation. Antioxidants suitable for use in accordance with the present invention include, but are not limited to, butylated hydroxytoluene, ascorbic acid, sodium ascorbate, calcium ascorbate, ascorbic palmitate, butylated hydroxyanisole, 2,4, 5-trihydroxybutyrophenone, 4-hydroxymethyl-2,6-di-tert-butylphenol, erythorbic acid, gum guaiac, propyl gallate, thiodipropionic acid, dilauryl thiodipropionate, tert-butylhydroquinone and tocopherols such as vitamin E, and the like, including pharmaceutically acceptable salts and esters of these compounds. Preferably, the antioxidant is butylated hydroxytoluene, butylated hydroxyanisole, propyl gallate, ascorbic acid, pharmaceutically acceptable salts or esters thereof, or mixtures thereof. Most preferably, the antioxidant is butylated hydroxytoluene. These materials are available from Ruger Chemical Co, (Irvington, N.J.). Antioxidants that may be incorporated into the formulations of the invention include natural antioxidants prepared from plant extracts, such as extracts from aloe vera; avocado; chamomile; *echinacea; ginko biloba*; ginseng; green tea; heather; jojoba; lavender; lemon grass; licorice; mallow; oats; peppermint; St. John's wort; willow; wintergreen; wheat wild yam extract; marine extracts; and mixtures thereof.

When the topical formulations of the present invention contain at least one antioxidant, the total amount of antioxidant present is from about 0.001 to 0.5 wt %, preferably 0.05 to about 0.5 wt %, more preferably 0.1%.

The topical pharmaceutical compositions may also comprise suitable preservatives. Preservatives are compounds added to a pharmaceutical formulation to act as an antimicrobial agent. Among preservatives known in the art as being effective and acceptable in parenteral formulations are benzalkonium chloride, benzethonium, chlorohexidine, phenol, m-cresol, benzyl alcohol, methylparaben, propylparaben and other parabens, chlorobutanol, o-cresol, p-cresol, chlorocresol, phenylmercuric nitrate, thimerosal, benzoic acid, and various mixtures thereof. See, e.g., Wallhausser, K.-H., Develop. Biol. Standard, 24:9-28 (1974) (S. Krager, Basel). Preferably, the preservative is selected from methylparaben, propylparaben and mixtures thereof. These materials are available from Inolex Chemical Co (Philadelphia, Pa.) or Spectrum Chemicals.

When the topical formulations of the present invention contain at least one preservative, the total amount of preservative present is from about 0.01 to about 0.5 wt %, preferably from about 0.1 to 0.5%, more preferably from about 0.03 to about 0.15. Preferably the preservative is a mixture of methylparaben and proplybarben in a 5/1 ratio. When alcohol is used as a preservative, the amount is usually 15 to 20%.

The topical pharmaceutical compositions may also comprise suitable chelating agents to form complexes with metal cations that do not cross a lipid bilayer. Examples of suitable chelating agents include ethylene diamine tetraacetic acid (EDTA), ethylene glycol-bis(beta-aminoethyl ether)-N,N,N', N'-tetraacetic acid (EGTA) and 8-Amino-2-[(2-amino-5-methylphenoxy)methyl]-6-methoxyquinoline-N,N,N',N'-tetraacetic acid, tetrapotassium salt (QUIN-2). Preferably the chelating agents are EDTA and citric acid. A chelating agent may comprise salts of the above, such as edetate disodium, for example. These materials are available from Spectrum Chemicals.

When the topical formulations of the present invention contain at least one chelating agent, the total amount of chelating agent present is from about 0.005% to 2.0% by weight, preferably from about 0.05% to about 0.5 wt %, more preferably about 0.1% by weight.

The topical pharmaceutical compositions may also comprise suitable neutralizing agents used to adjust the pH of the formulation to within a pharmaceutically acceptable range. Examples of neutralizing agents include but are not limited to trolamine, tromethamine, sodium hydroxide, hydrochloric acid, sodium carbonate, citric acid, acetic acid and corresponding acids or bases thereof. Such materials are available from are available from Spectrum Chemicals (Gardena, Calif.).

When the topical formulations of the present invention contain at least one neutralizing agent, the total amount of neutralizing agent present is from about 0.1 wt to about 10 wt %, preferably 0.1 wt % to about 5.0 wt %, and more preferably about 1.0 wt %. The neutralizing agent is generally added in whatever amount is required to bring the formulation to the desired pH. In one embodiment, the pH is about 6.0 to about 8.0. In one embodiment, the pH is about 3.0 to about 4.0.

The topical pharmaceutical compositions may also comprise suitable thickening or viscosity increasing agents. These components are diffusible compounds capable of increasing the viscosity of a polymer-containing solution through the interaction of the agent with the polymer. For example, CARBOPOL ULTREZ 10, polymethyl methacrylate (PMMA), and fumed silica may be used as a viscosity-increasing agent. These materials are available from Noveon Chemicals, Cleveland, Ohio Other examples of thickeners include monoglycerides and fatty alcohols, fatty acid esters of alcohols having from about 3 to about 16 carbon atoms. Examples of suitable monoglycerides are glyceryl monostearate and glyceryl monopalmitate. Examples of fatty alcohols are cetyl alcohol and stearyl alcohol. Examples of suitable esters are myristyl stearate and cetyl stearate. The monoglyceride also functions as an auxilliary emulsifier. Other emollients or oleaginous material which may be employed include petrolatum, glyceryl monooleate, myristyl alcohol, and isopropyl palmitate. In one embodiment, the thickener is used in combination with an emulsifying agent.

When the topical formulations of the present invention contain at least one viscosity increasing agent, the total amount of viscosity increasing agent present is from about 0.25% to about 5.0% by weight, preferably from about 0.25% to about 1.0 wt %, and more preferably from about 0.4% to about 0.6% by weight.

The topical pharmaceutical compositions may also comprise a disintegrating agent including starch, e.g., a natural starch such as corn starch or potato starch, a pregelatinized starch such as National 1551 or Amijele®, or sodium starch glycolate such as Promogel® or Explotab®; a cellulose such as a wood product, microcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose; a cross-linked starch such as sodium starch glycolate; a cross-linked polymer such as crosspovidone; a cross-linked polyvinylpyrrolidone; alginate such as alginic acid or a salt of alginic acid such as sodium alginate; a clay such as Veegum® HV (magnesium aluminum silicate); a gum such as agar, guar, locust bean, Karaya, pectin, or tragacanth; sodium starch glycolate; bentonite; a natural sponge; a surfactant; a resin such as a cation-exchange resin; citrus pulp; sodium lauryl sulfate; sodium lauryl sulfate in combination starch; and the like.

The topical pharmaceutical compositions may also comprise suitable nail penetration enhancers. Examples of nail penetration enhancers include mercaptan compounds, sulfites and bisulfites, keratolytic agents and surfactants. Nail penetration enhancers suitable for use in the invention are described in greater detail in Malhotra et al., *J. Pharm. Sci.*, 91:2, 312-323 (2002), which is incorporated herein by reference in its entirety.

The topical pharmaceutical compositions may also comprise an anti-foaming anti-whitening agent that increases the elegancy of the cream or lotion and inhibits the formation of a white soapy look upon rubbing the cream or lotion on the skin. An example of such material includes silicone fluid. Other anti-foaming agents include simethicone, polyglycol, and sorbitan sesquioleate.

The topical pharmaceutical compositions may also comprise a post-foaming agent. "Post-foaming" refers to a gel that remains a gel as it is expelled from a container but foams up after it is spread over the skin. Post-foaming agents include saturated aliphatic hydrocarbons having from 4-6 carbon atoms, such as butane, pentane and hexane (in particular is opentane and isobutene). Other suitable post-foaming agents include partially, or wholly halogenated hydrocarbons, such as trichlorofluroethane. Also, mixtures of aliphatic and halogenated hydrocarbon propellants, or post-foaming agents can be used. Generally suitable post-foaming agents are those substances that have a low solubility in water, for example less than about 20 cc of gas in 100 grams of water at one atmosphere and 20.degree. C.

The topical pharmaceutical compositions may also comprise one or more suitable solvents. The ability of any solid substance (solute) to dissolve in any liquid substance (solvent) is dependent upon the physical properties of the solute and the solvent. When solutes and solvents have similar physical properties the solubility of the solute in the solvent will be the greatest. This gives rise to the traditional understanding that "like dissolves like." Solvents can be characterized in one extreme as non-polar, lipophilic oils, while in the other extreme as polar hydrophilic solvents. Oily solvents dissolve other non-polar substances by Van der Wals interactions while water and other hydrophilic solvents dissolve polar substances by ionic, dipole, or hydrogen bonding interactions. All solvents can be listed along a continuum from the least polar, i.e. hydrocarbons such as decane, to the most polar solvent being water. A solute will have its greatest solubility in solvents having equivalent polarity. Thus, for drugs having minimal solubility in water, less polar solvents will provide improved solubility with the solvent having polarity nearly equivalent to the solute providing maximum solubility. Most drugs have intermediate polarity, and thus experience maximum solubility in solvents such as propylene glycol or ethanol, which are significantly less polar than water. If the drug has greater solubility in propylene glycol (for example 8% (w/w)) than in water (for example 0.1% (w/w)), then addition of water to propylene glycol should decrease the maximum amount of drug solubility for the solvent mixture compared with pure propylene glycol. Addition of a poor solvent to an excellent solvent will decrease the maximum solubility for the blend compared with the maximum solubility in the excellent solvent.

When compounds are incorporated into topical formulations the concentration of active ingredient in the formulation may be limited by the solubility of the active ingredient in the chosen solvent and/or carrier. Non-lipophilic drugs typically display very low solubility in pharmaceutically acceptable solvents and/or carriers. For example, the solubility of some compounds in the invention in water is less than 0.00025% wt/wt. The solubility of the same compounds in the invention can be less than about 2% wt/wt in either propylene glycol or isopropyl myristate.

Examples of solubilizing excipients include polyethoxylated fatty acids, PEG-fatty acid diesters, PEG-fatty acid mono-ester and di-ester mixtures, polyethylene glycol glycerol fatty acid esters, alcohol-oil transesterification products, polyglycerized fatty acids, propylene glycol fatty acid esters, mixtures of propylene glycol esters-glycerol esters, mono- and diglycerides, sterol and sterol derivatives, polyethylene glycol sorbitan fatty acid esters, polyethylene glycol alkyl ethers, sugar esters, polyethylene glycol alkyl phenols, polyoxyethylene-polyoxypropylene block copolymers, sorbitan fatty acid esters, lower alcohol fatty acid esters, ionic surfactants, tocopherol esters, and sterol esters. In one embodiment of the present invention, ethylhexyl hydroxystearate is the solvent used to dissolve the compounds described herein. In one embodiment of the present invention, diethylene glycol monoethyl ether (DGME) is the solvent used to dissolve the compounds described herein. In one embodiment of the present invention, diethylene glycol monoethyl ether (DGME) is the solvent used to dissolve a compound of the invention. The compounds in the invention useful in the present formulation are believed to have a solubility of from about 10% wt/wt to about 25% wt/wt in DGME. In another embodiment a DGME water cosolvent system is used to dissolve the compounds described herein. In another embodiment a DGME water cosolvent system is used to dissolve a compound of the invention. The solvent capacity of DGME drops when water is added; however, the DGME/water cosolvent system can be designed to maintain the desired concentration of from about 0.1% to about 5% wt/wt active ingredient. Preferably the active ingredient is present from about 0.5% to about 3% wt/wt, and more preferably at about 1% wt/wt, in the as-applied topical formulations. Because DGME is less volatile than water, as the topical formulation evaporates upon application, the active agent becomes more soluble in the cream formulation. This increased solubility reduces the likelihood of reduced bioavailability caused by the drug precipitating on the surface of the skin, nail, hair, claw or hoof.

In one embodiment, the vehicle is lipophilic. Lipophilic materials include oleaginous material such as petrolatum, mineral oil thickened or gelled with polyethylene, high molecular weight paraffin waxes, mono and diglycerides of fatty acids gelled with high molecular weight fatty acids or polyamide complex of hydroxystearate, propylene glycol isostearate or isostearyl alcohol gelled with high molecular weight fatty acids, and mixtures thereof.

Liquid forms, such as lotions suitable for topical administration or suitable for cosmetic application, may include a suitable aqueous or nonaqueous vehicle with buffers, suspending and dispensing agents, thickeners, penetration enhancers, and the like. Solid forms such as creams or pastes or the like may include, for example, any of the following ingredients, water, oil, alcohol or grease as a substrate with surfactant, polymers such as polyethylene glycol, thickeners, solids and the like. Liquid or solid formulations may include enhanced delivery technologies such as liposomes, microsomes, microsponges and the like. Liposomal formulations, which help allow compounds to enter the skin, are described in U.S. Pat. Nos. 5,169,637; 5,000,958; 5,049,388; 4,975,282; 5,194,266; 5,023,087; 5,688,525; 5,874,104; 5,409,704; 5,552,155; 5,356,633; 5,032,582; 4,994,213; and PCT Publication No. WO 96/40061.

Additionally, the compounds can be delivered using a sustained-release system, such as semipermeable matrices of solid hydrophobic polymers containing the therapeutic agent. Various sustained-release materials have been established and are well known by those skilled in the art. Thus, at least two different dosage forms, each of which contains a compound of the invention, may be formulated for topical administration by including such dosage forms in an oil-in-water emulsion, or a water-in-oil emulsion. In such a formulation, the delayed release dosage forms are in the continuous phase, and the delayed sustained release dosage form is in a discontinuous phase. The formulation may also be produced in a manner for delivery of three dosage forms as hereinabove described. For example, there may be provided an oil-in-water-in-oil emulsion, with oil being a continuous phase that contains the third delayed sustained release component, water dispersed in the oil containing a first delayed release dosage form, and oil dispersed in the water containing a second delayed release dosage form.

Topical treatment regimens according to the practice of this invention comprise applying the composition directly to the skin, nail, hair, claw or hoof at the application site, from one to several times daily.

Formulations of the present invention can be used to treat, ameliorate or prevent conditions or symptoms associated with bacterial infections, acne, inflammation and the like.

In an exemplary embodiment, the pharmaceutical formulation includes a simple solution. In an exemplary embodiment, the simple solution includes a polyether. In an exemplary embodiment, the polyether is polyethylene glycol or polypropylene glycol. In an exemplary embodiment, the simple solution includes an alcohol. In an exemplary embodiment, the alcohol is methanol, ethanol, propanol, isopropanol or butanol. In an exemplary embodiment, the simple solution includes a polyether and an alcohol. In another exemplary embodiment, the simple solution includes a polypropylene glycol and ethanol. In another exemplary embodiment, the simple solution is a member selected from about 10% polypropylene glycol and about 90% ethanol; about 20% polypropylene glycol and about 80% ethanol; about 30% polypropylene glycol and about 70% ethanol; about 40% polypropylene glycol and about 60% ethanol; about 50% polypropylene glycol and about 50% ethanol; about 60% polypropylene glycol and about 40% ethanol; about 70% polypropylene glycol and about 30% ethanol; about 80% polypropylene glycol and about 20% ethanol; about 90% polypropylene glycol and about 10% ethanol.

In an exemplary embodiment, the simple solution includes acetone. In an exemplary embodiment, the simple solution includes acetone and an alcohol. In an exemplary embodiment, the simple solution includes acetone and a member selected from methanol, ethanol, propanol, isopropanol or butanol. In an exemplary embodiment, the simple solution includes acetone, an alcohol and a polyether. In another exemplary embodiment, the simple solution includes acetone, an alcohol and a member selected from polyethylene glycol and polypropylene glycol. In an exemplary embodiment, the simple solution includes acetone and ethanol. In another exemplary embodiment, the simple solution is a member selected from about 10% acetone and about 90% ethanol; about 20% acetone and about 80% ethanol; about 30% acetone and about 70% ethanol; about 40% acetone and about 60% ethanol; about 50% acetone and about 50% ethanol; about 60% acetone and about 40% ethanol; about 70% acetone and about 30% ethanol; about 80% acetone and about 20% ethanol; about 90% acetone and about 10% ethanol.

In an exemplary embodiment, the pharmaceutical formulation is a lacquer.

V. b) Additional Active Agents

The following are examples of the cosmetic and pharmaceutical agents that can be added to the topical pharmaceutical formulations of the present invention. The following agents are known compounds and are readily available commercially.

Anti-inflammatory agents include, but are not limited to, bisabolol, mentholatum, dapsone, aloe, hydrocortisone, and the like.

Vitamins include, but are not limited to, Vitamin B, Vitamin E, Vitamin A, Vitamin D, and the like and vitamin derivatives such as tazarotene, calcipotriene, tretinoin, adapalene and the like.

Anti-aging agents include, but are not limited to, niacinamide, retinol and retinoid derivatives, AHA, Ascorbic acid, lipoic acid, coenzyme Q 10, beta hydroxy acids, salicylic acid, copper binding peptides, dimethylaminoethyl (DAEA), and the like.

Sunscreens and or sunburn relief agents include, but are not limited to, PABA, jojoba, aloe, padimate-O, methoxycinnamates, proxamine HCl, lidocaine and the like. Sunless tanning agents include, but are not limited to, dihydroxyacetone (DHA). Ultraviolet (UV) light blockers include, for example, amino benzoic acids, benzophenones, camphors, cinnamates, dibenzoyl methanes, salicylates, metal oxides, and mixtures thereof.

Psoriasis-treating agents and/or acne-treating agents include, but are not limited to, salicylic acid, benzoyl peroxide, coal tar, selenium sulfide, zinc oxide, pyrithione (zinc and/or sodium), tazarotene, calcipotriene, tretinoin, adapalene and the like.

Agents that are effective to control or modify keratinization, including without limitation: tretinoin, tazarotene, and adapalene.

The compositions comprising an compound/active agent described herein, and optionally at least one of these additional agents, are to be administered topically. In a primary application, this leads to the compounds of the invention and any other active agent working upon and treating the skin, nail, hair, claw or hoof Alternatively, any one of the topically applied active agents may also be delivered systemically by transdermal routes.

In such compositions an additional cosmetically or pharmaceutically effective agent, such as an anti-inflammatory agent, vitamin, anti-aging agent, sunscreen, and/or acne-treating agent, for example, is usually a minor component (from about 0.001% to about 20% by weight or preferably from about 0.01% to about 10% by weight) with the remainder being various vehicles or carriers and processing aids helpful for forming the desired dosing form.

V. c) Testing

Preferred compounds for use in the present topical formulations will have certain pharmacological properties. Such properties include, but are not limited to, low toxicity, low serum protein binding and desirable in vitro and in vivo half-lives. Assays may be used to predict these desirable pharmacological properties. Assays used to predict bioavailability include transport across human intestinal cell monolayers, including Caco-2 cell monolayers. Serum protein binding may be predicted from albumin binding assays. Such assays are described in a review by Oravcova et al. (1996, *J. Chromat. B*677: 1-27). Compound half-life is inversely proportional to the frequency of dosage of a compound. In vitro half-lives of compounds may be predicted from assays of microsomal half-life as described by Kuhnz and Gleschen (Drug Metabolism and Disposition, (1998) volume 26, pages 1120-1127).

Toxicity and therapeutic efficacy of such compounds can be determined by standard pharmaceutical procedures in cell cultures or experimental animals, e.g., for determining the LD50 (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds that exhibit high therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. The exact formulation, route of administration and dosage can be chosen by the individual physician in view of the patient's condition. (See, e.g. Fingl et al., 1975, in "The Pharmacological Basis of Therapeutics", Ch. 1, p. 1).

V. d) Administration

For any compound used in the method of the invention, the therapeutically effective dose can be estimated initially from cell culture assays, as disclosed herein. For example, a dose can be formulated in animal models to achieve a circulating concentration range that includes the $EC_{50}$ (effective dose for 50% increase) as determined in cell culture, i.e., the concentration of the test compound which achieves a half-maximal inhibition of bacterial cell growth. Such information can be used to more accurately determine useful doses in humans.

In general, the compounds prepared by the methods, and from the intermediates, described herein will be administered in a therapeutically or cosmetically effective amount by any of the accepted modes of administration for agents that serve similar utilities. It will be understood, however, that the specific dose level for any particular patient will depend upon a variety of factors including the activity of the specific compound employed, the age, body weight, general health, sex, diet, time of administration, route of administration, and rate of excretion, drug combination, the severity of the particular disease undergoing therapy and the judgment of the prescribing physician. The drug can be administered from once or twice a day, or up to 3 or 4 times a day.

Dosage amount and interval can be adjusted individually to provide plasma levels of the active moiety that are sufficient to maintain bacterial cell growth inhibitory effects. Usual patient dosages for systemic administration range from 0.1 to 1000 mg/day, preferably, 1-500 mg/day, more preferably 10-200 mg/day, even more preferably 100-200 mg/day. Stated in terms of patient body surface areas, usual dosages range from 50-91 mg/m²/day.

The amount of the compound in a formulation can vary within the full range employed by those skilled in the art. Typically, the formulation will contain, on a weight percent (wt %) basis, from about 0.01-10 wt % of the drug based on the total formulation, with the balance being one or more suitable pharmaceutical excipients. Preferably, the compound is present at a level of about 0.1-3.0 wt %, more preferably, about 1.0 wt %.

In an exemplary embodiment, the pharmaceutical formulation is an ointment, and comprises a compound of the invention. In an exemplary embodiment, the pharmaceutical formulation is an ointment which includes C17. In an exemplary embodiment, the pharmaceutical formulation is an ointment which includes C27.

In another exemplary embodiment, the pharmaceutical formulation includes C17 and at least one surfactant described herein. In another exemplary embodiment, the pharmaceutical formulation includes C27 and at least one surfactant described herein. In another exemplary embodiment, the formulation comprises a hydroxystearate. In another exemplary embodiment, the hydroxystearate is a member selected from glyceryl monostearate, ethylhexyl hydroxystearate and octyl hydroxystearate.

In another exemplary embodiment, the pharmaceutical formulation includes C17 and an alcohol. In another exemplary embodiment, the pharmaceutical formulation includes C27 and an alcohol. In another exemplary embodiment, the alcohol is a long chain alcohol or a fatty alcohol. In another exemplary embodiment, the alcohol is a member selected from benzyl alcohol, octyldodecanol, stearyl alcohol, cetyl alcohol, oleyl alcohol. In an exemplary embodiment, the formulation comprises a member selected from benzyl alcohol, octyl comprises at least one compound which is a member selected from hydrocarbon oils, waxes, silicone, cetyl alcohol, isopropyl myristate, stearyl alcohol, oleyl alcohol, ethylhexyl hydroxystearate, octyl hydroxystearate, glycerin, other fatty alcohols hydroxystearate.

In another exemplary embodiment, the pharmaceutical formulation comprises a compound of the invention and at least one emollient described herein.

In another exemplary embodiment, the pharmaceutical formulation includes a compound of the invention, and petrolatum.

In an exemplary embodiment, the pharmaceutical formulation comprises C17 and petrolatum. In an exemplary embodiment, the pharmaceutical formulation comprises C27 and petrolatum. In an exemplary embodiment, the pharmaceutical formulation comprises C17 and a member selected from hydrocarbon oils, waxes, silicone, cetyl alcohol, isopropyl myristate, stearyl alcohol, oleyl alcohol, ethylhexyl hydroxystearate, octyl hydroxystearate, glycerin, other fatty alcohols hydroxystearate. In an exemplary embodiment, the pharmaceutical formulation comprises C27 and a member selected from hydrocarbon oils, waxes, silicone, cetyl alcohol, isopropyl myristate, stearyl alcohol, oleyl alcohol, ethylhexyl hydroxystearate, octyl hydroxystearate, glycerin, other fatty alcohols hydroxystearate. In an exemplary embodiment, the pharmaceutical formulation comprises C17 and ethylhexyl hydroxystearate and/or octyl hydroxystearate. In an exemplary embodiment, the pharmaceutical formulation comprises C27 and ethylhexyl hydroxystearate and/or octyl hydroxystearate. In an exemplary embodiment, the pharmaceutical formulation comprises C17, petrolatum and a member selected from hydrocarbon oils, waxes, silicone, cetyl alcohol, isopropyl myristate, stearyl alcohol, oleyl alcohol, ethylhexyl hydroxystearate, octyl hydroxystearate, glycerin, other fatty alcohols hydroxystearate. In an exemplary embodiment, the pharmaceutical formulation comprises C27, petrolatum and a member selected from hydrocarbon oils, waxes, silicone, cetyl alcohol, isopropyl myristate, stearyl alcohol, oleyl alcohol, ethylhexyl hydroxystearate, octyl hydroxystearate, glycerin, other fatty alcohols hydroxystearate. In an exemplary embodiment, the pharmaceutical formulation comprises C17, petrolatum, oleyl alcohol and ethylhexyl hydroxystearate. In an exemplary embodiment, the pharmaceutical formulation comprises C27, petrolatum, oleyl alcohol and ethylhexyl hydroxystearate.

In an exemplary embodiment, the pharmaceutical formulation is a cream, and comprises a compound of the invention. In an exemplary embodiment, the compound is C17. In an exemplary embodiment, the compound is C27.

In another exemplary embodiment, the pharmaceutical formulation comprises a compound of the invention and a preservative. In an exemplary embodiment, the preservative is a member selected from benzalkonium chloride, benzethonium, chlorohexidine, phenol, m-cresol, benzyl alcohol, methylparaben, propylparaben and other parabens, chlorobutanol, o-cresol, p-cresol, chlorocresol, phenylmercuric nitrate, thimerosal, benzoic acid, and various mixtures thereof. In an exemplary embodiment, the compound is C17. In an exemplary embodiment, the compound is C27. In an exemplary embodiment, the perservative is a paraben. In an exemplary embodiment, the perservative is a member selected from methyl paraben and propyl paraben.

In another exemplary embodiment, the pharmaceutical formulation comprises a compound of the invention and a chelating agent. In another exemplary embodiment, the pharmaceutical formulation comprises C17 and a chelating agent.

In another exemplary embodiment, the pharmaceutical formulation comprises C27 and a chelating agent. In an exemplary embodiment, the chelating agent is edetate sodium.

Exemplary embodiments are summarized herein below.

In an exemplary embodiment, the invention provides a compound having a structure according to the formula:

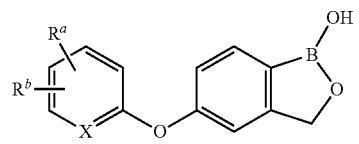

wherein $R^a$ is a member selected from CN, $C(O)NR^1R^2$, $C(O)OR^3$; wherein $R^3$ is a member selected from H and substituted or unsubstituted alkyl, X is a member selected from N, CH and $CR^b$, $R^b$ is a member selected from halogen and substituted or unsubstituted alkyl, $C(O)R^4$, $C(O)OR^4$, $OR^4$, $NR^4R^5$, wherein R', $R^2$, $R^4$ and $R^5$ are members independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, with the proviso that $R^1$ and $R^2$, together with the atoms to which they are attached, are optionally combined to form a 4- to 8-membered substituted or unsubstituted heterocycloalkyl ring; with the proviso that $R^4$ and $R^5$, together with the atoms to which they are attached, are optionally combined to form a 4- to 8-membered substituted or unsubstituted heterocycloalkyl ring, and salts thereof.

In an exemplary embodiment, according to the above paragraph, $R^3$ is a member selected from H and unsubstituted alkyl.

In an exemplary embodiment, according to any of the above paragraphs, the compound has a structure according to the formula:

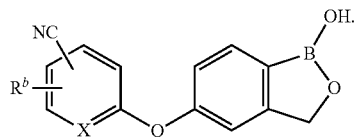

In an exemplary embodiment, according to any of the above paragraphs, the compound has a formula which is a member selected from:

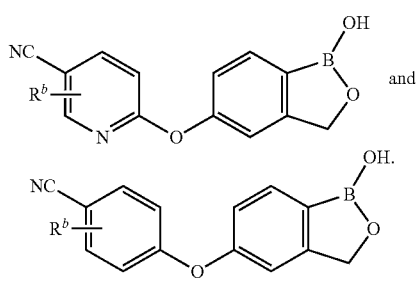

In an exemplary embodiment, according to any of the above paragraphs, the compound has a formula which is a member selected from:

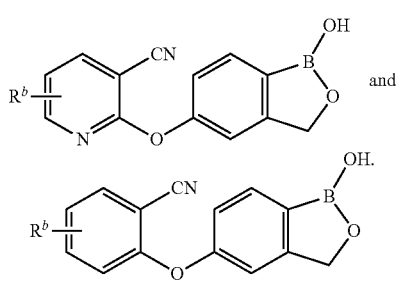

In an exemplary embodiment, according to any of the above paragraphs, the compound has a formula which is a member selected from:

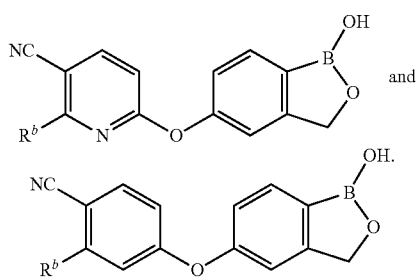

In an exemplary embodiment, according to any of the above paragraphs, the compound has a formula which is a member selected from:

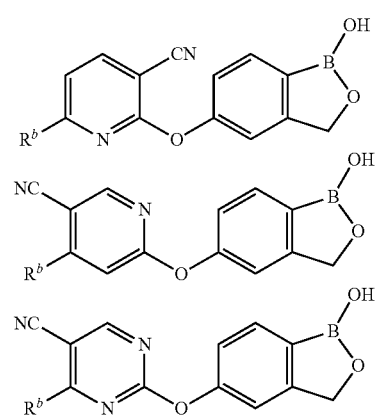

-continued

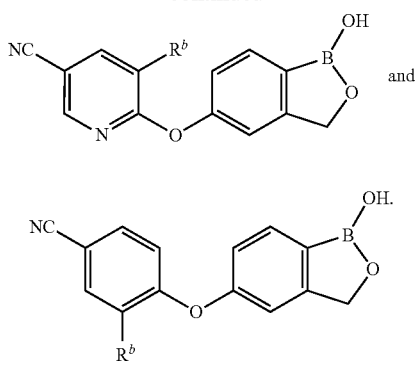

In an exemplary embodiment, according to any of the above paragraphs, the compound has a structure according to the formula:

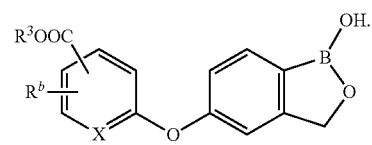

In an exemplary embodiment, according to any of the above paragraphs, the compound has a formula which is a member selected from:

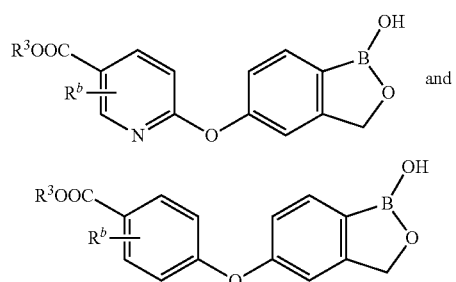

In an exemplary embodiment, according to any of the above paragraphs, the compound has a formula which is a member selected from:

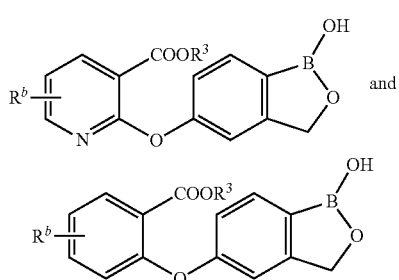

In an exemplary embodiment, according to any of the above paragraphs, the compound has a formula which is a member selected from:

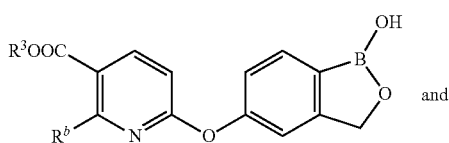

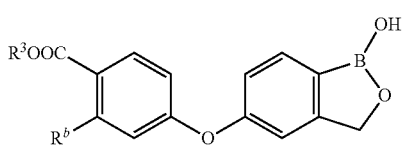

In an exemplary embodiment, according to any of the above paragraphs, the compound has a formula which is a member selected from:

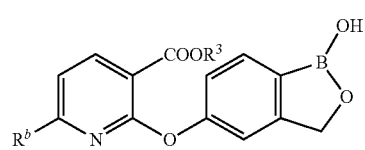

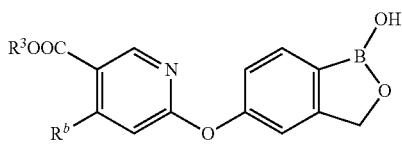

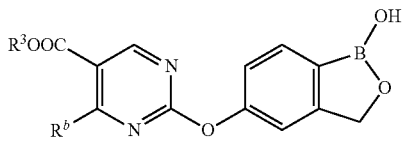

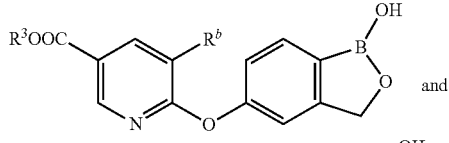

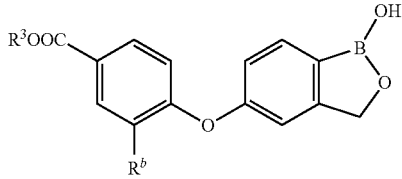

In an exemplary embodiment, according to any of the above paragraphs, the compound has a structure according to the formula:

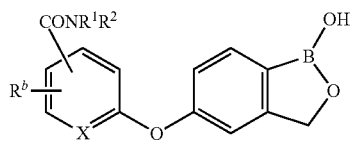

the compound has a formula which is a member selected from:

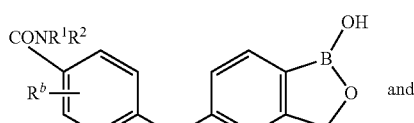

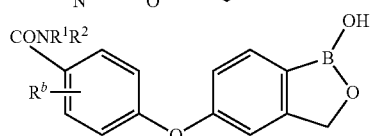

In an exemplary embodiment, according to any of the above paragraphs, the compound has a formula which is a member selected from:

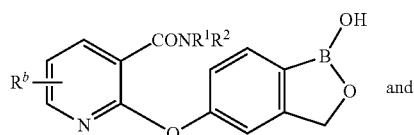

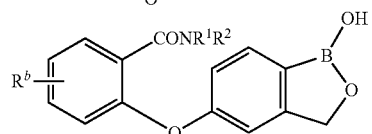

In an exemplary embodiment, according to any of the above paragraphs, the compound has a formula which is a member selected from:

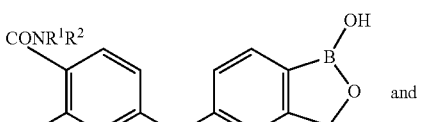

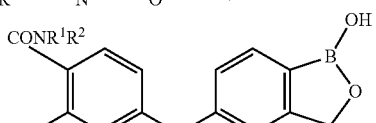

In an exemplary embodiment, according to any of the above paragraphs, the compound has a formula which is a member selected from:

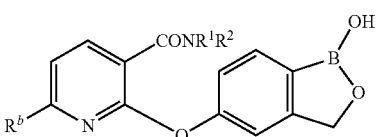

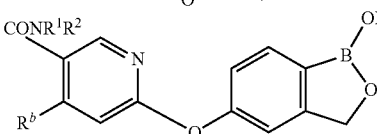

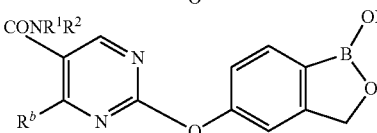

-continued

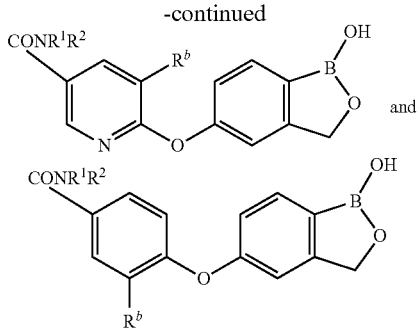

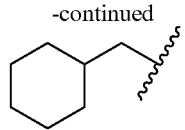

In an exemplary embodiment, according to any of the above paragraphs, $R^b$ is a member selected from fluorine and chlorine.

In an exemplary embodiment, according to any of the above paragraphs, $R^b$ is a member selected from $OR^4$ and $NR^4R^5$.

In an exemplary embodiment, according to any of the above paragraphs, $R^b$ is $OR^4$, and $R^4$ is a member selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In an exemplary embodiment, according to any of the above paragraphs, $R^b$ is $OR^4$, and $R^4$ is a member selected from H, substituted or unsubstituted alkyl, substituted or unsubstituted heteroalkyl and substituted or unsubstituted cycloalkyl.

In an exemplary embodiment, according to any of the above paragraphs, $R^b$ is $OR^4$, and $R^4$ is unsubstituted $C_1$-$C_6$ alkyl.

In an exemplary embodiment, according to any of the above paragraphs, $R^b$ is $OR^4$, and $R^4$ is unsubstituted cycloalkyl.

In an exemplary embodiment, according to any of the above paragraphs, $R^b$ is $OR^4$, and $R^4$ is alkyl, substituted with a member selected from substituted or unsubstituted $C_1$-$C_6$ alkoxy.

In an exemplary embodiment, according to any of the above paragraphs, $R^b$ is $OR^4$, and $R^4$ is alkyl, substituted with at least one halogen.

In an exemplary embodiment, according to any of the above paragraphs, $R^b$ is $OR^4$, and $R^4$ is alkyl, substituted with at least one oxo moiety.

In an exemplary embodiment, according to any of the above paragraphs, $R^b$ is $OR^4$, and $R^4$ is a member selected from —$CH_3$, —$CH_2CH_3$, —$(CH_2)_2CH_3$, —$CH(CH_3)_2$, —$CH_2CF_3$, —$CH_2CHF_2$, —$CH_2CH_2(OH)$, —$CH_2CH_2(OCH_3)$, —$CH_2CH_2(OC(CH_3)_2)$, —$C(O)CH_3$, —$CH_2CH_2OC(O)CH_3$, —$CH_2C(O)OCH_2CH_3$, —$CH_2C(O)OC(CH_3)_3$, —$(CH_2)_3C(O)CH_3$, —$CH_2C(O)OC(CH_3)_3$, cyclopentyl, cyclohexyl

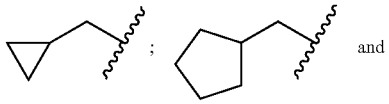

-continued

In an exemplary embodiment, according to any of the above paragraphs, $R^b$ is $OR^4$, wherein $R^4$ is alkyl is optionally substituted with at least one halogen, hydroxyl, ether, carboxy or ester moiety.

In an exemplary embodiment, according to any of the above paragraphs, $R^b$ is $OR^4$, wherein $R^4$ is unsubstituted alkyl.

In an exemplary embodiment, according to any of the above paragraphs, $R^b$ is $OR^4$, wherein $R^4$ is unsubstituted $C_1$ or $C_2$ or $C_3$ alkyl.

In an exemplary embodiment, according to any of the above paragraphs, $R^b$ is $OR^4$, wherein $R^4$ is unsubstituted $C_4$ or $C_5$ or $C_6$ alkyl.

In an exemplary embodiment, according to any of the above paragraphs, $R^b$ is $OR^4$, wherein $R^4$ is methyl or ethyl or propyl or isopropyl or isobutyl.

In an exemplary embodiment, according to any of the above paragraphs, $R^b$ is —$O(CH_2)_{m1}OC(O)R^{4d}$, wherein m1 is a number selected from 1 or 2 or 3 or 4 or 5 or 6 and $R^{4d}$ is unsubstituted alkyl. In an exemplary embodiment, m1 is 1 or 2 or 3. In an exemplary embodiment, m1 is 2. In an exemplary embodiment, $R^{4d}$ is unsubstituted $C_1$ or $C_2$ or $C_3$ alkyl. In an exemplary embodiment, $R^{4d}$ is unsubstituted $C_4$ or $C_5$ or $C_6$ alkyl. In an exemplary embodiment, $R^{4d}$ is methyl. In an exemplary embodiment, $R^b$ is —$O(CH_2)_2OC(O)CH_3$.

In an exemplary embodiment, according to any of the above paragraphs, $R^b$ is —$O(CH_2)_{m1}C(O)R^{4d}$, wherein m1 is a number selected from 1 or 2 or 3 or 4 or 5 or 6 and $R^{4d}$ is unsubstituted alkyl. In an exemplary embodiment, m1 is 2 or 3 or 4. In an exemplary embodiment, m1 is 3. In an exemplary embodiment, $R^{4d}$ is unsubstituted $C_1$ or $C_2$ or $C_3$ alkyl. In an exemplary embodiment, $R^{4d}$ is unsubstituted $C_4$ or $C_5$ or $C_6$ alkyl. In an exemplary embodiment, $R^{4d}$ is methyl. In an exemplary embodiment, $R^b$ is —$O(CH_2)_3C(O)CH_3$.

In an exemplary embodiment, according to any of the above paragraphs, $R^b$ is —$O(CH_2)_{m1}C(O)OR^{4d}$, wherein m1 is a number selected from 1 or 2 or 3 or 4 or 5 or 6 and $R^{4d}$ is H or unsubstituted alkyl.

In an exemplary embodiment, according to any of the above paragraphs, $R^b$ is —$OCH_2C(O)OR^{4d}$, wherein $R^{4d}$ is as described herein.

In an exemplary embodiment, according to any of the above paragraphs, $R^{4d}$ is H or methyl or ethyl or t-butyl.

In an exemplary embodiment, according to any of the above paragraphs, $R^b$ is —$O(CH_2)C(O)OCH_2CH_3$ or —$O(CH_2)C(O)OH$ or —$O(CH_2)C(O)OC(CH_3)_3$.

In an exemplary embodiment, according to any of the above paragraphs, $R^b$ is $OR^4$, wherein $R^4$ is alkyl substituted with a substituted or unsubstituted amino.

In an exemplary embodiment, according to any of the above paragraphs, $R^b$ is —$O(CH_2)_{m2}C(O)NR^{4e}R^{4f}$, wherein m2 is a number selected from 1 or 2 or 3 or 4 or 5 or 6, and $R^{4e}$ and $R^{4f}$ are independently selected from H or unsubstituted alkyl, or $R^{4e}$ and $R^{4f}$, together with the nitrogen to which they are attached, are optionally joined to form a substituted or unsubstituted 4 to 8 membered ring.

In an exemplary embodiment, according to any of the above paragraphs, $R^b$ is $OR^4$, wherein $R^4$ is substituted or unsubstituted cycloalkyl.

In an exemplary embodiment, according to any of the above paragraphs, $R^b$ is $OR^4$, wherein $R^4$ is unsubstituted cycloalkyl.

In an exemplary embodiment, according to any of the above paragraphs, $R^b$ is $—O(CH_2)_{m5}OR^{30}$, wherein m5 is 1 or 2 or 3 or 4 or 5 or 6 and $R^{30}$ is H or unsubstituted alkyl or unsubstituted tetrahydropyran.

In an exemplary embodiment, according to any of the above paragraphs, X is N.

In an exemplary embodiment, according to any of the above paragraphs, X is CH.

In an exemplary embodiment, according to any of the above paragraphs, X is $CR^b$.

In an exemplary embodiment, according to any of the above paragraphs, $R^b$ is $NR^4R^5$, wherein $R^4$ and $R^5$ are members independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In an exemplary embodiment, according to any of the above paragraphs, $R^b$ is $NR^4R^5$, wherein $R^4$ is H or unsubstituted alkyl; and $R^5$ is unsubstituted alkyl or alkyl substituted with a member selected from hydroxyl, phenyl, unsubstituted alkoxy and alkoxy substituted with a phenyl.

In an exemplary embodiment, according to any of the above paragraphs, $R^b$ is $NR^4R^5$.

In an exemplary embodiment, according to any of the above paragraphs, $R^4$ is a member selected from H or $CH_3$.

In an exemplary embodiment, according to any of the above paragraphs, $R^b$ is $NR^4R^5$ wherein $R^4$ and $R^5$ are each members independently selected from substituted or unsubstituted alkyl.

In an exemplary embodiment, according to any of the above paragraphs, $R^b$ is $NR^4R^5$, wherein $R^5$ is alkyl, substituted with a member selected from OH, unsubstituted arylalkoxy, unsubstituted alkoxy, and unsubstituted aryl. In an exemplary embodiment, $R^b$ is $NR^4R^5$, wherein $R^5$ is $—(CH_2)_{m8}Ph$.

In an exemplary embodiment, according to any of the above paragraphs, $R^b$ is $NR^4R^5$, wherein $R^5$ is $—(CH_2)_{m8}OR^{26}$, wherein m8 is a number selected from 1 or 2 or 3 or 4 or 5 or 6 and $R^{26}$ is a member selected from H, unsubstituted or arylsubstituted $C_1$ or $C_2$ or $C_3$ or $C_4$ or $C_5$ or $C_6$ alkyl.

In an exemplary embodiment, according to any of the above paragraphs, $R^b$ is $NR^4R^5$, wherein $R^5$ is $—(CH_2)_{m8}O(CH_2)_{m9}Ph$, wherein m8 and m9 are each independently selected from 1 or 2 or 3.

In an exemplary embodiment, according to any of the above paragraphs, $R^b$ is $NR^4R^5$, wherein $R^4$ is unsubstituted alkyl; and $R^5$ is substituted or unsubstituted alkyl.

In an exemplary embodiment, according to any of the above paragraphs, $R^b$ is $NR^4R^5$, wherein $R^4$ is unsubstituted alkyl; and $R^5$ is alkyl, substituted with a member selected from substituted or unsubstituted alkoxy and hydroxyl.

In an exemplary embodiment, according to any of the above paragraphs, $R^b$ is $NR^4R^5$, wherein $R^4$ is unsubstituted alkyl; and $R^5$ is alkyl, substituted with unsubstituted alkoxy.

In an exemplary embodiment, according to any of the above paragraphs, $R^b$ is a member selected from $N(CH_3)_2$, $N(CH_3)(CH_2CH_2(OCH_3))$, $N(CH_3)(CH_2CH_2OH)$, $NH_2$, $NHCH_3$, $NH(CH_2CH_2(OCH_3))$, $NH(CH_2CH_2(OCH_2Ph))$, $NH(CH_2Ph)$, $NH(C(CH_3)_3)$ and $NH(CH_2CH_2OH)$.

In an exemplary embodiment, according to any of the above paragraphs, $R^b$ is $NR^4R^5$, wherein $R^4$ and $R^5$, together with the nitrogen to which they are attached, are combined to form a 4- to 8-membered substituted or unsubstituted heterocycloalkyl ring.

In an exemplary embodiment, according to any of the above paragraphs, $R^b$ is $NR^4R^5$, wherein $R^4$ and $R^5$, together with the nitrogen to which they are attached, are combined to form a 5- or 6-membered substituted or unsubstituted heterocycloalkyl ring.

In an exemplary embodiment, according to any of the above paragraphs, $R^b$ is a member selected from:

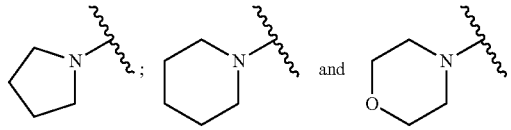

In an exemplary embodiment, the invention provides a pharmaceutical formulation comprising: (a) a compound according to any of the above paragraphs; and (b) a pharmaceutically acceptable excipient.

In an exemplary embodiment, according to any of the above paragraphs, the formulation is in a unit dosage form.

In an exemplary embodiment, according to any of the above paragraphs, the formulation is for oral or topical use.

In an exemplary embodiment, the invention provides a method of decreasing the release of a cytokine or a chemokine, the method comprising: contacting a cell with a compound according to any of the above paragraphs or a pharmaceutically acceptable salt thereof, wherein the release of the cytokine or chemokine by the cell is decreased.

In an exemplary embodiment, according to any of the above paragraphs, the cytokine is a member selected from IL-1α, IL-1β, IL-2, IL-3, IL-6, IL-7, IL-9, IL-12, IL-17, IL-18, IL-23, TNF-α, LT, LIF, Oncostatin, IFNα, IFNβ and IFN-γ.

In an exemplary embodiment, according to any of the above paragraphs, the cytokine is a member selected from IL-1β, IL-2, IL-4, IL-5, IL-6, IL-8, IL-1β, IL-12, IL-23, TNF-α and IFN-γ.

In an exemplary embodiment, according to any of the above paragraphs, the cytokine is a member selected from IL-2, IL-5, IL-1β, IL-12, IL-23, TNF-α and IFN-γ.

In an exemplary embodiment, according to any of the above paragraphs, the chemokine is a member selected from IL-8, Gro-α, MIP-1, MCP-1, PGE2, ENA-78, and RANTES.

In an exemplary embodiment, the invention provides a method of treating a condition, in an animal, the method comprising administering to the animal a therapeutically effective amount of a compound according to any of the above paragraphs, or a pharmaceutically acceptable salt thereof, thereby treating the condition.

In an exemplary embodiment, according to any of the above paragraphs, the condition is a member selected from arthritis, rheumatoid arthritis, an inflammatory bowel disease, psoriasis, a pulmonary disease, multiple sclerosis, a neurodegenerative disorder, congestive heart failure, stroke, aortic valve stenosis, kidney failure, lupus, pancreatitis, allergy, fibrosis, anemia, atherosclerosis, a metabolic disease, a bone disease, a cardiovascular disease, a chemotherapy/radiation related complication, diabetes type I, diabetes type II, a liver disease, a gastrointestinal disorder, an ophthamological disease, allergic conjunctivitis, diabetic retinopathy, Sjogren's syndrome, uveitis, a pulmonary disorder, a renal disease, dermatitis, HIV-related cachexia, cerebral malaria, ankylosing spondolytis, leprosy, anemia and fibromyalgia.

In an exemplary embodiment, according to any of the above paragraphs, the condition is a member selected from psoriasis, atopic dermatitis, rheumatoid arthritis, an inflammatory bowel disease, asthma and chronic obstructive pulmonary disease.

In an exemplary embodiment, according to any of the above paragraphs, the condition is psoriasis, said psoriasis is a member selected from plaque psoriasis, flexural psoriasis, Guttate psoriasis, pustular psoriasis, nail psoriasis and erythrodermic psoriasis.

In an exemplary embodiment, according to any of the above paragraphs, the psoriasis is a member selected from plaque psoriasis and nail psoriasis.

In an exemplary embodiment, according to any of the above paragraphs, the animal is a human.

In an exemplary embodiment, according to any of the above paragraphs, the animal is in need of treatment.

In an exemplary embodiment, according to any of the above paragraphs, the animal is a human.

In an exemplary embodiment, according to any of the above paragraphs, the animal is not already in need of treatment by the compound.

In an exemplary embodiment, the invention provides a method of inhibiting a phosphodiesterase (PDE), the method comprising: contacting the phosphodiesterase with a compound according to any of the above paragraphs, or a pharmaceutically acceptable salt thereof, thereby inhibiting the phosphodiesterase.

In an exemplary embodiment, according to any of the above paragraphs, the phosphodiesterase is a member selected from phosphodiesterase4 (PDE4) and phosphodiesterase? (PDE7).

The invention is further illustrated by the Examples that follow. The Examples are not intended to define or limit the scope of the invention.

EXAMPLES

Proton NMR are recorded on Varian AS 300 (300 MHz) or AS400 (400 MHz) spectrometer and chemical shifts are reported as δ (ppm) down field from tetramethylsilane. Mass spectra are determined on Agilent 1200 series plus 6120 Quadrupole LC/MS, Micromass Quattro II or Waters MS consisting of an Alliance 2795 (LC) and Waters Micromass ZQ detector. The mass spectrometer was equipped with an electrospray ion source (ES) operated in a positive or negative mode.

The following abbreviations have been used: aqueous is aq.; O-(7-azabenzotriazol-1-yl)-N,N,N',N'-tetramethyluronium hexafluorophosphate is HATU; N-(3-dimethylaminopropyl)-N'-ethylcarbodiimide hydrochloride m-CPBA3-chloroperoxybenzoic acid is EDCI; equivalent is eq.; diisopropyl azodicarboxylate is DIAD; N,N-dimethylformamide is DMF; dimethylsulfoxide is DMSO; acetic acid is HOAc; sodium cyanoborohydride is NaCNBH$_3$; room temperature is r.t.; overnight is O/N; tetrahydrofuran is THF; Di-tert-butyl dicarbonate is Boc$_2$O; methanol is MeOH; ethanol is EtOH; trifluoroacetic acid is TFA; Diisopropylethylamine is DIPEA; 1-propanol is PrOH; 2-propanol is iPrOH and melting point is mp.

All solvents used were commercially available and were used without further purification. Reactions were typically run using anhydrous solvents under an inert atmosphere of nitrogen.

Compounds are named either manually or by using Chem-Draw, or using their catalogue name if commercially available.

HPLC analyses were performed on a Water 600 Controller system with a Waters 717 Plus Autosampler and a Waters 2996 Photodiode Array Detector. The column used was an ACE C$_{18}$, 5 µm, 4.6×150 mm. A linear gradient was applied, starting at 95% A (A: 0.1% H$_3$PO$_4$ in water) and ending at 90% B (B: MeCN) over 6 min and then maintained at 90% B until the 10 min mark. The column is then re-equilibrated over 3 min to 95:5 with a total run time of 20 min. The column temperature was at ambient temperature with the flow rate of 1.0 mL/min. The Diode Array Detector was scanned from 200-400 nm.

Thin layer chromatography (TLC) was performed on Alugram (Silica gel 60 F$_{254}$) from Mancherey-Nagel and UV was typically used to visualize the spots. Additional visualization methods were also employed in some cases. In these cases the TLC plate was developed with iodine (generated by adding approximately 1 g of I$_2$ to 10 g silica gel and thoroughly mixing), vanillin (generated by dissolving about 1 g vanillin in 100 mL 10% H$_2$SO$_4$), ninhydrin (available commercially from Aldrich), or Magic Stain (generated by thoroughly mixing 25 g (NH$_4$)$_6$Mo$_7$O$_{24}$.4H$_2$O, 5 g (NH$_4$)$_2$Ce(IV)(NO$_3$)$_6$ in 450 mL water and 50 mL concentrated H$_2$SO$_4$) to visualize the compound. Flash chromatography was preformed using typically 40-63 µm (230-400 mesh) silica gel from Silicycle following analogous techniques to those disclosed in Still, W. C.; Kahn, M.; and Mitra, M. Journal of Organic Chemistry, 1978, 43, 2923-2925. Typical solvents used for flash chromatography or thin layer chromatography were mixtures of chloroform/methanol, dichloromethane/methanol, ethyl acetate/methanol and hexanes/ethyl acetate. Reverse phase column chromatography were performed on a Biotage® using a Biotage C$_{18}$ cartridges and a water/methanol gradient (typically eluting from 5% MeOH/H$_2$O to 90% MeOH/H$_2$O).

Preparative chromatography was performed on either a Waters Prep LC 4000 System using a Waters 2487 Diode Array or on a Waters LC Module 1 plus. The column used was a Waters XTerra Prep C$_{18}$, 5 µm, 30×100 mm or Phenomenex Luna C$_{18}$, 5 µm, 21.6×250 mm or Phenomenex Gemini C$_{18}$, 5 µm, 100×30 mm. Narrow gradients with acetonitrile/water, with the water containing either 0.1% trifluoroacetic acid or 0.1% acetic acid, were used to elute the compound at a flow rate of approximately 20 mL/min and a total run time between 20-30 min.

Example 1

Preparation of 3 from 1

1.1 Reduction of Carboxylic Acid

To a solution of 1 (23.3 mmol) in anhydrous THF (70 mL) under nitrogen was added dropwise a BH$_3$ THF solution (1.0 M, 55 mL, 55 mmol) at 0° C. and the reaction mixture was stirred overnight at room temperature. Then the mixture was cooled again with ice bath and MeOH (20 mL) was added dropwise to decompose excess BH$_3$. The resulting mixture was stirred until no bubble was released and then 10% NaOH (10 mL) was added. The mixture was concentrated and the residue was mixed with water (200 mL) and extracted with EtOAc. The residue from rotary evaporation was purified by flash column chromatography over silica gel to give 20.7 mmol of 3.

1.2 Results

Exemplary compounds of structure 3 prepared by the method above include: 1.2.a 2-Bromo-5-chlorobenzyl Alcohol; 1.2.b 2-Bromo-5-methoxybenzyl Alcohol.

Example 2

Preparation of 3 from 2

2.1. Reduction of Aldehyde

To a solution of 2 (Z=H, 10.7 mmol) in methanol (30 mL) was added sodium borohydride (5.40 mol), and the mixture was stirred at room temperature for 1 h. Water was added, and the mixture was extracted with ethyl acetate. The organic layer was washed with brine and dried on anhydrous sodium sulfate. The solvent was removed under reduced pressure to afford 9.9 mmol of 3.

Exemplary compounds of structure 3 prepared by the method include: 2.2.a 2-Bromo-5-(4-cyanophenoxy)benzyl Alcohol; 2.2.b 2-Bromo-4-(4-cyanophenoxy)benzyl Alcohol; 2.2.c 5-(4-Cyanophenoxy)-1-Indanol; 2.2.d 2-Bromo-5-(tert-butyldimethylsiloxy)benzyl Alcohol.

Additional examples of compounds which can be produced by this method include 2-bromo-4-(3-cyanophenoxy) benzyl alcohol; 2-bromo-4-(4-chlorophenoxy)benzyl alcohol; 2-bromo-4-phenoxybenzyl alcohol; 2-bromo-5-(3,4-dicyanophenoxy)benzyl alcohol; 2-(2-bromo-5-fluorophenyl)ethyl alcohol; 2-bromo-5-fluorobenzyl alcohol; and 1-bromo-2-naphthalenemethanol.

Example 3

Preparation of 4 from 3

3.1 Protective Alkylation

Compound 3 (20.7 mmol) was dissolved in $CH_2Cl_2$ (150 mL) and cooled to 0° C. with ice bath. To this solution under nitrogen were added in sequence N,N-diisopropyl ethyl amine (5.4 mL, 31.02 mmol, 1.5 eq) and chloromethyl methyl ether (2 mL, 25.85 mmol, 1.25 eq). The reaction mixture was stirred overnight at room temperature and washed with $NaHCO_3$-saturated water and then NaCl-saturated water. The residue after rotary evaporation was purified by flash column chromatography over silica gel to give 17.6 mmol of 4.

3.2 Results

Exemplary compounds of structure 4 prepared by the method above include: 3.2.a 2-Bromo-5-chloro-1-(methoxymethoxymethyl)benzene; 3.2.b 2-Bromo-5-fluoro-1-[1-(methoxymethoxy)ethyl]benzene; 3.2.c 2-Bromo-5-fluoro-1-[2-(methoxymethoxy)ethyl]benzene; 3.2.d 2-Bromo-4,5-difluoro-1-(methoxymethoxymethyl)benzene; 3.2.e 2-Bromo-5-cyano-1-(methoxymethoxymethyl)benzene; 3.2.f 2-Bromo-5-methoxy-1-(methoxymethoxymethyl)benzene; 3.2.g 1-Benzyl-1-(2-bromophenyl)-1-(methoxymethoxy)ethane; 3.2.h 2-Bromo-6-fluoro-1-(methoxymethoxymethyl)benzene; 3.2.i 2-Bromo-4-(4-cyanophenoxy)-1-(methoxymethoxymethyl)benzene; 3.2.j 2-Bromo-5-(tert-butyldimethylsiloxy)-1-(methoxymethoxymethyl)benzene; 3.2.k 2-Bromo-5-(2-cyanophenoxy)-1-(methoxymethoxymethyl)benzene; 3.2.l 2-Bromo-5-phenoxy-1-(methoxymethoxymethyl)benzene.

Additional examples of compounds which can be produced by this method include 2-bromo-1-(methoxymethoxymethyl)benzene; 2-bromo-5-methyl-1-(methoxymethoxymethyl)benzene; 2-bromo-5-(methoxymethoxymethyl)-1-(methoxymethoxymethyl)benzene; 2-bromo-5-fluoro-1-(methoxymethoxymethyl) benzene; 1-bromo-2-(methoxymethoxymethyl)naphthalene; 2-bromo-4-fluoro-1-(methoxymethoxymethyl)benzene; 2-phenyl-1-(2-bromophenyl)-1-(methoxymethoxy)ethane; 2-bromo-5-(4-cyanophenoxy)-1-(methoxymethoxy methyl) benzene; 2-bromo-4-(3-cyanophenoxy)-1-(methoxymethoxymethyl)benzene; 2-bromo-4-(4-chlorophenoxy)-1-(methoxymethoxymethyl)benzene; 2-bromo-4-phenoxy-1-(methoxymethoxymethyl)benzene; 2-bromo-5-(3,4-dicyanophenoxy)-1-(methoxymethoxymethyl)benzene.

Example 4

Preparation of 1 from 4 via 5

4.1 Metallation and Boronylation

To a solution of 4 (17.3 mmol) in anhydrous THF (80 mL) at −78° C. under nitrogen was added dropwise tert-BuLi or n-BuLi (11.7 mL) and the solution became brown colored. Then, $B(OMe)_3$ (1.93 mL, 17.3 mmol) was injected in one portion and the cooling bath was removed. The mixture was warmed gradually with stirring for 30 min and then stirred with a water bath for 2 h. After addition of 6N HCl (6 mL), the mixture was stirred overnight at room temperature and about 50% hydrolysis has happened as shown by TLC analysis. The solution was rotary evaporated and the residue was dissolved in MeOH (50 mL) and 6N HCl (4 mL). The solution was refluxed for 1 h and the hydrolysis was completed as indicated by TLC analysis. Rotary evaporation gave a residue which was dissolved in EtOAc, washed with water, dried and then evaporated. The crude product was purified by flash column chromatography over silica gel to provide a solid with 80% purity. The solid was further purified by washing with hexane to afford 7.2 mmol of I.

4.2 Results

Analytical data for exemplary compounds of structure I prepared by the method above include: 4.2.a 5-Chloro-1,3-dihydro-1-hydroxy-2,1-benzoxaborole (C1); 4.2.b 1,3-Dihydro-1-hydroxy-2,1-benzoxaborole (C2); 4.2. c 5-Fluoro-1,3-dihydro-1-hydroxy-3-methyl-2,1-benzoxaborole (C3); 4.2.d 6-Fluoro-1-hydroxy-1,2,3,4-tetrahydro-2,1-benzoxaborine (C4); 4.2.e 5,6-Difluoro-1,3-dihydro-1-hydroxy-2,1-benzoxaborole (C5); 4.2.f 5-Cyano-1,3-dihydro-1-hydroxy-2,1-benzoxaborole (C6); 4.2.g 1,3-Dihydro-1-hydroxy-5-methoxy-2,1-benzoxaborole (C7); 4.2.h 1,3-Dihydro-1-hydroxy-5-methyl-2,1-benzoxaborole (C8); 4.2.i 1,3-Dihydro-1-hydroxy-5-hydroxymethyl-2,1-benzoxaborole (C9); 4.2.k 1,3-Dihydro-2-oxa-1-cyclopenta[α]naphthalene (C11); 4.2.l 7-Hydroxy-2,1-oxaborolano[5,4-c]pyridine (C12); 4.2.m 1,3-Dihydro-6-fluoro-1-hydroxy-2,1-benzoxaborole (C13); 4.2.n 3-Benzyl-1,3-dihydro-1-hydroxy-3-methyl-2,1-benzoxaborole (C14); 4.2.o 3-Benzyl-1,3-dihydro-1-hydroxy-2,1-benzoxaborole (C15); 4.2.p 1,3-Dihydro-4-fluoro-1-hydroxy-2,1-benzoxaborole (C16); 4.2.q 5-(4-Cyanophenoxy)-1,3-dihydro-1-hydroxy-2,1-benzoxaborole (C17); 4.2.r 6-(4-Cyanophenoxy)-1,3-dihydro-1-hydroxy-2,1-benzoxaborole (C18); 4.2.s 6-(3-Cyanophenoxy)-1,3-dihydro-1-hydroxy-2,1-benzoxaborole (C19); 4.2.t 6-(4-Chlorophenoxy)-1,3-dihydro-1-hydroxy-2,1-benzoxaborole (C20); 4.2.u 6-Phenoxy-1,3-dihydro-1-hydroxy-2,1-benzoxaborole (C21); 4.2.v 5-(4-Cyanobenzyloxy)-1,3-dihydro-1-hydroxy-2,1-benzoxaborole (C22); 4.2.w 5-(2-Cyanophenoxy)-1,3-dihydro-1-hydroxy-2,1-benzoxaborole (C23); 4.2.x 5-Phenoxy-1,3-dihydro-1-hydroxy-2,1-benzoxaborole (C24); 4.2.y 5-[4-(N,N-Diethylcarbamoyl)phenoxy]-1,3-dihydro-1-hydroxy-2,1-benzoxaborole (C25); 4.2.z 1,3-Dihydro-1-hydroxy-5-[4-(morpholinocarbonyl)phenoxy]-2,1-benzoxaborole (C26); 4.2.aa 5-(3,4-Dicyanophenoxy)-1,3-dihydro- 1-hydroxy-2,1-benzoxaborole (C27); 4.2.ab 6-Phenylthio-1,3-dihydro-1-hydroxy-2,1-benzoxaborole (C28); 4.2.ac 6-(4-trifluoromethoxyphenoxy)-1,3-dihydro-1-hydroxy-2,1-benzoxaborole (C29); 4.2.ad 5-(N-Methyl-N-phenylsulfonylamino)-1,3-dihydro-1-hydroxy-2,1-benzoxaborole (C30); 4.2.ae 6-(4-Methoxyphenoxy)-1,3-dihydro-1-hydroxy-2,1-benzoxaborole (C31); 4.2.af 6-(4-Methoxyphenylthio)-1,3-dihydro-1-hydroxy-2,1-benzoxaborole (C32); 4.2.ag 6-(4-Methoxyphenylsulfonyl)-1,3-dihydro-1-hydroxy-2,1-benzoxaborole (C33); 4.2.ah 6-(4-Methoxyphenylsulfinyl)-1,3-dihydro-1-hydroxy-2,1-benzoxaborole (C34); 4.2.ai 5-Trifluoromethyl-1,3-dihydro-1-hydroxy-2,1-benzoxaborole (C35) and 4.2.aj 4-(4-Cyanophenoxy)-1,3-dihydro-1-hydroxy-2,1-benzoxaborole (C36).

For coupling reaction between 4-fluorobenzonitrile and substituted phenol to give starting material 2, see Igarashi, S.; et al. Chemical & Pharmaceutical Bulletin (2000), 48(11), 1689-1697.

7-(4-Cyanophenoxy)-1,3-dihydro-1-hydroxy-2,1-benzoxaborole (C100)

For coupling reaction between 4-fluorobenzonitrile and substituted phenol to give starting material 2, see Igarashi, S.; et al. Chemical & Pharmaceutical Bulletin (2000), 48(11), 1689-1697.

4.2.ak 5-(3-Cyanophenoxy)-1,3-dihydro-1-hydroxy-2,1-benzoxaborole (C37)

For coupling between 3-fluorobenzonitrile and substituted phenol to give starting material 2: Li, F. et al., Organic Letters (2003), 5(12), 2169-2171.

4.2.al
5-(4-Carboxyphenoxy)-1-hydroxy-2,1-benzoxaborole (C38)

To a solution of 5-(4-cyanophenoxy)-1-hydroxy-2,1-benzoxaborole obtained in C17 (430 mg, 1.71 mmol) in ethanol (10 mL) was added 6 mol/L sodium hydroxide (2 mL), and the mixture was refluxed for 3 hours. Hydrochloric acid (6 mol/L, 3 mL) was added, and the mixture was extracted with ethyl acetate. The organic layer was washed with brine and dried on anhydrous sodium sulfate. The solvent was removed under reduced pressure, and the residue was purified by silica gel column chromatography (ethyl acetate) followed by trituration with diisopropyl ether to give the target compound (37 mg, 8%).

4.2.am 1-Hydroxy-5-[4-(tetrazole-1-yl)phenoxy]-2,1-benzoxaborole (C39)

A mixture of 5-(4-cyanophenoxy)-1-hydroxy-2,1-benzoxaborole (200 mg, 0.797 mmol), sodium azide (103 mg, 1.59 mmol), and ammonium chloride (85 mg, 1.6 mmol) in N,N-dimethylformamide (5 mL) was stirred at 80° C. for two days. Water was added, and the mixture was extracted with ethyl acetate. The organic layer was washed with water and brine, and dried on anhydrous sodium sulfate. The solvent was removed under reduced pressure, and the residue was purified by silica gel column chromatography (ethyl acetate) followed by trituration with ethyl acetate to give the target compound (55 mg, 23%).

Example 5

Preparation of 1 from 2 via 6

5.1 Catalytic Boronylation, Reduction and Cyclization

A mixture of 2 (10.0 mmol), bis(pinacolato)diboron (2.79 g, 11.0 mmol), $PdCl_2(dppf)$ (250 mg, 3 mol %), and potassium acetate (2.94 g, 30.0 mmol) in 1,4-dioxane (40 mL) was stirred at 80° C. for overnight. Water was added, and the mixture was extracted with ethyl acetate. The organic layer was washed with brine and dried on anhydrous sodium sulfate. The solvent was removed under reduced pressure. The crude product was dissolved in tetrahydrofuran (80 mL), then sodium periodate (5.56 g, 26.0 mmol) was added. After stirring at room temperature for 30 min, 2N HCl (10 mL) was added, and the mixture was stirred at room temperature for overnight. Water was added, and the mixture was extracted with ethyl acetate. The organic layer was washed with brine and dried on anhydrous sodium sulfate. The solvent was removed under reduced pressure, and the residue was treated with ether to afford 6.3 mmol of the corresponding boronic acid. To the solution of the obtained boronic acid (0.595 mmol) in methanol (5 mL) was added sodium borohydride (11 mg, 0.30 mmol), and the mixture was stirred at room temperature for 1 h. Water was added, and the mixture was extracted with ethyl acetate. The organic layer was washed with brine and dried on anhydrous sodium sulfate. The solvent was removed under reduced pressure, and the residue was purified by silica gel column chromatography to give 0.217 mmol of I.

Example 6

Preparation of 1 from 3

6.1 One-Pot Boronylation and Cyclization

To a solution of 3 (4.88 mmol) and triisopropyl borate (1.35 mL, 5.86 mmol) in tetrahydrofuran (10 mL) was added n-butyllithium (1.6 mol/L in hexanes; 6.7 mL, 10.7 mmol) dropwise over 15 min at –78° C. under nitrogen atmosphere, and the mixture was stirred for 2 h while allowing to warm to room temperature. The reaction was quenched with 2N HCl, and extracted with ethyl acetate. The organic layer was washed with brine and dried on anhydrous sodium sulfate. The solvent was removed under reduced pressure, and the residue was purified by silica gel column chromatography and treated with pentane to give 0.41 mmol of I.

Example 7

Preparation of 1 from 3

7.1 One-Pot Boronylation and Cyclization with Distillation

To a solution of 3 (4.88 mmol) in toluene (20 mL) was added triisopropyl borate (2.2 mL, 9.8 mmol), and the mixture was heated at reflux for 1 h. The solvent, the generated isopropyl alcohol and excess triisopropyl borate were removed under reduced pressure. The residue was dissolved in tetrahydrofuran (10 mL) and cooled to –78° C. n-Butyllithium (3.2 mL, 5.1 mmol) was added dropwise over 10 min, and the mixture was stirred for 1 h while allowing to warm to room temperature. The reaction was quenched with 2N HCl, and extracted with ethyl acetate. The organic layer was washed with brine and dried on anhydrous sodium sulfate. The solvent was removed under reduced pressure, and the residue was purified by silica gel column chromatography to give 1.54 mmol of I.

Example 8

Preparation of 8 from 7

8.1 Bromination

To a solution of 7 (49.5 mmol) in carbon tetrachloride (200 mL) were added N-bromosuccinimide (8.81 g, 49.5 mmol) and N,N-azoisobutylonitrile (414 mg, 5 mol %), and the mixture was heated at reflux for 3 h. Water was added, and the mixture was extracted with chloroform. The organic layer was washed with brine and dried on anhydrous sodium sulfate. The solvent was removed under reduced pressure to give the crude methyl-brominated intermediate 8.

Example 9

Preparation of 3 from 8

9.1 Hydroxylation

To crude 8 (49.5 mmol) were added dimethylformamide (150 mL) and sodium acetate (20.5 g, 250 mmol), and the mixture was stirred at 80° C. for overnight. Water was added, and the mixture was extracted with ether. The organic layer was washed with water and brine, and dried on anhydrous sodium sulfate. The solvent was removed under reduced pressure. To the residue was added methanol (150 mL) and 1N sodium hydroxide (50 mL), and the mixture was stirred at room temperature for 1 h. The reaction mixture was concentrated to about a third of volume under reduced pressure. Water and hydrochloric acid were added, and the mixture was extracted with ethyl acetate. The organic layer was washed with water and brine, and dried on anhydrous sodium sulfate. The solvent was removed under reduced pressure, and the residue was purified by silica gel column chromatography followed by trituration with dichloromethane to give 21.8 mmol of 3.

9.2 Results

Exemplary compounds of structure 3 prepared by the method above include: 9.2.a 2-Bromo-5-cyanobenzyl Alcohol.

Additional examples of compounds which can be produced by this method include 2-bromo-5-(4-cyanophenoxy) benzyl alcohol.

Example 10

Preparation of 9 from 2

10.1 Reaction

A mixture of 2 (20.0 mmol), (methoxymethyl)triphenylphosphonium chloride (8.49 g, 24.0 mmol), and potassium tert-butoxide (2.83 g, 24.0 mol) in N,N-dimethylformamide (50 mL) was stirred at room temperature for overnight. The reaction was quenched with 6 N HCl, and the mixture was extracted with ethyl acetate. The organic layer was washed with water (×2) and brine, and dried on anhydrous sodium sulfate. The solvent was removed under reduced. To the residue were added tetrahydrofuran (60 mL) and 6 N HCl, and the mixture was heated at reflux for 8 h. Water was added, and the mixture was extracted with ether. The organic layer was washed with brine and dried on anhydrous sodium sulfate. The solvent was removed under reduced pressure to afford 16.6 mmol of 9.

Example 11

Preparation Method of Step 13

11.1 Reaction

A solution of I in an appropriate alcohol solvent ($R^1$—OH) was refluxed under nitrogen atmosphere and then distilled to remove the alcohol to give the corresponding ester.

Example 12

Preparation of Ib from Ia 12.1 Reaction

To a solution of Ia in toluene was added amino alcohol and the participated solid was collected to give Ib.

12.2 Results (500 mg, 3.3 mmol) was dissolved in toluene (37 mL) at 80° C. and ethanolamine (0.20 mL, 3.3 mmol) was added. The mixture was cooled to room temperature, then ice bath, and filtered to give C38 as a white powder (600.5 mg, 94%).

Example 13

5-(4-Carboxyphenoxy)-1-hydroxy-2,1-benzoxaborole (C38)

To a solution of 5-(4-cyanophenoxy)-1-hydroxy-2,1-benzoxaborole obtained in C17 (430 mg, 1.71 mmol) in ethanol (10 mL) was added 6 mol/L sodium hydroxide (2 mL), and the mixture was refluxed for 3 hours. Hydrochloric acid (6 mol/L, 3 mL) was added, and the mixture was extracted with ethyl acetate. The organic layer was washed with brine and dried on anhydrous sodium sulfate. The solvent was removed under reduced pressure, and the residue was purified by silica gel column chromatography (ethyl acetate) followed by trituration with diisopropyl ether to give the target compound (37 mg, 8%).

Example 14

1-Hydroxy-5-[4-(tetrazole-1-yl)phenoxy]-2,1-benzoxaborole (C39)

A mixture of 5-(4-cyanophenoxy)-1-hydroxy-2,1-benzoxaborole (200 mg, 0.797 mmol), sodium azide (103 mg, 1.59 mmol), and ammonium chloride (85 mg, 1.6 mmol) in N,N-dimethylformamide (5 mL) was stirred at 80° C. for two days. Water was added, and the mixture was extracted with ethyl acetate. The organic layer was washed with water and brine, and dried on anhydrous sodium sulfate. The solvent was removed under reduced pressure, and the residue was purified by silica gel column chromatography (ethyl acetate) followed by trituration with ethyl acetate to give the target compound (55 mg, 23%).

Example 15

4-(4-Cyanophenoxy)phenylboronic acid (C97)

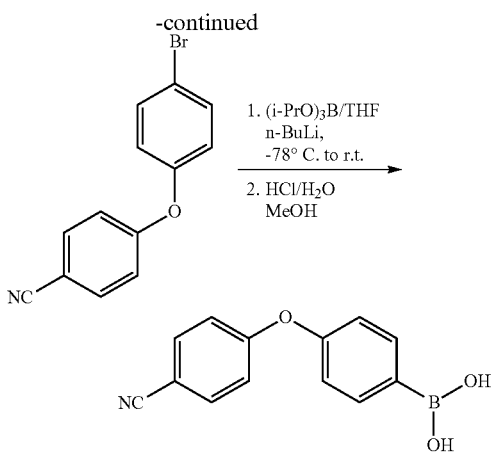

(a) (4-cyanophenyl)(4-bromophenyl)ether

Under nitrogen, the mixture of 4-fluorobenzonitrile (7.35 g, 60.68 mmol), 4-bromophenol (10 g, 57.8 mmol) and potassium carbonate (12 g, 1.5 eq) in DMF (100 mL) was stirred at 100° C. for 16 h and then filtered. After rotary evaporation, the residue was dissolved in ethyl acetate and washed with 1N NaOH solution to remove unreacted phenol. The organic solution was dried and passed through a short silica gel column to remove the color and minor phenol impurity. Evaporation of the solution gave (4-cyanophenyl)(4-bromophenyl) ether (13.82 g, yield 87.2%) as a white solid. $^1$H NMR (300 MHz, DMSO-$d_6$): δ 7.83 (d, 2H), 7.63 (d, 2H), 7.13 (d, 2H) and 7.10 (d, 2H) ppm.

(b) 4-(4-cyanophenoxy)phenylboronic acid

The procedure described in Example 2d was used for the synthesis of 4-(4-cyanophenoxy)phenylboronic acid using (4-cyanophenyl)(4-bromophenyl)ether as starting material. The title compound was obtained as a white solid. M.p. 194-198° C. MS: m/z=239 (M+), 240 (M+1) (ESI+) and m/z=238 (M−1) (ESI−). HPLC: 95.3% purity at 254 nm and 92.1% at 220 nm. $^1$H NMR (300 MHz, DMSO-$d_6$+$D_2O$): δ 7.83-7.76 (m, 4H), 7.07 (d, 2H) and 7.04 (d, 2H) ppm.

Example 16

3-(4-Cyanophenoxy)phenylboronic acid (C98)

By following the procedures described for the synthesis of C21, the title compound was acquired from (4-cyanophenyl) (3-bromophenyl)ether that was prepared using 3-bromophenol and 4-fluorobenzonitrile as starting materials. The product was obtained as a white solid.

Example 17

4-(4-Cyanophenoxy)-2-Methylphenylboronic acid (C99)

By following the procedures described for the synthesis of C21, the title compound was acquired from (4-cyanophenyl) (4-bromo-3-methylphenyl)ether that was prepared using 4-bromo-3-methylphenol and 4-fluorobenzonitrile as starting materials. The product was obtained as a cream solid.

Example 18

Cyclic Boronic Esters

Additional compounds can be produced by the methods described herein. By choosing the appropriate starting material such as 1 or 3, the methods described herein can be used to formulate the following compounds.

Exemplary compounds of structure I are provided: 18a Ethyl 2-(1-hydroxy-1,3-dihydrobenzo[c][1,2]oxaborol-5-yloxy)acetate (C41); 18b 2-(1-hydroxy-1,3-dihydrobenzo[c] [1,2]oxaborol-5-yloxy)acetic acid (C42); 18c 6-(thiophen-2-ylthio)benzo[c][1,2]oxaborol-1(3H)-ol (C43); 18d 6-(4-fluorophenylthio)benzo[c][1,2]oxaborol-1(3H)-ol (C44); 18e 1-(3((1-hydroxy-1,3-dihydrobenzo[c][1,2]oxaborol-5-yloxy)methyl)phenyl)pentan-1-one (C45); 18f 2-(1-hydroxy-1,3-dihydrobenzo[c][1,2]oxaborol-5-yloxy)-1-(piperidin-1-yl)ethanone (C46); 18g 2-(1-hydroxy-1,3-dihydrobenzo[c][1,2]oxaborol-5-yloxy)-1-(4-(pyrimidin-2-yl)piperazin-1-yl)ethanone (C47); 18h 6-(4-(pyridin-2-yl) piperazin-1-yl)benzo[c][1,2]oxaborol-1(3H)-ol (C48); 18i 6-nitrobenzo[c][1,2]oxaborol-1(3H)-ol (C49); 18j 6-aminobenzo[c][1,2]oxaborol-1(3H)-ol (C50); 18k 6-(dimethylamino)benzo[c][1,2]oxaborol-1(3H)-ol (C51); 18l N-(1-hydroxy-1,3-dihydrobenzo[c][1,2]oxaborol-6-yl)benzamide (C52); 18m 6-(4-phenylpiperazin-1-yl)benzo[c][1,2]oxaborol-1(3H)-ol (C53); 18n 6-(1H-indol-1-yl)benzo[c][1,2] oxaborol-1(3H)-ol (C55); 18o 6-morpholinobenzo[c][1,2] oxaborol-1(3H)-ol (C56); 18p 6-(1-hydroxy-1,3-dihydrobenzo[c][1,2]oxaborol-5-yloxy)nicotinonitrile (C57); 18q 5-fluoro-6-nitrobenzo[c][1,2]oxaborol-1(3H)-ol (C58); 18r 5-bromo-6-(hydroxymethyl)benzo[c][1,2]oxaborol-1(3H)-ol (C59); 18s 3,7-dihydro-1,5-dihydroxy-1H, 3H-Benzo[1,2-c:4,5-c']bis[1,2]oxaborole (C60); 18t 1-(1-hydroxy-1,3-dihydrobenzo[c][1,2]oxaborol-6-yl)-3-phenylurea (C61); 18u N-(1-hydroxy-1,3-dihydrobenzo[c] [1,2]oxaborol-6-yl)benzenesulfonamide (C62); 18v N-(1-hydroxy-1,3-dihydrobenzo[c][1,2]oxaborol-6-yl)acetamide (C63); 18w 7-(hydroxymethyl)benzo[c][1,2]oxaborol-1 (3H)-ol (C64); 18x 7-methylbenzo[c][1,2]oxaborol-1(3H)-ol (C65); 18y 6-(3-(phenylthio)-1H-indol-1-yl)benzo[c][1,2] oxaborol-1(3H)-ol (C66); 18z 3-(1-(1-hydroxy-1,3-dihydrobenzo[c][1,2]oxaborol-6-yl)-1H-indol-3-ylthio)propanenitrile (C67); 18aa 6-(5-methoxy-1H-indol-1-yl)benzo [c][1,2]oxaborol-1(3H)-ol (C68); 18ab 5,6-methylenedioxybenzo[c][1,2]oxaborol-1(3H)-ol. (C69); 18ac 6-amino-5-fluorobenzo[c][1,2]oxaborol-1(3H)-ol (C70); 18ad 6-(benzylamino)-5-fluorobenzo[c][1,2]oxaborol-1(3H)-ol (C71); 18ae 6-(5-methoxy-3-(phenylthio)-1H-indol-1-yl)benzo[c][1,2]oxaborol-1(3H)-ol (C72); 18af 3-(1-(1-hydroxy-1,3-dihydrobenzo[c][1,2]oxaborol-6-yl)-5-methoxy-1H-indol-3-ylthio)propanenitrile (C73); 18ag 4-(1-hydroxy-1,3-dihydrobenzo[c][1,2]oxaborol-7-yloxy)benzonitrile (C74); 18ah 6-(5-chloro-1H-indol-1-yl)benzo[c][1, 2]oxaborol-1(3H)-ol (C75); 18ai 3-(5-chloro-1-(1-hydroxy-1,3-dihydrobenzo[c][1,2]oxaborol-6-yl)-1H-indol-3-ylthio) propanenitrile (C76); 18aj 6-(benzylamino)benzo[c][1,2] oxaborol-1(3H)-ol (C77); 18ak 6-(dibenzylamino)benzo[c] [1,2]oxaborol-1(3H)-ol (C78); 18al 7-(4-(1H-tetrazol-5-yl) phenoxy)benzo[c][1,2]oxaborol-1(3H)-ol (C79); 18am 6-(5-chloro-3-(phenylthio)-1H-indol-1-yl)benzo[c][1,2] oxaborol-1(3H)-ol (C80); 18an 6-(4-(pyrimidin-2-yl) piperazin-1-yl)benzo[c][1,2]oxaborol-1(3H)-ol (C82); 18ao 7-(benzyloxy)benzo[c][1,2]oxaborol-1(3H)-ol (C83); 18ap 4-(1-hydroxy-1,3-dihydrobenzo[c][1,2]oxaborol-6-ylthio) pyridinium chloride (C84); 18aq 6-(pyridin-2-ylthio)benzo [c][1,2]oxaborol-1(3H)-ol (C85); 18ar 7-fluorobenzo[c][1,2]

oxaborol-1(3H)-ol (C86); 18as 6-(4-(trifluoromethyl)phenoxy)benzo[c][1,2]oxaborol-1(3H)-ol (C87); 18at 6-(4-chlorophenylthio)benzo[c][1,2]oxaborol-1(3H)-ol (C88); 18au 6-(4-chlorophenylsulfinyl)benzo[c][1,2]oxaborol-1(3H)-ol (C89); 18av 6-(4-chlorophenylsulfonyl)benzo[c][1,2]oxaborol-1(3H)-ol (C90); 18aw N-(1-hydroxy-1,3-dihydrobenzo[c][1,2]oxaborol-5-yl)-N-(phenylsulfonyl)benzenesulfonamide (C91); 18ax 6-(4-(trifluoromethyl)phenylthio)benzo[c][1,2]oxaborol-1(3H)-ol (C92); 18ay 6-(4-(trifluoromethyl)phenylsulfinyl)benzo[c][1,2]oxaborol-1(3H)-ol (C93); 18az 6-(4-(methylthio)phenylthio)benzo[c][1,2]oxaborol-1(3H)-ol (C94); 18ba 6-(p-tolylthio)benzo[c][1,2]oxaborol-1(3H)-ol (C95); 18bb 3-((1-hydroxy-1,3-dihydrobenzo[c][1,2]oxaborol-5-yloxy)methyl)benzonitrile (C96).

Example 19

19a 5-(4-Cyanobenzyloxy)-1,3-dihydro-1-hydroxy-2,1-benzoxaborole (D1)

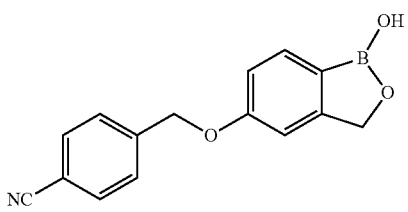 [SMILES: N#Cc1ccc(COc2ccc3c(c2)COB3O)cc1]

A mixture of 4-bromo-3-formylphenol (25.2 g, 125 mmol), tert-butyldimethylchlorosilane (21.4 g, 138 mmol), and imidazole (9.63 g, 140 mmol) in dichloromethane (300 mL) was stirred at room temperature for 3 hours. Water was added, and the mixture was extracted with chloroform. The organic layer was washed with brine and dried on anhydrous sodium sulfate. The solvent was removed under reduced pressure to give the crude silyl ether (40.9 g, quant). To a solution of the crude silyl ether (36.8 g, 117 mmol) in methanol (300 mL) was added sodium borohydride (2.22 g, 58.4 mmol) portionwise at 0° C., and the mixture was stirred at room temperature for 1 hour. Water was added slowly, and the solvent was removed under reduced pressure to about a third of volume. The mixture was extracted with ethyl acetate. The organic layer was washed with brine and dried on anhydrous sodium sulfate. The solvent was removed under reduced pressure to give 2-bromo-5-tert-butyldimethylsiloxybenzylalcohol (36.9 g, quant).

$^1$H-NMR (300 MHz, CDCl$_3$) δ (ppm) 0.20 (s, 6H), 0.98 (s, 9H), 4.67 (br s, 1H), 6.65 (dd, J=8.2, 2.6 Hz, 1H), 6.98 (d, J=2.9 Hz, 1H), 7.36 (d, J=8.8 Hz, 1H).

To a solution of 2-bromo-5-tert-butyldimethylsiloxybenzylalcohol (36.9 g, 116 mmol) and diisopropylethylamine (26.0 mL, 150 mmol) in dichloromethane (300 mL) was added chloromethyl methyl ether (11.0 mL, 145 mmol), and the mixture was stirred at room temperature for overnight. Water was added, and the mixture was extracted with chloroform. The organic layer was washed with brine and dried on anhydrous sodium sulfate. The solvent was removed under reduced pressure, and the residue was purified by silica gel column chromatography (96:4 hexane/ethyl acetate) to give 1-bromo-4-tert-butyldimethylsiloxy-2-methoxymethoxymethylbenzene (39.3 g, 94%).

$^1$H-NMR (300 MHz, CDCl$_3$) δ (ppm) 0.19 (s, 6H), 0.98 (s, 9H), 3.43 (s, 3H), 4.59 (s, 2H), 4.75 (s, 2H), 6.64 (dd, J=8.5, 2.9 Hz, 1H), 6.98 (d, J=2.9 Hz, 1H), 7.36 (d, J=8.5 Hz, 1H).

To a solution of 1-bromo-4-tert-butyldimethylsiloxy-2-methoxymethoxymethylbenzene (34.2 g, 94.8 mmol) in tetrahydrofuran (100 mL) was added tetrabutylammonium fluoride (1 mol/L in tetrahydrofuran, 50 mL), and the mixture was stirred at room temperature for 1 hour. Water was added, and the mixture was extracted with ethyl acetate. The organic layer was washed with brine and dried on anhydrous sodium sulfate. The solvent was removed under reduced pressure, and the residue was purified by silica gel column chromatography (2:1 hexane/ethyl acetate) to give 4-bromo-3-(methoxymethoxymethyl)phenol (25.9 g, quant).

$^1$H-NMR (300 MHz, CDCl$_3$) δ (ppm) 3.44 (s, 3H), 4.61 (s, 2H), 4.77 (s, 2H), 6.66 (dd, J=8.5, 2.9 Hz, 1H), 7.00 (d, J=2.9 Hz, 1H), 7.37 (d, J=8.5 Hz, 1H).

A mixture of 4-bromo-3-(methoxymethoxymethyl)phenol (2.47 g, 10.0 mmol), 4-cyanobenzyl bromide (1.88 g, 9.50 mmol), and potassium carbonate (1.66 g, 12.0 mmol) in N,N-dimethylformamide (20 mL) was stirred at 70° C. for overnight. Water was added, and the mixture was extracted with ethyl acetate. The organic layer was washed with brine and dried on anhydrous sodium sulfate. The solvent was removed under reduced pressure to give 4-[4-bromo-3-(methoxymethoxymethyl)phenoxymethyl]benzonitrile (1.88 g, 95%).

The above compound was converted into the target compound in a similar manner to Example 4.2.q (C17).

$^1$H-NMR (300 MHz, DMSO-d$_6$) δ (ppm) 4.90 (s, 2H), 5.25 (s, 2H), 6.98 (dd, J=7.9, 2.1 Hz, 1H), 7.03 (d, J=1.8 Hz, 1H), 7.62 (d, J=7.9 Hz, 1H), 7.64 (d, J=8.5 Hz, 2H), 7.86 (d, J=8.5 Hz, 1H), 9.01 (s, 1H).

19b 5-(3-Chloro-4-cyanophenoxy)-1,3-dihydro-1-hydroxy-2,1-benzoxaborole (D2)

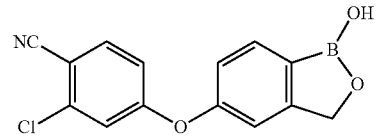 [SMILES: N#Cc1ccc(Oc2ccc3c(c2)COB3O)cc1Cl]

A mixture of 2-bromo-5-hydroxybenzaldehyde (60.0 g, 299 mmol), ethylene glycol (56 mL, 1.00 mol), and p-toluenesulfonic acid (1.14 g, 5.98 mmol) in toluene (450 mL) was refluxed with Dean-Stark head for overnight. Potassium carbonate (3 g) was added, and the mixture was extracted with ethyl acetate. The organic layer was washed with brine and dried on anhydrous sodium sulfate. The solvent was removed under reduced pressure to give 4-bromo-3-(1,3-dioxolan-2-yl)phenol (66.1 g, 90%).

$^1$H-NMR (300 MHz, DMSO-d$_6$) δ (ppm) 3.9-4.1 (m, 4H), 5.81 (s, 1H), 6.71 (dd, J=8.5, 2.9 Hz, 1H), 6.96 (d, J=2.9 Hz, 1H), 7.36 (d, J=7.9 Hz, 1H), 9.81 (br s, 1H).

A mixture of 2-chloro-4-fluorobenzonitrile (4.43 g, 28.4 mmol), 4-bromo-3-(1,3-dioxolan-2-yl)phenol (6.96 g, 28.4 mmol), and potassium carbonate (4.70 g, 34.1 mmol) in N,N-dimethylformamide (60 mL) was stirred at 100° C. under nitrogen atmosphere overnight. The mixture was poured into ethyl acetate/water. The organic layer was washed with brine and dried on anhydrous sodium sulfate. The solvent was removed under reduced pressure to give crude 4-(4-bromo- 3-(1,3-dioxolan-2-yl)phenoxy)-3-chlorobenzonitrile (10.8 g), which was used for the next step without purification.

The compound obtained above (10.8 g) was dissolved in tetrahydrofuran (40 mL) and 3 M HCl (20 mL) was added, and the mixture was refluxed for 2 h. Water was added, and the mixture was extracted with ethyl acetate. The organic layer was washed with brine and dried on anhydrous sodium sulfate. The solvent was removed under reduced pressure to give 4-(4-bromo-3-formylphenoxy)-3-chlorobenzonitrile (9.76 g, quant.).

$^1$H-NMR (300 MHz, CDCl$_3$) δ (ppm) 6.94 (dd, J=8.5, 2.3 Hz, 1H), 7.06 (d, J=2.3 Hz, 1H), 7.21 (dd, J=8.5, 2.9 Hz, 1H), 7.59 (d, J=2.9 Hz, 1H), 7.64 (d, J=8.5 Hz, 1H), 7.73 (d, J=8.5 Hz, 1H), 10.2 (s, 1H).

To a solution of 4-(4-bromo-3-formylphenoxy)-3-chlorobenzonitrile (9.25 g, 27.4 mmol) in methanol (80 mL) was added sodium borohydride (522 mg, 13.7 mmol) portionwise at 0° C., and the mixture was stirred at room temperature for 1 h. The solvent was removed to about a half volume, 1 M HCl was added, and the mixture was poured into ethyl acetate/water. The organic layer was washed with brine and dried on anhydrous sodium sulfate. The solvent was removed under reduced pressure and the residue was purified by silica gel chromatography (8:2 to 7:3 hexane/ethyl acetate) to give 4-(4-bromo-3-(hydroxymethyl)phenoxy)-3-chlorobenzonitrile (8.19 g, 3 steps, 85%).

$^1$H-NMR (300 MHz, CDCl$_3$) δ (ppm) 1.87 (br s, 1H), 4.75 (s, 2H), 6.89 (dd, J=8.5, 2.9 Hz, 1H), 6.92 (dd, J=8.8, 2.6 Hz, 1H), 7.03 (d, J=2.6 Hz, 1H), 7.27 (d, J=2.9 Hz, 1H), 7.58 (d, J=8.8 Hz, 1H), 7.61 (d, J=8.8 Hz, 1H).

To a solution of 4-(4-bromo-3-(hydroxymethyl)phenoxy)-3-chlorobenzonitrile (4.08 g, 12 mmol) in toluene (160 mL) was added triisopropyl borate (4.15 mL, 18.0 mmol), and the solvent was distilled out through Dean-Stark head to a volume of ca. 3 mL. Tetrahydrofuran (3 mL) was added, and the mixture was cooled down to −78° C. Then n-butyllithium (1.6 M in hexanes, 7.5 mL, 12 mmol) was added dropwise, and the mixture was allowed to warm to room temperature. The reaction was quenched with 1 M HCl, and the mixture was extracted with ethyl acetate. The organic layer was washed with brine and dried on anhydrous sodium sulfate. The solvent was removed under reduced pressure and the residue was purified by silica gel chromatography (70:30 to 55:45 hexane/ethyl acetate) followed by trituration with isopropyl ether to give 5-(3-Chloro-4-cyanophenoxy)-1-hydroxy-2,1-benzoxaborole (1.64 g, 39%).

$^1$H-NMR (300 MHz, DMSO-d$_6$) δ (ppm) 4.97 (s, 2H), 7.08 (dd, J=8.9, 2.3 Hz, 1H), 7.13 (dd, J=7.9, 2.1 Hz, 1H), 7.20 (d, J=2.1 Hz, 1H), 7.36 (d, J=2.3 Hz, 1H), 7.80 (d, J=7.9 Hz, 1H), 7.96 (d, J=8.8 Hz, 1H), 9.25 (s, 1H).

19c 5-(4-Cyano-3-methylphenoxy)-1,3-dihydro-1-hydroxy-2,1-benzoxaborole (D3)

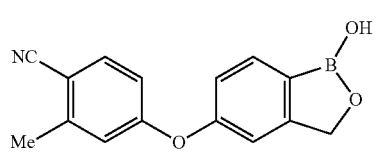

This compound was obtained in a similar manner to Example 19b (D2) from 4-fluoro-2-methylbenzonitrile and 4-bromo-3-(1,3-dioxolan-2-yl)phenol.

$^1$H-NMR (300 MHz, DMSO-d$_6$) δ (ppm) 2.43 (s, 3H), 4.95 (s, 2H), 6.94 (dd, J=8.5, 2.6 Hz, 1H), 7.06 (dd, J=7.9, 2.3 Hz, 1H), 7.08 (d, J=2.3 Hz, 1H), 7.12 (d, J=2.1 Hz, 1H), 7.77 (d, J=8.5 Hz, 2H), 9.21 (s, 1H).

19d 5-(2-Chloro-4-cyanophenoxy)-1,3-dihydro-1-hydroxy-2,1-benzoxaborole (D4)

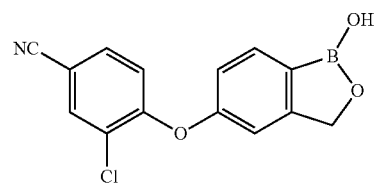

This compound was obtained in a similar manner to Example 19b (D2) from 3-chloro-4-fluorobenzonitrile and 4-bromo-3-(1,3-dioxolan-2-yl)phenol.

$^1$H-NMR (300 MHz, DMSO-d$_6$) δ (ppm) 4.94 (s, 2H), 7.07 (d, J=8.2 Hz, 1H), 7.11 (d, J=0.9 Hz, 1H), 7.12 (dd, J=8.8, 1.2 Hz, 1H), 7.7-7.9 (m, 2H), 8.24 (d, J=2.1 Hz, 1H), 9.23 (s, 1H).

19e 5-(4-Cyano-3-trifluoromethylphenoxy)-1,3-dihydro-1-hydroxy-2,1-benzoxaborole (D5)

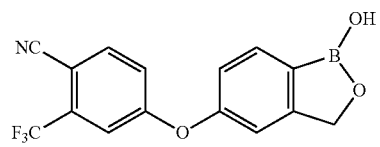 [SMILES: N#Cc1ccc(Oc2ccc3c(c2)COB3O)cc1C(F)(F)F]

This compound was obtained in a similar manner to Example 19b (D2) from 4-fluoro-2-trifluoromethylbenzonitrile and 4-bromo-3-(1,3-dioxolan-2-yl)phenol.

$^1$H-NMR (300 MHz, DMSO-d$_6$) δ (ppm) 4.97 (s, 2H), 7.16 (dd, J=7.0, 2.1 Hz, 1H), 7.24 (d, J=2.1 Hz, 1H), 7.35 (dd, J=8.5, 2.3 Hz, 1H), 7.60 (d, J=2.6 Hz, 1H), 7.81 (d, J=8.2 Hz, 1H), 8.14 (d, J=8.5 Hz, 1H), 9.27 (s, 1H).

19f 5-(4-Cyano-3-methoxycarbonylphenoxy)-1,3-dihydro-1-hydroxy-2,1-benzoxaborole (D6)

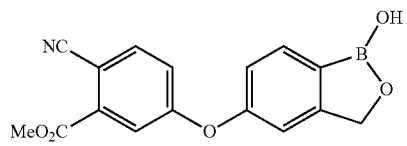 [SMILES: COC(=O)c1cc(Oc2ccc3c(c2)COB3O)ccc1C#N]

A mixture of methyl 2-cyano-5-fluorobenzoate (4.48 g, 25.0 mmol), 2-bromo-5-hydroxybenzaldehyde (5.03 g, 25.0 mmol), and potassium carbonate (4.14 g, 30.0 mmol) in N,N-dimethylformamide (50 mL) was stirred at 80° C. overnight. Water was added, and the mixture was extracted with ethyl acetate. The organic layer was washed with brine and dried on anhydrous sodium sulfate. The solvent was removed under reduced pressure and the residue was purified by silica gel chromatography (chloroform) to give methyl 5-(4-bromo-3-formylphenoxy)-2-cyanobenzoate (5.35 g, 71%).

$^1$H-NMR (300 MHz, CDCl$_3$) δ (ppm) 3.98 (s, 3H), 7.18-7.24 (m, 2H), 7.58 (d, J=2.9 Hz, 1H), 7.66 (d, J=2.6 Hz, 1H), 7.72 (d, J=8.8 Hz, 1H), 7.78 (d, J=8.5 Hz, 1H), 10.3 (s, 1H).

A mixture of methyl 5-(4-bromo-3-formylphenoxy)-2-cyanobenzoate (11.9 g, 33.1 mmol), bis(pinacolato)diboron (8.89 g, 35.0 mmol), [1,1'-bis(diphenylphosphino)ferrocene]dichloropalladium(II) (678 mg, 0.828 mmol), and potassium acetate (9.75 g, 99.0 mmol) in 1,4-dioxane (160 mL) was stirred under nitrogen atmosphere at 80° C. overnight. The mixture was filtered through a Celite pad, and the solvent was removed under reduced pressure. Silica gel column (65:35 hexane/ethyl acetate) gave methyl 2-cyano-5-(3-formyl-4-(4,4,5,5-tetramethyl-1,3,2-dioxaborolan-2-yl)phenoxy)benzoate (15.7 g).

To a solution of methyl 2-cyano-5-(3-formyl-4-(4,4,5,5-tetramethyl-1,3,2-dioxaborolan-2-yl)phenoxy)benzoate (15.7 g) in methanol (150 mL) was added sodium borohydride (646 mg, 17.0 mmol) portionwise at 0° C. The mixture was stirred at room temperature for 1 h. The mixture was acidified with 6 M HCl, and extracted with ethyl acetate. The organic layer was washed with brine and dried on anhydrous sodium sulfate. The solvent was removed under reduced pressure and the residue was purified by silica gel chromatography (6:4 to 4:6 hexane/ethyl acetate) followed by recrystallization from methanol/water to give 5-(4-cyano-3-methoxycarbonylphenoxy)-1-hydroxy-2,1-benzoxaborole (6.34 g, 62%).

$^1$H-NMR (300 MHz, DMSO-d$_6$) δ (ppm) 3.86 (s, 3H), 7.13 (dd, J=7.9, 2.1 Hz, 1H), 7.20 (d, J=2.1 Hz, 1H), 7.39 (dd, J=8.6, 2.6 Hz, 1H), 7.55 (d, J=2.6 Hz, 1H), 7.80 (d, J=7.9 Hz, 1H), 8.01 (d, J=8.8 Hz, 1H), 9.25 (s, 1H).

19g 5-(4-Carbamoyl-3-methoxycarbonylphenoxy)-1,3-dihydro-1-hydroxy-2,1-benzoxaborole (D7)

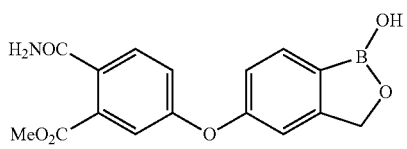

A mixture of 5-(4-Cyano-3-methoxycarbonylphenoxy)-1-hydroxy-2,1-benzoxaborole (5.25 g, 17.0 mmol) and 1 M NaOH (50 mL) in methanol (150 mL) was stirred at room temperature for 1 h. The mixture was acidified with 6 M HCl and extracted with ethyl acetate. The organic layer was washed with brine and dried on anhydrous sodium sulfate. The solvent was removed under reduced pressure and the residue was purified by silica gel chromatography (ethyl acetate) followed by trituration with diisopropyl ether to give 5-(4-Carbamoyl-3-methoxycarbonylphenoxy)-1-hydroxy-2,1-benzoxaborole (1.09 g, 19%)

$^1$H-NMR (300 MHz, DMSO-d$_6$) δ (ppm) 3.70 (s, 3H), 4.94 (s, 2H), 7.0-7.1 (m, 2H), 7.15-7.25 (m, 2H), 7.40 (br s, 1H), 7.61 (d, J=8.8 Hz, 1H), 7.75 (d, J=7.9 Hz, 1H), 7.90 (br s, 1H), 9.19 (s, 1H).

19h 5-(3-Carboxy-4-cyanophenoxy)-1,3-dihydro-1-hydroxy-2,1-benzoxaborole (D8)

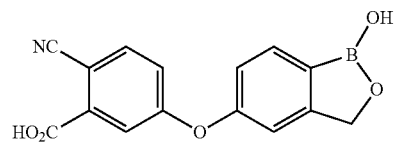 [SMILES: N#Cc1ccc(Oc2ccc3c(c2)COB3O)cc1C(=O)O]

A mixture of 5-(4-Cyano-3-methoxycarbonylphenoxy)-1-hydroxy-2,1-benzoxaborole (5.25 g, 17.0 mmol) and 1 M NaOH (50 mL) in methanol (150 mL) was stirred at room temperature for 1 h. The mixture was acidified with 6 M HCl and extracted with ethyl acetate. The organic layer was washed with brine and dried on anhydrous sodium sulfate. The solvent was removed under reduced pressure and the residue was purified by silica gel chromatography (ethyl acetate to 3:1 chloroform/methanol) followed by trituration with ethyl acetate to give 5-(3-carboxy-4-cyanophenoxy)-1-hydroxy-2,1-benzoxaborole (810 mg, 16%)

$^1$H-NMR (300 MHz, DMSO-d$_6$) δ (ppm) 4.95 (s, 2H), 7.04-7.16 (m, 3H), 7.43 (d, J=2.3 Hz, 1H), 7.71 (d, J=8.5 Hz, 1H), 7.78 (d, J=8.0 Hz, 1H), 9.27 (br s, 1H).

19i 5-(1,3-Dihydro-1-hydroxy-2,1-benzoxaborol-5-yloxy)isoindoline-1,3-dione (D9)

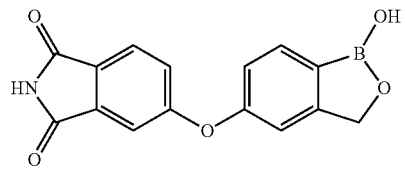 [SMILES: O=C1NC(=O)c2cc(Oc3ccc4c(c3)COB4O)ccc21]

A mixture of 5-(4-Carbamoyl-3-methoxycarbonylphenoxy)-1-hydroxy-2,1-benzoxaborole (560 mg, 1.71 mmol) and 1 M NaOH (5 mL) in methanol (15 mL) was stirred at room temperature for 10 min. The mixture was acidified with 6 M HCl, and extracted with ethyl acetate. The organic layer was washed with brine and dried on anhydrous sodium sulfate. The solvent was removed under reduced pressure and the residue was triturated with ethyl acetate to give 5-(1,3-Dihydro-1-hydroxy-2,1-benzoxaborol-5-yloxy)isoindoline-1,3-dione (380 mg, 75%).

$^1$H-NMR (300 MHz, DMSO-d$_6$) δ (ppm) 4.96 (s, 2H), 7.11 (dd, J=7.9, 1.5 Hz, 1H), 7.17 (s, 1H), 7.25 (d, J=2.3 Hz, 1H), 7.38 (dd, J=8.2, 2.3 Hz, 1H), 7.82 (d, J=8.2 Hz, 1H), 7.83 (d, J=8.2 Hz, 1H), 9.23 (s, 1H), 11.3 (br s, 1H).

19j 5-(4-Cyano-3-hydroxyphenoxy)-1,3-dihydro-1-hydroxy-2,1-benzoxaborole (D10)

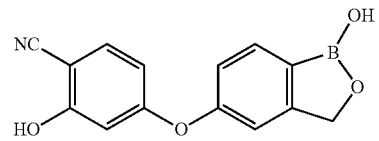

This compound was obtained in a similar manner to Example 19n (D14) from 4-fluoro-3-hydroxybenzonitrile and 4-bromo-3-(1,3-dioxolan-2-yl)phenol.

¹H-NMR (300 MHz, DMSO-d₆) δ (ppm) 4.96 (s, 2H), 6.49 (d, J=2.3 Hz, 1H), 6.55 (dd, J=8.8, 2.3 Hz, 1H), 7.08 (dd, J=7.9, 2.1 Hz, 1H), 7.15 (d, J=1.8 Hz, 1H), 7.60 (d, J=8.5 Hz, 1H), 7.78 (d, J=8.2 Hz, 1H), 9.23 (s, 1H), 11.2 (s, 1H).

19k 5-(4-Cyano-3-acetoxyphenoxy)-1,3-dihydro-1-hydroxy-2,1-benzoxaborole (D11)

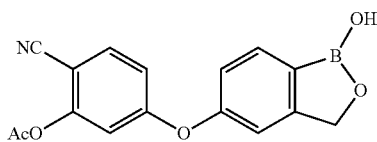

A mixture of 5-(4-cyano-3-hydroxyphenoxy)-1,3-dihydro-1-hydroxy-2,1-benzoxaborole (900 mg, 3.37 mmol), acetic anhydride (1.7 mL, 18 mmol), triethylamine (1.4 mL, 10 mL) in N,N-dimethylformamide (10 mL) was stirred at room temperature overnight. The mixture was acidified with 1 M HCl and extracted with ethyl acetate. The organic layer was washed with brine and dried on anhydrous sodium sulfate. The solvent was removed under reduced pressure and the residue was purified by silica gel chromatography (1:1 hexane/ethyl acetate) to give 5-(4-cyano-3-acetoxyphenoxy)-1, 3-dihydro-1-hydroxy-2,1-benzoxaborole (818 mg, 79%).

¹H-NMR (300 MHz, DMSO-d₆) δ (ppm) 2.31 (s, 3H), 4.96 (s, 2H), 7.04 (dd, J=8.5, 2.6 Hz, 1H), 7.07 (d, J=2.3 Hz, 1H), 7.12 (dd, J=7.9, 2.1 Hz, 1H), 7.20 (d, J=2.0 Hz, 1H), 7.80 (d, J=7.9 Hz, 1H), 7.91 (d, J=8.6 Hz, 1H), 9.25 (s, 1H).

19l 5-(4-Cyano-3-methoxyphenoxy)-1,3-dihydro-1-hydroxy-2,1-benzoxaborole (D12)

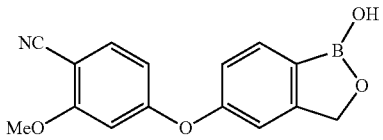 [SMILES: CC(=O)Oc1cc(Oc2ccc3c(c2)COB3O)ccc1C#N]

To a solution of 5-(4-cyano-3-hydroxyphenoxy)-1,3-dihydro-1-hydroxy-2,1-benzoxaborole (100 mg, 0.375 mmol) and iodomethane (0.070 mL, 1.1 mmol) in N,N-dimethylformamide (10 mL) was added sodium hydride (60% oil dispersion, 45 mg, 1.1 mmol) at 0° C. under nitrogen atmosphere, and the mixture was stirred at room temperature for 2 h. Water and 1 M HCl were added and the mixture was extracted with ethyl acetate. The organic layer was washed with brine and dried on anhydrous sodium sulfate. The solvent was removed under reduced pressure and the residue was treated with hexane/diisopropyl ether to give 5-(4-cyano-3-methoxyphenoxy)-1,3-dihydro-1-hydroxy-2,1-benzoxaborole (92 mg, 87%).

¹H-NMR (300 MHz, DMSO-d₆) δ (ppm) 3.86 (s, 3H), 4.96 (s, 2H), 6.56 (dd, J=8.5, 2.1 Hz, 1H), 6.93 (d, J=2.3 Hz, 1H), 7.09 (dd, J=8.2, 2.1 Hz, 1H), 7.14 (s, 1H), 7.70 (d, J=8.5 Hz, 1H), 7.77 (d, J=7.9 Hz, 1H), 9.22 (s, 1H).

19m 5-(3-Chloro-2-cyanophenoxy)-1,3-dihydro-1-hydroxy-2,1-benzoxaborole (D13)

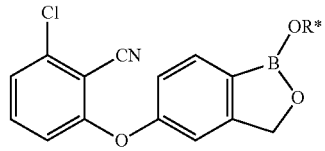

This compound was obtained in a similar manner to Example 19b (D2) from 2-chloro-6-fluorobenzonitrile and 4-bromo-3-(1,3-dioxolan-2-yl)phenol.

¹H-NMR (300 MHz, DMSO-d₆) δ (ppm) 4.96 (s, 2H), 6.97 (d, J=8.5 Hz, 1H), 7.16 (dd, J=7.9, 2.1 Hz, 1H), 7.21 (d, J=2.1 Hz, 1H), 7.49 (d, J=8.2 Hz, 1H), 7.66 (t, J=8.2 Hz, 1H), 7.79 (d, J=8.2 Hz, 1H), 9.25 (s, 1H).

19n 5-(4-Cyano-2-hydroxyphenoxy)-1,3-dihydro-1-hydroxy-2,1-benzoxaborole (D14)

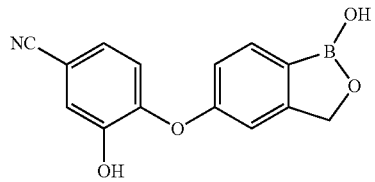 [SMILES: N#Cc1ccc(Oc2ccc3c(c2)COB3O)c(O)c1]

To a solution of 4-fluoro-3-hydroxybenzonitrile (25.0 g, 182 mmol), diisopropylethylamine (47.7 mL, 273 mmol) in dichloromethane (530 mL) was added chloromethyl methyl ether (16.6 mL, 219 mmol) dropwise at 0° C., and the mixture was stirred at room temperature overnight. Water was added, and the mixture was extracted with dichloromethane. The organic layer was washed with brine and dried on anhydrous sodium sulfate. The solvent was removed under reduced pressure to give 4-fluoro-3-methoxymethoxybenzonitrile (33.0 g, quant.), which was used for the next step without purification.

A mixture of 4-fluoro-3-methoxymethoxybenzonitrile (33.0 g, 182 mmol), 4-bromo-3-(1,3-dioxolan-2-yl)phenol (44.6 g, 182 mmol), and potassium carbonate (30.1 g, 218 mmol) in N,N-dimethylformamide (370 mL) was stirred at 100° C. under nitrogen atmosphere overnight. The mixture was poured into ethyl acetate/water. The organic layer was washed with brine and dried on anhydrous sodium sulfate. The solvent was removed under reduced pressure, and the residue was passed silica gel short column (3:1 hexane/ethyl acetate) followed by trituration with hexane/ethyl acetate to give 4-(4-bromo-3-(1,3-dioxolan-2-yl)phenoxy)-3-methoxymethoxybenzonitrile (32.6 g, 44%), ¹H-NMR (300 MHz, CDCl₃) δ (ppm) 3.46 (s, 3H), 4.0-4.2 (m, 4H), 5.20 (s, 2H), 6.03 (s, 1H), 6.86 (dd, J=8.5, 2.9 Hz, 1H), 6.93 (d, J=8.5 Hz, 1H), 7.24-7.30 (m, 2H), 7.54 (d, J=8.8 Hz, 1H), 7.54 (d, J=2.1 Hz, 1H).

To a solution of 4-(4-bromo-3-(1,3-dioxolan-2-yl)phenoxy)-3-methoxymethoxybenzonitrile (32.2 g, 79.3 mmol) in tetrahydrofuran (300 mL) was added 3 M HCl (100 mL), and the mixture was refluxed for 2 h. Water was added, and the mixture was extracted with ethyl acetate. The organic layer was washed with brine and dried on anhydrous sodium sulfate. The solvent was removed under reduced pressure to give 4-(4-bromo-3-formylphenoxy)-3-hydroxybenzonitrile (25.8 g, quant.).

A mixture of 4-(4-bromo-3-formylphenoxy)-3-hydroxybenzonitrile (20.5 g, 64.5 mmol), bis(pinacolato)diboron (17.2 g, 67.7 mmol), [1,1'-bis(diphenylphosphino)ferrocene] dichloropalladium(II) (1.32 g, 1.61 mmol), and potassium acetate (19.1 g, 194 mmol) in 1,4-dioxane (260 mL) was stirred under nitrogen atmosphere at 80° C. overnight. The mixture was filtered through a Celite pad, and the solvent was removed under reduced pressure. Silica gel column (ethyl acetate) gave methyl 4-(3-formyl-4-(4,4,5,5-tetramethyl-1,3,2-dioxaborolan-2-yl)phenoxy)-3-hydroxybenzonitrile (25.1 g).

To a solution of methyl 4-(3-formyl-4-(4,4,5,5-tetramethyl-1,3,2-dioxaborolan-2-yl)phenoxy)-3-hydroxybenzonitrile (25.1 g) in methanol (300 mL) was added sodium borohydride (2.45 g, 64.5 mmol) portionwise at 0° C. The mixture was stirred at room temperature for 1 h. The solvent was removed under reduced pressure to about a third of volume. The mixture was acidified with 6 M HCl, and extracted with ethyl acetate. The organic layer was washed with brine and dried on anhydrous sodium sulfate. The solvent was removed under reduced pressure and the residue was purified by silica gel chromatography (7:3 to 6:4 hexane/acetone) followed by recrystallization from acetone/water and trituration with ethyl acetate to give 5-(4-cyano-2-hydroxyphenoxy)-1,3-dihydro-1-hydroxy-2,1-benzoxaborole (10.9 g, 63%).

$^1$H-NMR (300 MHz, DMSO-$d_6$) δ (ppm) 4.90 (s, 2H), 6.90-6.95 (m, 2H), 7.09 (d, J=7.9 Hz, 1H), 7.26-7.33 (m, 2H), 7.69 (d, J=7.9 Hz, 1H), 9.12 (s, 1H), 10.4 (br s, 1H).

19o 5-(4-Cyano-2-methoxyphenoxy)-1,3-dihydro-1-hydroxy-2,1-benzoxaborole (D15)

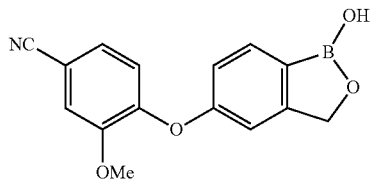

This compound was obtained in a similar manner to Example 271 (D12) from 5-(4-cyano-2-hydroxyphenoxy)-1,3-dihydro-1-hydroxy-2,1-benzoxaborole (D14) and iodomethane.

$^1$H-NMR (300 MHz, DMSO-$d_6$) δ (ppm) 3.80 (s, 3H), 4.90 (s, 2H), 6.90-6.96 (m, 2H), 7.12 (d, J=8.2 Hz, 1H), 7.44 (dd, J=8.2, 2.1 Hz, 1H), 7.67 (d, J=1.8 Hz, 1H), 7.69 (d, J=8.8 Hz, 1H), 9.13 (s, 1H).

19p 5-[4-Cyano-2-(ethoxycarbonylmethoxy)phenoxy]-1,3-dihydro-1-hydroxy-2,1-benzoxaborole (D16)

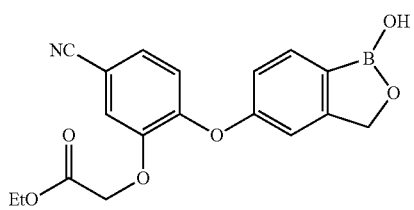 [SMILES: CCOC(=O)COc1cc(C#N)ccc1Oc1ccc2c(c1)COB2O]

This compound was obtained in a similar manner to Example 191 (D12) from 5-(4-cyano-2-hydroxyphenoxy)-1,3-dihydro-1-hydroxy-2,1-benzoxaborole (D14) and ethyl bromoacetate.

$^1$H-NMR (300 MHz, DMSO-$d_6$) δ (ppm) 1.17 (t, J=7.0 Hz, 3H), 4.12 (q, J=7.0 Hz, 2H), 4.91 (s, 4H), 6.94-6.99 (m, 2H), 7.13 (d, J=8.5 Hz, 1H), 7.47 (dd, J=8.5, 1.8 Hz, 1H), 7.66 (d, J=1.8 Hz, 1H), 7.70 (d, J=8.5 Hz, 1H), 9.14 (s, 1H).

19q 5-[12-(Carboxymethoxy)-4-cyanophenoxy]-1,3-dihydro-1-hydroxy-2,1-benzoxaborole (D17)

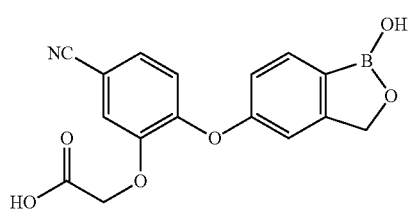 [SMILES: N#Cc1ccc(Oc2ccc3c(c2)COB3O)c(OCC(=O)O)c1]

A mixture of 5-[4-Cyano-2-(ethoxycarbonylmethoxy)phenoxy]-1,3-dihydro-1-hydroxy-2,1-benzoxaborole (D16) (216 mg, 0.612 mmol) and 1 M NaOH (2 mL in methanol (8 mL) was stirred at room temperature for 1 h. The mixture was acidified with 1 M HCl and extracted with ethyl acetate. The organic layer was washed with brine and dried on anhydrous sodium sulfate. The solvent was removed under reduced pressure and the residue was treated with hexane to give 5-[2-(Carboxymethoxy)-4-cyanophenoxy]-1,3-dihydro-1-hydroxy-2,1-benzoxaborole (82 mg, 41%)

$^1$H-NMR (300 MHz, DMSO-$d_6$) δ (ppm) 4.82 (s, 2H), 4.90 (s, 2H), 6.94-7.00 (m, 2H), 7.11 (d, J=8.2 Hz, 1H), 7.45 (dd, J=8.5, 1.8 Hz, 1H), 7.62 (s, 1H), 7.70 (d, J=8.5 Hz, 1H), 9.14 (s, 1H), 13.1 (br s, 1H).

19r 5-(4-Carboxy-2-hydroxyphenoxy)-1,3-dihydro-1-hydroxy-2,1-benzoxaborole (D18)

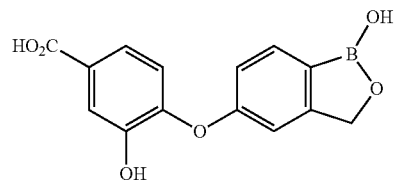 [SMILES: O=C(O)c1ccc(Oc2ccc3c(c2)COB3O)c(O)c1]

A mixture of 5-(4-cyano-2-hydroxyphenoxy)-1,3-dihydro-1-hydroxy-2,1-benzoxaborole (D14) (4.00 g, 15.0 mmol) and 6 M NaOH (30 mL) in methanol (60 mL) and 1,4-dioxane (60 mL) was refluxed for 5 days. The mixture was cooled on an ice bath and acidified with 6 M HCl, then extracted with ethyl acetate. The organic layer was washed with brine and dried on anhydrous sodium sulfate. The solvent was removed under reduced pressure and the residue was recrystallized from ethyl acetate to give 5-(4-carboxy-2-hydroxyphenoxy)-1,3-dihydro-1-hydroxy-2,1-benzoxaborole (1.29 g, 30%). Silica gel column (3:7 to 2:8 hexane/ethyl acetate) of the filtrate followed by trituration with ethyl acetate gave another 1.00 g (23%).

$^1$H-NMR (300 MHz, DMSO-$d_6$) δ (ppm) 4.89 (s, 2H), 6.85 (d, J=1.5 Hz, 1H), 6.90 (dd, J=7.9, 2.1 Hz, 1H), 7.03 (d, J=8.5

Hz, 1H), 7.41 (dd, J=8.2, 2.1 Hz, 1H), 7.54 (d, J=2.1 Hz, 1H), 7.66 (d, J=7.9 Hz, 1H), 9.08 (s, 1H), 9.98 (s, 1H), 12.8 (br s, 1H).

19s 5-(4-Ethoxycarbonyl-2-hydroxyphenoxy)-1,3-dihydro-1-hydroxy-2,1-benzoxaborole (D19)

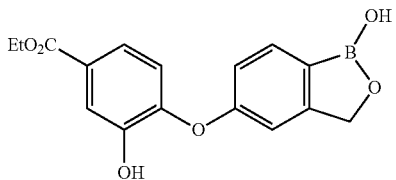

A mixture of 5-(4-carboxy-2-hydroxyphenoxy)-1,3-dihydro-1-hydroxy-2,1-benzoxaborole (1.95 g, 6.82 mmol) and sulfuric acid (1.5 mL) in ethanol (75 mL) was refluxed for 6 h. Water was added, and the mixture was extracted with ethyl acetate. The organic layer was washed with brine and dried on anhydrous sodium sulfate. The solvent was removed under reduced pressure. Silica gel column (6:4 to 5:5 hexane/acetone) followed by recrystallization from diisopropyl ether gave 5-(4-Ethoxycarbonyl-2-hydroxyphenoxy)-1,3-dihydro-1-hydroxy-2,1-benzoxaborole (1.65 g, 77%).

$^1$H-NMR (300 MHz, DMSO-$d_6$) δ (ppm) 1.29 (t, J=7.0 Hz, 3H), 4.27 (q, J=7.0 Hz, 1H), 4.89 (s, 2H), 6.86 (s, 1H), 6.91 (d, J=8.2 Hz, 1H), 7.05 (d, J=8.2 Hz, 1H), 7.43 (dd, J=8.5, 2.1 Hz, 1H), 7.56 (s, 1H), 7.67 (d, J=8.2 Hz, 1H), 9.09 (s, 1H), 10.1 (s, 1H).

19t 5-(4-Ethoxycarbonyl-2-methoxyphenoxy)-1,3-dihydro-1-hydroxy-2,1-benzoxaborole (D20)

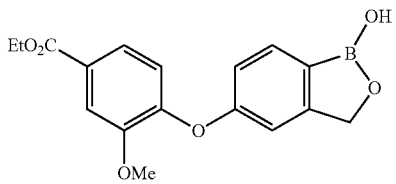

This compound was obtained in a similar manner to Example 191 (D12) from 5-(4-ethoxycarbonyl-2-hydroxyphenoxy)-1,3-dihydro-1-hydroxy-2,1-benzoxaborole (D19) and iodomethane.

$^1$H-NMR (300 MHz, DMSO-$d_6$) δ (ppm) 1.31 (t, J=7.0 Hz, 3H), 3.80 (s, 3H), 4.31 (q, J=7.0 Hz, 2H), 4.89 (s, 3H), 6.86-6.94 (m, 2H), 7.11 (d, J=8.5 Hz, 1H), 7.59 (dd, J=8.2, 1.8 Hz, 1H), 7.63 (d, J=2.1 Hz, 1H), 7.68 (d, J=7.9 Hz, 1H), 9.11 (s, 1H).

19u 5-[4-Ethoxycarbonyl-2-(cyclopentyloxy)phenoxy]-1,3-dihydro-1-hydroxy-2,1-benzoxaborole (D21)

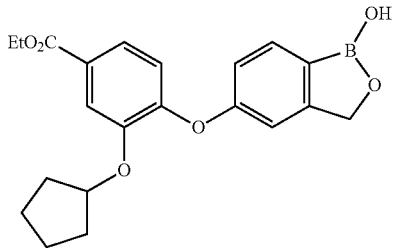 [SMILES: CCOC(=O)c1ccc(Oc2ccc3c(c2)COB3O)c(OC2CCCC2)c1]

This compound was obtained in a similar manner to Example 191 (D12) from 5-(4-ethoxycarbonyl-2-hydroxyphenoxy)-1,3-dihydro-1-hydroxy-2,1-benzoxaborole (D19) and cyclopentyl iodide.

$^1$H-NMR (300 MHz, DMSO-$d_6$) δ (ppm): 1.2-1.6 (m, 6H), 1.30 (t, J=7.0 Hz, 3H), 1.7-1.9 (m, 2H), 4.30 (q, J=7.0 Hz, 2H), 4.87 (s, 2H), 4.87 (m, 1H), 6.84 (s, 1H), 6.88 (d, J=7.9 Hz, 1H), 7.17 (d, J=7.9 Hz, 1H), 7.55-7.61 (m, 2H), 7.65 (d, J=7.9 Hz, 1H), 9.09 (s, 1H).

19v 5-[4-Ethoxycarbonyl-2-(4-cyanopyridin-2-yloxy)phenoxy]-1,3-dihydro-1-hydroxy-2,1-benzoxaborole (D22)

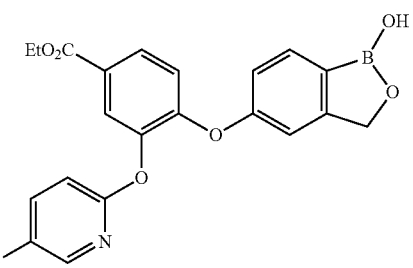

A mixture of 5-(4-ethoxycarbonyl-2-hydroxyphenoxy)-1,3-dihydro-1-hydroxy-2,1-benzoxaborole (D19) (200 mg, 0.637 mmol), 2-chloro-5-pyridin-5-carbonitrile (106 mg, 0.764 mmol), and potassium carbonate (264 mg, 1.90 mmol) in N,N-dimethylformamide (4 mL) was stirred at 70° C. under nitrogen atmosphere for 2 h. The mixture was poured into ethyl acetate/diluted HCl. The organic layer was washed with brine and dried on anhydrous sodium sulfate. The solvent was removed under reduced pressure and the residue was purified by silica gel column (6:4 hexane/acetone) and preparative TLC (5:5 hexane/acetone) to give 5-[4-Ethoxycarbonyl-2-(4-cyanopyridin-2-yloxy)phenoxy]-1,3-dihydro-1-hydroxy-2,1-benzoxaborole (133 mg, 50%).

$^1$H-NMR (300 MHz, DMSO-$d_6$) δ (ppm) 1.29 (t, J=7.0 Hz, 1H), 4.29 (q, J=7.0 Hz, 2H), 4.88 (s, 2H), 6.91 (dd, J=8.2, 2.3 Hz, 1H), 6.95 (d, J=2.1 Hz, 1H), 7.13 (d, J=8.8 Hz, 1H), 7.24 (d, J=8.8 Hz, 1H), 7.67 (d, J=7.9 Hz, 1H), 7.84-7.90 (m, 2H), 8.28 (dd, J=8.8, 2.3 Hz, 1H), 8.62 (d, J=2.3 Hz, 1H), 9.16 (s, 1H).

19w 5-(4-Cyano-2-formylphenoxy)-1,3-dihydro-1-hydroxy-2,1-benzoxaborole (D23)

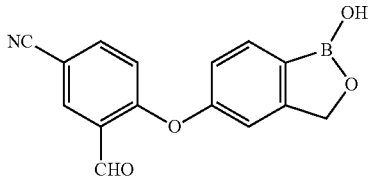 [SMILES: N#Cc1ccc(Oc2ccc3c(c2)COB3O)c(C=O)c1]

To a solution of 4-bromo-3-formylphenol (20.1 g, 100 mmol) in methanol (200 mL) was added sodium borohydride (1.90 g, 50.0 mmol) portionwise at 0° C., and the mixture was stirred at room temperature for 1 h. The solvent was removed under reduced pressure to a half volume, 6 M HCl (50 mL) was added, and the mixture was extracted with ethyl acetate.

The organic layer was washed with brine and dried on anhydrous sodium sulfate. The solvent was removed under reduced pressure to give 4-bromo-3-hydroxymethylphenol (19.4 g, 96%).

$^1$H-NMR (300 MHz, DMSO-d$_6$) δ (ppm) 4.39 (d, J=5.9 Hz, 2H), 5.35 (t, J=5.9 Hz, 1H), 6.56 (dd, J=8.5, 2.9 Hz, 1H), 6.97 (d, J=2.9 Hz, 1H), 7.28 (d, J=8.5 Hz, 1H), 9.61 (s, 1H).

A mixture of 4-fluoro-3-formylbenzonitrile (14.2 g, 96.0 mmol), 4-bromo-3-hydroxymethylphenol (19.4 g, 96 mmol), and potassium carbonate (15.2 g, 110 mmol) in N,N-dimethylformamide (200 mL) was stirred at 70° C. under nitrogen atmosphere for 2 h. The mixture was poured into ethyl acetate/water. The organic layer was washed with water twice and with brine, then dried on anhydrous sodium sulfate. The solvent was removed under reduced pressure, and the residue was purified by silica gel column (3:1 to 7:3 hexane/ethyl acetate) to give 4-[4-bromo-3-(hydroxymethyl)phenoxy]-3-formylbenzonitrile (26.0 g, 82%).

A mixture of 4-[4-bromo-3-(hydroxymethyl)phenoxy]-3-formylbenzonitrile (25.5 g, 76.8 mmol), 3,4-dihydro-2H-pyran (10.4 mL, 115 mmol), and dl-10-camphorsulfonic acid (356 mg, 2 mol %) in dichloromethane (300 mL) was stirred at room temperature for 2 h. Sodium carbonate (3 g) was added, and the mixture was poured into water/chloroform. The organic layer was washed with brine and dried on anhydrous sodium sulfate. The solvent was removed under reduced pressure, and the residue was purified by silica gel column (85:15 hexane/ethyl acetate) to give 4-[4-bromo-3-(2-tetrahydropyranyloxymethyl)phenoxy]-3-formylbenzonitrile (28.0 g, 88%).

A mixture of 4-[4-bromo-3-(2-tetrahydropyranyloxymethyl)phenoxy]-3-formylbenzonitrile (28.0 g, 67.3 mmol), bis(pinacolato)diboron (18.8 g, 74.0 mmol), [1,1'-bis(diphenylphosphino)ferrocene]dichloropalladium(II) (1.37 g, 2.5 mol %), and potassium acetate (19.8 g, 202 mmol) in 1,4-dioxane (270 mL) was stirred under nitrogen atmosphere at 80° C. overnight. The mixture was filtered through a Celite pad, and the solvent was removed under reduced pressure. The residue was dissolved in tetrahydrofuran (250 mL) and was added 6 M HCl (30 mL), and the mixture was stirred at room temperature for 2 h. The mixture was poured into ethyl acetate/water. The organic layer was washed with brine and dried on anhydrous sodium sulfate. The solvent was removed under reduced pressure, and the residue was purified by silica gel column (5:5 to 3:7 hexane/ethyl acetate) followed by recrystallization from ethyl acetate/hexane to give 5-(4-cyano-2-formylphenoxy)-1,3-dihydro-1-hydroxy-2,1-benzoxaborole (6.61 g, 35%).

$^1$H-NMR (300 MHz, DMSO-d$_6$) δ (ppm) 4.98 (s, 2H), 7.03 (d, J=8.5 Hz, 1H), 7.21 (d, J=8.2 Hz, 1H), 7.27 (s, 1H), 7.82 (d, J=7.9 Hz, 1H), 8.04 (dd, J=8.8, 2.3 Hz, 1H), 8.24 (d, J=2.3 Hz, 1H), 9.27 (s, 1H), 10.4 (s, 1H).

19x 5-[4-Cyano-2-(hydroxymethyl)phenoxy]-1,3-dihydro-1-hydroxy-2,1-benzoxaborole (D24)

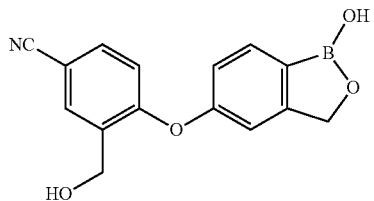 [SMILES: N#Cc1ccc(Oc2ccc3c(c2)COB3O)c(CO)c1]

To a solution of 5-(4-cyano-2-formylphenoxy)-1,3-dihydro-1-hydroxy-2,1-benzoxaborole (3.00 g, 10.8 mmol) in methanol (100 mL) was added sodium borohydride (400 mg, 10.8 mmol) portionwise at 0° C., and the mixture was stirred at room temperature for 1 h. The solvent was removed under reduced pressure to a half volume, 1 M HCl (50 mL) was added, and the mixture was extracted with ethyl acetate. The organic layer was washed with brine and dried on anhydrous sodium sulfate. The solvent was removed under reduced pressure, and the residue was treated with ethyl acetate/hexane to give 5-[4-cyano-2-(hydroxymethyl)phenoxy]-1,3-dihydro-1-hydroxy-2,1-benzoxaborole (1.83 g, 60%).

$^1$H-NMR (300 MHz, DMSO-d$_6$) δ (ppm) 4.58 (d, J=5.6 Hz, 2H), 4.93 (s, 2H), 5.44 (t, J=5.6 Hz, 1H), 6.91 (d, J=8.5 Hz, 1H), 7.03 (dd, J=8.2, 1.2 Hz, 1H), 7.05 (s, 1H), 7.71 (dd, J=8.5, 2.3 Hz, 1H), 7.75 (d, J=7.9 Hz, 1H), 7.88 (d, J=1.2 Hz, 1H), 9.20 (s, 1H).

19y 5-[4-Cyano-2-(formylaminomethyl)phenoxy]-1,3-dihydro-1-hydroxy-2,1-benzoxaborole (D25)

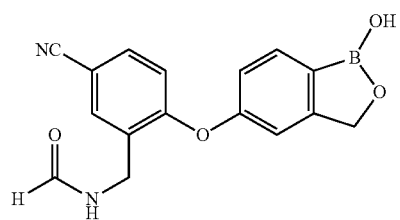 [SMILES: N#Cc1ccc(Oc2ccc3c(c2)COB3O)c(CNC=O)c1]

To a solution of 4-[4-bromo-3-(2-tetrahydropyranyloxymethyl)phenoxy]-3-formylbenzonitrile obtained in Example 19w (D23) (14.6 g, 34.9 mmol) in methanol (100 mL) was added sodium borohydride (664 mg g, 17.5 mmol) portionwise at 0° C., and the mixture was stirred at room temperature for 1 h. The solvent was removed under reduced pressure to a half volume, and the mixture was poured into ethyl acetate/water. The organic layer was washed with brine and dried on anhydrous sodium sulfate. The solvent was removed under reduced pressure to give 4-[4-bromo-3-(2-tetrahydropyranyloxymethyl)phenoxy]-3-(hydroxymethyl)benzonitrile (14.6 g, 100%).

$^1$H-NMR (300 MHz, DMSO-d$_6$) δ (ppm) 1.3-1.8 (m, 6H), 3.47 (m, 1H), 3.72 (m, 1H), 4.4-4.8 (m, 4H), 5.44 (t, J=5.9 Hz, 1H), 6.92 (d, J=8.5 Hz, 1H), 6.96 (dd, J=8.5, 2.9 Hz, 1H), 7.17 (d, J=2.9 Hz, 1H), 7.65 (d, J=8.5 Hz, 1H), 7.71 (dd, J=8.5, 1.8 Hz, 1H), 7.87 (d, J=1.2 Hz, 1H).

To a solution of 4-[4-bromo-3-(2-tetrahydropyranyloxymethyl)phenoxy]-3-(hydroxymethyl)benzonitrile (12.1 g, 28.9 mmol) in dichloromethane (100 mL) were added triethylamine (8.0 mL, 58 mmol) and methanesulfonyl chloride (2.5 mL, 32 mmol) at 0° C., and the mixture was stirred at room temperature for 1 h. The mixture was washed with water and brine, and dried on anhydrous sodium sulfate. The solvent was removed under reduced pressure. To a solution of the residue in N,N-dimethylformamide (100 mL) was added sodium diformylimide (3.29 g, 34.7 mmol), and the mixture was stirred at 50° C. for 2 h. The mixture was poured into ethyl acetate/water. The organic layer was washed with brine and dried on anhydrous sodium sulfate. The solvent was removed under reduced pressure. To a solution of the residue in 1,4-dioxane (80 mL) was added 3 M NaOH (10 mL), and the mixture was stirred at room temperature for 1 h. The mixture was poured into ethyl acetate/water. The organic layer was washed with brine and dried on anhydrous sodium sulfate. The solvent was removed under reduced pressure.

The residue was purified by silica gel column (5:5 to 4:6 hexane/ethyl acetate) to give 4-[4-bromo-3-(2-tetrahydropyranyloxymethyl)phenoxy]-3-(formylaminomethyl)benzonitrile (8.77 g, 68%).

$^1$H-NMR (300 MHz, DMSO-$d_6$) δ (ppm) 1.4-1.8 (m, 6H), 3.46 (m, 1H), 3.73 (m, 1H), 4.37 (d, J=5.9 Hz, 2H), 4.47 (d, J=13.8 Hz, 1H), 4.67 (d, J=13.8 Hz, 1H), 4.72 (br s, 1H), 6.92 (d, J=8.5 Hz, 1H), 7.00 (d, J=8.5 Hz, 1H), 7.21 (s, 1H), 7.67 (dd, J=8.8, 1.8 Hz, 1H), 7.72 (d, J=8.5 Hz, 1H), 7.76 (s, 1H), 8.14 (s, 1H), 8.53 (br t, 1H).

A mixture of 4-[4-bromo-3-(2-tetrahydropyranyloxymethyl)phenoxy]-3-(formylaminomethyl)benzonitrile (1.44 g, 3.24 mmol), bis(pinacolato)diboron (905 mg, 3.56 mmol), [1,1'-bis(diphenylphosphino)ferrocene]dichloropalladium (II) (87 mg, 3 mol %), and potassium acetate (1.01 g, 10.3 mmol) in 1,4-dioxane (25 mL) was stirred under nitrogen atmosphere at 80° C. overnight. The mixture was filtered through a Celite pad, and the solvent was removed under reduced pressure. The residue was passed short silica gel column (4:6 hexane/ethyl acetate). The crude product was dissolved in tetrahydrofuran (20 mL) and was added 6 M HCl (2 mL), and the mixture was stirred at room temperature overnight. The mixture was poured into ethyl acetate/water. The organic layer was washed with brine and dried on anhydrous sodium sulfate. The solvent was removed under reduced pressure, and the residue was purified by silica gel column (4:6 hexane/ethyl acetate to ethyl acetate to 2:1 ethyl acetate/methanol) followed by trituration with water to give 5-[4-cyano-2-(formylaminoethyl)phenoxy]-1,3-dihydro-1-hydroxy-2,1-benzoxaborole (685 mg, 68%).

$^1$H-NMR (300 MHz, DMSO-$d_6$) δ (ppm) 4.40 (d, J=5.9 Hz, 1H), 4.95 (s, 1H), 6.92 (d, J=8.5 Hz, 1H), 7.07 (dd, J=7.9, 1.8 Hz, 1H), 7.11 (s, 1H), 7.72 (dd, J=8.5, 2.1 Hz, 1H), 7.77 (d, J=8.2 Hz, 1H), 8.15 (s, 1H), 8.53 (br t, 1H), 9.21 (s, 1H).

19z 5-(2-Aminomethyl-4-cyanophenoxy)-1,3-dihydro-1-hydroxy-2,1-benzoxaborole hydrochloride (D26)

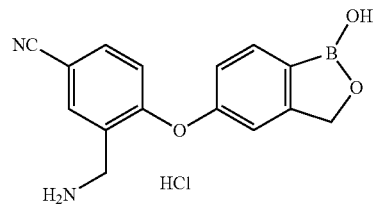 [SMILES: N#Cc1ccc(Oc2ccc3c(c2)COB3O)c(CN)c1 ; Cl]

To a solution of 5-[4-cyano-2-(formylaminomethyl)phenoxy]-1,3-dihydro-1-hydroxy-2,1-benzoxaborole (250 mg, 0.812 mmol) in ethanol (16 mL) was added 6 M HCl (4 mL), and the mixture was refluxed for 2 h. The solvent was removed under reduced pressure, and the residue was treated with ether to give 5-(2-aminomethyl-4-cyanophenoxy)-1,3-dihydro-1-hydroxy-2,1-benzoxaborole hydrochloride (247 mg, 98%).

$^1$H-NMR (300 MHz, DMSO-$d_6$) δ (ppm) 4.14 (br s, 2H), 4.97 (s, 2H), 6.88 (d, J=8.8 Hz, 1H), 7.16 (dd, J=7.9, 2.1 Hz, 1H), 7.21 (s, 1H), 7.78-7.86 (m, 2H), 8.08 (d, J=1.8 Hz, 1H), 8.54 (br s, 3H), 9.29 (s, 1H).

19aa Ethyl 2-ethoxy-6-(1-hydroxy-1,3-dihydrobenzo[c][1,2]oxaborol-5-yloxy)nicotinate (D27)

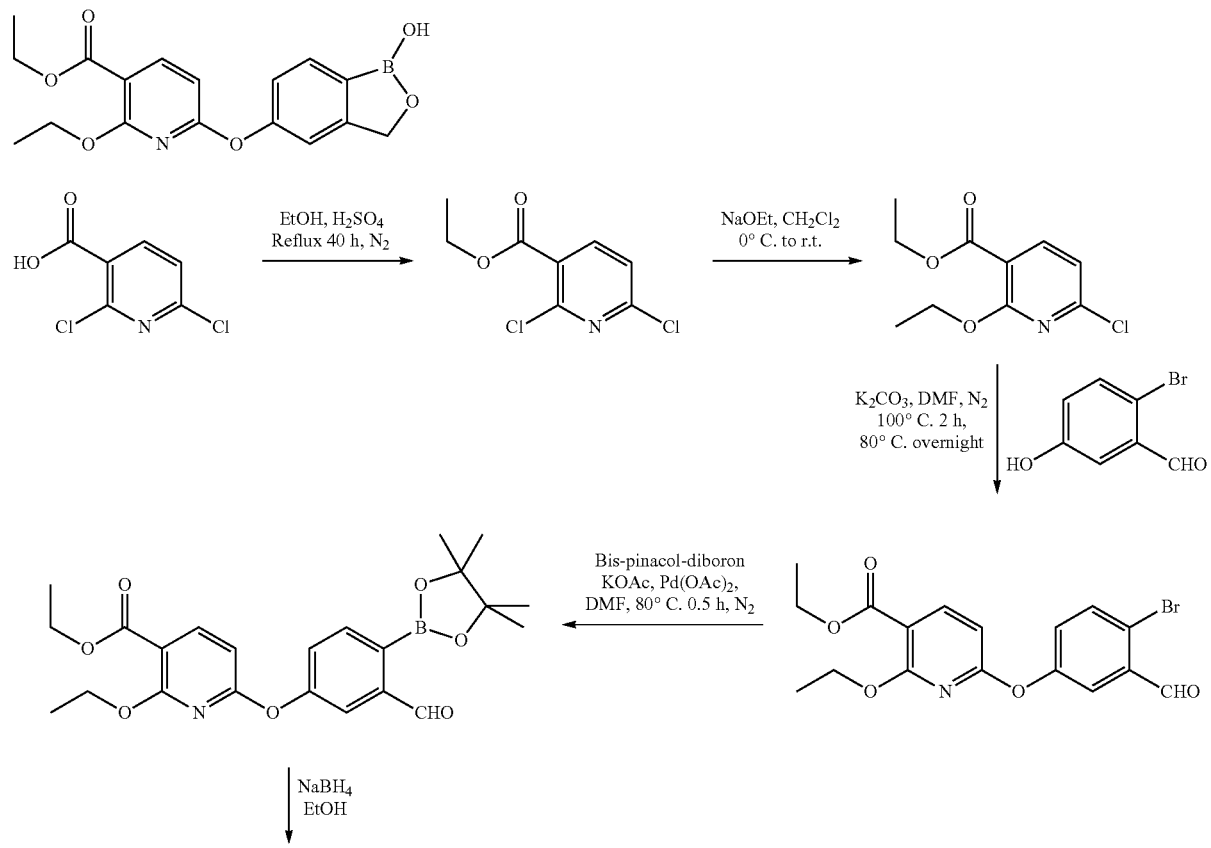

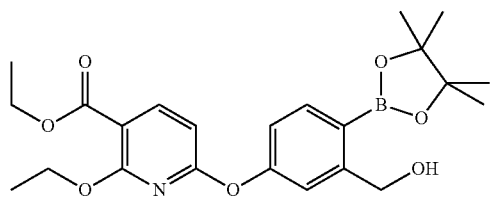 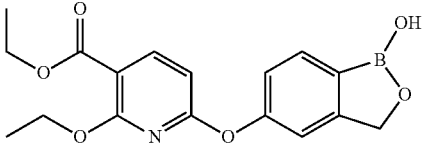

Esterification of 2,6-dichloronicotinic acid (25.5 g, 0.1328 mmol) in EtOH (200 proof, 200 mL) catalyzed with 96% $H_2SO_4$ (1.7 g) at refluxing temperature for 40 h under $N_2$ gave the desired ethyl 2,6-dichloronicotinate as grey solid (24.89 g, 0.1131 mmol, yield 85.2%) after a normal work-up.

$^1$H NMR (300 MHz, DMSO-$d_6$): δ 8.30 (d, J=8.1 Hz, 1H), 7.71 (d, J=8.1 Hz, 1H), 4.33 (q, J=7.2 Hz, 2H) and 1.30 (t, J=7.2 Hz, 3H) ppm.

Substitution of NaOEt (5.8 g, 1.5 eq) with ethyl 2,6-dichloronicotinate (12.5 g, 56.8 mmol) in $CH_2Cl_2$ was performed (Reference: US2005/0288299A1) by slow addition of the base solid to the bis-chloro ester solution at 0° C. and stirred for 3 h with the cooling, then overnight from 0° C. to r.t. More $CH_2Cl_2$ and water were added, separated, dried and evaporated giving a liquid (11.62 g) that crystallized slowly overnight. The solid was recrystallized from dry-ice-cooling pentane affording the desired ethyl 6-chloro-2-ethoxynicotinate as white crystals (9.45 g, 41.15 mmol, yield 72.4%).

M.p. 33-35° C. $^1$H NMR (300 MHz, DMSO-$d_6$): δ 8.13 (d, J=8.1 Hz, 1H), 8.16 (d, J=8.1 Hz, 1H), 4.34 (q, J=7.2 Hz, 2H), 4.24 (q, J=7.2 Hz, 2H), 1.31 (t, J=7.2 Hz, 3H) and 1.27 (t, J=7.2 Hz, 3H) ppm.

Coupling reaction of ethyl 6-chloro-2-ethoxynicotinate (9.45 g, 41.15 mmol) with 2-bromo-5-hydroxybenzaldehyde (8.27 g, 41.15 mmol) in the presence of $K_2CO_3$ (8.53 g, 1.5 eq) in DMF (100 mL) for 2 h at 100° C. and overnight at 80° C. under $N_2$ provided a crude residue after filtration and evaporation. The residue was purified by silica gel column chromatography (hexane:EtOAc=7:1, v/v) and recrystallization from hexane and pentane affording the desired ethyl 6-(4-bromo-3-formylphenoxy)-2-ethoxynicotinate as white solid (8.35 g, 21.15 mmol, yield 51.4%).

$^1$H NMR (300 MHz, DMSO-$d_6$): δ 10.17 (s, 1H), 8.21 (d, J=8.4 Hz, 1H), 7.85 (d, J=8.4 Hz, 1H), 7.67 (d, J=3.3 Hz, 1H), 7.54 (dd, J=8.4 & 2.8 Hz, 1H), 6.68 (d, J=8.4 Hz, 1H), 4.21 (q, J=7.5 Hz, 2H), 4.05 (q, J=7.2 Hz, 2H), 1.26 (t, J=7.2 Hz, 3H) and 1.14 (t, J=7.1 Hz, 3H) ppm.

Catalytic boronylation of ethyl 6-(4-bromo-3-formylphenoxy)-2-ethoxynicotinate (8.35 g, 21.15 mmol) with bis-pinacol-diboron (6.5 g, 25.38 mmol), KOAc (6.2 g, 63.45 mmol) and Pd(OAc)$_2$ (0.25 g) in DMF (100 mL) at 80° C. for 30 min under $N_2$ generated a single component as monitored by TLC, but another compound was showed up after overnight standing of the reaction mixture at r.t. Normal work-up gave a crude oil (13.5 g) containing the desired ethyl 2-ethoxy-6-(3-formyl-4-(4,4,5,5-tetramethyl-1,3,2-dioxaborolan-2-yl)phenoxy)nicotinate, which was used for the next reaction.

Reduction of the crude oil (13.5 g) containing ethyl 2-ethoxy-6-(3-formyl-4-(4,4,5,5-tetramethyl-1,3,2-dioxaborolan-2-yl)phenoxy)nicotinate with NaBH$_4$ (2.3 g) in EtOH (200 proof, 250 mL) at 0° C. for 30 min was completed as monitored by TLC.

HCl(6N) was added and then evaporated, dissolved in EtOAc, washed with water and purified by silica gel column chromatography (hexane:EtOAc=2:1). $^1$H NMR indicated the oil obtained was actually the uncyclized ethyl 2-ethoxy-6-(3-(hydroxymethyl)-4-(4,4,5,5-tetramethyl-1,3,2-dioxaborolan-2-yl)phenoxy)nicotinate.

Cyclization of ethyl 2-ethoxy-6-(3-(hydroxymethyl)-4-(4,4,5,5-tetramethyl-1,3,2-dioxa-borolan-2-yl)phenoxy)nicotinate obtained above was quickly performed in EtOH and 6N HCl and subsequent evaporation. Water was added to the residue and then acetone was slowly added with sonication to get the crystals that were filtered and washed with water and hexane. The solid was dried under high vacuum overnight giving the desired title compound ethyl 2-ethoxy-6-(1-hydroxy-1,3-dihydrobenzo[c][1,2]oxaborol-5-yloxy) nicotinate (2.287 g, 6.66 mmol).

$^1$H NMR (300 MHz, DMSO-$d_6$): δ 9.22 (s, 1H), 8.18 (d, J=8.1 Hz, 1H), 7.76 (d, J=7.8 Hz, 1H), 7.24 (s, 1H), 7.16 (dd, J=7.8 & 1.8 Hz, 1H), 6.57 (d, J=8.1 Hz, 1H), 4.97 (s, 2H), 4.21 (q, J=7.5 Hz, 2H), 4.09 (q, J=7.2 Hz, 2H), 1.25 (t, J=7.2 Hz, 3H) and 1.16 (t, J=7.2 Hz, 3H) ppm. Purity (HPLC): 100% at both 220 nm and 254 nm. MS: m/z=342 (M−1, ESI−).

19ab 2-(5-cyano-2-(1-hydroxy-1,3-dihydrobenzo[c][1,2]oxaborol-5-yloxy)phenoxy)-N,N-diethylacetamide (D28)

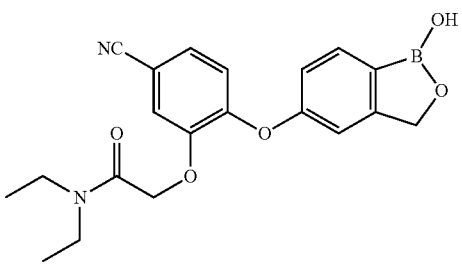 [SMILES: CCN(CC)C(=O)COc1cc(C#N)ccc1Oc1ccc2c(c1)COB2O]

A mixture of 5-[2-(Carboxymethoxy)-4-cyanophenoxy]-1,3-dihydro-1-hydroxy-2,1-benzoxaborole (D17) (1.00 g, 3.08 mmol), EDCI (1.77 g, 9.24 mmol), HOBT (1.25 g, 9.24 mmol), diethylamine (0.96 mL, 9.24 mmol), and 4-dimethylaminopyridine (75 mg, 0.62 mmol) in DMF (20 mL) was stirred at room temperature overnight. Water was added, and the mixture was extracted with ethyl acetate. The organic layer was washed with brine, dried over anhydrous sodium sulfate. The solvent was removed under reduced pressure and the residue was purified with silica gel chromatography (9:1 chloroform/methanol). The combined fractions were put under reduced pressure to remove solvent and then washed with water and toluene. The solvent was again removed under reduced pressure. Another silica gel chromatography column was used (5:5 acetone:hexane). The desired fractions were combined and the solvent was removed under reduced pressure. The residue was recrystallized using hexanes and diisopropylether. Pure 2-(5-cyano-2-(1-hydroxy-1,3-dihydrobenzo[c][1,2]oxaborol-5-yloxy)phenoxy)-N,N-diethylacetamide (0.662 g, 57%) was obtained.

¹H-NMR (300 MHz, DMSO-d₆) δ (ppm) 1.00 (t, J=6.75 Hz, 3H), 1.09 (t, J=7.03, 3H), 3.2-3.3 (m, 4H), 4.9 (d, J=9.01 Hz, 1H), 6.9-7.0 (m, 2H), 7.1-7.2 (dd, J=8.36, 1.03 Hz, 1H), 7.42 (m, 1H), 7.54 (s, 1H), 7.69 (m, 1H), 9.12 (d, J=1.17 Hz, 1H).

19ac 4-(2-(5-cyano-2-(1-hydroxy-1,3-dihydrobenzo[c][1,2]oxaborol-5-yloxy)phenoxy)acetyl)-1-methylpiperazine hydrochloride (D29)

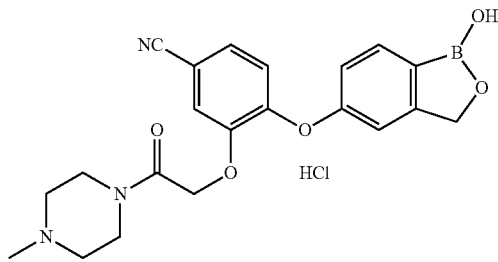 [SMILES: CN1CCN(C(=O)COc2cc(C#N)ccc2Oc2ccc3c(c2)COB3O)CC1 ; Cl]

This compound was prepared in the similar manner to that of (D28).

¹H-NMR (300 MHz, DMSO-d₆) δ (ppm) 2.73 (s, 3H), 2.9-3.1 (m, 4H), 3.3-3.5 (m, 2H), 3.8-3.9 (m, 1H), 4.3-4.4 (m, 1H), 4.90 (s, 2H), 5.02 (d, J=8.2 Hz, 2H), 6.96 (m, 2H), 7.14 (d, J=8.2 Hz, 1H), 7.45 (d, J=8.2 Hz, 1H), 7.62 (s, 1H), 7.71 (d, J=8.8 Hz, 1H), 9.15 (s, 1H), 10.91 (s, 1H).

19ad 5-[4-Cyano-2-(tert-butoxycarbonylmethoxy)phenoxy]-1,3-dihydro-1-hydroxy-2,1-benzoxaborole (D30)

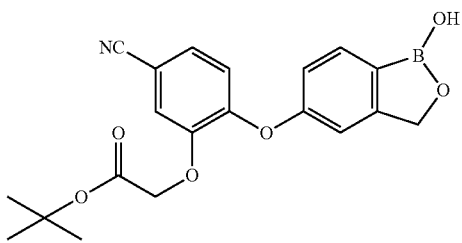 [SMILES: CC(C)(C)OC(=O)COc1cc(C#N)ccc1Oc1ccc2c(c1)COB2O]

This compound was obtained in a similar manner to Example 191 (D12) from 5-(4-cyano-2-hydroxyphenoxy)-1,3-dihydro-1-hydroxy-2,1-benzoxaborole (D14) and tertiary butyl bromoacetate.

¹H-NMR (300 MHz, DMSO-d₆) δ (ppm) 1.38 (s, 9H), 4.79 (s, 2H), 4.90 (s, 2H), 6.96 (m, 2H), 7.14 (d, J=8.5 Hz, 1H), 7.46 (dd, J=1.8, 8.5 Hz, 1H), 7.59 (d, J=1.0 Hz, 1H), 7.65 (m, 1H), 9.13 (s, 1H).

19ae 2-((5-cyano-2-(1-hydroxy-1,3-dihydrobenzo[c][1,2]oxaborol-5-yloxy)phenoxy)methyl)pyridine hydrochloride (D31)

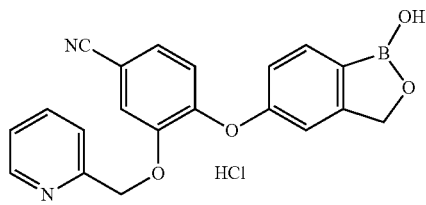 [SMILES: N#Cc1ccc(Oc2ccc3c(c2)COB3O)c(OCc2ccccn2)c1 ; Cl]

This compound was obtained in a similar manner to Example 191 (D12) from 5-(4-cyano-2-hydroxyphenoxy)-1,3-dihydro-1-hydroxy-2,1-benzoxaborole (D14) and 2-chlorometylpyridine hydrochloride.

¹H-NMR (300 MHz, DMSO-d₆) δ (ppm) 4.89 (s, 2H), 5.32 (s, 2H), 6.70 (m, 2H), 7.20 (d, J=8.2 Hz, 1H), 7.26 (d, J=7.9 Hz, 1H), 7.4-7.6 (m, 2H), 7.70 (d, J=8.8 Hz, 1H), 7.81 (s, 1H), 7.88 (t, J=7.9 Hz, 1H), 8.60 (d, J=5.0, 1H).

19af 4-(5-cyano-2-(1-hydroxy-1,3-dihydrobenzo[c][1,2]oxaborol-5-yloxy)benzyl)morpholine hydrochloride (D32)

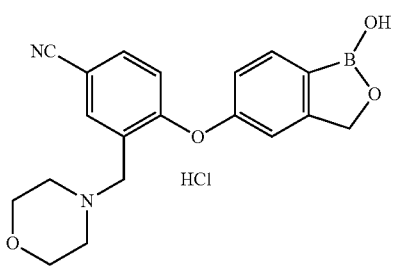 [SMILES: N#Cc1ccc(Oc2ccc3c(c2)COB3O)c(CN2CCOCC2)c1 ; Cl]

A mixture of 5-(4-Cyano-2-formylphenoxy)-1,3-dihydro-1-hydroxy-2,1-benzoxaborole (D23) (0.400 g, 1.43 mmol), morpholine (0.375 mL, 4.29 mmol), and acetic acid (0.246 mL, 4.29 mmol) in methanol (10 mL) was stirred for five minutes under nitrogen at room temperature. Cyanoborohydride (0.270 g, 4.29 mmol) was added, and the mixture was stirred at room temperature under nitrogen for two hours. Water was added and the mixture was extracted with ethyl acetate. The organic layer was washed with brine and dried over anhydrous sodium sulfate. The solvent was removed under reduced pressure and the residue was purified by silica gel chromatography (5:5 ethyl acetate: hexanes to 4:1 dichloromethane/methanol). The desired fractions were combined and the solvent was removed under reduced pressure. Water and toluene were added and removed under reduced pressure to give pure 4-(1-hydroxy-1,3-dihydrobenzo[c][1,2]oxaborol-5-yloxy)-3-(morpholinomethyl)benzonitrile (0.399 g, 80%).

¹H-NMR (300 MHz, DMSO-d₆) δ (ppm) 2.35 (m, 4H), 3.53 (m, 6H), 4.93 (s, 2H), 7.00 (m, 3H), 7.73 (dd, J=8.07, 2.50 Hz, 2H), 7.90 (d, 2.35 Hz, 1H), 9.18 (s, 1H).

A mixture of 4-(1-hydroxy-1,3-dihydrobenzo[c][1,2]oxaborol-5-yloxy)-3-(morpholinomethyl)benzonitrile (0.391 g, 1.12 mmol), 4 M HCl in dioxane (0.335 mL, 1.34 mmol), ether (10 mL), and THF (3 mL) were stirred at room temperature for five minutes. Filtered the precipitate and dried under reduced pressure. The solid was washed in THF and the solid was again filtered and dried under reduced pressure to give the target compound (0.258 g, 60%).

¹H-NMR (300 MHz, DMSO-d₆) δ (ppm) 3.2-3.3 (m, 3H), 3.7-4.0 (m, 5H), 4.47 (s, 2H), 4.98 (s, 2H), 6.90 (d, J=8.8 Hz, 1H), 7.20 (d, J=7.9 Hz, 1H), 7.27 (s, 1H), 7.8-7.9 (m, 2H), 8.28 (s, 1H), 9.29 (br s, 1H), 11.09 (br s, 1H).

19ag 1-(5-cyano-2-(1-hydroxy-1,3-dihydrobenzo[c][1,2]oxaborol-5-yloxy)benzyl)-4-methylpiperazine-1,4-diium (D33)

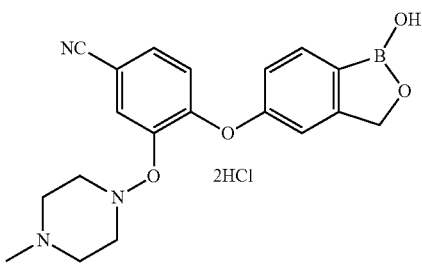 [SMILES: CN1CCN(Oc2cc(C#N)ccc2Oc2ccc3c(c2)COB3O)CC1 ; "2HCl"]

This compound was obtained in a similar manner to Example 19af (D32) from 5-(4-Cyano-2-formylphenoxy)-1,3-dihydro-1-hydroxy-2,1-benzoxaborole (D23) and 1-methylpiperazine.

$^1$H-NMR (300 MHz, DMSO-d$_6$) δ (ppm) 2.77 (s, 3H), 3.0-4.2 (m, 10H), 4.96 (s, 2H), 6.92 (d, J=8.8 Hz, 1H), 7.15 (d, J=7.6 Hz, 1H), 7.20 (s, 1H), 7.83 (m, 2H), 8.15 (s, 1H), 9.2 (br s, 1H), 11.1 (br s, 1H), 19ah 1-(5-cyano-2-(1-hydroxy-1,3-dihydrobenzo[c][1,2]oxaborol-5-yloxy)phenyl)-N,N-dimethylmethanaminium (D34)

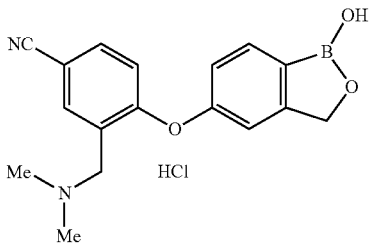 [SMILES: CN(C)Cc1cc(C#N)ccc1Oc1ccc2c(c1)COB2O ; Cl]

This compound was obtained in a similar manner to Example 19af (D32) from 5-(4-cyano-2-formylphenoxy)-1,3-dihydro-1-hydroxy-2,1-benzoxaborole (D23) and dimethylamine.

$^1$H-NMR (300 MHz, DMSO-d$_6$) δ (ppm) 2.77 (s, 6H), 4.41 (s, 2H), 4.97 (s, 2H), 6.90 (d, J=8.5 Hz, 1H), 7.19 (dd, J=8.05, 1.86 Hz, 1H), 7.26 (s, 1H), 7.84 (d, J=8.2, 1H), 7.88 (d, J=2.4, 1H), 8.25 (d, J=2.1, 1H), 9.32 (br s, 1H).

19ai Synthesis of 4-(1-Hydroxy-1,3-dihydro-benzo[c][1,2]oxaborol-5-yloxy)-2-methoxy-benzoic acid ethyl ester (D35)

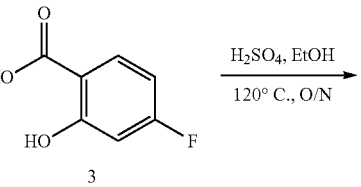

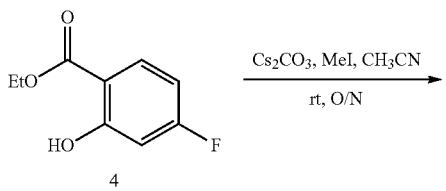

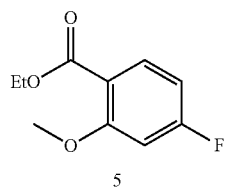

-continued

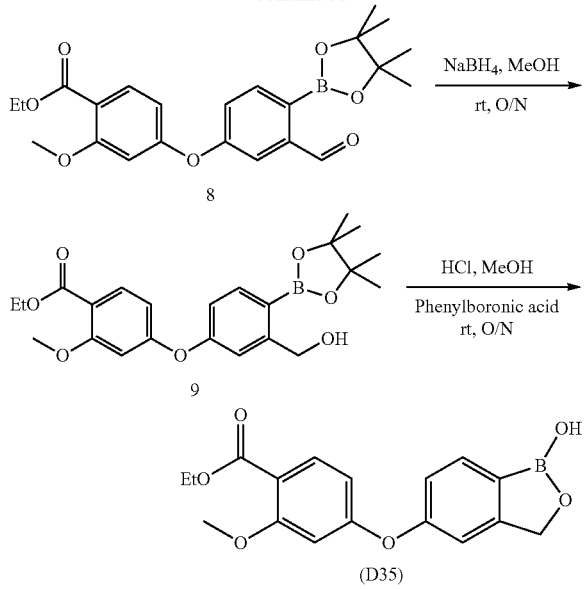

4-Bromo-3-[1,3]dioxolan-2-yl-phenol (2)

To a solution of 2-bromo-5-hydroxy-benzaldehyde compound 1 (15.0 g, 74.62 mmol) in toluene (100 mL) was added ethylene glycol (12.5 mL, 223.86 mmol) and p-TSA (1.42 g, 7.46 mmol). The solvent was removed under reduced pressure to give crude product 2 (20.0 g crude), which was used in the next step without further purification. $^1$H NMR 400 MHz (CDCl$_3$) δ: 7.38 (d, J=8.6 Hz, 1H), 7.01 (d, J=2.7 Hz, 1H), 6.62 (d, J=8.2, 2.3 Hz, 1H), 6.01 (s, 1H), 4.20-4.01 (m, 4H).

4-Fluoro-2-hydroxy-benzoic acid ethyl ester (4)

To a solution of 4-fluoro-2-hydroxybenzoic acid compound 3 (20.0 g, 128.11 mmol) in ethanol (100 mL) was added conc. sulfuric acid (10 mL). The resulting mixture was heated in a 120° C. oil bath O/N. The solvent was removed under reduced pressure to give crude product, which was purified by column chromatography (silica gel, 10% EtOAc in hexane) to afford the title compound 4 (19.9 g, 85%) as a colorless solid. $^1$H NMR 400 MHz (CDCl$_3$) δ: 11.15 (s, 1H), 7.83 (d, J=6.6 Hz, 1H), 7.81 (d, J=6.6 Hz, 1H), 6.62 (dd, J=10.1, 2.3 Hz, 1H), 6.61 (dd, J=7.0, 2.0 Hz, 1H), 4.41 (q, J=7.0 Hz, 2H), 1.42 (t, J=7.0 Hz, 3H); MS (ES) m/z: 185 (M+1)$^+$.

4-Fluoro-2-methoxy-benzoic acid ethyl ester (5)

To a solution of compound 4 (19.9 g, 0.109 mol) in acetonitrile (200 mL) was added cesium carbonate (42.0 g, 0.129 mol). The resulting mixture was stirred at rt for 30 min. followed by addition of methyl iodide (13.5 mL, 0.218 mol). The resulting mixture was stirred at rt O/N and filtered through Celite. The solvent was removed under reduced pressure to give crude product 5 (20.0 g, 93%) and used in the next step without further purification. $^1$H NMR 400 MHz (CDCl$_3$) δ: 7.81-7.78 (m, 1H), 6.60-6.58 (m, 2H), 4.38 (q, J=7.0 Hz, 2H), 3.82 (s, 3H), 1.39 (t, J=7.0 Hz, 3H); MS (ES) m/z: 199 (M+1)'.

4-(4-Bromo-3-[1,3]dioxolan-2-yl-phenoxy)-2-methoxy-benzoic acid ethyl ester (6)

To a solution of compound 2 (9.27 g, 37.83 mmol) in DMSO (50 mL) was added potassium carbonate (15.68 g, 113.48 mmol). The resulting mixture was stirred at rt for 30 min. followed by addition of compound 5 (8.99 g, 45.39 mmol). The resulting mixture was heated at 120° C. O/N. The reaction mixture was diluted with EtOAc (100 mL) and washed with water (50 mL). The organic layer was dried over Na$_2$SO$_4$, and concentrated under reduced pressure to give crude product, which was purified by column chromatography (silica gel, 10% EtOAc in hexane) to afford the title compound 6 (5.6 g, 35%) as a pale yellow solid. $^1$H NMR 400 MHz (CDCl$_3$) δ:
7.81 (d, J=9.0 Hz, 1H), 7.59 (d, J=8.6 Hz, 1H), 7.35 (s, 1H), 6.97 (dd, J=8.6, 2.7 Hz, 1H), 6.60 (d, J=2.3 Hz, 1H), 6.49 (dd, J=8.6, 2.4 Hz, 1H), 6.01 (s, 1H), 4.39 (q, J=7.4 Hz, 2H), 4.20-4.01 (m, 4H), 3.81 (s, 3H), 1.40 (t, J=7.4 Hz, 3H); MS (ES) m/z: 423 (M+1)$^+$, 425 (M+3)$^+$.

4-(4-Bromo-3-formyl-phenoxy)-2-methoxy-benzoic acid ethyl ester (7)

To a solution of compound 6 (5.6 g, 13.23 mmol) in THF (50 mL) at 0° C. was added 2N HCl (50 mL). The resulting mixture was stirred at rt O/N. The reaction mixture was diluted with EtOAc (100 mL) and washed with water (50 mL). The organic layer was dried over Na$_2$SO$_4$, and concentrated under reduced pressure to give crude product, which was purified by column chromatography (silica gel, 10% EtOAc in hexane) to afford the title compound 7 (3.0 g, 60%) as a pale yellow solid.
$^1$H NMR 400 MHz (CDCl$_3$) δ: 10.35 (s, 1H), 7.82 (d, J=8.6 Hz, 1H), 7.60 (d, J=8.6 Hz, 1H), 7.58 (d, J=2.7 Hz, 1H), 7.19 (dd, J=8.6, 3.1 Hz, 1H), 6.60 (d, J=2.0 Hz, 1H), 6.51 (dd, J=8.6, 2.3 Hz, 1H), 4.39 (q, J=7.0 Hz, 2H), 3.81 (s, 3H), 1.40 (t, J=7.0 Hz, 3H); MS (ES) m/z: 379 (M+1)$^+$, 381 (M+3)$^+$.

4-[3-Formyl-4-(4,4,5,5-tetramethyl-[1,3,2]dioxaborolan-2-yl)-phenoxy]-2-methoxy-benzoic acid ethyl ester (8)

To a solution of compound 7 (3.0 g, 7.91 mmol) in 1,4-dioxane (20 mL) was added bis(pinacolato)diboron (2.41 g, 9.49 mmol), potassium acetate (2.33 g, 23.73 mmol), and [1,1'-bis(diphenylphosphino)ferrocene]palladium(II)chloride (0.3 g, 0.40 mmol). Nitrogen gas was passed through the mixture for 10 min. and the suspension was heated at 80° C. for 1 h. The mixture was passed through Celite® and concentrated under reduced pressure to give crude product, which was purified by column chromatography (silica gel, 10% EtOAc in hexane) to afford the title compound 8 (3.22 g, 96%) as a colorless oil. $^1$H NMR 400 MHz (CDCl$_3$) δ: 10.61 (s, 1H), 7.98 (d, J=8.2 Hz, 1H), 7.81 (d, J=8.6 Hz, 1H), 7.60 (d, J=2.3 Hz, 1H), 7.35 (d, J=5.5 Hz, 2H), 6.62 (d, J=2.0 Hz, 1H), 6.58 (d, J=8.6 Hz, 1H), 4.39 (q, J=7.0 Hz, 2H), 3.81 (s, 3H), 1.42 (s, 12H), 1.20 (t, J=7.0 Hz, 3H).

4-[3-Hydroxymethyl-4-(4,4,5,5-tetramethyl-[1,3,2]dioxaborolan-2-yl)-phenoxy]-2-methoxy-benzoic acid ethyl ester (9)

To a solution of compound 8 (3.22 g, 7.55 mmol) in methanol (40 mL) was added sodium borohydride (0.373 g, 9.82 mmol) at 0° C. The resulting mixture was stirred at rt for 30 min. The solvent was removed under reduced pressure, diluted with water (50 mL) and extracted with EtOAc (2×50 mL). The combined organic layer was dried over Na₂SO₄, and concentrated under reduced pressure to give crude product and used in the next step without further purification. ¹H NMR 400 MHz (CDCl₃) δ: 7.91 (d, J=8.2 Hz, 1H), 7.82 (d, J=8.6 Hz, 1H), 7.01 (s, 1H), 6.98 (d, J=8.2 Hz, 1H), 6.60 (s, 1H), 6.67 (d, J=8.6 Hz, 1H), 4.65 (s, 2H), 4.39 (q, J=7.0 Hz, 2H), 3.81 (s, 3H), 1.42 (s, 12H), 1.20 (t, J=7.0 Hz, 3H).

19ai 4-(1-Hydroxy-1,3-dihydro-benzo[c][1,2]oxaborol-5-yloxy)-2-methoxy-benzoic acid ethyl ester (D35)

To a solution of compound 9 (2.0 g, 4.67 mmol) in methanol (50 mL) was added 6N HCl (10 mL) and phenylboronic acid (2.85 g, 23.36 mmol). The resulting mixture was stirred at rt O/N. The solvent was removed under reduced pressure to give crude product, which was purified by reverse phase prep HPLC using CH₃CN/H₂O (with 0.1% acetic acid) as the eluent to afford the title compound (D35) (0.66 g, 39%) as a white solid after lyophilization. Mp 64.9-65.2° C. ¹H NMR 400 MHz (DMSO-d₆) δ: 9.20 (s, 1H), 7.80 (d, J=8.2 Hz, 1H), 7.72 (d, J=8.6 Hz, 1H), 7.18 (s, 1H), 7.16 (dd, J=8.2, 2.0 Hz, 1H), 6.80 (s, 1H), 6.60 (dd, J=8.6, 2.3 Hz, 1H), 4.98 (s, 2H), 4.21 (q, J=7.0 Hz, 2H), 3.81 (s, 3H), 1.20 (t, J=7.0 Hz, 3H); MS (ES) m/z: 329 (M+1)⁺; HPLC purity: 99.46% (220 nm), 100% (254 nm).

19aj 4-(1-Hydroxy-1,3-dihydro-benzo[c][1,2]oxaborol-5-yloxy)-2-methoxy-benzoic acid (D36)

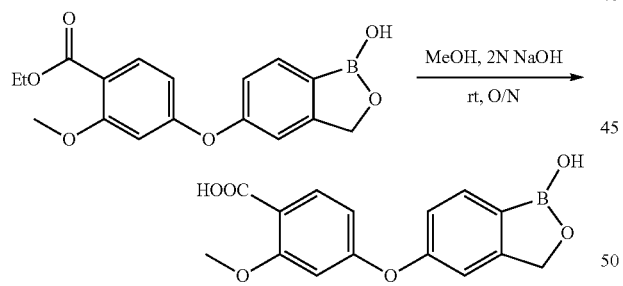

To a solution of compound (D35) (0.1 g, 0.31 mmol) in methanol (2 mL) was added 2N NaOH (1 mL). The resulting mixture was stirred at rt O/N. The solvent was removed under reduced pressure to give crude product, which was dissolved in H₂O (1 mL) and acidified using 1N HCl. The solid obtained which was filtered and washed with ether (10 mL) to afford the title compound (D36) (78 mg, 86%) as a white solid. Mp 109.6-110.1° C. ¹H NMR 400 MHz (DMSO-d₆) δ: 9.20 (s, 1H), 7.80 (d, J=8.2 Hz, 1H), 7.75 (d, J=8.6 Hz, 1H), 7.18 (s, 1H), 7.15 (d, J=9.4 Hz, 1H), 6.80 (s, 1H), 6.60 (d, J=8.6 Hz, 1H), 4.98 (s, 2H), 3.81 (s, 3H); MS (ES) m/z: 301 (M+1)⁺; HPLC purity: 100% (220 nm), 99.79% (254 nm).

19ak 2-Cyclopentyloxy-4-(1-hydroxy-1,3-dihydro-benzo[c][1,2]oxaborol-5-yloxy)-benzonitrile (D37)

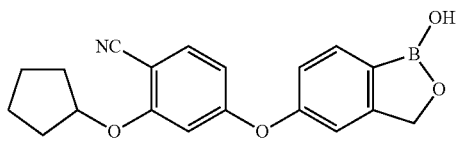 [SMILES: N#Cc1ccc(Oc2ccc3c(c2)COB3O)cc1OC1CCCC1]

To a solution of 2-hydroxy-4-(1-hydroxy-1,3-dihydro-benzo[c][1,2]oxaborol-5-yloxy)-benzonitrile (D10) (200 mg, 0.75 mmol) in THF (50 mL) and DMF (20 mL) was added NaH (47 mg, 95%, 1.87 mmol) portion-wise. The mixture was stirred at room temperature for 5 minutes, followed by the slow addition of cyclopentyl iodide (0.26 mL, 2.25 mmol). The reaction was stirred at room temperature for 24 hours. After the reaction, all volatile components were evaporated under vacuum. The residue was purified using silica gel column chromatography, eluting with 25% EtOAc/hexane, afforded 36 mg of the title compound in 12.6% yield. ¹H NMR 400 MHz (DMSO-d₆) δ: 9.23 (s, 1H), 7.78 (d, J=7.8 Hz, 1H) 7.69 (d, J=8.6 Hz, 1H), 7.17 (s, 1H), 7.10 (dd, J=2.0, 8.2 Hz, 1H), 6.90 (d, J=2.3 Hz, 1H), 6.56 (dd, J=1.9, 8.6 Hz, 1H), 4.96 (s, 2H), 4.95 (t, J=5.8 Hz, 1H), 1.95-1.55 (m, 8H); MS (ES) m/z: 336 (M+H)⁺; HPLC purity: 99.15% (220 nm), 99.62% (MaxPlot).

19al [2-Cyano-5-(1-hydroxy-1,3-dihydro-benzo[c][1,2]oxaborol-5-yloxy)-phenoxy]-acetic acid ethyl ester (D38)

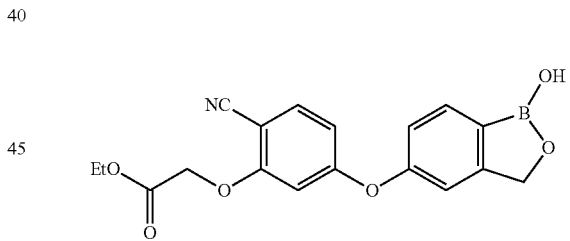

To a solution of 2-hydroxy-4-(1-hydroxy-1,3-dihydro-benzo[c][1,2]oxaborol-5-yloxy)-benzonitrile (D10) (300 mg, 1.12 mmol) in THF (50 mL) was added NaH (95 mg, 60%, 2.36 mmol) portion-wise. The mixture was stirred at room temperature for 5 minutes, followed by the slow addition of ethyl bromoacetate (0.262 mL, 2.36 mmol). The reaction was heated at 70° C. overnight.

After the cooling of the reaction solution to room temperature, the mixture was filtered. The filtrate was evaporated under vacuum. The residue was purified using reverse phase chromatography, eluting from 5% MeOH/H₂O to 90% MeOH/H₂O, afforded 320 mg of the title compound in 81% yield. ¹H NMR 400 MHz (DMSO-d₆) δ: 9.25 (s 1H), 7.78 (d, J=8.0 Hz, 1H), 7.75 (d, J=8.4 Hz, 1H), 7.14 (d, J=1.6 Hz, 1H), 7.08 (dd, J=1.6, 7.6 Hz, 1H), 6.86 (d, J=2.0 Hz, 1H), 6.64 (dd, J=2.4, 8.8 Hz, 1H), 5.00 (s, 2H), 4.97 (s, 2H), 4.13 (q, J=6.8

Hz, 2H), 1.16 (t, 6.8 Hz, 3H); MS (ES) m/z: 354 (M+H)⁺; HPLC purity: 99.11% (220 nm), 99.14% (254 nm).

19am [2-Cyano-5-(1-hydroxy-1,3-dihydro-benzo[c][1,2]oxaborol-5-yloxy)-phenoxy]-acetic acid (D39)

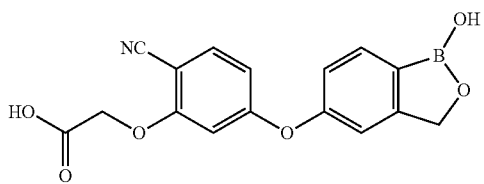 [SMILES: N#Cc1ccc(Oc2ccc3c(c2)COB3O)cc1OCC(=O)O]

To a clear solution of [2-cyano-5-(1-hydroxy-1,3-dihydro-benzo[c][1,2]oxaborol-5-yloxy)-phenoxy]-acetic acid ethyl ester ((D38), 90 mg, 0.25 mmol) in THF (20 mL) was added LiOH (15.3 mg, 0.76 mmol) and water (5 mL). The resulting mixture was stirred at room temperature for 2 hours. Then 1 N HCl was slowly added to pH 2. The mixture was evaporated under vacuum. The residue was purified with reverse phase chromatography, eluting from 5% MeOH/H₂O to 90% MeOH/H₂O, afforded 48 mg of the title compound in 58% yield. ¹H NMR 400 MHz (CD₃OD) δ: 7.70 (d, J=7.8 Hz, 1H), 7.59 (d, J=8.6 Hz, 1H), 7.09 (s, 1H), 7.05 (dd, J=1.9, 8.21 Hz, 1H), 6.66 (d, J=1.9 Hz, 1H), 6.63 (dd, J=1.9, 8.6 Hz, 1H), 5.06 (s, 2H), 4.78 (s, 2H); MS (ES) m/z: 326 (M+H)¹; HPLC purity: 96.33% (220 nm), 96.44% (254 nm).

19an [2-Cyano-5-(1-hydroxy-1,3-dihydro-benzo[c][1,2]oxaborol-5-yloxy)-phenoxy]-acetic acid tert-butyl ester (D40)

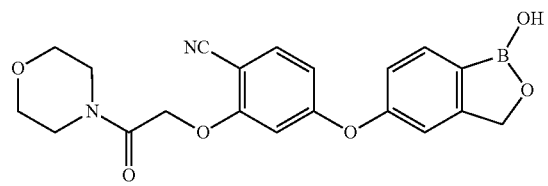

To a solution of 2-hydroxy-4-(1-hydroxy-1,3-dihydro-benzo[c][1,2]oxaborol-5-yloxy)-benzonitrile (D10) (200 mg, 0.75 mmol) in THF (50 mL) was added NaH (43 mg, 95%, 1.81 mmol) portion-wise. The mixture was stirred at room temperature for 5 minutes, followed by the slow addition of t-butyl bromoacetate (0.25 mL, 1.65 mmol). The reaction was heated at 70° C. for 24 hours.

After the cooling of the reaction solution to room temperature, the mixture was filtered. The filtrate was evaporated under vacuum. The residue was purified using reverse phase chromatography, eluting from 5% MeOH/H₂O to 90% MeOH/H₂O, afforded 36 mg of the title compound in 12.6% yield. ¹H NMR 400 MHz (DMSO-d₆) δ: 9.26 (s, 1H), 7.78 (d, J=8.2 Hz, 1H), 7.75 (d, J=8.6 Hz, 1H), 7.14 (s, 1H), 7.09 (dd, J=2.3, 8.2 Hz, 1H), 6.74 (d, J=2.3 Hz, 1H), 6.68 (dd, J=2.0, 8.6 Hz, 1H), 4.96 (s, 2H), 4.86 (s, 2H), 1.37 (s, 9H); MS (ES) m/z: 380 (M–H)⁻; HPLC purity: 99.11% (220 nm), 98.48% (254 nm).

General Procedure for Amide Coupling:

HATU (353 mg, 0.93 mmol) and diisopropylethylamine (0.32 mL, 1.86 mmol) were added to a solution of [2-cyano-5-(1-hydroxy-1,3-dihydro-benzo[c][1,2]oxaborol-5-yloxy)-phenoxy]-acetic acid ((D39), 150 mg, 0.46 mmol) in DMF (4 mL) at rt and stirred for 1 minute. The corresponding amine (0.93 mmol) was added and the reaction mixture was stirred overnight at rt. The reaction mixture was diluted with distilled water (300 mL) and extracted with ethyl acetate (4×400 mL). The organic extracts were combined, dried over Na₂SO₄ and concentrated to give a crude oil. All crudes were purified by reverse phase HPLC using a biphasic solvent system of 0.1% AcOH (aqueous) and acetonitrile which eluted as a gradient. Pure fractions obtained from column were combined and lyophilized to give final product in good purity.

19ao 4-(1-Hydroxy-1,3-dihydro-benzo[c][1,2]oxaborol-5-yloxy)-2-(2-morpholin-4-yl-2-oxo-ethoxy)-benzonitrile (D41)

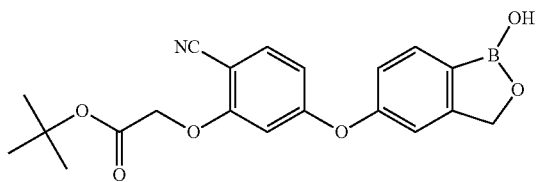 [SMILES: CC(C)(C)OC(=O)COc1cc(Oc2ccc3c(c2)COB3O)ccc1C#N]

Following the general procedure, morpholine (80 μL, 0.93 mmol) was coupled with [2-cyano-5-(1-hydroxy-1,3-dihydro-benzo[c][1,2]oxaborol-5-yloxy)-phenoxy]-acetic acid ((D39), 150 mg, 0.46 mmol) to give a crude oil containing (D41). Purification by reverse phase HPLC followed by lyophilization gave a white solid of (D41) (38 mg, 21%). ¹H NMR 400 MHz (d₆-DMSO) δ: 9.32 (br s, 1H), 7.86 (d, J=8.5 Hz, 1H), 7.78 (d, J=8.5 Hz, 1H), 7.21 (br s, 1H), 7.15 (dd, J=9.0, 1.5 Hz, 1H), 6.90 (d, J=1.5 Hz, 1H), 6.65 (dd, J=8.5, 1.5 Hz, 1H), 5.17 (s, 2H), 5.03 (s, 2H), 3.65-3.55 (m, 4H), 3.49-3.40 (m, 4H); MS (ES) m/z: 395 (M+H)⁺; HPLC purity 96.02% (Maxplot), 97.64% (220 nm) and 97.18% (254 nm).

19ap 4-(1-Hydroxy-1,3-dihydro-benzo[c][1,2]oxaborol-5-yloxy)-2-[2-(4-methyl-piperidin-1-yl)-2-oxo-ethoxy]-benzonitrile (D42)

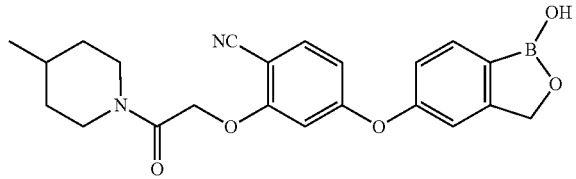 [SMILES: CC1CCN(C(=O)COc2cc(Oc3ccc4c(c3)COB4O)ccc2C#N)CC1]

Following the general procedure, 4-methyl piperidine (110 μL, 0.90 mmol) was coupled with cyano-5-(1-hydroxy-1,3-dihydro-benzo[c][1,2]oxaborol-5-yloxy)-phenoxy]-acetic acid ((D39), 97 mg, 0.30 mmol) to give a crude oil containing (D42). Purification by reverse phase HPLC followed by lyophilization gave a white solid of (D42) (42 mg, 35%). ¹H NMR 400 MHz (d₆-DMSO) δ: 9.25 (br s, 1H), 7.78 (d, J=7.0 Hz, 1H), 7.73 (d, J=7.0 Hz, 1H), 7.13 (br s, 1H), 7.08 (dd, J=7.5, 2.0 Hz, 1H), 6.74 (d, J=2.0 Hz, 1H), 6.62 (dd, J=7.5. 2.0 Hz, 1H), 5.08 (d, J=10.0 Hz, 1H), 5.02 (d, J=10.0 Hz, 1H), 4.95 (s, 2H), 4.22 (br d, J=10.5 Hz, 1H), 3.65 (br d, J=10.5 Hz), 2.93 (br t, J=10.5 Hz, 1H), 2.52 (br t, J=10.5 Hz, 1H), 1.63-1.50 (m, 3H), 1.08-0.96 (m, 1H), 0.88 (d, J=7.0 Hz, 3H), 0.90-0.80 (m, 1H); MS (ES) m/z: 407 (M+H)⁺; HPLC purity 99.51% (Maxplot), 99.12% (220 nm) and 98.77% (254 nm).

19aq 4-(1-Hydroxy-1,3-dihydro-benzo[c][1,2]ox-aborol-5-yloxy)-2-[2-(4-methyl-piperazin-1-yl)-2-oxo-ethoxy]-benzonitrile hexafluorophosphate (D43)

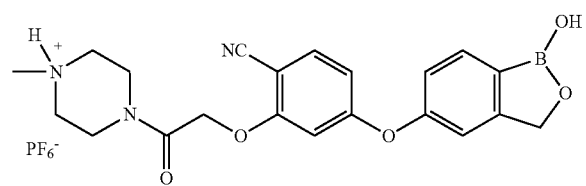

Following the general procedure, 4-methyl piperazine (150 µL, 0.90 mmol) was coupled with cyano-5-(1-hydroxy-1,3-dihydro-benzo[c][1,2]oxaborol-5-yloxy)-phenoxy]-acetic acid ((D39), 150 mg, 0.46 mmol) to give a crude oil containing (D43). Purification by reverse phase HPLC followed by lyophilization gave a white hexaflourophosphate salt (D43) (40 mg, 16% purity). $^1$H NMR 400 MHz (d$_6$-DMSO) δ: 9.65 (br s, 1H), 9.23 (s, 1H), 7.80 (d, J=8.0 Hz, 1H), 7.73 (d, J=8.0 Hz, 1H), 7.13 (s, 1H), 7.08 (d, J=8.0 Hz, 1H), 6.97 (s, 1H), 6.55 (d, J=8.0 Hz, 1H), 5.17 (s, 2H), 4.97 (s, 2H), 3.50-2.76 (br m, 5H), 3.35 (br s, 3H), 2.70 (br s, 3H); $^{19}$F NMR 376 MHz (d$_6$-DMSO) −70.6 (d, J=714 Hz, 6F) ppm; MS (ES) m/z: 408 (M+H)⁺; HPLC purity 94.56% (Maxplot), 95.06% (220 nm) and 95.77% (254 nm).

19ar 6-(1-Hydroxy-1,3-dihydro-benzo[c][1,2]ox-aborol-5-yloxy)-pyridine-2,3-dicarboxylic acid dimethyl ester (D44)

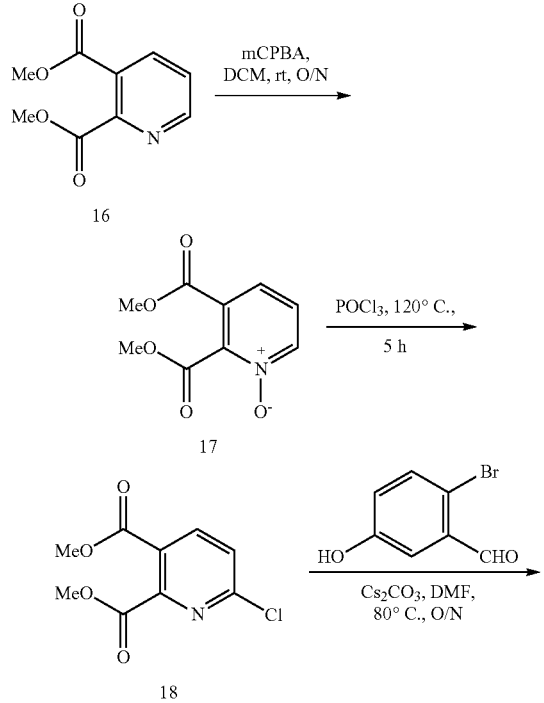

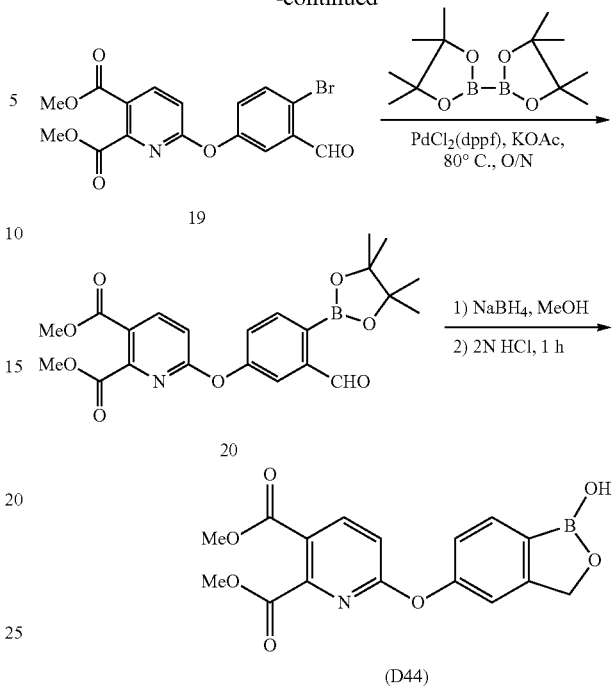

1-Oxy-pyridine-2,3-dicarboxylic acid dimethyl ester (17)

A mixture of pyridine-2,3-dicarboxylic acid dimethyl ester (16, 2.0 g, 10.24 mmol) and m-chloroperbenzoic acid (75% purity, 2.12 g, 12.28 mmol) in chloroform (50 mL) was stirred at room temperature for 16 h. Solid separated was filtered and the filtrate was washed with saturated aq. NaHCO$_3$ (2×50 mL), dried over Na$_2$SO$_4$, filtered, and concentrated to give crude product (2.3 g, quantitative) as yellow solid, which was used for next step without purification. $^1$H NMR 400 MHz (DMSO-d$_6$) δ: 8.65 (d, J=6.6 Hz, 1H), 7.90 (d, J=7.8 Hz, 1H), 7.66 (dd, J=7.8, 6.6 Hz, 1H), 3.91 (s, 6H); MS (ES) m/z: 212 (M+1)⁺.

6-Chloro-pyridine-2,3-dicarboxylic acid dimethyl ester (18)

Solution of 1-oxy-pyridine-2,3-dicarboxylic acid dimethyl ester (17, 4.0 g, 18.94 mmol) in phosphorus oxychloride (30 mL) was heated at 115° C. for 3 h. After being cooled, the mixture was treated with ice-water (50 mL) and chloroform (3×50 mL), basified with saturated aq. NaHCO$_3$ (3×50 mL), and separated the layers. The chloroform layer was dried over Na$_2$SO$_4$, filtered, and concentrated to give crude product (4.0 g) as brown oil, which was used for next step without purification. $^1$H NMR 400 MHz (DMSO-d$_6$) δ: 8.32 (d, J=8.2 Hz, 1H), 7.83 (d, J=8.2 Hz, 1H), 3.85 (s, 6H); MS (ES) m/z: 230 (M+1)⁺, 232 (M+3)⁺.

6-(4-Bromo-3-formyl-phenoxy)-pyridine-2,3-dicarboxylic acid dimethyl ester (19)

To a solution of 6-chloro-pyridine-2,3-dicarboxylic acid dimethyl ester (18, 4.0 g, 17.42 mmols) and 2-bromo-5-hydroxy-benzaldehyde (3.5 g, 17.42 mmol) in DMF (30 mL) was added cesium carbonate (11.35 g, 34.84 mmols). The resulting mixture was heated at 80° C. overnight. DMF was removed under reduced pressure, diluted with EtOAc (100 mL), washed with water (2×25 mL) and brine (50 mL) solution. The combined organic layers were dried over Na$_2$SO$_4$, filtered, and concentrated to give crude product which was purified by column chromatography (Silica gel 20% EtOAc in hexane) to yield title compound 19 (1.14 g, 15%) as a light yellow oil. $^1$H NMR 400 MHz (DMSO-d$_6$) δ: 10.18 (s, 1H), 8.38 (d, J=8.6 Hz, 1H), 7.90 (d, J=8.5 Hz, 1H), 7.66 (s, 1H), 7.55-7.52 (m, 1H), 7.36 (d, J=8.6 Hz, 1H), 3.86 (s, 3H), 3.84 (s, 3H); MS (ES) m/z: 394 (M+1)$^+$, 396 (M+3)$^+$.

6-[3-Formyl-4-(4,4,5,5-tetramethyl-[1,3,2]dioxaborolan-2-yl)-phenoxy]-pyridine-2,3-dicarboxylic acid dimethyl ester (20)

To a degassed solution (30 min with nitrogen) of 6-(4-bromo-3-formyl-phenoxy)-pyridine-2,3-dicarboxylic acid dimethyl ester (19, 1.14 g, 2.89 mmol) in 1,4-dioxane (10 mL) was added bis(pinacolato)diboron (1.10 g, 4.33 mmol), potassium acetate (0.85 g, 8.67 mmol), and [1,1'-bis(diphenylphosphino)ferrocene]palladium(II)chloride (0.16 g, 0.23 mmol). Degassed again (10 min with nitrogen), and the suspension was heated at 90° C. overnight. The mixture was passed through Celite and concentrated under reduced pressure to give crude product, which was purified by column chromatography (silica gel, 20% EtOAc in hexane) to yield the title compound 20 (0.85 g, 70%) as a colorless oil. $^1$H NMR 400 MHz (DMSO-d$_6$) δ: 10.39 (s, 1H), 8.39 (d, J=8.6 Hz, 1H), 7.85 (d, J=7.8 Hz, 1H), 7.69 (s, 1H), 7.56-7.53 (m, 1H), 7.36 (d, J=8.6 Hz, 1H), 3.84 (s, 3H), 3.79 (s, 3H), 1.35 (s, 12H).

19ar 6-(1-Hydroxy-1,3-dihydro-benzo[c][1,2]oxaborol-5-yloxy)-pyridine-2,3-dicarboxylic acid dimethyl ester (D44)

To a solution of 6-[3-formyl-4-(4,4,5,5-tetramethyl-[1,3,2] dioxaborolan-2-yl)-phenoxy]-pyridine-2,3-dicarboxylic acid dimethyl ester (20, 0.77 g, 1.74 mmol) in absolute ethanol (10 mL) was added sodium borohydride (0.08 g, 2.09 mmol) at 0° C. After 1 h at 0° C., 2 M HCl was added until pH is 2-3. The solvent was removed under reduced pressure to give crude product, which was purified by reverse phase prep HPLC using CH$_3$CN/H$_2$O (using neutral condition) as the eluent to yield the title compound (D44) (0.18 g, 30%) as a white solid after lyophilization. Mp 67.5-69.2° C. $^1$H NMR 400 MHz (DMSO-d$_6$) δ: 9.24 (s, 1H), 8.33 (d, J=8.6 Hz, 1H), 7.77 (d, J=7.8 Hz, 1H), 7.25-7.22 (m, 2H), 7.15 (d, J=7.8 Hz, 1H), 4.98 (s, 2H), 3.81 (s, 3H), 3.77 (s, 3H); MS (ES) m/z: 344 (M+1)$^+$; HPLC purity: 99.42% (Maxplot), 99.03% (220 nm), 99.95% (254 nm).

19as 3-Cyano-6-(1-hydroxy-1,3-dihydro-benzo[c][1,2]oxaborol-5-yloxy)-pyridine-2-carboxylic acid ethyl ester (D45)

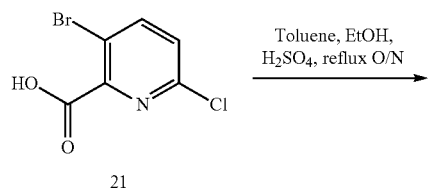

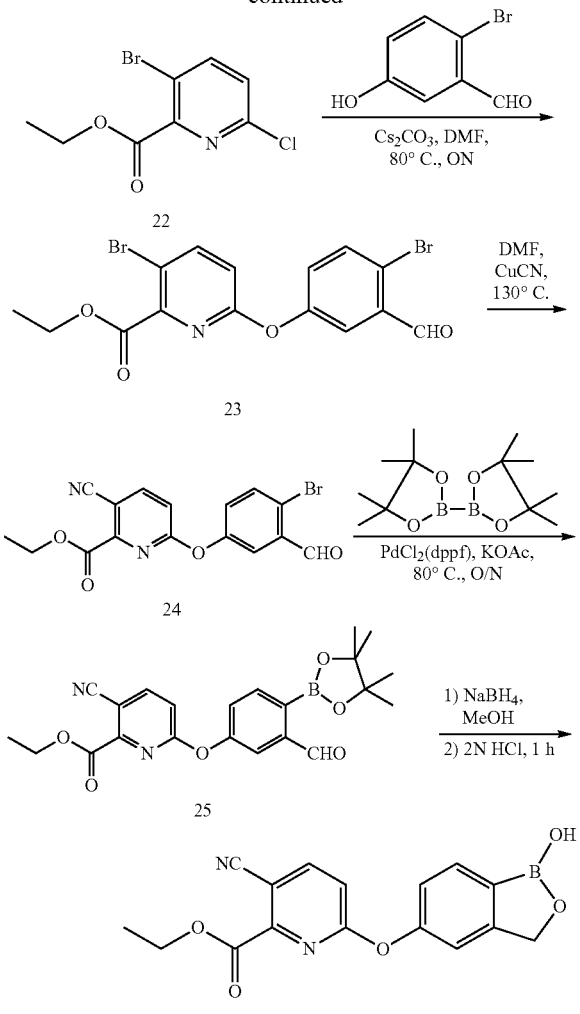

3-Bromo-6-chloro-pyridine-2-carboxylic acid ethyl ester (22)

To a solution of 3-bromo-6-chloropicolinic acid (21, 8.0 g, 33.83 mmols) in a mixture of toluene (80 mL) and ethanol (40 mL) was added sulfuric acid (0.66 mL, 6.76 mmols). The reaction mixture was refluxed for 16 h, then allowed to cool, and partitioned between CHCl$_3$ (200 mL) and saturated aq. NaHCO$_3$ (250 mL). The aqueous layer was extracted with CHCl$_3$ (2×100 mL), and the combined organic layers were dried over Na$_2$SO$_4$, filtered, and concentrated to give crude product which was purified by column chromatography (Silica gel 10% EtOAc in hexane) to yield title compound 22 (9.0 g, quantitative) as transparent oil. $^1$H NMR 400 MHz (DMSO-d$_6$) δ: 8.31 (d, J=8.6 Hz, 1H), 7.68 (d, 1H, J=8.2 Hz), 4.39 (q, J=7.0 Hz, 2H), 1.33 (t, J=7.2 Hz, 3H).

3-Bromo-6-(4-bromo-3-formyl-phenoxy)-pyridine-2-carboxylic acid ethyl ester (23)

To a solution of 3-bromo-6-chloro-pyridine-2-carboxylic acid ethyl ester (22, 8.0 g, 30.24 mmol) and 2-bromo-5-hydroxy-benzaldehyde (7.29 g, 36.29 mmol) in DMF (100 mL) was added cesium carbonate (22.6 g, 69.55 mmol). The resulting mixture was heated at 80° C. overnight. DMF was removed under reduced pressure, and the residue was diluted with EtOAc (200 mL), washed with water (2×50 mL) and brine (50 mL) solution. The combined organic layers were dried over Na₂SO₄, filtered, and concentrated to give crude product which was purified by column chromatography (Silica gel 20% EtOAc in hexane) to yield title compound 23 (4.0 g, 31%) as transparent oil. ¹H NMR 400 MHz (DMSO-d₆) δ: 10.18 (s, 1H), 8.27 (d, J=8.6 Hz, 1H), 7.87 (d, J=7.6 Hz, 1H), 7.65 (s, 1H), 7.51 (dd, J=8.7, 2.9 Hz, 1H), 7.26 (d, J=8.9 Hz, 1H), 4.29 (q, J=7.1 Hz, 2H), 1.25 (t, J=7.0 Hz, 3H); MS (ES) m/z: 430 (M+1)⁺.

6-(4-Bromo-3-formyl-phenoxy)-3-cyano-pyridine-2-carboxylic acid ethyl ester (24)

To a solution of 3-bromo-6-(4-bromo-3-formyl-phenoxy)-pyridine-2-carboxylic acid ethyl ester (23, 1.8 g, 4.19 mmol) in DMF (6 mL) was added CuCN (0.75 g, 8.38 mmol) in portions at 130° C. and heated for 4 hour. The mixture was cooled to room temperature and ethyl acetate (100 mL) was added. The mixture was stirred for 10 minutes, filtered, and washed with ethyl acetate (2×50 mL). The filtrate was washed with water (2×50 mL) and brine (50 mL), dried over anhydrous sodium sulfate, filtered and evaporated in vacuo. The residue was purified by column chromatography (25% ethyl acetate/hexanes) to yield compound 24 (0.3 g, 19%) as a white solid. ¹H NMR 400 MHz (DMSO-d₆) δ: 10.20 (s, 1H), 8.51 (d, J=8.6 Hz, 1H), 7.91 (d, J=8.9 Hz, 1H), 7.76 (s, 1H), 7.59 (d, J=2.7 Hz, 1H), 7.55 (dd, J=8.5, 2.7 Hz, 1H), 4.32 (q, J=7.1 Hz, 2H), 1.26 (t, J=7.0 Hz, 3H); MS (ES) m/z: 377 (M+1)⁺.

3-Cyano-6-[3-formyl-4-(4,4,5,5-tetramethyl-[1,3,2]dioxaborolan-2-yl)-phenoxy]-pyridine-2-carboxylic acid ethyl ester (25)

To a degassed solution (30 min with nitrogen) of 6-(4-bromo-3-formyl-phenoxy)-3-cyano-pyridine-2-carboxylic acid ethyl ester (24, 0.30 g, 0.79 mmol) in 1,4-dioxane (6 mL) was added bis(pinacolato)diboron (0.30 g, 1.19 mmol), potassium acetate (0.23 g, 2.39 mmol), and [1,1'-bis(diphenylphosphino)ferrocene]palladium(II) chloride (0.03 g, 0.03 mmol). Degassed again (10 min nitrogen), and the suspension was heated at 80° C. overnight. The mixture was passed through Celite® and concentrated under reduced pressure to give crude product, which was purified by column chromatography (silica gel, 25% EtOAc in hexane) to yield the title compound 25 (0.11 g, 29%) as a colorless oil. ¹H NMR 400 MHz (DMSO-d₆) δ: 10.38 (s, 1H), 8.51 (d, J=8.9 Hz, 1H), 7.83 (d, J=8.2 Hz, 1H), 7.76 (s, 1H), 7.51 (d, J=2.7 Hz, 1H), 7.49 (d, J=8.5 Hz, 1H), 4.32 (q, J=7.1 Hz, 2H), 1.39 (s, 12H), 1.21 (t, J=7.0 Hz, 3H).

19as 3-Cyano-6-(1-hydroxy-1,3-dihydro-benzo[c][1,2]oxaborol-5-yloxy)-pyridine-2-carboxylic acid ethyl ester (D45)

To a solution of 3-cyano-6-[3-formyl-4-(4,4,5,5-tetramethyl-[1,3,2]dioxaborolan-2-yl)-phenoxy]-pyridine-2-carboxylic acid ethyl ester (25, 0.11 g, 0.23 mmol) in methanol (5 mL) was added sodium borohydride (0.01 g, 0.27 mmol) at 0° C. After 1 h at 0° C., 2 M HCl was added until pH is 2-3. The solvent was removed under reduced pressure to give crude product, which was purified by reverse phase prep HPLC using CH₃CN/H₂O (0.1% AcOH) as the eluent to yield the title compound (D45) (0.08 g, 20%) as a white solid after lyophilization. Mp 204-206° C.
¹H NMR 400 MHz (DMSO-d₆) δ: 9.26 (s, 1H), 8.47 (d, J=9.0 Hz, 1H), 7.80 (d, J=9.4 Hz, 1H), 7.39 (d, J=8.6 Hz, 1H), 7.32 (s, 1H), 7.24-7.19 (m, 1H), 4.99 (s, 2H), 4.32-4.23 (m, 2H), 1.39-1.20 (m, 3H); MS (ES) m/z: 325 (M+1)⁺; HPLC purity: 96.01% (Maxplot), 98.13% (220 nm), 97.47% (254 nm).

19at 6-(1-Hydroxy-1,3-dihydro-benzo[c][1,2]oxaborol-5-yloxy)-2-methoxy-nicotinonitrile (D46) and

19au 2-(1-Hydroxy-1,3-dihydro-benzo[c][1,2]oxaborol-5-yloxy)-6-methoxy-nicotinonitrile (D47)

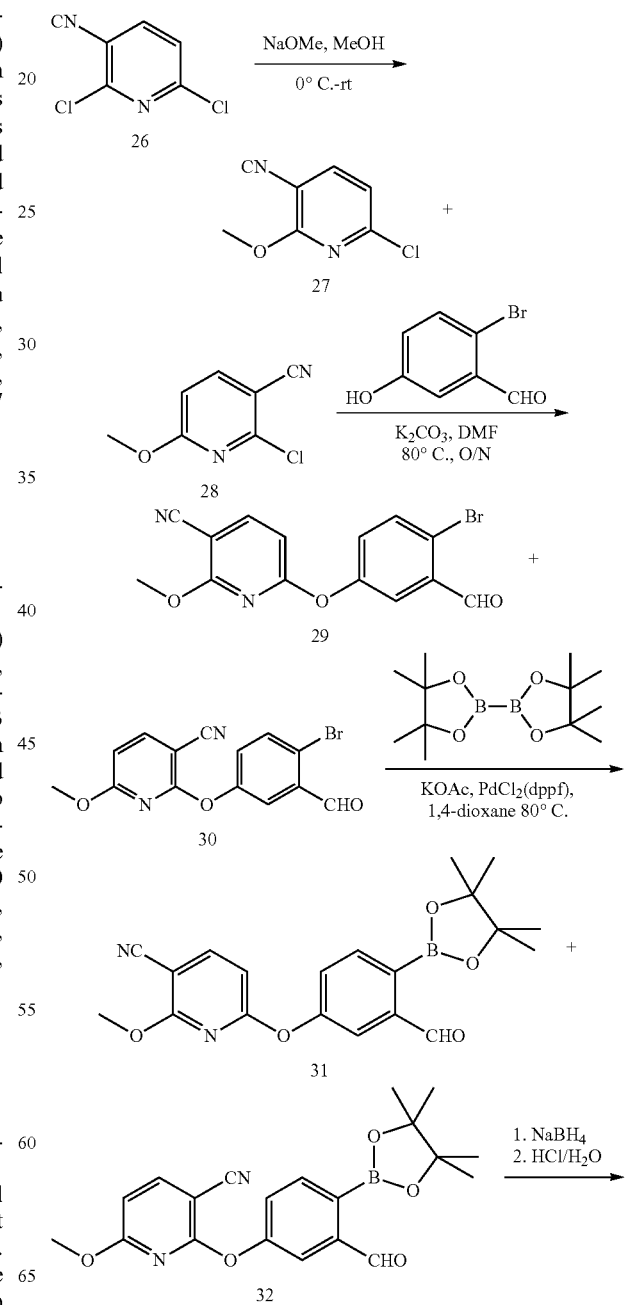

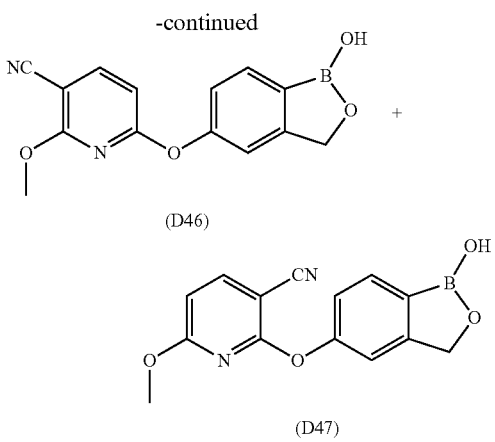

(D46)

(D47)

6-Chloro-2-methoxy-nicotinonitrile and 2-Chloro-6-methoxy-nicotinonitrile (27 and 28)

To a solution of 2,6-dichloro-nicotinonitrile (26, 5.0 g, 28.90 mmol) in methanol (25 mL) was added sodium methoxide (25% solution in methanol, 6.24 mL, 28.90 mmol) slowly at 0° C. and stirred for 16 h at room temperature. Methanol was distilled off and the residue was diluted with EtOAc (150 mL), washed with water (2×50 mL) and brine (50 mL), dried over $Na_2SO_4$, filtered, and concentrated to give crude mixture, which was recrystallized from ether to give inseparable mixture of compounds 27 and 28 in a ratio of 1:2 (4.8 g, quantitative) as white solid. $^1$H NMR 400 MHz (DMSO-$d_6$) δ: 8.30 (d, J=8.2 Hz, 1H), 8.27 (d, J=8.6 Hz, 1H), 7.31 (d, J=7.7 Hz, 1H), 7.00 (d, J=8.6 Hz, 1H), 3.98 (s, 3H), 3.92 (s, 3H).

6-(4-Bromo-3-formyl-phenoxy)-2-methoxy-nicotinonitrile and 2-(4-Bromo-3-formyl-phenoxy)-6-methoxy-nicotinonitrile (29 and 30)

To a mixture of 6-chloro-2-methoxy-nicotinonitrile and 2-chloro-6-methoxy-nicotinonitrile (27 and 28, 5.0 g, 29.65 mmol) and 2-bromo-5-hydroxy-benzaldehyde (5.96 g, 29.65 mmol) in DMF (100 mL) was added potassium carbonate (6.14 g, 44.47 mmol). The resulting mixture was heated at 80° C. overnight. DMF was removed under reduced pressure, residue was dissolved in EtOAc (150 mL), washed with water (2×50 mL) and brine (50 mL) solution, dried over $Na_2SO_4$, filtered, and concentrated to give brown oil, which was recrystallized from diethyl ether (50 mL) to give inseparable mixture of compounds 29 and 30 in a ratio of 1:2 (5.8 g, 60%) as white solid. $^1$H NMR 400 MHz (DMSO-$d_6$) δ: 10.17 (s, 2H), 8.28-8.23 (m, 2H), 7.87 (dd, J=8.5, 2.7 Hz, 2H), 7.75 (d, J=2.7 Hz, 1H), 7.71 (d, J=3.1 Hz, 1H), 7.62-7.55 (m, 2H), 6.79 (d, J=8.2 Hz, 1H), 6.73 (d, J=8.6 Hz, 1H), 3.71 (s, 3H), 3.61 (s, 3H); MS (ES) m/z: 335 (M+1)$^+$.

6-[3-Formyl-4-(4,4,5,5-tetramethyl-[1,3,2]dioxaborolan-2-yl)-phenoxy]-2-methoxy-nicotinonitrile and 2-[3-Formyl-4-(4,4,5,5-tetramethyl-[1,3,2]dioxaborolan-2-yl)-phenoxy]-6-methoxy-nicotinonitrile (31 and 32)

To a degassed solution (30 min with nitrogen) of 6-(4-bromo-3-formyl-phenoxy)-2-methoxy-nicotinonitrile and 2-(4-bromo-3-formyl-phenoxy)-6-methoxy-nicotinonitrile (29 and 30, 4.80 g, 14.40 mmol) in 1,4-dioxane (70 mL) was added bis(pinacolato)diboron (5.48 g, 21.61 mmol), potassium acetate (4.24 g, 43.20 mmol), and [1,1'-bis(diphenylphosphino)ferrocene]palladium(II)chloride (0.54 g, 0.72 mmol). Degassed again (10 min with nitrogen), and the suspension was heated at 90° C. overnight. The mixture was passed through Celite and concentrated under reduced pressure to give crude product, which was purified by column chromatography (silica gel, 25% EtOAc in hexane) to yield the title compounds 31 and 32 in a ratio of 1:1.5 (4.60 g, 85%) as a colorless oil. $^1$H NMR 400 MHz (DMSO-$d_6$) δ: 10.37 (s, 2H), 8.28-8.24 (m, 2H), 7.83-7.57 (m, 4H), 7.64-7.57 (m, 2H), 6.80-6.73 (m, 2H), 3.71 (s, 3H), 3.61 (s, 3H), 1.39 (s, 24H).

19at 6-(1-Hydroxy-1,3-dihydro-benzo[c][1,2]oxaborol-5-yloxy)-2-methoxy-nicotinonitrile (D46) and 19au 2-(1-Hydroxy-1,3-dihydro-benzo[c][1,2]oxaborol-5-yloxy)-6-methoxy-nicotinonitrile (D47)

To a solution of 6-[3-formyl-4-(4,4,5,5-tetramethyl-[1,3,2]dioxaborolan-2-yl)-phenoxy]-2-methoxy-nicotinonitrile and 2-[3-formyl-4-(4,4,5,5-tetramethyl-[1,3,2]dioxaborolan-2-yl)-phenoxy]-6-methoxy-nicotinonitrile (31 and 32, 2.6 g, 6.83 mmol) in methanol (15 mL) was added sodium borohydride (0.31 g, 8.19 mmol) at 0° C. and left at the same temperature for 1 h. 2 M HCl was added until pH reached 2~3. The solvent was removed under reduced pressure to give a mixture of regioisomers which were separated by chiral column (Chiralcel_OJ_10um_4-6×250 mm, eluting with 90 hexane/5iPrOH/5EtOH) to yield the title compounds (D46) (1.70 g, 58%) and (D47) (0.40 g, 23%) as white solids after lyophilization.

19at 6-(1-Hydroxy-1,3-dihydro-benzo[c][1,2]oxaborol-5-yloxy)-2-methoxy-nicotinonitrile (D46)

$^1$H NMR 400 MHz (DMSO-$d_6$) δ: 9.24 (s, 1H), 8.21 (d, J=8.2 Hz, 1H), 7.77 (d, J=7.8 Hz, 1H), 7.29 (s, 1H), 7.19 (d, J=8.6 Hz, 1H), 6.64 (d, J=8.2 Hz, 1H), 4.97 (s, 2H), 3.74 (s, 3H); MS (ES) m/z: 283 (M+1)$^+$; HPLC purity: 99.77% (Maxplot), 99.27% (220 nm), 99.77% (254 nm).

19au 2-(1-Hydroxy-1,3-dihydro-benzo[c][1,2]oxaborol-5-yloxy)-6-methoxy-nicotinonitrile (D47)

$^1$H NMR 400 MHz (DMSO-$d_6$) δ: 9.24 (s, 1H), 8.25 (d, J=7.2 Hz, 1H), 7.78 (d, J=7.8 Hz, 1H), 7.32 (s, 1H), 7.25-7.23 (m, 1H), 6.73 (d, J=8.6 Hz, 1H), 5.00 (s, 2H), 3.63 (s, 3H); MS (ES) m/z: 283 (M+1)$^+$; HPLC purity: 100% (Maxplot), 98.76% (200 nm), 99.59% (254 nm).

19av Ethyl 5-chloro-6-(1-hydroxy-1,3-dihydrobenzo[c][1,2]oxaborol-5-yloxy)nicotinate (D48)

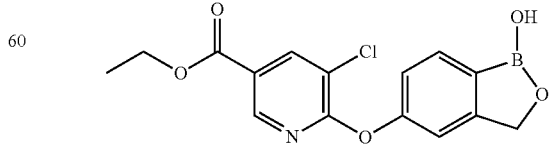

The title compound was prepared by procedures similar to that described below for D60.

Mp 149-153° C. ¹H NMR (300 MHz, DMSO-d₆): δ 9.24 (s, 1H), 8.57 (d, J=1.8 Hz, 1H), 8.42 (dd, J=2.1 & 0.6 Hz, 1H), 7.77 (d, J=8.1 Hz, 1H), 7.25 (d, 1H), 7.17 (dd, J=7.8 & 2.1 Hz, 1H), 4.97 (s, 2H), 4.31 (q, J=7.2 Hz, 2H) and 1.30 (t, J=7.2 Hz, 3H) ppm. Purity (HPLC): 95% at 220 nm and 95% at 254 nm. MS: m/z=334 (M+1, ESI+) and m/z=332 (M−1, ESI−).

19aw 5-Chloro-6-(1-hydroxy-1,3-dihydrobenzo[c][1,2]oxaborol-5-yloxy)nicotinic acid (D49)

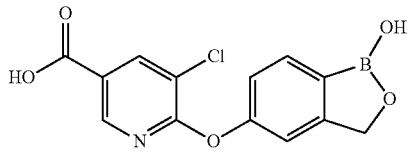 [SMILES: O=C(O)c1cnc(Oc2ccc3c(c2)COB3O)c(Cl)c1]

Hydrolysis of ethyl 5-chloro-6-(1-hydroxy-1,3-dihydrobenzo[c][1,2]oxaborol-5-yloxy) nicotinate (0.9 g, 2.7 mmol) with 1N NaOH (11 mL) in MeOH (50 mL) overnight at r.t. followed by acidification with 6N HCl, work-up and recrystallization from EtOAc and hexane afforded off-white solid of the title carboxylic acid compound (0.76 g, 2.49 mmol, yield 92%).

Mp 185-190° C. (dec.). ¹H NMR (300 MHz, DMSO-d₆): δ 13.50 (s, 1H), 9.23 (s, 1H), 8.54 (d, J=2.1 Hz, 1H), 8.37 (d, J=2.1 Hz, 1H), 7.77 (d, J=7.8 Hz, 1H), 7.25 (d, J=1.5 Hz, 1H), 7.16 (dd, J=7.8 & 1.5 Hz, 1H) and 4.97 (s, 2H) ppm. Purity (HPLC): >95% at 254 nm. MS: m/z=306 (M+1, ESI+) and m/z=260 (M−45, ESI−).

19ax 5-(2-Fluoro-4-methoxycarbonylphenoxy)-1-hydroxy-2,1-benzoxaborole (D50)

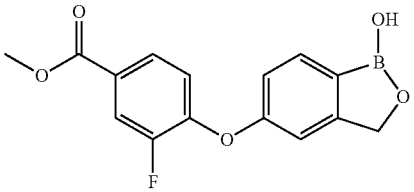 [SMILES: COC(=O)c1ccc(Oc2ccc3c(c2)COB3O)c(F)c1]

A mixture of 4-bromo-3-(1,3-dioxolan-2-yl)phenol (7.1 g, 29 mmol, 1 eq), methyl 3,4-difluorobenzorate (5 g, 29 mmol, 1 eq), potassium carbonate (6 g, 43.5 mmol, 1.5 eq) in DMF (29 mL). Reaction was stirred at 100° C. over night. TLC showed that reaction was completed. After cooling to room temperature, the residue was removed by filtration. The residue was washed with EtOAc. The organics were combined and concentrated via Rota vapor. The residue was poured into EtOAc and water. The organic layers was separated and washed with brine and dried over sodium sulfate anhydrous. Filter and concentrated to get methyl 4-(4-bromo-3-(1,3-dioxolan-2-yl)phenoxy)-3-fluorobenzoate as crude, light brown oil, which was used for next step without purification.

To a solution of methyl 4-(4-bromo-3-(1,3-dioxolan-2-yl)phenoxy)-3-fluorobenzoate in 30 mL of THF was added 20 ml of 3M HCl (made from 6M HCl and water 1:1), refluxed for 2 hour. TLC showed no SM (Hexane: EtOAc 7:3). The reaction was cooled to RT. Add 1N NaOH (60 ml), Rota vapor to remove half of the solvent, extracted with EtOAc. The organics were washed with water, brine, dried over Na2SO4, filtered, and concentrated to get light brown oil. Standby over weekend to get solidified solid. Filtered, washed with Hexane/EtOAc to collect methyl 4-(4-bromo-3-formylphenoxy)-3-fluorobenzoate as a off-white powder (10.2 g, 100%)

To a solution of methyl 4-(4-bromo-3-formylphenoxy)-3-fluorobenzoate; (10 g, 28.3 mmol), KOAc (8.33 g, 84.9 mmol), bis(pinacolato)diboron (8.63 g, 34 mmol) in anhydrous 1,4-dioxane (120 mL) was added PdCl₂(dppf)₂ (578 mg; 2.5 mol % CAS#72287-26-4, Aldrich catalog#379670). The reaction mixture was degassed with N₂, and then heated at 80° C. with magnetic stirring. The reaction was monitored with TLC and was completed overnight. The mixture was cooled to room temperature, filtered through Celite and washed with ethyl acetate and then evaporated. The residue was dissolved in minimum EtOAc and passed through a very short but big silica gel column eluted with a mixed solvent of hexane: EtOAc (3:1, v/v) to remove dark color giving light yellow oil. Chromatography on silica gel again (Hexane/EtOAc 7:3). The first portion is white solid, NMR indicated as bis(pinacolato)diboron (no aromatic signals). The product was collected and concentrated to afford methyl 3-fluoro-4-(3-formyl-4-(4,4,5,5-tetramethyl-1,3,2-dioxaborolan-2-yl)phenoxy)benzoate as colorless oil (9.5 g, 84%).

¹H NMR (DMSO-d6, 300 MHz): δ=10.38 (s, 1H), 7.91 (dd, J=2.1, 13.2 Hz, 1H), 7.82 (d, J=7.8 Hz, 2H), 7.42 (d, J=2.7 Hz, 2H), 7.32 (d, J=8.4 Hz, 1H), 3.85 (s, 3H), and 1.32 (s, 12H) ppm.

To a solution of methyl 3-fluoro-4-(3-formyl-4-(4,4,5,5-tetramethyl-1,3,2-dioxaborolan-2-yl)phenoxy)benzoate (5 g, 12.5 mmol) in MeOH (125 mL) was added NaBH₄ (709 mg; 18.75 mmol) in portions under N2 at 0° C. in an ice-bath. The reaction was stirred at 0° C. to room temperature. The reaction was monitored with TLC and was completed overnight. The mixture was cooled to rt. Solvent was evaporated to half volume via Rota vapor. The mixture was then cooled to 0° C., and quenched by adding water (12 mL) following by adding 6 N HCl(12 mL). Stirred at rt for 30 min, white Solid precipitated out. Filtered. The solid was gummy. The solid was suspended in water, sonicated for 1 hr. Filtered, washed with more water. Filtered, dried to get target compound as a white solid (2.1 g, 56%).

¹H NMR (DMSO-d6, 300 MHz): δ=9.19 (s, 1H), 7.88 (dd, J=1.8, 11.1 Hz, 1H), 7.80 (d, J=8.4 Hz, 1H), 7.75 (d, J=8.1 Hz, 1H), 7.21 (d, J=8.4 Hz, 1H), 7.07 (d, J=8.4 Hz, 2H), 4.93 (s, 2H), and 3.84 (s, 3H)

19ay 5-(2-Fluoro-4-ethoxycarbonylphenoxy)-1-hydroxy-2,1-benzoxaborole (D51)

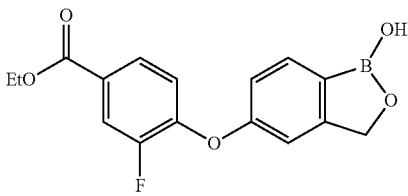 [SMILES: CCOC(=O)c1ccc(Oc2ccc3c(c2)COB3O)c(F)c1]

This compound was obtained in a similar manner to Example 19ax (D50) from ethyl 3,4-difluorobenzorate and 4-bromo-3-formylphenol.

ESI-MS (m/z) 315 (M−H)

19az 5-(2,6-Difluoro-4-methoxycarbonylphenoxy)-
1-hydroxy-2,1-benzoxaborole (D52)

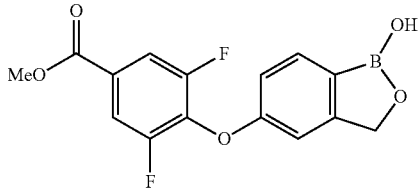 [SMILES: COC(=O)c1cc(F)c(Oc2ccc3c(c2)COB3O)c(F)c1]

This compound was obtained in a similar manner to Example 19ax (D50) from methyl 3,4,5-trifluorobenzorate and 4-bromo-3-formylphenol.
ESI-MS (m/z) 319 (M−H)⁻

19ba 5-(5-Chloro-2-fluoro-4-ethoxycarbonylphenoxy)-1-hydroxy-2,1-benzoxaborole (D53)

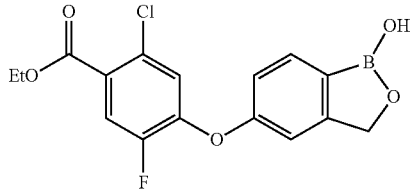

This compound was obtained in a similar manner to Example 19ax (D50) from ethyl 2-chloro-4,5-difluorobenzorate and 4-bromo-3-formylphenol.
ESI-MS (m/z) 349 (M−H)⁻

19bb 5-(4-Ethoxycarbonyl-2-trifluoromethylphenoxy)-1-hydroxy-2,1-benzoxaborole (D54)

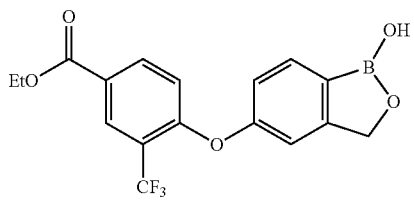 [SMILES: CCOC(=O)c1ccc(Oc2ccc3c(c2)COB3O)c(C(F)(F)F)c1]

This compound was obtained in a similar manner to Example 19ax (D50) from ethyl 4-fluoro-3-trifluromethylbenzorate and 4-bromo-3-formylphenol.
ESI-MS (m/z) 365 (M−H)⁻

19 bc 5-(2-Fluoro-4-isopropyloxycarbonylphenoxy)-
1-hydroxy-2,1-benzoxaborole (D55)

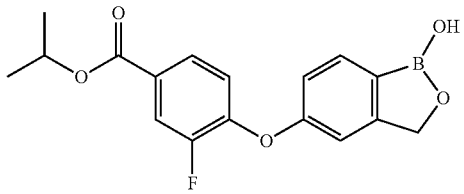 [SMILES: CC(C)OC(=O)c1ccc(Oc2ccc3c(c2)COB3O)c(F)c1]

This compound was obtained in a similar manner to Example 19ax (D50) from isopropyl 3,4-difluorobenzorate and 4-bromo-3-formylphenol.
ESI-MS (m/z) 329 (M−H)⁻

19 bd 5-(2,6-Difluoro-4-ethoxycarbonylphenoxy)-1-
hydroxy-2,1-benzoxaborole (D56)

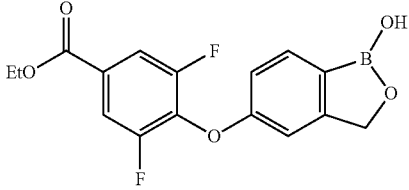 [SMILES: CCOC(=O)c1cc(F)c(Oc2ccc3c(c2)COB3O)c(F)c1]

This compound was obtained in a similar manner to Example 19ax (D50) from ethyl 3,4,5-trifluorobenzorate and 4-bromo-3-formylphenol.
ESI-MS (m/z) 333 (M−H)⁻

19 be 5-(3-Chloro-4-ethoxycarbonylphenoxy)-1-
hydroxy-2,1-benzoxaborole (D57)

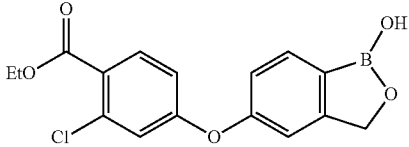 [SMILES: CCOC(=O)c1ccc(Oc2ccc3c(c2)COB3O)cc1Cl]

This compound was obtained in a similar manner to Example 19ax (D50) from ethyl 2-chloro-4-fluorobenzorate and 4-bromo-3-formylphenol.
ESI-MS (m/z) 331 (M−H)⁻

19bf 5-(2-Chloro-5-fluoro-4-ethoxycarbonylphenoxy)-1-hydroxy-2,1-benzoxaborole (D58)

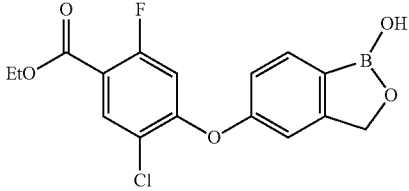 [SMILES: CCOC(=O)c1cc(Cl)c(Oc2ccc3c(c2)COB3O)cc1F]

This compound was obtained in a similar manner to Example 19ax (D50) from ethyl 5-chloro-2,4-difluorobenzorate and 4-bromo-3-formylphenol.
ESI-MS (m/z) 349 (M−H)⁻

19bi (4-(1-Hydroxy-1,3-dihydrobenzo[c][1,2]oxaborol-5-yloxy)phenyl)methanaminium chloride (D59)

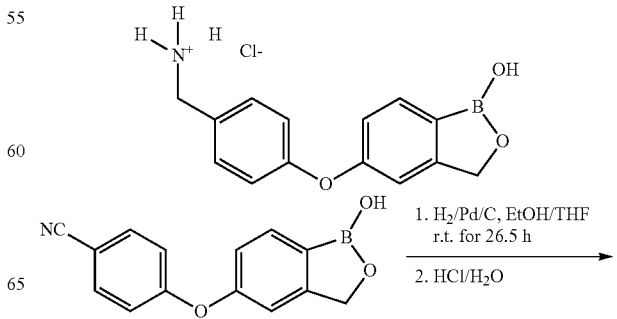

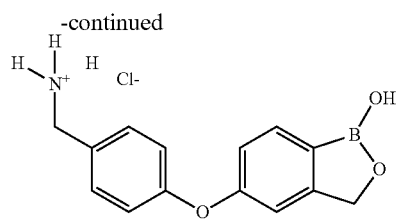

The title compound was synthesized by the same procedure as described above for the preparation of its regional isomer. Yield 66.7%.

Mp>250° C. $^1$H NMR (DMSO-d$_6$, 300 MHz): δ 9.18 (s, 1H), 8.43 (br. s, 3H), 7.74 (d, J=8.1 Hz, 2H), 7.52 (d, J=8.7 Hz, 2H), 7.08 (d, J=8.7 Hz, 1H), 6.98-6.94 (m, 2H), 4.91 (s, 2H) and 3.99 (br. q, J=4.8 Hz, 2H) ppm. Purity (HPLC): 92.2% at 220 nm and 94.9% at 254 nm. MS: m/z=256 (M+1, ESI+) and m/z=255 (M−, ESI−).

19bj Ethyl 6-(1-hydroxy-1,3-dihydrobenzo[c][1,2]oxaborol-5-yloxy)nicotinate (D60)

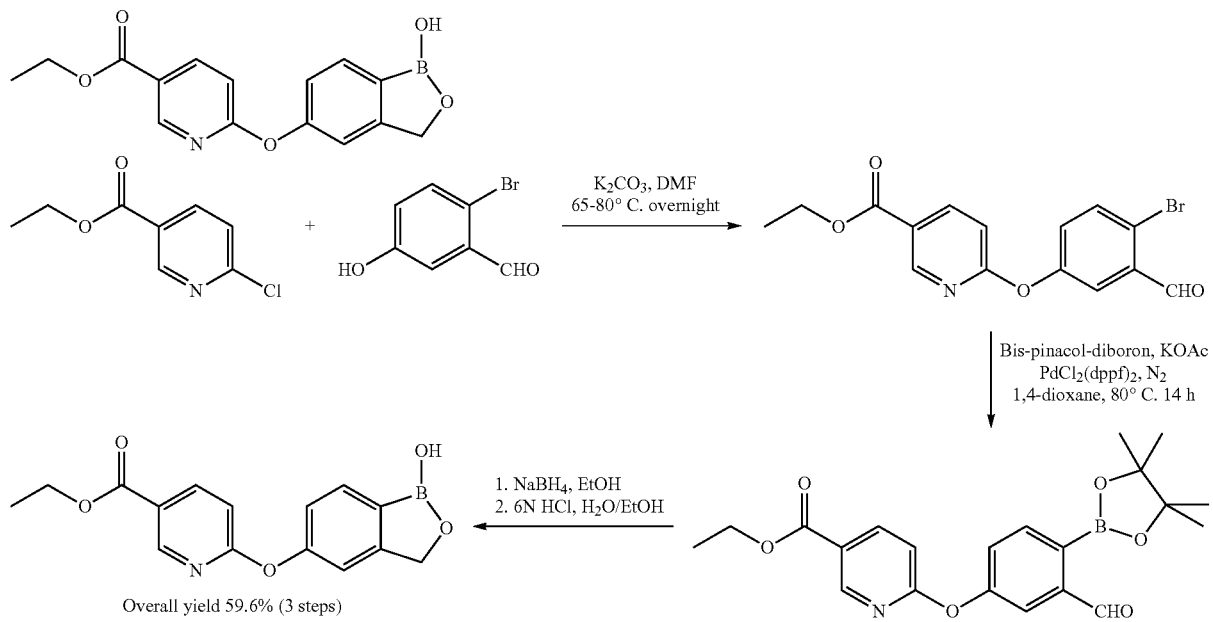

Overall yield 59.6% (3 steps)

To a mixture of ethyl 6-chloronicotinate (18.6 g, 0.1 mol) and 2-bromo-5-hydroxy benzaldehyde (20.1 g, 0.1 mol) in dry DMF (200 mL) was added K$_2$CO$_3$ (20.8 g, 1.5 eq) under nitrogen atmosphere and the mixture was stirred at 65-80° C. for 30.5 h. After being cooled to room temperature, the mixture was filtered, evaporated and pumped overnight to give brown oil (38.26 g) with 81.5% coupling conversion to ethyl 6-(4-bromo-3-formylphenoxy)nicotinate as indicated by NMR.

$^1$H NMR (300 MHz, DMSO-d$_6$): δ 10.17 (s, 1H), 8.66-8.65 (m, 1H), 8.33 (dd, J=8.7&2.4 Hz, 1H), 7.86 (d, J=8.7 Hz, 1H), 7.60 (d, J=2.7 Hz, 1H), 7.50 (dd, J=8.4&2.7 Hz, 1H), 7.23 (dd, J=8.7& 0.6 Hz, 1H), 4.30 (q, J=7.2 Hz, 2H) and 1.29 (t, J=7.2 Hz, 3H) ppm.

To the solution of the resulting oil intermediate in 1,4-dioxane (450 mL) was added bis-pinacol-diboron (30.5 g, 0.12 mol), KOAc (29.5 g, 0.3 mol) and PdCl$_2$(dppf)$_2$ (1.95 g, 2.5% mol), and the mixture was degassed with N$_2$ and heated at 80° C. for 14 h with stirring. The resulting dark mixture was filtered and evaporated. The residue was dissolved in minimum EtOAc, passed through a short silica gel column eluted with hexane:EtOAc (2:1) to remove the dark color giving brown oil (46.4 g) mainly containing ethyl 6-(3-formyl-4-(4,4,5,5-tetramethyl-1,3,2-dioxaborolan-2-yl)phenoxy)nicotinate.

$^1$H NMR (300 MHz, DMSO-d$_6$): δ 10.39 (s, 1H), 8.67-8.65 (m, 1H), 8.35-8.31 (m, 1H), 7.83 (d, J=8.1 Hz, 1H), 7.64 (d, J=2.7 Hz, 1H), 7.50 (dd, J=7.8 & 2.7 Hz, 1H), 7.24 (d, J=8.1 Hz, 1H), 4.30 (q, J=7.2 Hz, 2H), 1.34 (s, 12H) and 1.29 (t, J=7.2 Hz, 3H) ppm.

To the solution of the pinacolboron aldehyde (46.4 g) in EtOH (450 mL, 200 proof) at 0° C. was added NaBH$_4$ (5 g) in portions and the mixture was stirred overnight with slow increasing to room temperature. The mixture was cooled with ice bath again and water (50 mL) was added and followed with slow addition of 6N HCl (50 mL). After being stirred for 30 min, the mixture was evaporated to remove EtOH and then water (200 mL) was added, neutralized with NaHCO$_3$-saturated water. The mixture was extracted with EtOAc, concentrated and loaded to a short and big silica gel column eluted with hexane:EtOAc (2:1, v/v) to remove dark impurity. The oil obtained contained pinacol impurity that also complicates the proton NMR spectrum. The oil was dissolved in minimum acetone, and then water was added slowly with sonication at same time to participate the solid product. The solid was collected by filtration and washed with pentane and hexane, dried overnight under high vacuum to give ethyl 6-(1-hydroxy-1,3-dihydrobenzo[c][1,2]oxaborol-5-yloxy)nicotinate as a cream solid (17.84 g) in 59.6% overall yield (3 steps).

M.p. 110-113° C. $^1$H NMR (300 MHz, DMSO-d$_6$): δ 9.21 (s, 1H), 8.68 (d, J=2.4 Hz, 1H), 8.30 (dd, J=8.4 & 2.1 Hz, 1H), 7.76 (d, J=8.1 Hz, 1H), 7.21 (d, J=1.5 Hz, 1H), 7.15 (d, J=8.7 Hz, 1H), 7.12 (dd, J=7.8 & 2.1 Hz, 1H), 4.97 (s, 2H), 4.30 (q, J=7.5 Hz, 2H) and 1.29 (t, J=7.5 Hz, 3H) ppm. Purity (HPLC): 95.3% at 220 nm and 95.4% at 254 nm. MS: m/z=300 (M+1, ESI+) and m/z=298 (M−1, ESI−).

19bk 6-(1-Hydroxy-1,3-dihydrobenzo[c][1,2]oxaborol-5-yloxy)nicotinic acid (D61)

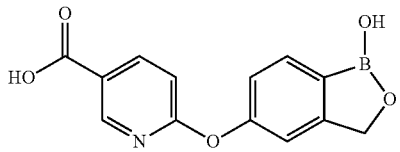 [SMILES: O=C(O)c1ccc(Oc2ccc3c(c2)COB3O)nc1]

The title bis-acid compound was prepared by hydrolysis of the corresponding carboxylic acid ethyl ester. Ethyl 6-(1-hydroxy-1,3-dihydrobenzo[c][1,2]oxaborol-5-yloxy)nicotinate (2.99 g, 10 mmol) was dissolved in freshly opened THF (100 mL), and 1N NaOH (38 mL) was added. The mixture was stirred at room temperature under $N_2$ overnight. Then 6N HCl (6.5 mL) was added, rotary evaporated to remove THF, filtered and washed with water and then hexane. The solid was dried overnight under high vacuum to afford the title bis-acid compound (2.57 g, 9.48 mmol, yield 94.8%) as a slightly brown solid.

M.p.>200° C. $^1$H NMR (300 MHz, DMSO-$d_6$): δ 13.21 (s, 1H), 9.21 (s, 1H), 8.65 (d, J=2.1 Hz, 1H), 8.28 (dd, J=8.4 & 2.4 Hz, 1H), 7.76 (d, J=7.8 Hz, 1H), 7.21 (d, J=1.5 Hz, 1H), 7.14-7.11 (m, 2H) and 4.97 (s, 2H) ppm. Purity (HPLC): 97.2% at 220 nm and 97.8% at 254 nm. MS: m/z=272 (M+1, ESI+) and m/z=270 (M−1, ESI−).

19bl N,N-diethyl-6-(1-hydroxy-1,3-dihydrobenzo[c][1,2]oxaborol-5-yloxy)nicotinamide (D62)

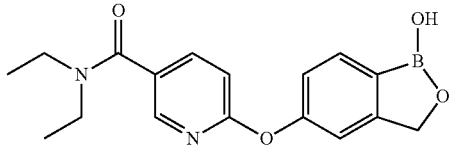 [SMILES: CCN(CC)C(=O)c1ccc(Oc2ccc3c(c2)COB3O)nc1]

To the solution of 6-(1-Hydroxy-1,3-dihydrobenzo[c][1,2]oxaborol-5-yloxy)nicotinic acid (0.813 g, 3 mmol) in anhydrous DMF (70 mL) was added diethylamine (3.2 mL, 30 mmol) and DIPEA (1.6 mL, 9 mmol) under $N_2$. The mixture was cooled with ice bath and a coupling agent PyCloP (Aldrich#26564, 1.4 g, 3.3 mmol) was added. The reaction mixture was stirred at 0° C. for 10 min and at room temperature overnight, and then rotary evaporated. The residue was dissolved in EtOAc and washed with water, evaporated and purified by flash column chromatography over silica gel eluted with EtOAc to provide the title amide compound as a white solid (0.92 g, 2.82 mmol, yield 94%).

Mp 85-95° C. $^1$H NMR (300 MHz, DMSO-$d_6$): δ 9.18 (s, 1H), 8.15 (dd, J=2.4 & 0.6 Hz, 1H), 7.86 (dd, J=8.7 & 2.4 Hz, 1H), 7.75 (d, J=8.1 Hz, 1H), 7.19 (dd, J=2.1 & 0.6 Hz, 1H), 7.13-7.07 (m, 2H) and 4.96 (s, 2H), 3.48-3.12 (broad m, 4H) and 1.16-1.02 (broad s, 6H) ppm. Purity (HPLC): 97.0% at 220 nm and 96.9% at 254 nm. MS: m/z=327 (M+1, ESI+) and m/z=325 (M−1, ESI−).

19bm N-Ethyl-6-(1-hydroxy-1,3-dihydrobenzo[c][1,2]oxaborol-5-yloxy)nicotinamide (D63)

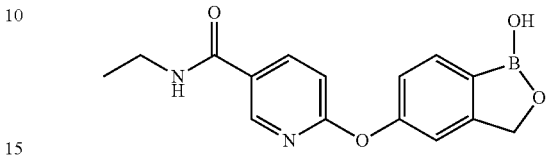

The title compound was synthesized from the corresponding carboxylic acid using the same methodology described for the diethyl amide analogue. Yield 78.3%.

Mp 100-120° C. (hydroscopic). $^1$H NMR (300 MHz, DMSO-$d_6$): δ 9.20 (s, 1H), 8.57 (d, J=2.1 Hz, 1H), 8.54 (broad t, J=5.4 Hz, 1H), 8.23 (dd, J=8.4 & 2.4 Hz, 1H), 7.75 (d, J=7.8 Hz, 1H), 7.17 (d, J=1.8 Hz, 1H), 7.12-7.08 (m, 2H), 4.96 (s, 2H), 3.32-3.22 (m, 2H) and 1.10 (t, J=7.2 Hz, 3H) ppm. Purity (HPLC): 97.2% at 220 nm and 98.1% at 254 nm. MS: m/z=299 (M+1, ESI+) and m/z=297 (M−1, ESI−).

19bn 5-(5-(Hydroxymethyl)pyridin-2-yloxy)benzo[c][1,2]oxaborol-1(3H)-ol (D64)

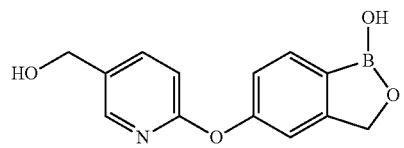 [SMILES: OCc1ccc(Oc2ccc3c(c2)COB3O)nc1]

Reduction of ethyl 6-(1-hydroxy-1,3-dihydrobenzo[c][1,2]oxaborol-5-yloxy)nicotinate (2 g, 6.68 mmol) in THF (130 mL) with Super Hydride (LiEt$_3$BH, 1M in THF, 26.7 mL) at 0° C. to r.t. overnight with normal work-up gave the title alcohol as white solid (1.03 g, yield 60%).

Mp 210-212° C. $^1$H NMR (300 MHz, DMSO-$d_6$): δ 9.18 (s, 1H), 8.08-8.07 (m, 1H), 7.81-7.78 (m, 1H), 7.72 (d, J=7.8 Hz, 1H), 7.09 (s, 1H), 7.05-7.01 (m, 2H), 5.28 (broad s, 1H), 4.94 (s, 2H) and 4.46 (s, 2H) ppm. Purity (HPLC): 96.5% at 220 nm and 98.3% at 254 nm. MS: m/z=258 (M+1, ESI+) and m/z=256 (M−1, ESI−).

19bo Methyl 6-(1-hydroxy-1,3-dihydrobenzo[c][1,2]oxaborol-5-yloxy)nicotinate (D65)

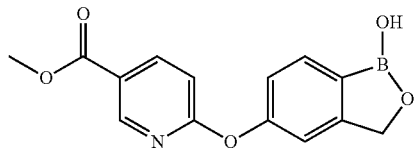 [SMILES: COC(=O)c1ccc(Oc2ccc3c(c2)COB3O)nc1]

The mixture of the corresponding carboxylic acid (0.8 g, 2.95 mmol) and 96% $H_2SO_4$ (1 g) in MeOH (130 mL) was refluxed overnight under $N_2$. Normal work-up and flash column chromatography over silica gel eluted with hexane:E- tOAc (1:1, v/v) provided the title methyl ester compound as a white solid (0.127 g, yield 15.1%).

Mp 156-158° C. $^1$H NMR (300 MHz, DMSO-d$_6$): δ 9.22 (s, 1H), 8.68 (dd, J=2.4 & 0.6 Hz, 1H), 8.31 (dd, J=8.7 & 2.4 Hz, 1H), 7.76 (d, J=7.8 Hz, 1H), 7.22 (d, J=1.2 Hz, 1H), 7.17-7.11 (m, 2H), 4.97 (s, 2H) and 3.84 (s, 3H) ppm. Purity (HPLC): 98.0% at 220 nm and 100% at 254 nm. MS: m/z=286 (M+1, ESI+) and m/z=284 (M-1, ESI-).

19bp n-Propyl 6-(1-hydroxy-1,3-dihydrobenzo[c][1,2]oxaborol-5-yloxy)nicotinate (D66)

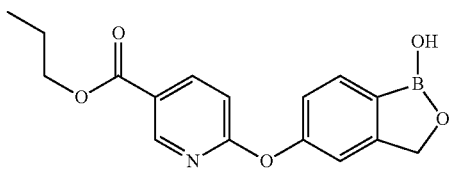 [SMILES: CCCOC(=O)c1ccc(Oc2ccc3c(c2)COB3O)nc1]

The mixture of the corresponding carboxylic acid (0.5 g, 1.84 mmol) and a coupling agent CDI (0.66 g, 4.06 mmol, 2.2 eq) in a mixed solvent of CH$_2$Cl$_2$ (50 mL), THF (30 mL) and DMF (40 mL) was stirred at r.t. overnight under N$_2$. Then anhydrous n-PrOH (30 mL) was injected into the mixture, and catalytic amount of NaH (60%, 10 mg) was added. The mixture was refluxed under N$_2$ for 2 h and then evaporated. The residue was dissolved in EtOAc, washed with 0.5N HCl, then with NaHCO$_3$ solution (pH=8), dried and evaporated. The sticky solid was dissolved in minimum acetone followed by addition of hexane with sonication and cooling to generate the title n-propyl ester product as an off-white solid (0.354 g, 1.13 mmol, yield 61.3%).

Mp 89-94° C. $^1$H NMR (300 MHz, DMSO-d$_6$): δ 9.22 (s, 1H), 8.69 (d, J=2.4 Hz, 1H), 8.31 (dd, J=8.7 & 2.7 Hz, 1H), 7.76 (d, J=7.8 Hz, 1H), 7.22 (s, 1H), 7.17-7.12 (m, 2H), 4.97 (s, 2H), 4.22 (t, J=6.3 Hz, 2H), 1.70 (sextet, J=6.9 Hz, 2H) and 0.94 (t, J=7.2 Hz, 3H) ppm. Purity (HPLC): 98.3% at 220 nm and 98.3% at 254 nm. MS: m/z=314 (M+1, ESI+) and m/z=312 (M-1, ESI-).

19bq Isopropyl 6-(1-hydroxy-1,3-dihydrobenzo[c][1,2]oxaborol-5-yloxy)nicotinate (D67)

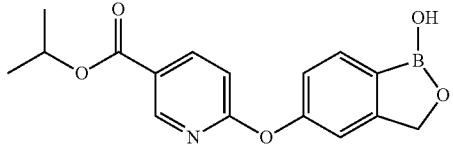 [SMILES: CC(C)OC(=O)c1ccc(Oc2ccc3c(c2)COB3O)nc1]

The title isopropyl ester compound was prepared by adapting the procedure described above for the n-propyl ester with increase of refluxing time to 4 h. Yield 71.8%.

Mp 95-101° C. $^1$H NMR (300 MHz, DMSO-d$_6$): δ 9.21 (s, 1H), 8.66 (d, J=2.4 Hz, 1H), 8.29 (dd, J=8.7 & 2.1 Hz, 1H), 7.76 (d, J=7.8 Hz, 1H), 7.21 (d, J=1.8 Hz, 1H), 7.16-7.11 (m, 2H), 5.12 (septet, J=6.0 Hz, 1H), 4.97 (s, 2H) and 1.30 (d, J=6.3 Hz, 6H) ppm. Purity (HPLC): 98.2% at 220 nm and 96.6% at 254 nm. MS: m/z=314 (M+1, ESI+) and m/z=312 (M-1, ESI-).

19br n-Butyl 6-(1-hydroxy-1,3-dihydrobenzo[c][1,2]oxaborol-5-yloxy)nicotinate (D68)

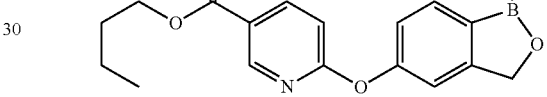

The title n-butyl ester compound was prepared by adapting the procedure described above for the n-propyl ester with increase of refluxing time to 4 h. Yield 68.5%.

Mp 75-80° C. $^1$H NMR (300 MHz, DMSO-d$_6$): δ 9.22 (s, 1H), 8.68-8.67 (m, 1H), 8.32-8.29 (dm, J$_d$=8.7 Hz, 1H), 7.76 (d, J=7.5 Hz, 1H), 7.22 (s, 1H), 7.17-7.12 (m, 2H), 4.97 (s, 2H), 4.26 (t, J=6.3 Hz, 2H), 1.66 (pentatet, J=7.5 Hz, 2H), 1.39 (sextet, J=7.5 Hz, 2H) and 0.90 (t, J=7.5 Hz, 3H) ppm. Purity (HPLC): 100% at 220 nm and 100% at 254 nm. MS: m/z=328 (M+1, ESI+).

19bs 6-(1-Hydroxy-1,3-dihydrobenzo[c][1,2]oxaborol-5-yloxy)nicotinaldehyde (D69)

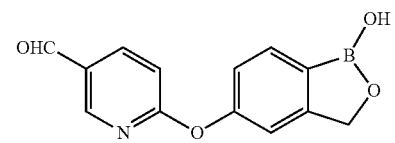

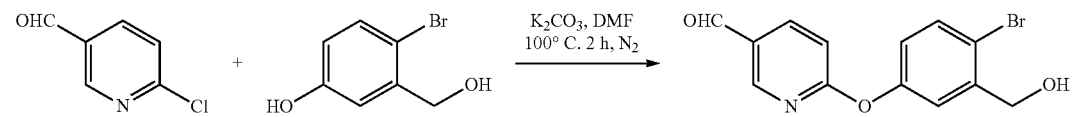

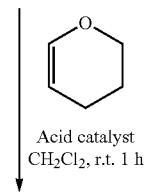

Acid catalyst
CH$_2$Cl$_2$, r.t. 1 h

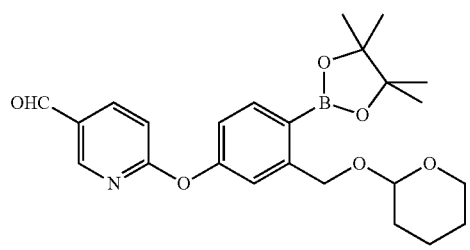 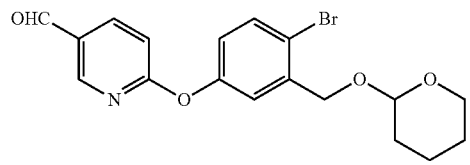

-continued

Bis-pinacol-diboron
KOAc, PdCl₂(dppf)₂
1,4-dioxane, 80° C. 20 h
N₂

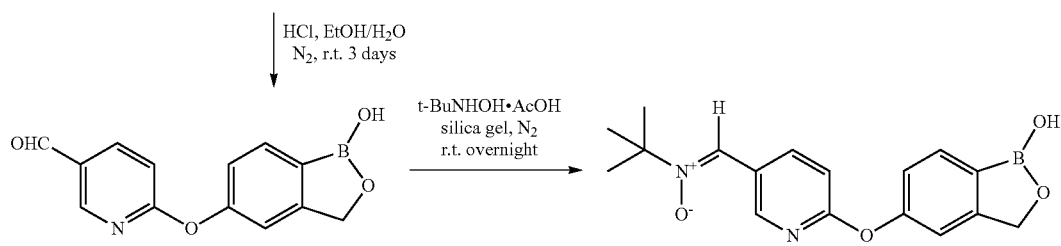

HCl, EtOH/H₂O
N₂, r.t. 3 days t-BuNHOH·AcOH
silica gel, N₂
r.t. overnight

Coupling reaction of 6-chloronicotinaldehyde (5.4 g, 38.15 mmol) and 4-bromo-3-(hydroxymethyl)phenol (8.15 g, 38.15 mmol) in the presence of K₂CO₃ (8.5 g, 1.5 eq) in DMF (100 mL) for 2 h at 100° C. under N₂ gave the desired 6-(4-bromo-3-(hydroxymethyl)phenoxy)nicotinaldehyde (8.03 g, 26.1 mmol, yield 68.3%) as a white solid after silica gel column purification (hexane:EtOAc=3:1, v/v).

$^1$H NMR (300 MHz, DMSO-d$_6$): δ 9.98 (s, 1H), 8.68 (d, J=2.4 Hz, 1H), 8.27 (ddd, J=8.7 & 2.4 & 0.6 Hz, 1H), 7.63 (d, J=7.8 Hz, 1H), 7.29 (d, J=2.4 Hz, 1H), 7.24 (d, J=8.7 Hz, 1H), 7.07 (dd, J=8.1 & 2.4 Hz, 1H), 5.54 (t, J=5.4 Hz, 1H) and 4.50 (d, J=5.4 Hz, 2H) ppm.

THP protection of 6-(4-bromo-3-(hydroxymethyl)phenoxy)nicotinaldehyde (2.4 g, 7.78 mmol) with 3,4-dihydro-2H-pyran (2.2 mL) catalyzed with (1S)-(+)-10-camphorsulfonic acid in CH₂Cl₂ (80 mL) at r.t. for 1 h provided the desired 6-(4-bromo-3-((tetrahydro-2H-pyran-2-yloxy)methyl)phenoxy)nicotinaldehyde as colorless oil (3.07 g, 7.8 mmol, yield 100%) after silica gel column purification (hexane:EtOAc=3:1, v/v).

$^1$H NMR (300 MHz, DMSO-d$_6$): δ 9.98 (s, 1H), 8.68 (d, J=2.4 Hz, 1H), 8.27 (ddd, J=8.4 & 2.4 & 0.6 Hz, 1H), 7.68 (dd, J=8.4 & 0.6 Hz, 1H), 7.31 (d, J=2.4 Hz, 1H), 7.25 (d, J=8.1 Hz, 1H), 7.12 (dd, J=8.4 & 3.0 Hz, 1H), 4.75-4.74 (m, 1H), 4.70 (d, J=13.5 Hz, 1H), 4.48 (d, J=13.5 Hz, 1H), 3.80-3.72 (m, 1H), 3.50-3.44 (m, 1H) and 1.80-1.40 (m, 6H) ppm.

Catalytic boronylation of 6-(4-bromo-3-((tetrahydro-2H-pyran-2-yloxy)methyl)phenoxy) nicotinaldehyde (3.07 g, 7.83 mmol) with bis-pinacol-diboron (3.05 g, 12 mmol), KOAc (2.3 g, 23.5 mmol) and PdCl₂(dppf)₂ (0.163 g, 2.5% mmol) in 1,4-dioxane (100 mL) at 80° C. overnight under N₂ afforded the desired 6-(3-((tetrahydro-2H-pyran-2-yloxy)methyl)-4-(4,4,5,5-tetramethyl-1,3,2-dioxaborolan-2-yl)phenoxy)nicotinaldehyde as oil (3 g, 6.83 mmol, yield 87.2%) after silica gel column purification (hexane:EtOAc=3:1, v/v).

$^1$H NMR (300 MHz, DMSO-d$_6$): δ 9.98 (s, 1H), 8.68 (d, J=2.4 Hz, 1H), 8.27 (dd, J=8.7 & 2.4 Hz, 1H), 7.73 (d, J=8.4 Hz, 1H), 7.24-7.21 (m, 2H), 7.10 (dd, J=8.4 & 2.4 Hz, 1H), 4.82 (d, J=12.9 Hz, 1H), 4.70-4.66 (m, 2H), 3.79-3.72 (m, 1H), 3.47-3.40 (m, 1H), 1.75-1.43 (m, 6H) and 1.29 (s, 12H) ppm.

Hydrolysis and simultaneous cyclization of 6-(3-((tetrahydro-2H-pyran-2-yloxy)methyl)-4-(4,4,5,5-tetramethyl-1,3,2-dioxaborolan-2-yl)phenoxy)nicotinaldehyde (3 g, 6.83 mmol) in acidic aqueous EtOH under N₂ during a long weekend produced the desired cyclic boronic acid 6-(1-hydroxy-1,3-dihydrobenzo[c][1,2]oxaborol-5-yloxy)nicotinaldehyde as a white solid (1.12 g, 4.39 mmol, yield 64.3%) after a normal work-up without column chromatography.

Mp 179-182° C. $^1$H NMR (300 MHz, DMSO-d$_6$): δ 9.98 (s, 1H), 9.23 (s, 1H), 8.69 (d, J=2.4 Hz, 1H), 8.26 (ddd, J=8.4 & 2.4 & 0.9 Hz, 1H), 7.77 (d, J=8.1 Hz, 1H), 7.24-7.21 (m, 2H), 7.15 (dd, J=8.1 & 1.2 Hz, 1H) and 4.98 (s, 2H) ppm. Purity (HPLC): 95% at 220 nm and 95% at 254 nm. MS: m/z=256 (M+1, ESI+) and m/z=254 (M−1, ESI−).

19bt (Z)—N-((6-(1-hydroxy-1,3-dihydrobenzo[c][1,2]oxaborol-5-yloxy)pyridin-3-yl)methylene)-2-methylpropan-2-amine oxide (D70)

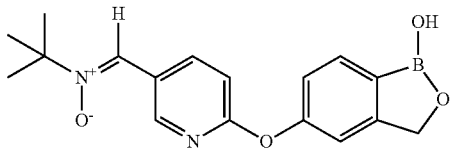 [SMILES: CC(C)(C)/[N+]([O-])=C/c1ccc(Oc2ccc3c(c2)COB3O)nc1]

Reaction of the aldehyde cyclic boronic acid 6-(1-hydroxy-1,3-dihydrobenzo[c][1,2]oxaborole-5-yloxy)nicotinaldehyde (0.18 g, 0.7 mmol) with t-BuNHOH AcOH salt (0.25 g, 2 eq) and silica gel (0.5 g) in EtOH (30 mL) at r.t. overnight under N₂ generated the desired title nitronyl cyclic boronic acid compound as white solid (0.1985 g, 0.6085 mmol, yield 86.9%) after filtration, evaporation and recrystallization from EtOAc and hexane with sonication.

Mp 156-164° C. 1H NMR (300 MHz, DMSO-d$_6$): δ 9.18 (s, 1H), 9.02 (d, J=2.1 Hz, 1H), 8.90 (dd, J=8.7 & 2.1 Hz, 1H), 7.92 (s, 1H), 7.75 (d, J=8.1 Hz, 1H), 7.15 (d, J=2.1 Hz, 1H), 7.11-7.06 (m, 2H), 4.96 (s, 2H) and 1.48 (s, 12H) ppm. Purity (HPLC): >95% at 220 nm and >95% at 254 nm. MS: m/z=327 (M+1, ESI+).

General Procedure for Ester Formation from Carboxylic Acid:

To a solution of 4-(1-hydroxy-1,3-dihydro-benzo[c][1,2]oxaborol-5-yloxy)-benzoic acid ((C38), 800 mg, 2.96 mmol) in the appropriate alcohol (50 mL) was added 4 drops of conc.

$H_2SO_4$. The resulting solution was heated to reflux until complete. All organic solvent was evaporated under vacuum. The residue was dissolved in EtOAc (30 mL) and washed with sat. $NaHCO_3$ (30 mL). Then the mixture was acidified to pH 3 by adding 1 M HCl. The organic layer was dried over $MgSO_4$, filtered, and evaporated under vacuum. The product was purified using silica gel column chromatography.

19bu 4-(1-Hydroxy-1,3-dihydro-benzo[c][1,2]oxaborol-5-yloxy)-benzoic acid methyl ester (D71)

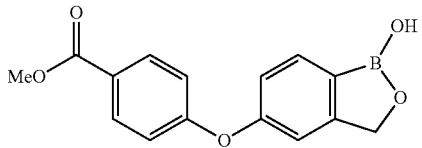 [SMILES: COC(=O)c1ccc(Oc2ccc3c(c2)COB3O)cc1]

Using the general procedure for ester formation with MeOH and purification by silica gel (eluting with 10% EtOAc/hexane) provided 630 mg of the title compound in 75% yield. $^1$H NMR 400 MHz (DMSO-$d_6$) δ: 9.22 (s, 1H), 7.98 (d, J=9.0 Hz, 2H), 7.78 (d, J=7.8 Hz, 1H), 7.30-7.10 (m, 4H), 4.97 (s, 2H), 3.83 (s, 3H); MS (ES) m/z: 285 (M+H)$^+$; HPLC purity: 96.21% (220 nm), 96.22% (254 nm).

19bv 4-(1-Hydroxy-1,3-dihydro-benzo[c][1,2]oxaborol-5-yloxy)-benzoic acid ethyl ester (D72)

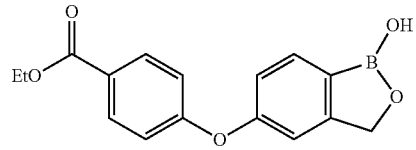 [SMILES: CCOC(=O)c1ccc(Oc2ccc3c(c2)COB3O)cc1]

Using the general procedure for ester formation with EtOH and purification by silica gel (eluting with 10% EtOAc/hexane) provided 350 mg the title compound in 39% yield. $^1$H NMR 400 MHz (DMSO-$d_6$) δ: 9.21 (s 1H), 7.98 (d, J=9.0 Hz, 2H), 7.78 (d, J=8.2 Hz, 1H), 7.107-7.03 (m, 4H), 4.96 (s, 2H), 4.30 (q, J=7.4 Hz, 2H), 1.31 (t, J=7.0 Hz, 3H); MS (ES) m/z: 299 (M+H)$^+$; HPLC purity: 97.7% (220 nm), 99.5% (254 nm).

19bw 4-(1-Hydroxy-1,3-dihydro-benzo[c][1,2]oxaborol-5-yloxy)-benzoic acid propyl ester (D73)

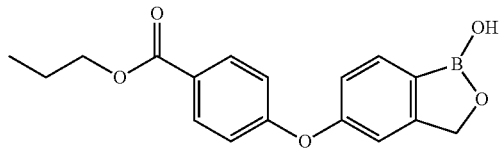 [SMILES: CCCOC(=O)c1ccc(Oc2ccc3c(c2)COB3O)cc1]

Using the general procedure for ester formation with PrOH and purification by silica gel (eluting with 10% EtOAc/hexane) provided 360 mg of the title compound in 39% yield. $^1$H NMR 400 MHz (DMSO-$d_6$) δ: 9.21 (s, 1H), 7.99 (d, J=9.0 Hz, 2H), 7.78 (d, J=7.8 Hz, 1H), 7.16-7.05 (m, 4H), 4.96 (s, 2H), 4.22 (t, J=6.7 Hz, 2H), 1.76-1.65 (m, 2H), 0.96 (t, 7.41 Hz, 3H); MS (ES) m/z: 313 (M+H)$^+$; HPLC purity: 96.5% (220 nm), 97.6% (254 nm).

19bx 4-(1-Hydroxy-1,3-dihydro-benzo[c][1,2]oxaborol-5-yloxy)-benzoic acid isopropyl ester (D74)

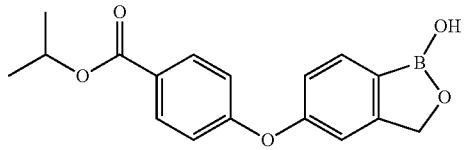 [SMILES: CC(C)OC(=O)c1ccc(Oc2ccc3c(c2)COB3O)cc1]

Using the general procedure for ester formation with iPrOH and purification by silica gel (eluting with 10% EtOAc/hexane) provided 550 mg the title compound in 60% yield. $^1$H NMR 400 MHz (DMSO-$d_6$) δ: 9.22 (s, 1H), 7.98 (d, 2H), 7.78 (d, 1H), 7.13-7.05 (m, 4H), 5.16-5.08 (m, 1H), 4.96 (s, 2H), 1.33 (d, 6H); MS (ES) m/z: 313 (M+H)$^+$; HPLC purity: 97.39% (220 nm), 98.23% (254 nm).

19by 4-(1-Hydroxy-1,3-dihydro-benzo[c][1,2]oxaborol-5-yloxy)-benzoic acid 2-dimethylamino-ethyl ester (D75)

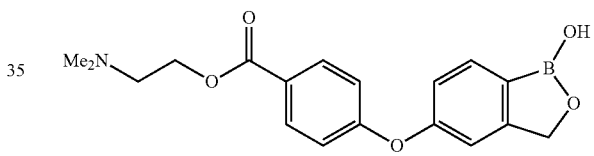

To a clear solution of 4-(1-hydroxy-1,3-dihydro-benzo[c][1,2]oxaborol-5-yloxy)-benzoic acid ((C38), 0.5 g, 1.75 mmol) in DMF (20 mL) were added N,N-dimethylamino ethanol (0.37 mL, 3.7 mmol) and EDCI (0.71 g, 3.7 mmol). The reaction was stirred at room temperature overnight. Then DMF was evaporated under vacuum. The residue was purified over sililca gel, eluting with 5% MeOH/DCM, to afford the 0.35 g of the title compound in 56% yield. $^1$H NMR 400 MHz (DMSO-$d_6$) δ: 7.97 (d, J=8.9 Hz, 2H), 7.76 (d, J=7.8 Hz, 1H), 7.15-7.07 (m, 4H), 4.95 (s, 2H), 4.33 (t, J=5.5 Hz, 2H), 2.58 (t, J=5.9 Hz, 2H), 2.20 (s, 6H); MS (ES) m/z: 342 (M+H)$^+$; HPLC purity: 91.90% (220 nm), 94.99% (254 nm).

Amide Analogues:

General Procedure for Amide Formation from Carboxylic Acid:

To a solution of 4-(1-hydroxy-1,3-dihydro-benzo[c][1,2]oxaborol-5-yloxy)-benzoic acid (C38, 1 g, 3.70 mmol) and the amine (3.70 mmol) were added HATU (1.67 g, 4.44 mmol) and DIPEA (1.55 mL, 8.88 mmol) in DMF (20 mL). The reaction was stirred at room temperature overnight. All organic solvent was evaporated. The residue was dissolved in EtOAc (50 mL) and washed with water (3×30 mL). The organic layer was evaporated under vacuum.

19bz N-Benzyl-4-(1-hydroxy-1,3-dihydro-benzo[c][1,2]oxaborol-5-yloxy)-benzamide (D76)

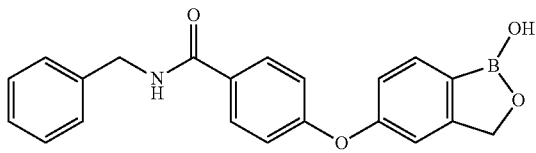 [SMILES: O=C(NCc1ccccc1)c1ccc(Oc2ccc3c(c2)COB3O)cc1]

Using the general procedure for amide formation with benzyl amine (0.396 g, 3.70 mmol) and purification using silica gel column chromatography (25% EtOAc/hexane) afforded 0.8 g of the title compound in 60% yield. $^1$H NMR 400 MHz (DMSO-$d_6$) δ: 9.08 (s, 1H), 9.00 (t, 1H), 7.97 (d, 2H), 7.78 (d, 1H), 7.40-7.23 (m, 4H), 7.12-7.02 (m, 4H), 4.97 (s, 2H), 4.48 (d, 2H); MS (ES) m/z: 360 (M+H)$^+$; HPLC purity: 96.5% (220 nm), 99.4% (254 nm).

19ca 4-(1-Hydroxy-1,3-dihydro-benzo[c][1,2]oxaborol-5-yloxy)-N-(2-hydroxy-ethyl)-benzamide (D77)

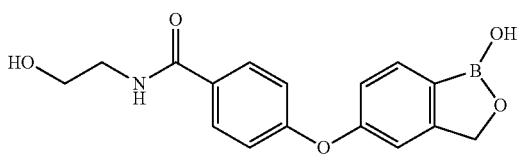 [SMILES: O=C(NCCO)c1ccc(Oc2ccc3c(c2)COB3O)cc1]

Using the general procedure for amide formation with 2-aminoethanol (0.23 g, 3.70 mmol) and purification by reverse phase chromatography, eluting from 5% MeOH/H$_2$O to 90% MeOH/H$_2$O, afforded 0.57 g of the title compound in 49% yield. $^1$H NMR 400 MHz (DMSO-$d_6$) δ: 9.16 (s, 1H), 8.38 (t, J=5.5 Hz, 1H), 7.90 (d, J=7.0 Hz, 2H), 7.75 (d, J=8.2 Hz, 1H), 7.08 (m, 4H), 4.95 (s, 2H), 4.72 (t, J=5.5 Hz, 1H), 3.49 (q, J=6.2 Hz, 2H); MS (ES) m/z: 314 (M+H)$^+$; HPLC purity: 94.6% (220 nm), 95.4% (254 nm).

19cb 4-(1-Hydroxy-1,3-dihydro-benzo[c][1,2]oxaborol-5-yloxy)-N-pyridin-2-ylmethyl-benzamide (D78)

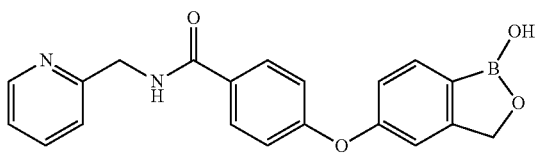 [SMILES: O=C(NCc1ccccn1)c1ccc(Oc2ccc3c(c2)COB3O)cc1]

Using the general procedure for amide formation with 2-aminomethyl pyridine (0.4 g, 3.70 mmol) and purification by reverse phase chromatography, eluting from 5% MeOH/H$_2$O to 90% MeOH/H$_2$O, afforded 0.55 g of the title compound in 41% yield. $^1$H NMR 400 MHz (DMSO-$d_6$) δ: 9.20 (s, 1H), 9.10 (t, J=5.8 Hz, 1H), 8.51 (d, J=4.7 Hz, 1H), 7.97 (d, J=8.6 Hz, 2H), 7.79-7.73 (m, 2H), 7.31 (d, J=7.8 Hz, 1H), 7.29-7.25 (m, 1H), 7.12 (d, J=8.6 Hz, 1H), 7.09-7.03 (m, 1H), 4.95 (s, 2H), 4.56 (d, 6.24 Hz, 2H); MS (ES) m/z: 361 (M+H)$^+$; HPLC purity: 98.4% (220 nm), 99.5% (254 nm).

19cc [4-(1-Hydroxy-1,3-dihydro-benzo[c][1,2]oxaborol-5-yloxy)-phenyl]-(4-methyl-piperazin-1-yl)-methanone (D79)

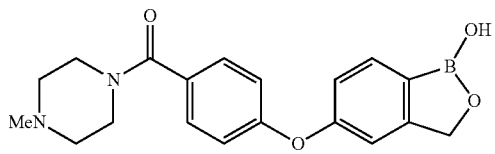 [SMILES: CN1CCN(C(=O)c2ccc(Oc3ccc4c(c3)COB4O)cc2)CC1]

Using the general procedure for amide formation with 1-methylpiperazine (0.41 g, 3.70 mmol) and purification by reverse phase chromatography, eluting from 5% MeOH/H$_2$O to 90% MeOH/H$_2$O, afforded 0.23 g of the title compound in 18% yield. $^1$H NMR 400 MHz (DMSO-$d_6$) δ: 9.20 (s, 1H), 7.78 (d, 1H), 7.42 (d, 2H), 7.14-7.06 (m, 4H), 4.96 (s, 2H), 3.58 (br, 4H), 2.32 (br, 4H), 2.20 (s, 3H); MS (ES) m/z: 353 (M+H)$^+$; HPLC purity: 96.24% (220 nm), 97.00% (254 nm).

19cd 1-{4-[4-(1-Hydroxy-1,3-dihydro-benzo[c][1,2]oxaborol-5-yloxy)-benzoyl]-piperazin-1-yl}-ethanone (D80)

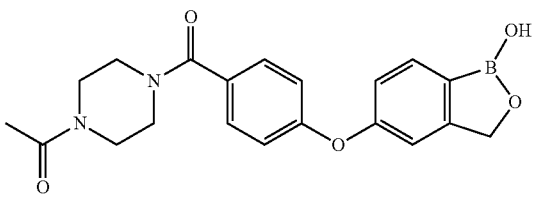 [SMILES: CC(=O)N1CCN(C(=O)c2ccc(Oc3ccc4c(c3)COB4O)cc2)CC1]

Using the general procedure for amide formation with 1-acetylpiperazine (0.474 g, 3.70 mmol) and purification by reverse phase chromatography, eluting from 5% MeOH/H$_2$O to 90% MeOH/H$_2$O, afforded 0.98 g of the title compound in 70% yield. $^1$H NMR 400 MHz (DMSO-$d_6$) δ: 9.19 (s, 1H), 7.75 (d, J=7.8 Hz, 1H), 7.47 (d, J=7.3 Hz, 2H), 7.12-7.02 (m, 4H), 4.96 (s, 2H), 2.02 (s, 3H), 3.46 (br, 8H); MS (ES) m/z: 381 (M+H)$^+$; HPLC purity: 97.17% (220 nm), 99.67% (254 nm).

19ce N-(2-Dimethylamino-ethyl)-4-(1-hydroxy-1,3-dihydro-benzo[c][1,2]oxaborol-5-yloxy)-benzamide (D81)

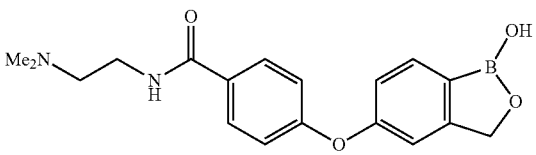 [SMILES: CN(C)CCNC(=O)c1ccc(Oc2ccc3c(c2)COB3O)cc1]

Using the general procedure for amide formation with 2-amino-1-dimethylaminoethane (0.4 g, 3.70 mmol) and purification by reverse phase chromatography, eluting from 5% MeOH/H$_2$O to 90% MeOH/H$_2$O, afforded 0.55 g of the title compound in 41% yield. $^1$H NMR 400 MHz (DMSO-d$_6$) δ: 9.21 (s, 1H), 8.65 (t, 1H), 7.92 (d, 2H), 7.78 (d, 1H), 7.16 (d, 2H), 7.06-7.01 (m, 2H), 4.98 (s, 2H), 3.59 (q, 2H), 3.26-3.20 (m, 2H), 2.82 (s, 6H); MS (ES) m/z: 341 (M+H)$^+$; HPLC purity: 96.13% (220 nm), 98.38% (254 nm).

19cj 6-(1-hydroxy-1,3-dihydrobenzo[c][1,2]ox-aborol-5-yloxy)nicotinonitrile (D82)

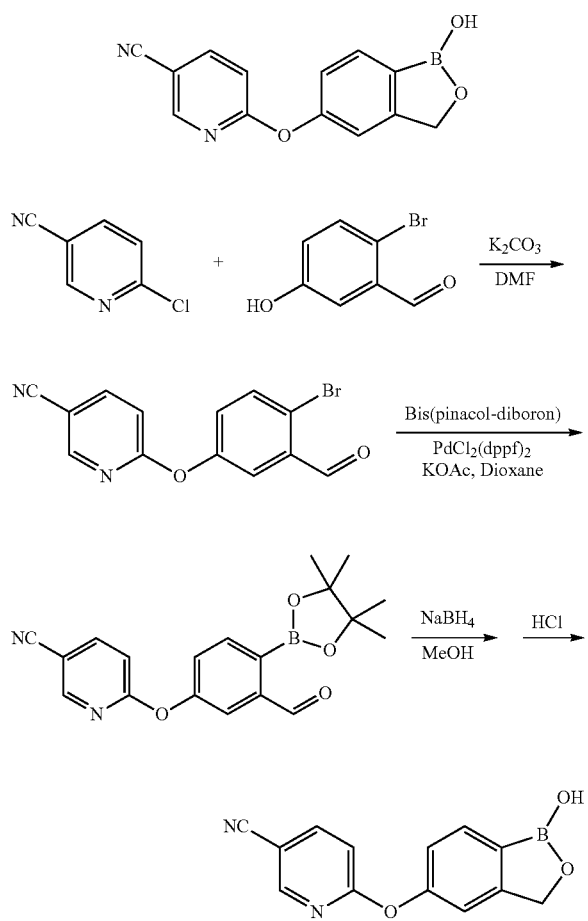

To a solution of 6-chloro-nicotinonitrile (3.5 g, 25.0 mmol, 1.0 eq.), 2-bromo-5-hydroxy-benzaldehyde (5.0 g, 25.0 mmol, 1.0 eq.) in DMF (40.0 mL) was added K$_2$CO$_3$ (4.1 g, 30.0 mmol, 1.2 eq.) under nitrogen atmosphere. The mixture was heated at 80° C. overnight. After cooling to room temperature, the mixture was poured into EtOAc (30 mL) and H$_2$O (30 mL). The layers were separated and the aqueous phase was extracted with EtOAc (3×20 mL). Combined organic extracts was washed with brine (30 mL), dried over MgSO$_4$, filtered and the filtrate was concentrated under reduced pressure. The residue was applied to silica chromatography eluting with MeOH/DCM (0:100 to 10:90) to give 6-(4-bromo-3-formyl-phenoxy)-nicotinonitrile as a white solid. $^1$H NMR (CHLOROFORM-d) δ: 10.35 (s, 1H), 8.43 (dd, J=2.3, 0.6 Hz, 1H), 7.98 (dd, J=8.6, 2.3 Hz, 1H), 7.69-7.77 (m, 2H), 7.30 (dd, J=8.6, 3.0 Hz, 1H), 7.12 (dd, J=8.6, 0.8 Hz, 1H). Amount obtained, 5.92 g, 78% yield.

To a solution of 6-(4-bromo-3-formyl-phenoxy)-nicotinonitrile (4.16 g, 13.7 mmol, 1.0 eq.) in 1,4-dioxane (120 mL) was added bis-pinacol-diboron (3.83 g, 15.1 mmol, 1.1 eq.), KOAc (4.03 g, 41.1 mmol, 3.0 eq.) and PdCl$_2$(dppf)$_2$ (300 mg, 0.4 mmol, 0.03 eq.). The mixture was degassed with N$_2$ and heated at 80° C. overnight. After cooling to room temperature, the mixture was filtered though a short pack of celite and the filtrate was concentrated under reduced pressure. The residue was applied to silica chromatography eluting with EtOAc/Heptanes (0:100 to 70:30) to give 6-[3-formyl-4-(4,4,5,5-tetramethyl-[1,3,2]dioxaborolan-2-yl)-phenoxy]-nicotinonitrile as a yellow solid. $^1$H NMR (CHLOROFORM-d) δ: 10.67-10.69 (m, 1H), 8.42-8.45 (m, 1H), 8.01-8.05 (m, 1H), 7.94-7.98 (m, 1H), 7.74-7.77 (m, 1H), 7.36-7.41 (m, 1H), 7.07-7.11 (m, 1H), 1.38-1.40 (m, 12H). Amount obtained, 4.1 g, 85.4% yield.

To a suspension of 6-[3-formyl-4-(4,4,5,5-tetramethyl-[1,3,2]dioxaborolan-2-yl)-phenoxy]-nicotinonitrile (1.67 g, 4.8 mmol, 1.0 eq.) in EtOH (30 mL) at 0° C. was added NaBH$_4$ (180.4 mg, 4.76 mmol, 1.0 eq.) in small portions. The mixture was stirred at 0° C. for 20 minutes and allowed to warm to room temperature in another 1 h. After cooling to 0° C., the clear solution was carefully treated with H$_2$O (1 mL), followed by slow addition of HCl (10 mL, 3N). The resulting yellow suspension was allowed to ward to room temperature gradually and stirred for 2 h. The mixture was then treated with sat. NaHCO$_3$ drop wise until PH reaching 7. The precipitate was collected by filtration, washed with H$_2$O to give 6-(1-hydroxy-1,3-dihydro-benzo[c][1,2]oxaborol-5-yloxy)-nicotinonitrile as a white solid. LCMS (m/z) 253 (M+H); $^1$H NMR (DMSO-d$_6$) δ: 9.19 (s, 1H), 8.60-8.66 (m, 1H), 8.31 (dd, J=8.7, 2.4 Hz, 1H), 7.76 (d, J=8.0 Hz, 1H), 7.20-7.28 (m, 2H), 7.13 (dd, J=8.0, 2.0 Hz, 1H), 4.96 (s, 2H). Amount obtained, 1.1 g, 92.4% yield.

19ck 4-(1-Hydroxy-1,3-dihydro-benzo[c][1,2]ox-aborol-5-yloxy)-benzoic acid butyl ester (D83)

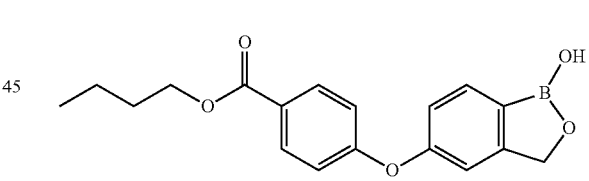

Using the general procedure for ester formation with BuOH and purification by silica gel.

19cl 3-fluoro-4-(1-hydroxy-1,3-dihydrobenzo[c][1,2]oxaborol-5-yloxy)benzonitrile (D84)

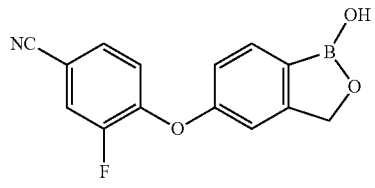 [SMILES: N#Cc1ccc(Oc2ccc3c(c2)COB3O)c(F)c1]

This compound was obtained in a similar manner to Example 19b (D2) from 3,4-difluorobenzonitrile and 4-bromo-3-(1,3-dioxolan-2-yl)phenol.

19cm 3-methyl-4-(1-hydroxy-1,3-dihydrobenzo[c][1,2]oxaborol-5-yloxy)benzonitrile (D85)

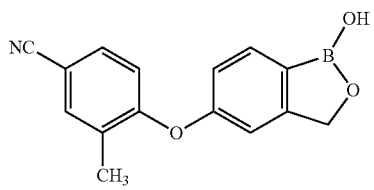 [SMILES: Cc1cc(C#N)ccc1Oc1ccc2c(c1)COB2O]

This compound was obtained in a similar manner to Example 19b (D2) from 4-fluoro-3-methylbenzonitrile and 4-bromo-3-(1,3-dioxolan-2-yl)phenol.

19cn 4-(1-Hydroxy-1,3-dihydro-benzo[c][1,2]oxaborol-5-yloxy)-2-(2-methoxyethoxy)-benzonitrile (D86)

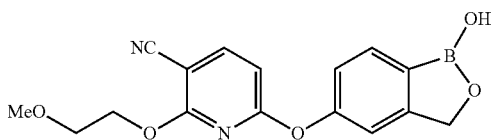 [SMILES: COCCOc1nc(Oc2ccc3c(c2)COB3O)ccc1C#N]

This compound was prepared in a similar manner to Example 19at (D46) using 2-methoxyethanol and sodium hydride instead of sodium methoxide.

$^1$H NMR 400 MHz (d$_6$-DMSO) δ3.22 (s, 3H), 3.53 (t, J=4.7 Hz, 2H), 4.24 (t, J=4.7 Hz, 2H), 4.99 (s, 2H), 6.71 (d, J=8.2 Hz, 1H), 7.21 (d, J=7.8 Hz, 1H), 7.30 (s, 1H), 7.79 (d, J=8.2 Hz, 1H), 8.25 (d, J=8.6 Hz, 1H), 9.26 (s, 1H). Mass Spectrum [M+H$^+$]=327.

19co 5-(4-Fluorophenoxy)-1,3-dihydro-1-hydroxy-2,1-benzoxaborole (D87)

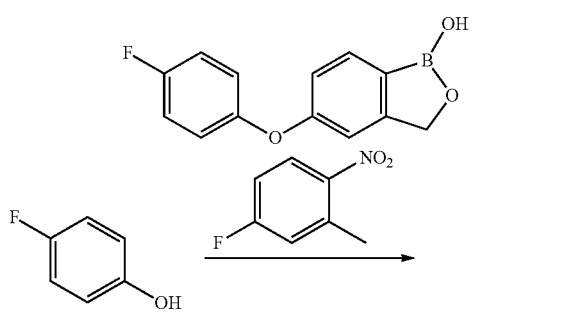

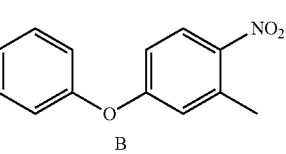

To a solution of A (7.22 g) and K$_2$CO$_3$ (17.8 g) in DMF (200 ml) was added 5-fluoro-2-nitrotoluene (10 g) under Ar. The reaction mixture was stirred at 80° C. overnight and filtrated, extracted with ether. The organic layer was separated, dried (Na$_2$SO$_4$), filtered, and the solvent was evaporated to give compound B (16 g; 99%). LC-MS: 248 (M+H)$^+$.

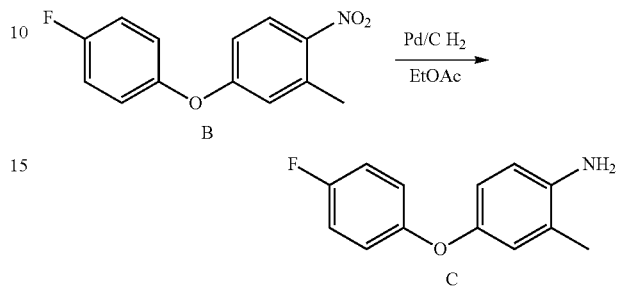

To the solution of B (16 g) in EtOAc (200 ml) was added Pd/C (2 g). The reaction mixture was stirred at room temperature under H$_2$ overnight and filtrated, and the solvent was evaporated to obtained compound C (13 g; 99%). LC-MS: 218 (M+H)$^+$.

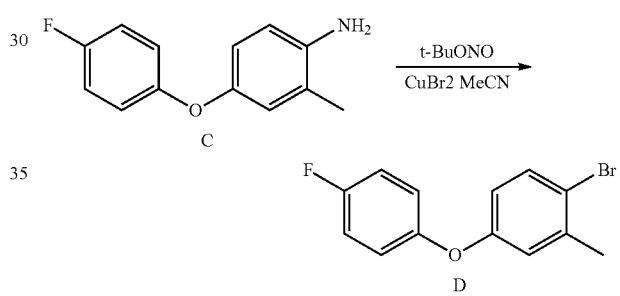

To a solution of CuBr$_2$ (16 g) in MeCN (140 ml) was added t-BuONO (10 ml) at −10° C. After 0.5 h, to the reaction mixture was added C (16 g) in MeCN (10 ml). The reaction mixture was stirred at −10° C. overnight and filtrated, the solvent was evaporated and the residue was purified by chromatography to give D (2.4 g; 15%). GC-MS: 281.

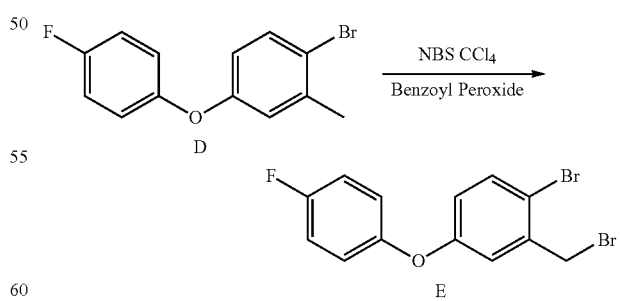

To a solution of D (2.4 g) and NBS (1.6 g) in CCl$_4$ (25 ml) was added benzoyl peroxide (200 mg). The reaction mixture was stirred at 70° C. overnight, filtrated, and washed with water. The organic layer was dried (Na$_2$SO$_4$), filtered, and the solvent was evaporated to give compound E (2.7 g; 99%)

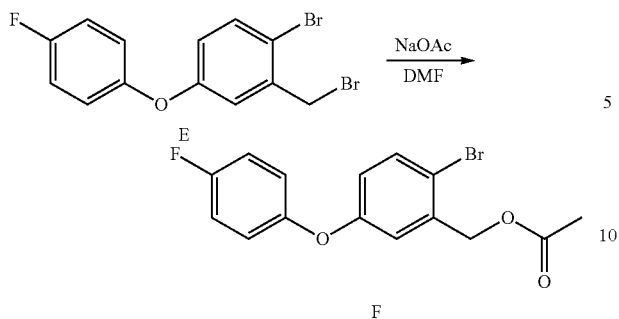

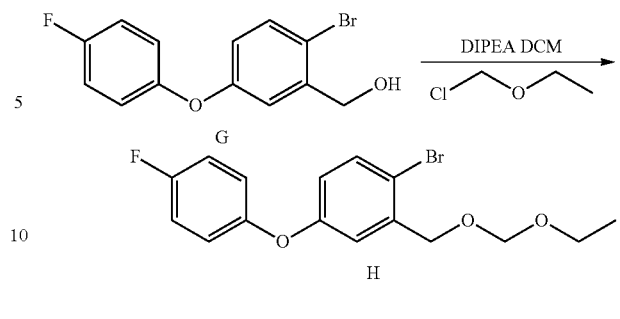

To a solution of E (2.7 g) in DMF (50 ml) was added NaOAc (4 g). The reaction mixture was stirred at 70° C. for 5 h, filtrated, and extracted with ether. The organic layer was To a solution of G (1.5 g) and DIPEA (0.97 g) in DCM (20 ml) was added (chloromethoxy)ethane (0.7 g). The reaction mixture was stirred at room temperature overnight and was evaporated. Purification of the residue by chromatography gave compound H (1 g; 58%). LC-MS: 356 (M+H)$^+$.

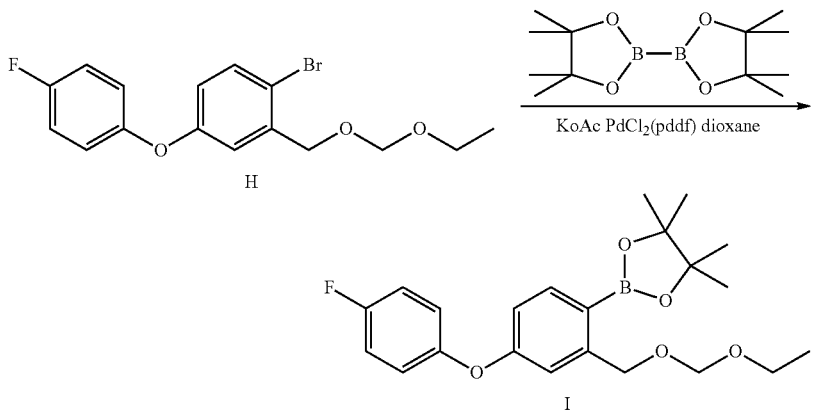

separated, dried (Na$_2$SO$_4$), filtered, and the solvent was evaporated to give compound F (2 g; 99%).

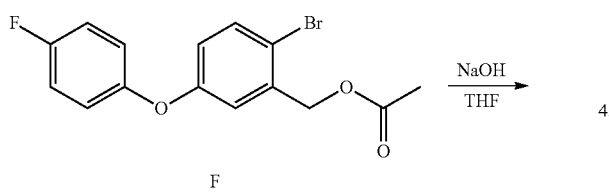

To the solution of H (1 g), KOAc (0.8 g) and PdCl$_2$(dppf) (0.12 g) in dioxane (5 ml) was added bis(pinacolato)diboron (1 g) under Ar. The reaction mixture was stirred at 70° C. overnight, washed with water, extracted with DCM, and the organic layer was evaporated. The residue was purified by HPLC to give compound I (800 mg; 70%).

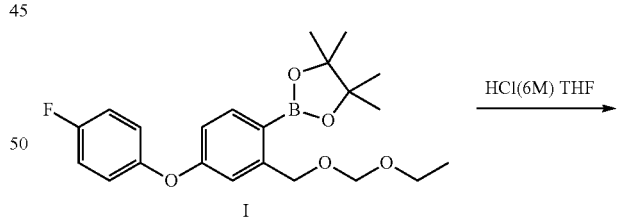

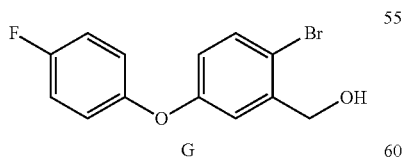

To a solution of F (2 g) in THF (20 ml) was added NaOH/H$_2$O (10%; 20 ml). The reaction mixture was stirred at room temperature overnight, HCl/H$_2$O (4 M) was added to ca. pH 7, and the mixture was extracted with EtOAc. The organic layer was dried (Na$_2$SO$_4$), filtered, and the solvent was evaporated to give G (1.5 g; 88%). LC-MS: 297 (M+H)$^+$.

To a solution of I (800 mg) in THF (20 ml) was added HCl/H$_2$O (6M; 20 ml). The reaction mixture was stirred at room temperature overnight and extracted with DCM. The organic layer was dried and evaporated. The residue was purified by HPLC to give the desired compound (300 mg; 60%). LC-MS: 245 (M+H)⁺.

19cp 5-(4-Chlorophenoxy)-1,3-dihydro-1-hydroxy-2,1-benzoxaborole (D88)

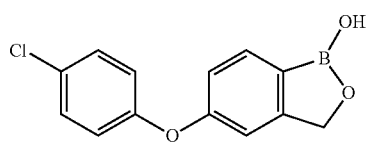

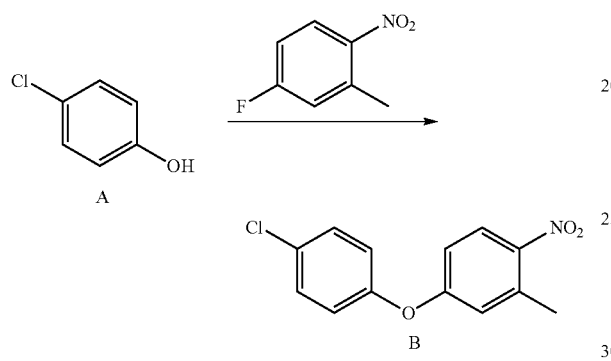

To a solution of A (18 g) and K₂CO₃ (36 g) in DMF (200 ml) was added 5-fluoro-2-nitrotoluene (20 g) under Ar. The reaction mixture was stirred at 70° C. overnight, filtrated, diluted with water and extracted with ether. The organic layer was separated, dried (Na₂SO₄), filtered, and the solvent was evaporated to obtained compound B (36 g; 99%). LC-MS: 264 (M+H)

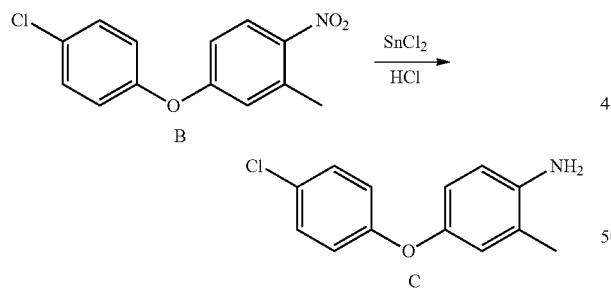

To a solution of B (36 g) in HCl(150 ml) was added SnCl₂ (116 g). The reaction mixture was stirred at room temperature for 1 h. filtered, extracted with EtOAc and the solvent was evaporated to obtained compound C (30 g; 97%). LC-MS: 234 (M+H)⁺.

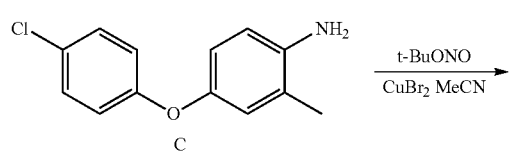

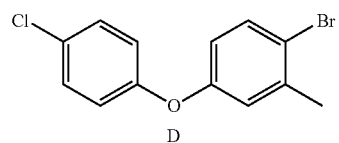

To a solution of CuBr₂ (42 g) in MeCN (500 ml) was added t-BuONO (22 ml) at −10° C. After 0.5 h, to the reaction mixture was added ANA-PO4209-3A-3 (30 g) in MeCN (10 ml). The reaction mixture was stirred at −10 overnight, filtered, and the solvent was evaporated. The residue was purified by chromatography to give compound ANA-PO4209-3A-4 (8.4 g; 22%). GC-MS: 297.

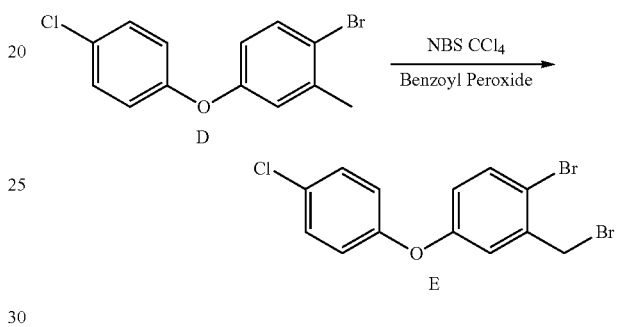

To a solution of D (8.4 g) and NBS (5.5 g) in CCl₄ (200 ml) was added benzoyl peroxide (800 mg). The reaction mixture was stirred at 70° C. overnight, filtered, and washed with water. The organic layer was dried (Na₂SO₄), filtered, and the solvent was evaporated to give compound E (10 g; 99%)

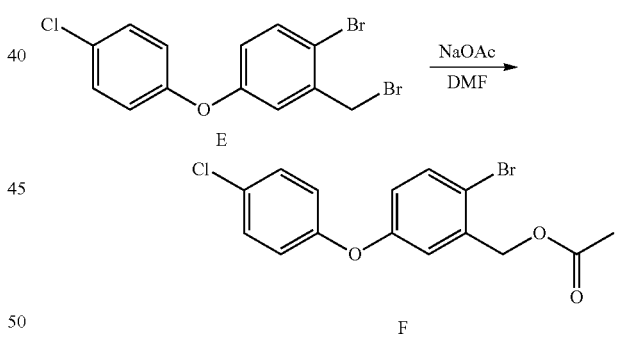

To a solution of E (10 g) in DMF (250 ml) was added NaOAc (15 g). The reaction mixture was stirred at 70° C. for 5 h, filtrated, diluted with water and extracted with ether. The organic layer was separated, dried (Na₂SO₄), filtered, and the solvent was evaporated to give compound F (9.6 g; 99%).

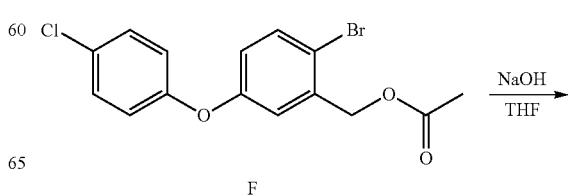

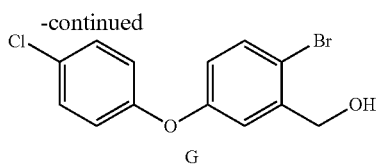
G

To a solution of F (9.6 g) in THF (50 ml) was added NaOH/H$_2$O (10%; 50 ml). The reaction mixture was stirred at room temperature overnight, HCl/H$_2$O (4 M) was added to ca. pH7, and the whole was extracted with EtOAc. The organic layer was dried (Na$_2$SO$_4$), filtered, and the solvent was evaporated to give compound G (7.5 g; 89%). LC-MS: 313 (M+H)$^+$.

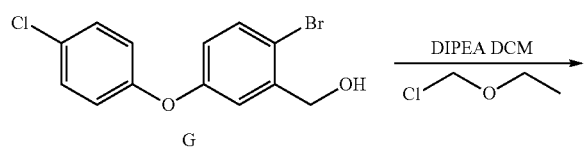

To a solution of G (7.5 g) and DIPEA (3.87 g) in DCM (200 ml) was added (chloromethoxy)ethane (2.9 g). The reaction mixture was stirred at room temperature overnight and was evaporated purified by chromatography to give compound H (9 g; 99%). LC-MS: 372 (M+H)$^+$.

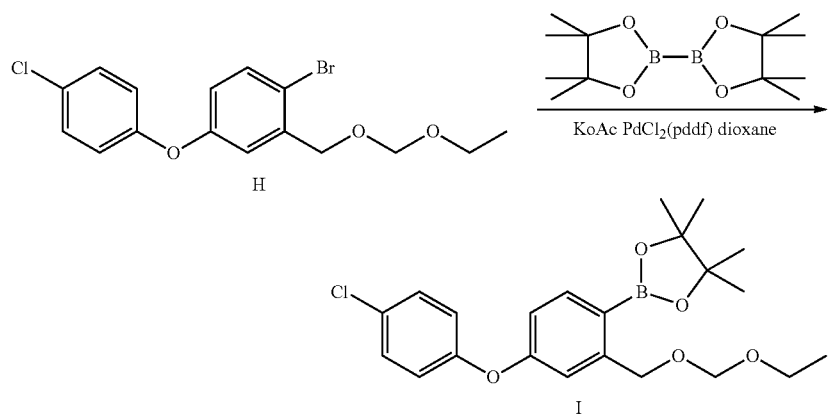

To a solution of H (9 g), KOAc (7 g) and PdCl$_2$(dppf) (0.98 g) in dioxane (100 ml) was added bis(pinacolato)diboron (9.1 g) under Ar. The reaction mixture was stirred at 70° C. overnight, diluted with water, extracted with DCM, and the organic layer was evaporated and purified by HPLC to give compound I (8 g; 80%).

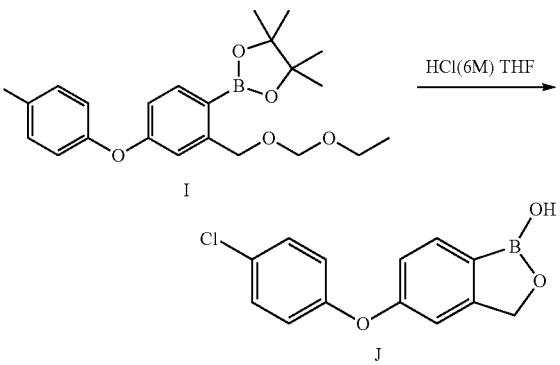

To a solution of I (8 g) in THF (80 ml) was added HCl/H$_2$O (6 M; 80 ml). The reaction mixture was stirred at room temperature overnight, extracted with DCM, and evaporated. The residue was purified by HPLC to give the desired compound (2 g; 40%). LC-MS: 261 (M+H)$^+$.

19cq 5-(4-Methylphenoxy)-1,3-dihydro-1-hydroxy-2,1-benzoxaborole (D89)

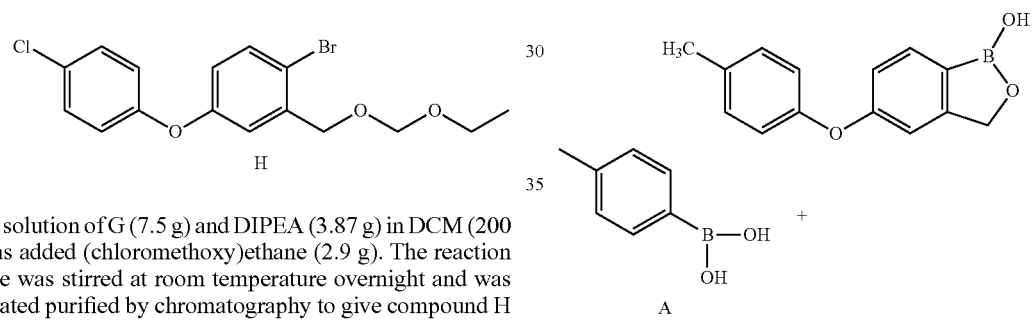

+

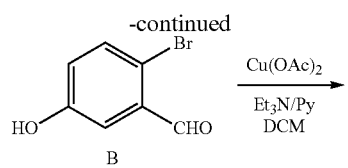
B

-continued

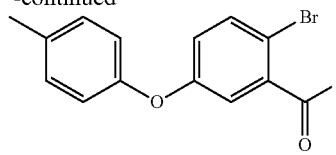

C

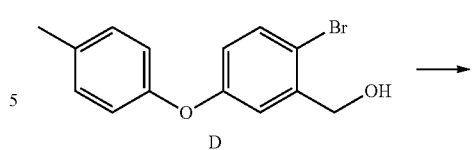

Compound A (8 g, 58.8 mmol), compound B (8 g, 39.8 mmol), Cu(OAc)$_2$ (8.4 g, 47.8 mmol) and 4 A MS (11 g) were suspended in dry DCM (100 mL), Et$_3$N (11.2 mL) and pyridine (33.6 mL) were added, and the reaction was stirred at room temperature under Ar for 48 h, filtered and washed by 1 M HCl, the organic layer was combined and dried over MgSO$_4$. The crude was purification by chromatography using 20:1 PE/EA to give compound C (4.2 g, 30%). GC-MS 290 (M+H)$^+$; $^1$H NMR (400 MHz, CDCl$_3$) δ 10.299 (s, 1H), 7.589 (d, J=8.8 Hz, 1H), 7.458 (d, J=2.8 Hz, 1H), 7.195 (d, J=8.0 Hz, 2H), 7.107 (dd, J=2.8 Hz, J=8.4 Hz, 1H), 6.936 (d, J=8.4 Hz, 2H), 2.366 (s, 1H).

A mixture of compound D (1.6 g, 5.5 mmol) and NaH (217 mg, 9.0 mmol) in DMF (20 mL) was stirred for 30 min at 0° C. EOM-Cl (800 mg, 8.5 mmol) was added, and the mixture was stirred for 1 h at ambient temperature and evaporated. The residue was purification by chromatography using 10:1 PE/EA to give compound E (1.6 g, 84%). $^1$H NMR (400 MHz, CDCl$_3$) δ 7.470 (d, J=9.2 Hz, 1H), 7.168-7.146 (m, 3H), 6.929 (d, J=8.4 Hz, 2H), 6.811 (d, J=9.2 Hz, 1H), 4.803 (s, 2H), 4.636 (s, 2H), 3.661-3.645 (m, 2H), 2.352 (s, 3H), 1.255-1.220 (m, 3H).

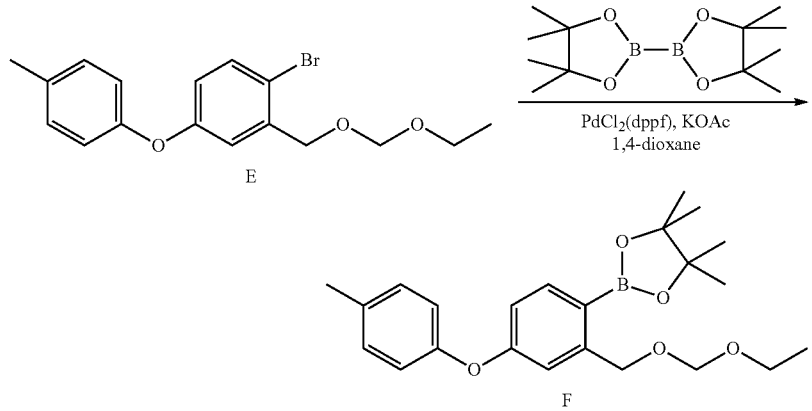

A mixture of compound E (1.6 g, 4.6 mmol), bis(pinacolato)diboron (1.7 g, 7.1 mmol), PdCl$_2$(dppf) (98 mg) and KOAc (1.3 g, 13.2 mmol) in 1,4-dioxane (20 mL) was stirred overnight at 80° C. under Ar. The solvent was evaporated. The residue was purification by chromatography using 10:1 PE/EA to give compound F (1.6 g, 89%). $^1$H NMR (400 MHz, CDCl$_3$) δ 7.778 (d, J=8.0 Hz, 1H), 7.159 (d, J=8.8 Hz, 2H), 6.942 (d, J=8.0 Hz, 2H), 6.856 (m, 1H), 4.854 (s, 2H), 4.797 (s, 2H), 3.659-3.606 (m, 2H), 2.349 (s, 3H), 1.333 (s, 12H), 1.240-1.206 (m, 3H).

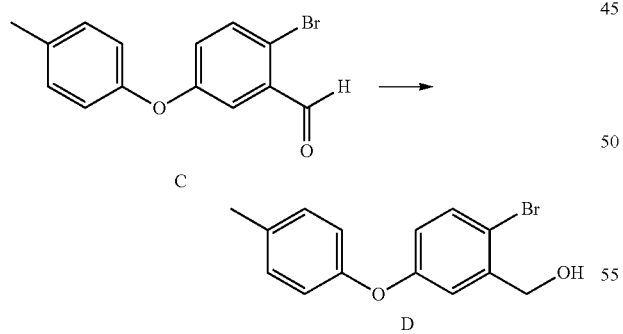

A mixture of compound C (5 g, 17.2 mmol) and NaBH$_4$ (320 mg, 8.6 mmol) in MeOH (50 mL) was stirred for 1 h at ambient temperature and evaporated. The residue was purification by chromatography using 6:1 PE/EA to give compound D (5 g, 100%). GC-MS 292 (M+H)$^+$; $^1$H NMR (400 MHz, CDCl$_3$) δ 7.465 (d, J=8.0 Hz, 1H), 7.272 (d, J=8.0 Hz, 2H), 7.171-7.133 (m, 1H), 6.931 (d, J=8.4 Hz, 2H), 6.811 (d, J=8.0 Hz, 1H), 4.701 (s, 2H), 2.351 (s, 3H).

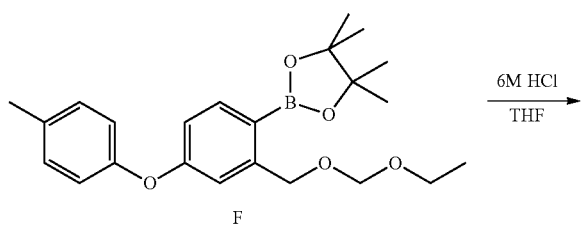

-continued

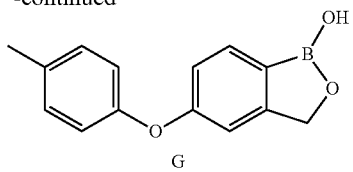

G

A mixture of compound F (1.6 g, 4.0 mmol) in 6 M HCl (8 mL) and THF (8 mL) was stirred overnight at ambient temperature and evaporated. The residue was purification by prepared-HPLC to give the desired compound (600 mg, 63%). LC-MS 241 (M+H)$^+$; $^1$H NMR (400 MHz, CDCl$_3$) δ 7.684 (d, J=8.4 Hz, 1H), 7.197 (d, J=7.6 Hz, 2H), 7.007-6.956 (m, 3H), 6.875 (s, 1H), 5.026 (s, 2H), 2.368 (s, 3H).

19cr 5-(4-Trifluoromethyl)-1,3-dihydro-1-hydroxy-2,1-benzoxaborole (D90)

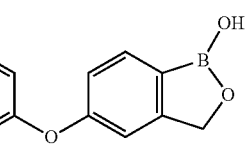

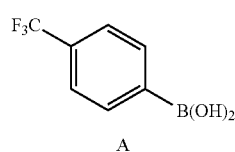

A

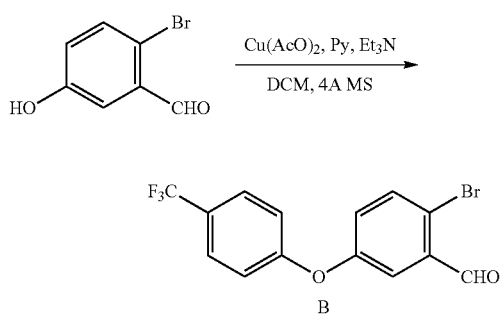

To a solution of A (10.1 g, 53.3 mmol), 2-bromo-5-hydroxybenzaldehyde (6.7 g, 33.3 mmol), 4 A MS (25 g) and Cu(OAc)$_2$ (7.84 g, 43.3 mmol) in dry CH$_2$Cl$_2$ (150 ml) was added pyridine (4.74 g, 59.9 mmol) and Et$_3$N (8.4 ml, 59.9 mmol) under Ar. The reaction mixture was stirred at ambient temperature overnight and filtrated, washed with 2N HCl, extracted with CH$_2$Cl$_2$. The organic layer was separated, dried (Na$_2$SO$_4$), filtered, and the solvent was evaporated. The residue was purified by column chromatography over silica gel (eluent: petroleum ether/EtOAc 25/1). The pure fractions were collected, and the solvent was evaporated to afford B (3.49 g, 30%): $^1$H NMR (CDCl$_3$) δ 7.07 (2H, d, J=8.8 Hz), 7.18 (1H, dd, J=2.8, 8.4 Hz), 7.55 (1H, d, J=2.8 Hz), 7.61-7.67 (3H, m), 10.32 (1H, s).

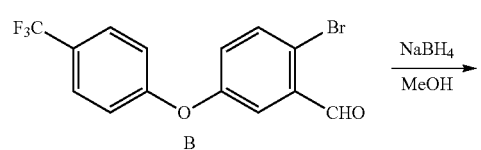

B

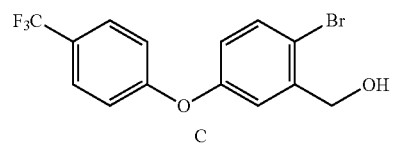

C

To a solution of B (3.49 g, 10.1 mmol) in MeOH (40 ml) was added NaBH$_4$ (192 mg, 5.06 mmol). The reaction mixture was stirred at ambient temperature for 0.5 h. The solvent was evaporated. The residue was purified by column chromatography over silica gel (eluent: petroleum ether/EtOAc 15/1). The pure fraction was collected, and the solvent was evaporated to afford C (3.25 g, 93%): $^1$H NMR (CDCl$_3$) δ 1.79 (1H, s), 4.73 (2H, s), 6.87 (1H, dd, J=2.4, 8.8 Hz), 7.05 (2H, d, J=8.4 Hz), 7.23 (1H, d, J=2 Hz), 7.53 (1H, d, J=9.2 Hz), 7.59 (2H, d, J=8.8 Hz).

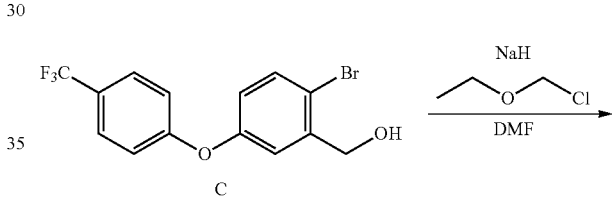

C

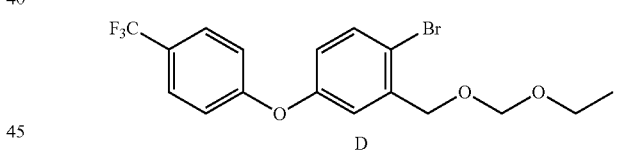

D

To a solution of C (3.7 g, 10.6 mmol) in dry DMF (20 ml) was added NaH (462 mg, 10.6 mmol, 55%) under Ar. The reaction mixture was stirred at 0° C. for 0.5 h, then (chloromethoxy)ethane (1.3 g, 13.8 mmol) was added. The reaction mixture was stirred at ambient temperature for 1 h and quenched with i-PrOH. The solvent was evaporated under high vacuum. The residue was dissolved in EtOAc, washed with water. The organic layer was separated, dried (Na$_2$SO$_4$), filtered, and the solvent was evaporated. The residue was purified by column chromatography over silica gel (eluent: petroleum ether/EtOAc 100/1). The pure fractions were collected, and the solvent was evaporated to afford D (3.1 g, 76%): $^1$H NMR (CDCl$_3$) δ 1.22 (3H, t, J=6.8 Hz), 3.61-3.66 (2H, m), 4.64 (2H, s), 4.80 (2H, s), 6.85 (1H, dd, J=2.8, 8.8 Hz), 7.04 (2H, d, J=8.8 Hz), 7.23 (1H, d, J=2.8 Hz), 7.53 (1H, d, J=8.8 Hz), 7.58 (2H, d, J=9.2 Hz).

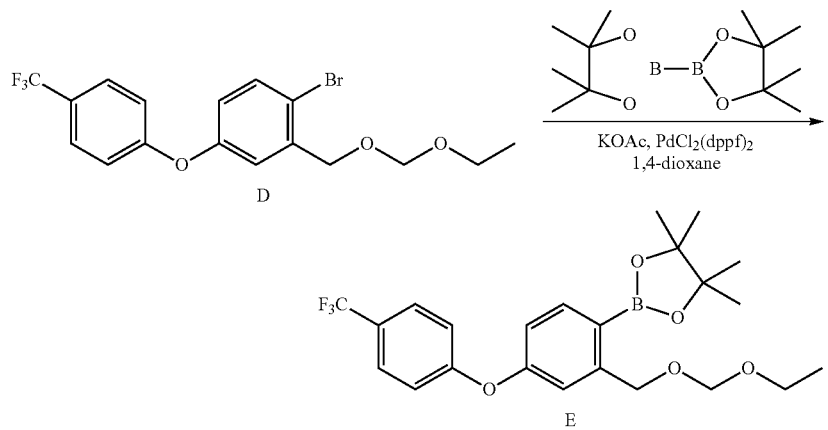

A mixture of D (3.1 g, 7.7 mmol), bis(pinacolato)diboron (5.87 g, 23.1 mmol), PdCl$_2$(dppf)$_2$ (186 mg, 0.23 mmol) and KOAc (2.26 g, 23.1 mmol) in 1,4-dioxane (40 mL) was stirred at 80° C. overnight under Ar. The organic layer was removed. The residue was purified by column chromatography over silica gel (eluent: petroleum ether). The pure fractions were collected, and the solvent was evaporated to afford E (2.6 g, 75%): $^1$H NMR (CDCl$_3$) δ 1.21 (3H, t, J=6.8 Hz), 1.33 (12H, s), 3.59-3.64 (2H, m), 4.79 (2H, s), 4.86 (2H, s), 6.92 (1H, dd, J=2.8, 7.6 Hz), 7.05 (2H, d, J=8.4 Hz), 7.19 (1H, d, J=1.6 Hz), 7.56 (2H, d, J=8.0 Hz), 7.83 (1H, d, J=7.6 Hz).

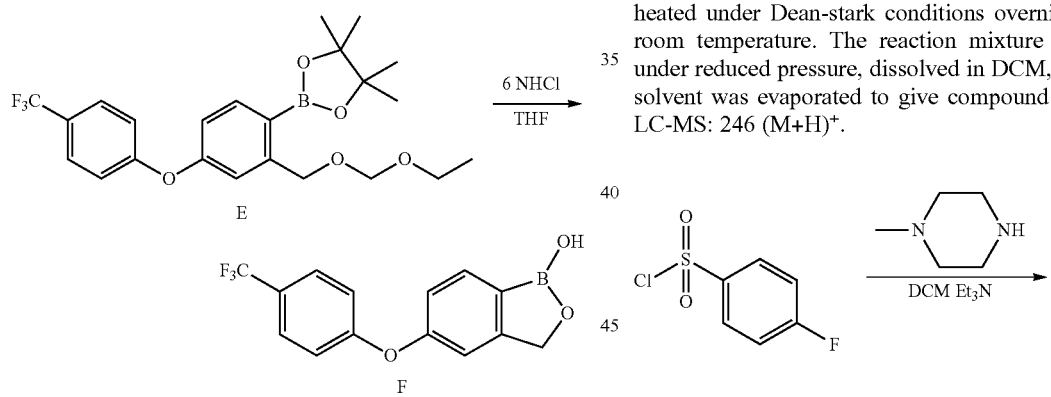

A mixture of E (2.6 g, 5.75 mmol) in 6 M HCl (26 mL) and THF (26 mL) was stirred at ambient temperature overnight. The solvents were removed. The residue was purification by preparative HPLC to obtain the desired compound (370 mg, 22%): $^1$H NMR (DMSO-d$_6$) δ 4.96 (2H, s), 7.08 (1H, m), 7.13 (1H, s), 7.20 (2H, d, J=8.5 Hz), 7.77 (3H, m), 9.21 (1H, s).

19cs 5-(4-(4-methylpiperazin-1-ylsulfonyl)phenoxy) benzo[c][1,2]oxaborol-1(3H)-ol (D91)

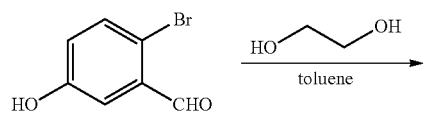

-continued

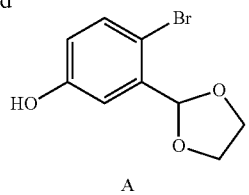

A

To a solution of 2-bromo-5-hydroxybenzaldehyde (14 g) and p-toluenesulfonic acid (1.4 g) in toluene (400 ml) was added ethane-1,2-diol (6.5 g). The reaction mixture was heated under Dean-stark conditions overnight and cool to room temperature. The reaction mixture was evaporated under reduced pressure, dissolved in DCM, filtered, and the solvent was evaporated to give compound A (15 g; 88%). LC-MS: 246 (M+H)$^+$.

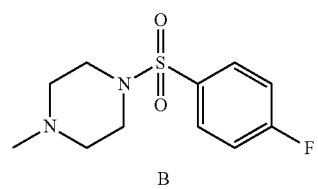

B

To a solution of 1-methylpiperazine (5.5 g) in DCM (200 ml) was added Et$_3$N (10.5 g) at 0° C. After stirring 0.5 h, to the reaction mixture was added 4-fluorobenzene-1-sulfonyl (10 g) dropwise. The reaction mixture was stirred at 0° C. for 2 h, then was stirred at room temperature overnight and washed with water. The organic layer was dried (Na$_2$SO$_4$), filtered, and the solvent was evaporated to give compound B (13 g; 97%). LC-MS: 259 (M+H)$^+$.

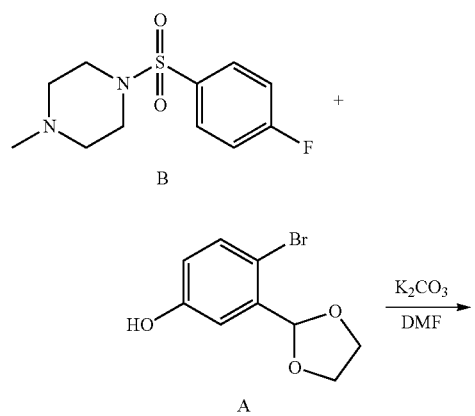

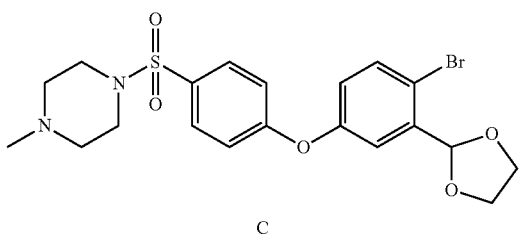

To a solution of B (8 g) and K$_2$CO$_3$ (8.3 g) in DMF (250 ml) was added A (8.3 g) under Ar. The reaction mixture was stirred at 150° C. for 3 h filtrated, diluted with ether and washed with water. The organic layer was separated, dried (Na$_2$SO$_4$), filtered, and the solvent was evaporated to obtained compound C (14 g; 96%). LC-MS: 484 (M+H)$^+$.

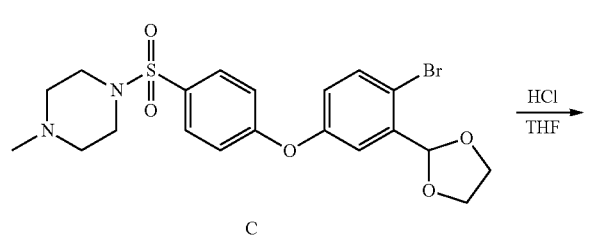

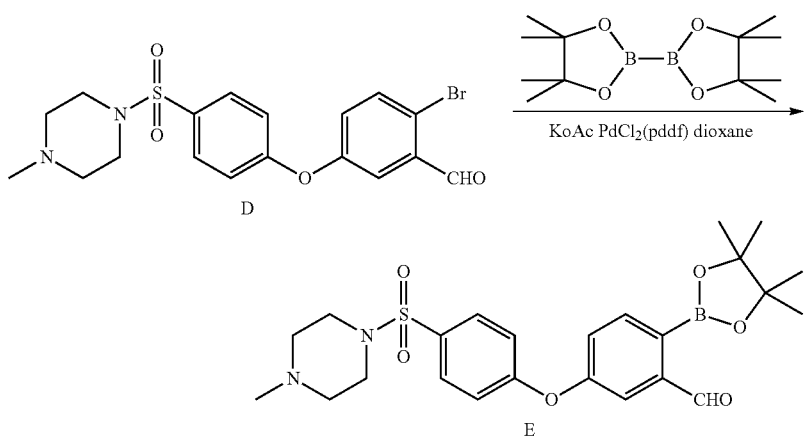

To a solution of C (14 g) in THF (100 ml) was added HCl (12 M; 100 ml). The reaction mixture was stirred at room temperature overnight and extracted with DCM. The organic layer was separated, dried (Na$_2$SO$_4$), filtered, and the solvent was evaporated to give compound D (12 g; 94%). LC-MS: 440 (M+H)$^+$.

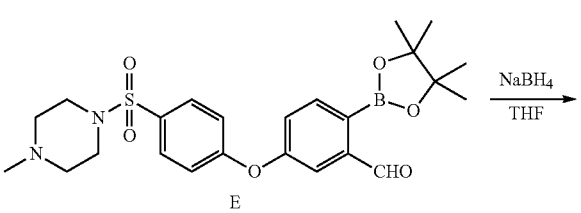

To the solution of D (12 g), KOAc (7.9 g) and PdCl$_2$(dppf) (1.1 g) in dioxane (80 ml) was added bis(pinacolato)diboron (10.4 g) under Ar. The reaction mixture was stirred at 70° C. overnight, diluted with water, and extracted with DCM. The organic layer was separated, dried (Na$_2$SO$_4$), filtered, and the solvent was evaporated to give compound E (5 g; 37%)

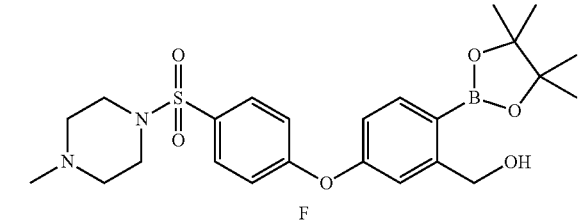

To a solution of E (5 g) in THF (40 ml) was added NaBH$_4$ (1 g). The reaction mixture was stirred at room temperature overnight, HCl/H$_2$O (4 M) was added, and the whole extracted with EtOAc. The organic layer was separated, dried (Na$_2$SO$_4$), filtered, and the solvent was evaporated to give compound F (800 mg; 16%). LC-MS: 489 (M+H)$^+$.

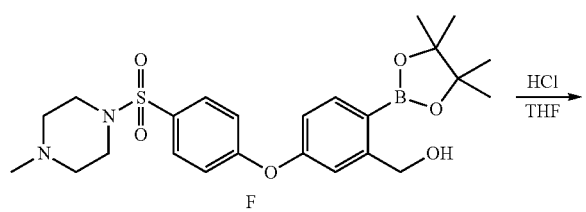

To a solution of F (800 mg) in THF (20 ml) was added HCl/H$_2$O (6 M; 20 ml). The reaction mixture was stirred at room temperature overnight and extracted with DCM. The organic layer was evaporated and the residue was purified by HPLC to give the desired compound (100 mg; 16%). LC-MS: 389 (M+H)$^+$.

19ct N,N-diethyl-4-(1-hydroxy-1,3-dihydrobenzo[c][1,2]oxaborol-5-yloxy)benzenesulfonamide (D92)

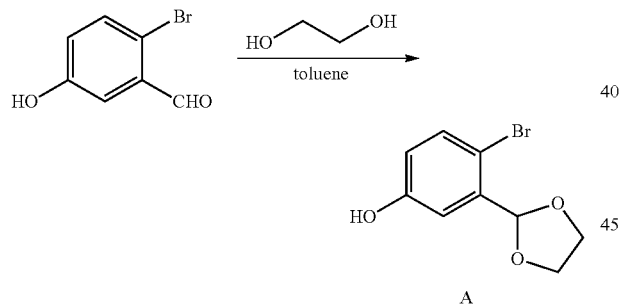

To a solution of 2-bromo-5-hydroxybenzaldehyde (5 g) and toluenesulfonic acid (0.13 g) in toluene (200 ml) was added ethane-1,2-diol (3.8 g). The reaction mixture was heated under Dean-stark conditions overnight and cool to room temperature. The reaction mixture was evaporated under reduced pressure, DCM was added, the mixture filtered, and the solvent was evaporated to give compound A (5 g; 83%). LC-MS: 246 (M+H)$^+$.

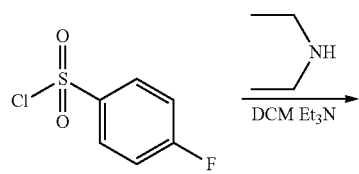

-continued

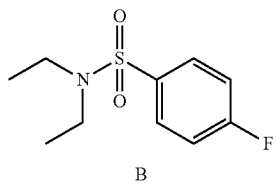

To a solution of diethylamine (1 g) in DCM (50 ml) was added Et$_3$N (2.8 g) at 0° C. After stirring 0.5 h, to the reaction mixture was added 4-fluorobenzene-1-sulfonyl (2.9 g) dropwise. The reaction mixture was stirred at 0° C. for 2 h, then was stirred at room temperature overnight and washed with water. The organic layer was dried (Na$_2$SO$_4$), filtered, and the solvent was evaporated to give compound B (2.5 g; 78%). LC-MS: 232 (M+H)$^+$.

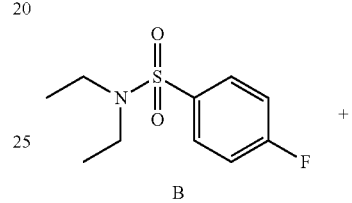

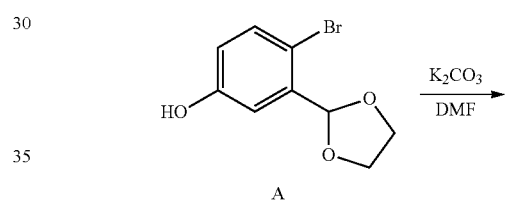

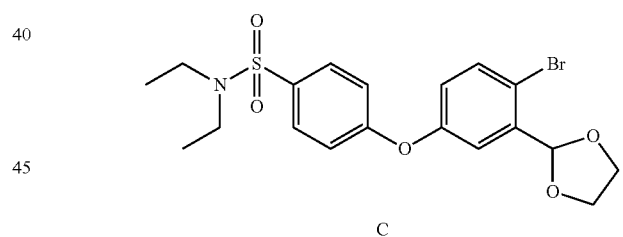

To a solution of B (2.5 g) and K$_2$CO$_3$ (2.7 g) in DMF (100 ml) was added A (2.5 g) under Ar$_e$. The reaction mixture was stirred at 150° C. for 3 h, filtered, and extracted with ether. The organic layer was separated, dried (Na$_2$SO$_4$), filtered, and the solvent was evaporated to give compound C (5 g; 100%). LC-MS: 458 (M+H)$^+$.

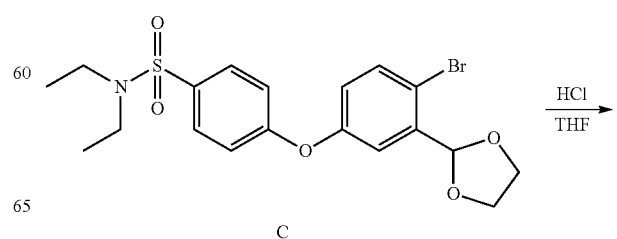

-continued

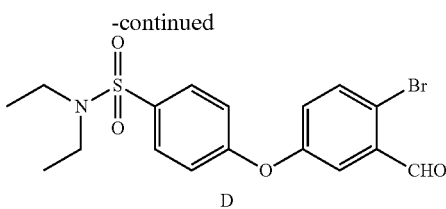
D

To a solution of C (5 g) in THF (40 ml) was added HCl (12 M; 40 ml). The reaction mixture was stirred at room temperature overnight and extracted with DCM. The organic layer was separated, dried (Na$_2$SO$_4$), filtered, and the solvent was evaporated to give compound D (4.1 g; 100%). LC-MS: 414 (M+H)$^+$.

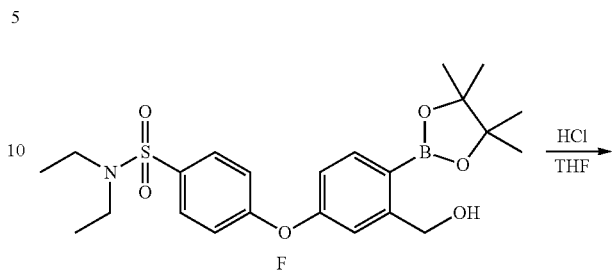

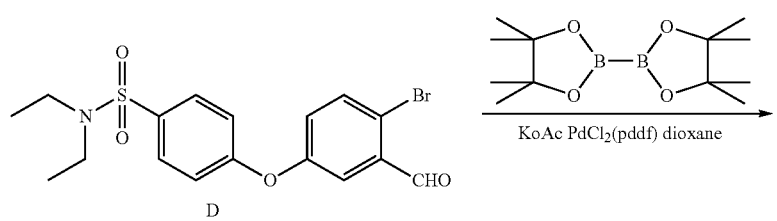
E

To the solution of D (4.1 g), KOAc (2.9 g) and PdCl$_2$(dppf) (0.4 g) in dioxane (80 ml) was added bis(pinacolato)diboron (3.8 g) under Ar. The reaction mixture was stirred at 70° C. overnight diluted with water, and extracted with DCM. The organic layer was separated, dried (Na$_2$SO$_4$), filtered, and the solvent was evaporated to give compound E (3 g; 66%)

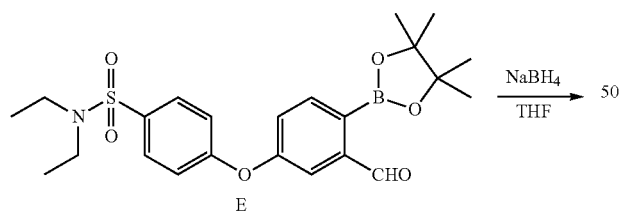
E

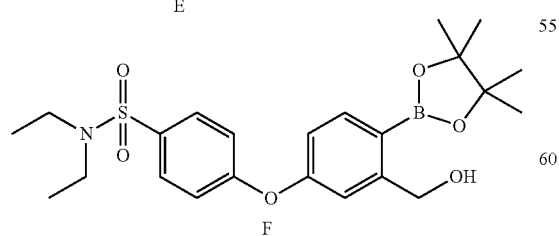
F

To a solution of E (3 g) in THF (40 ml) was added NaBH$_4$ (1 g). The reaction mixture was stirred at room temperature overnight and added HCl/H$_2$O (4 M), extracted with EtOAc.

The organic layer was separated, dried (Na$_2$SO$_4$), filtered, and the solvent was evaporated to obtained compound F (1.3 g; 43%). LC-MS: 462 (M+H)$^+$.

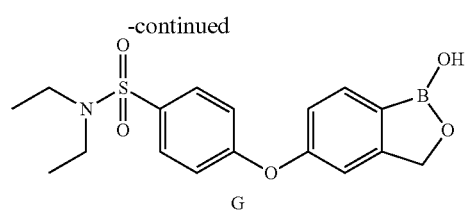
F

-continued

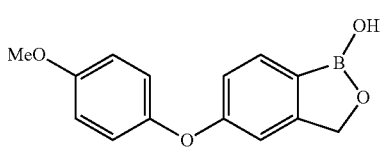 [SMILES: COc1ccc(Oc2ccc3c(c2)COB3O)cc1]
G

To a solution of F (1.3 g) in THF (30 ml) was added HCl/H$_2$O (6 M; 30 ml). The reaction mixture was stirred at room temperature overnight, extracted with DCM, evaporated and purified by HPLC to obtained the desired compound (300 mg; 30%). LC-MS: 362 (M+H)$^+$.

19cu
5-(4-methoxyphenoxy)benzo[c][1,2]oxaborol-1(3H)-ol
(D93)

Preparation of B

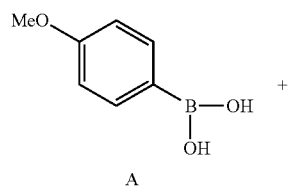

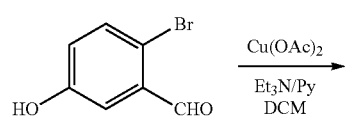

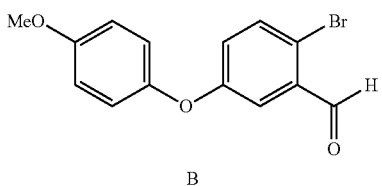

A (11 g, 5.97 mol), 2-bromo-5-hydroxybenzaldehyde (9 g, 45 mmol), Cu(OAc)$_2$ (9.8 g, 54 mmol) and 4 A MS (20 g) were suspended in dry DCM (100 mL), Et$_3$N (12.6 mL) and pyridine (37.8 mL) were added, and the reaction was stirred at room temperature under Ar for 48 h. The mixture was filtered and extracted by 1 M HCl. The organic layer was combined and dried over MgSO$_4$. The crude was purification by chromatography using 20:1 PE/EA to give compound B (2.2 g, 15%). GC-MS 308 (M+H)$^+$.

Preparation of C

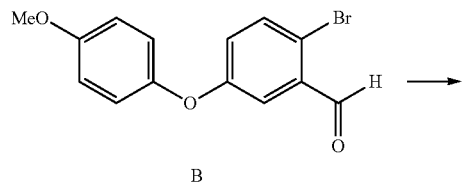

A mixture of B (80 mg, 0.26 mmol) and NaBH$_4$ (5 mg, 0.13 mmol) in MeOH (3 mL) was stirred for 1 h at ambient temperature. The solvent was removed. The residue was purified by chromatography using 6:1 PE/EA to give C (70 mg, 88%). $^1$HNMR (400 MHz, CDCl$_3$) δ 7.447 (d, J=8.4 Hz, 1H), 7.100 (d, J=2.1 Hz, 1H), 6.993 (d, J=9.2 Hz, 2H), 6.909 (d, J=9.2 Hz, 2H), 6.768 (dd, J=2.4 Hz, J=8.0 Hz, 1H), 4.688 (s, 2H), 3.820 (s, 3H).

Preparation of D

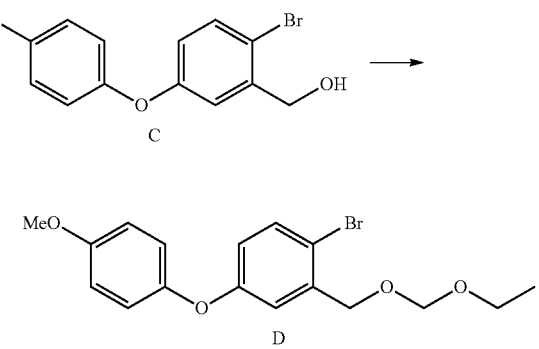

A mixture of C (1.45 g, 4.7 mmol) and NaH (187 mg, 7.8 mmol) in DMF (20 mL) was stirred for 30 min at 0° C. EOM-Cl (689 mg, 7.3 mmol) was added, and the mixture was stirred for 1 h at ambient temperature. The solvent was removed. The residue was purified by chromatography using 10:1 PE/EA to give D (1.4 g, 82%). $^1$H NMR (400 MHz, CDCl$_3$) δ 7.449 (d, J=9.2 Hz, 1H), 7.128 (d, J=3.6 Hz, 1H), 6.987 (d, J=8.4 Hz, 2H), 6.904 (d, J=9.6 Hz, 1H), 6.747 (dd, J=3.2 Hz, J=8.4 Hz, 1H), 4.797 (s, 2H), 4.622 (s, 2H), 3.819 (s, 3H), 3.674-3.622 (m, 2H), 1.251-1.215 (m, 3H).

Preparation of E

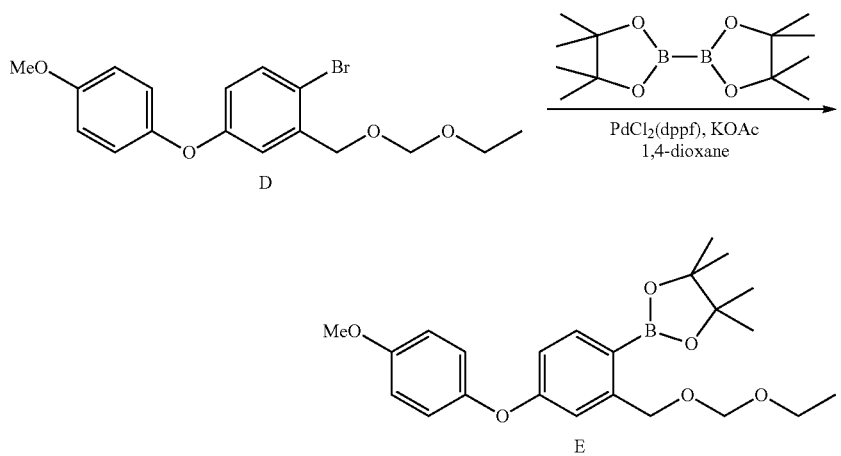

A mixture of D (700 mg, 1.9 mmol), bis(pinacolato)diboron (741 mg, 3.0 mmol), PdCl$_2$(dppf) (42 mg) and KOAc (570 mg, 5.5 mmol) in 1,4-dioxane (10 mL) was stirred overnight at 80° C. under Ar. The solvent was removed. The residue was purification by chromatography using 10:1 PE/EA to give E (700 mg, 89%). $^1$H NMR (400 MHz, CDCl$_3$) δ 7.767 (d, J=8.4 Hz, 1H), 7.092 (s, 1H), 7.001 (d, J=8.8 Hz, 2H), 6.903 (d, J=9.2 Hz, 2H), 6.814 (dd, J=1.6 Hz, J=8.0 Hz, 1H), 4.840 (s, 2H), 4.795 (s, 2H), 3.659-3.606 (m, 2H), 3.819 (s, 3H), 3.659-3.607 (m, 2H), 1.330 (s, 12H), 1.242-1.207 (m, 3H).

Preparation of (D93)

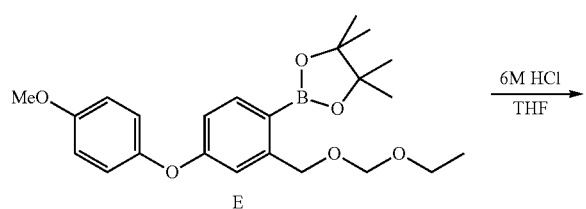

E

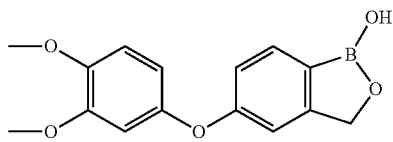 [SMILES: COc1ccc(Oc2ccc3c(c2)COB3O)cc1OC]

A mixture of E (700 mg, 1.7 mmol) in 6 M HCl (4 mL) and THF (4 mL) was stirred overnight at ambient temperature. The solvents were removed. The residue was purified by preparative-HPLC to give the desired compound (300 mg, 69%). LC-MS 257 (M+H)$^+$; $^1$H NMR (400 MHz, CDCl$_3$) δ 7.665 (d, J=8.0 Hz, 1H), 7.026 (d, J=9.2 Hz, 2H), 6.976 (dd, J=2.0 Hz, J=8.0 Hz, 1H), 6.926 (d, J=9.2 Hz, 2H), 6.826 (d, J=1.6 Hz, 1H), 5.014 (s, 2H), 3.823 (s, 3H).

19cv 5-(3,4-dimethoxyphenoxy)benzo[c][1,2]oxaborol-1(3H)-ol (D94)

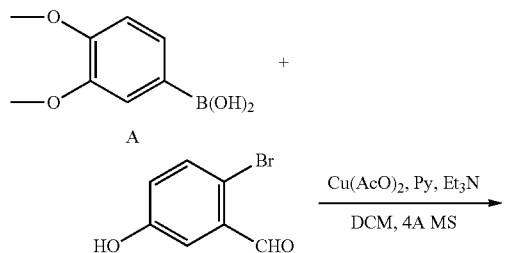

Preparation of B

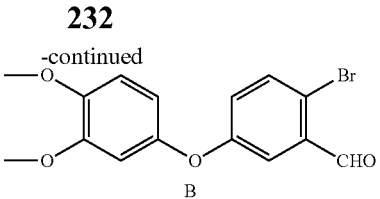

B

To a solution of A (14.6 g, 80.2 mmol), 2-bromo-5-hydroxybenzaldehyde (10.08 g, 50.2 mmol), 4 A MS (30 g) and Cu(OAc)$_2$ (10.88 g, 60.2 mmol) in dry CH$_2$Cl$_2$ (200 ml) was added pyridine (7.12 g, 90.2 mmol) and Et$_3$N (12.7 ml, 90.2 mmol) under Ar. The reaction mixture was stirred at ambient temperature overnight and filtrated, washed with 2N HCl, and extracted with CH$_2$Cl$_2$. The organic layer was combined, dried (Na$_2$SO$_4$), filtered, and the solvent was evaporated. The residue was purified by column chromatography over silica gel (eluent: petroleum ether/EtOAc 15/1). The pure fraction was collected, and the solvent was evaporated to afford B (1.84 g, 11%): $^1$H NMR (CDCl$_3$) δ 3.84 (3H, s), 3.89 (3H, s), 6.56-6.62 (2H, m), 6.84 (1H, d, J=8.8 Hz), 7.10 (1H, dd, J=2.8, 8.4 Hz), 7.43 (1H, d, J=2.8 Hz), 7.56 (1H, d, J=9.2 Hz), 10.29 (1H, s).

Preparation of Compound C

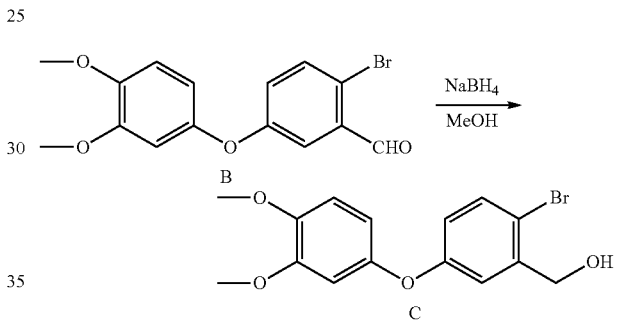

To a solution of B (2.16 g, 6.42 mmol) in MeOH (150 ml) was added NaBH$_4$ (120 mg, 3.15 mmol). The reaction mixture was stirred at ambient temperature for 0.5 h. The solvent was evaporated. The residue was purified by column chromatography over silica gel (eluent: petroleum ether/EtOAc 3/1). The pure fractions were collected, and the solvent was evaporated to afford C (2.2 g, 99%): $^1$H NMR (CDCl$_3$) δ 1.57 (1H, s), 3.83 (3H, s), 3.87 (3H, s), 4.69 (2H, d, J=6.0 Hz), 6.56 (1H, dd, J=2.4, 8.8 Hz), 6.62 (1H, d, J=2.4 Hz), 6.76 (1H, dd, J=2.4, 8.8 Hz), 6.82 (1H, d, J=9.2 Hz), 7.11 (1H, d, J=2.4 Hz), 7.43 (1H, d, J=8.4 Hz).

Preparation of D

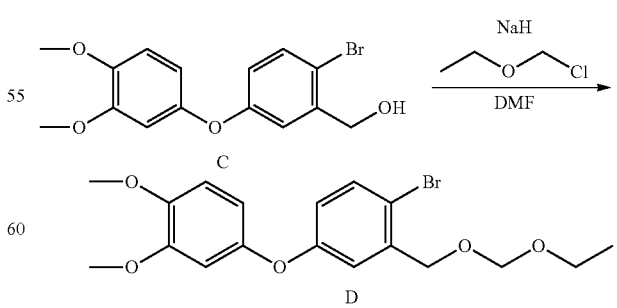

To a solution of C (2.2 g, 6.4 mmol) in dry DMF (25 ml) was added NaH (279 mg, 6.4 mmol, 55%) under Ar. The reaction mixture was stirred at 0° C. for 0.5 h, then (chloromethoxy)ethane (782 mg, 8.32 mmol) was added. The reaction mixture was stirred at ambient temperature for 1 h and quenched with i-PrOH. The solvent was evaporated under high vacuum. The residue was dissolved in EtOAc, washed with water. The organic layer was separated, dried (Na$_2$SO$_4$), filtered, and the solvent was evaporated. The residue was purified by column chromatography over silica gel (eluent: petroleum ether/EtOAc 10/1). The pure fraction was collected, and the solvent was evaporated to afford D (1.8 g, 71%): $^1$H NMR (CDCl$_3$) δ 1.22 (3H, t, J=8.0 Hz), 3.61-3.66 (2H, m), 3.83 (3H, s), 3.88 (3H, s), 4.61 (2H, s), 4.79 (2H, s), 6.55 (1H, dd, J=2.8, 8.4 Hz), 6.62 (1H, d, J=2.0 Hz), 6.74 (1H, dd, J=2.4, 9.2 Hz), 6.82 (1H, d, J=8.4 Hz), 7.12 (1H, d, J=2.4 Hz), 7.44 (1H, d, J=8.4 Hz).

Preparation of E

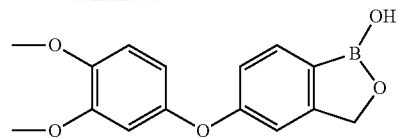

A mixture of E (1.84 g, 4.14 mmol) in 6 M HCl (40 mL) and THF (60 mL) was stirred at ambient temperature overnight. The solvents were removed. The residue was purification by preparative HPLC to give the desired compound (615 mg, 52%): $^1$H NMR (DMSO-d$_6$) δ 3.73 (3H, s), 3.76 (3H, s), 4.91 (2H, s), 6.59 (1H, dd, J=2.5, 9.0 Hz), 6.77 (1H, d, J=2.5 Hz), 6.89 (1H, s), 6.94 (1H, dd, J=1.5, 8.0 Hz), 6.97 (1H, d, J=8.5 Hz), 7.69 (1H, d, J=8.0 Hz), 9.11 (1H, s).

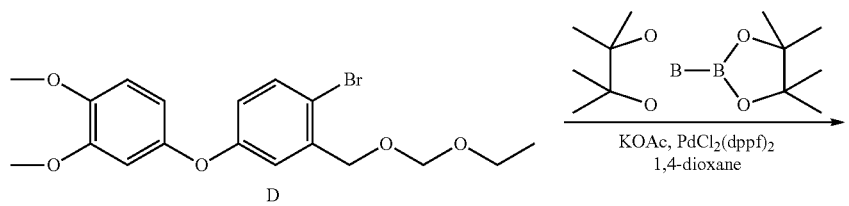

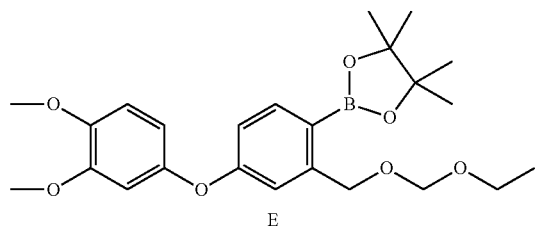

A mixture of D (1.8 g, 4.53 mmol), bis(pinacolato)diboron (3.45 g, 13.6 mmol), PdCl$_2$(dppf)$_2$ (109 mg, 0.13 mmol) and KOAc (1.33 g, 13.6 mmol) in 1,4-dioxane (20 mL) was stirred at 80° C. overnight under Ar. The organic layer was removed. The residue was purified by column chromatography over silica gel (eluent: petroleum ether/EtOAc 15/1). The pure fractions were collected, and the solvent was evaporated to afford E (1.84 g, 82%): $^1$H NMR (CDCl$_3$) δ 1.21 (3H, t, J=6.8 Hz), 1.32 (12H, s), 3.60-3.65 (2H, m), 3.81 (3H, s), 3.88 (3H, s), 4.79 (2H, s), 4.83 (2H, s), 6.59 (1H, dd, J=2.4, 8.4 Hz), 6.64 (1H, d, J=2.8 Hz), 6.80-6.83 (2H, m), 7.10 (1H, d, J=2.0 Hz), 7.75 (1H, d, J=8.4 Hz).

Preparation of (D94)

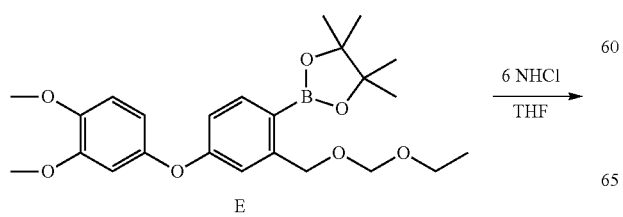

19cw 2-Dimethylamino-6-(1-hydroxy-1,3-dihydro-benzo[c][1,2]oxaborol-5-yloxy)-nicotinonitrile (D95)

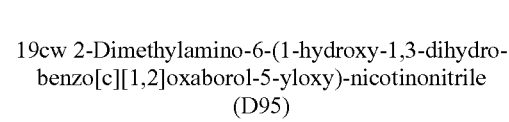

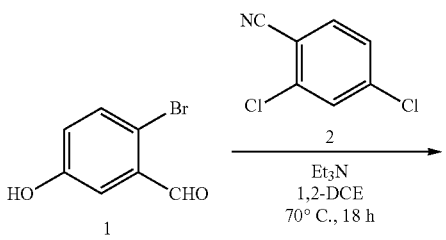

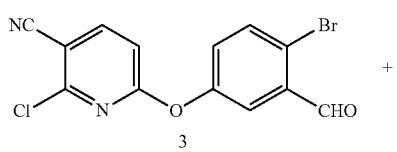

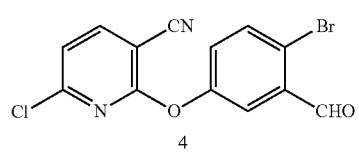

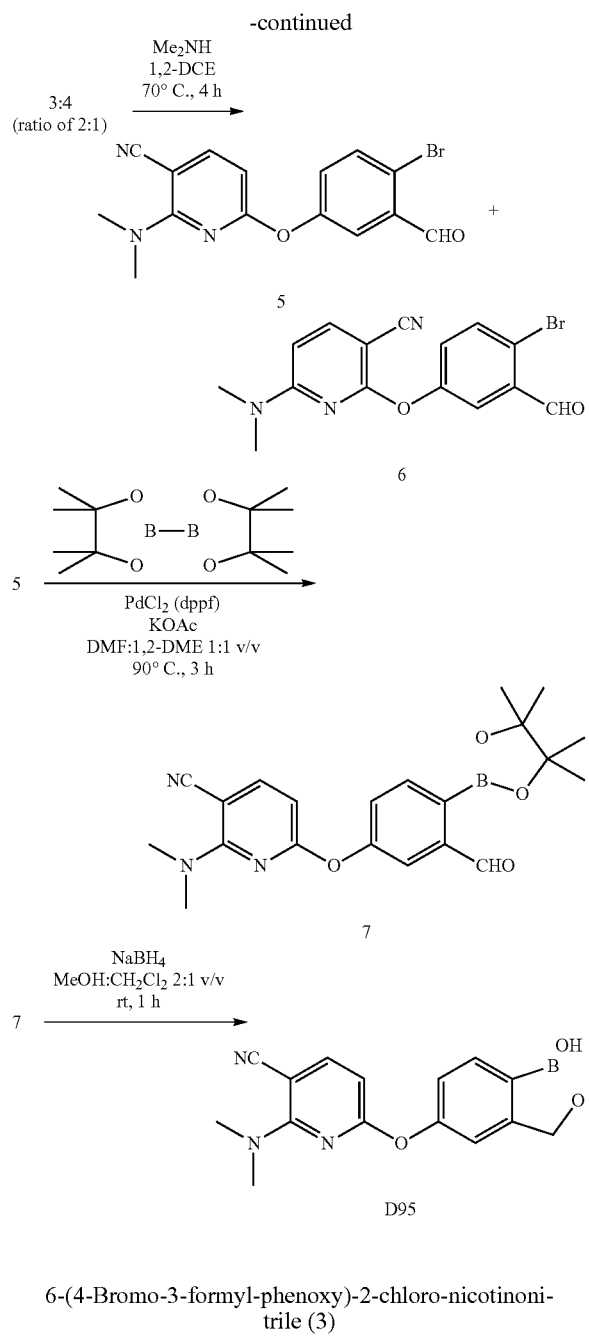

6-(4-Bromo-3-formyl-phenoxy)-2-chloro-nicotinonitrile (3)

Triethylamine (11.0 mL, 78.0 mmol) was added to a solution of 2-bromo-5-hydroxy-benzaldehyde (1) (7.84 g, 39.0 mmol) and 2,6-dichloro-nicotinonitrile (2) (7.42 g, 42.9 mmol) in a sealable reaction vessel. The reaction vessel was sealed with a teflon cap and heated at 70° C. for 18 hr. The reaction was left to cool to room temperature and concentrated to give an orange oil (18.0 g). The oil was diluted with CH$_2$Cl$_2$ (200 mL) followed by the addition of silica gel (70 g, 230-400 mesh) and concentrated to dryness. This was loaded onto a silica gel column (70 g, 230-400 mesh) and eluted with gradient 5-40% EtOAc/hexanes. Isolated a mixture of 6-(4-bromo-3-formyl-phenoxy)-2-chloro-nicotinonitrile (3) and 2-(4-bromo-3-formyl-phenoxy)-6-chloro-nicotinonitrile (4) in a ratio of 2:1, respectively (5.80 g) as a clear oil which later solidified to a white solid. The mixture was carried forward with further purification.

6-(4-bromo-3-formyl-phenoxy)-2-chloro-nicotinonitrile (3) $^1$H NMR 400 MHz (CDCl$_3$) δ 10.35 (s, 1H), 7.99 (d, J=8.6 Hz, 1H), 7.73 (d, J=8.6 Hz, 1H), 7.69 (d, J=2.7 Hz, 1H), 7.30 ppm (dd, J=8.6, 2.7 Hz, 1H), 7.02 (d, J=8.6 Hz, 1H).

2-(4-bromo-3-formyl-phenoxy)-6-chloro-nicotinonitrile (4) $^1$H NMR 400 MHz (CDCl$_3$) δ 10.35 (s, 1H), 7.97 (d, J=7.8 Hz, 1H), 7.75 (d, J=7.8 Hz, 1H), 7.73 (d, J=2.3 Hz, 1H), 7.34 (dd, J=7.8, 2.3 Hz, 1H), 7.17 (d, J=7.8 Hz, 1H).

6-(4-Bromo-3-formyl-phenoxy)-2-dimethylamino-nicotinonitrile (5)

A mixture of 6-(4-bromo-3-formyl-phenoxy)-2-chloro-nicotinonitrile (3) and 2-(4-bromo-3-formyl-phenoxy)-6-chloro-nicotinonitrile (4) in a ratio of 2:1, respectively (2.47 g, 7.34 mmol) was dissolved in 1,2-dichloroethane (40 mL) in a sealable reaction vessel. Then dimethylamine (18.3 mL, 36.7 mmol) was added and the reaction vessel was sealed with a teflon cap. The reaction was heated at 70° C. for 4 hr [Note: A white precipitate formed overtime]. The reaction mixture was cooled to room temperature and then concentrated to give an orange coloured solid which contained a mixture of 6-(4-bromo-3-formyl-phenoxy)-2-dimethylamino-nicotinonitrile (5) and 2-(4-bromo-3-formyl-phenoxy)-6-dimethylamino-nicotinonitrile (6) in a ratio of 2:1, respectively (2.80 g). The solid was dissolved with CH$_2$Cl$_2$ (200 mL) followed by the addition of silica gel (50 g, 230-400 mesh) and concentrated to dryness. This was loaded onto a silica gel column (100 g, 230-400 mesh) and eluted with gradient 5-10% EtOAc/hexanes. Pure fractions were combined and concentrated to give the title compound (5) as a white solid (1.10 g, 43% isolated yield).

6-(4-bromo-3-formyl-phenoxy)-2-dimethylamino-nicotinonitrile (5) $^1$H NMR 400 MHz (CDCl$_3$) δ 10.34 (s, 1H), 7.78 (d, J=2.7 Hz, 1H), 7.72 (d, J=8.2 Hz, 1H), 7.66 (d, J=8.6 Hz, 1H), 7.27 (dd, J=8.6, 2.7 Hz, 1H), 6.24 (d, J=8.2 Hz, 1H), 3.11 (s, 6H).

2-(4-bromo-3-formyl-phenoxy)-6-dimethylamino-nicotinonitrile (6) $^1$H NMR 400 MHz (CDCl$_3$) δ 10.35 (s, 1H), 7.85 (d, J=2.7 Hz, 1H), 7.66 (d, J=8.6 Hz, 1H), 7.64 (d, J=8.6 Hz, 1H), 7.32 (dd, J=8.6, 2.7 Hz, 1H), 6.19 (d, J=8.6 Hz, 1H), 2.95 (s, 6H).

2-Dimethylamino-6-[3-formyl-4-(4,4,5,5-tetramethyl-[1,3,2]dioxaborolan-2-yl)-phenoxy]-nicotinonitrile (7)

6-(4-Bromo-3-formyl-phenoxy)-2-dimethylamino-nicotinonitrile (5) (1.10 g, 3.18 mmol), bis(pinacolato)diboron (1.21 g, 4.77 mmol) and potassium acetate (624 mg, 6.36 mmol) in a mixture of dimethylformamide:1,2-dimethoxyethane (20 mL:20 mL) in a sealable reaction vessel was heated at 90° C. for 5 min. Then PdCl$_2$(dppf) (233 mg, 0.32 mmol) was added, the teflon cap was replaced and the reaction was heated at 90° C. for 3 hr. The reaction was left to cool to room temperature, then diluted with benzene (600 mL) and concentrated to give a black oil (3.0 g). The oil was diluted with CH$_2$Cl$_2$ (300 mL) followed by the addition of silica gel (30 g, 230-400 mesh) and concentrated to dryness. This was loaded onto a silica gel column (60 g, 230-400 mesh) and eluted with gradient 10-40% EtOAc/hexanes. Pure fractions were combined and concentrated to give the title compound (7) as an oil which later solidified to give a white solid (530 mg, 42% isolated yield). $^1$H NMR 400 MHz (CDCl$_3$) δ 10.61 (s, 1H), 7.92 (d, J=8.2 Hz, 1H), 7.78 (d, J=2.3 Hz, 1H), 7.68

(d, J=8.2 Hz, 1H), 7.35 (dd, J=8.2, 2.3 Hz, 1H), 6.20 (d, J=8.2 Hz, 1H), 3.08 (s, 6H), 1.28 (s, 12H).

19cx 2-Dimethylamino-6-(1-hydroxy-1,3-dihydro-benzo[c][1,2]oxaborol-5-yloxy)-nicotinonitrile (D95)

A solution of 2-dimethylamino-6-[3-formyl-4-(4,4,5,5-tetramethyl-[1,3,2]dioxaborolan-2-yl)-phenoxy]-nicotinonitrile (7) (370 mg, 0.94 mmol) in CH$_2$Cl$_2$ (5 mL) was added to a mixture of NaBH$_4$ (26 mg, 0.66 mmol) in anhydrous methanol (10 mL) at room temperature. Additional solid NaBH$_4$ (82 mg, 2.2 mmol) was then added portionwise over a period of 10 minutes. The reaction mixture was then stirred for a further 1 h at room temperature. The reaction was quenched by the addition of a solution of glacial acetic acid (0.2 mL) and distilled water (0.2 mL) followed by stirring for 10 minutes. The reaction was concentrated to give an oil (~550 mg). The oil was dissolved in a mixture of acetic acid/methanol/CH$_2$Cl$_2$ (1/2/100 v/v/v, 100 mL) followed by the addition of silica gel (5 g, 230-400 mesh) and concentrated to dryness to give a free flowing impregnated silica. This was loaded onto a silica column (10 g, 230-400 mesh) and eluted with acetic acid/methanol/CH$_2$Cl$_2$ (1/2/100 v/v/v). The fractions containing D95 were collected and concentrated to give a light yellow coloured oil. The oil was freeze dried by first diluting with MeOH/CH$_2$Cl$_2$ (1/1 v/v, 15 mL) followed by the addition of deionised water (200 mL), the resultant white suspension was frozen in a dry-ice acetone bath and placed overnight on freeze-dryer. A white solid of D95 was obtained (70 mg, 25% isolated yield). $^1$H NMR 400 MHz (d$_6$-DMSO) δ9.23 (s, 1H), 7.95 (d, J=8.6 Hz, 1H), 7.77 (d, J=7.8 Hz, 1H), 7.23 (d, J=0.5 Hz, 1H), 7.16 (dd, J=7.8, 0.5 Hz, 1H), 6.31 (d, J=8.6 Hz, 1H), 4.98 (s, 2H), 3.14 (s, 6H). Mass Spectrum [M+H$^+$]=296. HPLC purity 95.04% (Maxplot), 94.63% (220 nm), 92.41% (254 nm).

19cy 6-(1-hydroxy-1,3-dihydro-benzo[c][1,2]oxaborol-5-yloxy)-2-[(2-methoxy-ethyl)-methyl-amino]-nicotinonitrile (D96)

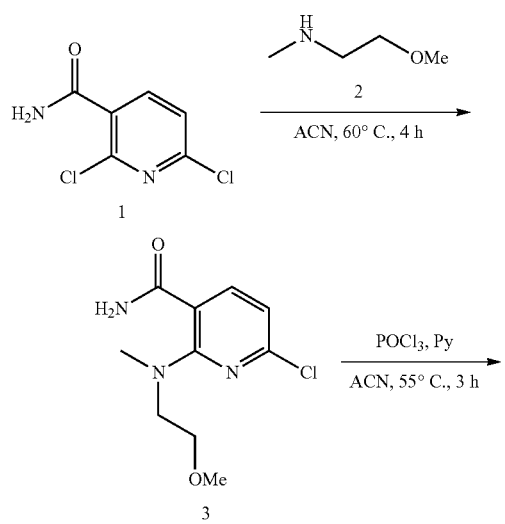

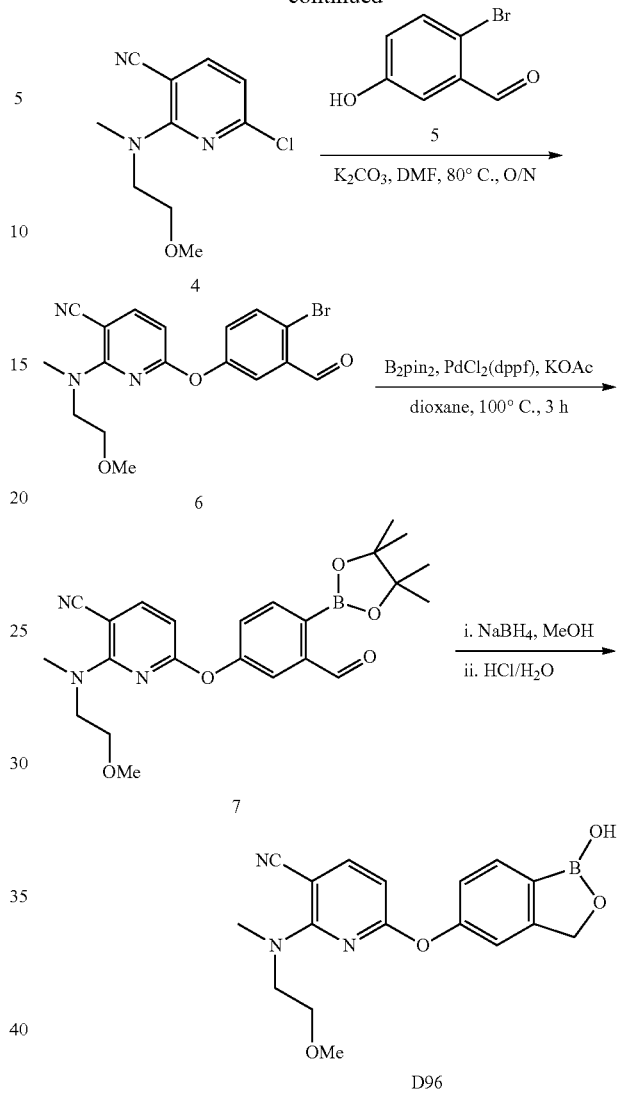

6-Chloro-2-[(2-methoxy-ethyl)-methyl-amino]-nicotinamide (3)

To a solution of 2,6-dichloro-nicotinamide (1) (10 g, 52.9 mmol) in acetonitrile (anhydrous, 200 mL) was added (2-methoxy-ethyl)-methyl-amine (2) (18.8 g, 212 mmol). The reaction was heated at 60° C. for 1.5 hours. 5% NaOH solution (1000 mL) was slowly added. The solution was then extracted with EtOAc (3×250 mL). The combined organic layer was dried over MgSO$_4$, filtered, and evaporated in vacuo. Purification was accomplished by silica gel chromatography, eluting with 5%-30% EtOAc/hexanes gradient, to afford 11.66 g (91% yield) of the title compound. $^1$H NMR (400 MHz, CHLOROFORM-d) δ ppm 8.07 (d, J=8.6 Hz, 1 H), 7.76 (br. s., 1H), 6.93 (d, J=8.2 Hz, 1H), 5.66 (br. s., 1H), 3.66-3.51 (m, 4H), 3.32 (s, 3H), 2.93 (s, 3H).

6-Chloro-2-[(2-methoxy-ethyl)-methyl-amino]-nicotinonitrile (4)

To a solution of 6-chloro-2-[(2-methoxy-ethyl)-methyl-amino]-nicotinamide (3) (14 g, 58 mmol) in acetonitrile (anhydrous, 360 mL) were added pyridine (37.5 mL, 463.8 mmol) and POCl₃ (21.2 mL, 232 mmol). The reaction was heated at 55° C. for 3 hours. After cooling to room temperature, NaOH solution (10% aq.) was slowly added till pH 9. The solution was extracted with EtOAc (3×200 mL). The combined organic layer was dried over MgSO₄, filtered, and evaporated in vacuo. Purification was accomplished by silica gel chromatography, eluting with 5%-30% EtOAc/hexanes gradient, to afford 11.6 g (90% yield) of the desired product. ¹H NMR (400 MHz, CHLOROFORM-d) δ ppm 7.61 (d, J=7.4 Hz, 1H), 6.58 (d, J=7.8 Hz, 1H), 3.87 (t, J=5.3 Hz, 2H), 3.64 (t, J=5.3 Hz, 2H), 3.38 (s, 3H), 3.36 (s, 3H).

6-(4-Bromo-3-formyl-phenoxy)-2-[(2-methoxy-ethyl)-methyl-amino]-nicotinonitrile (6)

To a solution of 6-chloro-2-[(2-methoxy-ethyl)-methyl-amino]-nicotinonitrile (4) (11.6 g, 51.9 mmol) in DMF (anhydrous, 300 mL) were added 2-bromo-5-hydroxy-benzaldehyde (10.4 g, 51.9 mmol) and K₂CO₃ (14.3 g, 103.8 mmol). The reaction was heated at 80° C. for 16 hours. DMF was evaporated in vacuo. Purification was accomplished by silica gel chromatography, eluting with 5%-30% EtOAc gradient, to afford 15 g (75% yield) of the title compound. ¹H NMR (400 MHz, CHLOROFORM-d) δ ppm 10.34 (s, 1H), 7.75-7.69 (m, 2H), 7.67 (d, J=8.6 Hz, 1H), 7.28-7.23 (m, 1H), 6.26 (d, J=8.6 Hz, 1H), 3.56 (t, J=5.5 Hz, 2H), 3.36 (t, J=5.5 Hz, 2H), 3.25 (s, 3H), 3.24 (s, 3H).

6-[3-Formyl-4-(4,4,5,5-tetramethyl-[1,3,2]dioxaborolan-2-yl)-phenoxy]-2-[(2-methoxy-ethyl)-methyl-amino]-nicotinonitrile (7)

To a solution of 6-(4-bromo-3-formyl-phenoxy)-2-[(2-methoxy-ethyl)-methyl-amino]-nicotinonitrile (6) (15 g, 38.5 mmol) in 1,4-dioxane (anhydrous, 360 mL) were added bispinacolatodiboron (11.7 g, 46.2 mmol), PdCl₂(dppf) (2.8 g, 3.85 mmol) and KOAc (11.3 g, 115.3 mmol). The solution was stirred at r.t. with N₂ bubbling for 30 minutes. Then the reaction was heated at 100° C. for 3 hours. After the reaction, the solution was filtered and concentrated in vacuo. Purification was accomplished by silica gel chromatography, eluting with 2.5%-20% EtOAc/hexanes gradient, to afford 15 g (89% yield) of the title compound. ¹H NMR (400 MHz, CHLOROFORM-d) δ ppm 10.64 (s, 1H), 7.94 (d, J=7.8 Hz, 1H), 7.76 (d, J=2.3 Hz, 1H), 7.72-7.69 (m, 1H), 7.35 (dd, J=8.0, 2.5 Hz, 1H), 6.25 (d, J=8.6 Hz, 1H), 3.56 (t, J=5.5 Hz, 2H), 3.36 (t, J=5.5 Hz, 2H), 3.25 (s, 3H), 3.22 (s, 3H), 1.40 (s, 12H)

6-(1-Hydroxy-1,3-dihydro-benzo[c][1,2]oxaborol-5-yloxy)-2-[(2-methoxy-ethyl)-methyl-amino]-nicotinonitrile (D96)

To a clear solution of 6-[3-formyl-4-(4,4,5,5-tetramethyl-[1,3,2]dioxaborolan-2-yl)-phenoxy]-2-[(2-methoxy-ethyl)-methyl-amino]-nicotinonitrile (7) (15 g, 343 mmol) in MeOH (anhydrous, 300 mL) was slowly added NaBH₄ (7.83 g, 206 mmol). The reaction was stirred at room temperature 4 hours, before the addition of HCl solution (1 M, 200 mL). The stirring was kept at room temperature overnight. Then the solution was slowly evaporated in vacuo. Purification was accomplished by reverse phase Biotage with 10%-100% MeOH/H₂O gradient to afford 3 g (26% yield) of the title compound. ¹H NMR (400 MHz, CHLOROFORM-d) δ ppm 7.74 (d, J=8.6 Hz, 1H), 7.70 (d, J=8.2 Hz, 1H), 7.13-7.09 (m, 2H), 6.23 (d, J=8.2 Hz, 1H), 5.08 (s, 2H), 4.78 (s, 1H), 3.56 (t, J=5.7 Hz, 2H), 3.36 (t, J=5.7 Hz, 2H), 3.27 (s, 3H), 3.23 (s, 3H); ES-MS: m/z 340 (M+H)⁺; HPLC: 99.38% (220 nm), 98.71% (MaxPlot).

19cz 6-(1-Hydroxy-1,3-dihydro-benzo[c][1,2]oxaborol-5-yloxy)-2-pyrrolidin-1-yl-nicotinonitrile (D97)

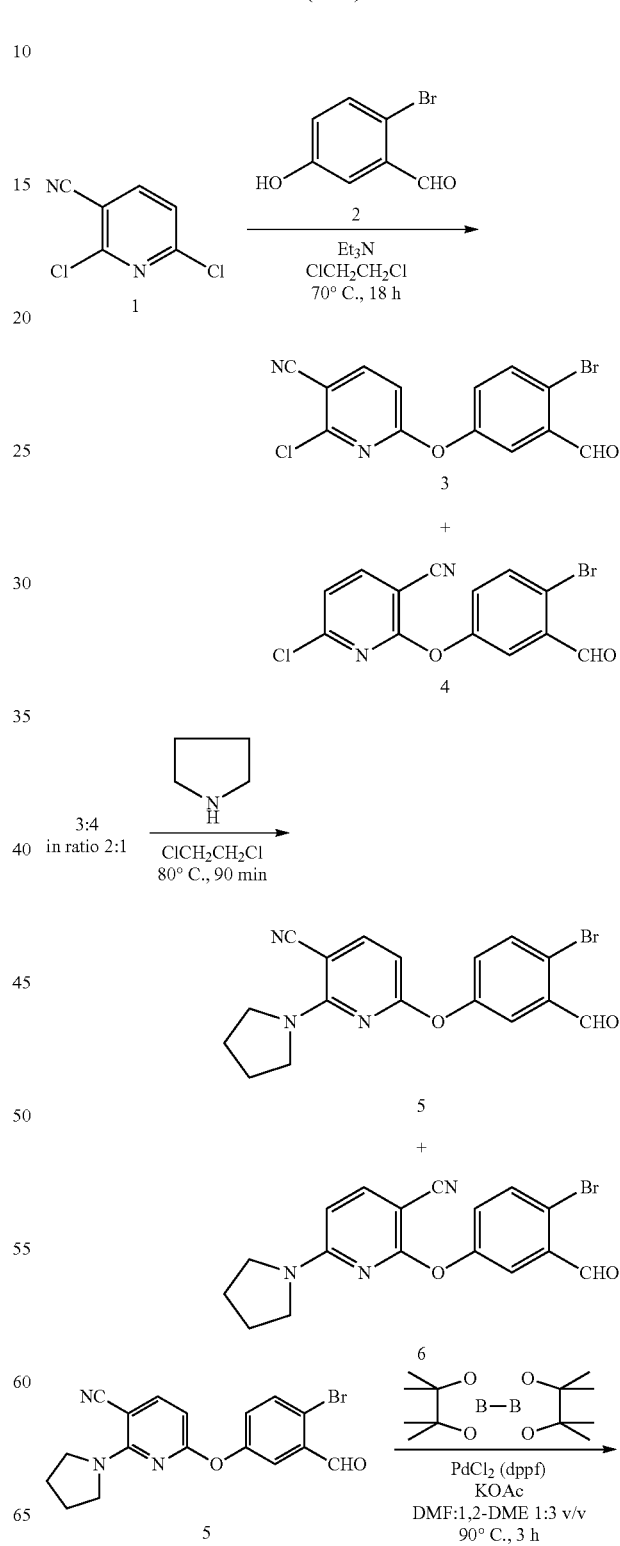

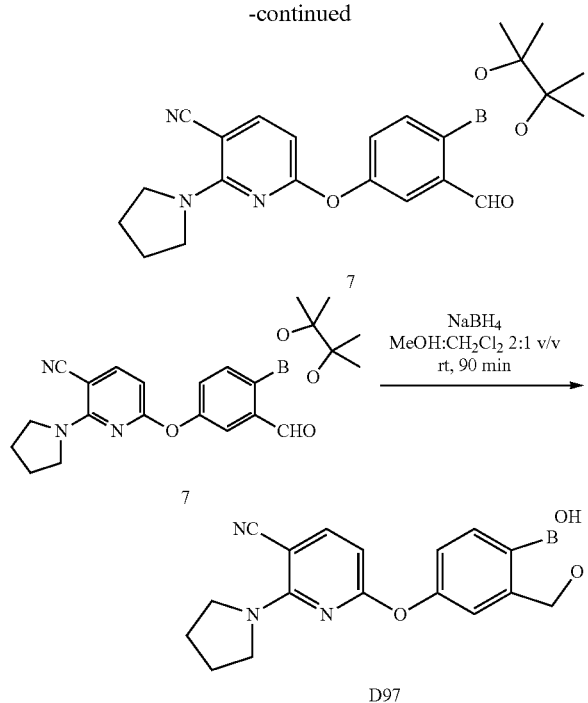

6-(4-Bromo-3-formyl-phenoxy)-2-chloro-nicotinonitrile (3)

2,6-Dichloronicotinonitrile (7.42 g, 42.9 mmol), 2-bromo-5-hydroxybenzaldehyde (7.84 g, 39.0 mmol) and triethylamine (7.89 g, 11.0 mL, 78.0 mmol) in 1,2-dichloroethane (50 mL) in a sealed reaction vessel was heated to 70° C. for 18 h. The reaction was cooled to room temperature and concentrated to give a mixture of 6-(4-bromo-3-formyl-phenoxy)-2-chloro-nicotinonitrile (3) and 2-(4-bromo-3-formyl-phenoxy)-6-chloro-nicotinonitrile (4) in a ratio of 1.8:1, respectively (18 g). TLC of 3 gave $R_f$=0.4 and 4 gave $R_f$=0.35 when eluted with 25% EtOAc/hexanes and rendered with UV lamp. The mixture was fractionated by dry-pack column chromatography as follows: The oil was diluted with $CH_2Cl_2$ (200 mL) followed by the addition of silica gel (70 g, 230-400 mesh) and concentrated to dryness. This was loaded onto a silica column (70 g, 230-400 mesh) and eluted with gradient 5-40% EtOAc/hexanes. Three major fractions where collected; fraction 1 with 3:4 in ratio 1:1.5 (3.40 g), fraction 2 with 3:4 in ratio 1.8:1 (3.70 g) and fraction 3 with 3:4 in ratio 2.0:1 (2.10 g). Fraction 3, which was the most enriched fraction in desired compound 3, was carried forward without further purification.

Compound 3: $^1$H NMR 400 MHz (CDCl$_3$) δ 10.34 (s, 1H), 7.99 (d, J=8.6 Hz, 1H), 7.73 (d, J=8.6 Hz, 1H), 7.69 (d, J=2.7 Hz, 1H), 7.30 (dd, J=8.9, 2.3 Hz, 1H), 7.02 (d, J=8.6 Hz, 1H).

Compound 4: $^1$H NMR 400 MHz (CDCl$_3$) δ 10.34 (s, 1H), 7.97 (d, J=7.8 Hz, 1H), 7.75 (d, J=10.5 Hz, 1H), 7.73 (d, J=2.3 Hz, 1H), 7.34 (dd, J=9.0, 3.1 Hz, 1H), 7.17 (d, J=7.8 Hz, 1H).

6-(4-Bromo-3-formyl-phenoxy)-2-pyrrolidin-1-yl-nicotinonitrile (5)

A mixture of 6-(4-bromo-3-formyl-phenoxy)-2-chloro-nicotinonitrile (3): 2-(4-bromo-3-formyl-phenoxy)-6-chloro-nicotinonitrile (4) in a ratio of 2.0:1 (1.14 g, 3.39 mmol) and pyrrolidine (723 mg, 0.85 mL, 10.2 mmol) in 1,2-dichloroethane (30 mL) in a sealed reaction vessel was heated to 80° C. for 90 min. The reaction was cooled to room temperature and concentrated to give a mixture of 6-(4-bromo-3-formyl-phenoxy)-2-pyrrolidin-1-yl-nicotinonitrile (5) and 2-(4-bromo-3-formyl-phenoxy)-6-pyrrolidin-1-yl-nicotinonitrile (6) in a ratio of 2:1 (2.10 g). TLC of 6-(4-bromo-3-formyl-phenoxy)-2-pyrrolidin-1-yl-nicotinonitrile (5) gave $R_f$=0.6 and 2-(4-bromo-3-formyl-phenoxy)-6-pyrrolidin-1-yl-nicotinonitrile (6) gave $R_f$=0.4 when eluted with 25% EtOAc/hexanes and rendered with UV lamp or a solution of phosphomolybdic acid in ethanol. The mixture was fractionated by dry-pack column chromatography as follows: The oil was diluted with 10% MeOH/$CH_2Cl_2$ (100 mL) followed by the addition of silica gel (10 g, 230-400 mesh) and concentrated to dryness. This was loaded onto a silica column (30 g, 230-400 mesh) and eluted with 10% EtOAc/hexanes. The mixture was separable and gave 5 (550 mg, white solid, 43% yield) and 6 (120 mg, white solid, 10% yield).

Compound 5: $^1$H NMR 400 MHz (CDCl$_3$) δ 10.34 (s, 1H), 7.79 (d, J=3.1 Hz, 1H), 7.69 (d, J=8.2 Hz, 1H), 7.65 (d, J=8.6 Hz. 1H), 7.28 (dd, J=9.0, 3.1 Hz, 1H), 6.18 (d, J=8.2 Hz, 1H), 3.60-3.52 (4H), 1.93-1.87 (4H).

Compound 6: $^1$H NMR 400 MHz (CDCl$_3$) δ 10.35 (s, 1H), 7.88 (d, J=2.7 Hz, 1H), 7.66 (d, J=8.6 Hz, 1H), 7.60 (d, J=8.6 Hz, 1H), 7.33 (dd, J=8.2, 2.7 Hz, 1H), 6.05 (d, J=8.6 Hz, 1H), 3.40-3.20 (4H), 2.13-1.81 (4H).

6-[3-Formyl-4-(4,4,5,5-tetramethyl-[1,3,2]dioxaborolan-2-yl)-phenoxy]-2-pyrrolidin-1-yl-nicotinonitrile (7)

6-(4-Bromo-3-formyl-phenoxy)-2-pyrrolidin-1-yl-nicotinonitrile (5) (505 mg, 1.36 mmol), bispinacolatodiboron (689 mg, 2.71 mmol) and KOAc (333 mg, 3.39 mmol) in a mixture of DMF (5 mL) and 1,2-dimethoxyethane (15 mL) in a sealed reaction vessel was heated to 90° C. for 5 min. PdCl$_2$(dppf) (99 mg, 0.13 mmol) was then added and the reaction mixture was stirred vigorously at 90° C. for 3 h. The reaction was cooled to room temperature and diluted with benzene (300 mL) and concentrated to give a black solid which contained product 7 (1.70 g) [Note: addition of benzene followed by evaporation allowed for the azeotropic removal of DMF]. TLC of 7 gave $R_f$=0.4 when eluted with 25% EtOAc/hexanes and rendered with UV lamp or a solution of phosphomolybdic acid in ethanol. The crude black solid was fractionated by dry-pack column chromatography as follows: The solid was dissolved with 10% MeOH/$CH_2Cl_2$ (200 mL) followed by the addition of silica gel (10 g, 230-400 mesh) and concentrated to dryness. This was loaded onto a silica column (30 g, 230-400 mesh) and eluted with 10% EtOAc/hexanes. Isolated 7 as a white solid (308 mg, 54%). $^1$H NMR 400 MHz (CDCl$_3$) δ 10.62 (s, 1H), 7.93 (d, J=8.2 Hz, 1H), 7.82 (d, J=2.3 Hz, 1H), 7.68 (d, J=8.6 Hz, 1H), 7.38 (dd, J=8.2, 2.3 Hz, 1H), 6.17 (d, J=8.2 Hz, 1H), 3.60-3.51 (4H), 1.93-1.83 (4H), 1.41 (s, 12H).

6-(1-Hydroxy-1,3-dihydro-benzo[c][1,2]oxaborol-5-yloxy)-2-pyrrolidin-1-yl-nicotinonitrile (D97)

A solution of NaBH$_4$ (35 mg, 0.93 mmol) in MeOH (5 mL) was added to a solution of 6-[3-formyl-4-(4,4,5,5-tetramethyl-[1,3,2]dioxaborolan-2-yl)-phenoxy]-2-pyrrolidin-1-yl-nicotinonitrile (7) (250 mg, 0.60 mmol) in CH$_2$Cl$_2$ (2.5 mL) at room temperature and the reaction was stirred for 5 minutes. Additional NaBH$_4$ solid (100 mg, 2.64 mmol) was added in portions over 25 minutes and the reaction was stirred for another 60 minutes at room temperature. A solution of glacial acetic acid (0.2 mL) in distilled water (0.2 mL) was added and the reaction was stirred for 15 minutes at room temperature. The reaction mixture was concentrated to dryness and dried under high vacuum to give 450 mg of a white solid. The white solid was fractionated by dry-pack column chromatography as follows: The solid was dissolved in AcOH/MeOH/CH$_2$Cl$_2$ (1:1:100, 200 mL) followed by the addition of silica gel (10 g, 230-400 mesh) and concentrated to dryness. This was loaded onto a silica column (20 g, 230-400 mesh) and eluted with AcOH/MeOH/CH$_2$Cl$_2$ (1:1:100). Isolated was D97 as a white sticky solid (110 mg). This sticky solid was dissolved in 30% MeOH/CH$_2$Cl$_2$ (30 mL) followed by addition of distilled water (300 mL) and freeze dried to give a free-flowing white solid D97 (90 mg, 47% yield). $^1$H NMR 400 MHz (CDCl$_3$) δ 9.19 (s, 1H), 7.89 (d, J=8.6 Hz, 1H), 7.73 (d, J=8.2 Hz, 1H), 7.20 (br s, 1H), 7.13 (br d, J=7.8 Hz, 1H), 6.22 (d, J=8.6 Hz, 1H), 4.96 (s, 2H), 3.48-3.40 (4H), 1.86-1.77 (4H); Mass Spectrum (M+H)$^+$=322; HPLC purity 96.73% (Maxplot), 97.50% (220 nm), 97.63% (254 nm).

19da 2-(1-hydroxy-1,3-dihydro-benzo[c][1,2]oxaborol-5-yloxy)-6-[(2-hydroxy-ethyl)-methyl-amino]-nicotinonitrile (D98)

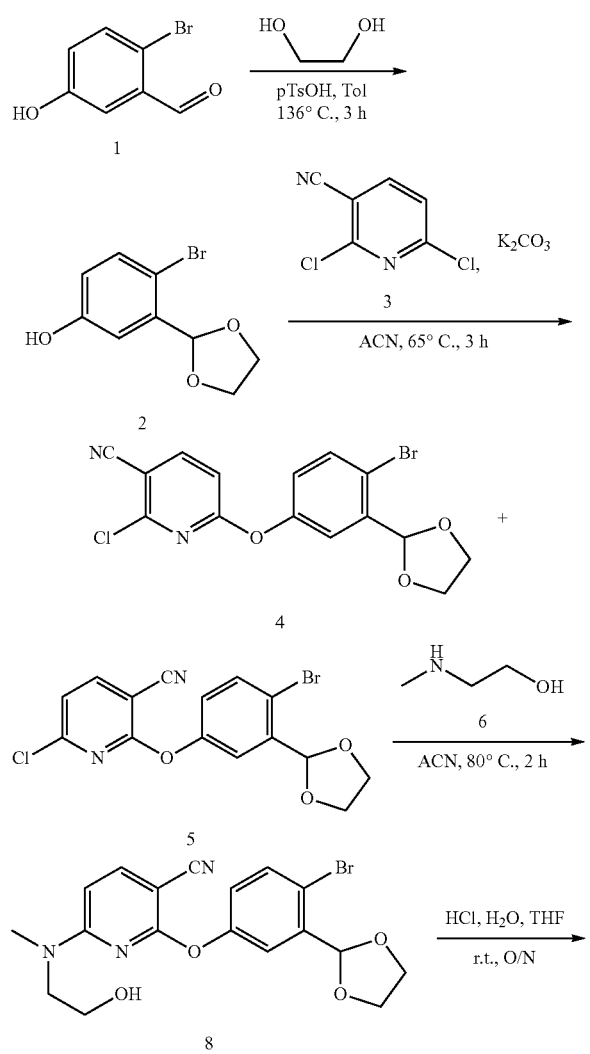

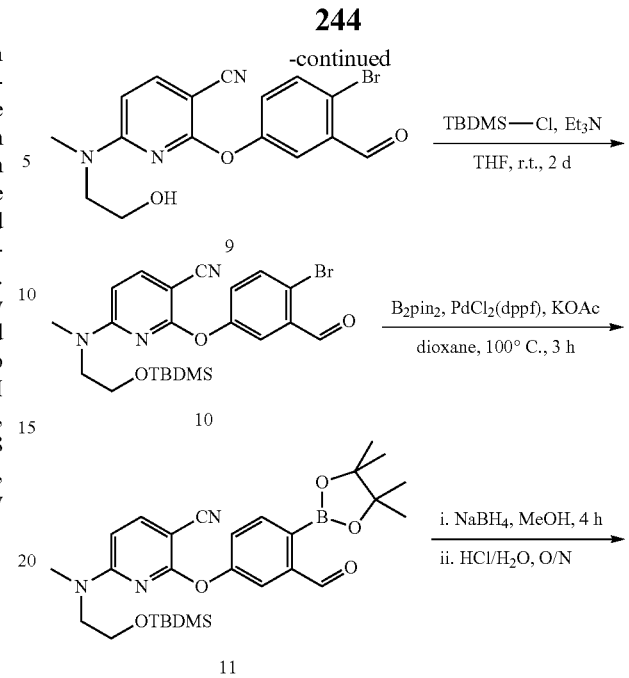

4-Bromo-3-[1,3]dioxolan-2-yl-phenol (2)

To a solution of 2-bromo-5-hydroxy-benzaldehyde (1) (10 g, 49.8 mmol) in toluene (200 mL) were added ethylene glycol (9.25 g, 149.3 mmol) and catalytic amount of p-TsOH (200 mg). After attaching a Dean-Stark trap, the reaction was heated at 136° C. for 3 hours. After the solution was cooled to room temperature, it was washed with saturated NaHCO$_3$ (200 mL). The organic layer was dried over Na$_2$SO$_4$, filtered and evaporated in vacuo to provide the 11.6 g (95% yield) of the title compound. $^1$H NMR (400 MHz, CHLOROFORM-d) δ ppm 7.40 (d, J=8.6 Hz, 1H), 7.09 (d, J=3.1 Hz, 1H), 6.72 (dd, J=8.6, 3.1 Hz, 1H), 6.04 (s, 1H), 4.18-4.04 (m, 4H)

6-(4-Bromo-3-[1,3]dioxolan-2-yl-phenoxy)-2-chloro-nicotinonitrile+2-(4-bromo-3-[1,3]dioxolan-2-yl-phenoxy)-6-chloro-nicotinonitrile (4+5)

To a solution of 2,6-dichloro-nicotinonitrile (3) (7.06 g, 40.8 mmol) in acetonitrile (anhydrous, 300 mL) were added 4-bromo-3-[1,3]dioxolan-2-yl-phenol (2) (10 g, 40.8 mmol) and K$_2$CO$_3$ (5.63 g, 40.8 mmol). The reaction was heated at 65° C. for 3 hours. The solution was filtered and evaporated in vacuo to afford 15.6 g of the product mixture. $^1$H NMR (400 MHz, CHLOROFORM-d) δ ppm 7.94 (d, J=9.0 Hz, 2H), 7.62 (d, J=8.6 Hz, 2H), 7.46 (d, J=3.1 Hz, 1H), 7.41 (d, J=3.1 Hz, 1H), 7.18-7.08 (m, 2H), 7.05 (dd, J=8.8, 2.93 Hz, 1H), 6.93 (d, J=8.2 Hz, 1H), 6.11 (s, 1H), 6.09 (s, 1H), 4.19-3.99 (m, 8H).

2-(4-Bromo-3-[1,3]dioxolan-2-yl-phenoxy)-6-[(2-hydroxy-ethyl)-methyl-amino]-nicotinonitrile (8)

To a solution of compound mixture, 6-(4-bromo-3-[1,3] dioxolan-2-yl-phenoxy)-2-chloro-nicotinonitrile and 2-(4- bromo-3-[1,3]dioxolan-2-yl-phenoxy)-6-chloro-nicotinonitrile, (4+5, 1 g, 2.6 mmol) in acetonitrile (anhydrous, 30 mL) was added 2-methylamino-ethanol (6, 2.1 mL, 26 mmol). The reaction was heated at 80° C. for 2 hours. After the reaction, all volatile components were evaporated under vacuum. Purification was accomplished by silica gel chromatography, eluting with 10%-80% EtOAc/Hexane gradient, affording the title compound 400 mg in 36% yield. $^1$H NMR 400 MHz (CDCl$_3$) δ 7.62 (d, J=8.6 Hz, 1H), 7.59 (d, J=8.6 Hz, 1H), 7.47 (d, J=3.1 Hz, 1H), 7.06 (dd, J=8.6 Hz, 3.1 Hz, 1H), 6.18 (d, J=8.6 Hz, 1H), 6.08 (s, 1H), 4.20-4.02 (m, 4H), 3.55 (t, J=3.2 Hz, 2H), 3.42 (t, J=3.2 Hz, 2H), 3.02 (s, 3H).

2-(4-Bromo-3-formyl-phenoxy)-6-[(2-hydroxy-ethyl)-methyl-amino]-nicotinonitrile (9)

To a solution of 2-(4-bromo-3-[1,3]dioxolan-2-yl-phenoxy)-6-[(2-hydroxy-ethyl)-methyl-amino]-nicotinonitrile (8) (400 mg, 0.95 mmol) in THF (30 mL) was added HCl solution (1 M, 10 mL). The reaction was stirred at room temperature overnight. After the reaction, all THF was evaporated under vacuum. The aqueous solution was extracted with EtOAc (2×50 mL). The organic layer was washed with water (3×50 mL). The organic layer was dried over MgSO$_4$, filtered and evaporated under vacuum to afford the desired product 320 mg (89% yield) that was used without further purification. $^1$H NMR (400 MHz, CHLOROFORM-d) δ ppm 10.35 (s, 1H), 7.91 (d, J=2.7 Hz, 1H), 7.67 (t, J=9.2 Hz, 2H), 7.32 (dd, J=8.6, 2.7 Hz, 1H), 6.24 (d, J=8.6 Hz, 1H), 3.70-3.62 (m, 2H), 3.56-3.49 (m, 2H), 3.04 (s, 3H).

2-(4-Bromo-3-formyl-phenoxy)-6-{[2-(tert-butyl-dimethyl-silanyloxy)-ethyl]-methyl-amino}-nicotinonitrile: (10)

To a solution of 2-(4-bromo-3-formyl-phenoxy)-6-[(2-hydroxy-ethyl)-methyl-amino]-nicotinonitrile (9) (400 mg, 1.06 mmol) in THF (anhydrous, 30 mL) were added TBDMS-Cl (193 mg, 1.28 mmol) and Et$_3$N (0.178 mL, 1.28 mmol). The solution was stirred at room temperature for 2 days. The solution was filtered and concentrated in vacuo. Purification was accomplished by silica gel chromatography, eluting with 2.5%-20% EtOAc/hexanes gradient, to afford 420 mg (81% yield) of the title compound. $^1$H NMR 400 MHz (CDCl$_3$) δ 10.4 (s, 1H), 7.83 (s, 1H), 7.76-7.68 (m, 2H), 7.40-7.33 (m, 1H), 6.30 (br s, 1H), 3.62 (br s, 2H), 3.48 (s, 2H), 3.02 (s, 3H), 0.89 (s, 9H), 0.02 (s, 6H).

6-{[2-(tert-Butyl-dimethyl-silanyloxy)-ethyl]-methyl-amino}-2-[3-formyl-4-(4,4,5,5-tetramethyl-[1,3,2]dioxaborolan-2-yl)-phenoxy]-nicotinonitrile: (11)

To a solution of 2-(4-bromo-3-formyl-phenoxy)-6-{[2-(tert-butyl-dimethyl-silanyloxy)-ethyl]-methyl-amino}-nicotinonitrile (10) (520 mg, 1.06 mmol) in 1,4-dioxane (anhydrous, 60 mL) were added bispinacolatodiboron (323 mg, 1.27 mmol), PdCl$_2$(dppf) (78 mg, 0.106 mmol) and KOAc (312 mg, 3.18 mmol). The solution was stirred at r.t. with N$_2$ bubbling for 30 minutes. Then the reaction was heated at 100° C. for 3 hours. The solution was filtered and concentrated in vacuo. Purification was accomplished by silica gel chromatography, eluting with 2.5%-20% EtOAc/hexanes gradient to afford 485 mg (85% yield) of the title compound. $^1$H NMR 400 MHz (CDCl$_3$) δ 10.6 (s, 1H), 7.93 (d, J=8.6 Hz, 1H), 7.82 (s, 1H), 7.60 (d, J=8.6 Hz, 1H), 7.39 (d, J=8.6 Hz, 1H), 6.20 (br s, 1H), 3.52 (br s, 2H), 3.39 (s, 2H), 2.98 (s, 3H), 1.37 (s, 12H), 0.79 (s, 9H), —0.09 (s, 6H).

2-(1-Hydroxy-1,3-dihydro-benzo[c][1,2]oxaborol-5-yloxy)-6-[(2-hydroxy-ethyl)-methyl-amino]-nicotinonitrile: (D98)

To a clear solution of 6-{[2-(tert-butyl-dimethyl-silanyloxy)-ethyl]-methyl-amino}-2-[3-formyl-4-(4,4,5,5-tetramethyl-[1,3,2]dioxaborolan-2-yl)-phenoxy]-nicotinonitrile (11) (485 mg, 0.903 mmol) in MeOH (anhydrous, 100 mL) was slowly added NaBH$_4$ (101 mg, 2.65 mmol). The reaction was stirred at room temperature for 4 hours, before the addition of HCl solution (1 M, 60 mL). The stirring was kept at room temperature overnight. Then the solution was slowly evaporated in vacuo. Purification was accomplished by reverse phase Biotage with 10%-100% MeOH/H$_2$O gradient to afford 51 mg (13.8% yield) of the desired product. $^1$H NMR (400 MHz, DMSO-d$_6$) δ ppm 9.22 (s, 1H), 7.92 (d, J=8.6 Hz, 1H), 7.75 (d, J=8.2 Hz, 1H), 7.24 (s, 1H), 7.16 (dd, J=7.8, 2.0 Hz, 1H), 6.43 (br. s., 1H), 4.98 (s, 2H), 3.90 (br. s., 1H), 3.47 (br. s., 2H), 3.39 (s, 2H, masked), 2.95 (br. s., 3H); HPLC: 98.18% (220 nm), 99.15% (254 nm), 99.16 (Max-Plot).

19db 6-(1-Hydroxy-1,3-dihydro-benzo[c][1,2]oxaborol-5-yloxy)-2-(2-hydroxy-ethoxy)-nicotinonitrile (D99)

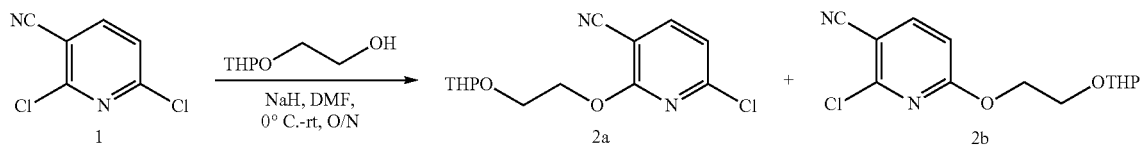

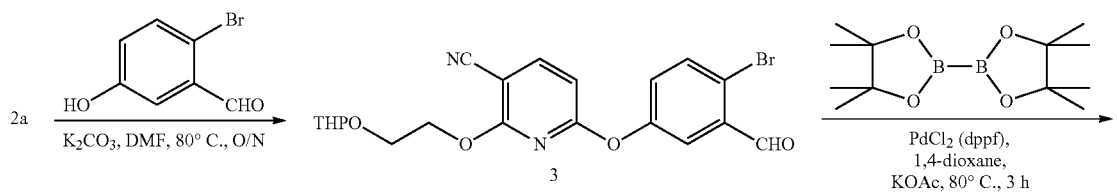

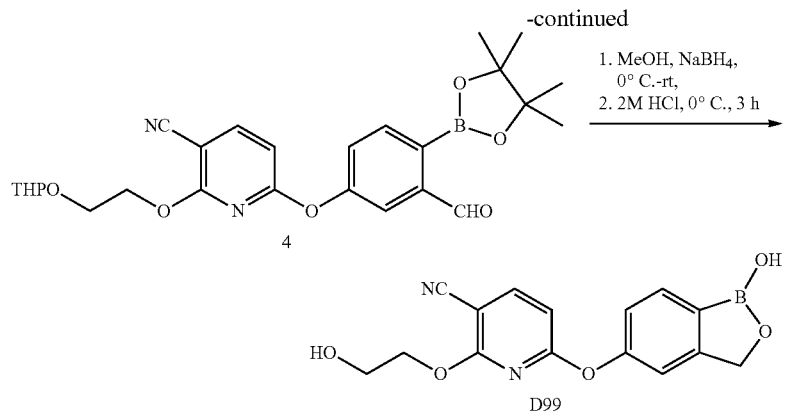

6-Chloro-2-[2-(tetrahydro-pyran-2-yloxy)-ethoxy]-nicotinonitrile (2a)

To a solution of 2-(tetrahydro-pyran-2-yloxy)-ethanol (12.65 mL, 86.70 mmol) in DMF (50 mL) at 0° C. was added sodium hydride (95% in mineral oil, 2.19 g, 86.70 mmol) portion-wise. After 1 h at room temperature, this mixture was slowly added to a solution of 2,6-dichloro-nicotinonitrile (10.0 g, 57.80 mmol) in DMF (30 mL) at 0° C. After overnight, DMF was removed under reduced pressure, and the resulting mixture was diluted with EtOAc (200 mL), washed with water (2×25 mL) and brine (2×25 mL) solution, dried over anhydrous $Na_2SO_4$, filtered, and concentrated to give a mixture of regioisomers 2a and 2b as an oil, Purification was accomplished by flash chromatography on silica gel using 2-25% EtOAc/hexanes gradient elution to yield the title compound (4.0 g, 26%) as a transparent oil. $^1$H NMR (400 MHz, $CDCl_3$) δ ppm 7.89-7.75 (m, 1H), 7.08-6.96 (m, 1H), 4.74 (br. s., 1H), 4.63 (t, J=4.9 Hz, 2H), 4.19-4.00 (m, 1H), 3.98-3.74 (m, 2H), 3.62-3.43 (m, 1H), 1.63-1.91 (m, 2H), 1.68-1.47 (m, 4H).

6-(4-Bromo-3-formyl-phenoxy)-2-[2-(tetrahydro-pyran-2-yloxy)-ethoxy]-nicotinonitrile (3)

To a mixture of 6-chloro-2-[2-(tetrahydro-pyran-2-yloxy)-ethoxy]-nicotinonitrile (2.4 g, 8.48 mmol) and 2-bromo-5-hydroxy-benzaldehyde (1.87 g, 9.33 mmol) in DMF (25 mL) was added potassium carbonate (1.75 g, 12.69 mmol). The resulting mixture was heated at 80° C. overnight. DMF was removed under reduced pressure, the residue was diluted with EtOAc (200 mL), washed with water (20 mL) and brine (3×20 mL), dried over $Na_2SO_4$, filtered, and concentrated to give white solid. Purification was accomplished by flash chromatography on silica gel using 5-25% EtOAc/hexanes as gradient elution yielding the title compound (2.7 g, 71%) as white solid. $^1$H NMR (400 MHz, $CDCl_3$) δ ppm 10.35 (s, 1H), 7.88 (d, J=8.2 Hz, 1H), 7.75 (d, J=2.7 Hz, 1H), 7.70 (d, J=8.2 Hz, 1H), 7.28 (dd, J=8.6, 3.5 Hz, 1H), 6.60 (d, J=8.2 Hz, 1H), 4.64 (s, 1H), 4.28 (t, J=4.9 Hz, 2H), 3.97-3.80 (m, 2H), 3.72-3.60 (m, 1H), 3.55-3.42 (m, 1H), 1.84-1.64 (m, 2H), 1.61-1.49 (m, 4H).

6-[3-Formyl-4-(4,4,5,5-tetramethyl-[1,3,2]dioxaborolan-2-yl)-phenoxy]-2-[2-(tetrahydro-pyran-2-yloxy)-ethoxy]-nicotinonitrile (4)

To a degassed solution of 6-(4-bromo-3-formyl-phenoxy)-2-[2-(tetrahydro-pyran-2-yloxy)-ethoxy]-nicotinonitrile (2.7 g, 6.03 mmol) in 1,4-dioxane (25 mL) was added bis(pinacolato)diboron (1.76 g, 6.94 mmol), potassium acetate (1.77 g, 18.0 mmol), and [1,1'-bis(diphenylphosphino)ferrocene]palladium(II)chloride (0.22 g, 0.30 mmol). After purging with $N_2$ again, the suspension was heated at 80° C. for 3 h. The mixture was cooled to room temperature and passed through Celite® and diluted with EtOAc (150 mL), organic layer was washed with water (20 mL) and brine (20 mL) solution, dried over $Na_2SO_4$, filtered, and concentrated. Purification was accomplished by flash chromatography on silica gel using 5-25% EtOAc/hexanes gradient elution yielding the title compound (2.10 g, 72%) as white solid. $^1$H NMR (400 MHz, DMSO-$d_6$) δ ppm 10.37 (s, 1H), 8.28 (d, J=8.6 Hz, 1H), 7.82 (d, J=8.2 Hz, 1H), 7.71 (s, 1H), 7.57 (d, J=8.2 Hz, 1H), 6.81 (d, J=8.2 Hz, 1H), 4.51 (s, 1H), 4.29-4.10 (m, 2H), 3.85-3.60 (m, 2H), 3.60-3.50 (m, 1H), 3.46-3.36 (m, 1H), 1.75-1.48 (m, 2H), 1.50-1.33 (m, 4H), 1.33 (s, 12H).

6-(1-Hydroxy-1,3-dihydro-benzo[c][1,2]oxaborol-5-yloxy)-2-(2-hydroxy-ethoxy)-nicotinonitrile (D99)

To a solution of 6-[3-formyl-4-(4,4,5,5-tetramethyl-[1,3,2]dioxaborolan-2-yl)-phenoxy]-2-[2-(tetrahydro-pyran-2-yloxy)-ethoxy]-nicotinonitrile (2.5 g, 5.15 mmol) in methanol (15 mL) at 0° C. was added sodium borohydride (0.38 g, 10.32 mmol). After 1 h at rt, the solution was cooled in an ice bath and 2M HCl was added until pH reached to 3-4. The resulting mixture was stirred at 0° C. for 2 h and then at room temperature for 30 min. The solvent was removed under reduced pressure purification was accomplished by reverse phase prep HPLC using $CH_3CN/H_2O$ (0.1% AcOH) as the eluent to yield the title compound D99 (1.0 g, 40%) as white solid. $^1$H NMR (400 MHz, DMSO-$d_6$) δ ppm 9.23 (s, 1H), 8.22 (d, J=8.2 Hz, 1H), 7.77 (d, J=8.2 Hz, 1H), 7.27 (s, 1H), 7.18 (d, J=8.2 Hz, 1H), 6.66 (d, J=8.6 Hz, 1H), 4.97 (s, 2H), 4.82 (t, 1H), 4.12 (t, J=4.9 Hz, 2H), 3.73-3.50 (m, 2H); MS (ES) m/z: 313 (M+1)$^+$; HPLC purity 98.78% (Maxplot), 98.58% (220 nm).

19dc 2-Cyclopentyloxy-6-(1-hydroxy-1,3-dihydro-benzo[c][1,2]oxaborol-5-yloxy)-nicotinonitrile (D100)

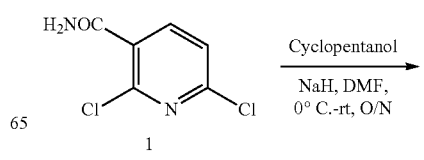

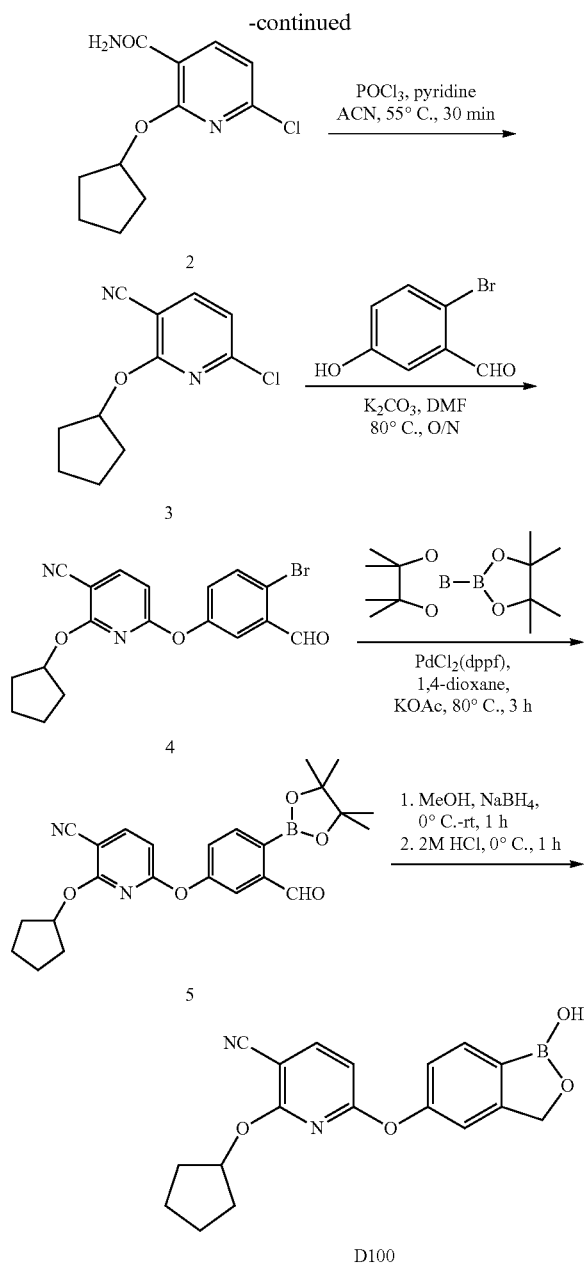

6-Chloro-2-cyclopentyloxy-nicotinamide (2)

To a solution of cyclopentanol (1.42 mL, 15.70 mmol) in DMF (5 mL) at 0° C. was added sodium hydride (95% in mineral oil, 0.39 g, 15.70 mmol) in portions and stirred for 1 h at room temperature. This mixture was slowly added to a solution of 2,6-dichloro-nicotinamide (2.0 g, 10.47 mmol) in DMF (10 mL) at 0° C. The reaction mixture was stirred at room temperature overnight. DMF was removed under reduced pressure, and the resulting mixture was diluted with EtOAc (100 mL), washed with water (2×25 mL) and brine (2×25 mL) solution, dried over anhyd. $Na_2SO_4$, filtered, and concentrated to give yellow oil, which was purified by flash chromatography on silica gel using 10-25% EtOAc/hexanes as eluent to yield the title compound (1.94 g, 51%) as a transparent oil. $^1$H NMR (400 MHz, $CDCl_3$) δ 8.44 (d, J=7.8 Hz, 1H), 7.65 (br. s., 1H), 7.03 (d, J=8.2 Hz, 1H), 5.74 (br. s., 1H), 5.70-5.57 (m, 1H), 2.25-1.95 (m, 2H), 1.90-1.66 (m, 6H).

6-Chloro-2-cyclopentyloxy-nicotinonitrile (3)

To a solution of 6-chloro-2-cyclopentyloxy-nicotinamide (1.56 g, 6.48 mmol) and pyridine (3.14 mL, 38.88 mmol) in acetonitrile (30 mL), phosphorus oxychloride (1.77 mL, 19.44 mmol) was added over a period of 5 min. The reaction was stirred at 55° C. for 1 h. Acetonitrile was evaporated in vacuo and the resulting residue was then neutralized with 1N NaOH at 0° C. until pH reached to ~7. The reaction mixture was extracted with EtOAc (100 mL). The organic layer was collected and the aqueous was further extracted with EtOAc (3×50 mL). All organics were combined washed with brine (2×25 mL), dried over anhyd. $Na_2SO_4$, filtered, and concentrated to give the title compound (1.63 g, 94%) as yellow oil, which was carried forward without further purification. $^1$H NMR (400 MHz, DMSO-$d_6$) δ 8.26 (d, J=7.8 Hz, 1H), 7.26 (d, J=7.8 Hz, 1H), 5.49-5.42 (m, 1H), 2.25-1.78 (m, 2H), 1.80-1.64 (m, 4H), 1.60 (t, J=6.8 Hz, 2H).

6-(4-Bromo-3-formyl-phenoxy)-2-cyclopentyloxy-nicotinonitrile (4)

To a mixture of 6-chloro-2-cyclopentyloxy-nicotinonitrile (1.32 g, 5.92 mmol) and 2-bromo-5-hydroxy-benzaldehyde (1.43 g, 7.10 mmol) in DMF (10 mL) was added potassium carbonate (1.22 g, 8.88 mmol). The resulting mixture was heated at 69° C. overnight. DMF was removed under reduced pressure, the residue was diluted with EtOAc (100 mL), washed with water (30 mL) and brine (30 mL), dried over $Na_2SO_4$, filtered, and concentrated to give white solid, which was purified by flash chromatography on silica gel using 10-25% EtOAc/hexanes as eluent to yield the title compound (2.30 g, quantitative) as white solid. $^1$H NMR (400 MHz, DMSO-$d_6$) δ 10.19 (s, 1H), 8.24 (d, J=8.2 Hz, 1H), 7.88 (d, J=8.6 Hz, 1H), 7.70 (s, 1H), 7.60-7.46 (m, 1H), 6.79 (d, J=8.2 Hz, 1H), 4.95 (br. s., 1H), 1.87-1.50 (m, 6H), 1.52-1.30 (m, 2H).

2-Cyclopentyloxy-6-[3-formyl-4-(4,4,5,5-tetramethyl-[1,3,2]dioxaborolan-2-yl)-phenoxy]-nicotinonitrile (5)

To a degassed solution of 6-(4-bromo-3-formyl-phenoxy)-2-cyclopentyloxy-nicotinonitrile (2.20 g, 5.68 mmol) in 1,4-dioxane (25 mL) was added bis(pinacolato)diboron (1.73 g, 6.81 mmol), potassium acetate (1.67 g, 17.04 mmol), and [1,1'-bis(diphenylphosphino)ferrocene]palladium(II)chloride (0.20 g, 0.28 mmol). Degassed again, and the suspension was heated at 80° C. overnight. The mixture was passed through Celite® washed with EtOAc (100 mL), organic layer was washed with water (30 mL) and brine (30 mL) solution, dried over $Na_2SO_4$, filtered, and concentrated to give crude product, which was purified by flash chromatography on silica gel using 10-25% EtOAc/hexanes as eluent to yield the title compound (2.0 g, 83%) as white solid. $^1$H NMR (400 MHz, DMSO-$d_6$) δ 10.38 (s, 1H), 8.24 (d, J=8.2 Hz, 1H), 7.82 (d, J=8.2 Hz, 1H), 7.74 (s, 1H), 7.56 (d, J=8.2 Hz, 1H), 6.78 (d, J=8.2 Hz, 1H), 4.96 (br. s., 1H), 1.80-1.54 (m, 6H), 1.50-1.40 (m, 2H), 1.34 (s, 12H).

2-Cyclopentyloxy-6-(1-hydroxy-1,3-dihydro-benzo[c][1,2]oxaborol-5-yloxy)-nicotinonitrile (D100)

To a solution of 2-cyclopentyloxy-6-[3-formyl-4-(4,4,5,5-tetramethyl-[1,3,2]dioxaborolan-2-yl)-phenoxy]-nicotinonitrile (2.0 g, 4.60 mmol) in methanol (15 mL) at 0° C. was added sodium borohydride (0.26 g, 6.90 mmol). After 1 h at rt, 2 M HCl was added to it at 0° C. until pH reached to 3-4. The resulting mixture was stirred at 0° C. for 30 min and then sonicated to give white solid which was filtered and lyophilized to yield D100 (0.85 g, 56%) as white solid. $^1$H NMR (400 MHz, DMSO-$d_6$) δ 9.24 (s, 1H), 8.20 (d, J=8.2 Hz, 1H), 7.77 (d, J=7.8 Hz, 1H), 7.27 (d, J=1.2 Hz, 1H), 7.18 (dd, J=8.2, 1.9 Hz, 1H), 6.69 (d, J=8.2 Hz, 1H), 4.97 (br. s., 3H), 1.75-1.54 (m, 6H), 1.52-1.33 (m, 2H); MS (ES) m/z: 337 (M+1)$^+$; HPLC purity 99.36% (Maxplot), 99.35% (220 nm); Elemental analysis for $C_{18}H_{17}BN_2O_4 \cdot 0.25\ H_2O$: Calculated C=63.46%, H=5.18%, N=8.22%. Found C=63.34%, H=5.17%, N=8.34%.

19dd 2-(1-Hydroxy-1,3-dihydro-benzo[c][1,2]oxaborol-5-yloxy)-6-(2-methoxy-ethylamino)-nicotinonitrile (D101)

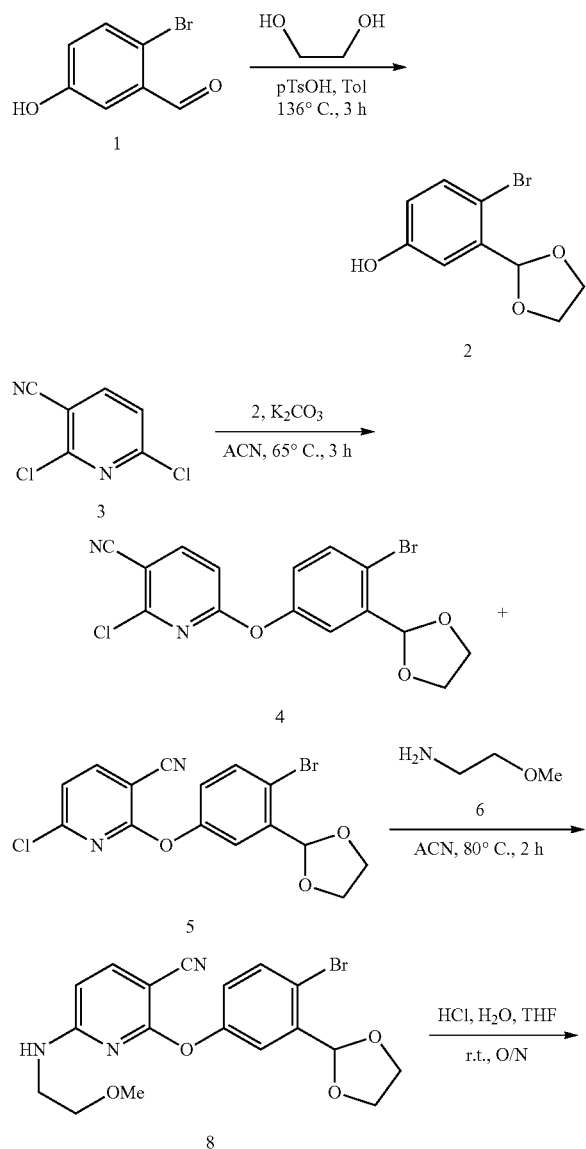

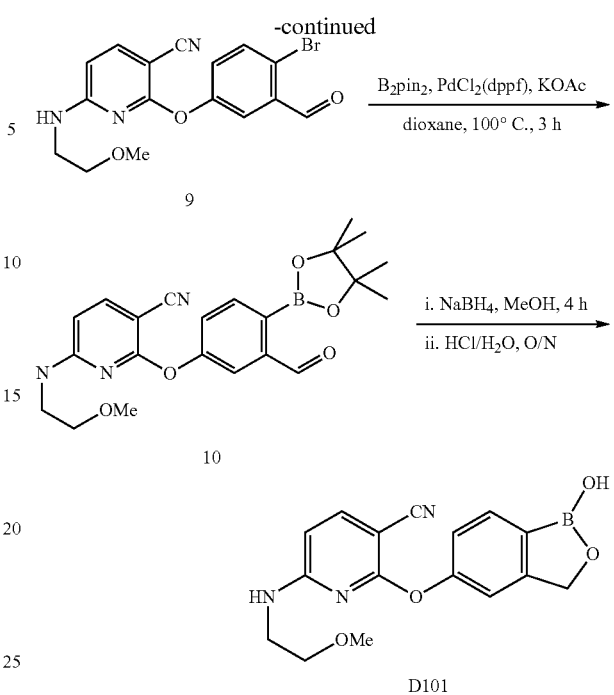

4-Bromo-3-[1,3]dioxolan-2-yl-phenol (2)

To a solution of 2-bromo-5-hydroxy-benzaldehyde (1) (10 g, 49.8 mmol) in toluene (200 mL) were added ethylene glycol (9.25 g, 149.3 mmol) and catalytic amount of p-TsOH (200 mg). After attaching a Dean-Stark trap, the reaction was heated at 136° C. for 3 hours. After the solution cooled to room temperature, it was washed with saturated NaHCO$_3$ (200 mL). The organic layer was dried over Na$_2$SO$_4$, filtered and evaporated in vacuo to provide 11.6 g (95% yield) of the title compound. $^1$H NMR (400 MHz, CHLOROFORM-d) δ ppm 7.40 (d, J=8.6 Hz, 1H), 7.09 (d, J=3.1 Hz, 1H), 6.72 (dd, J=8.6, 3.1 Hz, 1H), 6.04 (s, 1H), 4.18-4.04 (m, 4H)

6-(4-Bromo-3-[1,3]dioxolan-2-yl-phenoxy)-2-chloro-nicotinonitrile+2-(4-bromo-3-[1,3]dioxolan-2-yl-phenoxy)-6-chloro-nicotinonitrile (4+5)

To a solution of 2,6-dichloro-nicotinonitrile (3) (7.06 g, 40.8 mmol) in acetonitrile (anhydrous, 300 mL) were added 4-bromo-3-[1,3]dioxolan-2-yl-phenol (2) (10 g, 40.8 mmol) and K$_2$CO$_3$ (5.63 g, 40.8 mmol). The reaction was heated at 65° C. for 3 hours. The solution was filtered and evaporated in vacuo to afford 15.6 g of the mixture. $^1$H NMR (400 MHz, chloroform-d) δ ppm 7.94 (d, J=9.0 Hz, 2H), 7.62 (d, J=8.6 Hz, 2H), 7.46 (d, J=3.1 Hz, 1H), 7.41 (d, J=3.1 Hz, 1H), 7.18-7.08 (m, 2H), 7.05 (dd, J=8.8, 2.93 Hz, 1H), 6.93 (d, J=8.2 Hz, 1H), 6.11 (s, 1H), 6.09 (s, 1H), 4.19-3.99 (m, 8H).

2-(4-Bromo-3-[1,3]dioxolan-2-yl-phenoxy)-6-(2-methoxy-ethylamino)-nicotinonitrile (8)

To a solution of compound mixture, 6-(4-bromo-3-[1,3] dioxolan-2-yl-phenoxy)-2-chloro-nicotinonitrile and 2-(4-bromo-3-[1,3]dioxolan-2-yl-phenoxy)-6-chloro-nicotinonitrile (4+5, 2.5 g, 6.6 mmol) in acetonitrile (anhydrous, 50 mL) was added 2-methoxy-ethylamine (5.7 mL, 66 mmol). The reaction was heated at 80° C. for 2 hours. After the reaction, all volatile components were evaporated under vacuum. Purification was achieved by silica gel chromatography, eluting with 10%-80% EtOAc/hexanes gradient, affording 1.0 g (36% yield) of the title compound. ¹H NMR (400 MHz, chloroform-d) δ ppm 7.58-7.47 (m, 2H), 7.41 (d, J=3.1 Hz, 1H), 7.04 (dd, J=8.6, 2.7 Hz, 1H), 6.09-6.03 (m, 2H), 5.37 (t, J=5.1 Hz, 1H), 4.14-3.99 (m, 4H), 3.37 (t, J=5.1 Hz, 2H), 3.31-3.23 (m, 5H).

2-(4-Bromo-3-formyl-phenoxy)-6-(2-methoxy-ethylamino)-nicotinonitrile (9)

To a solution of 2-(4-bromo-3-[1,3]dioxolan-2-yl-phenoxy)-6-(2-methoxy-ethylamino)-nicotinonitrile (8) (1.0 g, 2.38 mmol) in THF (50 mL) was added HCl solution (1M/H₂O, 20 mL). After overnight, the THF was evaporated under vacuum. The aqueous solution was extracted with EtOAc (2×50 mL). The organic layer was washed with water (3×50 mL), dried over MgSO₄, filtered and evaporated in vacuo. Purification was accomplished by silica gel chromatography, eluting with 25%-100% EtOAc/hexanes gradient, to afford the desired product 780 mg (87% yield) as a white solid. ¹H NMR (400 MHz, chloroform-d) δ ppm 10.34 (s, 1H), 7.80 (d, J=2.7 Hz, 1H), 7.67 (d, J=8.6 Hz, 1H), 7.60 (d, J=8.2 Hz, 1H), 7.30 (dd, J=8.8, 2.9 Hz, 1H), 6.13 (d, J=8.2 Hz, 1H), 5.24 (br. s., 1H), 3.42 (t, J=4.9 Hz, 2H), 3.35-3.27 (m, 5H).

2-[3-Formyl-4-(4,4,5,5-tetramethyl-[1,3,2]dioxaborolan-2-yl)-phenoxy]-6-(2-methoxy-ethylamino)-nicotinonitrile (10)

To a solution of 2-(4-bromo-3-formyl-phenoxy)-6-(2-methoxy-ethylamino)-nicotinonitrile (9) (780 mg, 2.0 mmol) in 1,4-dioxane (anhydrous, 100 mL) were added bispinacolatodiboron (630 mg, 2.5 mmol), PdCl₂(dppf) (150 mg, 0.2 mmol) and KOAc (610 mg, 6.2 mmol). The solution was stirred at r.t. with N₂ bubbling for 30 minutes. Then the reaction was heated at 100° C. for 3 hours. After cooling to room temperature, the solution was filtered and concentrated in vacuo. Purification was accomplished by silica gel chromatography, eluting with 25%-100% EtOAc/hexanes gradient to afford 440 mg (50% yield) of the title compound product. ¹H NMR (400 MHz, chloroform-d) δ ppm 10.62 (s, 1H), 7.94 (d, J=7.8 Hz, 1H), 7.82 (d, J=2.0 Hz, 1H), 7.59 (d, J=8.6 Hz, 1H), 7.40 (dd, J=8.2, 2.3 Hz, 1H), 6.12 (d, J=8.6 Hz, 1H), 5.37 (t, J=4.9 Hz, 1H), 3.40 (t, J=4.9 Hz, 2H), 3.33-3.25 (m, 5H), 1.40 (s, 12H).

2-(1-Hydroxy-1,3-dihydro-benzo[c][1,2]oxaborol-5-yloxy)-6-(2-methoxy-ethylamino)-nicotinonitrile (D101)

To a clear solution of 2-[3-formyl-4-(4,4,5,5-tetramethyl-[1,3,2]dioxaborolan-2-yl)-phenoxy]-6-(2-methoxy-ethylamino)-nicotinonitrile (10) (440 mg, 1.04 mmol) in MeOH (anhydrous, 100 mL) was slowly added NaBH₄ (120 mg, 3.12 mmol). The reaction was stirred at room temperature for 4 hours, before the addition of HCl solution (1 M, 50 mL). The stirring was kept at room temperature overnight. Then the solution was slowly concentrated in vacuo. Purification was accomplished by preparative HPLC to afford the title compound (108 mg, 32% yield) as a white lyophilizate. ¹H NMR (400 MHz, DMSO-d₆) δ ppm 9.23 (br. s., 1H), 7.86 (br. s., 1H), 7.79-7.68 (m, 2H), 7.24 (s, 1H), 7.18-7.13 (m, 1H), 6.30 (d, J=8.6 Hz, 1H), 4.98 (s, 2H), 3.20 (d, J=1.6 Hz, 2H), 3.17-3.06 (m, 5H); ES-MS m/z=326 (M+H)⁺; HPLC: 99.39% (220 nm), 99.24% (MaxPlot).

19de 6-(1-Hydroxy-1,3-dihydro-benzo[c][1,2]oxaborol-5-yloxy)-2-morpholin-4-yl-nicotinonitrile (D102)

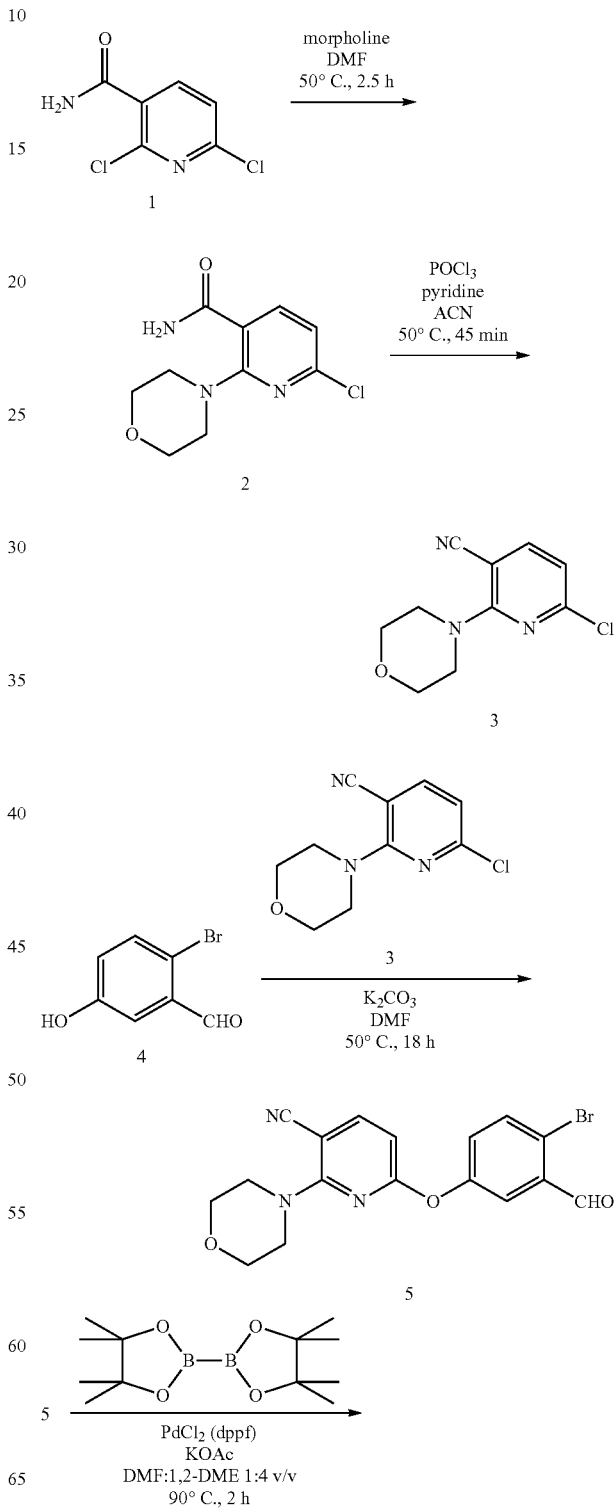

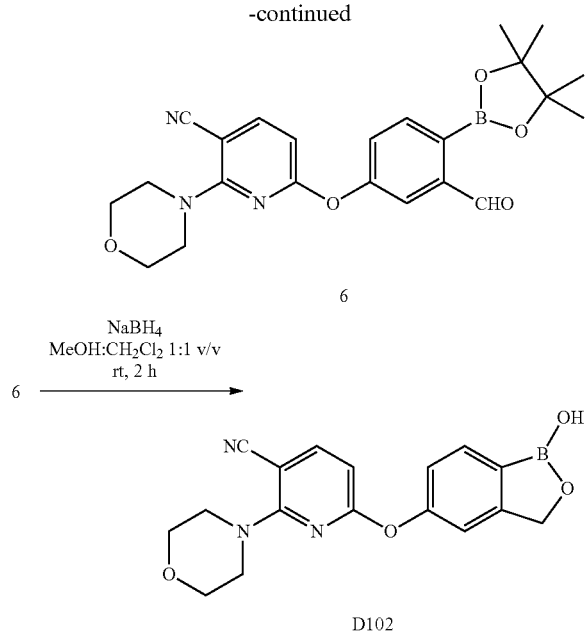

6-Chloro-2-morpholin-4-yl-nicotinamide (2)

Refer to synthesis of (D46) for preparation of 2,6-dichloro-nicotinamide (1). A sealed reaction vessel containing 2,6-dichloro-nicotinamide (1) (1.85 g, 9.70 mmol) and morpholine (1.69 mL, 19.4 mmol) in anhydrous dimethylformamide (20 mL) was heated to 50° C. for 2.5 h. The reaction was then cooled to room temperature and diluted with 0.1 M NaOH (600 mL) and extracted with ethyl acetate (3×500 mL). All organics were combined, dried over $Na_2SO_4$, filtered and concentrated to give the title compound (2.49 g) as an orange oil, which later solidified upon standing. Compound 6-Chloro-2-morpholin-4-yl-nicotinamide (2) was carried forward without further purification. $^1$H NMR 400 MHz ($d_6$-DMSO) δ 7.89 (br s, 1H), 7.67 (d, J=7.8 Hz, 1H), 7.56 (br s, 1H), 6.88 (d, J=7.8 Hz, 1H), 3.67 (br t, J=4.7 Hz, 4H), 3.31 (br t, J=4.7 Hz, 4H).

6-Chloro-2-morpholin-4-yl-nicotinonitrile (3)

Experimental procedure for synthesis of 6-chloro-2-morpholin-4-yl-nicotinonitrile (3) is the same as that described in synthesis of (D46). The reaction of 6-chloro-2-morpholin-4-yl-nicotinamide (2) (2.49 g) with phosphorus oxychloride (2.7 mL, 29 mmol) and pyridine (4.7 mL, 58 mmol) in acetonitrile (60 mL) gave a crude black oil upon workup. The black oil was fractionated by dry-pack column chromatography as follows: the oil was diluted with $CH_2Cl_2$ (300 mL) followed by the addition of silica gel (20 g, 230-400 mesh) and concentrated to dryness. This was loaded onto a silica column (60 g, 230-400 mesh) and eluted with 10% EtOAc/hexanes. Pure fractions were combined and concentrated to give the title compound as a white solid (1.97 g, 91% isolated yield over 2 steps with respect to 1.85 g of compound 1). TLC eluted with 50% EtOAc/hexanes and rendered with UV lamp gave $R_f$=0.8; $^1$H NMR 400 MHz ($CDCl_3$) δ 7.69 (d, J=8.2 Hz, 1H), 6.75 (d, J=7.8 Hz, 1H), 3.85-3.77 (8H).

6-(4'-Bromo-3'-formyl-phenoxy)-2-morpholin-4-yl-nicotinonitrile (5)

Experimental procedure for synthesis of 6-(4'-bromo-3'-formyl-phenoxy)-2-morpholin-4-yl-nicotinonitrile (5) is the same as that described in synthesis of D46 except that the reaction was heated at 50° C. for 18 h. The reaction of 6-chloro-2-morpholin-4-yl-nicotinonitrile (3) (1.58 g, 7.06 mmol), 2-bromo-5-hydroxy-benzaldehyde (4) (2.13 g, 10.6 mmol) and $K_2CO_3$ (1.95 g, 14.1 mmol) in DMF (30 mL) gave crude oil upon workup. The oil was fractionated by dry-pack column chromatography as follows: the oil was diluted with $CH_2Cl_2$ (300 mL) followed by the addition of silica gel (40 g, 230-400 mesh) and concentrated to dryness. This was loaded onto a silica column (80 g, 230-400 mesh) and eluted with gradient 10-20% EtOAc/hexanes. Pure fractions were combined and concentrated to give the title compound as a white solid (1.69 g, 61% isolated yield). TLC eluted with 25% EtOAc/hexanes and rendered with UV lamp and phosphomolybdic acid solution gave $R_f$=0.4; $^1$H NMR 400 MHz ($CDCl_3$) δ 10.34 (s, 1H), 7.77 (d, J=8.6 Hz, 1H), 7.76 (d, J=3.1, 1H), 7.68 (d, J=9.0 Hz, 1H), 7.25 (dd, J=8.6, 3.1 Hz, 1H), 6.38 (d, J=8.2 Hz, 1H), 3.71 (br t, J=4.3 Hz, 4H), 3.59 (br t, J=4.3 Hz, 4H).

6-[3-Formyl-4-(4,4,5,5-tetramethyl-[1,3,2]dioxaborolan-2-yl)-phenoxy]-2-morpholin-4-yl-nicotinonitrile (6)

Experimental procedure for synthesis of 6-[3-formyl-4-(4,4,5,5-tetramethyl-[1,3,2]dioxaborolan-2-yl)-phenoxy]-2-morpholin-4-yl-nicotinonitrile (6) is the same as that described in synthesis of (D46). The reaction of 5 (1.69 g, 4.37 mmol), bis(pinacolato)diboron (3.32 g, 13.1 mmol) and potassium acetate (1.28 g, 13.1 mmol) in a solvent mixture of dimethylformamide (10 mL) and 1,2-dimethoxyethane (40 mL) gave a brown oil. The brown oil was fractionated by dry-pack column chromatography as follows: the oil was diluted with $CH_2Cl_2$ (400 mL) followed by the addition of silica gel (40 g, 230-400 mesh) and concentrated to dryness. This was loaded onto a silica column (80 g, 230-400 mesh) and eluted with gradient 10-20% EtOAc/hexanes. The pure fractions were combined and concentrated to give the title compound as a white solid (1.24 g, 65% isolated yield). TLC with two elutions of 25% EtOAc/hexanes and rendered with UV lamp gave $R_f$=0.3; $^1$H NMR 400 MHz ($CDCl_3$) δ 10.64 (s, 1H), 7.95 (d, J=8.2 Hz, 1H), 7.79 (d, J=2.3 Hz, 1H), 7.76 (d, J=8.6 Hz, 1H), 7.36 (dd, J=8.2, 2.3 Hz, 1H), 6.39 (d, J=8.2 Hz, 1H), 3.71 (br t, J=5.1 Hz, 4H), 3.59 (br t, J=5.1 Hz, 4H), 1.40 (s, 12H).

6-(1-Hydroxy-1,3-dihydro-benzo[c][1,2]oxaborol-5-yloxy)-2-morpholin-4-yl-nicotinonitrile (D102)

Experimental procedure for synthesis of 6-(1-hydroxy-1,3-dihydro-benzo[c][1,2]oxaborol-5-yloxy)-2-morpholin-4-yl-nicotinonitrile (D102) is the same as that described in synthesis of (D46). The reaction of 6-[3-formyl-4-(4,4,5,5-tetramethyl-[1,3,2]dioxaborolan-2-yl)-phenoxy]-2-morpholin-4-yl-nicotinonitrile (6) (1.20 g, 2.76 mmol) with $NaBH_4$ (417 mg, 11.0 mmol) gave an orange oil containing D102 upon workup. The oil was fractionated by dry-pack column chromatography as follows: The oil was diluted with 30% MeOH/$CH_2Cl_2$ (400 mL) followed by the addition of silica gel (40 g, 230-400 mesh) and concentrated to dryness. This was loaded onto a silica column (120 g, 230-400 mesh) and eluted with 1:1:100 acetic acid:MeOH:$CH_2Cl_2$. The fractions containing D102 were collected and concentrated to give a light yellow coloured oil. The oil was freeze dried by first diluting with acetonitrile (40 mL) followed by the addition of de-ionised water (400 mL), the resultant white suspension was frozen in a dry-ice acetone bath and placed overnight on freeze-dryer. A white solid of D102 was obtained (740 mg, 94% purity by HPLC). To increase purity of D102, it was re-subjected to column chromatography and freeze-dried following the same conditions as before to give D102 as a white solid (405 mg, 98% purity by HPLC, 44% isolated yield). TLC eluted with 1:2:100 acetic acid:MeOH:$CH_2Cl_2$ and rendered with UV lamp gave $R_f$=0.5; $^1$H NMR 400 MHz ($d_6$-DMSO) δ 9.23 (s, 1H), 8.06 (d, J=8.6 Hz, 1H), 7.77 (d, J=8.2 Hz, 1H), 7.25 (d, J=1.9 Hz, 1H), 7.16 (dd, J=8.2, 1.9 Hz, 1H), 6.46 (d, J=8.6 Hz, 1H), 4.98 (s, 2H), 3.61 (br t, J=4.5 Hz, 4H), 3.49 (br t, J=4.5 Hz, 4H); Mass Spectrum [M+H]$^+$=338; HPLC purity 96.50% (Maxplot), 98.28% (220 nm), 97.23 (254 nm).

19df 5-(4-(methylsulfonyl)phenoxy)benzo[c][1,2]oxaborol-1(3H)-ol (D103)

Preparation of B

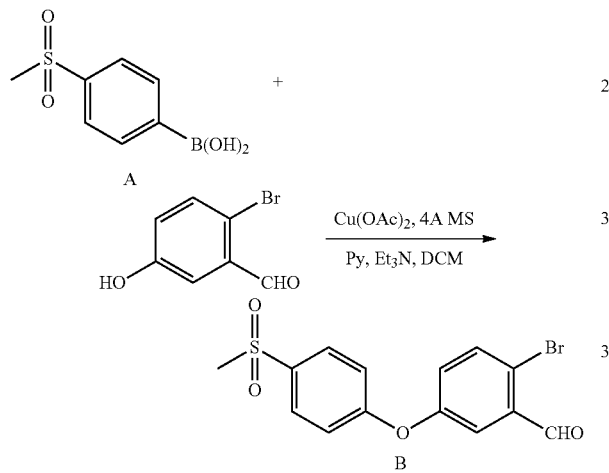

To the solution of A (15.4 g, 77 mmol), 2-bromo-5-hydroxybenzaldehyde (9.67 g, 48 mmol), 4 A MS (35 g) and Cu(OAc)$_2$ (11.32 g, 62.6 mmol) in dry $CH_2Cl_2$ (250 ml) was added pyridine (6.84 g, 86.6 mmol) and $Et_3N$ (12.2 ml, 86.6 mmol) under Ar. The reaction mixture was stirred at ambient temperature overnight and filtrated, washed with 2N HCl, extracted with $CH_2Cl_2$. The organic layer was separated, dried ($Na_2SO_4$), filtered, and the solvent was evaporated. The residue was purified by column chromatography over silica gel (eluent: petroleum ether/EtOAc 10/1 to 4/1). The pure fraction was collected, and the solvent was evaporated to afford B (2.9 g, 7.8%): $^1$H NMR (DMSO, 500 MHz): δ 10.17 (1H, S), 7.95 (2H, d, J=8.5 Hz), 7.89 (1H, d, J=8.5 Hz), 7.49 (1H, d, J=2 Hz), 7.45 (1H, dd, J=2.0, 8.5 Hz), 7.27 (2H, d, J=8.5 Hz), 3.22 (3H, s).

Preparation of C

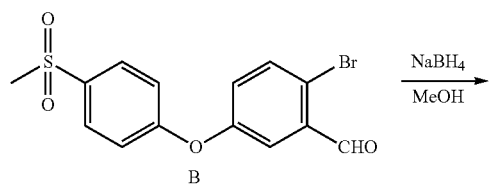

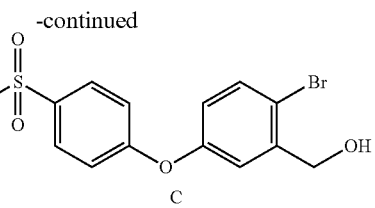

To the solution of B (4.0 g, 11.3 mmol) in MeOH (250 ml) was added NaBH$_4$ (214 mg, 5.65 mmol). The reaction mixture was stirred at ambient temperature for 0.5 h. The solvent was evaporated. The residue was purified by column chromatography over silica gel (eluent: petroleum ether/EtOAc 2/1). The pure fraction was collected, and the solvent was evaporated to afford C (3.25 g, 93%): $^1$H NMR (DMSO, 500 MHz): δ 3.20 (3H, s), 4.50 (2H, d, J=5.5 Hz), 5.55 (1H, t, J=5.5 Hz), 7.02 (1H, dd, J=3.0, 8.5 Hz), 7.20 (2H, m), 7.24 (1H, d, J=2.5 Hz), 7.65 (1H, d, J=8.5 Hz), 7.93 (2H, m).

Preparation of D

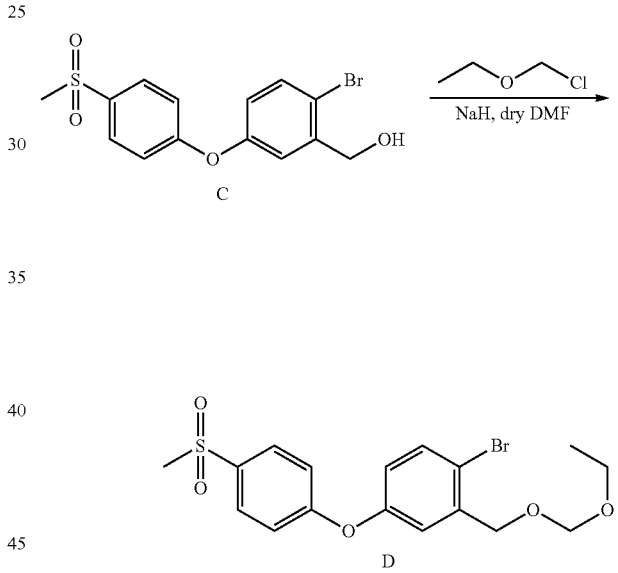

To the solution of C (400 mg, 1.12 mmol) in dry DMF (6 ml) was added NaH (49 mg, 1.12 mmol, 55%) under Ar. The reaction mixture was stirred at 0° C. for 0.5 h, then (chloromethoxy)ethane (137 mg, 1.46 mmol) was added. The reaction mixture was stirred at ambient temperature for 1 h and quenched with i-PrOH. The solvent was evaporated under high vacuum. The residue was dissolved in EtOAc, washed with water. The organic layer was separated, dried ($Na_2SO_4$), filtered, and the solvent was evaporated. The residue was purified by column chromatography over silica gel (eluent: petroleum ether/EtOAc 5/1). The pure fraction was collected, and the solvent was evaporated to afford D (350 mg, 75%): $^1$H NMR (CDCl$_3$, 400 MHz): δ 1.22 (3H, m), 3.05 (3H, s), 3.64 (2H, m), 4.65 (2H, s), 4.80 (2H, s), 6.88 (1H, dd, J=3.2, 8.8 Hz), 7.08 (2H, m), 7.25 (1H, d, J=3.2 Hz), 7.57 (1H, d, J=8.8 Hz), 7.89 (2H, m).

Preparation of E

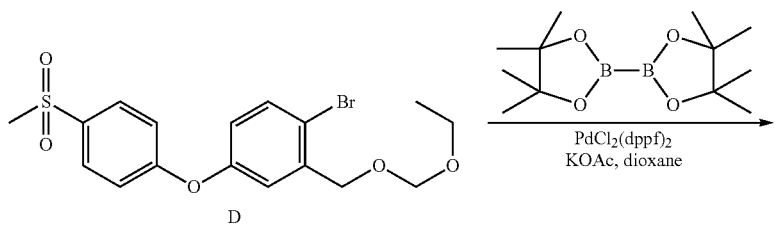

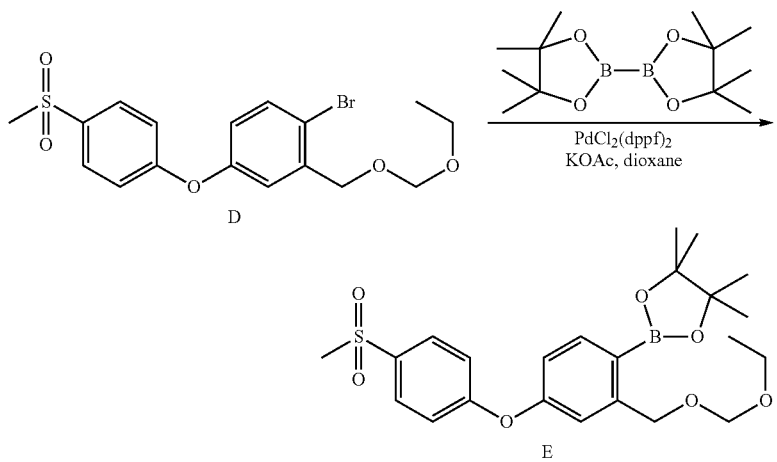

A mixture of D (340 mg, 0.82 mmol), bis(pinacolato)diboron (625 mg, 2.46 mmol), PdCl$_2$(dppf)$_2$ (19.8 mg, 0.0246 mmol) and KOAc (241 mg, 2.46 mmol) in 1,4-dioxane (5 mL) was stirred at 80 overnight under Ar. The organic layer was removed. The residue was purified by column chromatography over silica gel (eluent: petroleum ether/EtOAc 5/1). The pure fraction was collected, and the solvent was evaporated to afford E (360 mg, 95%): $^1$H NMR (CDCl$_3$, 500 MHz): δ 1.20 (3H, t, J=4.5 Hz), 1.32 (12H, s), 3.05 (3H, s), 3.63 (2H, m), 4.80 (2H, s), 4.87 (2H, s), 6.96 (1H, dd, J=2.5, 10 Hz), 7.09 (2H, dd, J=2.5, 9.0 Hz), 7.20 (1H, d, J=3.0 Hz), 7.86 (3H, m).

Preparation of (D103)

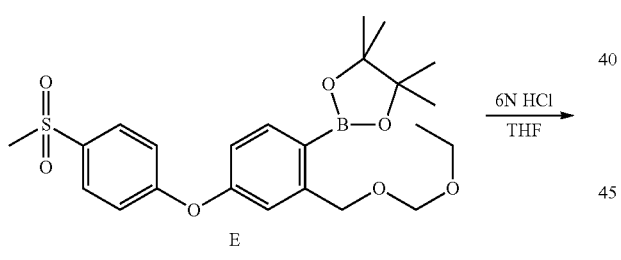

A mixture of E (300 mg, 0.66 mmol) in 6 N HCl (6 mL) and THF (9 mL) was stirred at ambient temperature overnight. The solvents were removed. The residue was purification by preparation HPLC to obtain the desired compound (100 mg, 50%): $^1$H NMR (DMSO-d$_6$, 500 MHz): δ 3.20 (3H, s), 4.97 (2H, s), 7.11 (1H, dd, J=2.0, 8.0 Hz), 7.16 (1H, d, J=1.5 Hz), 7.21 (2H, m), 7.80 (1H, d, J=8.0 Hz), 7.93 (2H, m), 9.23 (1H, s).

19dg 5-(4-(isopropylsulfonyl)phenoxy)benzo[c][1,2]oxaborol-1(3H)-ol (D104)

Preparation of B

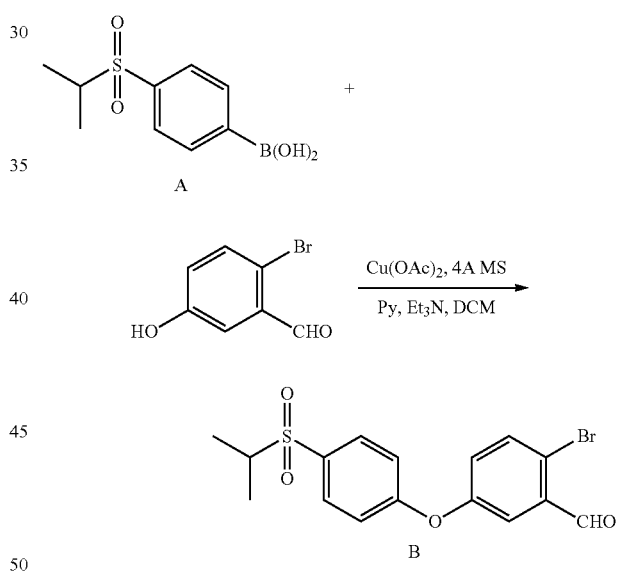

To the solution of A (15.0 g, 65.8 mmol), 2-bromo-5-hydroxybenzaldehyde (8.26 g, 41.1 mmol), 4 A MS (35 g) and Cu(OAc)$_2$ (9.68 g, 53.4 mmol) in dry CH$_2$Cl$_2$ (250 ml) was added pyridine (5.85 g, 74 mmol) and Et$_3$N (10.4 ml, 74 mmol) under Ar. The reaction mixture was stirred at ambient temperature overnight and filtrated, washed with 2N HCl, extracted with CH$_2$Cl$_2$. The organic layer was separated, dried (Na$_2$SO$_4$), filtered, and the solvent was evaporated. The residue was purified by column chromatography over silica gel (eluent: petroleum ether/EtOAc 10/1 to 5/1). The pure fraction was collected, and the solvent was evaporated to afford B (2.2 g, 14%): $^1$H NMR (DMSO, 500 MHz): δ 10.33 (1H, S), 7.86 (1H, m), 7.85 (1H, m), 7.70 (1H, d, J=8.5 Hz), 7.61 (1H, d, J=3.0 Hz), 7.21 (1H, dd, J=3.0, 8.5 Hz), 7.11 (1H, m), 7.09 (1H, m), 3.19 (1H, m), 1.32 (3H, s), 1.31 (3H, s).

Preparation of C

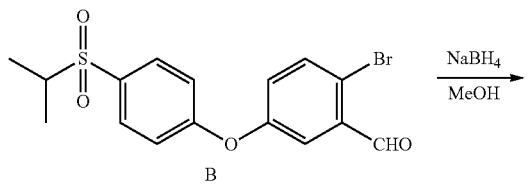

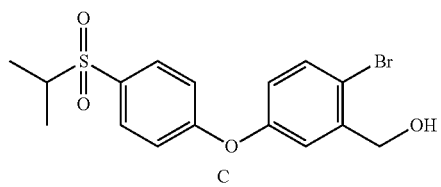

To the solution of B (2.9 g, 7.6 mmol) in MeOH (150 ml) was added NaBH₄ (144 mg, 3.8 mmol). The reaction mixture was stirred at ambient temperature for 0.5 h. The solvent was evaporated. The residue was purified by column chromatography over silica gel (eluent: petroleum ether/EtOAc 3/1). The pure fraction was collected, and the solvent was evaporated to afford C (2.6 g, 89%): ¹H NMR (DMSO, 500 MHz): δ 1.14 (3H, s), 1.15 (3H, s), 3.36 (1H, m), 4.50 (2H, d, J=5.0 Hz), 5.57 (1H, t, J=6.0 Hz), 7.03 (1H, dd, J=3.5, 8.5 Hz), 7.20 (2H, d, J=9.0 Hz), 7.26 (1H, d, J=3.0 Hz), 7.64 (1H, d, J=8.5 Hz), 7.84 (2H, d, J=8.5 Hz).

Preparation of D

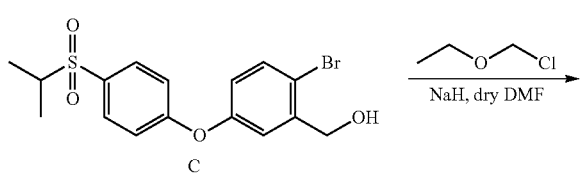

To the solution of C (2.7 g, 7.0 mmol) in dry DMF (50 ml) was added NaH (305 mg, 7.0 mmol, 55%) under Ar. The reaction mixture was stirred at 0° C. for 0.5 h, then (chloromethoxy)ethane (861 mg, 9.1 mmol) was added. The reaction mixture was stirred at ambient temperature for 1 h and quenched with i-PrOH. The solvent was evaporated under high vacuum. The residue was dissolved in EtOAc, washed with water. The organic layer was separated, dried (Na₂SO₄), filtered, and the solvent was evaporated. The residue was purified by column chromatography over silica gel (eluent: petroleum ether/EtOAc 5/1). The pure fraction was collected, and the solvent was evaporated to afford D (2.5 g, 81%).

Preparation of E

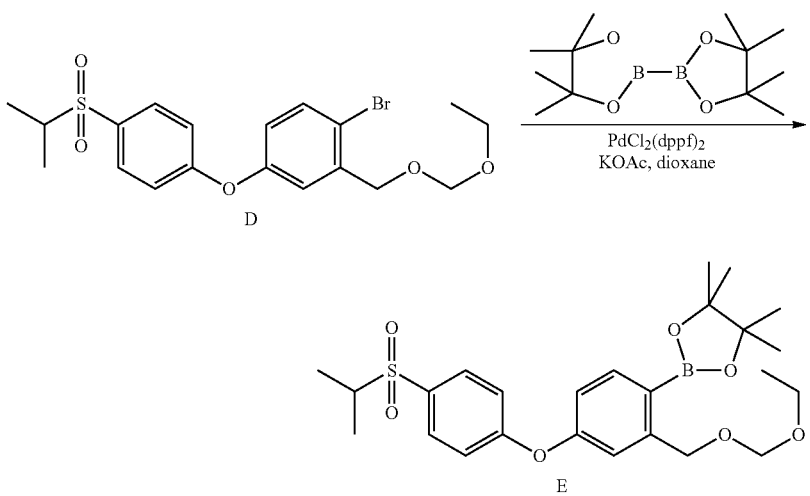

A mixture of D (2.5 g, 5.64 mmol), bis(pinacolato)diboron (4.3 g, 16.9 mmol), PdCl₂(dppf)₂ (184 mg, 0.226 mmol) and KOAc (1.65 g, 16.9 mmol) in 1,4-dioxane (50 mL) was stirred at 80 overnight under Ar. The organic layer was removed. The residue was purified by column chromatography over silica gel (eluent: petroleum ether/EtOAc 5/1). The pure fraction was collected, and the solvent was evaporated to afford E (2.7 g, 99%).

Preparation of compound D104

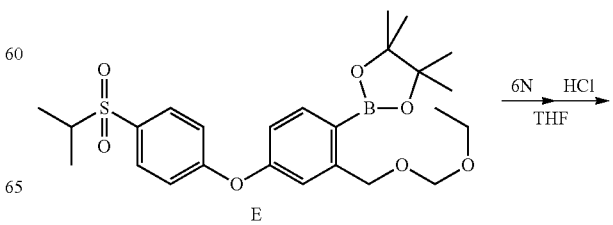

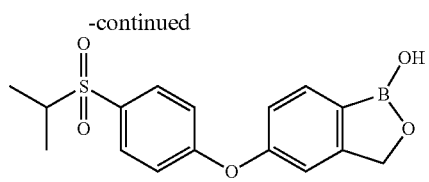

A mixture of E (2.7 g, 5.6 mmol) in 6 N HCl (20 mL) and THF (30 mL) was stirred at ambient temperature overnight. The solvents were removed. The residue was purification by preparation HPLC to obtain the desired compound (1.3 g, 70%): $^1$H NMR (DMSO-$d_6$, 500 MHz): δ 1.15 (3H, s), 1.16 (3H, s), 3.38 (1H, m), 4.97 (2H, s), 7.13 (1H, dd, J=2.0, 8.0 Hz), 7.20 (1H, d, J=5 Hz), 7.22 (2H, m), 7.80 (1H, d, J=8.0 Hz), 7.85 (2H, m), 9.23 (1H, s).

19dh 5-(4-(ethylsulfonyl)phenoxy)benzo[c][1,2]oxaborol-1(3H)-ol (D105)

Preparation of B

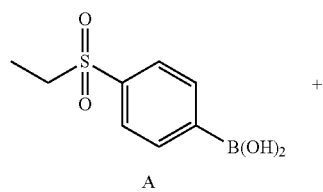

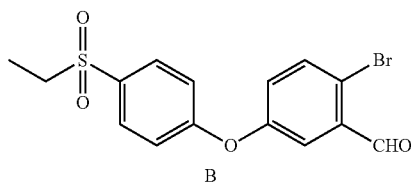

To the solution of A (10.3 g, 48.1 mmol), 2-bromo-5-hydroxybenzaldehyde (6.0 g, 30 mmol), 4 A MS (25 g) and Cu(OAc)$_2$ (7.0 g, 39 mmol) in dry CH$_2$Cl$_2$ (200 ml) was added pyridine (4.22 g, 54 mmol) and Et$_3$N (7.5 ml, 54 mmol) under Ar. The reaction mixture was stirred at ambient temperature overnight and filtrated, washed with 2N HCl, extracted with CH$_2$Cl$_2$. The organic layer was separated, dried (Na$_2$SO$_4$), filtered, and the solvent was evaporated. The residue was purified by column chromatography over silica gel (eluent: petroleum ether/EtOAc 10/1 to 4/1). The pure fraction was collected, and the solvent was evaporated to afford B (3.9 g, 35%): $^1$H NMR (DMSO, 500 MHz): δ 10.18 (1H, S), 7.90 (3H, m), 7.51 (1H, d, J=3.5 Hz), 7.46 (1H, dd, J=3.0, 9.0 Hz), 7.27 (2H, d, J=8.5 Hz), 3.28 (2H, m), 1.11 (3H, t, J=7.5 Hz).

Preparation of C

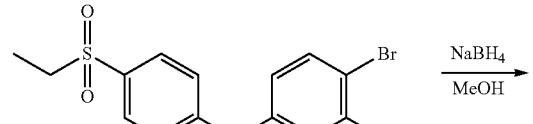

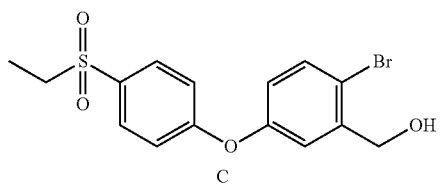

To the solution of B (3.9 g, 10.6 mmol) in MeOH (250 ml) was added NaBH$_4$ (200 mg, 5.3 mmol). The reaction mixture was stirred at ambient temperature for 0.5 h. The solvent was evaporated. The residue was purified by column chromatography over silica gel (eluent: petroleum ether/EtOAc 3/1). The pure fraction was collected, and the solvent was evaporated to afford C (3.66 g, 93.4%): $^1$H NMR (DMSO, 500 MHz): δ 1.10 (3H, t, J=8.0 Hz), 3.26 (2H, m), 4.50 (2H, d, J=5.5 Hz), 5.54 (1H, t, J=6.0 Hz), 7.03 (1H, dd, J=3.0, 9.0 Hz), 7.20 (2H, m), 7.26 (1H, d, J=3.0 Hz), 7.65 (1H, d, J=8.5 Hz), 7.88 (2H, m).

Preparation of D

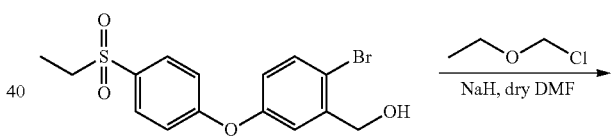

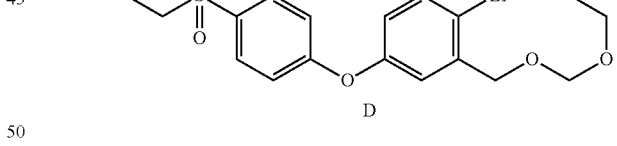

To the solution of C (3.66 g, 9.9 mmol) in dry DMF (50 ml) was added NaH (432 mg, 9.9 mmol, 55%) under Ar. The reaction mixture was stirred at 0° C. for 0.5 h, then (chloromethoxy)ethane (1.22 g, 13 mmol) was added. The reaction mixture was stirred at ambient temperature for 1 h and quenched with i-PrOH. The solvent was evaporated under high vacuum. The residue was dissolved in EtOAc, washed with water. The organic layer was separated, dried (Na$_2$SO$_4$), filtered, and the solvent was evaporated. The residue was purified by column chromatography over silica gel (eluent: petroleum ether/EtOAc 5/1). The pure fraction was collected, and the solvent was evaporated to afford D (2.84 g, 67%): $^1$H NMR (CDCl$_3$, 500 MHz): δ 1.22 (3H, t, J=7.0 Hz), 1.29 (3H, t, J=7.0 Hz), 3.11 (2H, m), 3.64 (2H, m), 4.65 (2H, s), 4.81 (2H, s), 6.89 (1H, d, J=8.5 Hz), 7.08 (1H, d, J=8.0 Hz), 7.25 (1H, s), 7.57 (1H, d, J=8.5 Hz), 7.85 (2H, d, J=8.0 Hz).

Preparation of E

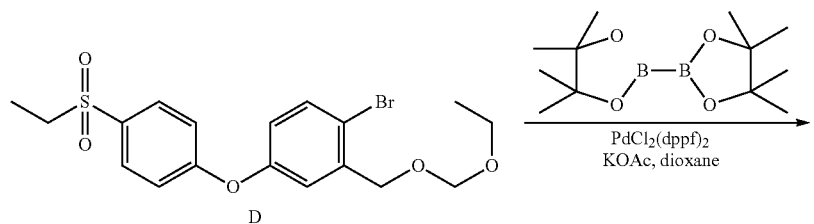

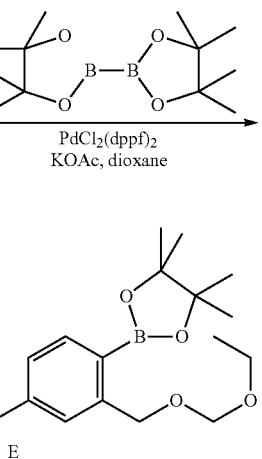

A mixture of D (2.84 g, 6.64 mmol), bis(pinacolato)diboron (5.08 g, 20 mmol), PdCl$_2$(dppf)$_2$ (161 mg, 0.2 mmol) and KOAc (1.96 g, 20 mmol) in 1,4-dioxane (50 mL) was stirred at 80 overnight under Ar. The organic layer was removed. The residue was purified by column chromatography over silica gel (eluent: petroleum ether/EtOAc 5/1). The pure fraction was collected, and the solvent was evaporated to afford E (2.83 g, 90%).

Preparation of D105

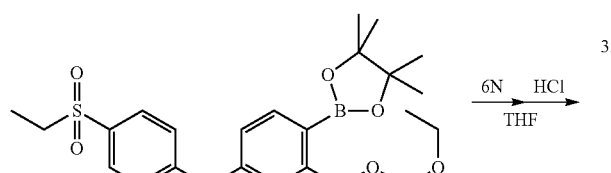

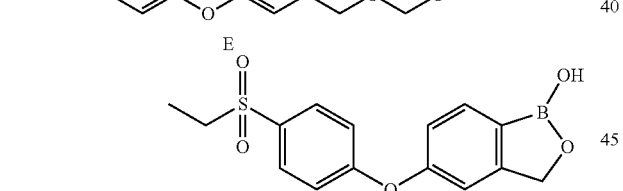

A mixture of E (2.83 g, 5.94 mmol) in 6 N HCl (40 mL) and THF (60 mL) was stirred at ambient temperature overnight. The solvents were removed. The residue was purification by preparation HPLC to obtain the desired compound (1.0 g, 53%): $^1$H NMR (CDCl$_3$, 500 MHz): δ 1.30 (3H, m), 3.12 (2H, m), 5.08 (2H, s), 7.02 (1H, d, J=1.5 Hz), 7.07 (1H, dd, J=2.0, 7.5 Hz), 7.12 (2H, m), 7.78 (1H, d, J=7.5 Hz), 7.87 (2H, m).

19di 2-(1-Hydroxy-1,3-dihydro-benzo[c][1,2]oxaborol-5-yloxy)-6-(2-hydroxy-ethylamino)-nicotinonitrile (D106)

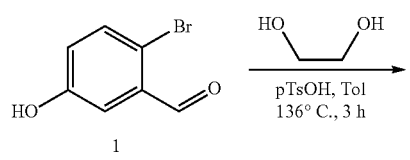

-continued

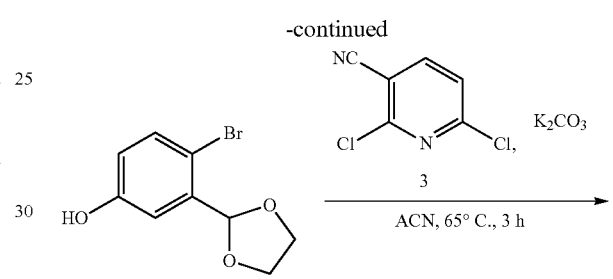

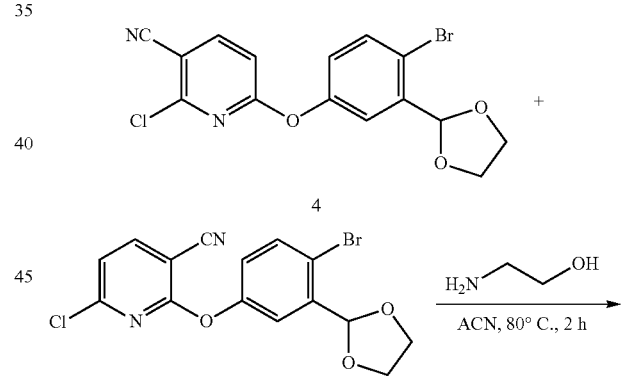

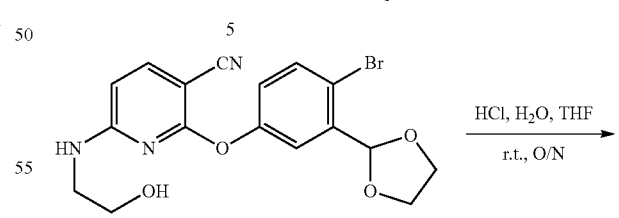

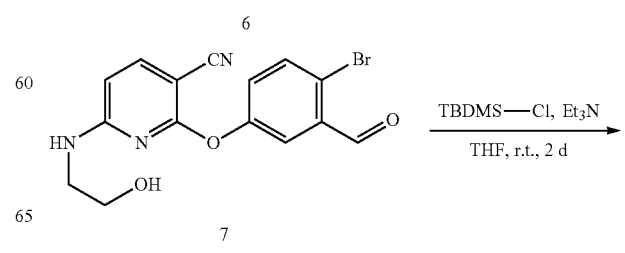

-continued

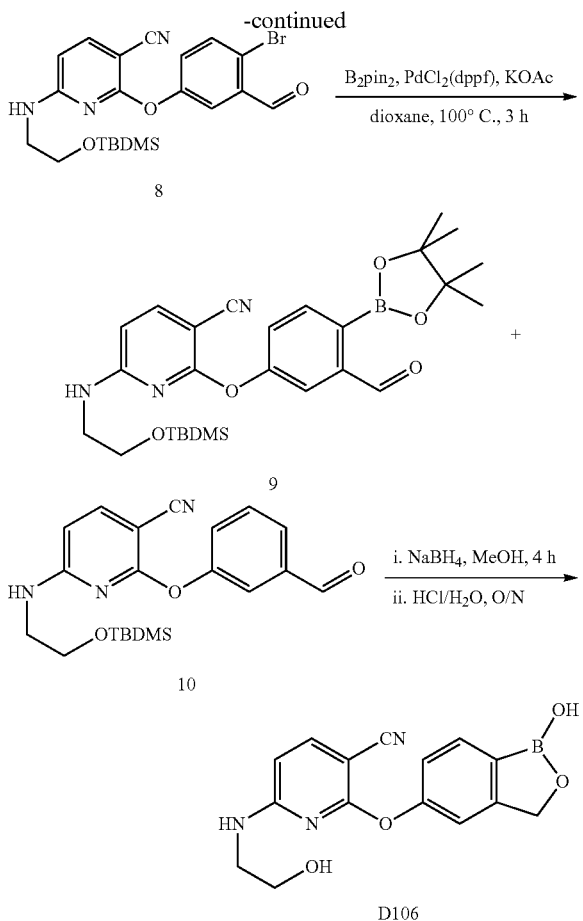

4-Bromo-3-[1,3]dioxolan-2-yl-phenol (2)

To a solution of 2-bromo-5-hydroxy-benzaldehyde (1) (10 g, 49.8 mmol) in toluene (200 mL) were added ethylene glycol (9.25 g, 149.3 mmol) and catalytic amount of p-TsOH (200 mg). After attaching a Dean-Stark trap, the reaction was heated in a 136° C. oil batch for 3 hours. After the solution was cooled to room temperature, it was washed with saturated NaHCO$_3$ (200 mL). The organic layer was dried over Na$_2$SO$_4$, filtered and concentrated in vacuo to provide the 11.6 g (95% yield) of the title compound. $^1$H NMR (400 MHz, CHLOROFORM-d) δ ppm 7.40 (d, J=8.6 Hz, 1H), 7.09 (d, J=3.1 Hz, 1H), 6.72 (dd, J=8.6, 3.1 Hz, 1H), 6.04 (s, 1H), 4.18-4.04 (m, 4H).

6-(4-Bromo-3-[1,3]dioxolan-2-yl-phenoxy)-2-chloro-nicotinonitrile+2-(4-bromo-3-[1,3]dioxolan-2-yl-phenoxy)-6-chloro-nicotinonitrile (4+5)

To a solution of 2,6-dichloro-nicotinonitrile (3) (7.06 g, 40.8 mmol) in acetonitrile (anhydrous, 300 mL) were added 4-bromo-3-[1,3]dioxolan-2-yl-phenol (2) (10 g, 40.8 mmol) and K$_2$CO$_3$ (5.63 g, 40.8 mmol). The reaction was heated at 65° C. for 3 hours. The solution was filtered and concentrated in vacuo to afford 15.6 g of the product mixture. $^1$H NMR (400 MHz, CHLOROFORM-d) δ ppm 7.94 (d, J=9.0 Hz, 2H), 7.62 (d, J=8.6 Hz, 2H), 7.46 (d, J=3.1 Hz, 1H), 7.41 (d, J=3.1 Hz, 1H), 7.18-7.08 (m, 2H), 7.05 (dd, J=8.8, 2.9 Hz, 1H), 6.93 (d, J=8.2 Hz, 1H), 6.11 (s, 1H), 6.09 (s, 1H), 4.19-3.99 (m, 8H).

2-(4-Bromo-3-[1,3]dioxolan-2-yl-phenoxy)-6-(2-hydroxy-ethylamino)-nicotinonitrile (6)

To a solution of 6-(4-bromo-3-[1,3]dioxolan-2-yl-phenoxy)-2-chloro-nicotinonitrile and 2-(4-bromo-3-[1,3]dioxolan-2-yl-phenoxy)-6-chloro-nicotinonitrile, (4+5, 2.5 g, 6.6 mmol) in acetonitrile (anhydrous, 50 mL) was added 2-amino-ethanol (2) (3.96 g, 66 mmol). The reaction was heated at 80° C. for 2 hours. After the reaction cooled to room temperature, all volatile components were removed in vacuo. Purification was accomplished by silica gel chromatography, eluting with 25%-100% EtOAc/Hexane gradient, to give 1.1 g of title compound in 41% yield.
$^1$H NMR (400 MHz, CHLOROFORM-d) δ ppm 7.57 (d, J=8.6 Hz, 2H), 7.45 (d, J=2.7 Hz, 1H), 7.06 (dd, J=8.8, 2.9 Hz, 1H), 6.09 (d, J=8.6 Hz, 1H), 6.08 (s, 1H), 5.34 (br. s., 1H), 4.04-4.18 (m, 4H), 3.60 (t, J=5.3 Hz, 2H), 3.28 (q, J=5.4 Hz, 2H).

2-(4-Bromo-3-formyl-phenoxy)-6-[(2-hydroxy-ethyl)-methyl-amino]-nicotinonitrile (7)

To a solution of 6 (2-(4-bromo-3-[1,3]dioxolan-2-yl-phenoxy)-6-(2-hydroxy-ethylamino)-nicotinonitrile, 1.1 g, 2.7 mmol) in THF (200 mL) was added a HCl solution (1 M, 100 mL). The reaction was stirred at room temperature overnight. The THF was evaporated in vacuo. The white solid that formed was filtered and air-dried to afford 0.94 g (55% yield for two steps) of the title compound.
$^1$H NMR (400 MHz, DMSO-d$_6$) δ ppm 10.19 (s, 1H), 7.88 (br. s, 1H), 7.85 (d, J=8.6 Hz, 1H), 7.72 (br. s., 1H), 7.65 (d, J=2.3 Hz, 1H), 7.52 (dd, J=8.8, 2.3 Hz, 1H), 6.34 (d, J=8.6 Hz, 1H), 4.61 (br. s., 1H), 3.40 (br. s, 2H), 3.05 (br. s, 2H)

2-(4-Bromo-3-formyl-phenoxy)-6-[2-(tert-butyl-dimethyl-silanyloxy)-ethylamino]-nicotinonitrile: (8)

To a solution of 2-(4-bromo-3-formyl-phenoxy)-6-[(2-hydroxy-ethyl)-methyl-amino]-nicotinonitrile (7, 0.94 g, 2.59 mmol) in THF (anhydrous, 100 mL) were added tert-butyl chloro-dimethyl silane (0.86 g, 5.7 mmol), Et$_3$N (0.8 mL, 5.7 mmol) and cat. amount of DMAP. The solution was stirred at room temperature overnight. The solution was filtered and concentrated in vacuo. Purification was accomplished by silica gel chromatography, eluting with 5%-50% EtOAc/hexanes gradient, to afford 1.1 g (89% yield) of the title compound.
$^1$H NMR (400 MHz, CHLOROFORM-d) δ ppm 10.34 (s, 1H), 7.79 (d, J=2.7 Hz, 1H), 7.66 (d, J=8.6 Hz, 1H), 7.60 (d, J=8.6 Hz, 1H), 7.30 (dd, J=8.6, 2.7 Hz, 1H), 6.14 (d, J=8.6 Hz, 1H), 5.23 (br. s., 1H), 3.64 (t, J=4.9 Hz, 2H), 3.25 (q, J=5.4 Hz, 2H), 0.86 (s, 9H), 0.02 (s, 6H).

6-[2-(tert-Butyl-dimethyl-silanyloxy)-ethylamino]-2-[3-formyl-4-(4,4,5,5-tetramethyl-[1,3,2]dioxaborolan-2-yl)-phenoxy]-nicotinonitrile: (9)

To a solution of 2-(4-bromo-3-formyl-phenoxy)-6-[2-(tert-butyl-dimethyl-silanyloxy)-ethylamino]-nicotinonitrile (8, 1.1 g, 2.3 mmol) in 1,4-dioxane (anhydrous, 150 mL) were added bispinacolatodiboron (0.71 g, 2.77 mmol), PdCl$_2$(dppf) (0.17 g, 0.23 mmol) and KOAc (0.68 g, 6.9 mmol). The solution was stirred at r.t. with N$_2$ bubbling for 30 minutes. Then the reaction was heated at 100° C. for 3 hours. The solution was filtered and concentrated in vacuo. Purification was accomplished by silica gel chromatography, eluting with 5%-25% EtOAc/hexanes gradient to afford the mixture of the title compound (9) and de-brominated compound, 6-[2-(tert-butyl-dimethyl-silanyloxy)-ethylamino]-2-(3-formyl-phenoxy)-nicotinonitrile (10). The material was used directly in the next step without further purification.

$^1$H NMR (400 MHz, CHLOROFORM-d) δ ppm 10.62 (s, 1H), 10.02 (s, 1H), 7.94 (d, J=8.20 Hz, 1H), 7.82 (d, J=1.95 Hz, 1H), 7.70-7.77 (m, 2H), 7.53-7.64 (m, 4H), 7.37-7.50 (m, 3H), 6.12-6.19 (m, 2H), 5.27-5.37 (m, 2H), 3.55-3.69 (m, 4H), 3.23 (m, 4H), 0.82-0.88 (m, 18H), 0.00 (d, 12H).

2-(1-Hydroxy-1,3-dihydro-benzo[c][1,2]oxaborol-5-yloxy)-6-(2-hydroxy-ethylamino)-nicotinonitrile: (D106)

To a clear solution of mixture of 9 and 10 (6-[2-(tert-butyl-dimethyl-silanyloxy)-ethylamino]-2-[3-formyl-4-(4,4,5,5-tetramethyl-[1,3,2]dioxaborolan-2-yl)-phenoxy]-nicotinonitrile and 6-[2-(tert-butyl-dimethyl-silanyloxy)-ethylamino]-2-(3-formyl-phenoxy)-nicotinonitrile) in MeOH (anhydrous, 200 mL) was slowly added NaBH$_4$ (0.26 g, 6.9 mmol). The reaction was stirred at room temperature for 4 hours, before the addition of HCl solution (1 M, 30 mL). After overnight at room temperature, the solution was slowly evaporated in vacuo. Purification was accomplished by reverse phase Biotage with 5%-100% MeOH/H$_2$O gradient to afford 120 mg (29% yield) of the title compound as a white solid.

$^1$H NMR (400 MHz, DMSO-d$_6$) δ ppm 9.23 (s, 1H), 7.86-7.80 (m, 1H), 7.75 (d, J=8.2 Hz, 1H), 7.70 (br. s., 1H), 7.22 (s, 1H), 7.14 (dd, J=8.0, 2.1 Hz, 1H), 6.31 (d, J=8.6 Hz, 1H), 4.98 (s, 2H), 4.64 (br. s, 1H), 3.43 (br. s, 2H), 3.07 (br. s, 2H); ES MS: m/z 312 (M+H)$^+$; HPLC: 97.41% (220 nm), 97.24 (Max-Plot).

19dj 2-Ethoxy-6-(1-hydroxy-1,3-dihydro-benzo[c][1,2]oxaborol-5-yloxy)-nicotinonitrile (D107)

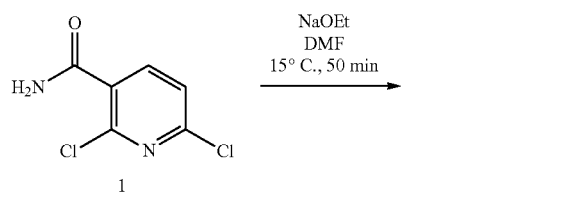

1

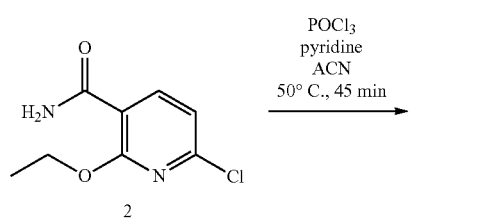

2

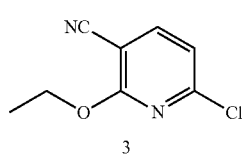

3

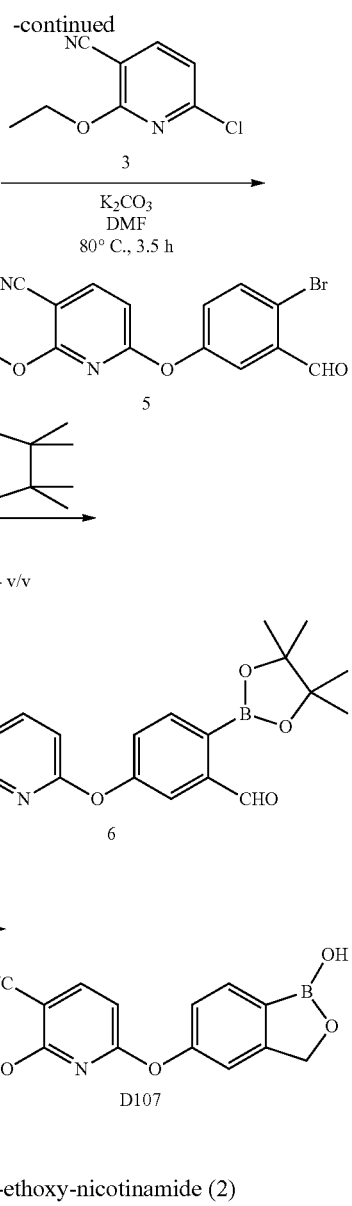

6-Chloro-2-ethoxy-nicotinamide (2)

Refer to synthesis of D46 for preparation of 2,6-dichloro-nicotinamide (1). Freshly prepared sodium ethoxide solution in ethanol (12.1 mL of 2.17 M, 26.2 mmol) was slowly added over 10 min to a solution of 1 (5.01 g, 26.2 mmol) in dimethylformamide (30 mL) at 15° C. [Note: a water bath was used to maintain reaction temperature around 14-16° C.; sodium ethoxide was prepared from reaction of Na solid (1.50 g, 65.2 mmol) with anhydrous EtOH (30.0 mL)]. Upon completion of sodium ethoxide addition, the reaction was stirred for 40 min at 14-16° C. [Note: An aliquot (0.3 mL) of reaction was concentrated. A $^1$H NMR of aliquot recorded in d$_6$-DMSO showed ~98% conversion to desired 2]. The reaction was poured into water (500 mL) and extracted with EtOAc (3×400 mL). All organics were combined, dried over Na$_2$SO$_4$, filtered and concentrated to give the title compound as a light gray solid (5.20 g, 95% purity as established by $^1$H NMR). The title compound was carried forward without further purification.

$^1$H NMR 400 MHz (d$_6$-DMSO) δ8.16 (d, J=8.2 Hz, 1H), 7.76 (br s, 1H), 7.57 (br s, 1H), 7.17 (d, J=7.8 Hz, 1H), 4.41 (q, J=7.0 Hz, 2H), 1.35 (t, J=7.0 Hz, 3H).

6-Chloro-2-ethoxy-nicotinonitrile (3)

Experimental procedure for synthesis of 6-chloro-2-ethoxy-nicotinonitrile (3) is the same as that described in synthesis of D46. The reaction of 6-chloro-2-morpholin-4-yl-nicotinamide (2) (5.20 g, 25.9 mmol) with phosphorus oxychloride (7.2 mL, 78 mmol) and pyridine (12.6 mL, 156 mmol) in acetonitrile (120 mL) gave a crude black oil upon workup. The black oil was fractionated by dry-pack column chromatography as follows: the oil was diluted with $CH_2Cl_2$ (300 mL) followed by the addition of silica gel (40 g, 230-400 mesh) and concentrated to dryness. This was loaded onto a silica column (120 g, 230-400 mesh) and eluted with 5% EtOAc/hexanes. Pure fractions were combined and concentrated to give the title compound as a white solid (4.20 g, 87% isolated). TLC eluted with 25% EtOAc/hexanes and rendered with UV lamp gave $R_f$=0.8; $^1$H NMR 400 MHz (CDCl$_3$) δ 7.80 (d, J=7.8 Hz, 1H), 6.99 (d, J=8.2 Hz, 1H), 4.51 (q, J=7.0 Hz, 2H), 1.45 (t, J=7.0 Hz, 3H).

6-(4'-Bromo-3'-formyl-phenoxy)-2-ethoxy-nicotinonitrile (5)

Experimental procedure for synthesis of 6-(4'-bromo-3'-formyl-phenoxy)-2-ethoxy-nicotinonitrile (5) is the same as that described in synthesis of D46 except that the reaction was heated at 80° C. for 3.5 h. The reaction of 6-chloro-2-ethoxy-nicotinonitrile (3) (3.52 g, 19.3 mmol), 2-bromo-5-hydroxy-benzaldehyde (4) (2.58 g, 12.9 mmol) and $K_2CO_3$ (3.55 g, 25.7 mmol) in DMF (40 mL) gave crude oil upon workup. The oil was fractionated by dry-pack column chromatography as follows: the oil was diluted with $CH_2Cl_2$ (500 mL) followed by the addition of silica gel (80 g, 230-400 mesh) and concentrated to dryness. This was loaded onto a silica column (120 g, 230-400 mesh) and eluted with gradient 10-30% EtOAc/hexanes. Pure fractions were combined and concentrated to give the title compound as a white solid (3.71 g, 61% isolated yield). TLC eluted twice with 25% EtOAc/hexanes and rendered with UV lamp gave $R_f$=0.5; $^1$H NMR 400 MHz (CDCl$_3$) δ 10.35 (s, 1H), 7.87 (d, J=8.6 Hz, 1H), 7.76 (d, J=3.1 Hz, 1H), 7.70 (d, J=8.6 Hz, 1H), 7.29 (dd, J=8.6, 3.1 Hz), 6.57 (d, J=8.2 Hz, 1H), 4.17 (q, J=7.0 Hz, 2H), 1.29 (t, J=7.0 Hz, 3H).

2-Ethoxy-6-[3-formyl-4-(4,4,5,5-tetramethyl-[1,3,2]dioxaborolan-2-yl)-phenoxy]-nicotinonitrile (6)

Experimental procedure for synthesis of 2-ethoxy-6-[3-formyl-4-(4,4,5,5-tetramethyl-[1,3,2]dioxaborolan-2-yl)-phenoxy]-nicotinonitrile (6) is the same as that described in synthesis of D46. The reaction of 6 (3.62 g, 10.5 mmol), bis(pinacolato)diboron (7.97 g, 31.4 mmol) and potassium acetate (3.08 g, 31.4 mmol) in a solvent mixture of dimethyl formamide (20 mL) and 1,2-dimethoxyethane (80 mL) gave a brown oil upon workup. The oil was fractionated by dry-pack column chromatography as follows: the oil was diluted with $CH_2Cl_2$ (400 mL) followed by the addition of silica gel (80 g, 230-400 mesh) and concentrated to dryness. This was loaded onto a silica column (80 g, 230-400 mesh) and eluted with gradient 10-20% EtOAc/hexanes. The pure fractions were combined and concentrated to give the title compound as a white solid (2.71 g, 74% isolated yield). TLC eluted with 25% EtOAc/hexanes and rendered with UV lamp gave $R_f$=0.4; $^1$H NMR 400 MHz (CDCl$_3$) δ 10.64 (s, 1H), 7.97 (d, J=8.2 Hz, 1H), 7.86 (d, J=8.6 Hz, 1H), 7.79 (d, J=2.0 Hz, 1H), 7.38 (dd, J=8.2, 2.3 Hz, 1H), 6.54 (d, J=8.2 Hz, 1H), 4.17 (q, J=7.0 Hz, 2H), 1.41 (s, 12H), 1.28 (t, J=7.0 Hz, 3H).

2-Ethoxy-6-(1-hydroxy-1,3-dihydro-benzo[c][1,2]oxaborol-5-yloxy)-nicotinonitrile (D107)

Experimental procedure for synthesis of 6-(1-hydroxy-1,3-dihydro-benzo[c][1,2]oxaborol-5-yloxy)-2-morpholin-4-yl-nicotinonitrile (D107) is the same as that described in synthesis of (D46). The reaction of 2-ethoxy-6-[3-formyl-4-(4,4,5,5-tetramethyl-[1,3,2]dioxaborolan-2-yl)-phenoxy]-nicotinonitrile (6) (2.71 g, 7.81 mmol) with NaBH$_4$ (886 mg, 23.4 mmol) gave an orange oil containing D107 upon workup. The oil was fractionated by dry-pack column chromatography as follows: the oil was diluted with 30% MeOH/$CH_2Cl_2$ (400 mL) followed by the addition of silica gel (80 g, 230-400 mesh) and concentrated to dryness. This was loaded onto a silica column (160 g, 230-400 mesh) and eluted with 1:1:100 acetic acid:MeOH:$CH_2Cl_2$. The fractions containing D107 were collected and concentrated to give a light yellow coloured oil. The oil was freeze dried by first diluting with methanol (30 mL) followed by the addition of deionised water (400 mL), the resultant white suspension was frozen in a dry-ice acetone bath and placed overnight on freeze-dryer. A white solid of D107 was obtained (1.82 g, with 30 mol % pinacoldiol present as established by H NMR). To increase purity of D107, it was resubjected to column chromatography and freeze-dried following the same conditions as before to give D107 (402 mg, 17% isolated yield) as a white solid. $^1$H NMR 400 MHz (d$_6$-DMSO) δ9.25 (s, 1H), 8.24 (d, J=8.2 Hz, 1H), 7.79 (d, J=7.8 Hz, 1H), 7.29 (d, J=2.0 Hz, 1H), 7.20 (dd, J=7.8, 2.0 Hz, 1H), 6.69 (d, J=8.2 Hz, 1H), 4.99 (s, 2H), 4.17 (q, J=7.0 Hz, 2H), 1.21 (t, J=7.0 Hz, 3H); Mass Spectrum [M+H$^+$]=297; HPLC purity 97.18% (Maxplot), 97.65% (220 nm).

19dk 2-hydroxy-6-(1-hydroxy-1,3-dihydrobenzo[c][1,2]oxaborol-5-yloxy)nicotinonitrile (D108)

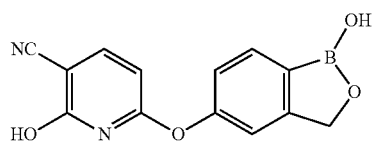

To a solution of 48% HBr (2 mL) and acetic acid (4 mL) was added 6-(1-hydroxy-1,3-dihydrobenzo[c][1,2]oxaborol-5-yloxy)-2-methoxynicotinonitrile (D46) (0.300 mg, 1.06 mmol). The reaction was stirred for 24 hours at 50° C. Water was added and the mixture was extracted with ethyl acetate. The organic layer was washed with water, brine, dried over anhydrous sodium sulfate, and then filtered. The solvent was removed under reduced pressure. The residue was purified by silica gel column (7:3 to 9:1 ethyl acetate/hexane). The material was further purified by reverse phase HPLC to give 2-hydroxy-6-(1-hydroxy-1,3-dihydrobenzo[c][1,2]oxaborol-5-yloxy)nicotinonitrile (0.027 g, 10% yield). ES(−)MS m/z=267 (M−H)$^-$; $^1$H NMR (300 MHz, DMSO-d$_6$) δ ppm 4.97 (s, 2H), 6.4 (br s, 1H), 7.15 (d, J=7.9 Hz, 1H), 7.25 (s, 1H), 7.77 (d, J=7.9 Hz, 1H), 8.09 (d, J=7.9 Hz, 1H), 9.24 (s, 1H), 12.7 (br s, 1H).

19dl 6-(1-Hydroxy-1,3-dihydro-benzo[c][1,2]oxaborol-5-yloxy)-4-methoxy-nicotinonitrile (D109)

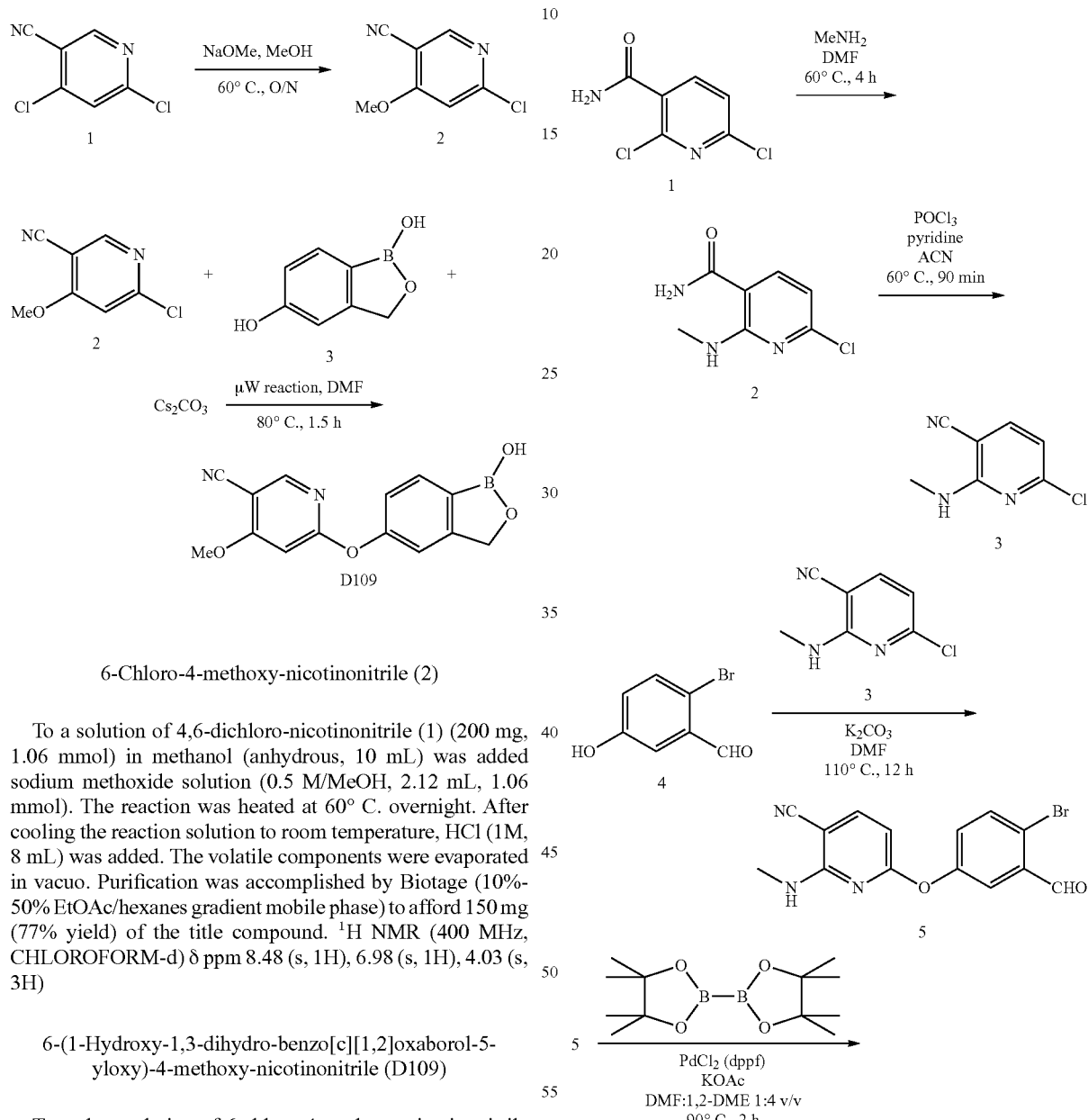

6-Chloro-4-methoxy-nicotinonitrile (2)

To a solution of 4,6-dichloro-nicotinonitrile (1) (200 mg, 1.06 mmol) in methanol (anhydrous, 10 mL) was added sodium methoxide solution (0.5 M/MeOH, 2.12 mL, 1.06 mmol). The reaction was heated at 60° C. overnight. After cooling the reaction solution to room temperature, HCl (1M, 8 mL) was added. The volatile components were evaporated in vacuo. Purification was accomplished by Biotage (10%-50% EtOAc/hexanes gradient mobile phase) to afford 150 mg (77% yield) of the title compound. $^1$H NMR (400 MHz, CHLOROFORM-d) δ ppm 8.48 (s, 1H), 6.98 (s, 1H), 4.03 (s, 3H)

6-(1-Hydroxy-1,3-dihydro-benzo[c][1,2]oxaborol-5-yloxy)-4-methoxy-nicotinonitrile (D109)

To a clear solution of 6-chloro-4-methoxy-nicotinonitrile (2) (200 mg, 1.2 mmol) in DMF (anhydrous, 15 mL) were added 3H-benzo[c][1,2]oxaborole-1,5-diol (3) (90 mg, 0.6 mmol) and Cs$_2$CO$_3$ (390 mg, 1.2 mmol). The reaction was heated at 80° C. for 1.5 hours by microwave. HCl (1 M) was added till pH 2. All volatile components were removed in vacuo. Purification was accomplished by reverse phase Biotage with 5%-100% MeOH/H$_2$O gradient to afford the 100 mg (30% yield) of the title compound. $^1$H NMR (400 MHz, DMSO-d$_6$) δ ppm 9.32 (s, 1H), 8.40 (s, 1H), 7.75 (d, J=7.8 Hz, 1H), 7.19 (s, 1H), 7.12-7.08 (m, 1H), 6.93 (s, 1H), 4.96 (s, 2H), 3.99 (s, 3H); ES-MS m/z=283 (M+H)$^+$; HPLC: 95.75% (220 nm), 95.81% (MaxPlot).

19dm 6-(1-Hydroxy-1,3-dihydro-benzo[c][1,2]oxaborol-5-yloxy)-2-methylamino-nicotinonitrile (D110)

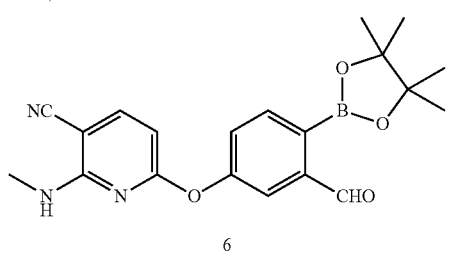

-continued

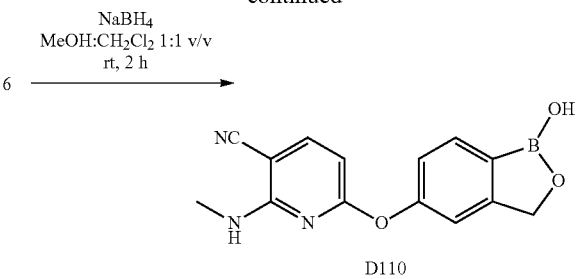

D110

6-Chloro-2-methylamino-nicotinamide (2)

Refer to synthesis of D46 for preparation of 2,6-dichloro-nicotinamide (1). A sealed reaction vessel containing 2,6-dichloro-nicotinamide (1) (6.23 g, 32.6 mmol) and methylamine (98 mL of 2M in THF, 196 mmol) in anhydrous dimethylformamide (60 mL) was heated to 60° C. for 4 h. The reaction was then cooled to room temperature and diluted with water (800 mL) and extracted with ethyl acetate (4×600 mL). All organics were combined, dried over $Na_2SO_4$, filtered and concentrated to give a light orange oil (7.10 g). The oil was diluted with $CH_2Cl_2$ (300 mL) followed by the addition of silica gel (50 g, 230-400 mesh) and concentrated to dryness. This was loaded onto a silica column (200 g, 230-400 mesh) and eluted with gradient 30-50% EtOAc/hexanes. Pure fractions were combined and concentrated to give the title compound as a white solid (4.73 g, 78% isolated yield). TLC eluted with 50% EtOAc/hexanes and rendered with UV lamp gave $R_f$=0.5; $^1$H NMR 400 MHz ($CDCl_3$) δ 7.47 (d, J=8.5 Hz, 1H), 7.90 (d, J=7.9 Hz, 1H), 1.48 (s, 3H).

6-Chloro-2-methylamino-nicotinonitrile (3)

Experimental procedure for synthesis of 6-chloro-2-methylamino-nicotinonitrile (3) is the same as that described in synthesis of D46. The reaction of 6-chloro-2-methylamino-nicotinamide (2) (4.70 g, 25.54 mmol) with phosphorus oxychloride (7.0 mL, 76.6 mmol) and pyridine (12.3 mL, 152 mmol) in acetonitrile (60 mL) at 60° C. for 90 min gave crude black oil. The black oil was fractionated by dry-pack column chromatography as follows: the oil was diluted with $CH_2Cl_2$ (300 mL) followed by the addition of silica gel (50 g, 230-400 mesh) and concentrated to dryness. This was loaded onto a silica column (100 g, 230-400 mesh) and eluted with 20% EtOAc/hexanes. Pure fractions were combined and concentrated to give the titled compound as a white solid (2.91 g, 69% isolated yield). TLC eluted with 10% EtOAc/hexanes and rendered with UV lamp gave $R_f$=0.4; $^1$H NMR 400 MHz ($d_6$-DMSO) δ7.91 (d, J=7.8 Hz, 1H), 7.52 (br q, J=4.7 Hz, 1H), 6.67 (d, J=7.8 Hz, 1H), 2.80 (d, J=4.7 Hz, 3H).

6-(4'-Bromo-3'-formyl-phenoxy)-2-methylamino-nicotinonitrile (5)

Experimental procedure for synthesis of 6-(4'-bromo-3'-formyl-phenoxy)-2-methylamino-nicotinonitrile (5) is the same as that described in synthesis of (D46) except that the reaction was heated at 110° C. for 12 h. The reaction of 6-Chloro-2-methylamino-nicotinonitrile (3) (1.90 g, 11.3 mmol), 2-Bromo-5-hydroxy-benzaldehyde (4) (1.52 g, 7.56 mmol) and $K_2CO_3$ (2.09 g, 15.1 mmol) in DMF (45 mL) gave crude oil upon workup. The oil was fractionated by dry-pack column chromatography as follows: the oil was diluted with $CH_2Cl_2$ (400 mL) followed by the addition of silica gel (50 g, 230-400 mesh) and concentrated to dryness. This was loaded onto a silica column (200 g, 230-400 mesh) and eluted with gradient 10-30% EtOAc/hexanes. Pure fractions were combined and concentrated to give the title compound as a white solid (1.42 g, 57% isolated yield). TLC eluted with 10% EtOAc/hexanes and rendered with UV lamp gave $R_f$=0.2; $^1$H NMR 400 MHz ($CDCl_3$) δ 10.35 (s, 1H), 7.80 (d, J=2.7 Hz, 1H), 7.67 (d, J=8.6 Hz, 1H), 7.64 (d, J=8.2 Hz, 1H), 7.30 (dd, J=8.6, 3.1 Hz, 1H), 6.20 (d, J=8.2 Hz, 1H), 5.20 (br s, 1H), 2.80 (d, J=4.7 Hz, 1H).

6-[3-Formyl-4-(4,4,5,5-tetramethyl-[1,3,2]dioxaborolan-2-yl)-phenoxy]-2-methylamino-nicotinonitrile (6)

Experimental procedure for synthesis of 6-[3-formyl-4-(4,4,5,5-tetramethyl-[1,3,2]dioxaborolan-2-yl)-phenoxy]-2-methylamino-nicotinonitrile (6) is the same as that described in synthesis of D46. The reaction of 6 (1.40 g, 4.21 mmol), bis(pinacolato)diboron (3.21 g, 12.6 mmol) and potassium acetate (1.24 g, 12.6 mmol) in a solvent mixture of dimethylformamide (15 mL) and 1,2-dimethoxyethane (45 mL) gave a black oil upon workup. The black oil was fractionated by dry-pack column chromatography as follows: the oil was diluted with $CH_2Cl_2$ (400 mL) followed by the addition of silica gel (50 g, 230-400 mesh) and concentrated to dryness. This was loaded onto a silica column (100 g, 230-400 mesh) and eluted with gradient 10-40% EtOAc/hexanes. Pure fractions were combined and concentrated to give the title compound as a light gray coloured solid (510 mg, 33% isolated yield). TLC with two elutions of 25% EtOAc/hexanes and rendered with UV lamp gave $R_f$=0.3; $^1$H NMR 400 MHz ($d_6$-DMSO) δ10.40 (s, 1H), 7.94 (d, J=8.2 Hz, 1H), 7.82 (d, J=8.2 Hz, 1H), 7.71 (d, J=2.3 Hz, 1H), 7.54 (dd, J=8.2, 2.3 Hz, 1H), 7.32 (br q, J=4.3 Hz, 1H), 6.26 (d, J=8.6 Hz, 1H), 2.58 (d, J=4.3 Hz, 3H), 1.35 (s, 12H).

6-(1-Hydroxy-1,3-dihydro-benzo[c][1,2]oxaborol-5-yloxy)-2-methylamino-nicotinonitrile (D110)

Experimental procedure for synthesis of 6-(1-hydroxy-1,3-dihydro-benzo[c][1,2]oxaborol-5-yloxy)-2-methylamino-nicotinonitrile (D110) is the same as that described in synthesis of (D46). The reaction of 6-[3-formyl-4-(4,4,5,5-tetramethyl-[1,3,2]dioxaborolan-2-yl)-phenoxy]-2-methylamino-nicotinonitrile (6) (490 mg, 1.35 mmol) with $NaBH_4$ (102 mg, 2.69 mmol) gave an orange oil containing D110 upon workup. The oil was fractionated by dry-pack column chromatography as follows: the oil was diluted with $CH_2Cl_2$ (300 mL) followed by the addition of silica gel (30 g, 230-400 mesh) and concentrated to dryness. This was loaded onto a silica column (150 g, 230-400 mesh) and eluted with 0.5:0.5:100 acetic acid:MeOH:$CH_2Cl_2$. The fractions containing D110 were collected and concentrated to give a light yellow coloured oil. The oil was freeze dried by first diluting with methanol (50 mL) followed by the addition of deionised water (300 mL), the resultant white suspension was frozen in a dry-ice acetone bath and placed overnight on freeze-dryer. A white solid of D110 was obtained (243 mg, 64% isolated yield). $^1$H NMR 400 MHz ($d_6$-DMSO) δ9.20 (s, 1H), 7.88 (d, J=8.2 Hz, 1H), 7.76 (d, J=8.2 Hz, 1H), 7.25 (br s, 1H), 7.24 (s, 1H), 7.15 (d, J=8.2 Hz, 1H), 6.13 (d, J=8.2 Hz, 1H), 4.98 (s, 2H), 2.61 (d, J=4.3 Hz, 3H); Mass Spectrum [M+H]⁺=282; HPLC purity 94.93% (Maxplot), 93.43% (220 nm).

19dn 6-(1-Hydroxy-1,3-dihydro-benzo[c][1,2]ox-aborol-5-yloxy)-2-(2-methoxy-ethylamino)-nicotinonitrile (D111)

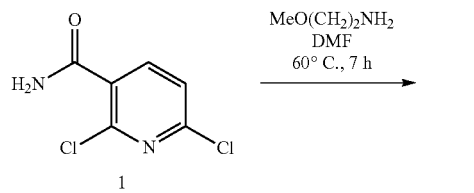

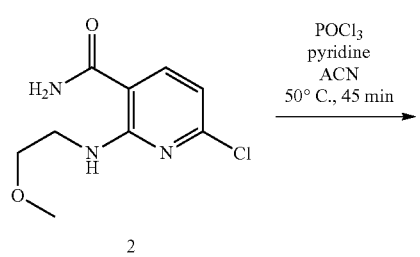

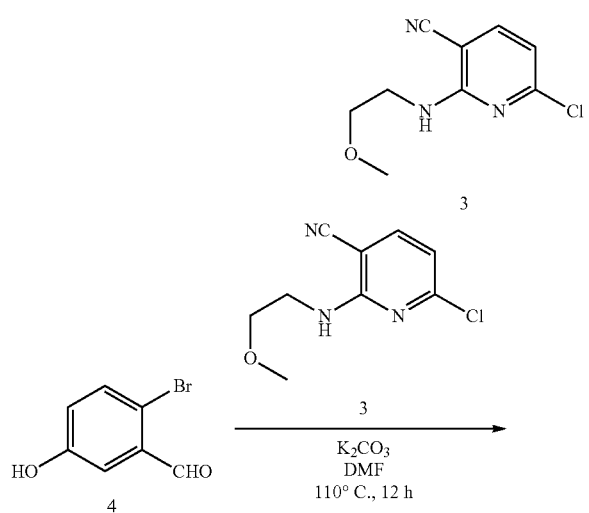

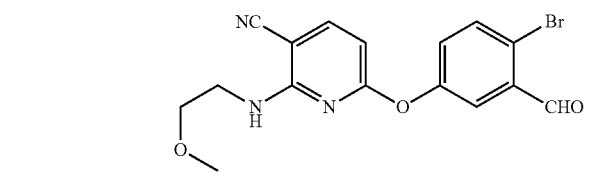

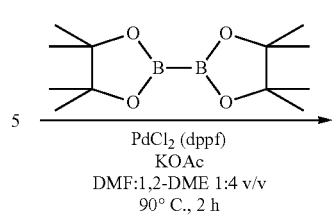

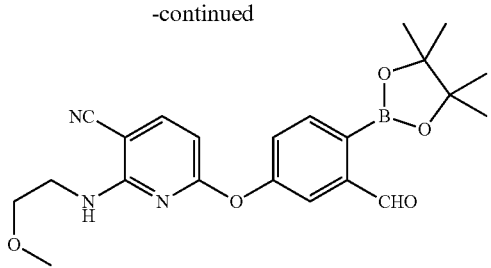

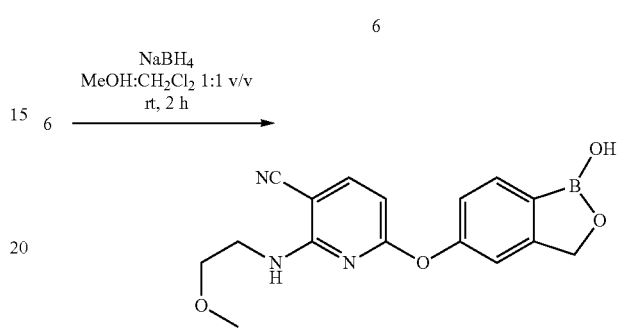

6-Chloro-2-(2-methoxy-ethylamino)-nicotinamide (2)

Refer to synthesis of D46 for preparation of 2,6-dichloro-nicotinamide (1). A sealed reaction vessel containing 2,6-dichloro-nicotinamide (1) (8.66 g, 45.3 mmol) and 2-methoxy-ethylamine (15.6 mL, 181 mmol) in anhydrous dimethylformamide (40 mL) was heated to 60° C. for 7 h. The reaction was then cooled to room temperature. Dimethylformamide was azeotropically removed by the addition and evaporation of toluene (6×700 mL) by rotary evaporation with water bath at 70° C. An orange oil was obtained (12.2 g). The oil was fractionated by dry-pack column chromatography as follows: the oil was diluted with $CH_2Cl_2$ (400 mL) followed by the addition of silica gel (100 g, 230-400 mesh) and concentrated to dryness. This was loaded onto a silica column (200 g, 230-400 mesh) and eluted with 50% EtOAc/hexanes. Pure fractions were combined and concentrated to give the title compound as a white solid (5.37 g, 64% isolated yield). $^1$H NMR 400 MHz ($d_6$-DMSO) δ7.79 (d, J=7.8 Hz, 1H), 7.30 (s, 1H), 6.76 (d, J=7.8 Hz, 1H), 6.52 (s, 1H), 4.04 (br t, J=4.7 Hz, 1H), 3.80 (td, J=5.5, 4.7 Hz, 2H), 3.63 (t, J=5.5 Hz, 2H), 2.94 (s, 3H).

6-Chloro-2-(2-methoxy-ethylamino)-nicotinonitrile (3)

Experimental procedure for synthesis of 6-chloro-2-(2-methoxy-ethylamino)-nicotinonitrile (3) is the same as that described in synthesis of (D46). The reaction of 6-chloro-2-(2-methoxy-ethylamino)-nicotinamide (2) (6.85 g, 36.9 mmol) with phosphorus oxychloride (10.1 mL, 111 mmol) and pyridine (17.9 mL, 221 mmol) in acetonitrile (90 mL) gave a black oil containing the title compound (6.97 g. 98% conversion) upon workup. The title compound was carried forward without further purification. $^1$H NMR 400 MHz ($d_6$-DMSO) δ7.94 (d, J=7.8 Hz, 1H), 7.50 (br s, 1H), 6.71 (d, J=8.2 Hz, 1H), 3.54-3.43 (m, 4H), 3.26 (s, 3H).

6-(4'-Bromo-3'-formyl-phenoxy)-2-(2-methoxy-ethylamino)-nicotinonitrile (5)

Experimental procedure for synthesis of 6-(4'-bromo-3'-formyl-phenoxy)-2-(2-methoxy-ethylamino)-nicotinonitrile (5) is the same as that described in synthesis of D46 except that the reaction was heated at 110° C. for 12 h. The reaction of 6-chloro-2-(2-methoxy-ethylamino)-nicotinonitrile (3) (5.13 g, 24.2 mmol), 2-bromo-5-hydroxy-benzaldehyde (4) (3.25 g, 16.2 mmol) and K$_2$CO$_3$ (4.47 g, 32.3 mmol) in DMF (45 mL) gave crude oil of 5 upon workup. The oil was fractionated by dry-pack column chromatography as follows: the oil was diluted with 10% MeOH/CH$_2$Cl$_2$ (300 mL) followed by the addition of silica gel (70 g, 230-400 mesh) and concentrated to dryness. This was loaded onto a silica column (140 g, 230-400 mesh) and eluted with gradient 10-40% EtOAc/hexanes. Pure fractions were combined and concentrated to give the title compound as a white solid (4.71 g, 52% isolated yield). TLC eluted with 25% EtOAc/hexanes and rendered with UV lamp gave R$_f$=0.3; $^1$H NMR 400 MHz (CDCl$_3$) δ 10.29 (s, 1H), 7.70 (d, J=3.0 Hz, 1H), 7.63 (d, J=8.6 Hz, 1H), 7.61 (d, J=8.2 Hz, 1H), 7.23 (dd, J=8.6, 3.0 Hz, 1H), 6.17 (d, J=8.2 Hz, 1H), 5.57 (br s, 1H), 3.37-3.27 (4H), 3.26 (s, 3H).

6-[3-Formyl-4-(4,4,5,5-tetramethyl-[1,3,2]diox-aborolan-2-yl)-phenoxy]-2-(2-methoxy-ethylamino)-nicotinonitrile (6)

Experimental procedure for synthesis of 6-[3-formyl-4-(4, 4,5,5-tetramethyl-[1,3,2]dioxaborolan-2-yl)-phenoxy]-2-(2-methoxy-ethylamino)-nicotinonitrile (6) is the same as that described in synthesis of (D46). The reaction of 5 (4.70 g, 12.5 mmol), bis(pinacolato)diboron (6.35 g, 25.0 mmol) and potassium acetate (2.45 g, 25.0 mmol) in 1,2-dimethoxy-ethane (120 mL) gave a brown oil. The brown oil was fractionated by dry-pack column chromatography as follows: the oil was diluted with CH$_2$Cl$_2$ (400 mL) followed by the addition of silica gel (70 g, 230-400 mesh) and concentrated to dryness. This was loaded onto a silica column (140 g, 230-400 mesh) and eluted with gradient 10-20% EtOAc/hexanes. The pure fractions were combined and concentrated to give the title compound as a light yellow solid (4.24 g, 80% isolated yield). $^1$H NMR 400 MHz (d$_6$-DMSO) δ 10.38 (s, 1H), 7.93 (d, J=8.2 Hz, 1H), 7.80 (d, J=8.2 Hz, 1H), 7.66 (d, J=2.3 Hz, 1H), 7.50 (dd, J=8.2, 2.3 Hz, 1H), 7.29 (br s, 1H), 6.29 (d, J=8.2 Hz, 1H), 3.32 (s, 3H), 3.17-3.13 (4H), 1.33 (s, 12H).

6-(1-Hydroxy-1,3-dihydro-benzo[c][1,2]oxaborol-5-yloxy)-2-(2-methoxy-ethylamino)-nicotinonitrile (D111)

Experimental procedure for synthesis of 6-(1-hydroxy-1, 3-dihydro-benzo[c][1,2]oxaborol-5-yloxy)-2-(2-methoxy-ethylamino)-nicotinonitrile (D111) is the same as that described in synthesis of (D46). The reaction of 6-[3-formyl-4-(4,4,5,5-tetramethyl-[1,3,2]dioxaborolan-2-yl)-phenoxy]-2-(2-methoxy-ethylamino)-nicotinonitrile (6) (4.20 g, 9.92 mmol) with NaBH$_4$ (750 mg, 19.8 mmol) gave an orange oil containing D111 upon workup. The oil was fractionated by dry-pack column chromatography as follows: the oil was diluted with 10% MeOH/CH$_2$Cl$_2$ (400 mL) followed by the addition of silica gel (70 g, 230-400 mesh) and concentrated to dryness. This was loaded onto a silica column (210 g, 230-400 mesh) and eluted with 1:1:100 acetic acid:MeOH:CH$_2$Cl$_2$. The fractions containing D111 were collected and concentrated to give a light yellow coloured oil. The oil was freeze dried by first diluting with acetonitrile (40 mL) followed by the addition of deionised water (400 mL), the resultant white suspension was frozen in a dry-ice acetone bath and placed overnight on freeze-dryer. A white solid of D111 was obtained (1.70 g with 30 mol % pinacoldiol as determined by $^1$H NMR). To increase purity of D111, it was re-subjected to column chromatography and freeze-dried following the same conditions as before to give D111 as a white solid (972 mg, 30% isolated yield). $^1$H NMR 400 MHz (d$_6$-DMSO) δ9.21 (s, 1H), 7.90 (d, J=8.2 Hz, 1H), 7.76 (d, J=7.8 Hz, 1H), 7.25 (br t, J=4.7 Hz, 1H), 7.24 (d, J=1.5 Hz, 1H), 7.14 (dd, J=7.8, 1.5 Hz, 1H), 6.22 (d, J=8.6 Hz, 1H), 4.97 (s, 2H), 3.33 (s, 3H), 3.25-3.15 (m, 4H); Mass Spectrum [M+H]$^+$=324; HPLC purity 97.36% (Maxplot), 97.21% (220 nm), 96.44% (254 nm).

19do 6-(1-Hydroxy-1,3-dihydro-benzo[c][1,2]ox-aborol-5-yloxy)-2-methoxy-nicotinamide (D112)

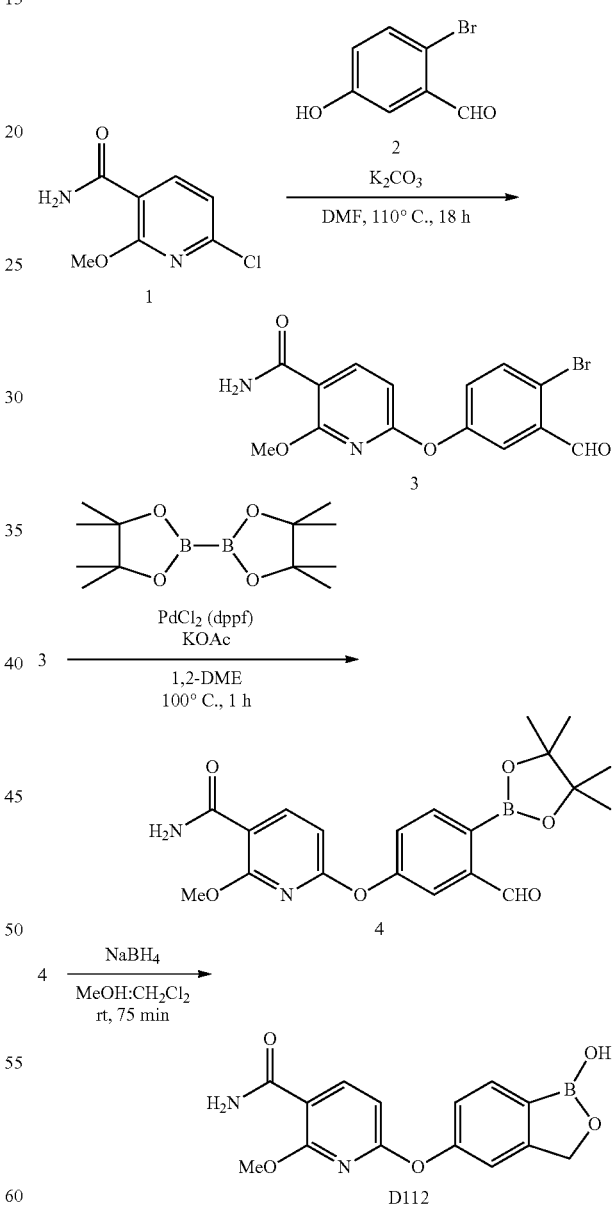

6-(4-Bromo-3-formyl-phenoxy)-2-methoxy-nicotinamide (3)

A mixture of 6-chloro-2-methoxy-nicotinamide (7.15 g, 38.3 mmol), 2-bromo-5-hydroxy-benzaldehyde (11.5 g, 57.5 mmol) and K₂CO₃ (15.9 g, 115 mmol) in dimethylformamide (60 mL) was heated to 110° C. for 18 hours. The reaction mixture was cooled to room temperature, diluted with H₂O (800 mL) and extracted with ethyl acetate (6×400 mL). The organic extracts were combined, dried over Na₂SO₄, filtered and concentrated. The residue was purified by silica gel flash column chromatography (50-80% ethyl acetate/hexanes) to give the title compound as a light brown solid (5.19 g, 39% yield).

¹H NMR 400 MHz (d₆-DMSO) δ 10.18 (s, 1H), 8.28 (d, J=8.2 Hz, 1H), 7.85 (d, J=8.6 Hz, 1H), 7.68 (d, J=2.7 Hz, 1H), 7.59 (br s, 1H), 7.53 (dd, J=8.6, 2.7 Hz, 1H), 7.53 (br s, 1H), 6.72 (d, J=8.2 Hz, 1H), 3.71 (s, 3H).

6-[3-Formyl-4-(4,4,5,5-tetramethyl-[1,3,2]diox-aborolan-2-yl)-phenoxy]-2-methoxy-nicotinamide (4)

A suspension of 6-(4-bromo-3-formyl-phenoxy)-2-methoxy-nicotinamide (4.05 g, 11.5 mmol) in 1,2-dimethoxyethane (240 mL) was heated to 100° C. for 20 minutes until all solid dissolved. Bispinacolatodiboron (5.86 g, 23.1 mmol) and KOAc (2.26 g, 23.1 mmol) were added and the reaction was stirred at 100° C. for an additional 10 minutes. PdCl₂(dppf) (0.84 g, 1.2 mmol) was added and the reaction mixture was stirred at 100° C. for 70 minutes. This was purified by silica gel flash column chromatography (50-80% ethyl acetate/hexanes) to give the title compound as a white solid (3.21 g, 69% yield).

¹H NMR 400 MHz (d₆-DMSO) δ 10.39 (s, 1H), 8.28 (d, J=8.2 Hz, 1H), 7.82 (d, J=8.2 Hz, 1H), 7.71 (d, J 2.3 Hz, 1H), 7.60 (br s, 1H), 7.53 (dd, J=8.2, 2.3 Hz, 1H), 7.53 (br s, 1H), 6.71 (d, J=8.2 Hz, 1H), 3.72 (s, 3H), 1.33 (s, 12H).

6-(1-Hydroxy-1,3-dihydro-benzo[c][1,2]oxaborol-5-yloxy)-2-methoxy-nicotinamide (D112)

A solution of NaBH₄ (0.077 g, 2.0 mmol) in anhydrous methanol (10 mL) was added to a solution of 6-[3-formyl-4-(4,4,5,5-tetramethyl-[1,3,2]dioxaborolan-2-yl)-phenoxy]-2-methoxy-nicotinamide (2.51 g, 6.30 mmol) in CH₂Cl₂ (40 mL) and stirred at room temperature for 5 minutes. Solid NaBH₄ (0.400 g, 10.6 mmol) was then added portionwise over 45 minutes at room temperature. The reaction was stirred for an additional 30 minutes then quenched by the addition of 50% aqueous acetic acid (1 mL). After stirring for an additional 30 minutes at room temperature, the solution was concentrated in vacuo. The residue was purified by silica gel flash column chromatography (AcOH/MeOH/CH₂Cl₂ 1:3:100 v/v/v) to give the title compound as a white fluffy solid (0.220 g, 12% yield).

¹H NMR 400 MHz (d₆-DMSO) δ9.20 (s, 1H), 8.25 (d, J=8.2 Hz, 1H), 7.76 (d, J=7.8 Hz, 1H), 7.58 (br s, 1H), 7.53 (br s, 1H), 7.25 (br s, 1H), 7.16 (br d, J=7.8 Hz, 1H), 6.58 (d, J=8.2 Hz, 1H), 4.97 (s, 2H), 3.75 (s, 3H).

Mass Spectrum [M+H⁺]=301.

HPLC purity 94.05% (Maxplot), 94.02% (220 nm), 92.23% (254 nm).

19dp 2-(2-Benzyloxy-ethylamino)-6-(1-hydroxy-1,3-dihydro-benzo[c][1,2]oxaborol-5-yloxy)-nicotinonitrile (D113)

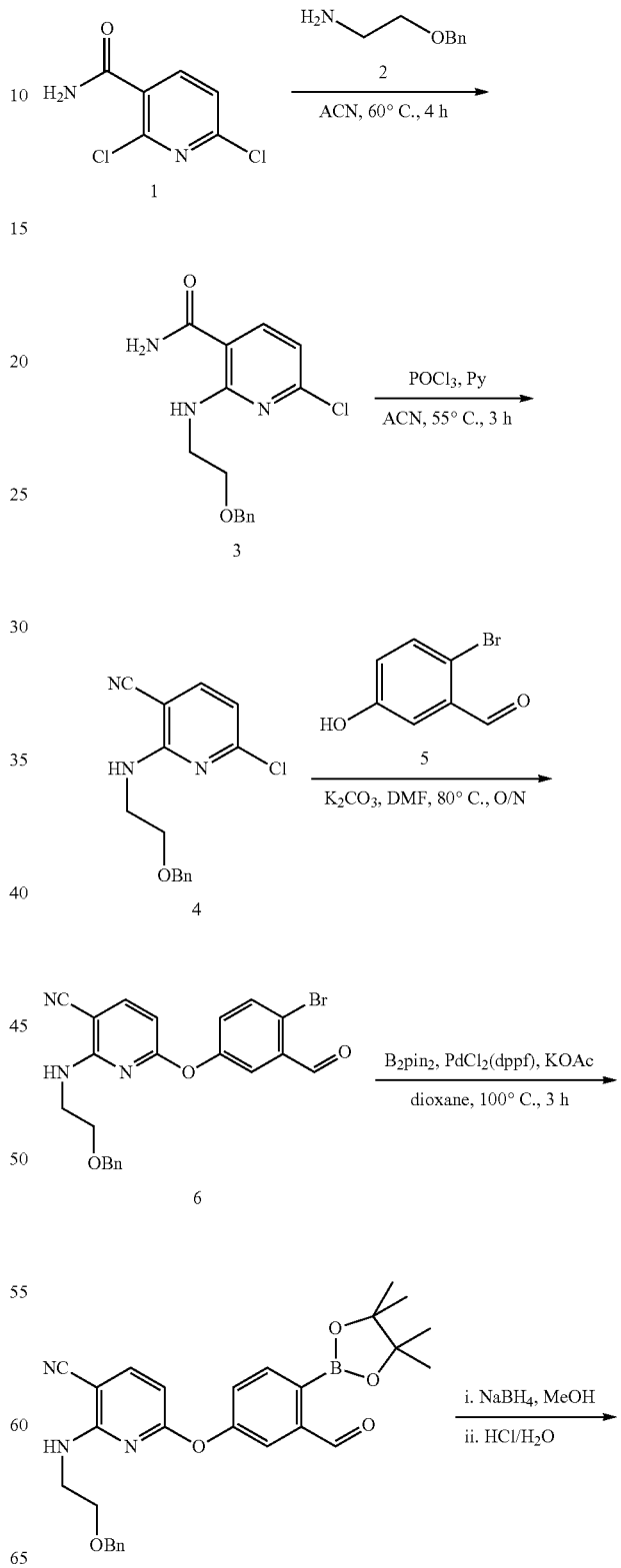

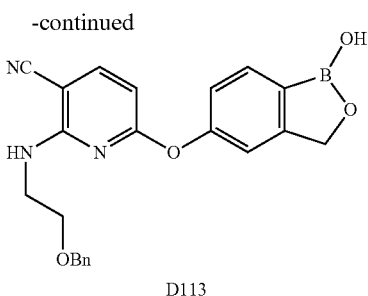

D113

2-(2-Benzyloxy-ethylamino)-6-chloro-nicotinamide (3)

To a solution of 2,6-dichloro-nicotinamide (1) (12.6 g, 66.1 mmol) in acetonitrile (anhydrous, 200 mL) were added 2-benzyloxy-ethylamine (2) (10 g, 66.1 mmol) and triethylamine (11 mL, 79.3 mmol). The reaction was heated at 60° C. for 2 days. The solution was cooled to room temperature and the suspension was filtered. The filtrate was evaporated in vacuo. The residue was purified by Biotage with 25%-100% EtOAc/hexanes to afford 15.8 g (78.3% yield) of the title compound.

$^1$H NMR (400 MHz, CHLOROFORM-d) δ ppm 8.70 (br. s., 1H), 7.46 (d, J=8.2 Hz, 1H), 7.40-7.23 (m, 5H), 6.44 (d, J=8.2 Hz, 1H), 5.97 (br. s., 2H), 4.58 (s, 2H), 3.75-3.66 (m, 4H).

2-(2-Benzyloxy-ethylamino)-6-chloro-nicotinonitrile (4)

To a solution of 2-(2-benzyloxy-ethylamino)-6-chloro-nicotinamide (3, 15.8 g, 51.7 mmol) in acetonitrile (anhydrous, 200 mL) were added pyridine (33.4 mL, 413 mmol) and POCl$_3$ (18.9 mL, 207 mmol). The reaction was heated at 55° C. for 3 hours. After cooling to room temperature, NaOH solution (10% aq.) was slowly added till pH 9. EtOAc (200 mL) was added and layers separated. The aqueous layer was extracted with EtOAc (2×200 mL). The combined organic layer was dried over MgSO$_4$, filtered, and evaporated in vacuo. Purification was accomplished by silica gel chromatography, eluting with 2%-20% EtOAc/hexanes gradient, to afford 10 g (67% yield) of the title product.

$^1$H NMR (400 MHz, CHLOROFORM-d) δ ppm 7.56 (d, J=7.8 Hz, 1H), 7.41-7.27 (m, 5H), 6.60 (d, J=7.8 Hz, 1H), 5.68 (br. s., 1H), 4.57 (s, 2H), 3.76-3.63 (m, 4H).

2-(2-Benzyloxy-ethylamino)-6-(4-bromo-3-formyl-phenoxy)-nicotinonitrile (6)

To a solution of 2-(2-benzyloxy-ethylamino)-6-chloro-nicotinonitrile (4, 10 g, 34.7 mmol) in DMF (anhydrous, 300 mL) were added 2-bromo-5-hydroxy-benzaldehyde (7 g, 34.7 mmol) and K$_2$CO$_3$ (9.6 g, 69.4 mmol). The reaction was heated at 80° C. for 16 hours. DMF was evaporated in vacuo. Purification was accomplished by silica gel chromatography, eluting with 2.5%-20% EtOAc/hexanes gradient, to afford 10 g (64% yield) of the title compound.

$^1$H NMR (400 MHz, CHLOROFORM-d) δ ppm 10.34 (s, 1H), 7.75-7.60 (m, 3H), 7.39-7.20 (m, 6H), 6.20 (d, J=6.6 Hz, 1H), 5.59 (br s, 1H), 4.43 (s, 2H), 3.50-3.36 (m, 4H).

2-(2-Benzyloxy-ethylamino)-6-[3-formyl-4-(4,4,5,5-tetramethyl-[1,3,2]dioxaborolan-2-yl)-phenoxy]-nicotinonitrile (7)

To a solution of 2-(2-benzyloxy-ethylamino)-6-(4-bromo-3-formyl-phenoxy)-nicotinonitrile (6, 10 g, 22.1 mmol) in 1,4-dioxane (anhydrous, 360 mL) were added bispinacolato-diboron (6.74 g, 26.5 mmol), PdCl$_2$(dppf) (1.62 g, 2.21 mmol) and KOAc (6.5 g, 66.3 mmol). The solution was stirred at r.t. with N$_2$ bubbling for 30 minutes. Then the reaction was heated at 100° C. for 3 hours. After the reaction, the solution was filtered and concentrated in vacuo. Purification was accomplished by silica gel chromatography, eluting with 2.5%-20% EtOAc/hexanes gradient, to afford 9 g (82% yield) of the title compound.

$^1$H NMR (400 MHz, CHLOROFORM-d) δ ppm 10.63 (s, 1H), 7.93 (d, J=8.2 Hz, 1H), 7.77 (s, 1H), 7.66-7.62 (m, 1H), 7.38-7.25 (m, 6H), 6.18 (d, J=8.2 Hz, 1H), 5.56 (br s, 1H), 4.48 (s, 2H), 3.47 (t, J=5.3 Hz, 2H), 3.39 (q, J=5.4 Hz, 2H), 1.39 (s, 12H).

2-(2-Benzyloxy-ethylamino)-6-(1-hydroxy-1,3-dihydro-benzo[c][1,2]oxaborol-5-yloxy)-nicotinonitrile (D113)

To a clear solution of 2-(2-benzyloxy-ethylamino)-6-[3-formyl-4-(4,4,5,5-tetramethyl-[1,3,2]dioxaborolan-2-yl)-phenoxy]-nicotinonitrile (7, 9 g, 18 mmol) in MeOH (anhydrous, 200 mL) was slowly added NaBH$_4$ (4.11 g, 108 mmol). The reaction was stirred at room temperature 4 hours, before the addition of HCl solution (1 M, 200 mL). The stirring was kept at room temperature overnight. Then the solution was slowly evaporated in vacuo. The solid formed was filtered, washed with water and air-dried to give 3.3 g (45.6% yield) of the title compound as a white solid.

$^1$H NMR (400 MHz, DMSO-d$_6$) δ ppm 7.91 (d, J=8.6 Hz, 2H), 7.76 (d, J=8.2 Hz, 2H), 7.35-7.18 (m, 5H), 7.15 (s, 1H), 7.08 (dd, J=8.2, 2.0 Hz, 1H), 6.23 (d, J=8.6 Hz, 1H), 4.94 (s, 2H), 4.29 (s, 2H), 3.34-3.21 (m, 4H); ES-MS: m/z 402 (M+H)$^+$; HPLC: 92.59% (220 nm), 93.22% (MaxPlot).

19dq 6-(4-Fluoro-1-hydroxy-1,3-dihydrobenzo[c][1,2]oxaborol-5-yloxy)-2-methoxynicotinonitrile (D114)

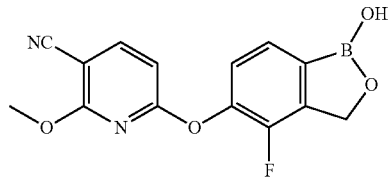 [SMILES: COc1nc(Oc2ccc3c(c2F)COB3O)ccc1C#N]

A solution of anhydrous tetrahydrofuran (50 mL) and diisopropylamine (11 mL) was cooled to 0° C. and had 1.6 M n-butyl lithium/hexanes (47 mL) added drop wise under nitrogen balloon. The mixture was stirred for 10 minutes at 0° C. and was then cooled to −78° C. with an acetone dry ice bath. A mixture of 4-bromo-2-fluoro-1-methoxybenzene (7.9 mL, 61 mmol) in anhydrous tetrahydrofuran (50 mL) was added drop wise, under nitrogen balloon, to the reaction. The mixture was then allowed to stir for 30 minutes at −78° C. N,N-dimethylformamide (7.5 mL) was added drop wise at −78° C. under a nitrogen balloon. The reaction was stirred for 1 hour at room temperature under a nitrogen balloon. Half of the solvent from the solution was removed under reduced pressure and the solution was extracted using ethyl acetate, water (300 mL), and 1 M HCl (65 mL). The organic layer was washed with brine, dried over anhydrous sodium sulfate, and filtered. The solvent was removed under reduced pressure. The residue was crystallized by washing with hexanes. The solid was collected via filtration and dried under reduced pressure to give 6-bromo-2-fluoro-3-methoxybenzaldehyde (8.21 g, 58% yield).

A solution of 6-bromo-2-fluoro-3-methoxybenzaldehyde (2 g, 8.58 mmol) in dichloromethane (43 mL) under a nitrogen balloon was cooled to −78° C. in an acetone dry ice bath. 1 M boron tribromide solution in dichloromethane (9.5 mL) was added drop wise under nitrogen balloon. The reaction was stirred at room temperature overnight. The reaction was then put on an ice water bath and the excess boron tribromide was quenched with ice chips. Water was added and the solution was extracted with dichloromethane. The aqueous layer was extracted two times with dichloromethane. The organic layers were combined, washed with brine, dried over anhydrous sodium sulfate, and filtered. The solvent was removed under reduced pressure to give 6-bromo-2-fluoro-3-hydroxybenzaldehyde (1.61 g, 86% yield).

A solution of 6-bromo-2-fluoro-3-hydroxybenzaldehyde (1.61 g, 7.35 mmol), ethylene glycol (2 mL, 36.8 mmol), para-toluenesulfonic acid (0.27 g, 0.147 mmol), and toluene (150 mL) was refluxed with a dean-stark head for 16 hours. An aqueous solution of sodium bicarbonate was added and the solution was extracted with ethyl acetate. The aqueous layer was extracted five more times with ethyl acetate. The organic layers were combined and washed with brine, dried over anhydrous sodium sulfate, and filtered. The solvent was removed under reduced pressure to give 4-bromo-3-(1,3-dioxolan-2-yl)-2-fluorophenol (1.81 g, 94% yield).

A solution of 6-chloro-2-methoxynicotinonitrile (1.16 g, 6.88 mmol), 4-bromo-3-(1,3-dioxolan-2-yl)-2-fluorophenol (1.81 g, 6.88 mmol), potassium carbonate (1.14 g, 8.26 mmol), and N,N-dimethylformamide (35 mL) was stirred at 80° C. overnight. Water was added and the solution was extracted with ethyl acetate. The organic layer was washed with brine, dried over anhydrous sodium sulfate, and filtered. The solvent was removed under reduced pressure and the residue was purified by silica gel column using Combiflash to give 6-(4-bromo-3-(1,3-dioxolan-2-yl)-2-fluorophenoxy)-2-methoxynicotinonitrile (2.31 g, 85% yield).

To a solution of 6-(4-bromo-3-(1,3-dioxolan-2-yl)-2-fluorophenoxy)-2-methoxynicotinonitrile (2.31 g, 5.85 mmol) in 1,4-dioxane (30 mL) was added potassium acetate, bis(pinacolato)diboron (1.64 g, 6.44 mmol), and 1,1'-Bis(diphenylphosphino)ferrocene]dichloropalladium(II) (0.119 g, 0.146 mmol). The reaction was stirred under nitrogen balloon at 80° C. overnight. The reaction was cooled to room temperature and filtered through Celite using ethyl acetate. The solvent was removed under reduced pressure. The residue was purified by silica gel column using Combiflash to give 6-(3-(1,3-dioxolan-2-yl)-2-fluoro-4-(4,4,5,5-tetramethyl-1,3,2-dioxaborolan-2-yl)phenoxy)-2-methoxynicotinonitrile (2.18 g, 85% yield).

A solution of 6-(3-(1,3-dioxolan-2-yl)-2-fluoro-4-(4,4,5,5-tetramethyl-1,3,2-dioxaborolan-2-yl)phenoxy)-2-methoxynicotinonitrile (2.18 g, 4.93 mmol) in tetrahydrofuran (6 mL) was added 3 M HCl (3 mL). The solution was refluxed for four hours. The solution was cooled to room temperature and water was added. The solution was extracted with ethyl acetate. The organic layer was washed with water, then washed with brine, dried over anhydrous sodium sulfate, and filtered. The solvent was removed under reduced pressure to give 6-(2-fluoro-3-formyl-4-(4,4,5,5-tetramethyl-1,3,2-dioxaborolan-2-yl)phenoxy)-2-methoxynicotinonitrile (1.45 g, 74% yield).

A solution of 6-(2-fluoro-3-formyl-4-(4,4,5,5-tetramethyl-1,3,2-dioxaborolan-2-yl)phenoxy)-2-methoxynicotinonitrile (1.45 g, 3.64 mmol) in methanol (15 mL) was put on an ice water bath. Sodium borohydride was added in portions. The reaction was stirred at 0° C. for five minutes and then stirred at room temperature for 2 hours. The reaction was cooled again to 0° C. on an ice water bath and sodium borohydride (0.034 g, 0.91 mmol) was added. The reaction was stirred at room temperature for 1 hour. The reaction was again cooled to 0° C. and sodium borohydride (0.034 g, 0.91 mmol) was again added. The reaction was stirred at room temperature for one hour. The reaction was neutralized to pH 6 to 7 using 1 M HCl. The solution was then extracted using ethyl acetate and 0.5 M boronic acid solution in water. The organic layer was washed two more times with the 0.5 M boronic acid solution, then washed with brine, dried over anhydrous sodium sulfate, and filtered. The solvent was removed under reduced pressure. The residue was purified by silica gel column using Combiflash to give 6-(4-fluoro-1-hydroxy-1,3-dihydrobenzo[c][1,2]oxaborol-5-yloxy)-2-methoxynicotinonitrile (0.220 g, 20% yield). ES(−)MS m/z=300 (M−H)⁻; $^1$H NMR (400 MHz, DMSO-$d_6$) δ ppm 3.67 (s, 3H), 5.11 (s, 2H), 6.82 (d, J=8.2 Hz, 1H), 7.39 (t, J=6.8, J=7.5 Hz, 1H), 7.60 (d, J=7.8 Hz, 1H), 8.28 (d, J=8.2 Hz, 1H), 9.47 (s, 1H).

19dr 6-(1-Hydroxy-1,3-dihydro-benzo[c][1,2]oxaborol-5-yloxy)-2-[(2-hydroxy-ethyl)-methylamino]-nicotinonitrile (D115)

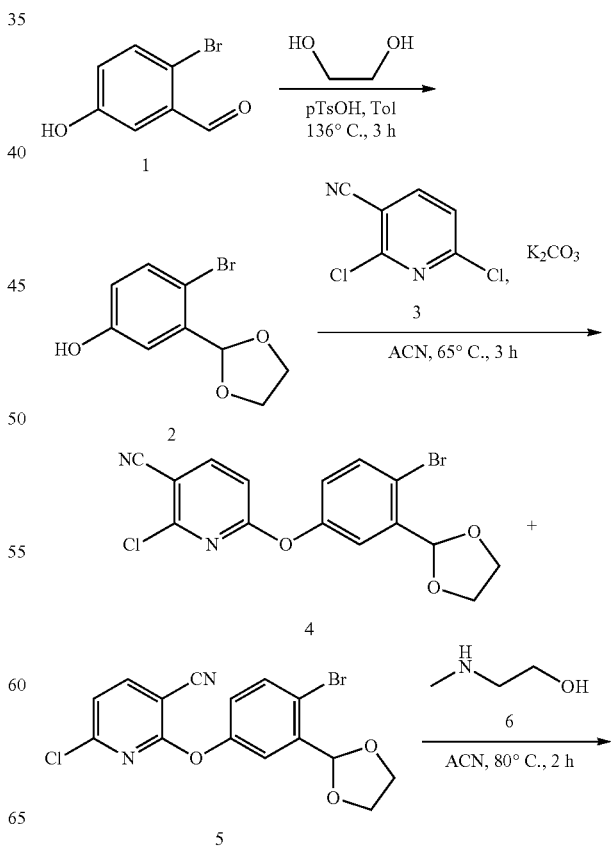

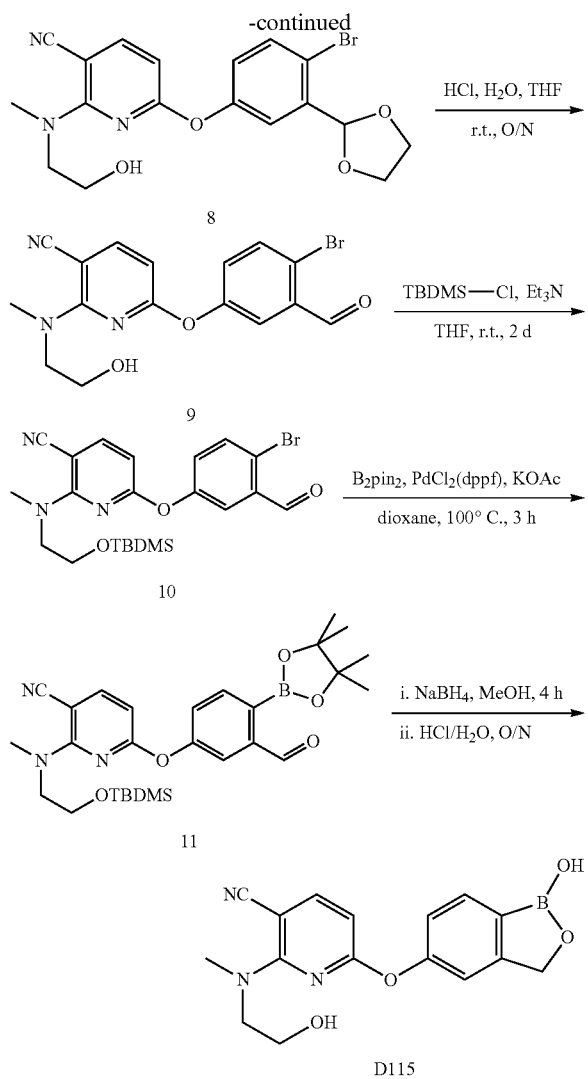

MHz, CHLOROFORM-d) δ ppm 7.94 (d, J=9.0 Hz, 2H), 7.62 (d, J=8.6 Hz, 2H), 7.46 (d, J=3.1 Hz, 1H), 7.41 (d, J=3.1 Hz, 1H), 7.18-7.08 (m, 2H), 7.05 (dd, J=8.8, 2.93 Hz, 1H), 6.93 (d, J=8.2 Hz, 1H), 6.11 (s, 1H), 6.09 (s, 1H), 4.19-3.99 (m, 8H).

6-(4-Bromo-3-[1,3]dioxolan-2-yl-phenoxy)-2-[(2-hydroxy-ethyl)-methyl-amino]-nicotinonitrile (8)

To a solution of compound mixture, 6-(4-bromo-3-[1,3]dioxolan-2-yl-phenoxy)-2-chloro-nicotinonitrile and 2-(4-bromo-3-[1,3]dioxolan-2-yl-phenoxy)-6-chloro-nicotinonitrile, (4+5, 1 g, 2.6 mmol) in acetonitrile (anhydrous, 30 mL) was added 2-methylamino-ethanol (6, 2.1 mL, 26 mmol). The reaction was heated at 80° C. for 2 hours. After the reaction, all volatile components were evaporated in vacuo. Purification was accomplished by silica gel chromatography, eluting with 10%-80% EtOAc/hexanes gradient, affording 400 mg (36% yield) of the title compound.

$^1$H NMR (400 MHz, CHLOROFORM-d) δ ppm 7.71-7.68 (m, 1H), 7.59 (d, J=8.6 Hz, 1H), 7.42 (d, J=2.7 Hz, 1H), 7.00 (dd, J=8.6, 3.0 Hz, 1H), 6.25 (d, J=8.6 Hz, 1H), 6.06 (s, 1H), 4.19-4.04 (m, 4H), 3.60-3.43 (m, 4H), 3.35-3.30 (m, 3H).

2-(4-Bromo-3-formyl-phenoxy)-6-[(2-hydroxy-ethyl)-methyl-amino]-nicotinonitrile (9)

To a solution of 6-(4-bromo-3-[1,3]dioxolan-2-yl-phenoxy)-2-[(2-hydroxy-ethyl)-methyl-amino]-nicotinonitrile (8, 7.6 g, 18.1 mmol) in THF (100 mL) was added HCl solution (1 M, 100 mL). The reaction was stirred at 50° C. overnight. After the reaction, all THF was evaporated in vacuo. The aqueous solution was extracted with EtOAc (2×50 mL). The organic layer was washed with water (3×50 mL), dried over MgSO$_4$, filtered and evaporated in vacuo to afford 6.8 g (100% yield) of the desired product.

$^1$H NMR (400 MHz, CHLOROFORM-d) δ ppm 10.34 (s, 1H), 7.80-7.65 (m, 3H), 7.26-7.22 (m, 1H), 6.28 (d, J=8.6 Hz, 1H), 3.71-3.64 (m, 2H), 3.58 (t, J=5.7 Hz, 2H), 3.29 (s, 3H), 2.03 (s, 1H).

6-(4-Bromo-3-formyl-phenoxy)-2-{[2-(tert-butyl-dimethyl-silanyloxy)-ethyl]-methyl-amino}-nicotinonitrile (10)

To a solution of 2-(4-bromo-3-formyl-phenoxy)-6-[(2-hydroxy-ethyl)-methyl-amino]-nicotinonitrile (9, 8 g, 21.3 mmol) in THF (anhydrous, 100 mL) were added TBDMS-Cl (3.21 g, 21.3 mmol) and Et$_3$N (3 mL, 21.3 mmol). The solution was stirred at room temperature for 2 days. The solution was filtered and concentrated in vacuo. Purification was accomplished by silica gel chromatography, eluting with 5%-50% EtOAc/hexanes gradient, to afford 10 g (85% yield) of the title compound.

$^1$H NMR (400 MHz, CHLOROFORM-d) δ ppm 10.37 (s, 1H), 7.78-7.73 (m, 2H), 7.69 (d, J=8.6 Hz, 1H), 7.30-7.26 (m, 1H), 6.28 (d, J=8.6 Hz, 1H), 3.66-3.57 (m, 4H), 3.28 (s, 3H), 0.87 (s, 9H), 0.00 (s, 6H).

2-{[2-(tert-Butyl-dimethyl-silanyloxy)-ethyl]-methyl-amino}-6-[3-formyl-4-(4,4,5,5-tetramethyl-[1,3,2]dioxaborolan-2-yl)-phenoxy]-nicotinonitrile: (11)

To a solution of 6-(4-bromo-3-formyl-phenoxy)-2-{[2-(tert-butyl-dimethyl-silanyloxy)-ethyl]-methyl-amino}-nicotinonitrile (10, 5 g, 10.2 mmol) in 1,4-dioxane (anhydrous, 150 mL) were added bispinacolatodiboron (3.11 g, 4-Bromo-3-[1,3]dioxolan-2-yl-phenol (2)

To a solution of 2-bromo-5-hydroxy-benzaldehyde (1) (10 g, 49.8 mmol) in toluene (200 mL) were added ethylene glycol (9.25 g, 149.3 mmol) and catalytic amount of p-TsOH (200 mg). After attaching a Dean-Stark trap, the reaction was heated at 136° C. for 3 hours. After the solution was cooled to room temperature, it was washed with saturated NaHCO$_3$ (200 mL). The organic layer was dried over Na$_2$SO$_4$, filtered and evaporated in vacuo to provide the 11.6 g (95% yield) of the title compound. $^1$H NMR (400 MHz, CHLOROFORM-d) δ ppm 7.40 (d, J=8.6 Hz, 1H), 7.09 (d, J=3.1 Hz, 1H), 6.72 (dd, J=8.6, 3.1 Hz, 1H), 6.04 (s, 1H), 4.18-4.04 (m, 4H).

6-(4-Bromo-3-[1,3]dioxolan-2-yl-phenoxy)-2-chloro-nicotinonitrile+2-(4-bromo-3-[1,3]dioxolan-2-yl-phenoxy)-6-chloro-nicotinonitrile (4+5)

To a solution of 2,6-dichloro-nicotinonitrile (3) (7.06 g, 40.8 mmol) in acetonitrile (anhydrous, 300 mL) were added 4-bromo-3-[1,3]dioxolan-2-yl-phenol (2) (10 g, 40.8 mmol) and K$_2$CO$_3$ (5.63 g, 40.8 mmol). The reaction was heated at 65° C. for 3 hours. The solution was filtered and evaporated in vacuo to afford 15.6 g of the product mixture. $^1$H NMR (400

12.2 mmol), PdCl$_2$(dppf) (0.75 g, 1.02 mmol) and KOAc (3 g, 30.6 mmol). The solution was stirred at r.t. with N$_2$ bubbling for 30 minutes. Then the reaction was heated at 100° C. for 3 hours. The solution was filtered and concentrated in vacuo. Purification was accomplished by silica gel chromatography, eluting with 5%-10% EtOAc/hexanes gradient to afford 5.2 g (95% yield) of the title compound.

$^1$H NMR (400 MHz, CHLOROFORM-d) δ ppm 10.70 (s, 1H), 7.98 (d, J=8.2 Hz, 1H), 7.81 (d, J=2.3 Hz, 1H), 7.77-7.73 (m, 1H), 7.39 (dd, J=8.2, 2.3 Hz, 1H), 6.28 (d, J=8.2 Hz, 1H), 3.71-3.51 (m, 4H), 3.29 (s, 3H), 1.44 (s, 12H), 0.87 (s, 9H), 0.00 (s, 6H).

6-(1-Hydroxy-1,3-dihydro-benzo[c][1,2]oxaborol-5-yloxy)-2-[(2-hydroxy-ethyl)-methyl-amino]-nicotinonitrile: (D115)

To a clear solution of 11 (5.2 g, 9.7 mmol) in MeOH (anhydrous, 150 mL) was slowly added NaBH$_4$ (2.2 g, 58 mmol). The reaction was stirred at room temperature for 4 hours, before the addition of HCl solution (1 M, 150 mL). The stirring was kept at room temperature overnight. Then the solution was slowly evaporated in vacuo. Purification was accomplished by reverse phase Biotage with 5%-100% MeOH/H$_2$O gradient to afford 786 mg (25% yield) of the desired product as a white solid.

1H NMR (400 MHz, DMSO-d$_6$) δ ppm 9.22 (s, 1H), 7.93 (d, J=8.6 Hz, 1H), 7.75 (d, J=8.2 Hz, 1H), 7.22 (s, 1H), 7.13 (dd, J=7.8, 2.0 Hz, 1H), 6.31 (d, J=8.6 Hz, 1H), 4.98 (s, 2H), 4.66 (t, J=5.1 Hz, 1H), 3.48-3.44 (m, 2H), 3.41 (t, J=5.1 Hz, 2H), 3.16 (s, 3H); ES MS: m/z 326 (M+H)$^+$; HPLC: 99.0% (220 nm), 98.21% (MaxPlot).

19ds 2-(1-Hydroxy-1,3-dihydro-benzo[c][1,2]oxaborol-5-yloxy)-4-methoxy-pyrimidine-5-carbonitrile (D116)

2-Chloro-4-methoxy-pyrimidine-5-carbonitrile (2)

To a solution of 2,4-dichloro-pyrimidine-5-carbonitrile (1) (300 mg, 1.72 mmol) in THF (anhydrous, 20 mL) was added sodium methoxide solution (0.5 M/MeOH, 3.45 mL, 1.72 mmol). The reaction was stirred at r.t. for 30 minutes. The volatile components were removed in vacuo. Purification was accomplished by Biotage silica gel chromatography (2%-30% EtOAc/hexanes gradient) to give 130 mg (45% yield) of the title compound. $^1$H NMR (400 MHz, CHLOROFORM-d) δ ppm 8.62 (s, 1H), 4.18 (s, 3H)

2-(1-Hydroxy-1,3-dihydro-benzo[c][1,2]oxaborol-5-yloxy)-4-methoxy-pyrimidine-5-carbonitrile To a clear solution of 2-chloro-4-methoxy-pyrimidine-5-carbonitrile (2) (500 mg, 2.95 mmol) in DMF (anhydrous, 30 mL) were added 3H-benzo[c][1,2]oxaborole-1,5-diol (3) (221 mg, 1.47 mmol) and Cs$_2$CO$_3$ (1054 mg, 3.24 mmol). The reaction was heated at 80° C. for 2 h by microwave. HCl (1 M) was added till pH 2. All volatile components were removed in vacuo. Purification was accomplished by reverse phase Biotage with 5%-100% MeOH/H$_2$O gradient to afford the 125 mg (30% yield) of the title compound as a white solid.

$^1$H NMR (400 MHz, DMSO-d$_6$) δ ppm 9.26 (s, 1H), 8.88 (s, 1H), 7.80 (d, J=8.0 Hz, 1H), 7.31 (s, 1H), 7.23 (dd, J=8.0, 1.8 Hz, 1H), 5.01 (s, 2H), 4.00 (s, 3H); ES-MS m/z=284 (M+H)$^+$; HPLC: 92.78% (220 nm), 94.74% (MaxPlot).

19dt 5-[5-Aminomethyl-6-(2-benzyloxy-ethylamino)-pyridin-2-yloxy]-3H-benzo[c][1,2]oxaborol-1-ol (D117)

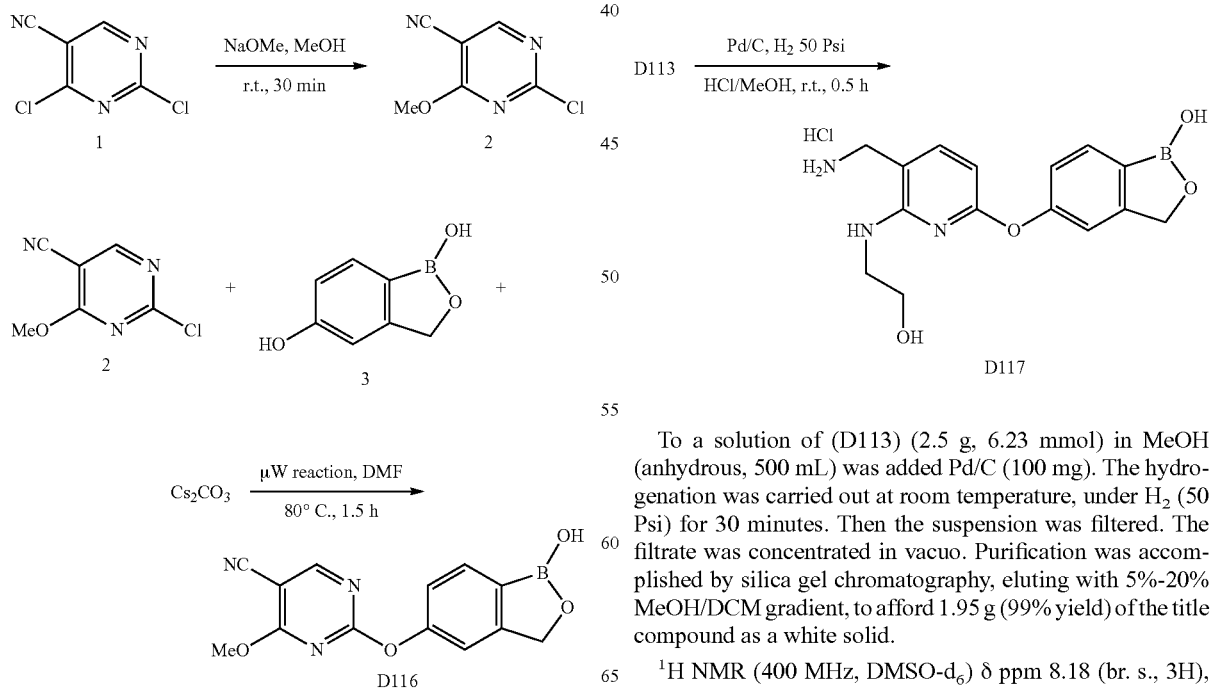

To a solution of (D113) (2.5 g, 6.23 mmol) in MeOH (anhydrous, 500 mL) was added Pd/C (100 mg). The hydrogenation was carried out at room temperature, under H$_2$ (50 Psi) for 30 minutes. Then the suspension was filtered. The filtrate was concentrated in vacuo. Purification was accomplished by silica gel chromatography, eluting with 5%-20% MeOH/DCM gradient, to afford 1.95 g (99% yield) of the title compound as a white solid.

$^1$H NMR (400 MHz, DMSO-d$_6$) δ ppm 8.18 (br. s., 3H), 7.74 (d, J=8.2 Hz, 1H), 7.54 (d, J=7.8 Hz, 1H), 7.10 (s, 1H), 7.06-7.01 (m, 1H), 6.09 (d, J=7.8 Hz, 1H), 4.96 (s, 2H), 3.94-3.88 (m, 3H), 3.41 (t, J=6.1 Hz, 2H), 3.17 (t, J=6.1 Hz, 2H); ES-MS: m/z 316 (M+H)+; HPLC: 96.08% (220 nm), 95.90% (MaxPlot).

19du 6-(1-Hydroxy-1,3-dihydro-benzo[c][1,2]oxaborol-5-yloxy)-4-[2-(tetrahydro-pyran-2-yloxy)-ethoxy]-nicotinonitrile (D118) and

19dv 6-(1-Hydroxy-1,3-dihydro-benzo[c][1,2]oxaborol-5-yloxy)-4-(2-hydroxy-ethoxy)-nicotinonitrile (D119)

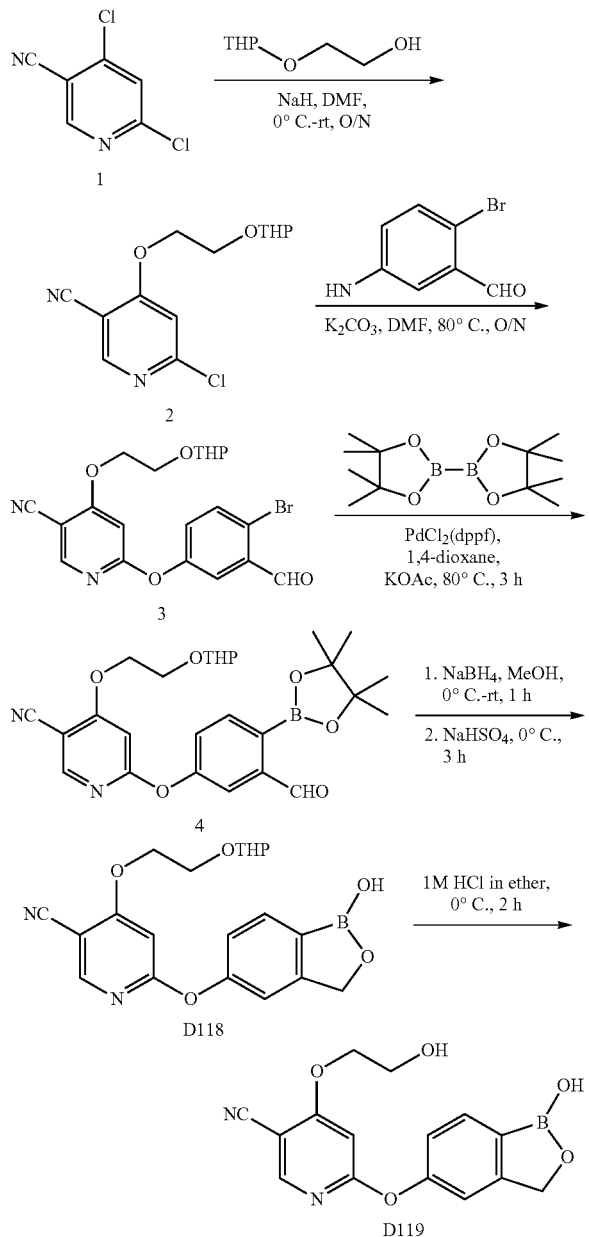

6-Chloro-4-[2-(tetrahydro-pyran-2-yloxy)-ethoxy]-nicotinonitrile (2)

To a solution of 2-(tetrahydro-pyran-2-yloxy)-ethanol (6.32 g, 43.30 mmol) in DMF (15 mL) at 0° C. was added sodium hydride (95% in mineral oil, 1.09 g, 43.30 mmol) portion-wise. After 1 h at room temperature, this mixture was slowly added to a solution of 4,6-dichloro-nicotinonitrile (5.0 g, 28.90 mmol) in DMF (25 mL) at 0° C. After overnight, DMF was removed under reduced pressure, and the resulting mixture was diluted with EtOAc (50 mL). The organic layer was washed with water (20 mL) and brine (3×20 mL) solution, dried over anhydrous $Na_2SO_4$, filtered, and concentrated. Purification was accomplished by flash chromatography on silica gel using 5-25% EtOAc/hexanes gradient elution to yield the title compound (4.9 g, 60%) as a transparent oil. $^1$H NMR (400 MHz, $CDCl_3$) δ ppm 8.47 (s, 1H), 7.10 (s, 1H), 4.70 (t, J=3.3 Hz, 1H), 4.32-4.45 (m, 2H), 4.19-4.08 (m, 1H), 3.91-3.80 (m, 2H), 3.59-3.50 (m, 1H), 1.83-1.68 (m, 2H), 1.65-1.50 (m, 4H).

6-(4-Bromo-3-formyl-phenoxy)-4-[2-(tetrahydro-pyran-2-yloxy)-ethoxy]-nicotinonitrile (3)

To a mixture of 6-chloro-4-[2-(tetrahydro-pyran-2-yloxy)-ethoxy]-nicotinonitrile (4.8 g, 16.62 mmol) and 2-bromo-5-hydroxy-benzaldehyde (4.01 g, 19.94 mmol) in DMF (30 mL) was added potassium carbonate (3.44 g, 24.93 mmol). The resulting mixture was heated at 80° C. overnight. DMF was removed under reduced pressure and the residue was diluted with EtOAc (200 mL). The organic layer was washed with water (20 mL) and brine (3×20 mL), dried over $Na_2SO_4$, filtered, and concentrated to give white solid. Purification was accomplished by flash chromatography on silica gel using 2-25% EtOAc/hexanes as gradient elution yielding the title compound (4.8 g, 64%) as a white solid. $^1$H NMR (400 MHz, DMSO-$d_6$) δ ppm 10.19 (s, 1H), 8.46 (s, 1H), 7.88 (d, J=8.6 Hz, 1H), 7.60 (d, J=2.7 Hz, 1H), 7.49 (dd, J=8.6, 2.7 Hz, 1H), 7.09 (s, 1H), 4.75-4.67 (m, 1H), 4.49-4.45 (m, 2H), 4.00-3.89 (m, 1H), 3.85-3.74 (m, 2H), 3.49-3.41 (m, 1H), 1.78-1.53 (m, 2H), 1.39-1.53 (m, 4H).

6-[3-Formyl-4-(4,4,5,5-tetramethyl-[1,3,2]dioxaborolan-2-yl)-phenoxy]-4-[2-(tetrahydro-pyran-2-yloxy)-ethoxy]-nicotinonitrile (4)

To a degassed solution of 6-(4-bromo-3-formyl-phenoxy)-4-[2-(tetrahydro-pyran-2-yloxy)-ethoxy]-nicotinonitrile (4.9 g, 10.09 mmol) in 1,4-dioxane (35 mL) was added bis(pinacolato)diboron (3.18 g, 12.54 mmol), potassium acetate (3.21 g, 37.7 mmol), and [1,1'-bis(diphenylphosphino)ferrocene] palladium(II)chloride (0.38 g, 0.52 mmol). After purging with $N_2$ again, the suspension was heated at 80° C. for 3 h. The mixture was cooled to room temperature and passed through Celite® and diluted with EtOAc (150 mL). The organic layer was washed with water (20 mL) and brine (20 mL) solution, dried over $Na_2SO_4$, filtered, and concentrated. Purification was accomplished by flash chromatography on silica gel using 5-25% EtOAc/hexanes gradient elution yielding the title compound (3.8 g, 64%) as a white solid. $^1$H NMR (400 MHz, DMSO-$d_6$) δ ppm 10.39 (s, 1H), 8.44 (s, 1H), 7.83 (d, J=7.8 Hz, 1H), 7.62 (d, J=2.3 Hz, 1H), 7.49 (dd, J=8.2, 2.3 Hz, 1H), 7.06 (s, 1H), 4.69 (s, 1H), 4.47-4.39 (m, 2H), 4.02-3.92 (m, 1H), 3.80-3.70 (m, 2H), 3.49-3.38 (m, 1H), 1.72-1.58 (m, 2H), 1.50-1.42 (m, 4H), 1.33 (s, 12H).

6-(1-Hydroxy-1,3-dihydro-benzo[c][1,2]oxaborol-5-yloxy)-4-[2-(tetrahydro-pyran-2-yloxy)-ethoxy]-nicotinonitrile (D118)

To a solution of 6-[3-formyl-4-(4,4,5,5-tetramethyl-[1,3,2] dioxaborolan-2-yl)-phenoxy]-4-[2-(tetrahydro-pyran-2- yloxy)-ethoxy]-nicotinonitrile (0.5 g, 1.02 mmol) in methanol (3 mL) at 0° C. was added sodium borohydride (0.07 g, 2.04 mmol). After 1 h at room temperature, the solution was cooled in an ice bath and 1M NaHSO₄ (2.6 mL, 2.6 mmol) was added until pH reached to 4-5. The resulting mixture was sonicated and stirred at 0° C. for 1 h. The white solid that separated was filtered, washed with MeOH and lyophilized to yield the title compound D118 (0.1 g, 25%) as a white solid. ¹H NMR (400 MHz, DMSO-$d_6$) δ ppm 9.22 (s, 1H), 8.46 (s, 1H), 7.77 (d, J=7.8 Hz, 1H), 7.21 (d, J=1.6 Hz, 1H), 7.15-7.09 (m, 1H), 7.02 (s, 1H), 4.99 (s, 2H), 4.71 (s, 1H), 4.49-4.40 (m, 2H), 4.02-3.91 (m, 1H), 3.84-3.73 (m, 2H), 3.49-3.41 (m, 1H), 1.72-1.58 (m, 2H), 1.55-1.41 (m, 4H); MS (ES) m/z: 397 (M+1)⁺; HPLC purity 97.55% (Maxplot), 97.65% (220 nm).

6-(1-Hydroxy-1,3-dihydro-benzo[c][1,2]oxaborol-5-yloxy)-4-(2-hydroxy-ethoxy)-nicotinonitrile (D119)

To a suspension of 6-(1-hydroxy-1,3-dihydro-benzo[c][1,2]oxaborol-5-yloxy)-4-[2-(tetrahydro-pyran-2-yloxy)-ethoxy]-nicotinonitrile (1.8 g, 4.54 mmol) in methanol (15 mL) at 0° C. was added 1M HCl in ether (5.45 ml, 5.45 mmol) and left at the same temperature for 2 h. The solid that formed was collected by filtration and dissolved in minimum volume of 10% MeOH/CHCl₃ and passed through a short column. The solvent was evaporated to yield the title compound (D119) (0.28 g, 20%) as a white solid. ¹H NMR (400 MHz, DMSO-$d_6$) δ ppm 9.23 (s, 1H), 8.45 (s, 1H), 7.77 (d, J=7.8 Hz, 1H), 7.22 (s, 1H), 7.15-7.09 (m, 1H), 7.01 (s, 1H), 5.04 (t, J=5.3 Hz, 1H), 4.99 (s, 2H), 4.30 (t, J=4.5 Hz, 2H), 3.79-3.76 (m, 2H); MS (ES) m/z: 313 (M+1)⁻; HPLC purity 99.27% (Maxplot), 99.66% (220 nm). Elemental analysis for $C_{15}H_{13}BN_2O_5$: Calculated C, 57.73; H, 4.20; N, 8.98. found C, 57.53; H, 4.31; N, 8.95.

19dw 4-Ethoxy-6-(1-hydroxy-1,3-dihydro-benzo[c][1,2]oxaborol-5-yloxy)-nicotinonitrile (D120)

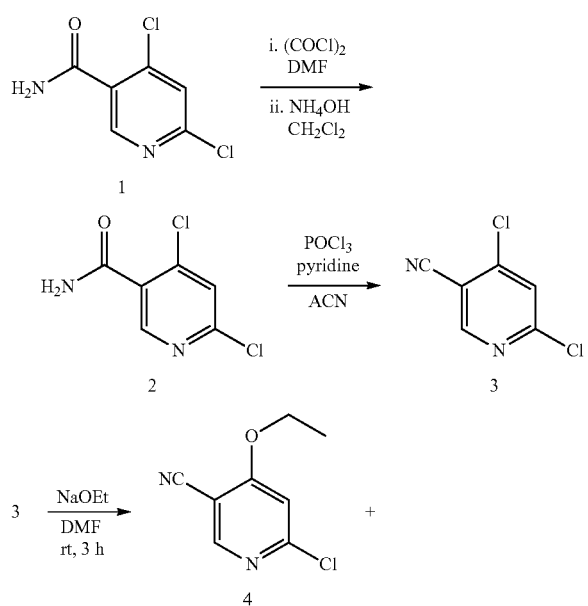

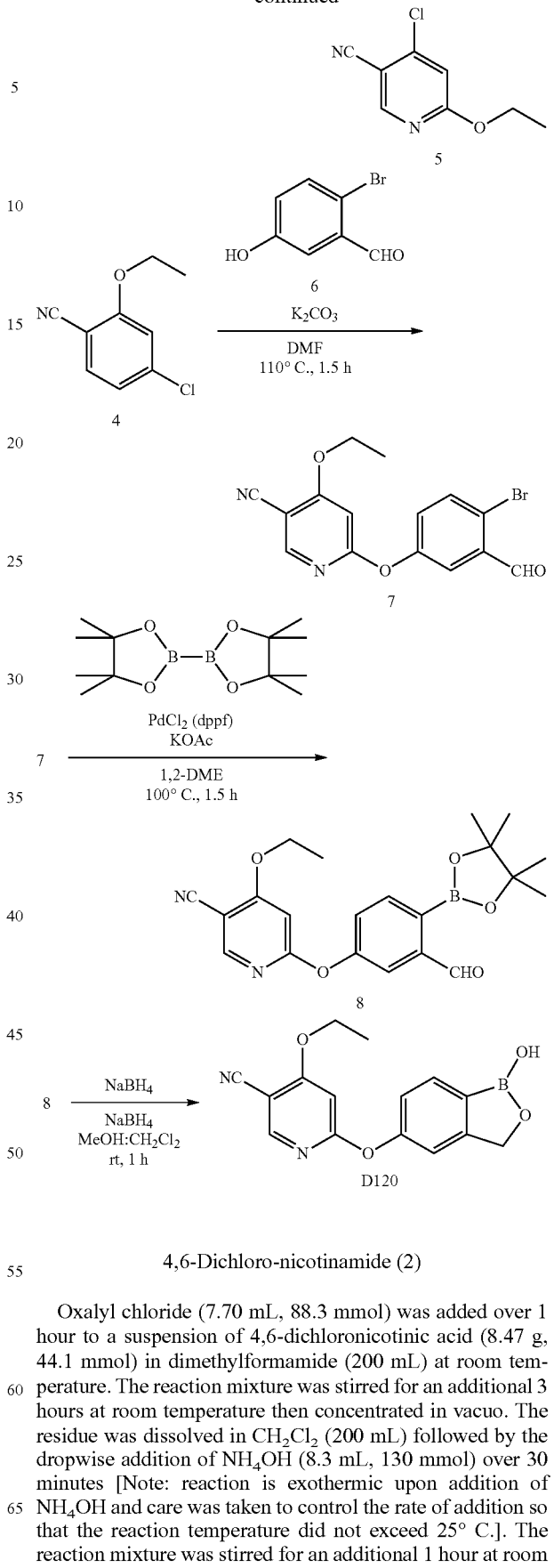

4,6-Dichloro-nicotinamide (2)

Oxalyl chloride (7.70 mL, 88.3 mmol) was added over 1 hour to a suspension of 4,6-dichloronicotinic acid (8.47 g, 44.1 mmol) in dimethylformamide (200 mL) at room temperature. The reaction mixture was stirred for an additional 3 hours at room temperature then concentrated in vacuo. The residue was dissolved in CH₂Cl₂ (200 mL) followed by the dropwise addition of NH₄OH (8.3 mL, 130 mmol) over 30 minutes [Note: reaction is exothermic upon addition of NH₄OH and care was taken to control the rate of addition so that the reaction temperature did not exceed 25° C.]. The reaction mixture was stirred for an additional 1 hour at room temperature then diluted with water (600 mL) and extracted with EtOAc (4×600 mL). The organic extracts were combined, dried over Na$_2$SO$_4$, filtered and concentrated to give the title compound as a light brown solid (8.05 g, 95% yield). This material was carried forward without further purification.

$^1$H NMR 400 MHz (d$_6$-DMSO) δ 8.48 (s, 1H), 8.10 (br s, 1H), 7.87 (br s, 2H).

4,6-Dichloro-nicotinonitrile (3)

Pyridine (20.3 mL, 250 mmol) was added to a suspension of 4,6-dichloro-nicotinamide (8.00 g, 41.9 mmol) in acetonitrile (180 mL) at room temperature POCl$_3$ (11.7 mL, 126 mmol) was added over 3 minutes at room temperature. The reaction mixture was heated at 60° C. with for 1.5 hours. The reaction solution was cooled to room temperature and poured into aqueous NaOH (0.8M, 600 mL) followed by extraction with EtOAc (6×400 mL). The organic extracts were combined, dried over Na$_2$SO$_4$, filtered and concentrated. The residue was purified by silica gel flash column chromatography (30% ethyl acetate/hexanes) to give the title compound as a light orange solid (6.41 g, 88%)

$^1$H NMR 400 MHz (CDCl$_3$) δ 8.67 (s, 1H), 7.58 (s, 1H).

6-Chloro-4-ethoxy-nicotinonitrile (4)

A solution of NaOEt in ethanol (1.93M, 18.8 mL, 36.3 mmol) was added over 10 minutes to a solution of 4,6-dichloro-nicotinonitrile (6.29 g, 36.3 mmol) in dimethylformamide (60 mL) at room temperature. The reaction was stirred for 3 hours, diluted with water (600 mL) and extracted with EtOAc (4×400 mL). The organic extracts were combined, dried over Na$_2$SO$_4$, filtered and concentrated. The residue was purified by silica gel flash column chromatography (20% ethyl acetate/hexanes) to give the title compound as a white solid (3.82 g, 58%) and 4-chloro-6-ethoxy-nicotinonitrile (0.41 g, 6.0%) as a white solid.

6-Chloro-4-ethoxy-nicotinonitrile (4): $^1$H NMR 400 MHz (CDCl$_3$) δ 8.47 (s, 1H), 6.93 (s, 1H), 4.24 (q, J=7.0 Hz, 2H), 1.54 (t, J=7.0 Hz, 3H).

4-Chloro-6-ethoxy-nicotinonitrile (5): $^1$H NMR 400 MHz (CDCl$_3$) δ 8.43 (s, 1H), 6.87 (s, 1H), 4.44 (q, J=7.0 Hz, 2H), 1.40 (t, J=7.0 Hz, 3H).

6-(4-Bromo-3-formyl-phenoxy)-4-ethoxy-nicotinonitrile (7)

A mixture of 6-chloro-4-ethoxy-nicotinonitrile (3.80 g, 20.8 mmol), 2-bromo-5-hydroxy-benzaldehyde (4.60 g, 22.9 mmol) and K$_2$CO$_3$ (4.31 g, 31.2 mmol) in dimethyl formamide (30 mL) was heated to 110° C. for 5 hours. The reaction mixture was diluted with H$_2$O (400 mL) and extracted with ethyl acetate (8×400 mL). The organic extracts were combined, dried over Na$_2$SO$_4$, filtered and concentrated. The residue was purified by silica gel flash column chromatography (15-50% ethyl acetate/hexanes) to give the title compound as a white solid (5.31 g, 73%).

$^1$H NMR 400 MHz (CDCl$_3$) δ 10.34 (s, 1H), 8.22 (s, 1H), 7.71 (d, J=8.6 Hz, 1H), 7.68 (d, J=3.1 Hz, 1H), 7.27 (dd, J=8.6, 3.1 Hz, 1H), 6.50 (s, 1H), 4.24 (q, J=7.0 Hz, 2H), 1.55 (t, J=7.0 Hz, 3H).

4-Ethoxy-6-[3-formyl-4-(4,4,5,5-tetramethyl-[1,3,2]dioxaborolan-2-yl)-phenoxy]-nicotinonitrile (8)

A mixture of 6-(4-bromo-3-formyl-phenoxy)-4-ethoxy-nicotinonitrile (5.30 g, 15.3 mmol), bispinacolatodiboron (7.75 g, 30.5 mmol) and KOAc (3.00 g, 30.5 mmol) in 1,2-dimethoxyethane (180 mL) was heated to 110° C. for 10 minutes. PdCl$_2$(dppf) (0.56 g, 0.76 mmol) was added and the reaction mixture was stirred vigorously at 110° C. for 1.5 hours. This was purified by silica gel flash column chromatography (20-40% ethyl acetate/hexanes) to give the title compound as a white solid (3.53 g, 59% yield).

$^1$H NMR 400 MHz (CDCl$_3$) δ10.68 (s, 1H), 8.23 (s, 1H), 8.01 (d, J=8.2 Hz, 1H), 7.73 (d, J=2.3 Hz, 1H), 7.36 (dd, J=8.2, 2.3 Hz, 1H), 6.49 (s, 1H), 4.23 (q, J=7.0 Hz, 2H), 1.54 (t, J=7.0 Hz, 3H), 1.39 (s, 12H).

4-Ethoxy-6-(1-hydroxy-1,3-dihydro-benzo[c][1,2]oxaborol-5-yloxy)-nicotinonitrile (D120)

A solution of NaBH$_4$ (0.10 g, 2.6 mmol) in anhydrous methanol (20 mL) was added to a solution of 4-ethoxy-6-[3-formyl-4-(4,4,5,5-tetramethyl-[1,3,2]dioxaborolan-2-yl)-phenoxy]-nicotinonitrile (3.53 g, 8.95 mmol) in CH$_2$Cl$_2$ (80 mL) and stirred at room temperature for 5 minutes. Solid NaBH$_4$ (0.58 g, 15.3 mmol) was then added portionwise over 30 minutes at room temperature. The reaction mixture was stirred for an additional 30 minutes, quenched by the addition 70% aqueous acetic acid (3 mL) then stirred for an additional 1 hour at room temperature. The reaction was concentrated and the residue purified by silica gel flash column chromatography (AcOH/MeOH/CH$_2$Cl$_2$ 1:1:100 v/v/v) to give the title compound as a viscous oil. The oil was lyophilized to give a white solid (0.781 g, 29% yield).

$^1$H NMR 400 MHz (d$_6$-DMSO) δ9.24 (s, 1H), 8.45 (s, 1H), 7.77 (d, J=8.2 Hz, 1H), 7.22 (s, 1H), 7.13 (dd, J=7.8, 1.6 Hz, 1H), 6.97 (s, 1H), 4.99 (s, 2H), 4.32 (q, J=7.0 Hz, 2H), 1.40 (t, J=7.0 Hz, 3H).

Mass Spectrum [M+H$^+$]=297.

HPLC purity 96.58% (Maxplot), 98.13% (220 nm), 97.49% (254 nm).

19dx 2-Benzylamino-6-(1-hydroxy-1,3-dihydro-benzo[c][1,2]oxaborol-5-yloxy)-nicotinonitrile (D121)

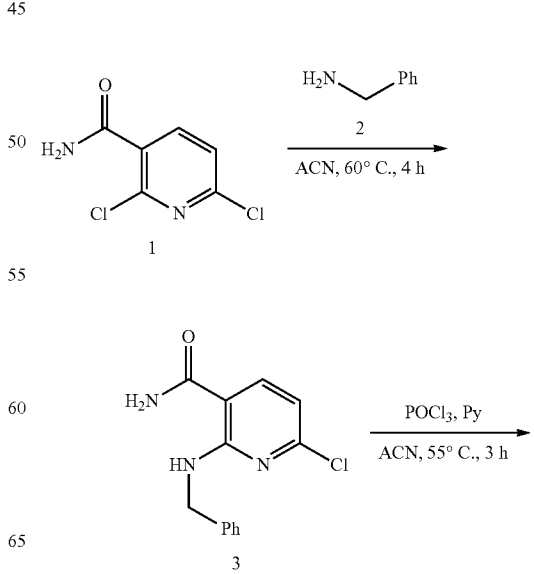

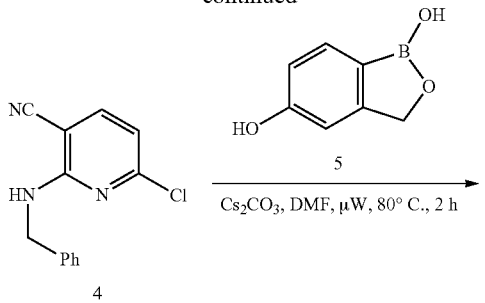

2-Benzylamino-6-chloro-nicotinamide (3)

To a solution of 2,6-dichloro-nicotinamide (1) (2.3 g, 12.2 mmol) in acetonitrile (anhydrous, 100 mL) were added 2-benzylamine (2) (1.3 g, 12.2 mmol) and triethylamine (1.7 mL, 12.2 mmol). The reaction was heated at 60° C. for 4 hours. The solution was cooled to room temperature and filtered. The filtrate was evaporated in vacuo. Purification was achieved by Biotage silica gel chromatography with 5%-50% EtOAc/hexanes gradient to afford 1.71 g (54% yield) of the title compound.

$^1$H NMR (400 MHz, CHLOROFORM-d) δ ppm 8.82 (br. s., 1H), 7.52 (d, J=8.2 Hz, 1H), 7.40-7.23 (m, 6H), 6.50 (d, J=8.2 Hz, 1H), 5.66 (br. s., 2H), 4.70 (d, J=5.5 Hz, 2H).

2-Benzylamino-6-chloro-nicotinonitrile (4)

To a solution of 2-benzylamino-6-chloro-nicotinamide (3, 1.71 g, 6.6 mmol) in acetonitrile (anhydrous, 80 mL) were added pyridine (4.26 mL, 52.7 mmol) and POCl$_3$ (2.41 mL, 264 mmol). The reaction was heated at 55° C. for 3 hours. After cooling to room temperature, NaOH solution (10% aq., 30 mL) was slowly added till pH 9. EtOAc (200 mL) was added and the layers separated. The aqueous layer was extracted with EtOAc (2×200 mL). The combined organic layer was dried over MgSO$_4$, filtered, and evaporated in vacuo. Purification was accomplished by silica gel chromatography, eluting with 2%-20% EtOAc/hexanes gradient, to afford 0.66 g (42% yield) of the title compound.

$^1$H NMR (400 MHz, CHLOROFORM-d) δ ppm 7.58 (d, J=8.2 Hz, 1H), 7.39-7.29 (m, 5H), 6.65 (d, J=7.8 Hz, 1H), 5.55 (br. s., 1H), 4.69 (d, J=5.5 Hz, 2H)

2-Benzylamino-6-(1-hydroxy-1,3-dihydro-benzo[c][1,2]oxaborol-5-yloxy)-nicotinonitrile (D121)

To a clear solution of 2-benzylamino-6-chloro-nicotinonitrile (4, 660 mg, 2.73 mmol) in DMF (anhydrous, 30 mL) were added 3H-benzo[c][1,2]oxaborole-1,5-diol (3) (205 mg, 1.37 mmol) and Cs$_2$CO$_3$ (880 mg, 2.73 mmol). The reaction was heated at 80° C. for 1.5 hours by microwave. HCl (1 M) was added till pH 2. All volatile components were removed in vacuo. Purification was accomplished by reverse phase Biotage with 10%-90% MeOH/H$_2$O gradient to afford the 480 mg (49.5% yield) of the title compound as a white solid.

$^1$H NMR (400 MHz, DMSO-d$_6$) δ ppm 9.25 (s, 1H), 8.00-7.95 (m, 1H), 7.91 (d, J=8.2 Hz, 1H), 7.76 (d, J=7.8 Hz, 1H), 7.20-7.05 (m, 5H), 6.87 (dd, J=7.4, 1.9 Hz, 1H), 6.25 (d, J=8.6 Hz, 1H), 4.93 (s, 2H), 4.17 (d, J=5.8 Hz, 2H), 3.32 (s, 1H); ES-MS: m/z 358 (M+H)$^+$; HPLC: 97.8% (220 nm), 97.61% (MaxPlot).

19dy 6-(6-Fluoro-1-hydroxy-1,3-dihydrobenzo[c][1,2]oxaborol-5-yloxy)-2-methoxynicotinonitrile (D122)

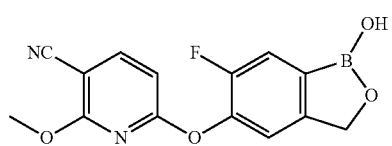 [SMILES: COc1nc(Oc2cc3c(cc2F)B(O)OC3)ccc1C#N]

A solution of 4-fluoro-3-methoxybenzaldehyde (4.3 g, 27.9 mmol), potassium bromide (16.6 g, 139.5 mmol), bromine (3.6 mL, 69.8 mmol), and water (45 mL) were stirred at room temperature for 24 hours. More bromine (1.43 mL, 27.9 mmol) was added and the reaction was stirred at room temperature overnight. The product precipitated out of solution and was collected via filtration and dried under reduced pressure to give 2-bromo-4-fluoro-5-methoxybenzaldehyde (6.01 g, 92% yield).

A solution of 2-bromo-4-fluoro-5-methoxybenzaldehyde (1.19 g, 8.20 mmol), 48% HBr (57 mL) and glacier acetic acid (57 mL) were refluxed at 130° C. for 5 hours. The glacier acetic acid was removed under reduced pressure. The solution was neutralized using sodium carbonate. Water was added and the mixture was extracted using ethyl acetate. The organic layer was washed with brine, dried over anhydrous sodium sulfate, and filtered. The solvent was removed under reduced pressure. The residue was purified by silica gel column using Combiflash to give 2-bromo-4-fluoro-5-hydroxybenzaldehyde (1.15 g, 64% yield).

The rest of the steps are identical to those of 6-(4-fluoro-1-hydroxy-1,3-dihydrobenzo[c][1,2]oxaborol-5-yloxy)-2-methoxynicotinonitrile. $^1$H NMR (400 MHz, DMSO-d$_6$) δ ppm 3.67 (s, 3H), 4.98 (s, 2H), 6.82 (d, J=8.4 Hz, 1H), 7.48 (d, J=6.6 Hz, 1H), 7.62 (d, J=9.8 Hz, 1H), 8.27 (d, J=8.4 Hz, 1H), 9.35 (s, 1H).

19dz 5-Hydroxy-6-(1-hydroxy-1,3-dihydro-benzo[c][1,2]oxaborol-5-yloxy)-nicotinonitrile (D123)

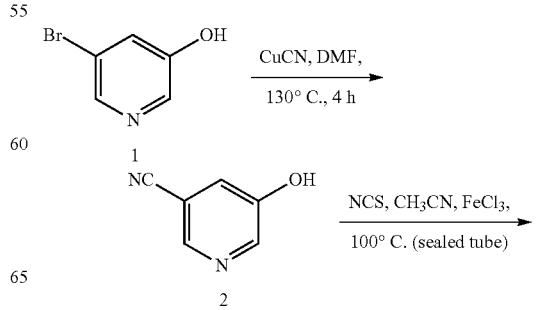

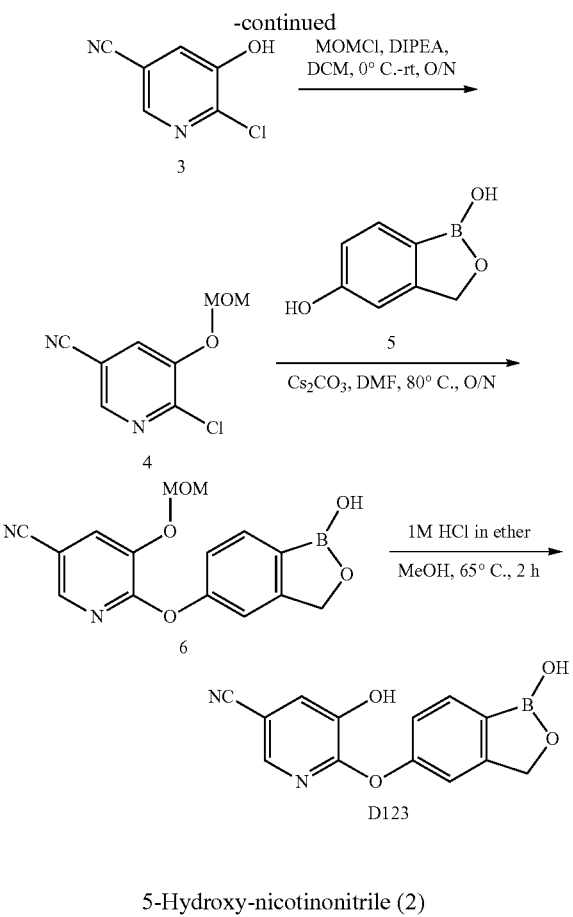

5-Hydroxy-nicotinonitrile (2)

A mixture of 5-bromo-pyridin-3-ol (9.94 mL, 54.0 mmol) and CuCN (7.4 g, 82.62 mmol) in DMF (20 mL) was heated at 135° C. for 5 hour. DMF was removed under reduced pressure, the residue was diluted with NH$_4$OH (10 mL) at 0° C. The mixture was bubbled with ammonia gas for 1 hour, cooled to 0° C. and acidified with conc. HCl (35 mL) until pH reached to ~4. The resulting mixture was extracted with EtOAc (5×100 mL). The organic layer was washed with water (2×100 mL) and brine (2×100 mL) solution, dried over anhydrous Na$_2$SO$_4$, filtered, and concentrated to give yellow solid. Purification was accomplished by flash chromatography on silica gel using 5-25% EtOAc/hexanes gradient elution to yield the title compound (2.5 g, 39%) as a yellow solid. $^1$H NMR (400 MHz, DMSO-d$_6$) δ ppm 10.78 (s, 1H), 8.46 (d, J=2.0 Hz, 1H), 8.41 (d, J=2.7 Hz, 1H), 7.61-7.57 (m, 1H).

6-Chloro-5-hydroxy-nicotinonitrile (3)

A mixture of 5-hydroxy-nicotinonitrile (2.0 g, 16.66 mmol), and N-chlorosuccinimide (3.3 g, 25.0 mmol) in acetonitrile (33 mL) was heated in a sealed tube at 107° C. overnight. Acetonitrile was removed under reduced pressure, the residue was diluted with EtOAc (100 mL). The organic layer was washed with water (10 mL) and brine (2×10 mL), dried over Na$_2$SO$_4$, filtered, and concentrated to give brown oil. Purification was accomplished by flash chromatography on silica gel using 20-80% EtOAc/hexanes gradient elution to yield the title compound (0.55 g, 36%) as a yellow solid. $^1$H NMR (400 MHz, DMSO-d$_6$) δ ppm 11.70 (s, 1H), 8.35 (d, J=2.0 Hz, 1H), 7.67 (d, J=2.0 Hz, 1H); MS (ES) m/z: 153 (M−1)$^-$.

6-Chloro-5-methoxymethoxy-nicotinonitrile (4)

To a solution of 6-chloro-5-hydroxy-nicotinonitrile (1.12 g, 7.24 mmol) in DCM (15 mL) was added N,N-diisopropyl ethylamine (1.57 mL, 9.05 mmol) followed by the addition of chloro-methyl methylether (0.66 mL, 8.69 mmol) slowly at 0° C. After overnight at room temperature, the reaction mixture was washed with saturated NaHCO$_3$ (10 mL) and brine (10 mL), dried over Na$_2$SO$_4$, filtered, and concentrated to give yellow oil. Purification was accomplished by flash chromatography on silica gel using 5-25% EtOAc/hexanes gradient elution to yield the title compound (0.68 g, 50%) as a transparent oil. $^1$H NMR (400 MHz, DMSO-d$_6$) δ ppm 8.53 (d, J=2.0 Hz, 1H), 8.14 (d, J=2.0 Hz, 1H), 5.42 (s, 2H), 3.40 (s, 3H); MS (ES) m/z: 199 (M+1)$^+$.

6-(1-Hydroxy-1,3-dihydro-benzo[c][1,2]oxaborol-5-yloxy)-5-methoxymethoxy-nicotinonitrile (6)

To a mixture of 6-chloro-5-methoxymethoxy-nicotinonitrile (0.68 g, 3.42 mmol) and 3H-benzo[c][1,2]oxaborole-1,5-diol (0.56 g, 3.76 mmol) in DMF (10 mL) was added cesium carbonate (2.45 g, 7.52 mmol). The resulting suspension was heated at 80° C. for overnight. DMF was removed under reduced pressure, the residue was diluted with EtOAc (50 mL), washed with water (10 mL) and brine (10 mL), dried over Na$_2$SO$_4$, filtered, and concentrated to give brown oil. Purification was accomplished by flash chromatography on silica gel using 1-100% MeOH/EtOAc gradient elution to yield the title compound (0.40 g, 40%) as a transparent oil. $^1$H NMR (400 MHz, DMSO-d$_6$) δ ppm 9.23 (s, 1H), 8.24 (s, 1H), 8.03 (s, 1H), 7.77 (d, J=8.6 Hz, 1H), 7.23 (s, 1H), 7.14 (d, J=7.4 Hz, 1H), 5.40 (s, 2H), 4.98 (s, 2H), 3.45 (s, 3H); MS (ES) m/z: 313 (M+1)$^+$.

5-Hydroxy-6-(1-hydroxy-1,3-dihydro-benzo[c][1,2]oxaborol-5-yloxy)-nicotinonitrile (D123)

To a suspension of 6-(1-hydroxy-1,3-dihydro-benzo[c][1,2]oxaborol-5-yloxy)-5-methoxymethoxy-nicotinonitrile (0.28 g, 0.89 mmol) in methanol (4 mL) was added 1 M HCl in ether (1.79 mL, 1.79 mmol) at 0° C. The reaction was heated at 65° C. for 2 hours. Methanol was removed under reduced pressure and the product was purified by reverse phase prep HPLC using CH$_3$CN/H$_2$O (0.1% AcOH) as the eluent to yield the title compound (0.10 g, 41%) as a white solid. $^1$H NMR (400 MHz, DMSO-d$_6$) δ ppm 9.22 (s, 1H), 8.02 (s, 1H), 7.76 (d, J=7.8 Hz, 1H), 7.57 (s, 1H), 7.19 (s, 1H), 7.15-7.09 (m, 1H), 4.98 (s, 2H); MS (ES) m/z: 267 (M−1)$^-$; HPLC purity 92.91% (Maxplot), 92.41% (220 nm).

19ea 2-Ethoxy-4-(1-hydroxy-1,3-dihydrobenzo[c][1,2]oxaborol-5-yloxy)benzonitrile (D124)

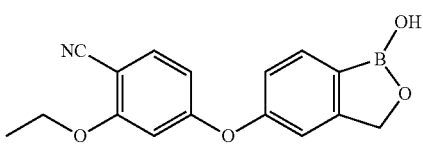 [SMILES: CCOc1cc(Oc2ccc3c(c2)COB3O)ccc1C#N]

A solution of 2-hydroxy-4-(1-hydroxy-1,3-dihydrobenzo[c][1,2]oxaborol-5-yloxy)benzonitrile (0.200 g, 0.749 mmol), iodoethane (0.182 mL, 2.25 mmol) and N,N-dimethylformamide (10 mL) under nitrogen balloon was put on an ice water bath. Sodium hydride (0.090 g, 2.25 mmol) was added and the mixture was stirred under nitrogen balloon at 0° C. for 15 minutes. The reaction was then stirred at room temperature for 2 hours. Water was added to quench the excess sodium hydride and the mixture was then neutralized using 1 M HCl. Water was added and the solution was extracted using ethyl acetate. The organic layer was washed with water, brine, dried over anhydrous sodium sulfate, and filtered. The solvent was removed under reduced pressure. The residue was solidified by adding isopropylether. The precipitate was filtered and dried under reduced pressure to give 2-ethoxy-4-(1-hydroxy-1,3-dihydrobenzo[c][1,2]oxaborol-5-yloxy)benzonitrile (0.131 g, 59% yield). ES(−)MS m/z=294 (M−H)⁻; ¹H NMR (400 MHz, DMSO-d₆) δ ppm 1.33 (t, J=6.9 Hz, 3H), 4.13 (q, J=7.0 Hz, 2H), 4.95 (s, 2H), 6.56 (dd, J=8.6, 1.9 Hz, 1H), 6.89 (d, J=1.9 Hz, 1H), 7.08 (dd, J=8.1, 1.6 Hz, 1H), 7.14 (s, 1H), 7.69 (d, J=8.6 Hz, 1H), 7.77 (d, J=7.8 Hz, 1H), 9.19 (s, 1H).

19eb 6-(1-Hydroxy-1,3-dihydro-benzo[c][1,2]oxaborol-5-yloxy)-2-(2,2,2-trifluoro-ethoxy)-nicotinonitrile (D125)

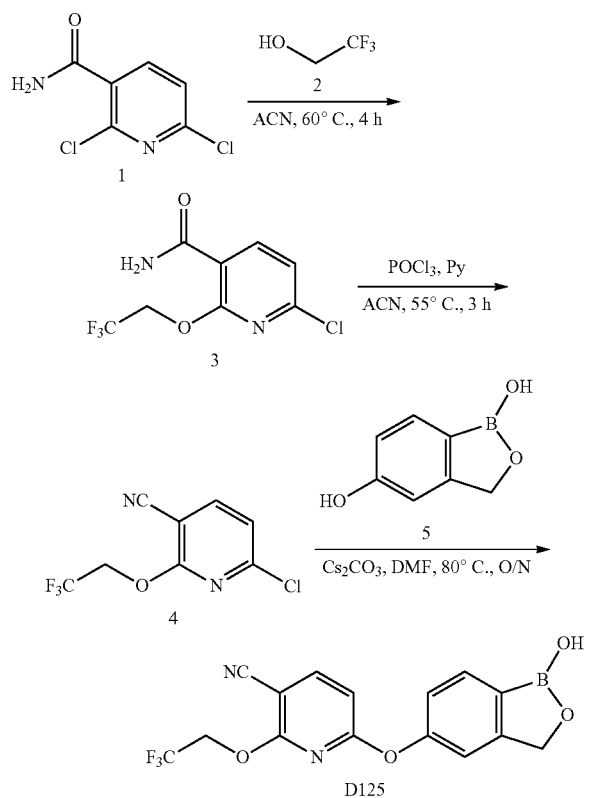

6-Chloro-2-(2,2,2-trifluoro-ethoxy)-nicotinamide (3)

To a solution of 2,2,2-trifluoro-ethanol (2) (4.8 mL, 67.8 mmol) was added sodium (0.52 g, 22.6 mmol). The reaction was kept O/N. Then to the solution was added 2,6-dichloro-nicotinamide (1, 4.32 g, 22.6 mmol) in DMF (30 mL). The reaction was kept at r.t. for 3 h. The suspension was filtered. The filtrate was concentrated in vacuo. Purification was accomplished by Biotage silica gel chromatography with 10%-60% EtOAc/hexanes gradient to afford 4.68 g (81% yield) of the title compound.

¹H NMR (400 MHz, CHLOROFORM-d) δ ppm 8.54 (d, J=7.8 Hz, 1H), 7.29 (br. s., 1H), 7.21 (d, J=7.8 Hz, 1H), 5.91 (br. s., 1H), 4.93-4.89 (m, 2H).

6-Chloro-2-(2,2,2-trifluoro-ethoxy)-nicotinonitrile (4)

To a solution of 6-chloro-2-(2,2,2-trifluoro-ethoxy)-nicotinamide (3, 4.68 g, 18.3 mmol) in acetonitrile (anhydrous, 100 mL) were added pyridine (11.86 mL, 146.8 mmol) and POCl₃ (6.72 mL, 73.4 mmol). The reaction was heated at 55° C. for 3 hours. After cooling to room temperature, NaOH solution (10% aq.) was slowly added till pH 9. EtOAc (200 mL) was added and layers separated. The aqueous layer was extracted with EtOAc (2×200 mL). The combined organic layer was dried over MgSO₄, filtered, and concentrated in vacuo. The purification was accomplished by silica gel chromatography, eluting with 2%-20% EtOAc/hexanes gradient, to afford 4 g (92% yield) of the titled product.

¹H NMR (400 MHz, CHLOROFORM-d) δ ppm 7.92 (d, J=7.9 Hz, 1H), 7.17 (d, J=7.9 Hz, 1H), 4.92-4.84 (m, 2H).

6-(1-Hydroxy-1,3-dihydro-benzo[c][1,2]oxaborol-5-yloxy)-2-(2,2,2-trifluoro-ethoxy)-nicotinonitrile (D125)

To a solution of 6-chloro-2-(2,2,2-trifluoro-ethoxy)-nicotinonitrile (4, 1.26 g, 5.33 mmol) in DMF (anhydrous, 30 mL) were added 3H-benzo[c][1,2]oxaborole-1,5-diol (400 mg, 2.67 mmol) and Cs₂CO₃ (1.91 g, 5.87 mmol). The reaction was heated at 80° C. for 2 h by microwave. After the reaction cooled to room temperature, HCl (1 M, 20 mL) was added. The volatiles were removed in vacuo. Purification was accomplished by preparative HPLC, eluting with 5%-90% ACN/water gradient, to afford 380 mg (41% yield) of the title compound as a white solid.

¹H NMR (400 MHz, DMSO-d₆) δ ppm 9.28 (s, 1H), 8.36 (d, J=8.2 Hz, 1H), 7.81 (d, J=7.8 Hz, 1H), 7.31 (s, 1H), 7.23 (dd, J=8.2, 2.0 Hz, 1H), 6.83 (d, J=8.2 Hz, 1H), 5.00 (s, 2H), 4.90-4.83 (m, 2H); ¹F NMR (376 MHz, DMSO-d₆) ppm −72.84; ES MS: m/z 351 (M+H)⁺; HPLC: 96.35% (220 nm), 97.02% (MaxPlot). Elemental analysis for C₁₅H₁₀BF₃N₂O₄, Calculated: C, 51.47%; H, 2.88%; N, 8.00%. Found: C, 51.44%; H, 2.86%; N, 8.30%.

19ec 2-[3-cyano-6-(1-hydroxy-1,3-dihydro-benzo[c][1,2]oxaborol-5-yloxy)-pyridin-2-yloxy]-ethyl acetate (D126)

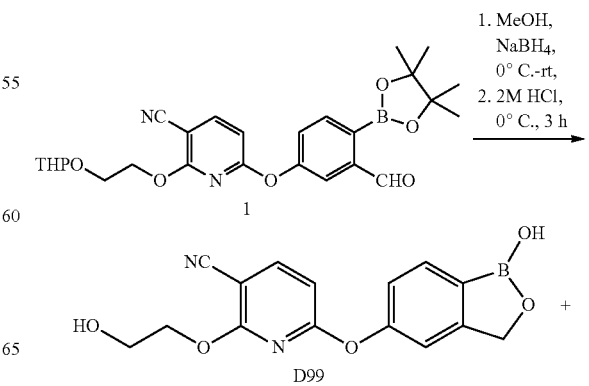

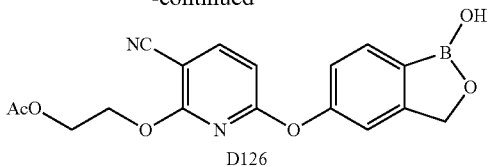

Acetic acid 2-[3-cyano-6-(1-hydroxy-1,3-dihydro-benzo[c][1,2]oxaborol-5-yloxy)-pyridin-2-yloxy]-ethyl ester (D126)

Refer to (D99) for the synthesis of D126, which was isolated as a by-product during the reverse phase preparative HPLC purification of D99. A gradient mixture of $CH_3CN/H_2O$ (0.1% AcOH) was used as the eluent to yield D126 (0.25 g, 20%), which was obtained as a white solid. $^1H$ NMR (400 MHz, DMSO-$d_6$) δ ppm 9.24 (s, 1H), 8.24 (d, J=8.2 Hz, 1H), 7.77 (d, J=8.2 Hz, 1H), 7.26 (s, 1H), 7.18 (d, J=7.8 Hz, 1H), 6.71 (d, J=8.2 Hz, 1H), 4.98 (s, 2H), 4.35-4.26 (m, 2H), 4.22-4.13 (m, 2H), 1.98 (s, 3H); $^{13}C$ NMR (400 MHz, DMSO-$d_6$) δ ppm 170.86, 164.58, 163.75, 156.71, 155.37, 147.67, 132.62, 120.87, 115.95, 114.86, 104.43, 89.54, 70.34, 65.92, 62.27, 21.22 (boron substituted C not observed); MS (ES) m/z: 355 (M+1)$^+$; HPLC purity 96.66% (Maxplot), 97.43% (220 nm). Elemental analysis for $C_{17}H_{15}BN_2O_6$: Calculated C=57.66%, H=4.27%, N=7.91%. Found C=57.58%, H=4.41%, N=7.71%.

19ed 2-(2,2-Difluoro-ethoxy)-6-(1-hydroxy-1,3-dihydro-benzo[c][1,2]oxaborol-5-yloxy)-nicotinonitrile (D127)

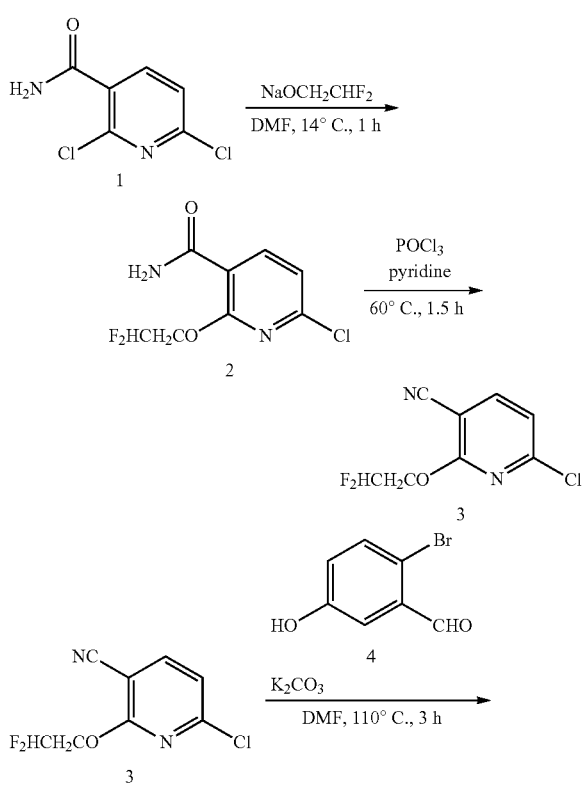

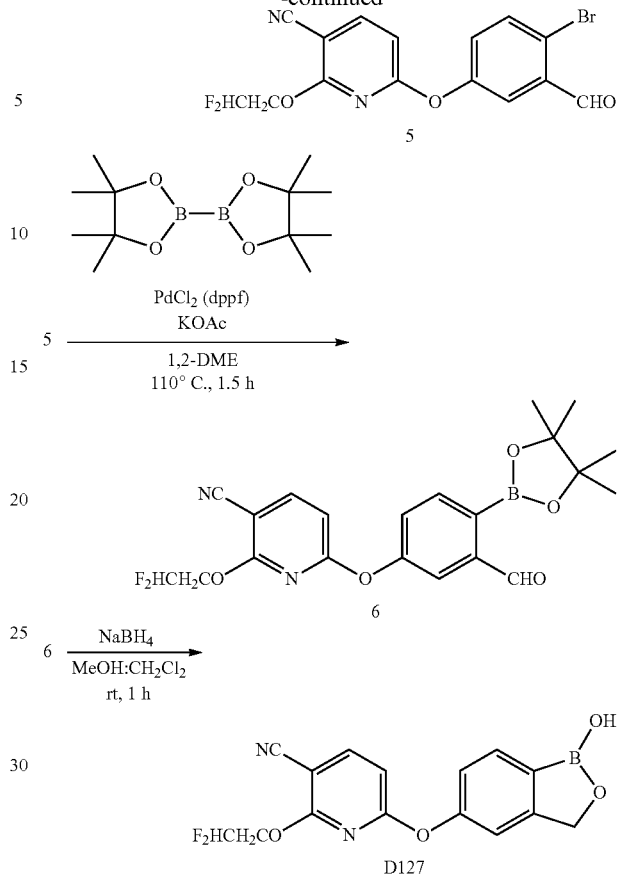

6-Chloro-2-(2,2-difluoro-ethoxy)-nicotinamide (2)

2,2-Difluoroethanol (3.51 mL, 55.5 mmol) was added dropwise over 30 minutes to a suspension of NaH (2.22 g, 60% w/w dispersion in oil) in 1,2-dimethoxyethane (40.0 mL) at 14° C. and stirred for 1 hour. A portion of this solution (25 mL, 35 mmol) was added dropwise over 10 minutes to a solution of 2,6-dichloro-nicotinamide (5.30 g, 27.7 mmol) in dimethylformamide (40 mL) at 14° C. The resultant suspension was stirred for an additional 1 hour at 14° C., diluted with water (600 mL) and extracted with EtOAc (3×400 mL). The organic extracts were combined, dried over $Na_2SO_4$, filtered and concentrated to give title compound as a light orange solid (6.39 g, 97%). This was used without further purification.

$^1H$ NMR 400 MHz ($d_6$-DMSO) δ8.19 (d, J=7.8 Hz, 1H), 7.87 (br s, 1H), 7.53 (br s, 1H), 7.28 (d, J=7.8 Hz, 1H), 6.47 (tt, J=54.7, 3.5 Hz, 1H), 4.66 (td, J=11.3, 3.5 Hz, 2H).

6-Chloro-2-(2,2-difluoro-ethoxy)-nicotinonitrile (3)

$POCl_3$ (7.5 mL, 81 mmol) was added to a solution of 6-chloro-2-(2,2-difluoro-ethoxy)-nicotinamide (6.39 g, 27.0 mmol) in acetonitrile (100 mL) at 14° C. over 5 minutes. The reaction mixture was heated to 60° C. for 1.5 hours then cooled to room temperature. The mixture was poured into an ice cold solution of aqueous NaOH (0.6M, 800 mL) and extracted with EtOAc (4×800 mL). The organic extracts were combined, dried over $Na_2SO_4$, filtered and concentrated. The residue was purified by silica gel flash column chromatography (20% ethyl acetate/hexanes) to give the title compound as a light yellow oil which solidified upon standing (5.10 g, 86%).

¹H NMR 400 MHz (CDCl₃) δ7.89 (d, J=8.2 Hz, 1H), 7.12 (d, J=8.2 Hz, 1H), 6.17 (tt, J=55.1, 3.5 Hz, 1H), 4.66 (td, J=13.3, 3.5 Hz, 2H).

6-(4-Bromo-3-formyl-phenoxy)-2-(2,2-difluoro-ethoxy)-nicotinonitrile (5)

A mixture of 6-chloro-2-(2,2-difluoro-ethoxy)-nicotinonitrile (5.01 g, 22.9 mmol), 2-bromo-5-hydroxy-benzaldehyde (3.84 g, 19.1 mmol) and K₂CO₃ (5.3 g, 38 mmol) in dimethylformamide (30 mL) was heated to 110° C. for 3 hours. The reaction mixture was cooled to room temperature, diluted with H₂O (800 mL) and extracted with ethyl acetate (4×800 mL). The organic extracts were combined, dried over Na₂SO₄, filtered and concentrated. The residue was purified by silica gel flash column chromatography (20% ethyl acetate/hexanes) to give the title compound as a white solid (6.62 g, 90%)

¹H NMR 400 MHz (CDCl₃) δ10.36 (s, 1H), 7.94 (d, J=8.2 Hz, 1H), 7.74 (d, J=3.1 Hz, 1H), 7.73 (d, J=8.6 Hz, 1H), 7.28 (dd, J=8.6, 3.1 Hz, 1H), 6.70 (d, J=8.2 Hz, 1H), 5.97 (tt, J=54.7, 4.3 Hz, 1H), 4.31 (td, J=13.3, 4.3 Hz, 2H).

2-(2,2-Difluoro-ethoxy)-6-[3-formyl-4-(4,4,5,5-tetramethyl-[1,3,2]dioxaborolan-2-yl)-phenoxy]-nicotinonitrile (6)

A mixture of 6-(4-bromo-3-formyl-phenoxy)-2-(2,2-difluoro-ethoxy)-nicotinonitrile (6.60 g, 17.2 mmol), bispinacolatodiboron (8.75 g, 34.5 mmol) and KOAc (3.38 g, 34.5 mmol) in 1,2-dimethoxyethane (180 mL) was heated to 110° C. for 10 minutes. PdCl₂(dppf) (0.630 g, 0.86 mmol) was added and the reaction mixture was stirred at 110° C. for 2 hours. This was purified by silica gel flash column chromatography (10-40% ethyl acetate/hexanes) to give the title compound as a light grey solid (5.22 g, 70% yield).

¹H NMR 400 MHz (d₆-DMSO) δ10.39 (s, 1H), 8.37 (d, J=8.6 Hz, 1H), 7.84 (d, J=8.2 Hz, 1H), 7.77 (d, J=2.7 Hz, 1H), 7.61 (dd, J=8.2, 2.3 Hz, 1H), 6.93 (d, J=8.2 Hz, 1H), 6.27 (tt, 54.3, 3.5 Hz, 1H), 4.39 (td, J=14.9, 3.5 Hz, 2H), 1.36 (s, 12H).

2-(2,2-Difluoro-ethoxy)-6-(1-hydroxy-1,3-dihydro-benzo[c][1,2]oxaborol-5-yloxy)-nicotinonitrile (D127)

A solution of NaBH₄ (0.100 g, 2.6 mmol) in anhydrous methanol (20 mL) was added to a solution of 2-(2,2-difluoro-ethoxy)-6-[3-formyl-4-(4,4,5,5-tetramethyl-[1,3,2]dioxaborolan-2-yl)-phenoxy]-nicotinonitrile (5.20 g, 12.1 mmol) in CH₂Cl₂ (80 mL) and stirred at room temperature for 5 minutes. Solid NaBH₄ (0.815 g, 21.5 mmol) was then added portionwise over 30 minutes to the reaction at room temperature and the reaction stirred for an additional 30 minutes. The reaction was quenched by the addition of 60% aqueous acetic acid (5 mL), stirred for 30 minutes at room temperature then concentrated in vacuo. The residue was purified by silica gel flash column chromatography (AcOH/MeOH/CH₂Cl₂ 1:1: 100 v/v/v) to give the title compound as a viscous oil which was lyophilized to give a white solid (1.92 g, 48% yield).

¹H NMR 400 MHz (d₆-DMSO) δ9.27 (s, 1H), 8.31 (d, J=8.2 Hz, 1H), 7.78 (d, J=7.9 Hz, 1H), 7.29 (d, J=1.5 Hz, 1H), 7.20 (dd, J=7.9, 1.5 Hz, 1H), 6.79 (d, J=8.2 Hz, 1H), 6.25 (tt, J=54.5, 3.5 Hz, 1H), 4.97 (s, 2H), 4.40 (td, J=11.4, 3.5 Hz, 2H).

Mass Spectrum [M+H⁺]=333.
HPLC purity 98.15% (Maxplot), 97.48% (220 nm), 97.44% (254 nm).

19ee 6-(1-Hydroxy-1,3-dihydro-benzo[c][1,2]oxaborol-5-yloxy)-2-isopropoxy-nicotinonitrile (D128)

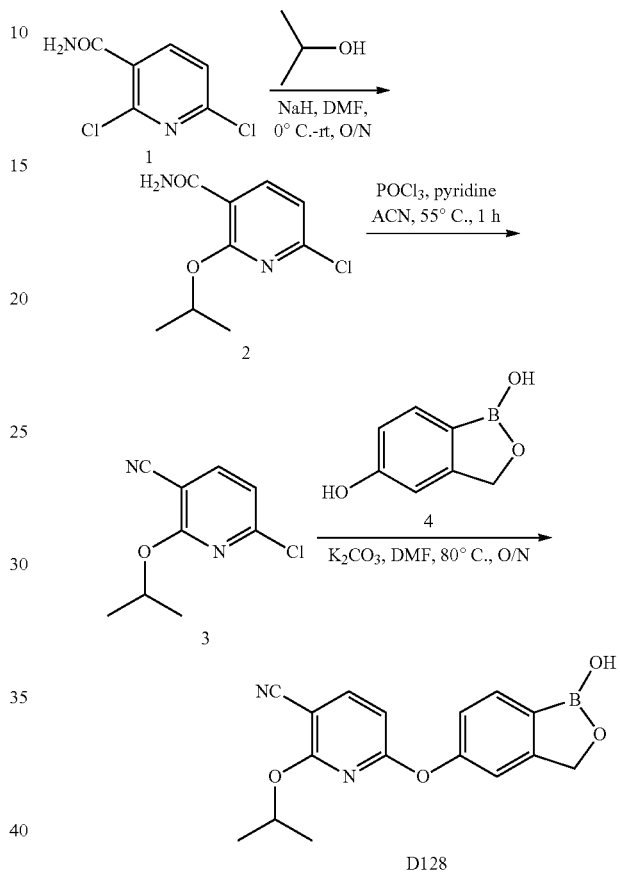

6-Chloro-2-isopropoxy-nicotinamide (2)

To a solution of propan-2-ol (2.94 mL, 39.26 mmol) in DMF (15 mL) at 0° C. was added sodium hydride (95% in mineral oil, 0.94 g, 39.26 mmol) in portions and stirred for 1 h at room temperature. This mixture was slowly added to a solution of 2,6-dichloro-nicotinamide (5.0 g, 26.17 mmol) in DMF (25 mL) at 0° C. The reaction mixture was stirred at room temperature overnight. DMF was removed under reduced pressure, and the resulting mixture was diluted with EtOAc (50 mL), washed with water (2×20 mL) and brine (2×10 mL) solution, dried over anhydrous Na₂SO₄, filtered, and concentrated to give yellow oil. Purification was accomplished by flash chromatography on silica gel using 5-50% EtOAc/hexanes gradient elution to yield the title compound (2.94 g, 64%) as a white solid. ¹H NMR (400 MHz, CDCl₃) δ ppm 8.45 (d, J=8.2 Hz, 1H), 7.73 (br. s., 1H), 7.03 (d, J=7.8 Hz, 1H), 5.84 (br. s., 1H), 5.64-5.47 (m, 1H), 1.45 (d, J=6.3 Hz, 6H).

6-Chloro-2-isopropoxy-nicotinonitrile (3)

To a solution of 6-chloro-2-isopropoxy-nicotinamide (2.87 g, 13.37 mmol) and pyridine (6.48 mL, 80.22 mmol) in acetonitrile (25 mL) was added phosphorus oxychloride (3.68 mL, 40.13 mmol) over a period of 5 min. The reaction was stirred at 55° C. for 1 h. Acetonitrile was evaporated in vacuo and the resulting residue was neutralized with 1N NaOH at 0° C. until pH reached to ~7. The reaction mixture was extracted with EtOAc (100 mL). The organic layer was collected and the aqueous layer was further extracted with EtOAc (3×50 mL). All organics were combined washed with brine (2×25 mL), dried over anhydrous $Na_2SO_4$, filtered, and concentrated to give yellow oil. Purification was accomplished by flash chromatography on silica gel using 5-25% EtOAc/hexanes gradient elution to yield the title compound (2.1 g, 81%) as a white solid. $^1$H NMR (400 MHz, DMSO-$d_6$) δ ppm 8.28 (d, J=8.2 Hz, 1H), 7.27 (d, J=8.2 Hz, 1H), 5.34-5.20 (m, 1H), 1.33 (d, J=6.2 Hz, 6H).

6-(1-Hydroxy-1,3-dihydro-benzo[c][1,2]oxaborol-5-yloxy)-2-isopropoxy-nicotinonitrile (D128)

To a mixture of 6-chloro-2-isopropoxy-nicotinonitrile (0.73 g, 4.0 mmol) and 3H-Benzo[c][1,2]oxaborole-1,5-diol (0.40 g, 2.66 mmol) in DMF (10 mL) was added potassium carbonate (1.10 g, 7.98 mmol). The resulting suspension was heated at 80° C. overnight. DMF was removed under reduced pressure, the residue was diluted with EtOAc (50 mL), washed with water (10 mL) and brine (2×10 mL), dried over $Na_2SO_4$, filtered, and concentrated to give brown oil. Purification was accomplished by reverse phase preparative HPLC using MeOH/$H_2O$ (0.1% AcOH) as the eluent to yield the title compound (0.21 g, 21%) as white solid. $^1$H NMR (400 MHz, DMSO-$d_6$) δ ppm 9.27 (s, 1H), 8.23 (d, J=8.6 Hz, 1H), 7.79 (d, J=7.8 Hz, 1H), 7.29 (s, 1H), 7.22-7.14 (m, 1H), 6.70 (d, J=8.2 Hz, 1H), 4.99 (s, 2H), 4.85 (sept., J=6.3 Hz, 1H), 1.19 (d, J=6.3 Hz, 6H); MS (ES) m/z: 311 (M+1)$^+$; HPLC purity 98.44% (Maxplot), 97.99% (220 nm).

19ef 2-tert-butylamino-6-(1-hydroxy-1,3-dihydro-benzo[c][1,2]oxaborol-5-yloxy)-nicotinonitrile (D129) and 19eg 2-amino-6-(1-hydroxy-1,3-dihydro-benzo[c][1,2]oxaborol-5-yloxy)-nicotinonitrile (D130)

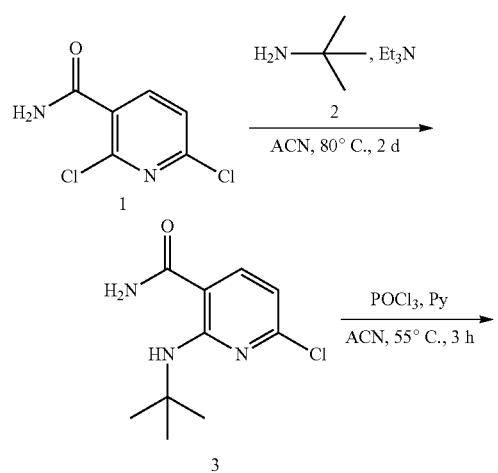

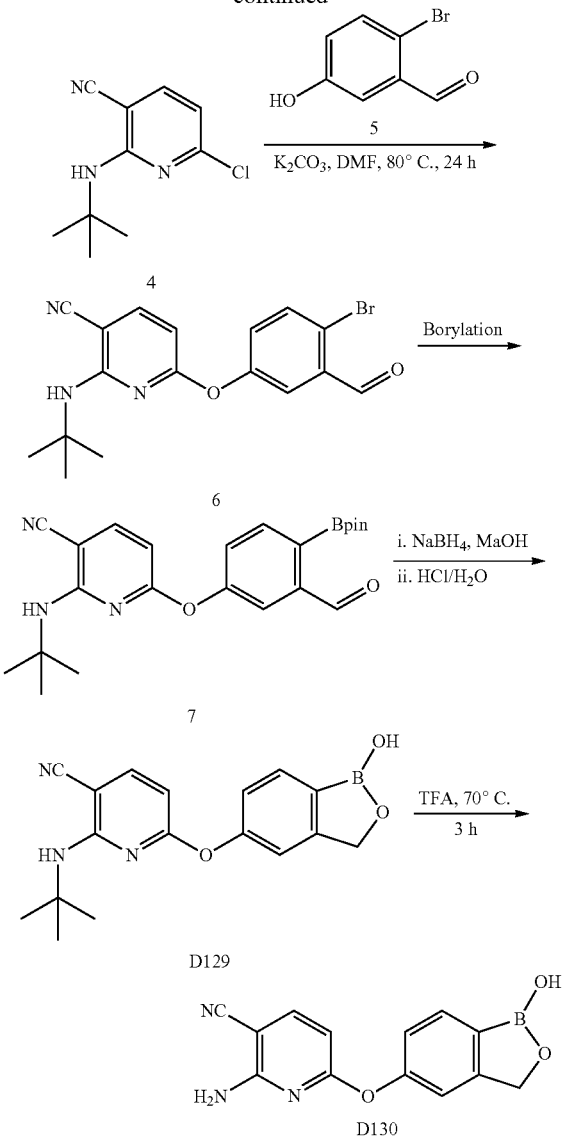

2-tert-Butylamino-6-chloro-nicotinamide (3)

To a solution of 2,6-dichloro-nicotinamide (1) (4 g, 20.9 mmol) in acetonitrile (anhydrous, 60 mL) were added tert-butylamine (2) (13.28 mL, 12.6 mmol) and triethylamine (15.7 mL, 12.6 mmol). The reaction was heated at 80° C. for 2 days. The solution was cooled to room temperature and the resulting suspension was filtered. The filtrate was concentrated in vacuo. The residue was purified by Biotage silica gel chromatography with 20%-100% EtOAc/hexanes gradient elution to afford 850 mg (18% yield) of the title compound. $^1$H NMR (400 MHz, CHLOROFORM-d) δ ppm 8.51 (br. s., 1H), 7.47 (d, J=7.8 Hz, 1H), 6.42 (d, J=7.8 Hz, 1H), 5.65 (br. s., 2H), 1.48 (s, 9H).

2-tert-Butylamino-6-chloro-nicotinonitrile (4)

To a solution of 2-tert-butylamino-6-chloro-nicotinamide (3, 850 mg, 3.73 mmol) in acetonitrile (anhydrous, 40 mL) were added pyridine (2.42 mL, 29.9 mmol) and POCl$_3$ (1.37 mL, 14.9 mmol). The reaction was heated at 55° C. for 3 hours. After cooling to room temperature, NaOH solution (10% aq.) was slowly added till pH 9. The solution was extracted with EtOAc (3×50 mL). The combined organic layer was dried over MgSO₄, filtered, and concentrated in vacuo. Purification was accomplished by Biotage silica gel chromatography, eluting with 2%-30% EtOAc/hexanes gradient, to afford 630 mg (80% yield) of the title product.
¹H NMR (400 MHz, CHLOROFORM-d) δ ppm 7.52 (d, J=7.9 Hz, 1H), 6.56 (d, J=7.9 Hz, 1H), 5.15 (br. s., 1H), 1.49 (s, 9H).

6-(4-Bromo-3-formyl-phenoxy)-2-tert-butylamino-nicotinonitrile (6)

To a solution of 2-tert-butylamino-6-chloro-nicotinonitrile (4, 630 mg, 3 mmol) in DMF (100 mL) were added 2-bromo-5-hydroxy-benzaldehyde (603 mg, 3 mmol) and K₂CO₃ (828 mg, 6 mmol). The reaction was heated at 80° C. for 24 h. After cooling to r.t., DMF was removed in vacuo. Purification was accomplished by Biotage silica gel chromatography with a 2.5%-10% EtOAc/hexanes gradient to afford 950 mg (85% yield) of the title compound.
¹H NMR (400 MHz, CHLOROFORM-d) δ ppm 10.34 (s, 1H), 7.71-7.67 (m, 2H), 7.62 (d, J=8.2 Hz, 1H), 7.24 (dd, J=8.6, 2.8 Hz, 1H), 6.24 (d, J=8.2 Hz, 1H), 5.04 (s, 1H), 1.12 (s, 9H)

2-tert-Butylamino-6-[3-formyl-4-(4,4,5,5-tetramethyl-[1,3,2]dioxaborolan-2-yl)-phenoxy]-nicotinonitrile (7)

To a solution of 6-(4-bromo-3-formyl-phenoxy)-2-tert-butylamino-nicotinonitrile (6, 950 mg, 2.54 mmol) in 1,4-dioxane (anhydrous, 100 mL) were added bispinacolatodiboron (0.775 g, 3.05 mmol), PdCl₂(dppf) (0.19 g, 0.25 mmol) and KOAc (0.75 g, 7.62 mmol). The solution was stirred at r.t. with N₂ bubbling for 30 minutes, then heated at 100° C. for 3 hours. The solution was filtered and concentrated in vacuo. Purification was accomplished by silica gel chromatography, eluting with 5%-30% EtOAc/hexanes gradient, producing 1 g (93.5%) of the title compound (7).
¹H NMR (400 MHz, CHLOROFORM-d) δ ppm 10.63 (s, 1H), 7.96 (d, J=8.2 Hz, 1H), 7.74 (d, J=2.2 Hz, 1H), 7.63-7.60 (m, 1H), 7.34 (dd, J=8.1, 2.1 Hz, 1H), 6.22 (d, J=8.2 Hz, 1H), 5.03 (br. s., 1H), 1.40 (s, 12H), 1.17 (s, 9H).

2-tert-butylamino-6-(1-hydroxy-1,3-dihydro-benzo[c][1,2]oxaborol-5-yloxy)-nicotinonitrile (D129)

To a solution of 2-tert-butylamino-6-[3-formyl-4-(4,4,5,5-tetramethyl-[1,3,2]dioxaborolan-2-yl)-phenoxy]-nicotinonitrile (7, 1 g, 2.38 mmol) in DMF (anhydrous, 100 mL) was added NaBH₄ (0.55 g, 14.25 mmol). The reaction was kept at r.t. for 4 h, before the addition of HCl (1 M, 30 mL). The reaction was kept O/N. All the volatile components were removed in vacuo. Purification was accomplished by preparative HPLC, eluting with 5%-80% ACN/water gradient, to afford 430 mg (56% yield) of the title compound as a white solid.
¹H NMR (400 MHz, DMSO-d₆) δ ppm 9.21 (s, 1H), 7.88 (d, J=8.2 Hz, 1H), 7.74 (d, J=8.2 Hz, 1H), 7.19 (s, 1H), 7.09 (dd, J=7.8, 1.9 Hz, 1H), 6.31 (d, J=8.2 Hz, 1H), 5.94 (s, 1H), 4.93 (s, 2H), 1.03 (s, 9H); ES MS: m/z 324 (M+H)⁺; HPLC: 96.97% (220 nm), 96.71% (MaxPlot).

2-amino-6-(1-hydroxy-1,3-dihydro-benzo[c][1,2]oxaborol-5-yloxy)-nicotinonitrile (D130)

A solution of (D129) (400 mg, 1.23 mmol) in TFA (25 mL) was heated at 70° C. for 3 h. All volatile components were removed in vacuo. Purification was accomplished by preparative HPLC with 5%-90% ACN/water gradient to afford 78 mg (24% yield) of the title compound.
¹H NMR (400 MHz, DMSO-d₆) δ ppm 9.23 (s, 1H), 7.88 (d, J=8.6 Hz, 1H), 7.76 (d, J=8.2 Hz, 1H), 7.21 (d, J=1.6 Hz, 1H), 7.12-7.09 (m, 1H), 6.98 (s, 2H), 6.19 (d, J=8.2 Hz, 1H), 4.98 (s, 2H); ES MS: m/z 268 (M+H)⁺; HPLC: 96.36% (220 nm), 97.08% (MaxPlot).

19eh 6-(1-Hydroxy-1,3-dihydro-benzo[c][1,2]oxaborol-5-yloxy)-2-propoxy-nicotinonitrile (D131)

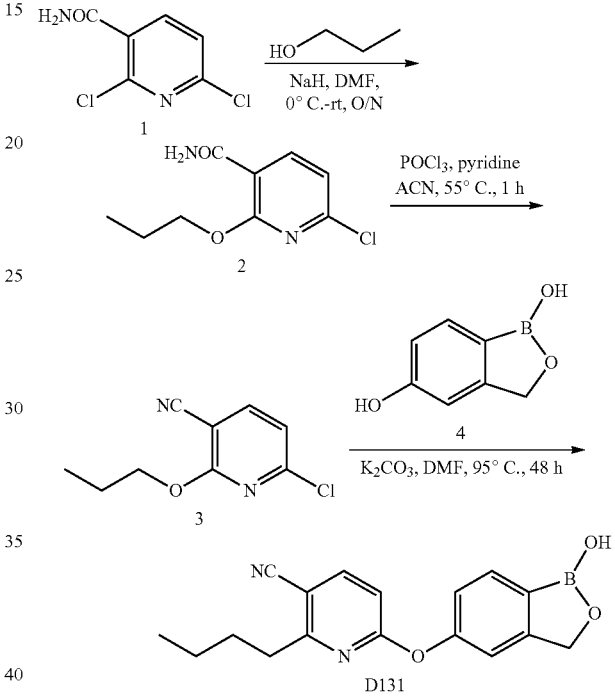

6-Chloro-2-propoxy-nicotinamide (2)

To a solution of propan-1-ol (2.94 mL, 39.26 mmol) in DMF (15 mL) at 0° C. was added sodium hydride (95% in mineral oil, 0.94 g, 39.26 mmol) in portions and stirred for 1 h at room temperature. This mixture was slowly added to a solution of 2,6-dichloro-nicotinamide (5.0 g, 26.17 mmol) in DMF (25 mL) at 0° C. The reaction mixture was stirred at room temperature overnight. DMF was removed under reduced pressure, and the resulting mixture was diluted with EtOAc (60 mL), washed with water (2×20 mL) and brine (2×10 mL) solution, dried over anhydrous Na₂SO₄, filtered, and concentrated to give yellow oil. Purification was accomplished by flash chromatography on silica gel using 5-60% EtOAc/hexanes gradient elution to yield the title compound (3.8 g, 68%) as a transparent oil. ¹H NMR (400 MHz, CDCl₃) δ ppm 8.46 (d, J=8.2 Hz, 1H), 7.69 (br. s., 1H), 7.06 (d, J=8.2 Hz, 1H), 5.86 (br. s., 1H), 4.48 (t, J=6.6 Hz, 2H), 1.99-1.79 (m, 2H), 1.07 (t, J=7.4 Hz, 3H).

6-Chloro-2-propoxy-nicotinonitrile (3)

To a solution of 6-chloro-2-propoxy-nicotinamide (3.80 g, 17.71 mmol) and pyridine (8.50 mL, 106.21 mmol) in acetonitrile (25 mL) was added phosphorus oxychloride (4.81 mL, 53.13 mmol) over a period of 5 min. The reaction was stirred at 55° C. for 1 h. Acetonitrile was evaporated in vacuo and the resulting residue was neutralized with 1N NaOH at 0° C. until pH reached to ~7. The reaction mixture was extracted with EtOAc (100 mL). The organic layer was collected and the aqueous layer was further extracted with EtOAc (3×50 mL). All organics were combined washed with brine (2×25 mL), dried over anhydrous Na$_2$SO$_4$, filtered, and concentrated to give yellow oil. Purification was accomplished by flash chromatography on silica gel using 5-25% EtOAc/hexanes gradient elution to yield the title compound (3.4 g, 98%) as a white solid. $^1$H NMR (400 MHz, DMSO-d$_6$) δ ppm 8.29 (d, J=7.9 Hz, 1H), 7.29 (d, J=7.9 Hz, 1H), 4.31 (t, J=6.5 Hz, 2H), 1.79-1.66 (m, 2H), 0.96 (t, J=7.5 Hz, 3H).

6-(1-Hydroxy-1,3-dihydro-benzo[c][1,2]oxaborol-5-yloxy)-2-isopropoxy-nicotinonitrile (D131)

To a mixture of 6-chloro-2-propoxy-nicotinonitrile (0.54 g, 3.0 mmol) and 3H-benzo[c][1,2]oxaborole-1,5-diol (0.40 g, 2.0 mmol) in DMF (10 mL) was added potassium carbonate (0.83 g, 6.0 mmol). The resulting suspension was heated at 95° C. for 48 h. DMF was removed under reduced pressure, the residue was diluted with EtOAc (50 mL), washed with water (10 mL) and brine (2×10 mL), dried over Na$_2$SO$_4$, filtered, and concentrated to give brown oil. Purification was accomplished by reverse phase preparative HPLC using MeOH/H$_2$O (0.1% AcOH) as the eluent to yield the title compound (0.25 g, 26%) as a white solid. $^1$H NMR (400 MHz, DMSO-d$_6$) δ ppm 9.25 (s, 1H), 8.24 (d, J=8.2 Hz, 1H), 7.79 (d, J=7.8 Hz, 1H), 7.29 (s, 1 H), 7.17-7.22 (m, 1H), 6.69 (d, J=8.6 Hz, 1H), 4.99 (s, 2H), 4.07 (t, J=6.8 Hz, 2H), 1.65-1.55 (m, 2H), 0.81 (t, J=7.4 Hz, 3H); MS (ES) m/z: 311 (M+1)$^+$; HPLC purity 98.36% (Maxplot), 97.66% (220 nm).

19ei 6-(1-hydroxy-1,3-dihydro-benzo[c][1,2]oxaborol-5-yloxy)-2-(2-hydroxy-ethylamino)-nicotinonitrile (D132)

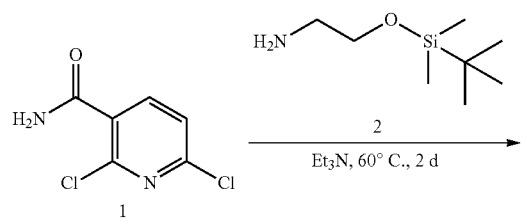

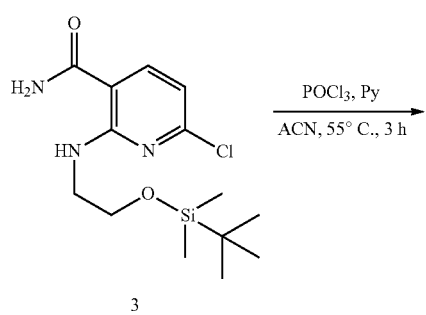

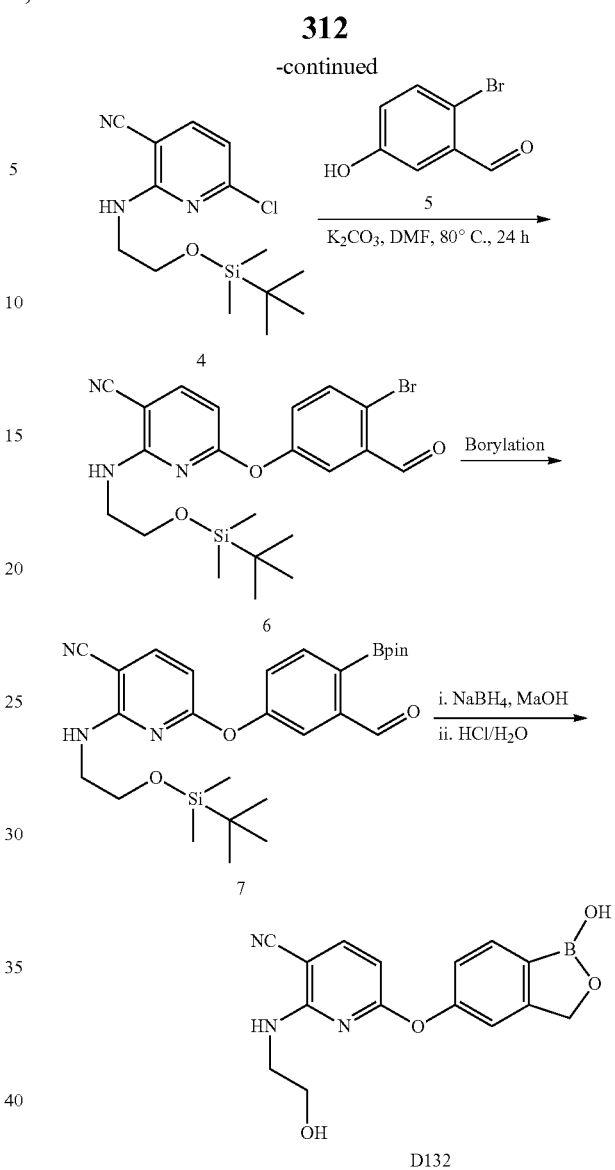

2-[2-(tert-Butyl-dimethyl-silanyloxy)-ethylamino]-6-chloro-nicotinamide (3)

To a solution of 2,6-dichloro-nicotinamide (1) (3 g, 15.7 mmol) in acetonitrile (anhydrous, 50 mL) were added 22-(tert-butyl-dimethyl-silanyloxy)-ethylamine (2) (2.75 g, 15.7 mmol) and triethylamine (2.2 mL, 15.7 mmol). The reaction was heated at 60° C. for 2 days. The solution was cooled to room temperature and filtered. The filtrate was concentrated in vacuo. Purification was accomplished by Biotage silica gel chromatography with 10%-100% EtOAc/hexanes to afford 2 g (40.6%) of the title compound.
$^1$H NMR (400 MHz, CHLOROFORM-d) δ ppm 8.64 (br. s., 1H), 7.51 (d, J=8.2 Hz, 1H), 6.47 (d, J=7.8 Hz, 1H), 5.66 (br. s., 2H), 3.79 (t, J=5.5 Hz, 2H), 3.62 (q, J=5.5 Hz, 2H), 0.91 (s, 9H), 0.07 (s, 6H).

2-[2-(tert-Butyl-dimethyl-silanyloxy)-ethylamino]-6-chloro-nicotinonitrile (4)

To a solution of 2-[2-(tert-butyl-dimethyl-silanyloxy)-ethylamino]-6-chloro-nicotinamide (3, 300 mg, 0.96 mmol)

in acetonitrile (anhydrous, 50 mL) were added pyridine (0.62 mL, 7.65 mmol) and POCl$_3$ (0.35 mL, 382 mmol). The reaction was heated at 60° C. for 1 hour. After cooling to room temperature, NaOH solution (10% aq.) was slowly added till pH 9. EtOAc (200 mL) was added and the layers separated. The aqueous layer was extracted with EtOAc (2×200 mL). The combined organic layer was dried over MgSO$_4$, filtered, and concentrated in vacuo. Purification was accomplished by silica gel chromatography, eluting with 1%-20% EtOAc/hexanes gradient, to afford 220 mg (78% yield) of the titled product.

$^1$H NMR (400 MHz, CHLOROFORM-d) δ ppm 7.48 (d, J=7.9 Hz, 1H), 6.51 (d, J=7.9 Hz, 1H), 5.62 (br. s., 1H), 3.71 (t, J=5.2 Hz, 2H), 3.54 (q, J=5.3 Hz, 2H), 0.83 (s, 9H), 0.00 (s, 6H).

6-(4-Bromo-3-formyl-phenoxy)-2-[2-(tert-butyl-dimethyl-silanyloxy)-ethylamino]-nicotinonitrile (6)

To a solution of 2-[2-(tert-butyl-dimethyl-silanyloxy)-ethylamino]-6-chloro-nicotinonitrile (4, 1.1 g, 3.5 mmol) in DMF (80 mL) were added 2-bromo-5-hydroxy-benzaldehyde (5, 0.75 g, 3.7 mmol) and K$_2$CO$_3$ (0.97 g, 7.05 mmol). The reaction was heated at 80° C. for 24 h. The DMF was removed in vacuo. Purification was accomplished by Biotage silica gel chromatography with 1%-3% EtOAc/hexanes gradient to afford 1.26 g (75% yield) of the title compound.

$^1$H NMR (400 MHz, CHLOROFORM-d) δ ppm 10.31 (s, 1H), 7.72 (d, J=2.8 Hz, 1H), 7.62 (dd, J=8.6, 3.8 Hz, 2H), 7.21-7.26 (m, 1H), 6.17 (d, J=8.3 Hz, 1H), 5.55 (t, J=4.9 Hz, 1H), 3.59 (t, J=5.3 Hz, 2H), 3.27 (q, J=5.2 Hz, 2H), 0.85 (s, 9H), 0.00 (s, 6H)

2-[2-(tert-Butyl-dimethyl-silanyloxy)-ethylamino]-6-[3-formyl-4-(4,4,5,5-tetramethyl-[1,3,2]dioxaborolan-2-yl)-phenoxy]-nicotinonitrile (7)

To a solution of 6-(4-bromo-3-formyl-phenoxy)-2-[2-(tert-butyl-dimethyl-silanyloxy)-ethylamino]-nicotinonitrile (6, 1.26 g, 2.65 mmol) in 1,4-dioxane (anhydrous, 150 mL) were added bispinacolatodiboron (0.807 g, 3.18 mmol), PdCl$_2$(dppf) (0.19 g, 0.26 mmol) and KOAc (0.78 g, 7.95 mmol). The solution was stirred at r.t. with N$_2$ bubbling for 30 minutes, then heated at 100° C. for 3 hours. The solution was filtered and concentrated in vacuo. Purification was accomplished by silica gel chromatography, eluting with 5%-25% EtOAc/hexanes gradient to afford 1.11 g (80% yield) of the title compound.

$^1$H NMR (400 MHz, CHLOROFORM-d) δ ppm 10.63 (s, 1H), 7.94 (d, J=8.2 Hz, 1H), 7.78 (d, J=1.9 Hz, 1H), 7.64 (d, J=8.2 Hz, 1H), 7.37 (dd, J=8.1, 2.1 Hz, 1H), 6.17 (d, J=8.2 Hz, 1H), 5.57 (br. s., 1H), 3.62 (t, J=5.1 Hz, 2H), 3.32 (q, J=5.1 Hz, 2H), 1.40 (s, 12H), 0.88 (s, 9H), 0.03 (s, 6H)

6-(1-hydroxy-1,3-dihydro-benzo[c][1,2]oxaborol-5-yloxy)-2-(2-hydroxy-ethylamino)-nicotinonitrile (D132)

To a solution of 2-[2-(tert-butyl-dimethyl-silanyloxy)-ethylamino]-6-[3-formyl-4-(4,4,5,5-tetramethyl-[1,3,2]dioxaborolan-2-yl)-phenoxy]-nicotinonitrile (7, 1.11 g, 2.12 mmol) in MeOH (anhydrous, 60 mL) was added NaBH$_4$ (0.48 g, 12.7 mmol). The reaction was stirred at r.t for 4 h, before the addition of HCl (1 M, 20 mL). After overnight stirring, all volatile components were removed. Purification was accomplished by preparative HPLC, eluting with 5%-90% ACN/water gradient, to afford 86.3 mg (13% yield) of the title compound as a white solid.

$^1$H NMR (400 MHz, DMSO-d$_6$) δ ppm 9.20 (s, 1H), 7.87 (d, J=8.6 Hz, 1H), 7.73 (d, J=8.2 Hz, 1H), 7.21 (s, 1H), 7.13-7.08 (m, 2H), 6.14 (d, J=8.2 Hz, 1H), 4.96 (s, 2H), 4.59-4.55 (m, 1H), 3.32-3.29 (m, 2H), 3.16-3.10 (m, 2H); ES MS: m/z 268 (M+H)$^+$; HPLC: 98.95% (220 nm), 98.66% (MaxPlot).

19ej 3-(cyclopentyloxy)-4-(1-hydroxy-1,3-dihydrobenzo[c][1,2]oxaborol-5-yloxy)benzonitrile (D133)

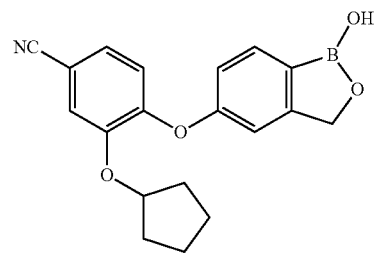 [SMILES: N#Cc1ccc(Oc2ccc3c(c2)COB3O)c(OC2CCCC2)c1]

A solution of 3-hydroxy-4-(1-hydroxy-1,3-dihydrobenzo[c][1,2]oxaborol-5-yloxy)benzonitrile (0.500 g, 1.87 mmol), cyclopentyl iodide (0.65 mL, 5.61 mmol), and N,N-dimethylformamide (30 mL) under a nitrogen balloon was cooled to 0° C. on an ice water bath. Sodium hydride (0.224 g, 5.61 mmol) was added and then the reaction was stirred for 5 minutes on the ice water bath. The reaction was then stirred at room temperature for 2 hours. More cyclopentyl iodide (0.22 mL, 1.87 mmol) was added and the reaction was cooled to 0° C. on an ice water bath. Sodium hydride was added (0.075 g, 1.87 mmol) and the reaction was stirred at 0° C. for 5 minutes. The reaction was then stirred at room temperature for another 2 hours. Water was added to quench excess sodium hydride and the reaction was then neutralized using 1 M HCl. Water was added and the solution was extracted using ethyl acetate. The organic layer was washed with water, brine, dried over anhydrous sodium sulfate, and filtered. The solvent was removed under reduced pressure. The residue was purified by silica gel column using Combiflash to give 3-(cyclopentyloxy)-4-(1-hydroxy-1,3-dihydrobenzo[c][1,2]oxaborol-5-yloxy)benzonitrile (0.396 g, 63% yield). $^1$H NMR (400 MHz, DMSO-d$_6$) δ ppm 1.25 (m, 2H), 1.38 (m, 2H), 1.50 (m, 2H), 1.73 (m, 2H), 4.86 (m, 2H), 6.84 (s, 1H), 6.87 (d, J=8.2 Hz, 1H), 7.18 (d, J=8.2 Hz, 1H), 7.40 (d, J=8.4 Hz, 1H), 7.58 (s, 1H), 7.64 (d, J=8.0 Hz, 1H), 9.06 (s, 1H).

19ek 3-(cyclopropylmethoxy)-4-(1-hydroxy-1,3-dihydrobenzo[c][1,2]oxaborol-5-yloxy)benzonitrile (D134)

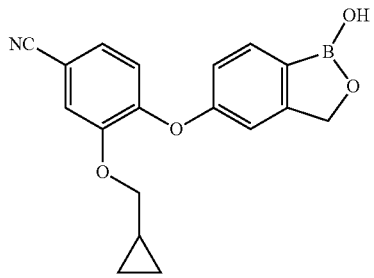 [SMILES: N#Cc1ccc(Oc2ccc3c(c2)COB3O)c(OCC2CC2)c1]

A solution of bromomethyl cyclopropane (0.544 mL, 5.61 mmol), sodium iodide (4.20 g, 28.05 mmol), and N,N-dimethylformamide (30 mL) under a nitrogen balloon were stirred at 70° C. for 3 hours. The reaction was cooled to room temperature and 3-hydroxy-4-(1-hydroxy-1,3-dihydrobenzo[c][1,2]oxaborol-5-yloxy)benzonitrile (0.500 g, 1.87 mmol) and more N,N-dimethylformamide (30 mL) was added. The reaction was cooled to 0° C. in an ice water bath and sodium hydride (0.224 g, 5.61 mmol) was added. The reaction was stirred under nitrogen balloon at 0° C. for 5 minutes and then at room temperature overnight. Water was added to quench excess sodium hydride and the solution was neutralized using 1 M HCl. Water was added and the solution was extracted using ethyl acetate. The organic layer was washed with water, brine, dried over anhydrous sodium sulfate, and filtered. The solvent was removed under reduced pressure. The residue was purified by silica gel column using Combiflash to give 3-(cyclopropylmethoxy)-4-(1-hydroxy-1,3-dihydrobenzo[c][1,2]oxaborol-5-yloxy)benzonitrile (0.225 g, 37% yield). $^1$H NMR (400 MHz, DMSO-d$_6$) δ ppm 0.15 (d, J=4.5 Hz, 2H), 0.43 (d, J=7.6 Hz, 2H), 1.06 (septet, J=6.7 Hz, 1H), 3.90, (d, J=6.9 Hz, 1H), 4.91 (s, 2H), 6.95 (m, 2H), 7.13 (d, J=8.2 Hz, 1H), 7.42 (d, J=8.4 Hz, 1H), 7.62 (s, 1H), 7.70 (d, J=8.6 Hz, 1H), 9.12 (s, 1H).

19el 3-(cyclopentylmethoxy)-4-(1-hydroxy-1,3-dihydrobenzo[c][1,2]oxaborol-5-yloxy)benzonitrile (D135)

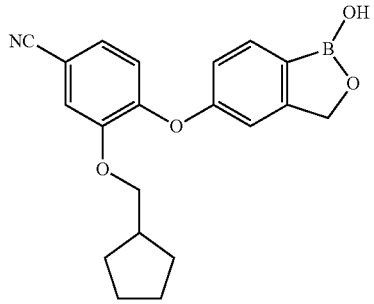 [SMILES: N#Cc1ccc(Oc2ccc3c(c2)COB3O)c(OCC2CCCC2)c1]

This compound was prepared in the similar manner to that of D133.

ES(–)MS m/z=348 (M–H)$^-$; $^1$H NMR (400 MHz, DMSO-d$_6$) δ ppm 1.05 (m, 2H), 1.37 (m, 4H), 1.47 (m, 2H), 2.07 (septet, J=7.2 Hz, 1H), 3.88 (d, J=6.4 Hz, 2H), 4.88 (s, 2H), 6.88 (s, 1H), 6.90 (dd, J=8.1, 2.2 Hz, 1H), 7.21 (d, J=8.4 Hz, 1H), 7.45 (dd, J=8.2, 2.0 Hz, 1H), 7.66 (m, 2H), 9.08 (s, 1H).

19em 6-(1-Hydroxy-1,3-dihydro-benzo[c][1,2]oxaborol-5-yloxy)-2-isobutoxy-nicotinonitrile (D136)

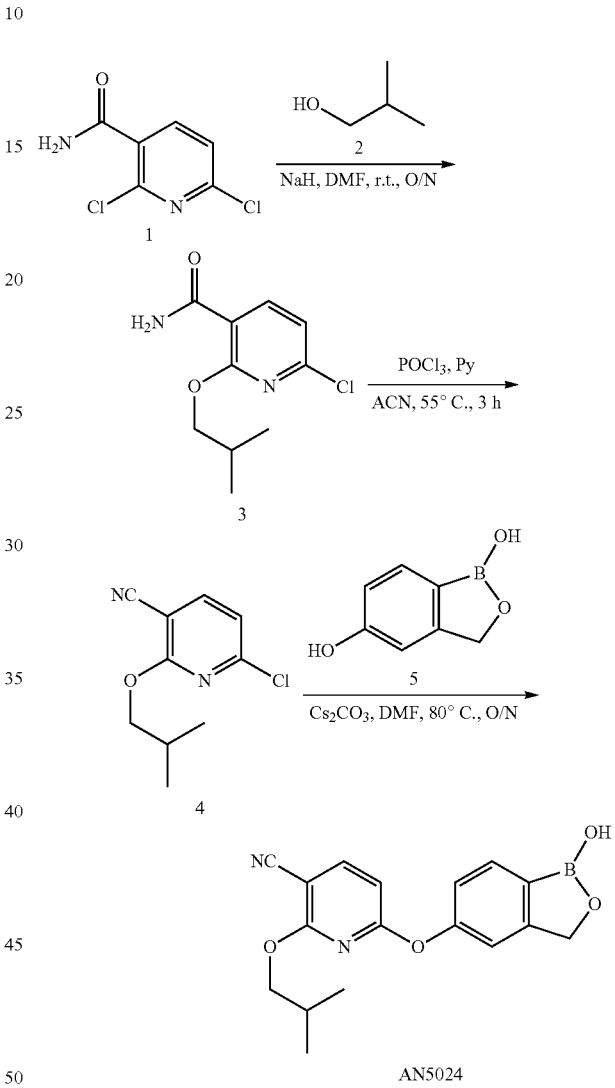

6-Chloro-2-isobutoxy-nicotinamide (3)

To a solution of 2,6-dichloro-nicotinamide (1) (3 g, 15.7 mmol) in acetonitrile (anhydrous, 30 mL) were added 2-methyl-propan-1-ol (2) (1.22 g, 16.5 mmol) and NaH (0.42 g, 16.5 mmol). The reaction was kept at r.t. O/N. The suspension was filtered and the filtrate was concentrated in vacuo. The residue was purified by Biotage silica gel chromatography with 10%-80% EtOAc/hexanes gradient elution to afford 2.39 g (66% yield) of the title compound.
$^1$H NMR (400 MHz, CHLOROFORM-d) δ ppm 8.46 (d, J=7.8 Hz, 1H), 7.70 (br. s., 1H), 7.06 (d, J=7.8 Hz, 1H), 6.09 (br. s., 1H), 4.30 (d, J=6.6 Hz, 2H), 2.25-2.11 (m, 1H), 1.07 (d, J=6.6 Hz, 6H).

6-Chloro-2-isobutylamino-nicotinonitrile (4)

To a solution of 6-chloro-2-isobutoxy-nicotinamide (3, 2.39 g, 10.4 mmol) in acetonitrile (anhydrous, 150 mL) were added pyridine (6.75 mL, 83.5 mmol) and POCl₃ (3.82 mL, 41.7 mmol). The reaction was heated at 55° C. for 3 hours. After cooling to room temperature, NaOH solution (10% aq.) was slowly added till pH 9. EtOAc (60 mL) was added and the layers separated. The aqueous layer was extracted with EtOAc (2×60 mL). The combined organic layer was dried over MgSO₄, filtered, and concentrated in vacuo. Purification was accomplished by silica gel chromatography, eluting with 2%-30% EtOAc/hexanes gradient, to afford 2 g (91% yield) of the title product.

¹H NMR (400 MHz, CHLOROFORM-d) δ ppm 7.80 (d, J=8.0 Hz, 1H), 6.99 (d, J=8.0 Hz, 1H), 4.20 (d, J=6.6 Hz, 2H), 2.21-2.09 (m, 1H), 1.05 (d, J=6.6 Hz, 6H).

6-(1-Hydroxy-1,3-dihydro-benzo[c][1,2]oxaborol-5-yloxy)-2-isobutoxy-nicotinonitrile (D136)

To a solution of 6-chloro-2-isobutylamino-nicotinonitrile (4, 1.12 g, 5.33 mmol) in DMF (anhydrous, 30 mL) were added 3H-benzo[c][1,2]oxaborole-1,5-diol (400 mg, 2.67 mmol) and Cs₂CO₃ (1.91 g, 5.87 mmol). The reaction was heated at 80° C. for 2 h by microwave. Then DMF was evaporated in vacuo. Purification was accomplished by preparative HPLC, eluting with 5%-90% ACN/water gradient, to afford 250 mg (29% yield) of the title compound as a white solid.

¹H NMR (400 MHz, DMSO-d₆) δ ppm 9.23 (br s, 1H), 8.20 (d, J=8.2 Hz, 1H), 7.77 (d, J=7.9 Hz, 1H), 7.17 (d, J=8.0 Hz, 1H), 6.66 (d, J=8.6 Hz, 1H), 4.97 (s, 2H), 3.89 (d, J=6.6 Hz, 2H), 1.95-1.80 (m, 1H), 0.80 (d, J=6.6 Hz, 6H); ES MS: m/z 323 (M−H)⁻; HPLC: 99.25% (220 nm), 99.43% (MaxPlot).

19en 5-[2-Cyano-4-(formylaminomethyl)phenoxy]-1,3-dihydro-1-hydroxy-2,1-benzoxaborole (D137)

This compound was prepared from 2-fluoro-5-formylbenzonitrile and 4-bromo-3-hydroxymethylphenol in the similar manner to that of D25.

¹H NMR (300 MHz, DMSO-d₆) ppm 4.30 (d, J=6.2 Hz, 2H), 4.94 (s, 2H), 7.0-7.1 (m, 3H), 7.56 (dd, J=8.8, 1.2 Hz, 1H), 7.7-7.8 (m, 2H), 8.13 (s, 1H), 8.56 (br s, 1H), 9.21 (s, 1H).

19eo 5-(2-Aminomethyl-4-cyanophenoxy)-1,3-dihydro-1-hydroxy-2,1-benzoxaborole hydrochloride (D138)

This compound was prepared from D137 in the similar manner to that of D26.

¹H NMR (300 MHz, DMSO-d₆) δ ppm 4.04 (br s, 2H), 4.96 (s, 2H), 7.06-7.16 (m, 3H), 8.05 (d, J=2.3 Hz, 1H), 8.45 (br s, 3H), 9.27 (s, 1H).

19ep Methyl 4-(1,3-dihydro-1-hydroxy-2,1-benzoxaborol-5-yloxy)-3-fluorobenzoate (D139)

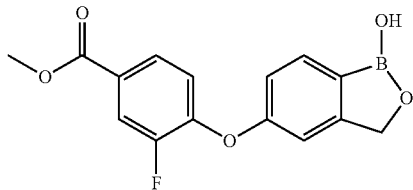 [SMILES: COC(=O)c1ccc(Oc2ccc3c(c2)COB3O)c(F)c1]

Step 1

A mixture of 4-bromo-3-(1,3-dioxolan-2-yl)phenol (7.1 g, 29 mmol, 1 eq), 3,4-difluoro-methylbenzorate (5 g, 29 mmol, 1 eq), potassium carbonate (6 g, 43.5 mmol, 1.5 eq) in DMF (29 mL). Reaction was stirred at 100° C. over night. TLC showed that reaction was completed. After cooling to room temperature, the residue was removed by filtration. The residue was washed with EtOAc. The organics were combined and concentrated via Rota vapor. The residue was poured into ETOAC and water. The Organic layers was separated and washed with brine and dried over sodium sulfate anhydrous. Filter and concentrated to get the titled compound as crude, light brown oil, which was used for next step without purification.

Step 2

-continued

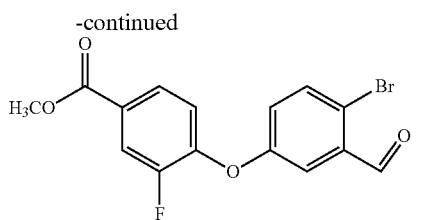

To a solution of methyl 4-(4-bromo-3-(1,3-dioxolan-2-yl)phenoxy)-3-fluorobenzoate in 30 mL of THF was added 20 ml of 3M HCl (made from 6M HCl and water 1:1), refluxed for 2 hour. TLC showed no SM (Hexane: EtOAc 7:3). The reaction was cooled to RT. Add 1N NaOH (60 ml), Rota vapor to remove half of the solvent, extracted with EtOAc. The organics were washed with water, brine, dried over Na2SO4, filtered, and concentrated to get light brown oil. Standby over weekend to get solidified solid. Filtered, washed with Hexane/EtOAc to collect the off-white powder 10.2 g 99.6 Yield % (two steps)

Step 3

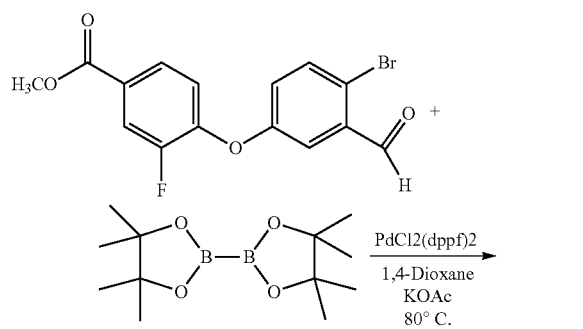

To a solution of methyl 4-(4-bromo-3-formylphenoxy)-3-fluorobenzoate; (10 g, 28.3 mmol), KOAc (8.33 g, 84.9 mmol), bis(pinacolato)diboron (8.63 g, 34 mmol) in anhydrous 1,4-dioxane (120 mL) was added PdCl2(dppf)2 (578 mg; 2.5 mol % CAS#72287-26-4, Aldrich catalog#379670). The reaction mixture was degassed with $N_2$, and then heated at 80° C. with magnetic stirring. The reaction was monitored with TLC and was completed overnight. The mixture was cooled to room temperature, filtered through celite and washed with ethyl acetate and then evaporated. The residue was dissolved in minimum EtOAc and passed through a very short but big silica gel column eluted with a mixed solvent of hexane: EtOAc (3:1, v/v) to remove dark color giving light yellow oil. Chromatography on silica gel again (Hexane/EtOAc 7:3). The first portion is white solid, NMR indicated as bis(pinacolato)diboron (no aromatic signals). The product was collected and concentrated to afford methyl 3-fluoro-4-(3-formyl-4-(4,4,5,5-tetramethyl-1,3,2-dioxaborolan-2-yl)phenoxy)benzoate as colorless oil 9.5 g. Yield 84% $^1$H NMR (DMSO-d6, 300 MHz): δ=10.38 (s, 1H), 7.91 (dd, J=2.1, 13.2 Hz, 1H), 7.82 (d, J=7.8 Hz, 2H), 7.42 (d, J=2.7 Hz, 2H), 7.32 (d, J=8.4 Hz, 1H), 3.85 (s, 3H), and 1.32 (s, 12H) ppm.

Step 4

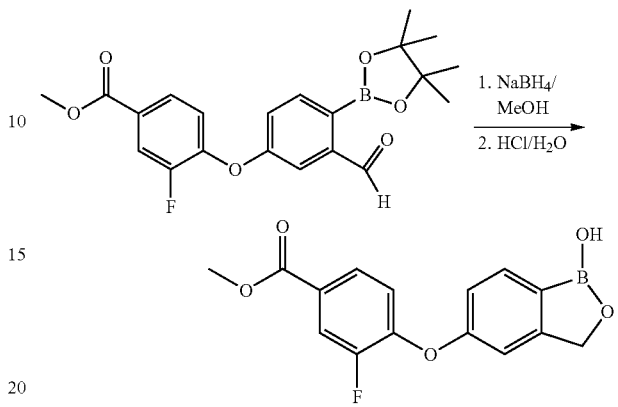

To a solution of methyl 3-fluoro-4-(3-formyl-4-(4,4,5,5-tetramethyl-1,3,2-dioxaborolan-2-yl)phenoxy)benzoate (5 g, 12.5 mmol) in MeOH (125 mL) was added NaBH$_4$ (709 mg; 18.75 mmol) in portions under N2 at 0° C. in an ice-bath. The reaction was stirred at 0° C. to room temperature. The reaction was monitored with TLC and was completed overnight. The mixture was cooled to rt. Solvent was evaporated to half volume via Rota vapor. The mixture was then cooled to 0° C., and quenched by adding water (12 mL) following by adding 6 N HCl(12 mL). Stirred at rt for 30 min, white Solid precipitated out. Filtered. The solid was gummy. The solid was suspended in water, sonicated for 1 hr. Filtered, washed with more water. Filtered, dried to get white solid. D139 (2.1 g). Yield 55.7%. M.p. 149-152° C. MS (ESI): m/z=303 (M+1, positive) and 301 (M−1, negative). HPLC (220 nm): 97.27% purity. (254 nM): 97.29% purity $^1$H NMR (DMSO-d6, 300 MHz): δ=9.19 (s, 1H), 7.88 (dd, J=1.8, 11.1 Hz, 1H), 7.80 (d, J=8.4 Hz, 1H), 7.75 (d, J=8.1 Hz, 1H), 7.21 (d, J=8.4 Hz, 1H), 7.07 (d, J=8.4 Hz, 2H), 4.93 (s, 2H), and 3.84 (s, 3H).

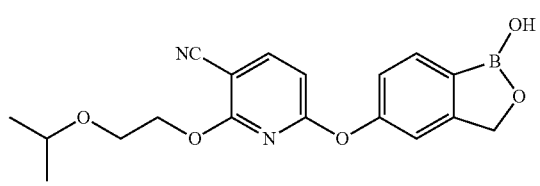 [SMILES: CC(C)OCCOc1nc(Oc2ccc3c(c2)COB3O)ccc1C#N]

19eq D140

This compound is made in a similar manner to D130 using 2-isopropoxyethanol instead of propanol.

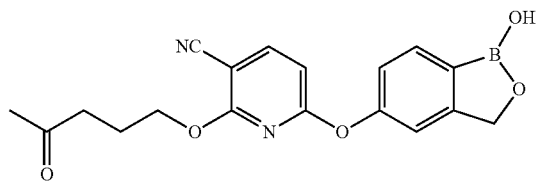 [SMILES: CC(=O)CCCOc1nc(Oc2ccc3c(c2)COB3O)ccc1C#N]

19er D141

This compound is made in a similar manner to D130 using 3-acetylpropanol instead of propanol.

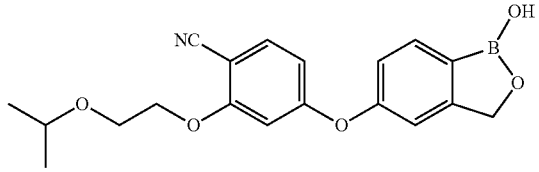 [SMILES: CC(C)OCCOc1cc(Oc2ccc3c(c2)COB3O)ccc1C#N]

19es D142

This compound is made from D10 and 2-isopropoxyethanol by Mitsunobu reaction.

19et D143

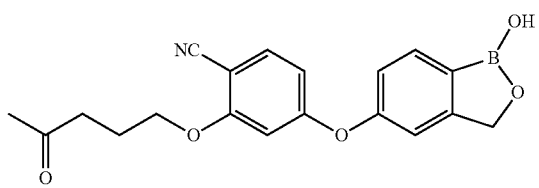 [SMILES: CC(=O)CCCOc1cc(Oc2ccc3c(c2)COB3O)ccc1C#N]

This compound is made from D10 and 3-acetylpropanol by Mitsunobu reaction.

19eu D144

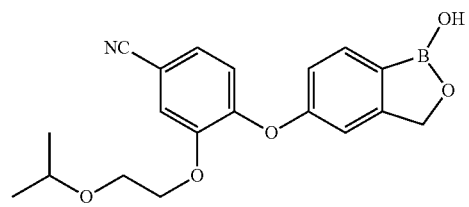 [SMILES: CC(C)OCCOc1cc(C#N)ccc1Oc1ccc2c(c1)COB2O]

This compound is made from D14 and 2-isopropoxyethanol by Mitsunobu reaction.

19ev D145

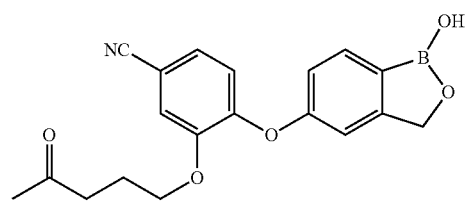 [SMILES: CC(=O)CCCOc1cc(C#N)ccc1Oc1ccc2c(c1)COB2O]

This compound is made from D14 and 3-acetylpropanol by Mitsunobu reaction.

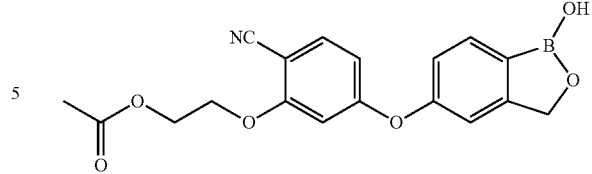

19ew D146

This compound is made from D10 and 2-hydroxyethyl acetate by Mitsunobu reaction.

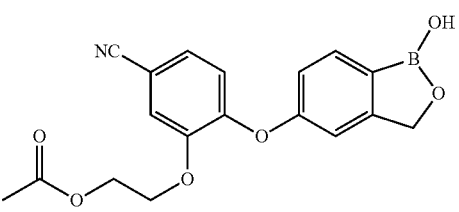 [SMILES: CC(=O)OCCOc1cc(C#N)ccc1Oc1ccc2c(c1)COB2O]

19ex D147

This compound is made from D14 and 2-hydroxyethyl acetate by Mitsunobu reaction.

N-[4-(1-Hydroxy-1,3-dihydro-benzo[c][1,2]oxaborol-5-yloxy)-benzyl]-4-methyl-benzenesulfonamide (D148)

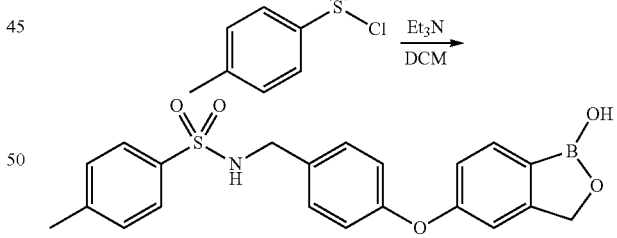

To a 20 mL scintillation vial containing 5-(4-aminomethyl-phenoxy)-3H-benzo[c][1,2]oxaborol-1-ol (144 mg, 0.56 mmol, 1.1 eq.), 4-methyl-benzenesulfonyl chloride (118.4 mg, 0.62 mmol, 1.1 eq.) in DCM (10.0 mL) was added $Et_3N$ (160 µL, 1.12 mmol, 2.0 eq.) drop wise. The mixture was stirred at room temperature overnight. The mixture was carefully treated with aqu. $NH_4Cl$ (10 mL) and the layers were separated. The aqueous was extracted with DCM (2×5 mL), combined organic phase was washed with $H_2O$ (10 mL), brine (10 mL), dried over $MgSO_4$, filtered and the filtrate was concentrated under reduced pressure. The residue was applied to silica chromatography eluting with EtOAc/Heptanes (0:100 to 80:20) to give N-[4-(1-hydroxy-1,3-dihydrobenzo[c][1,2]oxaborol-5-yloxy)-benzyl]-4-methyl-benzene-sulfonamide as a white solid. LCMS (m/z) 432 (M+23); $^1$H NMR (400 MHz, DMSO-d$^6$) δ ppm $^1$H NMR (DMSO-d$_6$) δ: 9.11 (s, 1H), 8.08 (t, J=6.3 Hz, 1H), 7.65-7.74 (m, 3H), 7.38 (d, J=8.0 Hz, 2H), 7.23-7.31 (m, J=8.6 Hz, 2H), 6.95-7.00 (m, 2H), 6.89-6.95 (m, 2H), 4.92 (s, 2H), 3.95 (d, J=6.3 Hz, 2H), 2.38 (s, 3H).

3-Chloro-N-[4-(1-hydroxy-1,3-dihydro-benzo[c][1,2]oxaborol-5-yloxy)-benzyl]-benzenesulfonamide (D149)

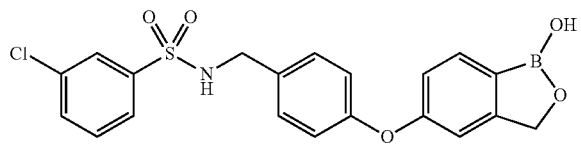 [SMILES: O=S(=O)(NCc1ccc(Oc2ccc3c(c2)COB3O)cc1)c1cccc(Cl)c1]

D149 was prepared using a procedure similar to that of D148. LCMS (m/z) 452 (M+23); $^1$H NMR (DMSO-d$_6$) δ: 9.11 (s, 1H), 8.36 (t, J=6.3 Hz, 1H), 7.66-7.77 (m, 4H), 7.59 (t, J=8.1 Hz, 1H), 7.25 (d, J=8.6 Hz, 2H), 6.87-6.98 (m, 4H), 4.93 (s, 2H), 4.05 (d, J=6.3 Hz, 2H).

2-Chloro-N-[4-(1-hydroxy-1,3-dihydro-benzo[c][1,2]oxaborol-5-yloxy)-benzyl]-benzenesulfonamide (D150)

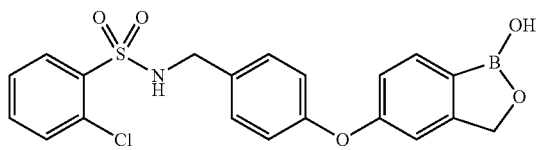 [SMILES: O=S(=O)(NCc1ccc(Oc2ccc3c(c2)COB3O)cc1)c1ccccc1Cl]

D150 was prepared using a procedure similar to that of D148. LCMS (m/z) 452 (M+23); $^1$H NMR (DMSO-d$_6$) δ: 9.11 (s, 1H), 8.45 (t, J=6.2 Hz, 1H), 7.88-7.93 (m, 1H), 7.71 (d, J=8.0 Hz, 1H), 7.57-7.61 (m, 2H), 7.44-7.51 (m, 1H), 7.23 (d, J=8.6 Hz, 2H), 6.84-6.92 (m, 4H), 4.94 (s, 2H), 4.11 (d, J=6.2 Hz, 2H).

N-[4-(1-Hydroxy-1,3-dihydro-benzo[c][1,2]oxaborol-5-yloxy)-benzyl]-methanesulfonamide (D151)

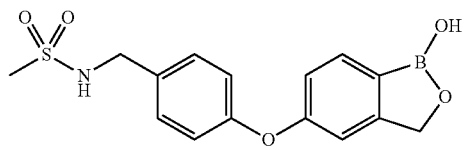 [SMILES: CS(=O)(=O)NCc1ccc(Oc2ccc3c(c2)COB3O)cc1]

D151 was prepared using a procedure similar to that of D148. LCMS (m/z) 356 (M+23); $^1$H NMR (DMSO-d$_6$) δ: 9.08 (s, 1H), 7.69 (d, J=7.9 Hz, 1H), 7.52 (t, J=6.3 Hz, 1H), 7.33-7.39 (m, J=8.6 Hz, 2H), 7.00-7.07 (m, 2H), 6.90-6.97 (m, 2H), 4.90 (s, 2H), 4.13 (d, J=6.3 Hz, 2H), 2.85 (s, 3H).

5-(5-Aminomethyl-pyridin-2-yloxy)-3H-benzo[c][1,2]oxaborol-1-ol (D152)

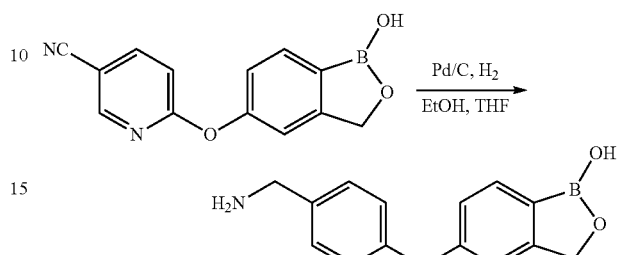

To a 50 mL round-bottom flask fitted with magnetic stirring bar was added 6-(1-hydroxy-1,3-dihydro-benzo[c][1,2]oxaborol-5-yloxy)-nicotinonitrile (1.0 g, 4.0 mmol, 1.0 eq.), followed by addition of EtOH (40 mL) and THF (15 mL). The flask was evacuated and recharged with N$_2$ twice. To the stirring solution was added 5% Pd/C (300 mg) and the flask was evacuated and recharged with H$_2$ three times. The resulting suspension was stirred under a H$_2$ balloon at room temperature over 3 days. The mixture was filtered through a short pack of celite and washed with EtOH (3×25 mL). The combined filtrate was concentrated under reduced pressure, the residue was applied to silica chromatography eluting with MeOH/DCM (0:100 to 10:90) to give a white solid. The solid was dissolved in minimum amount of MeOH and carefully treated with HCl in Et$_2$O. The precipitate was collected by filtration and washed with Et$_2$O to give 5-(5-aminomethyl-pyridin-2-yloxy)-3H-benzo[c][1,2]oxaborol-1-ol hydrochloride a white solid. $^1$H NMR (DMSO-d$_6$) δ: 9.95 (br. s., 1H), 8.28 (d, J=2.2 Hz, 1H), 8.11 (dd, J=8.5, 2.4 Hz, 1H), 7.75 (d, J=8.0 Hz, 1H), 7.07-7.14 (m, 2H), 7.05 (dd, J=7.9, 2.0 Hz, 1H), 4.94 (s, 2H), 4.14 (t, J=5.6 Hz, 2H).

5-{4-[(Cyclohexylmethyl-amino)-methyl]-phenoxy}-3H-benzo[c][1,2]oxaborol-1-ol (D153)

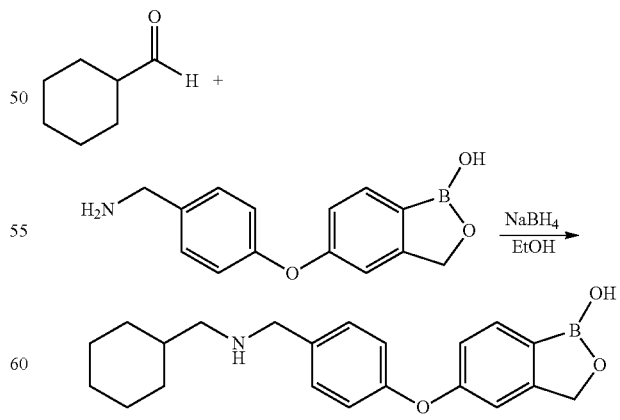

To a solution of 5-(4-aminomethyl-phenoxy)-3H-benzo[c][1,2]oxaborol-1-(150 mg, 0.59 mmol, 1.0 eq.) in EtOH (5.0 mL) was added cyclohexanecarbaldehyde (280 μL, 2.36 mmol, 4.0 eq.). The mixture was stirred at room temperature for 30 minutes. After cooling to 0° C., NaBH₄ (89 mg, 0.36 mmol, 4.0 eq.) was added in portions and the mixture was allowed to warm to room temperature and stirred for 2 h. The mixture was carefully treated with dilute HCl (5 mL) and aqueous phase was extracted with EtOAc (3×10 mL). Combined organic extracts was washed with brine (10 mL), dried over MgSO₄, filtered and the filtrate was concentrated under reduced pressure. The residue was applied to silica chromatography eluting with MeOH/DCM (0:100 to 10:90) to give 5-{4-[(cyclohexylmethyl-amino)-methyl]-phenoxy}-3H-benzo[c][1,2]oxaborol-1-ol as a white solid. LCMS (m/z) 352 (M+H); ¹H NMR (DMSO-d₆) δ: 9.08 (s, 1H), 7.68 (d, J=8.0 Hz, 1H), 7.30-7.37 (m, J=8.5 Hz, 2H), 6.95-7.02 (m, 2H), 6.88-6.95 (m, 2H), 4.89 (s, 2H), 3.64 (s, 2H), 2.31 (d, J=6.6 Hz, 2H), 1.67-1.77 (m, 2H), 1.56-1.66 (m, 3H), 1.30-1.44 (m, 1H), 1.02-1.23 (m, 3H), 0.77-0.91 (m, 2H).

5-(4-Cyclohexylaminomethyl-phenoxy)-3H-benzo[c][1,2]oxaborol-1-ol (D154)

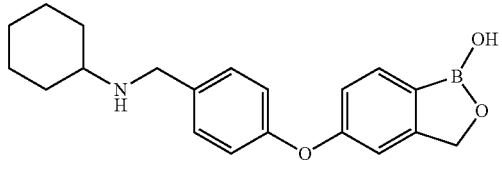 [SMILES: OB1OCc2cc(Oc3ccc(CNC4CCCCC4)cc3)ccc21]

D154 was prepared using a procedure similar to that of D153. LCMS (m/z) 338 (M+H); ¹H NMR (DMSO-d₆) δ: 9.08 (br. s., 1H), 7.68 (d, J=8.0 Hz, 1H), 7.31-7.38 (m, J=8.5 Hz, 2H), 6.95-7.00 (m, 2H), 6.89-6.95 (m, 2H), 4.89 (s, 2H), 3.68 (s, 2H), 2.35 (tt, J=9.9, 3.7 Hz, 1H), 1.78-1.88 (m, 2H), 1.59-1.70 (m, 2H), 1.47-1.56 (m, 1H), 0.97-1.22 (m, 5H).

5-(4-{[(1H-Pyrrol-2-ylmethyl)-amino]-methyl}-phenoxy)-3H-benzo[c][1,2]oxaborol-1-ol (D155)

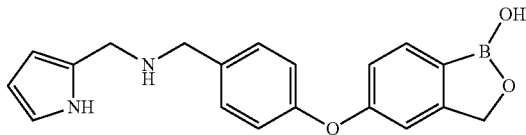 [SMILES: OB1OCc2cc(Oc3ccc(CNCc4ccc[nH]4)cc3)ccc21]

D155 was prepared using a procedure similar to that of D153. LCMS (m/z) 335 (M+H); ¹H NMR (DMSO-d₆) δ: 9.08 (br. s., 1H), 7.68 (d, J=7.9 Hz, 1H), 7.32-7.38 (m, J=8.5 Hz, 2H), 6.96-7.02 (m, 2H), 6.89-6.96 (m, 2H), 6.61 (td, J=2.6, 1.6 Hz, 1H), 5.89 (q, J=2.6 Hz, 1H), 5.83-5.87 (m, 1H), 4.90 (s, 2H), 4.07 (br. s., 1H), 3.63 (s, 2H), 3.60 (s, 2H), 3.31 (br. s., 1H).

5-{4-[(2-Bromo-benzylamino)-methyl]-phenoxy}-3H-benzo[c][1,2]oxaborol-1-ol (D156)

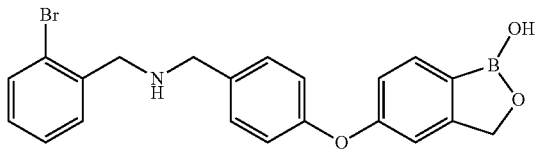 [SMILES: OB1OCc2cc(Oc3ccc(CNCc4ccccc4Br)cc3)ccc21]

D156 was prepared using a procedure similar to that of D153. LCMS (m/z) 424 (M⁺); ¹H NMR (CHLOROFORM-d) δ: 7.71 (br. s., 1H), 7.55 (d, J=7.9 Hz, 1H), 7.41 (dd, J=7.6, 1.5 Hz, 1H), 7.36 (d, J=8.4 Hz, 2H), 7.26-7.32 (m, 1H), 7.10-7.19 (m, 2H), 7.01 (d, J=8.5 Hz, 3H), 6.96 (br. s., 1H), 6.89 (s, 1H), 5.29 (br. s., 1H), 5.04 (br. s., 2H), 3.92 (s, 2H), 3.81 (s, 2H).

5-{4[(3-Bromo-benzylamino)-methyl]-phenoxy}-3H-benzo[c][1,2]oxaborol-1-ol (D157)

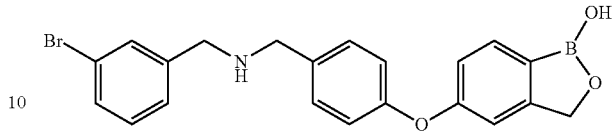

D157 was prepared using a procedure similar to that of D153. LCMS (m/z) 424 (M⁺); ¹H NMR (CHLOROFORM-d) δ: 7.68 (br. s., 1H), 7.52 (s, 1H), 7.38 (dt, J=7.9, 1.4 Hz, 1H), 7.33 (d, J=8.5 Hz, 2H), 7.26-7.29 (m, 1H), 7.19 (t, J=7.7 Hz, 1H), 6.96-7.03 (m, 1H), 7.01 (d, J=8.5 Hz, 2H), 6.89 (s, 1H), 5.02 (br. s., 2H), 3.80 (d, J=5.5 Hz, 4H), 2.17 (s, 1H).

5-{4-[(2-Methoxy-benzylamino)-methyl]-phenoxy}-3H-benzo[c][1,2]oxaborol-1-ol (D158)

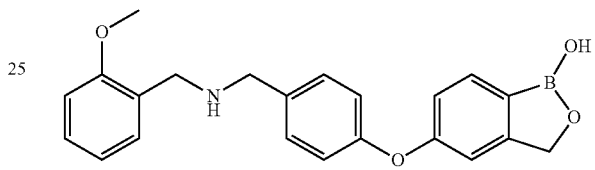

D158 was prepared using a procedure similar to that of D153. LCMS (m/z) 376 (M+H); ¹H NMR (CHLOROFORM-d) δ: 7.64 (s, 1H), 7.34 (d, J=8.4 Hz, 2H), 7.27 (s, 1H), 7.24 (br. s., 1H), 6.85-7.02 (m, 6H), 5.00 (s, 2H), 3.85 (s, 2H), 3.83 (s, 3H), 3.78 (s, 2H), 2.16 (s, 1H).

5-[4-(Benzylamino-methyl)-phenoxy]-3H-benzo[c][1,2]oxaborol-1-ol (D159)

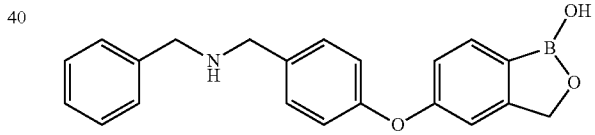

D159 was prepared using a procedure similar to that of D153. LCMS (m/z) 346 (M+H); ¹H NMR (CHLOROFORM-d) δ: 7.66 (br. s., 1H), 7.31-7.38 (m, 6H), 7.28 (d, J=2.5 Hz, 0H), 6.99 (s, 3H), 6.88 (br. s., 1H), 5.01 (s, 2H), 3.88 (s, 1H), 3.84 (s, 2H), 3.81 (s, 2H).

5-{4-[(2-Methyl-benzylamino)-methyl]-phenoxy}-3H-benzo[c][1,2]oxaborol-1-ol (D160)

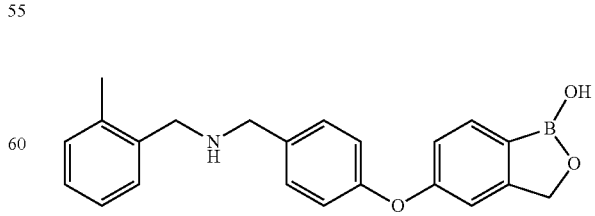

D160 was prepared using a procedure similar to that of D153. LCMS (m/z) 360 (M+H); ¹H NMR (CHLOROFORM-d) δ: 7.64-7.72 (m, 1H), 7.32-7.39 (m, 3H), 7.18 (dd, J=5.3, 3.4 Hz, 2H), 7.14-7.21 (m, 1H), 6.98 (d, J=8.5 Hz, 3H), 6.87 (s, 1H), 4.99 (s, 2H), 3.94 (d, J=1.4 Hz, 4H), 2.30 (s, 3H).

5-[4-(Isopropylamino-methyl)-phenoxy]-3H-benzo[c][1,2]oxaborol-1-ol (D161)

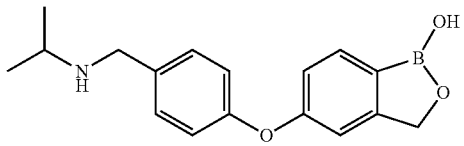 [SMILES: CC(C)NCc1ccc(Oc2ccc3c(c2)COB3O)cc1]

D161 was prepared using a procedure similar to that of D153. LCMS (m/z) 298 (M+H); $^1$H NMR (CHLOROFORM-d) δ: 7.61 (d, J=8.4 Hz, 3H), 6.99 (d, J=8.1 Hz, 2H), 6.85 (br. s., 2H), 5.00 (s, 2H), 3.98 (s, 2H), 2.15 (s, 1H), 1.42 (d, J=6.5 Hz, 6H).

3-{[4-(1-Hydroxy-1,3-dihydro-benzo[c][1,2]oxaborol-5-yloxy)-benzylamino]-methyl}-benzonitrile (D162)

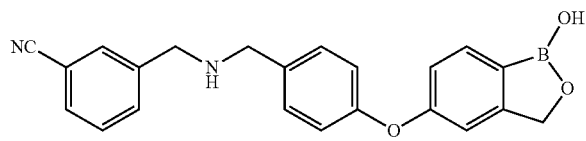 [SMILES: N#Cc1cccc(CNCc2ccc(Oc3ccc4c(c3)COB4O)cc2)c1]

D162 was prepared using a procedure similar to that of D153. LCMS (m/z) 239 (M−131); $^1$H NMR (DMSO-d$_6$) δ: 9.86 (br. s., 1H), 9.15 (br. s., 1H), 8.06 (s, 1H), 7.83-7.93 (m, 2H), 7.65-7.75 (m, 1H), 7.58-7.65 (m, 3H), 7.07 (d, J=8.6 Hz, 1H), 7.04-7.10 (m, 1H), 6.93-6.99 (m, 2H), 4.91 (s, 2H), 4.14 (br. s., 4H).

4-{[4-(1-Hydroxy-1,3-dihydro-benzo[c][1,2]oxaborol-5-yloxy)-benzylamino]-methyl}-benzonitrile (D163)

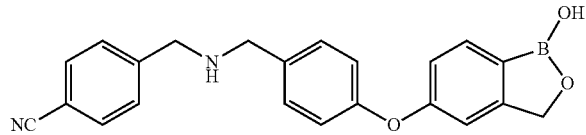 [SMILES: N#Cc1ccc(CNCc2ccc(Oc3ccc4c(c3)COB4O)cc2)cc1]

D163 was prepared using a procedure similar to that of D153. LCMS (m/z) 239 (M−131); $^1$H NMR (DMSO-d$_6$) δ: 9.46-9.73 (m, 1H), 9.13 (s, 1H), 7.90 (d, J=8.3 Hz, 2H), 7.72 (d, J=8.6 Hz, 3H), 7.52-7.56 (m, J=8.6 Hz, 2H), 7.06-7.10 (m, J=8.6 Hz, 2H), 6.96 (s, 1H), 6.95 (d, J=0.5 Hz, 1H), 4.91 (s, 2H), 4.22 (s, 2H), 4.09-4.17 (m, 2H).

5-{4-[(4-Nitro-benzylamino)-methyl]-phenoxy}-3H-benzo[c][1,2]oxaborol-1-ol (D164)

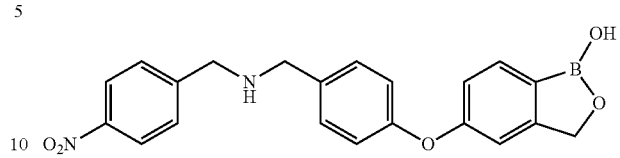

D164 was prepared using a procedure similar to that of D153. LCMS (m/z) 239 (M−151); $^1$H NMR (DMSO-d$_6$) δ: 9.11 (s, 1H), 8.22-8.27 (m, J=8.7 Hz, 2H), 7.70 (d, J=8.9 Hz, 3H), 7.47 (s, 2H), 7.04-7.08 (m, J=8.5 Hz, 2H), 6.93-6.97 (m, 2H), 4.90 (s, 2H), 4.09-4.23 (m, 2H), 3.94-4.05 (m, 2H).

N-(4-{[4-(1-Hydroxy-1,3-dihydro-benzo[c][1,2]oxaborol-5-yloxy)-benzylamino]-methyl}-phenyl)-acetamide (D165)

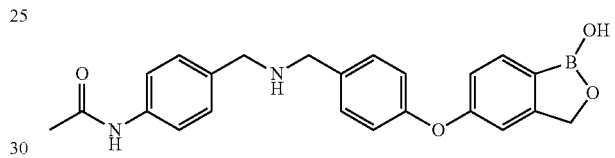

D165 was prepared using a procedure similar to that of D153. LCMS (m/z) 403 (M+H); $^1$H NMR (DMSO-d$_6$) δ: 10.18 (s, 1H), 9.66 (br. s., 1H), 9.16 (br. s., 1H), 7.74 (d, J=8.7 Hz, 1H), 7.59 (dd, J=16.0, 8.6 Hz, 4H), 7.45 (d, J=8.6 Hz, 2H), 7.06 (d, J=8.6 Hz, 2H), 6.95 (s, 1H), 6.96 (d, J=3.8 Hz, 1H), 4.91 (s, 2H), 4.04 (br. s., 4H), 2.03 (s, 3H).

N-[4-(1-Hydroxy-1,3-dihydro-benzo[c][1,2]oxaborol-5-yloxy)-benzyl]-acetamide (D166)

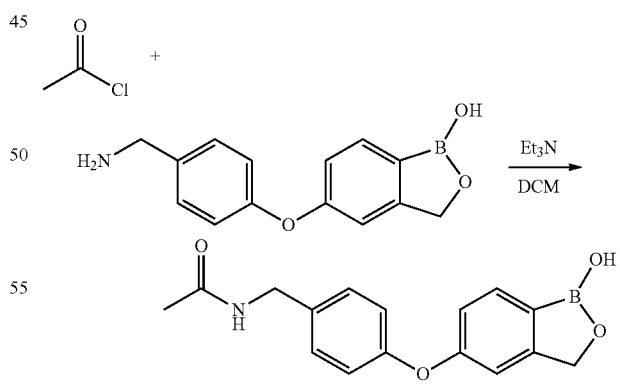

To a 20 mL scintillation vial containing 5-(4-aminomethyl-phenoxy)-3H-benzo[c][1,2]oxaborol-1-ol (150 mg, 0.59 mmol, 1.0 eq.) in DCM (5.0 mL) was added Et$_3$N (180 μL, 1.3 mmol, 2.2 eq.), followed by acetyl chloride (84 μL, 1.2 mmol, 2.0 eq.). The mixture was stirred at room temperature overnight. The mixture was concentrated under reduced pressure. The residue was applied to silica chromatography eluting with MeOH/DCM (0:100 to 10:90) to give N-[4-(1-hydroxy-1,3-dihydro-benzo[c][1,2]oxaborol-5-yloxy)-phenyl]-acetamide as a white solid. LCMS (m/z) 298 (M+H); $^1$H NMR (CHLOROFORM-d) δ: 7.55 (d, J=8.0 Hz, 1H), 7.11 (d, J=8.6 Hz, 2H), 6.74-6.83 (m, 3H), 6.68 (d, J=1.4 Hz, 1H), 4.79 (s, 2H), 4.21 (d, J=5.8 Hz, 2H), 1.84 (s, 3H). Amount obtained, 165 mg, 94.3% yield.

N-[4-(1-Hydroxy-1,3-dihydro-benzo[c][1,2]oxaborol-5-yloxy)-benzyl]-4-methyl-benzamide (D167)

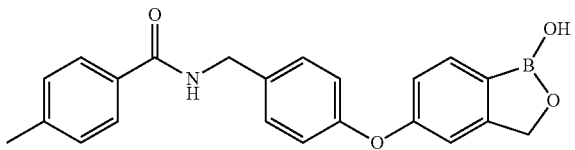 [SMILES: Cc1ccc(C(=O)NCc2ccc(Oc3ccc4c(c3)COB4O)cc2)cc1]

D167 was prepared using a procedure similar to that of D166. LCMS (m/z) 396 (M+23); $^1$H NMR (CHLOROFORM-d) δ: 7.69 (d, J=8.2 Hz, 2H), 7.35 (d, J=6.8 Hz, 2H), 7.23 (d, J=7.9 Hz, 2H), 6.95-7.04 (m, 3H), 6.88 (br. s., 1H), 6.83-6.93 (m, 1H), 6.38 (br. s., 1H), 5.02 (s, 2H), 4.63 (d, J=5.7 Hz, 2H), 2.39 (s, 3H).

N-[4-(1-Hydroxy-1,3-dihydro-benzo[c][1,2]oxaborol-5-yloxy)-benzyl]-3-methyl-benzamide (D168)

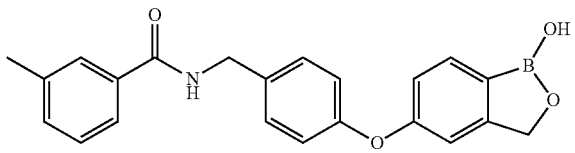 [SMILES: Cc1cccc(C(=O)NCc2ccc(Oc3ccc4c(c3)COB4O)cc2)c1]

D168 was prepared using a procedure similar to that of D166. LCMS (m/z) 374 (M+H); $^1$H NMR (CHLOROFORM-d) δ: 7.68 (d, J=8.2 Hz, 1H), 7.63 (s, 1H), 7.52-7.60 (m, 1H), 7.30-7.38 (m, 4H), 7.02 (dd, J=8.6, 2.7 Hz, 3H), 6.89 (br. s., 1H), 6.39 (br. s., 1H), 5.02 (s, 2H), 4.64 (d, J=5.7 Hz, 2H), 3.88 (s, 1H), 2.39 (s, 3H).

N-[4-(1-Hydroxy-1,3-dihydro-benzo[c][1,2]oxaborol-5-yloxy)-benzyl]-2-methyl-benzamide (D169)

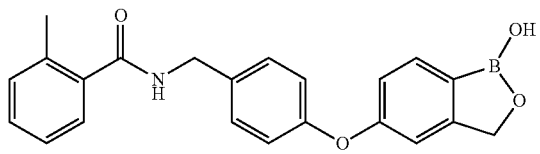 [SMILES: Cc1ccccc1C(=O)NCc1ccc(Oc2ccc3c(c2)COB3O)cc1]

D169 was prepared using a procedure similar to that of D166. LCMS (m/z) 374 (M+H); $^1$H NMR (DMSO-d$_6$) δ: 9.08 (s, 1H), 8.76 (s, 1H), 7.68 (d, J=8.0 Hz, 1H), 7.28-7.38 (m, 4H), 7.22 (d, J=7.4 Hz, 2H), 7.00-7.05 (m, 2H), 6.91-6.96 (m, 2H), 4.89 (s, 2H), 4.41 (d, J=6.1 Hz, 2H), 2.31 (s, 3H).

N-[4-(1-Hydroxy-1,3-dihydro-benzo[c][1,2]oxaborol-5-yloxy)-benzyl]-4-nitro-benzamide (D170)

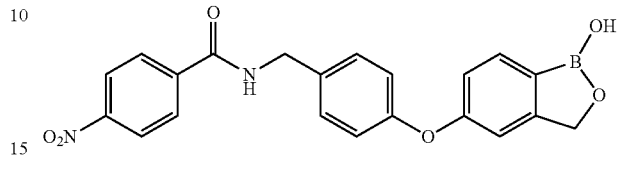

D170 was prepared using a procedure similar to that of D166. LCMS (m/z) 374 (M−30); $^1$H NMR (DMSO-d$_6$) δ: 9.36 (s, 1H), 9.08 (s, 1H), 8.28-8.32 (m, 2H), 8.08-8.12 (m, 2H), 7.68 (d, J=8.0 Hz, 1H), 7.34-7.38 (m, J=8.6 Hz, 2H), 6.99-7.04 (m, 2H), 6.89-6.95 (m, 2H), 4.89 (s, 2H), 4.48 (d, J=5.9 Hz, 2H).

4-Cyano-N-[4-(1-hydroxy-1,3-dihydro-benzo[c][1,2]oxaborol-5-yloxy)-benzyl]-benzamide (D171)

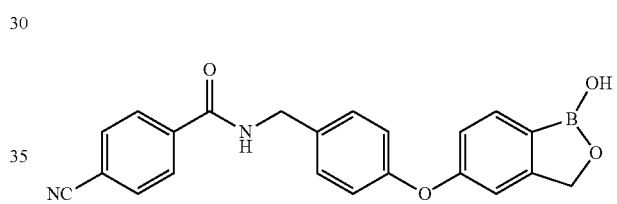

D171 was prepared using a procedure similar to that of D166. LCMS (m/z) 407 (M+23); $^1$H NMR (DMSO-d$_6$) δ: 9.28 (s, 1H), 9.08 (s, 1H), 8.00-8.05 (m, 2H), 7.93-7.97 (m, 2H), 7.68 (d, J=8.0 Hz, 1H), 7.32-7.37 (m, J=8.6 Hz, 2H), 6.99-7.04 (m, 2H), 6.89-6.95 (m, 2H), 4.88 (s, 2H), 4.47 (d, J=5.9 Hz, 2H).

N-[4-(1-Hydroxy-1,3-dihydro-benzo[c][1,2]oxaborol-5-yloxy)-benzyl]-4-methoxy-benzamide (D172)

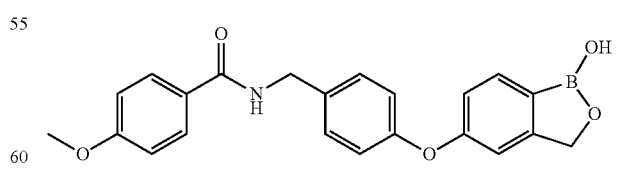

D172 was prepared using a procedure similar to that of D166. LCMS (m/z) 390 (M+H); $^1$H NMR (CHLOROFORM-d) δ: 7.74-7.78 (m, 1H), 7.76 (d, J=8.8 Hz, 2H), 7.31 (dd, J=8.4, 1.9 Hz, 2H), 6.97 (s, 1H), 6.95 (d, J=0.7 Hz, 1H), 6.92

(dd, J=8.1, 0.6 Hz, 1H), 6.85-6.89 (m, 2H), 6.81-6.84 (m, 1H), 4.97 (s, 1H), 4.94 (s, 1H), 4.57 (d, J=5.2 Hz, 2H), 3.80 (d, J=1.0 Hz, 3H).

4-Fluoro-N-[4-(1-hydroxy-1,3-dihydro-benzo[c][1,2]oxaborol-5-yloxy)-benzyl]-benzamide (D173)

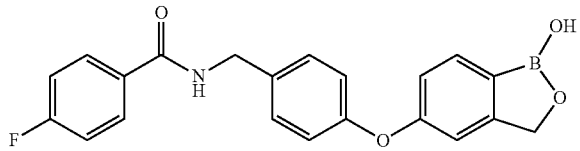 [SMILES: O=C(NCc1ccc(Oc2ccc3c(c2)COB3O)cc1)c1ccc(F)cc1]

D173 was prepared using a procedure similar to that of D166. LCMS (m/z) 400 (M+23); $^1$H NMR (CHLOROFORM-d) δ: 7.82 (dd, J=8.8, 5.3 Hz, 2H), 7.55-7.72 (m, 1H), 7.30 (dd, J=8.7, 2.3 Hz, 2H), 7.01-7.09 (m, 3H), 6.96 (d, J=8.5 Hz, 2H), 6.91 (dt, J=8.1, 2.3 Hz, 1H), 6.83 (d, J=2.0 Hz, 1H), 4.95 (d, J=12.8 Hz, 2H), 4.56 (d, J=5.7 Hz, 2H).

N-[4-(1-Hydroxy-1,3-dihydro-benzo[c][1,2]oxaborol-5-yloxy)-benzyl]-4-trifluoromethyl-benzamide (D174)

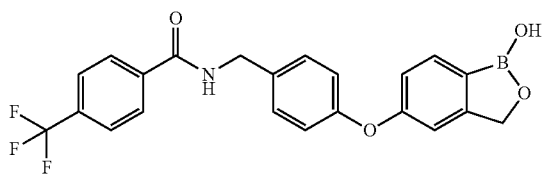 [SMILES: O=C(NCc1ccc(Oc2ccc3c(c2)COB3O)cc1)c1ccc(C(F)(F)F)cc1]

D174 was prepared using a procedure similar to that of D166. LCMS (m/z) 450 (M+23); $^1$H NMR (CHLOROFORM-d) δ: 8.20 (s, 1H), 7.89-7.94 (m, J=8.2 Hz, 2H), 7.79 (br. s., 1H), 7.64 (d, J=8.1 Hz, 1H), 7.56-7.62 (m, J=8.2 Hz, 2H), 7.27 (d, J=8.6 Hz, 2H), 6.88-6.93 (m, 2H), 6.85 (dd, J=8.1, 2.0 Hz, 1H), 6.78 (s, 1H), 4.88 (s, 2H), 4.52 (d, J=5.8 Hz, 2H).

Acetic acid 1-[4-(1-hydroxy-1,3-dihydro-benzo[c][1,2]oxaborol-5-yloxy)-benzylcarbamoyl]-1-methyl-ethyl ester (D175)

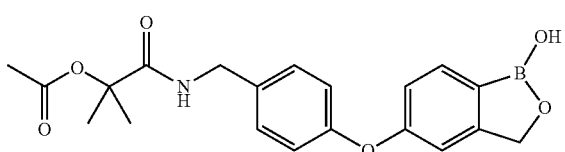

D175 was prepared using a procedure similar to that of D166. LCMS (m/z) 406 (M+23); $^1$H NMR (CHLOROFORM-d) δ: 7.68 (br. s., 1H), 7.23-7.28 (m, 2H), 6.95-7.02 (m, 3H), 6.88 (s, 1H), 6.40 (br. s., 1H), 5.01 (s, 2H), 4.46 (d, J=5.9 Hz, 2H), 2.06 (s, 3H), 2.03 (s, 1H), 1.66 (s, 6H).

N-[4-(1-Hydroxy-1,3-dihydro-benzo[c][1,2]oxaborol-5-yloxy)-benzyl]-isobutyramide (D176)

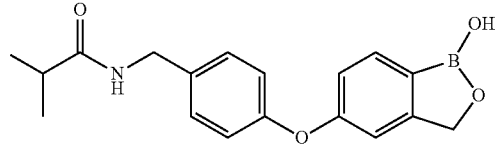 [SMILES: CC(C)C(=O)NCc1ccc(Oc2ccc3c(c2)COB3O)cc1]

D176 was prepared using a procedure similar to that of D166. LCMS (m/z) 326 (M+H); $^1$H NMR (CHLOROFORM-d) δ: 7.68 (br. s., 1H), 7.24-7.28 (m, 2H), 6.96-7.02 (m, 3H), 6.84-6.92 (m, 1H), 5.77 (br. s., 1H), 5.02 (s, 2H), 4.43 (d, J=5.8 Hz, 2H), 1.19 (d, J=6.9 Hz, 6H).

N-[4-(1-Hydroxy-1,3-dihydro-benzo[c][1,2]oxaborol-5-yloxy)-benzyl]-2,2-dimethyl-propionamide (D177)

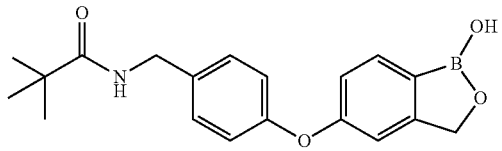 [SMILES: CC(C)(C)C(=O)NCc1ccc(Oc2ccc3c(c2)COB3O)cc1]

D177 was prepared using a procedure similar to that of D166. LCMS (m/z) 340 (M+H); $^1$H NMR (CHLOROFORM-d) δ: 7.66 (br. s., 1H), 7.21-7.26 (m, 2H), 6.99 (d, J=8.5 Hz, 2H), 6.94-7.00 (m, 1H), 6.88 (s, 1H), 6.02 (br. s., 1H), 5.01 (s, 2H), 4.42 (d, J=5.7 Hz, 2H), 3.82 (br. s., 1H), 1.23 (s, 9H).

N-[4-(1-Hydroxy-1,3-dihydro-benzo[c][1,2]oxaborol-5-yloxy)-benzyl]-propionamide (D178)

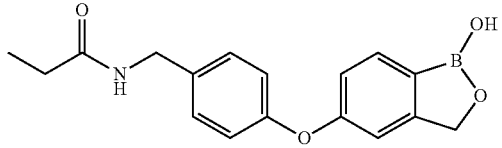 [SMILES: CCC(=O)NCc1ccc(Oc2ccc3c(c2)COB3O)cc1]

D178 was prepared using a procedure similar to that of D166. LCMS (m/z) 312 (M+H); $^1$H NMR (DMSO-$d_6$) δ: 9.08 (br. s., 1H), 8.24 (br. s., 1H), 7.68 (d, J=8.0 Hz, 1H), 7.23-7.29 (m, J=8.5 Hz, 2H), 6.97-7.03 (m, 2H), 6.93 (dd, J=8.0, 2.1 Hz, 1H), 6.90 (s, 1H), 4.89 (s, 2H), 4.23 (d, J=6.0 Hz, 2H), 2.12 (q, J=7.6 Hz, 2H), 1.00 (t, J=7.6 Hz, 3H).

Cyclopentanecarboxylic acid 4-(1-hydroxy-1,3-dihydro-benzo[c][1,2]oxaborol-5-yloxy)-benzylamide (D179)

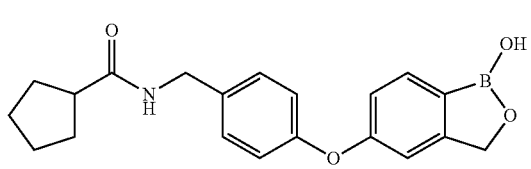

D179 was prepared using a procedure similar to that of D166. LCMS (m/z) 352 (M+H); $^1$H NMR (CHLOROFORM-d) δ: 7.66 (d, J=8.1 Hz, 1H), 7.19 (d, J=8.5 Hz, 2H), 6.85-6.93

(m, 3H), 6.79 (s, 1H), 6.31 (br. s., 1H), 4.91 (s, 2H), 4.34 (d, J=5.8 Hz, 2H), 1.64-1.83 (m, 6H), 1.45-1.54 (m, 2H).

Cyclohexanecarboxylic acid 4-(1-hydroxy-1,3-dihydro-benzo[c][1,2]oxaborol-5-yloxy)-benzylamide (D180)

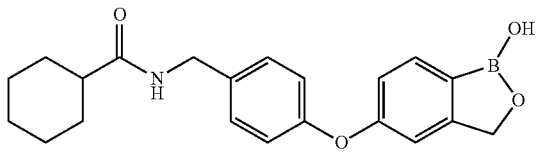 [SMILES: O=C(NCc1ccc(Oc2ccc3c(c2)COB3O)cc1)C1CCCCC1]

D180 was prepared using a procedure similar to that of D166. LCMS (m/z) 366 (M+H); $^1$H NMR (CHLOROFORM-d) δ: 7.71 (br. s., 1H), 7.24 (d, J=8.5 Hz, 2H), 6.97 (d, J=8.4 Hz, 3H), 6.87 (s, 1H), 5.96 (br. s., 1H), 5.01 (br. s., 2H), 4.42 (d, J=5.7 Hz, 2H), 1.88 (d, J=13.2 Hz, 2H), 1.77 (d, J=9.8 Hz, 2H), 1.66 (d, J=5.7 Hz, 1H), 1.46 (d, J=12.3 Hz, 2H), 1.16-1.31 (m, 3H).

Furan-2-carboxylic acid 4-(1-hydroxy-1,3-dihydro-benzo[c][1,2]oxaborol-5-yloxy)-benzylamide (D181)

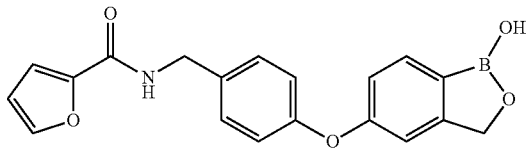 [SMILES: O=C(NCc1ccc(Oc2ccc3c(c2)COB3O)cc1)c1ccco1]

D181 was prepared using a procedure similar to that of D166. LCMS (m/z) 350 (M+H); $^1$H NMR (CHLOROFORM-d) δ: 8.01 (s, 1H), 7.67 (d, J=8.0 Hz, 1H), 7.38 (d, J=0.9 Hz, 1H), 7.24-7.31 (m, 2H), 7.08 (d, J=3.5 Hz, 1H), 6.87-6.96 (m, 4H), 6.81 (s, 1H), 6.44 (dd, J=3.4, 1.7 Hz, 1H), 4.92 (s, 2H), 4.53 (d, J=6.0 Hz, 2H).

Pyrrolidine-1-carboxylic acid 4-(1-hydroxy-1,3-dihydro-benzo[c][1,2]oxaborol-5-yloxy)-benzylamide (D182)

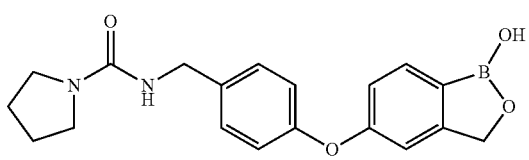 [SMILES: O=C(NCc1ccc(Oc2ccc3c(c2)COB3O)cc1)N1CCCC1]

D182 was prepared using a procedure similar to that of D166. LCMS (m/z) 353 (M+H); $^1$H NMR (CHLOROFORM-d) δ: 7.71 (d, J=8.1 Hz, 1H), 7.30 (d, J=8.4 Hz, 2H), 6.90-7.02 (m, 3H), 6.86 (d, J=1.1 Hz, 1H), 6.61 (br. s., 1H), 4.96-5.02 (m, 2H), 4.57 (br. s., 1H), 4.43 (d, J=5.7 Hz, 2H), 3.36 (t, J=6.5 Hz, 4H), 1.90 (t, J=3.0 Hz, 3H), 1.90 (d, J=13.4 Hz, 1H).

[4-(1-Hydroxy-1,3-dihydro-benzo[c][1,2]oxaborol-5-yloxy)-benzyl]-carbamic acid tert-butyl ester (D183)

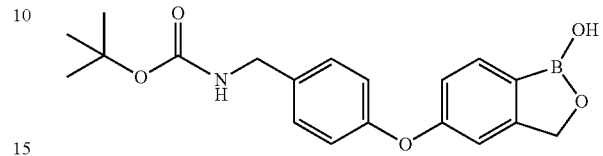

D183 was prepared using a procedure similar to that of D166. LCMS (m/z) 353 (M+H); $^1$H NMR (CHLOROFORM-d) δ: 7.68 (d, J=8.1 Hz, 1H), 7.27 (d, J=8.5 Hz, 2H), 6.96-7.03 (m, 1H), 7.00 (d, J=8.5 Hz, 2H), 6.87 (s, 1H), 5.00 (s, 2H), 4.30 (br. s., 2H), 1.46 (s, 9H).

1-[4-(1-Hydroxy-1,3-dihydro-benzo[c][1,2]oxaborol-5-yloxy)-benzyl]-3-phenyl-urea (D184)

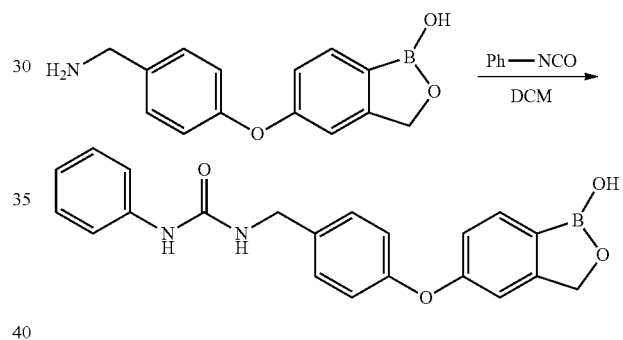

To a 20 mL scintillation vial containing 5-(4-aminomethylphenoxy)-3H-benzo[c][1,2]oxaborol-1-ol (150 mg, 0.59 mmol, 1.0 eq.) in DCM (5.0 mL) was added phenylisocyanate (71 μL, 0.65 mmol, 1.1 eq.). The mixture was stirred at room temperature overnight. The mixture was treated with H$_2$O (5 mL). The precipitate was collected by filtration and washed with H$_2$O to give 1-[4-(1-hydroxy-1,3-dihydro-benzo[c][1,2]oxaborol-5-yloxy)-benzyl]-3-phenyl-urea as a white solid. LCMS (m/z) 375 (M+H); $^1$H NMR (DMSO-d$_6$) δ: 9.07 (s, 1H), 8.51 (s, 1H), 7.67 (d, J=8.0 Hz, 1H), 7.37 (dd, J=8.6, 1.0 Hz, 2H), 7.30-7.35 (m, J=8.6 Hz, 2H), 7.19 (t, J=8.0 Hz, 2H), 6.99-7.04 (m, 2H), 6.88-6.95 (m, 3H), 6.58 (s, 1H), 4.89 (s, 2H), 4.27 (d, J=5.9 Hz, 2H).

1-Ethyl-3-[4-(1-hydroxy-1,3-dihydro-benzo[c][1,2]oxaborol-5-yloxy)-benzyl]-urea (D185)

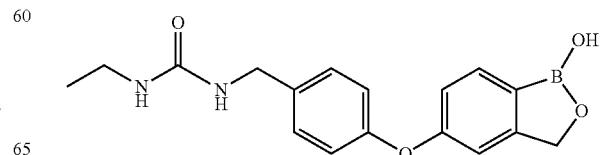

D185 was prepared using a procedure similar to that of D184. LCMS (m/z) 327 (M+H); $^1$H NMR (DMSO-$d_6$) δ: 9.07 (s, 1H), 7.67 (d, J=8.0 Hz, 1H), 7.23-7.28 (m, J=8.6 Hz, 2H), 6.97-7.02 (m, 2H), 6.87-6.94 (m, 2H), 6.27 (s, 1H), 5.85 (s, 1H), 4.88 (s, 2H), 4.16 (d, J=6.0 Hz, 2H), 3.00 (dd, J=7.1, 5.7 Hz, 2H), 0.97 (t, J=7.2 Hz, 3H).

1-[4-(1-Hydroxy-1,3-dihydro-benzo[c][1,2]oxaborol-5-yloxy)-benzyl]-3-p-tolyl-urea (D186)

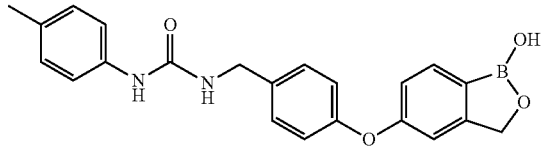 [SMILES: Cc1ccc(NC(=O)NCc2ccc(Oc3ccc4c(c3)COB4O)cc2)cc1]

D186 was prepared using a procedure similar to that of D184. LCMS (m/z) 389 (M+H); $^1$H NMR (DMSO-$d_6$) δ: 9.07 (s, 1H), 8.40 (s, 1H), 7.68 (d, J=8.0 Hz, 1H), 7.24-7.35 (m, 4H), 6.98-7.05 (m, 4H), 6.89-6.96 (m, 2H), 6.53 (s, 1H), 4.89 (s, 2H), 4.26 (d, J=5.9 Hz, 2H), 2.19 (s, 3H).

1-Cyclohexyl-3-[4-(1-hydroxy-1,3-dihydro-benzo[c][1,2]oxaborol-5-yloxy)-benzyl]-urea (D187)

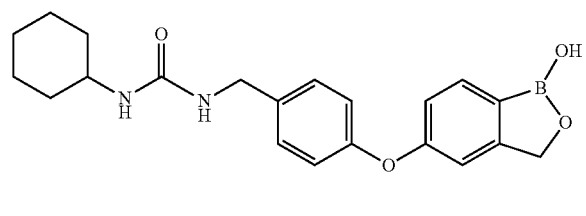 [SMILES: O=C(NCc1ccc(Oc2ccc3c(c2)COB3O)cc1)NC1CCCCC1]

D187 was prepared using a procedure similar to that of D184. LCMS (m/z) 381 (M+H); $^1$H NMR (DMSO-$d_6$) δ: 9.07 (s, 1H), 7.68 (d, J=8.0 Hz, 1H), 7.26 (d, J=8.6 Hz, 2H), 7.00 (d, J=8.5 Hz, 1H), 6.97-7.03 (m, 1H), 6.88-6.95 (m, 2H), 6.16 (s, 1H), 5.80 (d, J=8.0 Hz, 1H), 4.89 (s, 2H), 4.17 (d, J=6.0 Hz, 2H), 1.71 (br. s., 2H), 1.60 (br. s., 2H), 1.44-1.55 (m, 1H), 1.23 (br. s., 2H), 1.08 (br. s., 3H).

1-(4-Chlorophenyl)-3-[4-(1-hydroxy-1,3-dihydro-benzo[c][1,2]oxaborol-5-yloxy)-benzyl]-urea (D188)

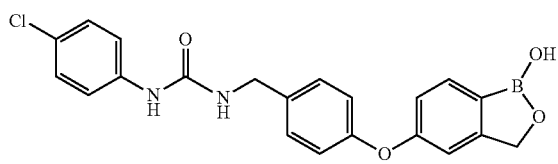 [SMILES: O=C(NCc1ccc(Oc2ccc3c(c2)COB3O)cc1)Nc1ccc(Cl)cc1]

D188 was prepared using a procedure similar to that of D184. LCMS (m/z) 409 (M+H); $^1$H NMR (DMSO-$d_6$) δ: 9.08 (br. s., 1H), 8.70 (s, 1H), 7.68 (d, J=8.0 Hz, 1H), 7.42 (d, J=8.9 Hz, 1H), 7.42 (q, J=5.2 Hz, 1H), 7.30-7.38 (m, 2H), 7.24 (d, J=8.9 Hz, 1H), 7.24 (q, J=5.1 Hz, 1H), 6.96-7.05 (m, 1H), 7.02 (d, J=8.5 Hz, 1H), 6.88-6.96 (m, 2H), 6.66 (s, 1H), 4.89 (s, 2H), 4.27 (d, J=5.9 Hz, 2H).

1-(4-Dimethylamino-phenyl)-3-[4-(1-hydroxy-1,3-dihydro-benzo[c][1,2]oxaborol-5-yloxy)-benzyl]-urea (D189)

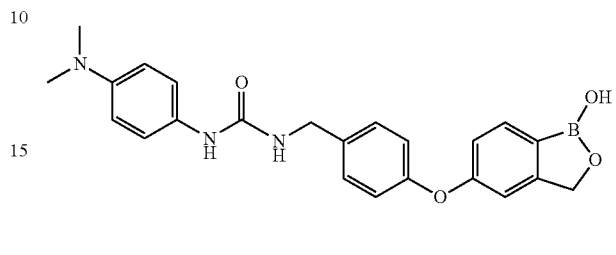

D189 was prepared using a procedure similar to that of D184. LCMS (m/z) 418 (M+H); $^1$H NMR (DMSO-$d_6$) δ: 9.07 (s, 1H), 8.13 (s, 1H), 7.67 (s, 1H), 7.31 (s, 2H), 7.18 (d, J=9.1 Hz, 2H), 7.02 (d, J=8.6 Hz, 2H), 6.90 (s, 2H), 6.63 (d, J=9.1 Hz, 2H), 6.41 (s, 1H), 4.89 (s, 2H), 4.26 (s, 2H), 2.78 (s, 6H).

{1-[4-(1-Hydroxy-1,3-dihydro-benzo[c][1,2]oxaborol-5-yloxy)-benzylcarbamoyl]-ethyl}-carbamic acid tert-butyl ester (D190)

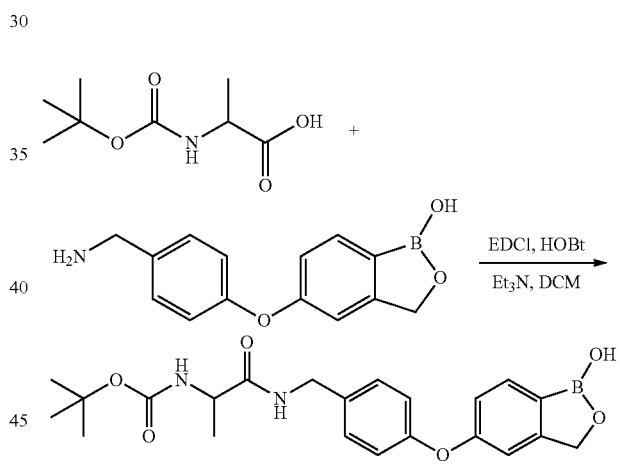

To a 40 mL scintillation vial containing 5-(4-aminomethyl-phenoxy)-3H-benzo[c][1,2]oxaborol-1-ol (350 mg, 1.37 mmol, 1.0 eq.), EDCI (314.4 mg, 1.64 mmol, 1.2 eq.), HOBt (221.6 mg, 1.64 mmol, 1.2 eq.) and Et$_3$N (0.46 mL mg, 3.29 mmol, 2.4 eq.) in DCM (15.0 mL) was added 2-tert-Butoxycarbonylamino-propionic acid (311.1 mg, 1.64 mmol, 1.2 eq.) drop wise. The mixture was stirred at room temperature overnight. The mixture was treated with H$_2$O (10 mL) and the layers were separated. The aqueous was extracted with DCM (2×10 mL), combined organic phase was washed with brine (10 mL), dried over MgSO$_4$, filtered and the filtrate was concentrated under reduced pressure. The residue was applied to silica chromatography eluting with MeOH/DCM (0:100 to 10:90) to give {1-[4-(1-hydroxy-1,3-dihydro-benzo[c][1,2]oxaborol-5-yloxy)-benzylcarbamoyl]-ethyl}-carbamic acid tert-butyl ester as a white solid. LCMS (m/z) 449 (M+23); $^1$H NMR (DMSO-$d_6$) δ: 9.08 (s, 1H), 8.26 (t, J=5.7 Hz, 1H), 7.68 (d, J=8.0 Hz, 1H), 7.22-7.31 (m, J=8.4 Hz, 2H), 6.96-7.01 (m, J=8.5 Hz, 2H), 6.88-6.95 (m, 3H), 4.89 (s, 2H), 4.21-4.30 (m, 2H), 3.88-4.02 (m, 1H), 1.35 (s, 9H), 1.18 (d, J=7.1 Hz, 3H).

{1-[4-(1-Hydroxy-1,3-dihydro-benzo[c][1,2]oxaborol-5-yloxy)-benzylcarbamoyl]-2-phenyl-ethyl}-carbamic acid tert-butyl ester) (D191)

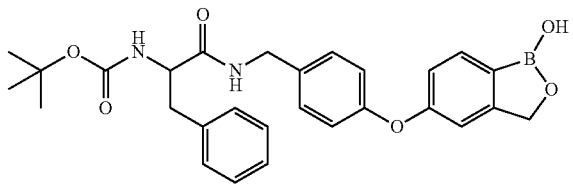 [SMILES: CC(C)(C)OC(=O)NC(Cc1ccccc1)C(=O)NCc1ccc(Oc2ccc3c(c2)COB3O)cc1]

D191 was prepared using a procedure similar to that of D190. LCMS (m/z) 525 (M+23); ¹H NMR (DMSO-d₆) δ: 9.08 (s, 1H), 8.39 (t, J=5.7 Hz, 1H), 7.68 (d, J=8.0 Hz, 1H), 7.18-7.27 (m, 8H), 6.89-6.99 (m, 4H), 4.89 (s, 2H), 4.26 (d, J=5.9 Hz, 2H), 4.11-4.21 (m, 1H), 2.89-3.03 (m, 1H), 2.71-2.86 (m, 1H), 1.29 (s, 9H).

{[4-(1-Hydroxy-1,3-dihydro-benzo[c][1,2]oxaborol-5-yloxy)-benzylcarbamoyl]-methyl}-carbamic acid tert-butyl ester (D192)

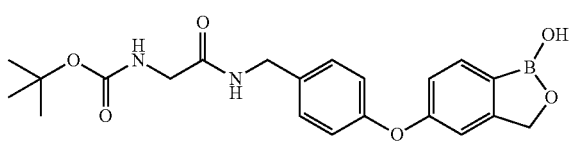 [SMILES: CC(C)(C)OC(=O)NCC(=O)NCc1ccc(Oc2ccc3c(c2)COB3O)cc1]

D192 was prepared using a procedure similar to that of D190. LCMS (m/z) 435 (M+23); ¹H NMR (CHLOROFORM-d) δ: 7.66 (br. s., 1H), 7.24 (d, J=6.2 Hz, 1H), 7.26 (s, 1H), 6.93-6.98 (m, 3H), 6.85 (s, 1H), 6.73 (br. s., 1H), 4.98 (br. s., 2H), 4.44 (d, J=5.9 Hz, 2H), 3.83 (d, J=6.1 Hz, 2H), 2.16 (s, 1H), 2.07 (s, 1H), 1.41 (s, 9H).

{1-[4-(1-Hydroxy-1,3-dihydro-benzo[c][1,2]oxaborol-5-yloxy)-benzylcarbamoyl]-3-methyl-butyl}-carbamic acid tert-butyl ester (D193)

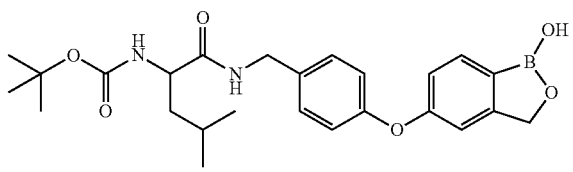 [SMILES: CC(C)CC(NC(=O)OC(C)(C)C)C(=O)NCc1ccc(Oc2ccc3c(c2)COB3O)cc1]

D193 was prepared using a procedure similar to that of D190. LCMS (m/z) 491 (M+23); ¹H NMR (DMSO-d₆) δ: 9.08 (s, 1H), 8.30 (t, J=5.9 Hz, 1H), 7.68 (d, J=8.0 Hz, 1H), 7.26 (d, J=8.5 Hz, 2H), 6.98 (d, J=8.5 Hz, 2H), 6.85-6.94 (m, 3H), 4.89 (s, 2H), 4.24 (d, J=5.9 Hz, 2H), 3.92-4.01 (m, 1H), 1.39-1.48 (m, 1H), 1.35 (s, 9H), 1.26-1.32 (m, 1H), 0.84 (dd, J=10.5, 6.6 Hz, 7H).

{[4-(1-Hydroxy-1,3-dihydro-benzo[c][1,2]oxaborol-5-yloxy)-benzylcarbamoyl]-methyl}-methyl-carbamic acid tert-butyl ester (D194)

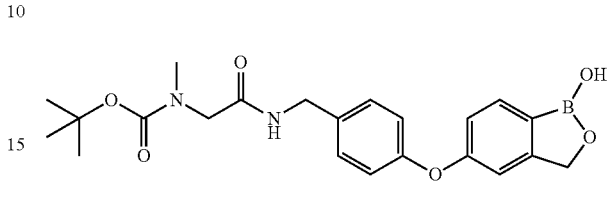

D194 was prepared using a procedure similar to that of D190. LCMS (m/z) 449 (M+23); ¹H NMR (DMSO-d₆) δ: 9.08 (s, 1H), 8.35 (t, J=5.5 Hz, 1H), 7.68 (d, J=8.0 Hz, 1H), 7.29 (d, J=7.8 Hz, 2H), 6.97-7.04 (m, 2H), 6.86-6.96 (m, 2H), 4.89 (s, 2H), 4.26 (d, J=6.0 Hz, 2H), 3.74-3.83 (m, 2H), 2.80 (br. s., 3H), 1.38 (s, 4H), 1.29 (s, 5H).

2-Dimethylamino-N-[4-(1-hydroxy-1,3-dihydro-benzo[c][1,2]oxaborol-5-yloxy)-benzyl]-acetamide (D195)

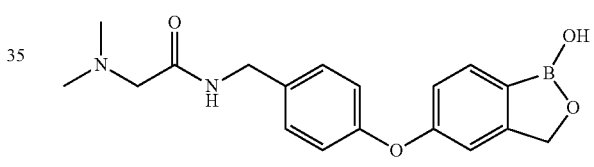

D195 was prepared using a procedure similar to that of D190. LCMS (m/z) 341 (M+H); ¹H NMR (DMSO-d₆) δ: 9.08 (s, 1H), 8.26 (t, J=6.2 Hz, 1H), 7.68 (d, J=8.1 Hz, 1H), 7.25-7.31 (m, 2H), 6.97-7.02 (m, 2H), 6.88-6.95 (m, 2H), 4.89 (s, 2H), 4.26 (d, J=6.2 Hz, 2H), 2.89 (s, 2H), 2.19 (s, 6H).

1-Methyl-pyrrolidine-2-carboxylic acid 4-(1-hydroxy-1,3-dihydro-benzo[c][1,2]oxaborol-5-yloxy)-benzylamide (D196)

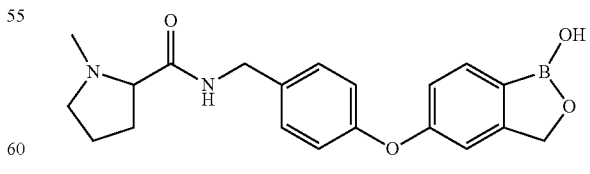

D196 was prepared using a procedure similar to that of D190. LCMS (m/z) 367 (M+H); ¹H NMR (DMSO-d₆) δ: 9.08 (s, 1H), 8.25 (t, J=6.2 Hz, 1H), 7.68 (d, J=8.0 Hz, 1H), 7.22-7.29 (m, J=8.6 Hz, 2H), 6.96-7.03 (m, 2H), 6.89-6.96 (m, 2H), 4.89 (s, 2H), 4.19-4.31 (m, 2H), 2.97-3.04 (m, 1H), 2.74 (dd, J=9.4, 5.8 Hz, 1H), 2.26 (s, 3H), 2.19-2.24 (m, 1H), 2.01-2.12 (m, 1H), 1.62-1.75 (m, 3H).

2-Dimethylamino-N-[4-(1-hydroxy-1,3-dihydro-benzo[c][1,2]oxaborol-5-yloxy)-benzyl]-3-phenyl-propionamide (D197)

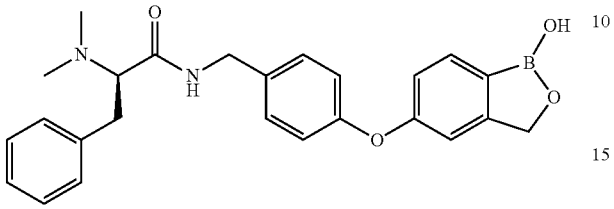

D197 was prepared using a procedure similar to that of D190. LCMS (m/z) 431 (M+H); $^1$H NMR (DMSO-d$_6$) δ: 9.08 (s, 1H), 8.24 (t, J=5.9 Hz, 1H), 7.68 (d, J=8.0 Hz, 1H), 7.12-7.24 (m, 5H), 7.03 (d, J=8.6 Hz, 2H), 6.87-6.93 (m, 4H), 4.90 (s, 2H), 4.25-4.32 (m, 1H), 4.10 (dd, J=14.7, 5.2 Hz, 1H), 3.27 (dd, J=9.5, 5.1 Hz, 1H), 2.96 (dd, J=13.1, 9.5 Hz, 1H), 2.76 (dd, J=13.1, 5.1 Hz, 1H), 2.25 (s, 6H).

(2-[4-(1-Hydroxy-1,3-dihydro-benzo[c][1,2]oxaborol-5-yloxy)-benzylcarbamoyl]-pyrrolidine-1-carboxylic acid tert-butyl ester (D198)

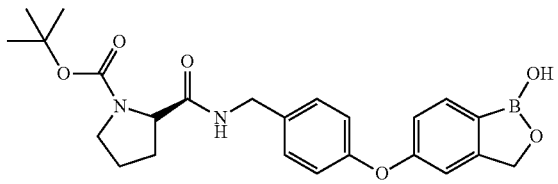

D198 was prepared using a procedure similar to that of D190. LCMS (m/z) 475 (M+23); $^1$H NMR (DMSO-d$_6$) δ: 9.08 (s, 1H), 8.29-8.40 (m, 1H), 7.68 (d, J=8.0 Hz, 1H), 7.25-7.34 (m, 2H), 6.95-7.03 (m, 2H), 6.87-6.95 (m, 2H), 4.89 (s, 2H), 4.26-4.35 (m, 1H), 4.01-4.25 (m, 2H), 3.33-3.43 (m, 1H), 3.22-3.30 (m, 2H), 1.66-1.87 (m, 3H), 1.38 (s, 3H), 1.25 (s, 6H).

2-[4-(1-Hydroxy-1,3-dihydro-benzo[c][1,2]oxaborol-5-yloxy)-benzylcarbamoyl]-piperidine-1-carboxylic acid tert-butyl ester (D199)

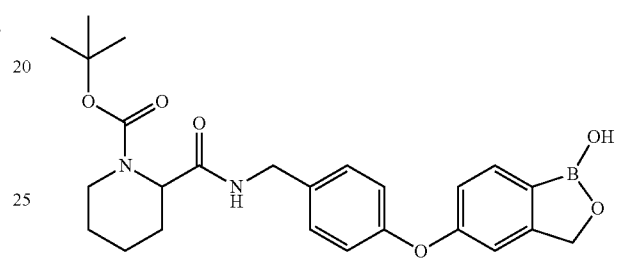

D199 was prepared using a procedure similar to that of D190. LCMS (m/z) 489 (M+23); $^1$H NMR (DMSO-d$_6$) δ: 9.08 (s, 4H), 7.68 (d, J=7.5 Hz, 3H), 7.67 (d, J=0.2 Hz, 1H), 7.27 (d, J=8.6 Hz, 7H), 6.97-7.02 (m, 7H), 4.89 (s, 7H), 3.29 (s, 5H), 2.48 (dt, J=3.7, 1.8 Hz, 17H), 2.48 (d, J=7.6 Hz, 17H).

2-Amino-N-[4-(1-hydroxy-1,3-dihydro-benzo[c][1,2]oxaborol-5-yloxy)-benzyl]-3-phenyl-propionamide (D200)

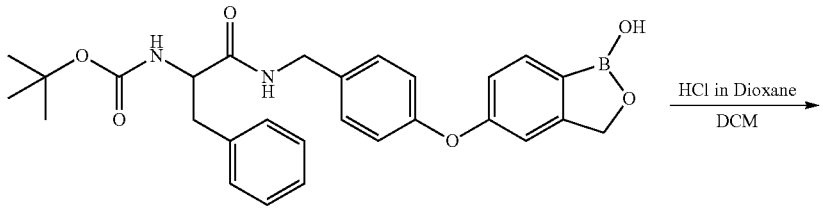

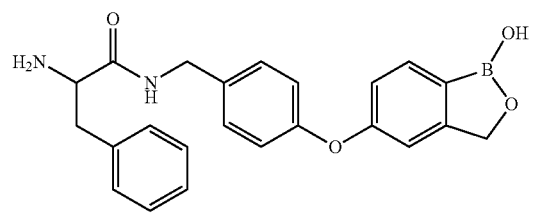

To a 20 mL scintillation vial {1-[4-(1-hydroxy-1,3-dihydro-benzo[c][1,2]oxaborol-5-yloxy)-benzylcarbamoyl]-2-phenyl-ethyl}-carbamic acid tert-butyl ester (190 mg, 0.38 mmol, 1.0 eq.) in DCM (5.0 mL) was added HCl (5.0 mL, 4.0M in 1,4-dioxane) and the mixture was stirred at room temperature overnight. The mixture was concentrated under reduced pressure to give 2-amino-N-[4-(1-hydroxy-1,3-dihydro-benzo[c][1,2]oxaborol-5-yloxy)-benzyl]-3-phenyl-propionamide as a light yellow glassy solid. LCMS (m/z) 403 (M+H); $^1$H NMR (DMSO-d$_6$) δ: 8.91 (br. s., 1H), 8.32 (br. s., 3H), 7.70 (d, J=8.0 Hz, 1H), 7.23-7.33 (m, 4H), 7.19-7.23 (m, 2H), 7.11 (d, J=8.6 Hz, 2H), 6.88-6.99 (m, 4H), 4.90 (s, 2H), 4.27-4.35 (m, 1H), 4.15-4.24 (m, 1H), 3.98-4.06 (m, 1H), 3.04 (d, J=7.2 Hz, 2H).

2-Amino-N-[4-(1-hydroxy-1,3-dihydro-benzo[c][1,2]oxaborol-5-yloxy)-benzyl]-propionamide (D201)

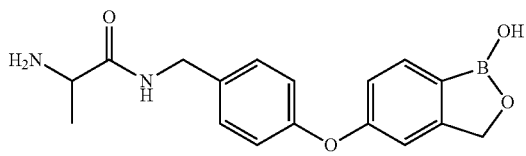 [SMILES: CC(N)C(=O)NCc1ccc(Oc2ccc3c(c2)COB3O)cc1]

D201 was prepared using a procedure similar to that of D200. LCMS (m/z) 327 (M+H); $^1$H NMR (DMSO-d$_6$) δ: 8.88 (s, 1H), 8.14 (br. s., 3H), 7.69 (d, J=8.0 Hz, 1H), 7.30 (d, J=8.6 Hz, 2H), 6.99-7.05 (m, 2H), 6.89-6.96 (m, 2H), 4.89 (s, 2H), 4.32 (t, J=5.3 Hz, 2H), 3.82-3.91 (m, 1H), 1.36 (d, J=7.0 Hz, 3H).

2-Amino-4-methyl-pentanoic acid 4-(1-hydroxy-1,3-dihydro-benzo[c][1,2]oxaborol-5-yloxy)-benzylamide (D202)

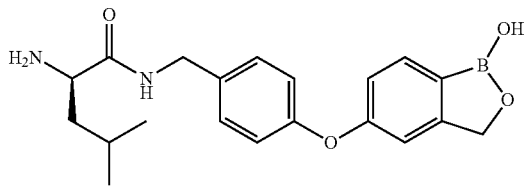 [SMILES: CC(C)C[C@@H](N)C(=O)NCc1ccc(Oc2ccc3c(c2)COB3O)cc1]

D202 was prepared using a procedure similar to that of D200. LCMS (m/z) 369 (M+H); $^1$H NMR (DMSO-d$_6$) δ: 9.07-9.15 (m, 2H), 8.29 (br. s., 3H), 7.71 (d, J=8.0 Hz, 1H), 7.29-7.36 (m, J=8.6 Hz, 2H), 6.99-7.06 (m, 2H), 6.88-6.96 (m, 2H), 4.90 (s, 2H), 4.26-4.36 (m, 2H), 3.72-3.83 (m, 1H), 1.53-1.66 (m, 3H), 0.87 (dd, J=7.6, 6.2 Hz, 6H).

N-[4-(1-Hydroxy-1,3-dihydro-benzo[c][1,2]oxaborol-5-yloxy)-benzyl]-2-methylamino-acetamide (D203)

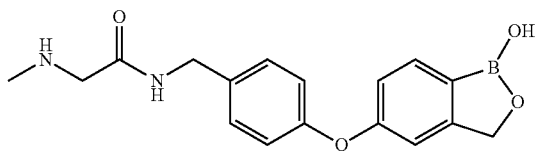 [SMILES: CNCC(=O)NCc1ccc(Oc2ccc3c(c2)COB3O)cc1]

D203 was prepared using a procedure similar to that of D200. LCMS (m/z) 327 (M+H); $^1$H NMR (DMSO-d$_6$) δ: 7.70 (d, J=8.0 Hz, 1H), 7.32 (d, J=8.4 Hz, 2H), 7.03 (d, J=8.6 Hz, 2H), 6.89-6.96 (m, 2H), 4.90 (s, 2H), 4.33 (d, J=5.9 Hz, 2H), 3.74 (t, J=5.7 Hz, 2H), 2.55 (dd, 3H).

Pyrrolidine-2-carboxylic acid 4-(1-hydroxy-1,3-dihydro-benzo[c][1,2]oxaborol-5-yloxy)-benzylamide (D204)

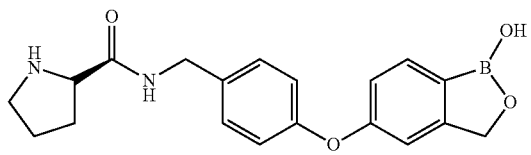

D204 was prepared using a procedure similar to that of D200. LCMS (m/z) 353 (M+H); $^1$H NMR (DMSO-d$_6$) δ: 9.11 (br. s., 1H), 9.06 (t, J=5.8 Hz, 1H), 7.70 (d, J=8.0 Hz, 1H), 7.31 (d, J=8.6 Hz, 2H), 7.03 (d, J=8.6 Hz, 1H), 7.03 (q, J=4.9 Hz, 1H), 6.89-6.97 (m, 2H), 4.90 (s, 2H), 4.33 (d, J=5.8 Hz, 2H), 4.18 (br. s., 1H), 3.17-3.26 (m, 2H), 2.23-2.35 (m, 1H), 1.79-1.94 (m, 3H).

Piperidine-2-carboxylic acid 4-(1-hydroxy-1,3-dihydro-benzo[c][1,2]oxaborol-5-yloxy)-benzylamide (D205)

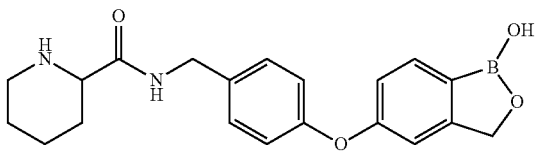 [SMILES: O=C(NCc1ccc(Oc2ccc3c(c2)COB3O)cc1)C1CCCCN1]

D205 was prepared using a procedure similar to that of D200. LCMS (m/z) 367 (M+H); $^1$H NMR (DMSO-d$_6$) δ: 9.12 (br. s., 1H), 9.03 (t, J=5.8 Hz, 1H), 8.62-8.72 (m, 1H), 7.71 (d, J=8.0 Hz, 1H), 7.30 (d, J=8.6 Hz, 2H), 6.99-7.05 (m, 2H), 6.89-6.96 (m, 2H), 4.90 (s, 2H), 4.32 (dd, J=5.6, 3.2 Hz, 2H), 3.73-3.82 (m, 1H), 3.25-3.40 (m, 2H), 3.20 (d, J=12.5 Hz, 1H), 2.86-2.95 (m, 0H), 2.12 (d, J=12.0 Hz, 1H), 1.44-1.79 (m, 3H).

4-(1-Hydroxy-1,3-dihydro-benzo[c][1,2]oxaborol-5-yloxy)-benzoic acid hydrazide (D206)

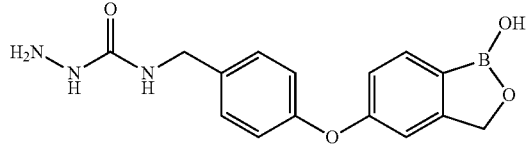 [SMILES: NNC(=O)NCc1ccc(Oc2ccc3c(c2)COB3O)cc1]

D206 was prepared using a procedure similar to that of D200. LCMS (m/z) 285 (M+H); $^1$H NMR (DMSO-d$_6$) δ:

11.68 (s, 1H), 7.92-8.04 (m, 2H), 7.79 (d, J=8.0 Hz, 1H), 7.08-7.15 (m, 3H), 7.06 (dd, J=8.0, 2.1 Hz, 1H), 4.94 (s, 2H).

2-Amino-N-[4-(1-hydroxy-1,3-dihydro-benzo[c][1,2]oxaborol-5-yloxy)-benzyl]-acetamide (D207)

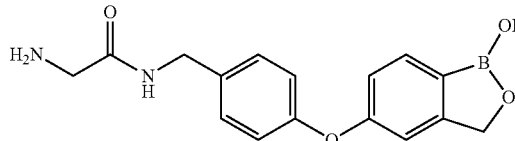

D207 was prepared using a procedure similar to that of D200. LCMS (m/z) 313 (M+23); $^1$H NMR (DMSO-d$_6$) δ: 8.95 (br. s., 1H), 8.16 (br. s., 2H), 7.71 (d, J=8.0 Hz, 1H), 7.29-7.36 (m, 2H), 6.98-7.06 (m, 2H), 6.88-6.97 (m, 2H), 4.90 (s, 2H), 4.32 (d, J=5.9 Hz, 2H), 3.47-3.67 (m, 2H).

6-(1-Hydroxy-3-methyl-1,3-dihydro-benzo[c][1,2]oxaborol-5-yloxy)-nicotinonitrile (D208)

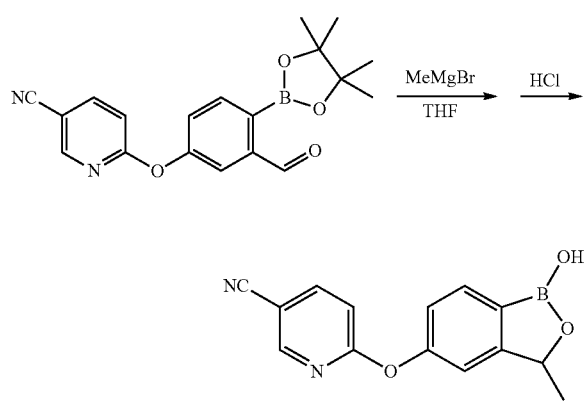

To a suspension of 6-[3-formyl-4-(4,4,5,5-tetramethyl-[1,3,2]dioxaborolan-2-yl)-phenoxy]-nicotinonitrile (105 mg, 0.3 mmol, 1.0 eq.) in THF (5.0 mL) at 0° C. was added MeMgBr (0.15 mL, 0.45 mmol, 1.5 eq.) drop wise. The mixture was stirred at 0° C. for 20 minutes and allowed to warm to room temperature in another 1 h. After cooling to 0° C., the clear solution was carefully treated with H$_2$O (1 mL), followed by slow addition of HCl (10 mL, 3N). The resulting yellow suspension was allowed to ward to room temperature gradually and stirred for 2 h. The mixture was then treated with sat. NaHCO$_3$ drop wise until PH reaching 1 and was extracted with EtOAc (3×10 mL). Combined organic extracts was washed with brine (10 mL), dried over MgSO$_4$, filtered and the filtrate was concentrated under reduced pressure. The residue was applied to silica chromatography eluting with MeOH/DCM (0:100 to 10:90) to give 6-(1-hydroxy-3-methyl-1,3-dihydro-benzo[c][1,2]oxaborol-5-yloxy)-nicotinonitrile as a white solid. LCMS (m/z) 267 (M+H); $^1$H NMR (DMSO-d$_6$) δ: 9.19 (s, 1H), 8.71 (dd, J=2.3, 0.6 Hz, 1H), 8.38 (dd, J=8.7, 2.4 Hz, 1H), 7.80 (d, J=7.9 Hz, 1H), 7.28-7.35 (m, 2H), 7.20 (dd, J=7.9, 2.0 Hz, 1H), 5.26 (q, J=6.5 Hz, 1H), 1.45 (d, J=6.6 Hz, 3H).

4-(1-Hydroxy-1,3-dihydro-benzo[c][1,2]oxaborol-5-yloxy)-benzaldehyde (D209)

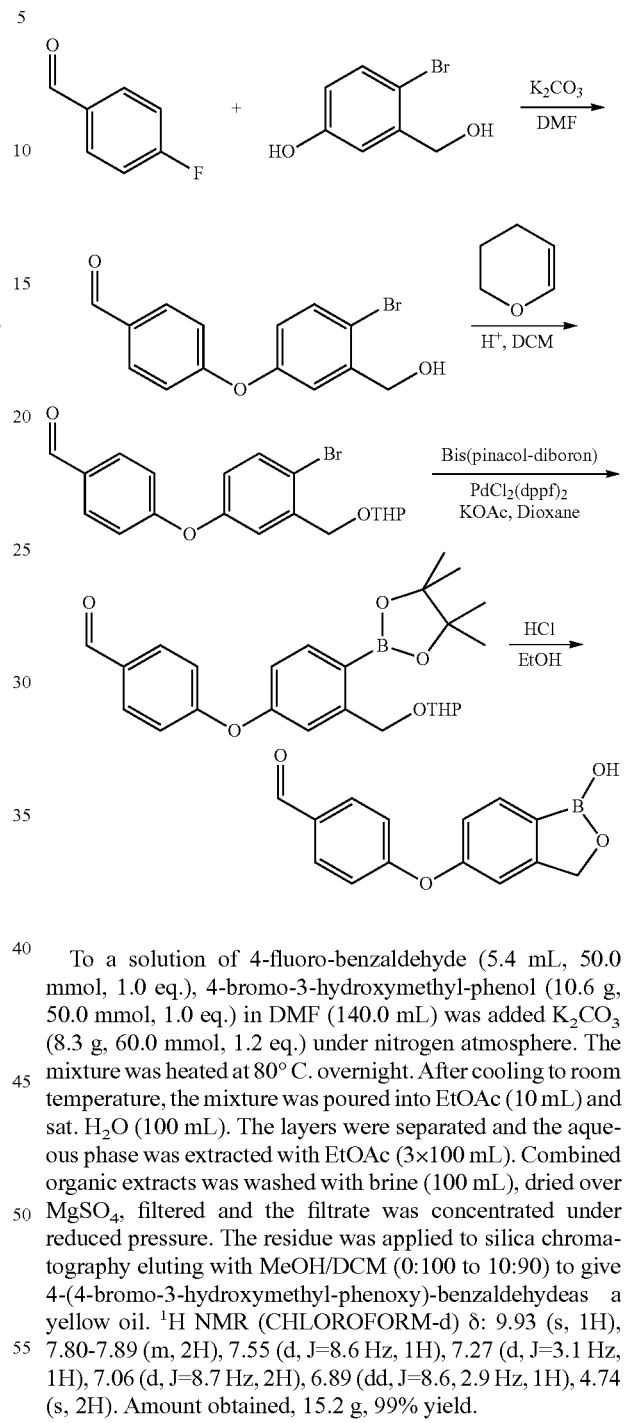

To a solution of 4-fluoro-benzaldehyde (5.4 mL, 50.0 mmol, 1.0 eq.), 4-bromo-3-hydroxymethyl-phenol (10.6 g, 50.0 mmol, 1.0 eq.) in DMF (140.0 mL) was added K$_2$CO$_3$ (8.3 g, 60.0 mmol, 1.2 eq.) under nitrogen atmosphere. The mixture was heated at 80° C. overnight. After cooling to room temperature, the mixture was poured into EtOAc (10 mL) and sat. H$_2$O (100 mL). The layers were separated and the aqueous phase was extracted with EtOAc (3×100 mL). Combined organic extracts was washed with brine (100 mL), dried over MgSO$_4$, filtered and the filtrate was concentrated under reduced pressure. The residue was applied to silica chromatography eluting with MeOH/DCM (0:100 to 10:90) to give 4-(4-bromo-3-hydroxymethyl-phenoxy)-benzaldehydeas a yellow oil. $^1$H NMR (CHLOROFORM-d) δ: 9.93 (s, 1H), 7.80-7.89 (m, 2H), 7.55 (d, J=8.6 Hz, 1H), 7.27 (d, J=3.1 Hz, 1H), 7.06 (d, J=8.7 Hz, 2H), 6.89 (dd, J=8.6, 2.9 Hz, 1H), 4.74 (s, 2H). Amount obtained, 15.2 g, 99% yield.

To a suspension of 44-(4-bromo-3-hydroxymethyl-phenoxy)-benzaldehydeas (15.2 g, 49.5 mmol, 1.0 eq) in DCM (250 mL) was added 3,4-dihydro-2H-pyran (6.7 mL, 74.2 mmol, 1.5 eq.), followed by camphorsulfonic acid (300 mg). The mixture was stirred at room temperature for 2 h. After adding K$_2$CO$_3$ (1 g), the mixture was washed with H$_2$O (150 mL), brine (150 mL). The organic phase was dried over MgSO$_4$, filtered and the filtrate was concentrated under reduced pressure. The oily residue was applied to silica chromatography eluting with EtOAc/Heptanes (0:100 to 50:50) to give 4-[4-bromo-3-(tetrahydro-pyran-2-yloxymethyl)-phenoxy]-benzaldehyde as a light yellow oil. $^1$H NMR (CHLOROFORM-d) δ: 9.93 (s, 1H), 7.81-7.89 (m, 2H), 7.54 (d, J=8.6 Hz, 1H), 7.29 (d, J=2.9 Hz, 1H), 7.04-7.11 (m, 2H), 6.87 (dd, J=8.6, 2.9 Hz, 1H), 4.81 (d, J=14.0 Hz, 1H), 4.76 (t, J=3.4 Hz, 1H), 4.55 (d, J=14.0 Hz, 1H), 3.88 (ddd, J=11.3, 8.6, 3.1 Hz, 1H), 3.51-3.61 (m, 1H), 1.71-1.88 (m, 6H).

To a solution of 4-[4-bromo-3-(tetrahydro-pyran-2-yloxymethyl)-phenoxy]-benzaldehyde (1.17 g, 3.0 mmol, 1.0 eq.) in 1,4-dioxane (20 mL) was added bis-pinacol-diboron (838 mg, 3.3 mmol, 1.1 eq.), KOAc (883 mg, 9.0 mmol, 3.0 eq.) and PdCl$_2$(dppf)$_2$ (65.8 mg, 0.09 mmol, 0.03 eq.). The mixture was degassed with N$_2$ and heated at 80° C. overnight. After cooling to room temperature, the mixture was filtered though a short pack of celite and the filtrate was concentrated under reduced pressure. The residue was applied to silica chromatography eluting with EtOAc/Heptanes (0:100 to 70:30) to give 4-[3-(tetrahydro-pyran-2-yloxymethyl)-4-(4,4,5,5-tetramethyl-[1,3,2]dioxaborolan-2-yl)-phenoxy]-benzaldehyde as a clear oil. $^1$H NMR (CHLOROFORM-d) δ: 9.93 (s, 1H), 7.84 (d, J=8.8 Hz, 2H), 7.26 (s, 1H), 7.05-7.11 (m, 2H), 6.95 (dd, J=8.2, 2.4 Hz, 1H), 4.95 (d, J=13.2 Hz, 1H), 4.84 (d, J=13.3 Hz, 1H), 4.75 (t, J=3.5 Hz, 1H), 3.89 (ddd, J=11.3, 8.4, 3.0 Hz, 1H), 3.48-3.59 (m, 1H), 1.55-1.75 (m, 6H), 1.34 (s, 12H).

To a suspension of 4-[3-(tetrahydro-pyran-2-yloxymethyl)-4-(4,4,5,5-tetramethyl-[1,3,2]dioxaborolan-2-yl)-phenoxy]-benzaldehyde (1.4 g, 3.2 mmol, 1.0 eq.) in EtOH (15 mL) at 0° C. was added HCl (15 mL, 3N). The mixture was stirred at 0° C. for 20 minutes and allowed to warm to room temperature in another 1 h. The mixture was then treated with sat. NaHCO$_3$ drop wise until PH reaching 7. The precipitate was collected by filtration, washed with H$_2$O to give 4-(1-hydroxy-1,3-dihydro-benzo[c][1,2]oxaborol-5-yloxy)-benzaldehyde as a white solid. LCMS (m/z) 255 (M+H); $^1$H NMR (DMSO-d$_6$) δ: 9.92 (s, 1H), 9.19 (s, 1H), 7.92 (d, J=8.8 Hz, 1H), 7.92 (q, J=4.6 Hz, 1H), 7.78 (d, J=8.0 Hz, 1H), 7.16 (d, J=8.7 Hz, 2H), 7.12-7.19 (m, 1H), 7.09 (dd, J=8.0, 2.1 Hz, 1H), 4.95 (s, 2H).

5-(4-Methylaminomethyl-phenoxy)-3H-benzo[c][1,2]oxaborol-1-ol (D210)

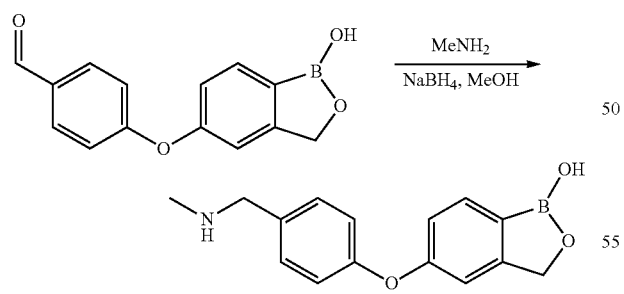

To a solution of 4-(1-hydroxy-1,3-dihydro-benzo[c][1,2]oxaborol-5-yloxy)-benzaldehyde (76.2 mg, 0.3 mmol, 1.0 eq.) in MeOH (3.0 mL) was added dimethylamine (170 µL, 0.33 mmol, 1.1 eq.). The mixture was stirred at room temperature for 30 minutes. After cooling to 0° C., NaBH$_4$ (11.3 mg, 0.3 mmol, 1.0 eq.) was added in portions and the mixture was allowed to warm to room temperature and stirred for 2 h. The mixture was carefully treated with dilute HCl (5 mL) and aqueous phase was extracted with EtOAc (3×10 mL). Combined organic extracts was washed with brine (10 mL), dried over MgSO$_4$, filtered and the filtrate was concentrated under reduced pressure. The residue was applied to silica chromatography eluting with MeOH/DCM (0:100 to 10:90) to give 5-(4-methylaminomethyl-phenoxy)-3H-benzo[c][1,2]oxaborol-1-ol as a white solid. LCMS (m/z) 270 (M+H); $^1$H NMR (DMSO-d$_6$) δ: 7.67-7.74 (m, 1H), 7.41-7.46 (m, J=8.5 Hz, 2H), 7.00-7.07 (m, 2H), 6.91-6.98 (m, 2H), 4.91 (s, 2H), 4.53 (s, 3H), 3.85 (s, 2H).

5-(4-Dimethylaminomethyl-phenoxy)-3H-benzo[c][1,2]oxaborol-1-ol (D211)

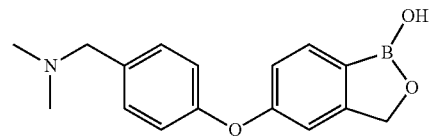 [SMILES: CN(C)Cc1ccc(Oc2ccc3c(c2)COB3O)cc1]

D211 was prepared using a procedure similar to that of D210. LCMS (m/z) 284 (M+H); $^1$H NMR (DMSO-d$_6$) δ: 9.09 (br. s., 1H), 7.67-7.73 (m, 1H), 7.29-7.35 (m, J=8.5 Hz, 2H), 6.97-7.03 (m, 2H), 6.92-6.97 (m, 2H), 4.90 (s, 2H), 4.54 (s, 6H), 3.45 (s, 2H).

4-(1-Hydroxy-1,3-dihydro-benzo[c][1,2]oxaborol-5-yloxy)-N-(4-methyl-benzyl)-benzamide (D212)

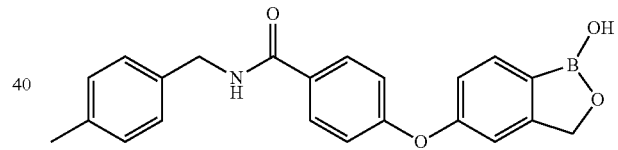

D212 was prepared using a procedure similar to that of D229. LCMS (m/z) 374 (M+H); $^1$H NMR (DMSO-d$_6$) δ: 9.16 (s, 1H), 8.96 (t, J=5.9 Hz, 1H), 7.90-7.98 (m, 2H), 7.75 (d, J=7.9 Hz, 1H), 7.17-7.22 (m, 2H), 7.07-7.15 (m, 4H), 7.02-7.07 (m, 2H), 4.95 (s, 2H), 4.43 (d, J=6.0 Hz, 2H), 2.27 (s, 3H).

4-(1-Hydroxy-1,3-dihydro-benzo[c][1,2]oxaborol-5-yloxy)-N-(4-methoxy-benzyl)-benzamide (D213)

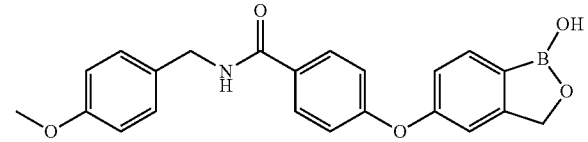 [SMILES: COc1ccc(CNC(=O)c2ccc(Oc3ccc4c(c3)COB4O)cc2)cc1]

D213 was prepared using a procedure similar to that of D229. LCMS (m/z) 412 (M+23); $^1$H NMR (DMSO-d$_6$) δ: 9.16 (s, 1H), 8.93 (t, J=6.0 Hz, 1H), 7.89-7.98 (m, 2H), 7.75

(d, J=7.9 Hz, 1H), 7.20-7.27 (m, 2H), 7.07-7.12 (m, 2H), 7.02-7.07 (m, 2H), 6.86-6.91 (m, 2H), 4.94 (s, 2H), 4.40 (d, J=6.0 Hz, 2H), 3.72 (s, 3H).

4-(1-Hydroxy-1,3-dihydro-benzo[c][1,2]oxaborol-5-yloxy)-N-phenyl-benzamide (D214)

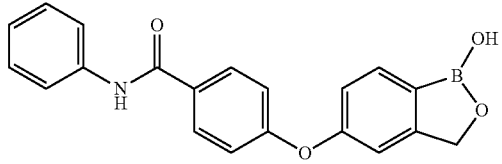 [SMILES: O=C(Nc1ccccc1)c1ccc(Oc2ccc3c(c2)COB3O)cc1]

D214 was prepared using a procedure similar to that of D229. LCMS (m/z) 368 (M+23); $^1$H NMR (DMSO-d$_6$) δ: 10.17 (s, 1H), 7.99 (d, J=8.6 Hz, 2H), 7.74 (dd, J=7.8, 4.7 Hz, 3H), 7.32 (t, J=7.8 Hz, 2H), 7.13 (d, J=8.6 Hz, 2H), 7.01-7.09 (m, 3H), 4.93 (s, 2H).

N-Cyclopropyl-4-(1-hydroxy-1,3-dihydro-benzo[c][1,2]oxaborol-5-yloxy)-benzamide (D215)

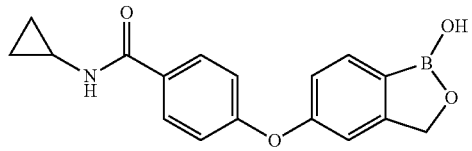 [SMILES: O=C(NC1CC1)c1ccc(Oc2ccc3c(c2)COB3O)cc1]

D215 was prepared using a procedure similar to that of D229. LCMS (m/z) 310 (M+H); $^1$H NMR (DMSO-d$_6$) δ: 9.13 (s, 1H), 8.36 (d, J=4.0 Hz, 1H), 7.83 (d, J=8.8 Hz, 2H), 7.66-7.77 (m, 1H), 6.98-7.11 (m, 4H), 4.92 (s, 2H), 2.81 (td, J=7.3, 3.7 Hz, 1H), 0.62-0.70 (m, 2H), 0.49-0.57 (m, 2H).

4-(1-Hydroxy-1,3-dihydro-benzo[c][1,2]oxaborol-5-yloxy)-N-(tetrahydro-furan-2-ylmethyl)-benzamide (D216)

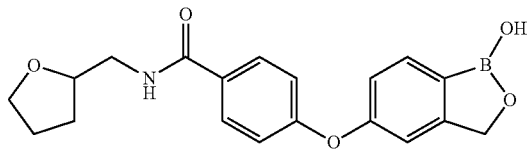 [SMILES: O=C(NCC1CCCO1)c1ccc(Oc2ccc3c(c2)COB3O)cc1]

D216 was prepared using a procedure similar to that of D229. LCMS (m/z) 376 (M+23); $^1$H NMR (METHANOL-d$_4$) δ: 8.38 (br. s., 1H), 7.81-7.88 (m, 2H), 7.66 (d, J=7.9 Hz, 1H), 6.99-7.07 (m, 4H), 5.02 (s, 2H), 4.10 (qd, J=6.8, 4.8 Hz, 1H), 3.89 (dt, J=8.1, 6.7 Hz, 1H), 3.72-3.79 (m, 1H), 3.46-3.54 (m, 1H), 3.37-3.45 (m, 1H), 1.84-2.07 (m, 3H), 1.61-1.70 (m, 1H)

4-(1-Hydroxy-1,3-dihydro-benzo[c][1,2]oxaborol-5-yloxy)-N-methyl-benzamide (D217)

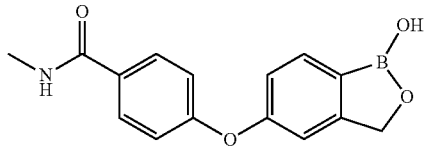 [SMILES: CNC(=O)c1ccc(Oc2ccc3c(c2)COB3O)cc1]

D217 was prepared using a procedure similar to that of D229. LCMS (m/z) 284 (M+H); $^1$H NMR (DMSO-d$_6$) δ: 9.13 (s, 1H), 8.36 (d, J=4.5 Hz, 1H), 7.82-7.87 (m, 2H), 7.73 (d, J=7.9 Hz, 1H), 6.99-7.08 (m, 4H), 4.92 (s, 2H), 2.75 (d, J=4.5 Hz, 3H).

4-(1-Hydroxy-1,3-dihydro-benzo[c][1,2]oxaborol-5-yloxy)-N,N-dimethyl-benzamide (D218)

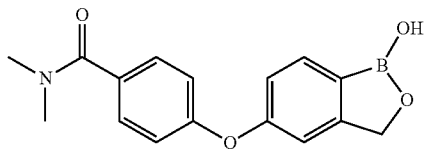 [SMILES: CN(C)C(=O)c1ccc(Oc2ccc3c(c2)COB3O)cc1]

D218 was prepared using a procedure similar to that of D229. LCMS (m/z) 298 (M+H); $^1$H NMR (DMSO-d$_6$) δ: 9.29 (s, 1H), 7.71 (d, J=8.0 Hz, 1H), 7.38-7.45 (m, 2H), 6.97-7.05 (m, 4H), 4.91 (s, 2H), 2.92 (br. s., 6H).

N'-[4-(1-Hydroxy-1,3-dihydro-benzo[c][1,2]oxaborol-5-yloxy)-benzoyl]-hydrazinecarboxylic acid tert-butylester (D219)

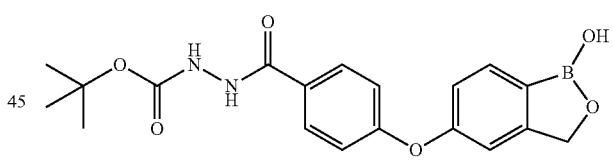

D219 was prepared using a procedure similar to that of D229. LCMS (m/z) 407 (M+23); $^1$H NMR (DMSO-d$_6$) δ: 10.13 (s, 1H), 9.15 (s, 1H), 8.87 (s, 1H), 7.88 (d, J=8.6 Hz, 2H), 7.75 (d, J=8.0 Hz, 1H), 7.02-7.10 (m, 4H), 4.93 (s, 2H), 1.41 (s, 9H).

4-(1-Hydroxy-1,3-dihydro-benzo[c][1,2]oxaborol-5-yloxy)-benzamide (D220)

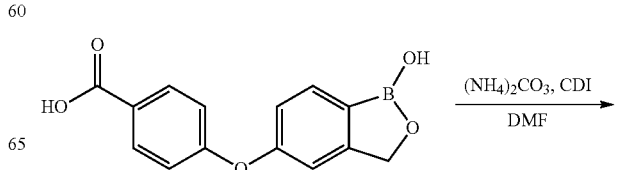

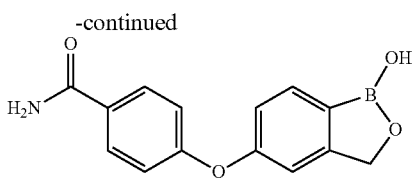

To a 40 mL scintillation vial containing 4-(1-hydroxy-1,3-dihydro-benzo[c][1,2]oxaborol-5-yloxy)-benzoic acid (77 mg, 0.28 mmol, 1.0 eq.) and CDI (101.3 mg, 0.62 mmol), 2.5 eq.) in DMF (3.0 mL) was added Ammonium carbonate (123.3 mg, 1.28 mmol, 4.5 eq.). The mixture was stirred at room temperature overnight. The mixture was treated with H₂O (5 mL) and the layers were separated. The aqueous was extracted with EtOAc (2×5 mL), combined organic phase was washed with brine (10 mL), dried over MgSO₄, filtered and the filtrate was concentrated under reduced pressure. The residue was applied to silica chromatography eluting with MeOH/DCM (0:100 to 10:90) to give 4-(1-hydroxy-1,3-dihydro-benzo[c][1,2]oxaborol-5-yloxy)-benzamide as a white solid. LCMS (m/z) 270 (M+H); ¹H NMR (DMSO-d₆) δ: 9.14 (s, 1H), 7.87-7.92 (m, 2H), 7.73 (d, J=7.8 Hz, 1H), 7.05 (d, J=8.8 Hz, 4H), 4.93 (s, 2H).

5-(4-Hydroxymethyl-phenoxy)-3H-benzo[c][1,2]oxaborol-1-ol (D221)

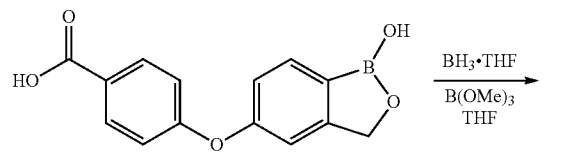

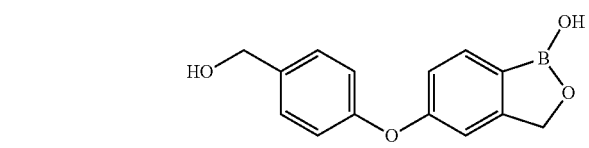

To a solution of 4-(1-hydroxy-1,3-dihydro-benzo[c][1,2]oxaborol-5-yloxy)-benzoic acid (200 mg, 0.74 mmol, 1.0 eq.), trimethyl borate (0.5 mL, 4.4 mmol, 6.0 eq.) in THF (7.0 mL) was added borane tetrahydrofuran complex solution (1.5 mL, 1.0 M in THF, 1.5 mmol, 2.0 eq.) dropwise under nitrogen atmosphere. The mixture was stirred at room temperature overnight. The mixture was carefully treated with MeOH (2 mL) and poured into EtOAc (10 mL) and sat. NaHCO₃ (10 mL). The layers were separated and the aqueous phase was extracted with EtOAc (3×10 mL). Combined organic extracts was washed with brine (10 mL), dried over MgSO₄, filtered and the filtrate was concentrated under reduced pressure. The residue was applied to silica chromatography eluting with MeOH/DCM (0:100 to 10:90) to give 5-(4-hydroxymethyl-phenoxy)-3H-benzo[c][1,2]oxaborol-1-ol as a white solid. LCMS (m/z) 279 (M+23); ¹H NMR (DMSO-d₆) δ: 9.09 (s, 1H), 7.70 (d, J=8.0 Hz, 1H), 7.34-7.38 (m, J=8.7 Hz, 2H), 7.01-7.05 (m, 2H), 6.96 (dd, J=8.0, 2.1 Hz, 1H), 6.91-6.93 (m, 1H), 5.18 (t, J=5.7 Hz, 1H), 4.91 (s, 2H), 4.49 (d, J=5.7 Hz, 2H).

5-(4-Nitro-phenoxy)-3H-benzo[c][1,2]oxaborol-1-ol (D222)

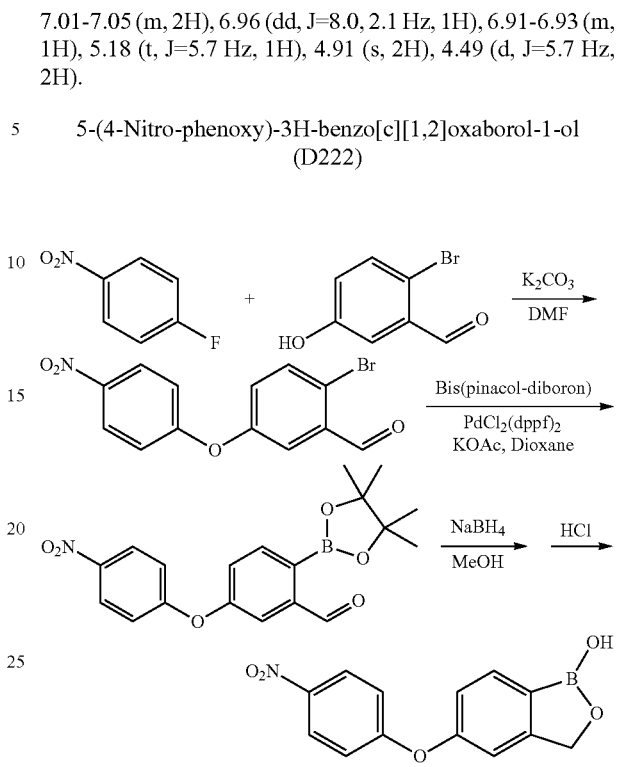

To a solution of 1-fluoro-4-nitro-benzene (1.1 mL, 10.0 mmol, 1.0 eq.), 2-bromo-5-hydroxy-benzaldehyde (2.0 g, 10.0 mmol, 1.0 eq.) in DMF (30.0 mL) was added K₂CO₃ (1.7 g, 12.0 mmol, 1.2 eq.) under nitrogen atmosphere. The mixture was heated at 100° C. overnight. After cooling to room temperature, the mixture was poured into EtOAc (30 mL) and sat. H₂O (30 mL). The layers were separated and the aqueous phase was extracted with EtOAc (3×20 mL). Combined organic extracts was washed with brine (30 mL), dried over MgSO₄, filtered and the filtrate was concentrated under reduced pressure. The residue was applied to silica chromatography eluting with EtOAc/Heptanes (0:100 to 100:0) to give 2-bromo-5-(4-nitro-phenoxy)-benzaldehyde as a yellow fine powder. ¹H NMR (CHLOROFORM-d) δ: 10.31-10.37 (m, 10H), 8.26 (dd, J=9.0, 0.3 Hz, 15H), 8.21-8.28 (m, 13H), 7.73 (d, J=8.6 Hz, 3H), 7.73 (dt, J=8.7, 0.5 Hz, 7H), 7.62 (dd, J=3.1, 0.3 Hz, 10H), 7.20-7.29 (m, 19H), 7.00-7.10 (m, 23H). Amount obtained, 2.6 g, 80.7% yield.

To a solution of 2-Bromo-5-(4-nitro-phenoxy)-benzaldehyde (966 mg, 3.0 mmol, 1.0 eq.) in 1,4-dioxane (25 mL) was added bis-pinacol-diboron (838 mg, 3.3 mmol, 1.1 eq.), KOAc (883 mg, 9.0 mmol, 3.0 eq.) and PdCl₂(dppf)₂ (66 mg, 0.09 mmol, 0.03 eq.). The mixture was degassed with N₂ and heated at 80° C. overnight. After cooling to room temperature, the mixture was filtered though a short pack of celite and the filtrate was concentrated under reduced pressure. The residue was applied to silica chromatography eluting with EtOAc/Heptanes (0:100 to 100:0) to give 5-(4-nitro-phenoxy)-2-(4,4,5-trimethyl-[1,3,2]dioxaborolan-2-yl)-benzaldehyde as a yellow solid. ¹H NMR (CHLOROFORM-d) δ: 10.65 (s, 1H), 8.19-8.29 (m, J=9.3 Hz, 2H), 8.01 (d, J=8.2 Hz, 1H), 7.66 (d, J=2.5 Hz, 1H), 7.32 (dd, J=8.2, 2.5 Hz, 1H), 7.04-7.10 (m, 2H), 1.41 (s, 12H). Amount obtained, 724 mg, 65.3% yield.

To a suspension of 5-(4-nitro-phenoxy)-2-(4,4,5-trimethyl-[1,3,2]dioxaborolan-2-yl)-benzaldehyde (721 mg, 1.9 mmol, 1.0 eq.) in EtOH (15 mL) at 0° C. was added NaBH₄

(73.8 mg, 1.9 mmol, 1.0 eq.) in small portions. The mixture was stirred at 0° C. for 20 minutes and allowed to warm to room temperature in another 1 h. After cooling to 0° C., the clear solution was carefully treated with H₂O (1 mL), followed by slow addition of HCl (5 mL, 3N). The resulting yellow suspension was allowed to ward to room temperature gradually and stirred for 2 h. The mixture was then treated with sat. NaHCO₃ drop wise until PH reaching 7. The precipitate was collected by filtration, washed with H₂O to give 5-(4-nitro-phenoxy)-3H-benzo[c][1,2]oxaborol-1-ol as a white powder. LCMS (m/z) 294 (M+23); $^1$H NMR (DMSO-d$_6$) δ: 7.26 (d, J=8.6 Hz, 1H), 6.93 (d, J=3.0 Hz, 1H), 6.56 (dd, J=8.5, 3.0 Hz, 1H), 4.37 (s, 2H). Amount obtained, 510 mg, 96.4% yield.

5-(4-Amino-phenoxy)-3H-benzo[c][1,2]oxaborol-1-ol (D223)

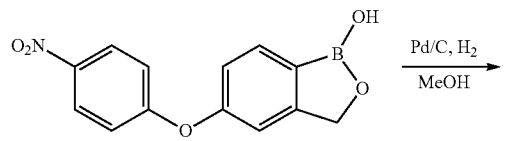

To a 25 mL round-bottom flask fitted with magnetic stirring bar was added 5-(4-nitro-phenoxy)-3H-benzo[c][1,2]oxaborol-1-01 (310 mg, 1.1 mmol, 1.0 eq.), followed by addition of MeOH (10 mL). The flask was evacuated and recharged with N₂ twice. To the stirring solution was added 5% Pd/C (60 mg) and the flask was evacuated and recharged with H₂ three times. The resulting suspension was stirred under a H₂ balloon at room temperature overnight. The mixture was filtered through a short pack of celite and washed with MeOH (3×10 mL). The combined filtrate was concentrated under reduced pressure to give a light yellow oil. The oil was dissolved in minimum amount of MeOH and carefully treated with HCl (conc.). The precipitate was collected by filtration, washed with heptanes to give 5-(4-amino-phenoxy)-3H-benzo[c][1,2]oxaborol-1-ol hydrochloride salt as a white solid. LCMS (m/z) 242 (M+H); $^1$H NMR (DMSO-d$_6$) δ: 9.03 (br. s., 1H), 7.64 (d, J=8.0 Hz, 1H), 6.77-6.89 (m, 4H), 6.64-6.77 (m, 2H), 4.86 (s, 2H), 3.30 (br. s., 2H).

N-[4-(1-Hydroxy-1,3-dihydro-benzo[c][1,2]oxaborol-5-yloxy)-phenyl]-acetamide (D224)

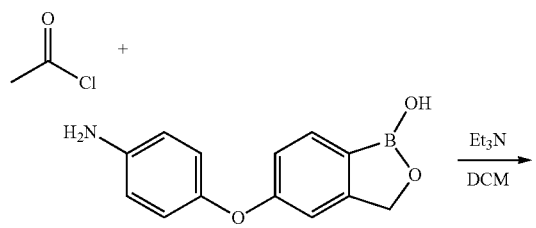

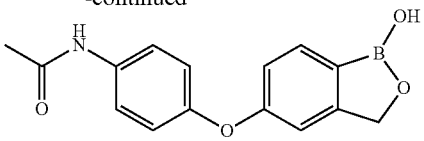

To a 20 mL scintillation vial containing 5-(4-amino-phenoxy)-3H-benzo[c][1,2]oxaborol-1-ol (68 mg, 0.28 mmol, 1.0 eq.) in DCM (3.0 mL) was added Et₃N (47 μL, 0.33 mmol, 1.2 eq.), followed by acetyl chloride (22 μL, 0.31 mmol, 1.1 eq.). The mixture was stirred at room temperature overnight. The mixture was concentrated under reduced pressure. The residue was applied to silica chromatography eluting with MeOH/DCM (0:100 to 10:90) to give N-[4-(1-hydroxy-1,3-dihydro-benzo[c][1,2]oxaborol-5-yloxy)-phenyl]-acetamide as a white solid. LCMS (m/z) 284 (M+H); $^1$H NMR (DMSO-d$_6$) δ: 10.17 (s, 1H), 7.68 (d, J=8.1 Hz, 1H), 7.58-7.63 (m, 2H), 6.94-6.99 (m, 2H), 6.88 (dd, J=8.0, 2.1 Hz, 1H), 6.84 (d, J=1.5 Hz, 1H), 4.85 (s, 2H), 3.12 (s, 1H), 2.00 (s, 3H).

N-[4-(1-Hydroxy-1,3-dihydro-benzo[c][1,2]oxaborol-5-yloxy)-phenyl]-methanesulfonamide (D225)

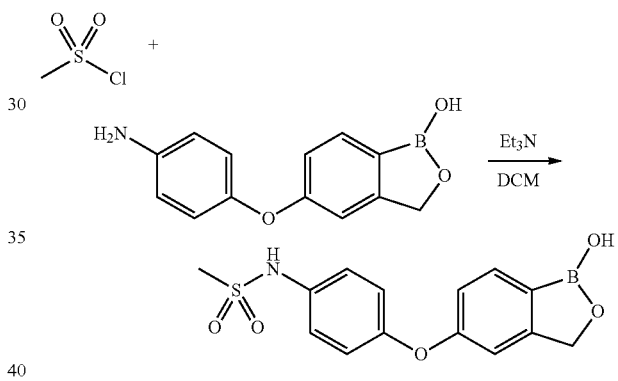

To a 20 mL scintillation vial containing 5-(4-amino-phenoxy)-3H-benzo[c][1,2]oxaborol-1-ol (50 mg, 0.21 mmol, 1.0 eq.) in DCM (3.0 mL) was added Et₃N (35 μL, 0.25 mmol, 1.2 eq.), followed by methanesulfonyl chloride (18 μL, 0.31 mmol, 1.1 eq.). The mixture was stirred at room temperature overnight. The mixture was concentrated under reduced pressure. The residue was applied to silica chromatography eluting with MeOH/DCM (0:100 to 10:90) to give N-[4-(1-hydroxy-1,3-dihydro-benzo[c][1,2]oxaborol-5-yloxy)-phenyl]-methanesulfonamide as a white solid. LCMS (m/z) 342 (M+23); $^1$H NMR (DMSO-d$_6$) δ: 9.72 (s, 1H), 7.65-7.79 (m, 1H), 7.21-7.26 (m, 2H), 7.01-7.05 (m, 2H), 6.91-6.94 (m, 1H), 6.89-6.91 (m, 1H), 4.88 (s, 2H), 2.94 (s, 3H).

4-(1-Hydroxy-1,3-dihydro-benzo[c][1,2]oxaborol-5-yloxy)-benzoic acid (D226)

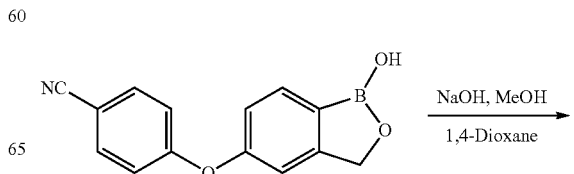

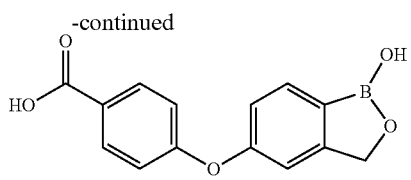

To a 250 mL round-bottom flask equipped with magnetic stirring bar containing 4-(1-hydroxy-1,3-dihydro-benzo[c][1,2]oxaborol-5-yloxy)-benzonitrile (5.0 g, 20.0 mmol, 1.0 eq.), MeOH (90 mL) and 1,4-dioxane (50 mL) was slowly added NaOH (6N, 20 mL). The flask was fitted with a air condenser and heated in a preheated 90° C. oil bath for 2 days. The flask was then immersed in an ice-bath and the solution was carefully treated with HCl (1N) until the PH value reached 2. The mixture was extracted with EtOAc (3×150 mL). Combined organic extracts was washed with $H_2O$ (200 mL) and brine (200 mL), dried over $MgSO_4$, filtered and the filtrate was concentrated under reduced pressure to give 4-(1-hydroxy-1,3-dihydro-benzo[c][1,2]oxaborol-5-yloxy)-benzoic acid as a white solid. LCMS (m/z) 271 (M+H); $^1$H NMR (DMSO-$d_6$) δ: 12.80 (br. s., 1H), 9.16 (s, 1H), 7.94 (d, J=8.6 Hz, 2H), 7.76 (d, J=8.0 Hz, 1H), 7.01-7.15 (m, 4H), 4.94 (s, 2H). Amount obtained, 4.7 g, 87.0% yield.

[4-(1-Hydroxy-1,3-dihydro-benzo[c][1,2]oxaborol-5-yloxy)-phenyl]-morpholin-4-yl-methanone (D227)

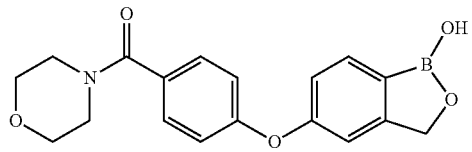 [SMILES: O=C(c1ccc(Oc2ccc3c(c2)COB3O)cc1)N1CCOCC1]

D227 was prepared using a procedure similar to that of D229. LCMS (m/z) 701 (2M+23); $^1$H NMR (DMSO-$d_6$) δ: 9.15 (s, 1H), 7.75 (d, J=7.9 Hz, 1H), 7.42-7.49 (m, 2H), 7.06-7.10 (m, 3H), 7.02-7.06 (m, 1H), 4.95 (s, 2H), 3.40-3.65 (m, 8H).

N-Cyclopentyl-4-(1-hydroxy-1,3-dihydro-benzo[c][1,2]oxaborol-5-yloxy)-benzamide (D228)

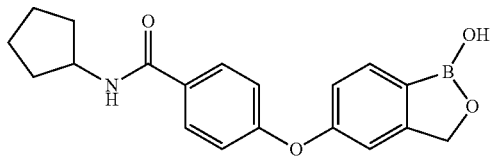 [SMILES: O=C(NC1CCCC1)c1ccc(Oc2ccc3c(c2)COB3O)cc1]

D228 was prepared using a procedure similar to that of D229. LCMS (m/z) 352 (M+H); $^1$H NMR (DMSO-$d_6$) δ: 9.15 (s, 1H), 8.15 (d, J=7.9 Hz, 1H), 7.86-7.92 (m, 2H), 7.75 (d, J=8.5 Hz, 1H), 7.05-7.11 (m, 2H), 7.00-7.05 (m, 2H), 4.94 (s, 2H), 3.69-3.81 (m, 1H), 1.77-1.86 (m, 2H), 1.67-1.77 (m, 2H), 1.56-1.65 (m, 1H), 1.22-1.37 (m, 4H), 1.04-1.20 (m, 1H).

N-Benzyl-4-(1-hydroxy-1,3-dihydro-benzo[c][1,2]oxaborol-5-yloxy)-benzamide (D229)

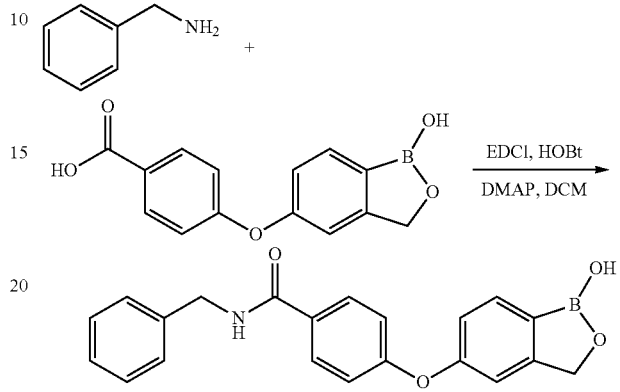

To a 40 mL scintillation vial containing 4-(1-hydroxy-1,3-dihydro-benzo[c][1,2]oxaborol-5-yloxy)-benzoic acid (150 mg, 0.55 mmol, 1.0 eq.), EDCI (157.2 mg, 0.82 mmol, 1.5 eq.), HOBt (111.5 mg, 0.82 mmol, 1.5 eq.) and DMAP (12 mg, 0.1 mmol, 0.2 eq.) in DCM (10.0 mL) was added benzylamine (24 μL, 2.2 mmol, 4.0 eq.) drop wise. The mixture was stirred at room temperature overnight. The mixture was treated with $H_2O$ (10 mL) and the layers were separated. The aqueous was extracted with DCM (2×5 mL), combined organic phase was washed with brine (10 mL), dried over $MgSO_4$, filtered and the filtrate was concentrated under reduced pressure. The residue was applied to silica chromatography eluting with MeOH/DCM (0:100 to 10:90) to give N-benzyl-4-(1-hydroxy-1,3-dihydro-benzo[c][1,2]oxaborol-5-yloxy)-benzamide as a white solid. LCMS (m/z) 360 (M+H); $^1$H NMR (DMSO-$d_6$) δ: 9.01 (t, J=6.0 Hz, 1H), 7.91-8.00 (m, 2H), 7.76 (d, J=7.9 Hz, 1H), 7.29-7.36 (m, 5H), 7.21-7.27 (m, 1H), 7.08-7.13 (m, 2H), 7.02-7.07 (m, 2H), 4.95 (s, 2H), 4.48 (d, J=6.0 Hz, 2H).

Example 20

In Vitro Assays

The ability of the compounds described herein to inhibit pro-inflammatory cytokines or phsophodiesterases were tested.

Cytokine Assay

Frozen human peripheral blood mononucleocytes (PBMC) were thawed and centrifuged. Cryopreservation media was aspirated off of the cell pellet, and the cells were resuspended in fresh culture media (CM) comprising RPMI 1640 and 10% FBS in 96 well plates. Test article was dissolved in DMSO to form a 10 mM sample (DMSO, 100%). The 10 mM samples were diluted to 100 μM in CM (DMSO, 1%), then further diluted to 10, 1, 0.1, 0.01 μM in 200 μl, of CM (n=3). Inducer (1 μg/mL LPS for TNF-α and IL-1β [and IL-6] or 20 ug/mL PHA for IFNγ, IL-2, IL-4, IL-5 and IL-1β. IL-23 was induced with 100 ng/ml IFN-g+1 mg/ml LPS, using THP-1 cells. Vehicle (1% DMSO) was used as a control for this experiment. Vehicle without inducer was used as a negative control. Cells were incubated at 37° C., 5% $CO_2$.

Supernatants were extracted at 24 hours (for TNF-α, IL-1β, IL-2, IL-6 and IFNγ) and 48 hours (for IL-4, IL-5, IL-10 and IL-23), and stored at −20° C. Supernatants were thawed and assayed for cytokine expression using the fluorochrome-labeled cytokine-specific beads and a BD FACSArray™. IL-23 was assayed using a commercial ELISA kit (R&D Systems).

| | IC50 (μM) or inhibition % at 10 μM | | | | |
|---|---|---|---|---|---|
| Cmpd | TNF-α | IL-2 | IFN-γ | IL-5 | IL-10 |
| C7 | + | + | + | + | + |
| C17 | ++++ | ++++ | ++++ | +++ | ++ |
| C18 | + | + | + | + | + |
| C23 | ++ | ++ | ++ | ++ | ++ |
| C24 | + | + | + | + | + |
| C25 | +++ | ++++ | +++ | ++ | +++ |
| C26 | ++++ | ++++ | ++++ | ++++ | ++++ |
| C31 | + | + | | + | + |
| C36 | + | +++ | + | ++ | + |
| C37 | ++ | +++ | +++ | ++ | ++ |
| C38 | + | + | + | + | + |
| C100 | + | + | + | + | + |
| D1 | ++ | +++ | +++ | +++ | + |
| D2 | ++++ | ++++ | ++++ | ++++ | + |
| D3 | ++++ | ++++ | ++++ | ++++ | + |
| D4 | ++++ | ++++ | ++++ | ++++ | + |
| D5 | ++++ | +++ | ++++ | ++++ | + |
| D6 | ++++ | ++++ | ++++ | ++ | ++ |
| D7 | ++++ | ++++ | ++++ | ++++ | ++++ |
| D8 | + | +++ | + | + | + |
| D9 | ++++ | ++++ | ++++ | ++++ | ++++ |
| D10 | ++++ | ++ | ++ | ++ | +++ |
| D11 | ++++ | +++ | +++ | ++ | +++ |
| D12 | ++++ | ++++ | ++++ | +++ | ++++ |
| D13 | ++ | +++ | +++ | +++ | +++ |
| D14 | ++++ | ++++ | ++++ | ++++ | +++ |
| D15 | ++++ | ++++ | ++++ | | |
| D16 | ++++ | +++ | ++++ | | |
| D17 | ++ | + | + | | |
| D18 | + | + | + | | |
| D19 | +++ | +++ | +++ | | |
| D20 | ++++ | ++++ | ++++ | | |
| D21 | +++ | ++++ | ++++ | | |
| D22 | ++++ | ++++ | ++++ | | |
| D23 | ++ | | | | |
| D24 | +++ | | | | |
| D25 | ++ | ++++ | +++ | ++++ | +++ |
| D26 | + | +++ | ++ | ++ | + |
| D27 | ++++ | ++++ | ++++ | | |
| D28 | ++++ | ++++ | ++++ | ++++ | +++ |
| D29 | ++++ | ++++ | ++++ | ++++ | + |
| D30 | ++++ | ++++ | ++++ | ++++ | ++++ |
| D31 | +++ | | | | |
| D32 | ++++ | ++++ | ++++ | ++++ | ++++ |
| D33 | ++++ | ++++ | ++++ | ++++ | ++++ |
| D34 | +++ | ++++ | ++++ | +++ | +++ |
| D35 | ++++ | ++++ | ++++ | | |
| D36 | + | + | + | | |
| D37 | ++++ | ++++ | ++++ | ++++ | ++++ |
| D38 | ++++ | ++++ | ++++ | ++++ | +++ |
| D39 | | | | | |
| D40 | ++++ | ++++ | ++++ | ++++ | ++++ |
| D41 | +++ | ++++ | ++++ | +++ | +++ |
| D42 | | | | | |
| D43 | | | | | |
| D44 | ++++ | ++++ | ++++ | | |
| D45 | ++++ | ++++ | ++++ | | |
| D46 | ++++ | ++++ | ++++ | ++++ | ++++ |
| D47 | ++++ | ++++ | ++++ | ++++ | +++ |
| D48 | ++++ | ++++ | ++++ | | |
| D49 | ++ | ++ | ++ | | |
| D50 | ++++ | ++++ | ++++ | +++ | ++ |
| D51 | +++ | +++ | +++ | ++ | +++ |
| D52 | + | ++ | ++ | + | + |
| D53 | ++++ | ++++ | ++++ | +++ | +++ |
| D54 | ++++ | ++++ | ++++ | +++ | ++++ |
| D55 | ++ | ++++ | ++++ | +++ | ++ |
| D56 | + | ++ | + | + | + |
| D57 | ++ | ++++ | +++ | ++++ | + |
| D58 | +++ | ++++ | ++++ | ++++ | + |
| D59 | | | | | |
| D60 | ++++ | ++++ | ++++ | ++++ | ++++ |
| D61 | | | | | |
| D62 | ++++ | ++++ | ++++ | +++ | +++ |
| D63 | ++++ | ++++ | +++ | +++ | +++ |
| D64 | +++ | ++ | ++ | + | ++ |
| D65 | ++++ | ++++ | ++++ | ++++ | ++++ |
| D66 | ++++ | ++++ | ++++ | ++++ | ++++ |
| D67 | ++++ | ++++ | ++++ | ++++ | ++++ |
| D68 | ++++ | ++++ | ++ | +++ | +++ |
| D69 | +++ | +++ | +++ | | |
| D70 | +++ | ++++ | +++ | | |
| D71 | +++ | +++ | +++ | ++ | + |
| D72 | +++ | +++ | +++ | ++ | + |
| D73 | +++ | +++ | ++ | +++ | + |
| D74 | +++ | ++++ | ++++ | +++ | +++ |
| D75 | +++ | +++ | ++ | ++ | + |
| D76 | +++ | ++++ | +++ | ++ | +++ |
| D77 | + | +++ | +++ | + | ++ |
| D78 | +++ | +++ | +++ | +++ | +++ |
| D79 | + | + | + | + | + |
| D80 | + | + | + | + | + |
| D81 | + | + | + | ++ | + |
| D82 | ++++ | ++++ | ++++ | +++ | ++++ |
| D84 | +++ | +++ | ++ | ++ | +++ |
| D85 | ++++ | ++++ | ++++ | ++++ | +++ |
| D86 | ++++ | ++++ | ++++ | ++++ | ++++ |
| D87 | | | | | |
| D88 | | | | | |
| D89 | | | | | |
| D90 | ++ | +++ | +++ | | |
| D91 | | | | | |
| D92 | | | | | |
| D93 | | | | | |
| D94 | +++ | +++ | +++ | +++ | + |
| D95 | ++++ | ++++ | ++++ | ++++ | +++ |
| D96 | ++++ | ++++ | ++++ | +++ | +++ |
| D97 | ++++ | ++++ | ++++ | ++++ | ++++ |
| D98 | ++++ | ++++ | ++++ | ++++ | ++++ |
| D99 | ++++ | ++++ | ++++ | ++++ | ++++ |
| D100 | ++++ | ++++ | ++++ | ++++ | ++++ |
| D101 | ++++ | ++++ | ++++ | ++++ | +++ |
| D102 | ++++ | ++++ | ++++ | ++++ | +++ |
| D103 | +++ | ++++ | ++++ | ++++ | +++ |
| D104 | +++ | +++ | +++ | ++ | ++ |
| D105 | +++ | +++ | +++ | ++ | +++ |
| D106 | ++++ | ++++ | ++++ | ++++ | ++ |
| D107 | ++++ | ++++ | ++++ | ++++ | ++++ |
| D109 | ++++ | ++++ | ++++ | ++++ | ++++ |
| D110 | ++++ | ++++ | ++++ | ++++ | + |
| D111 | ++++ | | | | |
| D112 | ++++ | ++++ | ++++ | +++ | ++++ |
| D113 | ++++ | ++++ | ++++ | ++++ | ++ |
| D114 | ++++ | ++++ | ++++ | ++++ | + |
| D115 | ++++ | ++++ | ++++ | ++++ | ++ |
| D116 | ++++ | ++++ | ++++ | ++++ | +++ |
| D117 | +++ | +++ | + | +++ | + |
| D118 | ++++ | ++++ | ++++ | ++++ | +++ |
| D119 | ++++ | ++++ | ++++ | ++++ | ++++ |
| D120 | ++++ | ++++ | ++++ | ++++ | ++++ |
| D121 | ++++ | ++++ | ++++ | ++++ | +++ |
| D122 | ++++ | ++++ | ++++ | ++++ | ++++ |
| D123 | ++++ | ++++ | ++++ | +++ | +++ |
| D124 | ++++ | ++++ | ++++ | ++++ | ++++ |
| D125 | ++++ | ++++ | ++++ | ++++ | ++++ |
| D126 | ++++ | ++++ | ++++ | ++++ | ++++ |
| D127 | ++++ | ++++ | ++++ | ++++ | ++++ |
| D128 | ++++ | ++++ | ++++ | ++++ | ++++ |
| D129 | ++++ | | | | |
| D130 | ++++ | ++++ | ++++ | ++++ | ++++ |
| D131 | ++++ | ++++ | ++++ | ++++ | ++++ |
| D132 | ++++ | ++++ | ++++ | ++++ | ++++ |
| D133 | ++++ | | | | |

-continued

| Cmpd | IC50 (μM) or inhibition % at 10 μM | | | | |
|---|---|---|---|---|---|
| | TNF-α | IL-2 | IFN-γ | IL-5 | IL-10 |
| D134 | ++++ | | | | |
| D135 | ++++ | | | | |
| D136 | ++++ | | | | |
| D137 | +++ | ^^^ | ^^^ | ^^ | ^^ |
| D138 | +++ | ^^^ | ^^ | ^^^ | ^^ |
| Rolipram | ++++ | ++++ | ++++ | ++++ | ++++ | wherein ^ is <30%, ^^ is 30 to <60%, ^^^ is 60 to <90%, ^^^^ is 90 to 100%.
wherein ++++ is <1 μM, +++ is 1 to <4 μM, ++ is 4 to 10 μM, + is >10 μM.

PDE Isoform Profiling

Recombinant human PDE enzymes were expressed in a baculoviral system. The assay is a modification of the 2-step method of Thompson & Appleman (Biochem. 10:311-316, 1971), which was adapted for 96-well plate format. Stock solutions were prepared at 40 mM in 100% DMSO. Final [DMSO] was 5%. Each compound was tested by performing 1 in 4 serial dilutions at starting concentration of 100 mM. Each concentration was tested in duplicate. IC50s were generated from 11-point curves and analyzed using Prism software (GraphPad Inc.). PDE isoforms tested include PDE1A3 (cAMP), PDE1A3 (cGMP), PDE2A3, PDE3Cat, PDE4Cat, PDE4A4, PDE4B2, PDE4C2, PDE4D3, PDE5Cat, PDE6AB, PDE7A1, PDE8A1, PDE9A1, PDE10A1 (cAMP), PDE10A1 (cGMP), PDE11A1 (cAMP) and PDE11A1 (cGMP).

PDE4 Assay

PDE4 partially purified from human U-937 myeloid leukemia cells was used. Test article and/or vehicle was incubated with 0.2 mg enzyme and 1 mM cAMP containing 0.01 mM [3H]cAMP in Tris buffer pH 7.5 for 20 minutes at 25° C. The reaction was terminated by boiling for 2 minutes and the resulting AMP is converted to adenosine by addition of 10 mg/ml snake venom nucleotidase and further incubation at 37° C. for 10 minutes. Unhydrolyzed cAMP is bound to AG1-X2 resin, and remaining [3H]Adenosine in the aqueous phase is quantitated by scintillation counting. Test articles were tested at 10, 3, 1, 0.3, 0.1, 0.03, 0.01, 0.003, and 0.001 μM for $IC_{50}$ determination.

| Cmpd | PDE4 |
|---|---|
| C17 | ++++ |
| C18 | + |
| C23 | +++ |
| C24 | ++ |
| C25 | +++ |
| C26 | ++++ |
| C31 | ++ |
| C36 | ++ |
| C37 | ++ |
| C38 | ++ |
| C100 | + |
| D1 | +++ |
| D2 | ++++ |
| D3 | ++++ |
| D4 | ++++ |
| D5 | ++++ |
| D6 | ++++ |
| D7 | ++++ |
| D9 | ++++ |
| D10 | +++ |
| D11 | ++++ |
| D12 | ++++ |
| D13 | +++ |
| D14 | ++++ |
| D15 | ++++ |
| D16 | ++++ |
| D17 | ++++ |
| D19 | ++++ |
| D20 | ++++ |
| D21 | ++++ |
| D22 | ++++ |
| D25 | ++++ |
| D26 | +++ |
| D27 | ++++ |
| D28 | ++++ |
| D29 | ++++ |
| D30 | ++++ |
| D32 | ++++ |
| D33 | ++++ |
| D34 | +++ |
| D35 | ++++ |
| D37 | ++++ |
| D38 | ++++ |
| D40 | ++++ |
| D41 | ++++ |
| D44 | ++++ |
| D45 | ++++ |
| D46 | ++++ |
| D47 | ++++ |
| D48 | ++++ |
| D49 | +++ |
| D50 | ++++ |
| D51 | ++++ |
| D52 | +++ |
| D53 | ++++ |
| D54 | ++++ |
| D55 | ++++ |
| D56 | +++ |
| D57 | ++++ |
| D58 | ++++ |
| D59 | + |
| D60 | ++++ |
| D62 | +++ |
| D63 | ++++ |
| D65 | ++++ |
| D66 | ++++ |
| D67 | ++++ |
| D68 | ++++ |
| D69 | ++++ |
| D70 | +++ |
| D71 | ++++ |
| D72 | ++++ |
| D73 | ++++ |
| D74 | ++++ |
| D76 | ++++ |
| D78 | ++++ |
| D82 | ++++ |
| D84 | ++++ |
| D85 | ++++ |
| D86 | ++++ |
| D87 | ++ |
| D88 | +++ |
| D89 | +++ |
| D90 | ++++ |
| D91 | + |
| D92 | +++ |
| D93 | +++ |
| D94 | ++++ |
| D95 | ++++ |
| D96 | ++++ |
| D97 | ++++ |
| D98 | ++++ |
| D99 | ++++ |
| D100 | ++++ |
| D101 | ++++ |
| D102 | ++++ |
| D103 | +++ |
| D104 | ++++ |
| D105 | +++ |
| D106 | ++++ |
| D107 | ++++ |
| D108 | ++ |

-continued

| Cmpd | PDE4 |
|---|---|
| D109 | ++++ |
| D110 | ++++ |
| D111 | ++++ |
| D112 | ++++ |
| D113 | ++++ |
| D114 | ++++ |
| D115 | ++++ |
| D116 | ++++ |
| D117 | ++++ |
| D118 | ++++ |
| D119 | ++++ |
| D120 | ++++ |
| D122 | ++++ |
| D123 | ++++ |
| D124 | ++++ |
| D125 | ++++ |
| D126 | ++++ |
| D127 | ++++ |
| D128 | ++++ |
| D129 | ++++ |
| D130 | ++++ |
| D131 | ++++ |
| D132 | ++++ |
| D133 | ++++ |
| D134 | ++++ |
| D135 | ++++ |
| D136 | ++++ |
| Rolipram | ++++ | wherein ++++ is <1 μM, +++ is 1 to <4 μM, ++ is 4 to 10 μM, + is >10 μM.

Example 21

In Vivo Assays

1. In Vivo Anti-Inflammation Activity in Phorbol Ester Induced Mouse Ear Edema Model Phorbol 12-myristate 13-acetate (PMA, 5 μg in 20 L of acetone) was applied topically to the anterior and posterior surfaces of the right ear to eight groups of CD-1 (Crl.) derived male mice of 5 each (weighing 22±2 g). Test substances and vehicle (acetone:ethanol/1:1, 20 μL/ear) were each applied to both ears topically 30 minutes before and 15 minutes after PMA challenge. Dexamethasone (1 mg/ear×2) used as the positive control was administered topically to test animals using the same application schedule. Ear swelling was then measured by a Dyer model micrometer gauge at 6 hours after PMA application as an index of inflammation. Percent inhibition was calculated according to the formula: [(Ic−It)/Ic]× 100%, where Ic and It refer to increase of ear thickness (mm) in control and treated mice, respectively. Percent inhibition of 30 percent or more in ear swelling was considered significant anti-inflammatory activity.

| Compound | Vehicle | Dose 20 μL/ear × 2 | % inhibition |
|---|---|---|---|
| C17 | | 1 mg/ear × 2 | *** |
| C26 | | 1 mg/ear × 2 | *** |
| C27 | | 3 mg/ear × 2 | *** |
| C27 | | 1 mg/ear × 2 | *** |
| D4 | Acetone:Ethanol/1:1 | 1 mg/ear × 2 | ** |
| D4 | Acetone:Ethano/1:1 | 1 mg/ear × 2 | *** |
| D5 | Acetone:Ethanol/1:1 | 1 mg/ear × 2 | ** |
| D6 | Acetone:Ethanol/1:1 | 1 mg/ear × 2 | ** |
| D6 | Acetone:Ethanol/1:1 | 0.2 mg/ear × 2 | * |
| D7 | Acetone:Ethanol/1:1 | 1 mg/kg × 2 | * |
| D10 | Acetone:Ethanol/1:1 | 1 mg/ear × 2 | *** |
| D12 | Acetone:Ethanol/1:1 | 1 mg/ear × 2 | ** |
| D12 | Acetone:Ethanol/1:1 | 0.2 mg/ear × 2 | * |
| D14 | Acetone:Ethanol/1:1 | 1 mg/ear × 2 | * |
| D14 | 95% Ethanol | 0.05 mg/ear × 2 | * |
| D14 | 95% Ethanol | 0.17 mg/ear × 2 | * |
| D14 | 95% Ethanol | 0.51 mg/ear × 2 | * |
| D14 | 95% Ethanol | 1 mg/ear × 2 | * |
| D15 | Acetone:Ethanol/1:1 | 1 mg/ear × 2 | ** |
| D16 | Acetone:Ethano/1:1 | 1 mg/ear × 2 | **** |
| D16 | Acetone:Ethano/1:1 | 0.2 mg/ear × 2 | *** |
| D24 | Acetone:Ethanol/1:1 | 1 mg/ear × 2 | *** |
| D29 | Acetone:Ethanol/1:1 | 1 mg/ear × 2 | * |
| D31 | Acetone:Ethanol/1:1 | 1 mg/ear × 2 | ** |
| D32 | Acetone:Ethanol/1:1 | 1 mg/ear | * |
| D32 | Acetone:Ethanol/1:1 | 1 mg/ear × 2 | * |
| D33 | Acetone:Ethanol/1:1 | 1 mg/ear | * |
| D34 | Acetone:Ethanol/1:1 | 1 mg/ear | * |
| D37 | Acetone:Ethanol/1:1 | 1 mg/ear × 2 | *** |
| D37 | 95% Ethanol | 3 mg/ear × 2 | *** |
| D46 | Acetone:Ethano/1:1 | 1 mg/ear × 2 | *** |
| D46 | Acetone:Ethanol/1:1 | 1 mg/ear × 2 | *** |
| D46 | Acetone:Ethanol/1:1 | 0.2 mg/ear × 2 | * |
| D46 | Acetone:Ethanol/1:1 | 0.1 mg/ear × 2 | * |
| D46 | 95% Ethanol | 0.05 mg/ear × 2 | * |
| D46 | 95% Ethanol | 0.17 mg/ear × 2 | * |
| D46 | 95% Ethanol | 0.5 mg/ear × 2 | * |
| D46 | 95% Ethanol | 3 mg/ear × 2 | *** |
| D48 | Acetone:Ethanol/1:1 | 1 mg/ear × 2 | * |
| D48 | Acetone:Ethanol/1:1 | 0.2 mg/ear × 2 | * |
| D50 | Acetone:Ethano/1:1 | 1 mg/ear × 2 | *** |
| D60 | Acetone:Ethanol/1:1 | 1 mg/ear × 2 | ** |
| D60 | Acetone:Ethanol/1:1 | 0.2 mg/ear × 2 | * |
| D60 | Acetone:Ethanol/1:1 | 0.1 mg/ear × 2 | * |
| D61 | Acetone:Ethanol/1:1 | 1 mg/ear × 2 | ** |
| D61 | Acetone:Ethanol/1:1 | 0.2 mg/ear × 2 | * |
| D61 | Acetone:Ethanol/1:1 | 0.1 mg/ear × 2 | * |
| D63 | Acetone:Ethanol/1:1 | 1 mg/ear × 2 | * |
| D65 | Acetone:Ethano/1:1 | 1 mg/ear × 2 | ** |
| D67 | Acetone:Ethanol/1:1 | 1 mg/ear × 2 | *** |
| D68 | Acetone:Ethanol/1:1 | 1 mg/ear × 2 | ** |
| D69 | | 1 mg/ear × 2 | ** |
| D73 | | 3 mg/ear × 2 | *** |
| D73 | | 1 mg/ear × 2 | ** |
| D86 | 95% Ethanol | 0.063 mg/ear × 2 | * |
| D86 | 95% Ethanol | 0.21 mg/ear × 2 | * |
| D86 | 95% Ethanol | 0.63 mg/ear × 2 | * |
| D86 | 95% Ethanol | 3 mg/ear × 2 | * |
| D90 | 95% EthanolAcetone:1/1 | 1 mg/ear × 2 | *** |
| D95 | 95% Ethanol | 0.02 mg/ear × 2 | * |
| D95 | 95% Ethanol | 0.06 mg/ear × 2 | * |
| D95 | 95% Ethanol | 0.2 mg/ear × 2 | * |
| D97 | 95% Ethanol | 0.056 mg/ear × 2 | * |
| D97 | 95% Ethanol | 0.19 mg/ear × 2 | * |
| D97 | 95% Ethanol | 0.56 mg/ear × 2 | ** |
| D98 | 95% Ethanol | 0.02 mg/ear × 2 | * |
| D98 | 95% Ethanol | 0.06 mg/ear × 2 | * |
| D98 | 95% Ethanol | 0.2 mg/ear × 2 | ** |
| D99 | 95% Ethanol | 0.02 mg/ear × 2 | * |
| D99 | 95% Ethanol | 0.067 mg/ear × 2 | * |
| D99 | 95% Ethanol | 0.2 mg/ear × 2 | * |
| D99 | 95% Ethanol | 3 mg/ear × 2 | *** |
| D100 | 95% Ethanol | 0.028 mg/ear × 2 | * |
| D100 | 95% Ethanol | 0.093 mg/ear × 2 | * |
| D100 | 95% Ethanol | 0.28 mg/ear × 2 | ** |
| D101 | 95% Ethanol | 0.8 mg/ear × 2 | * |
| D101 | 95% Ethanol | 2.4 mg/ear × 2 | * |
| D102 | 95% Ethanol | 0.02 mg/ear × 2 | * |
| D102 | 95% Ethanol | 0.067 mg/ear × 2 | * |
| D102 | 95% Ethanol | 0.2 mg/ear × 2 | * |
| D102 | 95% Ethanol | 3 mg/ear × 2 | ** |
| D102 | 95% Ethanol | 1 mg/ear × 2 | ** |
| D107 | 95% Ethanol | 0.24 mg/ear × 2 | ** |
| D107 | 95% Ethanol | 0.8 mg/ear × 2 | *** |
| D107 | 95% Ethanol | 2.4 mg/ear × 2 | *** |
| D107 | 95% Ethanol | 0.24 mg/ear × 2 | * |
| D107 | 95% Ethanol | 0.02 mg/ear × 2 | * |
| D107 | 95% Ethanol | 0.067 mg/ear × 2 | ** |

-continued

| Compound | Vehicle | Dose 20 μL/ear × 2 | % inhibition |
|---|---|---|---|
| D107 | 95% Ethanol | 0.2 mg/ear × 2 | *** |
| D107 | 95% Ethanol | 0.02 mg/ear × 2 | * |
| D107 | 95% Ethanol | 0.06 mg/ear × 2 | * |
| D109 | 95% Ethanol | 0.02 mg/ear × 2 | * |
| D109 | 95% Ethanol | 0.067 mg/ear × 2 | * |
| D109 | 95% Ethanol | 0.2 mg/ear × 2 | * |
| D110 | 95% Ethanol | 0.02 mg/ear × 2 | * |
| D110 | 95% Ethanol | 0.06 mg/ear × 2 | * |
| D110 | 95% Ethanol | 0.2 mg/ear × 2 | * |
| D111 | 95% Ethanol | 0.015 mg/ear × 2 | * |
| D111 | 95% Ethanol | 0.05 mg/ear × 2 | * |
| D111 | 95% Ethanol | 0.15 mg/ear × 2 | * |
| D111 | 95% Ethanol | 1 mg/ear × 2 | * |
| D124 | 95% Ethanol | 1 mg/ear × 2 | * |
| Dexamethasone | | 1 mg/ear × 2 | *** | wherein * is <30%,  is 30 to <60%, * is 60 to <90%, **** is 90 to 100%.

2. In Vivo Anti-Inflammation Activity in Oxazolone Induced Mouse Ear Edema Model Groups of 5 BALB/c male mice weighing 23±2 g were used. The preshaved abdomens of test animals were sensitized by application of 100 μL, of 1.5% oxazolone solution dissolved in acetone. Seven days after the initial sensitization, test substances, as well as vehicle (acetone:ethanol/1:1, 20 μL/ear) were each administered topically to the anterior and posterior surfaces of the right ear 30 minutes before, and 15 minutes after, challenge by a second application of oxazolone (1% in acetone, 20 ml/ear) via topical route. As a positive control, indomethacin (0.3 mg/ear×2) was administered topically using the same treatment regime as for the test compounds. Twenty-four hours after the second application of oxazolone, the ear thickness of each mouse was measured with a Dyer model micrometer gauge. A 30 percent or more inhibition in ear swelling relative to the vehicle control was considered significant and indicated possible anti-inflammatory activity.

| Compound | Vehicle | Dose 20 μL/ear × 2 | % inhibition |
|---|---|---|---|
| C27 | | 3 mg/ear × 2 | **** |
| D4 | Acetone:Ethanol/1:1 | 1 mg/ear × 2 | *** |
| D4 | Acetone:Ethanol/1:1 | 0.02 mg/ear × 2 | * |
| D5 | Acetone:Ethanol/1:1 | 1 mg/ear × 2 | *** |
| D6 | Acetone:Ethanol/1:1 | 1 mg/ear × 2 | * |
| D6 | Acetone:Ethanol/1:1 | 0.2 mg/ear × 2 | * |
| D7 | Acetone:Ethanol/1:1 | 1 mg/kg × 2 | * |
| D12 | Acetone:Ethanol/1:1 | 1 mg/ear × 2 | *** |
| D12 | Acetone:Ethanol/1:1 | 0.2 mg/ear × 2 | * |
| D15 | Acetone:Ethanol/1:1 | 1 mg/ear × 2 | **** |
| D16 | 95% Ethanol | 3 mg/ear × 2 | * |
| D22 | 95% Ethanol | 3 mg/ear × 2 | * |
| D27 | 95% Ethanol | 3 mg/ear × 2 | ** |
| D37 | Acetone:Ethanol/1:1 | 1 mg/ear × 2 | * |
| D46 | Acetone:Ethanol/1:1 | 1 mg/ear × 2 | * |
| D48 | Acetone:Ethanol/1:1 | 1 mg/ear × 2 | ** |
| D48 | Acetone:Ethanol/1:1 | 0.2 mg/ear × 2 | * |
| D60 | Acetone:Ethanol/1:1 | 1 mg/ear × 2 | * |
| D60 | Acetone:Ethanol/1:1 | 0.2 mg/ear × 2 | * |
| D60 | Acetone:Ethanol/1:1 | 0.1 mg/ear × 2 | * |
| D61 | Acetone:Ethanol/1:1 | 1 mg/ear × 2 | * |
| D61 | Acetone:Ethanol/1:1 | 0.2 mg/ear × 2 | * |
| D61 | Acetone:Ethanol/1:1 | 0.1 mg/ear × 2 | * |
| D67 | Acetone:Ethanol/1:1 | 1 mg/ear × 2 | * |
| D68 | Acetone:Ethanol/1:1 | 1 mg/ear × 2 | * |
| D96 | Acetone:Ethanol/1:1 | 1 mg/ear × 2 | * |
| D97 | 95% Ethanol | 0.56 mg/ear × 2 | * |
| D99 | 95% Ethanol | 0.02 mg/ear × 2 | * |
| D99 | Acetone:Ethanol/1:1 | 1 mg/ear × 2 | * |

-continued

| Compound | Vehicle | Dose 20 μL/ear × 2 | % inhibition |
|---|---|---|---|
| D102 | Acetone:Ethanol/1:1 | 1 mg/ear × 2 | * |
| D107 | 95% Ethanol | 2.4 mg/ear × 2 | * |
| D111 | 95% Ethanol | 0.15 mg/ear × 2 | * |
| D122 | Acetone:Ethanol/1:1 | 1 mg/ear × 2 | * |
| D124 | Acetone:Ethanol/1:1 | 1 mg/ear × 2 | * |
| Indomethacin | 95% Ethanol | 0.3 mg/ear × 2 | **** | wherein * is <20%,  is 20 to <30%, * is 30 to <40%, **** is 40 to 60%.

Example 22

Preclinical Toxicology of C17, a Novel Oxaborole in Development for the Topical Treatment of Psoriasis C17 (5-(4-cyanophenoxy)-1,3-dihydro-1-hydroxy-2,1-benzoxaborole) is a novel oxaborole compound with anti-inflammatory activity. Preclinical toxicity data is available for in vitro studies and in vivo studies following systemic and topical administration to shrews, ferrets, rats, and mice. C17 (1 μM) was classified as a low potency hERG-channel blocker, minim/zing concerns over cardiovascular safety. C17 (up to 5000 μg per plate) demonstrated no mutagenic activity in the presence or absence of Aroclor-induced S9 liver fraction against *Salmonella typhimurium* strains TA98, TA100, TA1535, and TA1537 and *Escherichia coli* strain WP2 uvrA. C17 (up to 500 μg/mL), demonstrated no clastogenic activity in the In Vitro Mammalian Chromosome Aberration Assay in the presence or absence of Aroclor-induced S9 using human peripheral blood lymphocytes. Following oral administration of 10, 30, and 100 mg/kg to shrews, (*Suncus murinus*), dose-responsive emetic effect was observed. The no-observed-effect level (NOEL) was 10 mg/kg, and was associated with significant plasma exposure. Following oral administration of 10, 30, and 100 mg/kg to ferrets, no emetic episodes were observed in any dose group. Following oral administration of 30, 100, and 300 mg/kg/day to male and female Sprague-Dawley rats for 14 consecutive days, the NOEL was determined to be 300 mg/kg/day. No mortality, adverse effects on clinical pathology, or microscopic or macroscopic changes were observed in any dose group. C17 was formulated as a 1%, 5%, and 10% solution in acetone/ethanol (50:50, v/v) and tested in a local lymph node assay for its potential to induce a hypersensitivity response. Topical treatment with C17 to female CBA/J mice did not result in a stimulation index of 3 or greater and therefore C17 was not considered to have skin sensitizing activity. C17 is a novel compound in development for the topical treatment of psoriasis and has been demonstrated to be safe in various preclinical toxicity studies.

Example 23

In Vitro Activity and Mechanism of Action of C17, a Novel Oxaborole in Development for Treatment of Psoriasis C17 (4-cyanophenoxy)-1-hydroxy-1,3-dihydro-2,1-benzoxaborole) is a broad spectrum anti-inflammatory compound currently under development for the topical treatment of plaque psoriasis. C17 inhibits TNF-α secretion from peripheral blood mononuclear cells (PBMCs) stimulated by lipopolysaccharide (LPS) and IL-2 and IFN-γ secretion after stimulation with phytohemagglutinin (PHA) in the nanomolar range. C17 inhibits TNF-α secretion with an $IC_{50}$ of 770 nM; however the pro-inflammatory cytokines IL-1 and IL-6 are not affected by C17. IL-2 and IFN-γ are inhibited with $IC_{50}$s of 460 nM and 270 nM respectively. IL-5 and IL-10 are inhibited by C17 in the low micromolar range. One mechanism of action of C17 to inhibit a broad range of cytokine secretion may be through inhibition of phosphodiesterase 4 (PDE4). C17 inhibits PDE4 enzyme activity in human U937 cells with an $IC_{50}$ of 0.49 μM, inhibiting all four PDE4 isoforms equally. C17 has been shown to be a competitive inhibitor of the substrate cAMP, as determined by enzyme kinetic analysis. C17 also inhibits PDE7 with an $IC_{50}$ of 0.73 μM but does not significantly inhibit PDE1, 2, 3, or 5. In contrast to classic PDE4 inhibitors, for example Rolipram, C17 inhibits production of IL-23 from human THP-1 macrophages with an $IC_{50}$ of 2.25 μM. This activity, with its inhibition of TNF-α and TH1 cytokines, suggests potential for C17 in the treatment of psoriasis.

TABLE 1

C17 inhibits LPS- and PHA-induced cytokine production by human PBMCs, as well as IL-23 production when human THP-1 monocytic cells are stimulated with IFN-g and LPS

| | IC50 (mM) | | | | | | | |
|---|---|---|---|---|---|---|---|---|
| | Pro-inflammatory Cytokines | | | | Th1 Cytokines | | Th2 Cytokines | |
| Compounds | TNFα | IL-1β | IL-6 | IL-23* | IL-2 | IFNg | IL-5 | IL-10 |
| C17 | ++++ | + | + | +++ | ++++ | ++++ | +++ | ++++ |
| Rolipram | ++++ | + | | | ++++ | ++++ | ++++ | ++++ |
| Cilomilast | ++++ | + | | | ++++ | ++++ | ++++ | +++ |

+ = >30
++ = 10-29
+++ = 1-10
++++ = <1

TABLE 2

C17 inhibits PDE 4 and PDE7, to a lesser extent PDE1 and PDE3. Standards: 8-methoxymethyl-IBMX, Cilostazol, Rolipram and BRL-50481 respectively.

| | IC50 (mM) | | | |
|---|---|---|---|---|
| Compound | PDE1A3 | PDE3 Cat | PDE4Cat | PDE7A1 |
| C17 | +++ | +++ | ++++ | ++++ |
| Standard | +++ | +++ | +++ | +++ |

Example 24

In Vivo Activity of C17, a Novel Oxaborole in Development for Treatment of Psoriasis C17 is a novel boron-containing oxaborole drug with anti-inflammatory activity based on the inhibition of the release of pro-inflammatory cytokines including TNF-α, IFN-γ, IL-1β, IL-2, IL-4, IL-5, IL-6, IL-8, IL-1β, IL-12, and IL-23. C17 also inhibits the release of the chemokine MCP-1 and PGE2. This activity is explained in part by the inhibition of phosphodiesterase-4 (PDE-4).

A single-center, random/zed, vehicle-controlled, observer-blind study enrolled 12 subjects with psoriasis in order to evaluate the antipsoriatic activity of C17. Six test fields per subject were treated (two active formulations: C17 Ointment, 5%, C17 Cream, 5%, two vehicles, and two comparators).

Study preparation 1 consisted of the C17 Ointment (preparation described herein), with a topical application of approximately 200 μl ointment per test field (1.1 cm²) once daily over a 12 day period (10 treatments). The dosage was approximately 10 mg active ingredient/day, for a total dosage of approximately 100 mg active ingredient.

Study preparation 2 consisted of the C17 Cream (preparation described herein), with a topical application of approximately 200 μl cream per test field (1.1 cm²) once daily over a 12 day period (10 treatments). The dosage was approximately 10 mg active ingredient/day, for a total dosage of approximately 100 mg active ingredient.

Study preparation 3 consisted of the vehicle of study preparation 1 (no C17 present), with a topical application of approximately 200 μl cream per test field (1.1 cm²) once daily over a 12 day period (10 treatments).

Study preparation 4 consisted of the vehicle of study preparation 2 (no C17 present), with a topical application of approximately 200 μl cream per test field (1.1 cm²) once daily over a 12 day period (10 treatments).

Comparator 1 consisted of Betnesol®-V Creme 0.1%, with topical application of approximately 200 μl cream per test field (1.1 cm²) once daily over a 12 day period (10 treatments). The dosage was approximately 0.2 mg betamethasone/day, for a total dosage of approximately 2 mg betamethasone.

Comparator 2 consisted of Protopic® Ointment 0.1%, with topical application of approximately 200 μl cream per test field (1.1 cm²) once daily over a 12 day period (10 treatments). The dosage was approximately 0.2 mg tacrolimus/day, for a total dosage of approximately 2 mg tacrolimus.

The test preparations were manufactured by Dow Pharmaceutical Sciences, 1330A Redwood Way, Petaluma, Calif. 94954, USA. The comparator Betnesol®-V Creme 0.1% was manufactured by GlaxoWellcome GmbH & Co. The comparator Protopic 0.1% was manufactured by Astellas Pharma GmbH, Neumarkter Str. 61, 81673 Munich, Germany. The labeling of the study preparations was performed at Anacor Pharmaceuticals, 1060 East Meadow Circle, Palo Alto, Calif. 94303-4230, USA.

200 μl of each study preparation and the comparators were applied to the test fields per treatment. The study preparations were applied under Duhring chambers (12 mm inside 0, 14 mm outside 0) seated in holes punched in a hydrocolloid dressing (Varihesive®, Bristol-Myers Squibb Gruppe, Munich, Germany). The amount completely filled the chambers. The chambers were fixed in place with adhesive patches (Fixomull®, BSN, Hamburg, Germany). In previous studies the hydrocolloid dressing had been shown to be well tolerated. The lack of a therapeutic influence of the dressing on the psoriasis had been verified by determination of the infiltrate thickness before and after application. The distance between chambers had to be at least 1.5 cm. This distance was sufficient to exclude interactions with neighboring fields. All fields were treated under occlusion 10 times over 12 days. Before each new application remaining preparation residues were removed by gently cleansing each test field with a separate soft tissue. On 10 of the study days treatments were performed (days 1-6 and 8-11). The hydrocolloid dressing stayed in place for maximal 7 days, it was renewed on study day 8.

Experimental measurements included sonography, photo documentation and clinical assessments with intra individual comparison of the treatments.

On the first day of the study the outline of the plaque was traced onto a transparent plastic sheet. The intended test fields were then drawn on the sheet, taking care to allow at least 1.5 cm between sites. The test fields were numbered from 1-6. The plastic sheets were attached to the case report form (CRF). Baseline sonographic measurements and photodocumentation were performed. Pretreatment clinical assessment scores were 0 by definition in all test fields. The hydrocolloid dressing was attached and the first treatment performed as described above.

On study days 2 to 6 and 8 to 11 the occluding chambers were removed and treatments renewed once daily. On study day 7 dressing and chambers remained in place until study day 8. On study days 8 and 12 the hydrocolloid dressing was also removed and sonography, clinical assessment and photodocumentation performed after removal of preparation residues. On the last day of the study the final clinical examination was made including safety laboratory testing (hematology, clinical chemistry and urinalysis).

Sonographic measurements were performed using a 20 MHz high frequency sonograph (DUB 20S, Taberna pro Medicum, Lueneburg). Serial A-scans were composed and represented on a monitor as a section of the skin. A lateral resolution of approximately 200 µm and an axial resolution of 80 µm are possible. Dependent on the echo patterns, components of the epidermis, dermis and subcutis were represented. Therefore exact measurement of skin thickness was possible. The inflammatory psoriatic infiltrate was seen as a clearly definable echo lucent band below the entrance echo. The thickness of the echo lucent psoriatic band was determined and documented. The thickness was measured in µm and was denoted as T.

Clinical assessment (global assessment) of the test fields was performed using a 5-point score: −1=worsened; 0=unchanged (no effect); 1=slight improvement; 2=clear improvement but not completely healed; 3=completely healed. Comparison was made with the untreated plaque beneath the hydrocolloid dressing. Clinically apparent differences in erythema and infiltration contributed to this global assessment.

The infiltrate thickness showed that treatment with C17 led to a relevant and clear improvement. The mean percent reduction in infiltrate thickness for both C17-formulations was 54% vs. no changes in the mean infiltrate thickness for the vehicles. The statistical comparisons showed that C17, 5% demonstrated a significantly higher reduction ($p<0.025$) in infiltrate thickness than the corresponding vehicles. For the comparator Protopic™ Ointment 0.1% the mean percent reduction in infiltrate thickness (48%) was lower. A higher reduction in the mean infiltrate thickness (72%) was noted for the comparator Betnesol™-V Creme, 0.1%. No significant differences were found between the C17 Ointment, 5% and the Betnesol™-V Creme 0.1% on study day 12. In all other comparisons Betnesol™-V Creme 0.1% demonstrated a significantly higher reduction in infiltrate thickness. The clinical assessments and other secondary endpoints paralleled the findings of the sonographic measurements.

Example 25

C27, a Novel Oxaborole Compound with Anti-Inflammatory Activity: Results of In Vivo Efficacy and Preclinical Safety Studies C27 is the second in a series of novel oxaborale compounds that decreases TNFα release through potent inhibition of phosphodiesterase 4 (PDE4). This new drug is currently in preclinical development for psoriasis and atopic dermatitis. C27 demonstrates significant in vivo activity in a model of acute skin irritation. In an acetone/ethanol vehicle, 5% C27 inhibits PMA induced ear edema greater than 15% dexamethasone (82% vs 73% inhibition, respectively, $p<0.01$) and is active in this model in an ointment vehicle at concentrations as low as 0.01%. Topical C27 also significantly inhibits oxazolone induced ear swelling (a model of allergic contact dermatitis). In vitro screening shows C27 to have no significant hERG or p450 enzyme inhibition. Pharmacokinetic analysis in the rat after oral dosing at 100 mg/kg demonstrates relatively low bioavailability (7%) and, after intravenous dosing at 20 mg/kg, a mean plasma residence time of 0.64 h. C27 is safe in a rat 14-day oral repeated dose study at 10, 100, and 300 mg/kg/day; no clinical chemistry or hematology effects were seen at any dose. It also shows less emetic effect than rolipram. The no effect Cmax plasma level of C27 in a shrew emesis assay was 12.4 µg/ml. Dermal application of 5% C27 ointment or cream over 15% body surface area on the Gottingen minipig results in undetectable plasma levels of the compound (LLOQ=0.01 µg/ml) and no dermal irritation after 24 hours of exposure. These early studies suggest that C27 has the required in vivo biological activity and good preclinical safety profile to enable clinical trials.

Example 26

Structure-Activity Studies of C17 and C27, Novel Oxaborole Compounds with Anti-Inflammatory Activity The structure-activity relationships of novel boron-containing anti-inflammatory agents was investigated. C17 (5-(4-cyanophenoxy)-1-hydroxy-1,3-dihydro-2,1-benzoxaborole) is a broad spectrum anti-inflammatory compound that is currently under development for the topical treatment of plaque psoriasis. C17 inhibited release of TNF-alpha from peripheral blood mononuclear cells (PBMCs) stimulated by lipopolysaccharide (LPS). C17 was found to inhibit the phosphodiesterase 4 (PDE4) enzyme derived from human U937 cells. Since the PDE4 inhibition was considered to be a part of its mechanism of action to inhibit the TNF-alpha release, investigation of structure-activity relationships around this compound was carried out to identify a more potent PDE4/TNF-alpha inhibitor.

Compounds were screened by a biochemical assay against PDE4 enzyme and cell-based cytokine release assays using PBMCs stimulated by LPS or phytohemagglutinin (PHA). The results showed that electron-withdrawing groups, such as cyano and N,N-dialkylcarbamoyl, at the para-position to the oxygen atom were important for the activity. Ester and pyridine analogs also showed potent activity. However, carboxy derivatives lost most of the activity in both assays. C27 showed potent inhibition against PDE4 ($IC_{50}$ 60 nM), while the $IC_{50}$ of C17 and rolipram were 490 nM and 860 nM, respectively. The regioisomers of the cyano group were less active. C27 also inhibited the release of cytokines, such as TNF-alpha ($IC_{50}$ 160 nM), IL-2 ($IC_{50}$ 180 nM), and interferon-gamma ($IC_{50}$ 220 nM). C27 did not show cytotoxicity against L929 and HepG2 cell lines up to 100 micro M.

Example 27

Ointment Formulations for C17 or C27

In the manufacturing vessel, add the required amounts of white petrolatum and heat to melt at 65±5° C. In stainless steel vessel, add C17 or C27, oleyl alcohol and Octyl hydroxystearate Propeller mix while heating to 65±5° C. until a clear solution (suspension in case of 5% C17) is obtained. Maintain the temperature. With Homogenizer mixing, add the C17 or C27 mixture to the manufacturing vessel. Homogenize at 65±5° C. for a minimum of 5 minutes. Remove the heat source and start cooling. Continue mixing until the ointment is homogenous.

The composition of an C17 ointment is provided below.

| Quantitative Composition of C17 Ointment, 0.5%, 2% and 5% | | | |
|---|---|---|---|
| Component | % w/w | % w/w | % w/w |
| C17 | 0.5 | 2.0 | 5.0 |
| Ethylhexyl Hydroxystearate | 10.0 | 10.0 | 10.0 |
| Oleyl Alcohol | 10.0 | 10.0 | 10.0 |
| White Petrolatum | 79.5 | 78.0 | 75.0 |

The composition of an C27 ointment is provided below.

| Quantitative Composition of C27 Ointment, 0.01, 0.1%, 1% and 2% | | | | |
|---|---|---|---|---|
| Component | % w/w | % w/w | % w/w | % w/w |
| C27 | 0.01 | 0.1 | 1.0 | 2.0 |
| Ethylhexyl Hydroxystearate | 10.0 | 10.0 | 10.0 | 10.0 |
| Oleyl Alcohol | 10.0 | 10.0 | 10.0 | 10.0 |
| White Petrolatum | 79.99 | 79.90 | 79.0 | 78.0 |

Example 28

C17 Cream Formulations

Cream Formulation A for C17

In stainless steel (SS) vessel 1, add purified water and Glycerin for preparation of Xanthum gum blend. With propeller mixing, add Xanthum Gum and mix until a smooth and uniform gel is formed. In stainless steel vessel 2, add purified Water and Sodium Hydroxide and mix with a stir bar until a clear 10% Sodium Hydroxide Solution is obtained. In stainless steel vessel 3, add C17, Oleyl Alcohol, Ethylhexyl Hydroxystearate, Glyceryl Monostearate SE, Cholesterol, and Butylated Hydroxytoluene. Propeller mix while heating to 80±5° C. until a clear solution is obtained. Maintain the temperature. With Homogenizer mixing, add the solution from SS Vessel 3 into the Manufacturing Vessel. Homogenize at 80±5° C. for a minimum of 5 minutes. Remove the heat source and start cooling. Continue with propeller mixing until a thin cream is formed and it reaches 30-35° C. With Homogenizer mixing, add the Xanthum Gum Blend from SS Vessel 1. Continue with Homogenization until the cream becomes thicker, smooth and homogeneous. Adjust pH of the cream with either 10% Sodium Hydroxide Solution or Diluted Hydrochloric Solution to pH 6.0±0.3. QS the batch to 100% with remaining amount of Purified Water. Mix with a propeller until the cream is smooth and homogeneous.

The composition of an C17 cream is provided below.

| Cream Formulation A for C17, 5% | |
|---|---|
| Component | % w/w |
| C17 | 5.0 |
| Methylparaben | 0.15 |
| Propylparaben | 0.03 |
| Propylene Glycol | 5.0 |
| Glycerol Monostearate SE | 7.0 |

-continued

| Cream Formulation A for C17, 5% | |
|---|---|
| Component | % w/w |
| Cholesterol | 0.8 |
| Oleyl Alcohol | 10.0 |
| Butylated Hydroxytoluene | 0.1 |
| Ethylhexyl Hydroxystearate | 12.0 |
| Xantham Gum Blend | 15.0 |
| Citric Acid, anhydrous | 0.12 |
| Sodium Citrate, anhydrous | 1.39 |
| 10% Sodium Hydroxide Solution | q.s. pH 6.0 |
| Dilute Hydrochloric Acid | q.s. pH 6.0 |
| Purified Water, (for Xanthum Gum Blend) | 40.0 |
| Purified Water, (for the entire composition) | q.s. 100% |

| Xantham Gum Blend | |
|---|---|
| Component | % w/w |
| Xantham Gum | 3.0 |
| Glycerin | 5.0 |
| Purified Water | 92.0 |

| 10% Sodium Hydroxide Solution | |
|---|---|
| Component | % w/w |
| Sodium Hydroxide | 10.0 |
| Purified Water | 90.0 |

Cream Formulation B for C17

In a stainless steel vessel, add oleyl alcohol, benzyl alcohol, diisopropyl adipate, glyceryl monostearate SE, octyldodecanol, butylated hydroxytoluene and C17. Propeller mix while heating to 60±5° C. until a clear solution is obtained. Maintain the temperature. With continuous propeller mixing, add pemulen TR-2. Mix until the oily components are visually homogeneous. Maintain the temperature. In a manufacturing vessel, add purified water, methylparaben, propylparaben, propylene glycol, and edetate disodium. Propeller mix while heating to 60±5° C. until a clear solution is obtained. Maintain the temperature.

With continuous propeller mixing, add carbopol ultrez 10. Mix until the aqueous phase is visually homogeneous. Maintain the temperature. With homogenizer mixing, add the oil phase into the aqueous phase in the manufacturing vessel. Homogenize at 60±5° C. for a minimum of 5 minutes. Remove the heat source and start cooling. Continue with propeller mixing and add 25% trolamine and mix until the cream becomes thicker, smooth and reaches room temperature.

The composition of another C17 cream is provided below.

| Cream Formulation B for C17, 0.3-2% | | | |
|---|---|---|---|
| Component | % w/w | % w/w | % w/w |
| C17 | 0.3 | 1.0 | 2.0 |
| Methylparaben | 0.15 | 0.15 | 0.15 |
| Propylparaben | 0.03 | 0.03 | 0.03 |
| Glyceryl Monostearate SE | 8.0 | 8.0 | 8.0 |
| Butylated Hydroxytoluene | 0.02 | 0.02 | 0.02 |
| Edetate Disodium | 0.05 | 0.05 | 0.05 |
| Pemulen TR-2 | 0.25 | 0.25 | 0.25 |

369

-continued

| Cream Formulation B for C17, 0.3-2% | | | |
|---|---|---|---|
| Component | % w/w | % w/w | % w/w |
| Carbopol Ultrez 10 | 0.20 | 0.20 | 0.20 |
| 25% Trolamine | 0.84 | 0.84 | 0.84 |
| Propylene Glycol | 5.0 | 5.0 | 5.0 |
| Octyldodecanol | 10.0 | 10.0 | 10.0 |
| Oleyl Alcohol | 10.0 | 10.0 | 10.0 |
| Benzyl Alcohol | 2.0 | 2.0 | 2.0 |
| Diisopropyl Adipate | 10.0 | 10.0 | 10.0 |
| Purified Water | QS 100 | QS 100 | QS 100 |

| 25% Trolamine Solution | |
|---|---|
| Component | % w/w |
| Trolamine | 25.0 |
| Purified Water | 75.0 |

Example 29

C27 Cream Formulation

In a stainless steel vessel, add Benzyl alcohol, Octyldodecanol, C27, Stearyl alcohol, Cetyl alcohol, BHT and Glyceryl monostearate. Propeller mix while heating to 65±5° C. until the solids have melted and a homogenous solution appears Maintain the temperature. In the manufacturing vessel, add purified water, Polysorbate 60, Propylene glycol, Methyl paraben, Propyl paraben and edetate sodium. Heat to 65±5° C. while mixing with a homogenizer until a clear solution is obtained Maintain the temperature. With homogenizer mixing, add the C27 oil phase components to the aqueous phase in the manufacturing vessel. Homogenize at 65±5° C. for a minimum of 5 minutes. Remove the heat source and start cooling. Continue with propeller mixing until the cream becomes thicker, smooth and reaches room temperature.

The composition of an C27 cream is provided below.

| Component | % w/w | % w/w | % w/w | % w/w |
|---|---|---|---|---|
| C27 | 0.01 | 0.1 | 1.0 | 2.0 |
| Benzyl alcohol | 1.0 | 1.0 | 1.0 | 1.0 |
| BHT | 0.01 | 0.01 | 0.01 | 0.01 |
| Octyldodecanol | 13.5 | 13.5 | 13.5 | 13.5 |
| Glyceryl monostearate | 8.0 | 8.0 | 8.0 | 8.0 |
| Stearyl alcohol | 10.0 | 10.0 | 10.0 | 10.0 |
| Cetyl alcohol | 5.0 | 5.0 | 5.0 | 5.0 |
| Polysorbate -60 | 3.0 | 3.0 | 3.0 | 3.0 |
| Methyl paraben | 0.15 | 0.15 | 0.15 | 0.15 |
| Propyl paraben | 0.03 | 0.03 | 0.03 | 0.03 |
| Edetate Disodium | 0.05 | 0.05 | 0.05 | 0.05 |
| Propylene glycol | 5.0 | 5.0 | 5.0 | 5.0 |
| Purified Water | QS 100 | QS 100 | QS 100 | QS 100 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

370

What is claimed is:

1. A compound having a structure according to the formula:

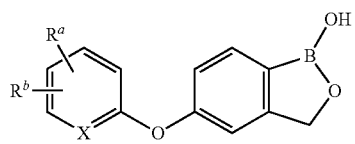

wherein
$R^a$ is C(O)OR$^3$
wherein $R^3$ is unsubstituted alkyl,
X is N or CH,
$R^b$ is OR$^4$
wherein $R^4$ is unsubstituted straight chain or branched chain alkyl, or straight chain or branched alkyl substituted with unsubstituted cycloalkyl, or unsubstituted cycloalkyl,
or a salt thereof.

2. The compound of claim 1, or a salt thereof, wherein the compound has a formula which is a member selected from:

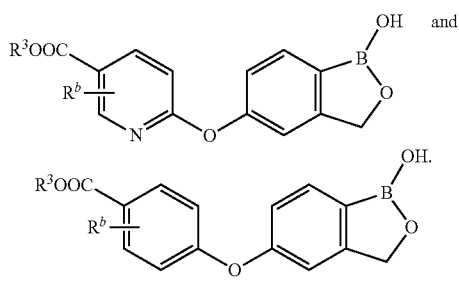

3. The compound of claim 1, or a salt thereof, wherein the compound has a formula which is a member selected from:

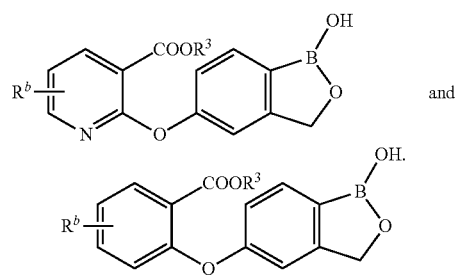

4. The compound of claim 1, or a salt thereof, wherein the compound has a formula which is a member selected from:

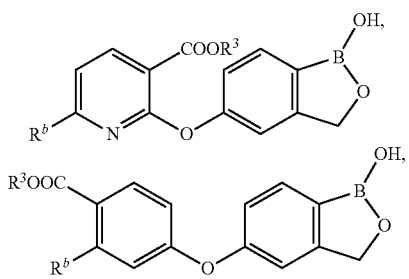

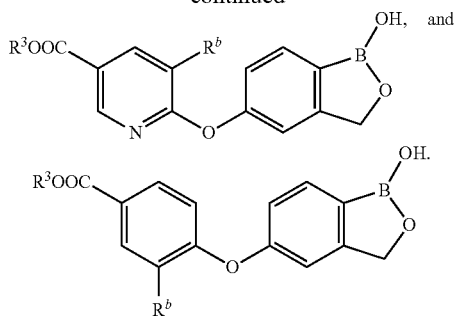

5. The compound of claim 4, or a salt thereof, wherein the compound is

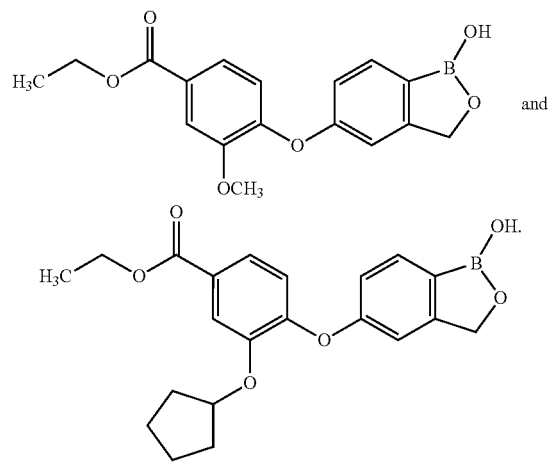

6. The compound of claim 1, or a salt thereof, wherein the compound has a formula which is a member selected from:

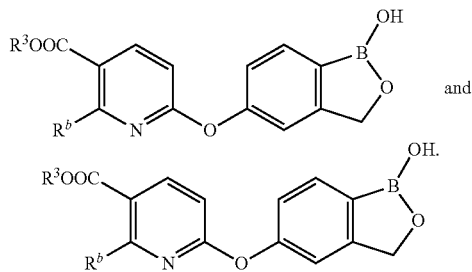

7. The compound of claim 6, or a salt thereof, wherein $R^3$ is methyl or $C_2$ alkyl or $C_3$ alkyl.

8. The compound of claim 6, or a salt thereof, wherein $R^3$ is $C_4$ alkyl or $C_5$ alkyl or $C_6$ alkyl.

9. The compound of claim 7, or a salt thereof, wherein $R^b$ is $OR^4$, and $R^4$ is unsubstituted $C_1$-$C_6$ straight chain or branched chain alkyl.

10. The compound of claim 9, or a salt thereof, wherein $R^4$ is unsubstituted $C_1$ or $C_2$ or $C_3$ straight chain or branched chain alkyl.

11. The compound of claim 9, or a salt thereof, wherein the compound is

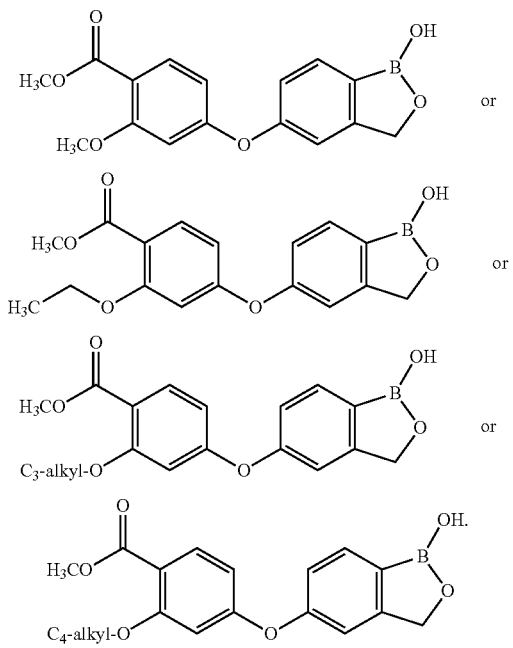

12. The compound of claim 9, or a salt thereof, wherein the compound is

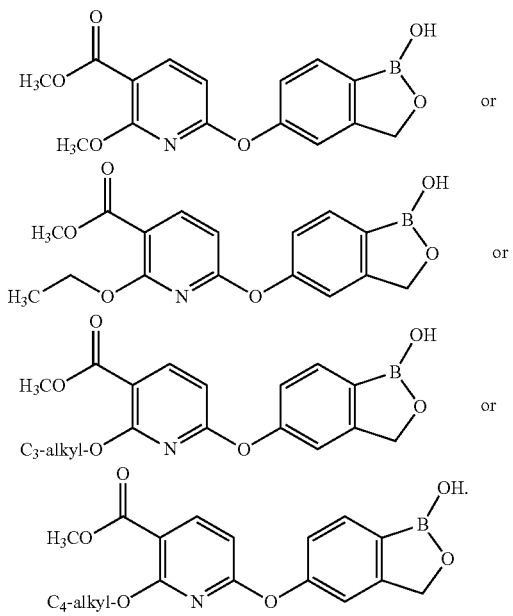

13. The compound of claim 9, or a salt thereof, wherein the compound is

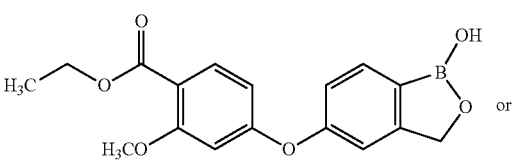

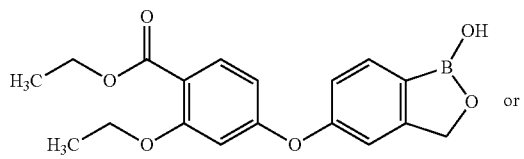

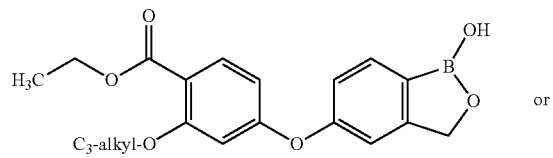

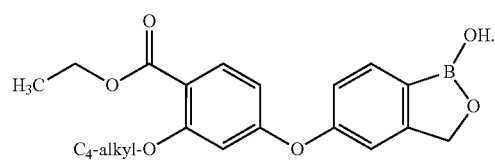

14. The compound of claim 9, or a salt thereof, wherein the compound is

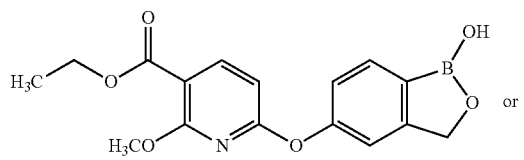

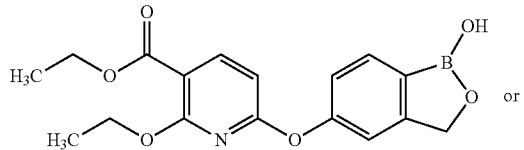

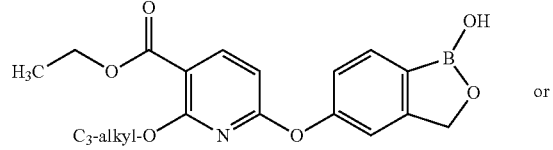

15. The compound of claim 1, or a salt thereof, wherein the compound is

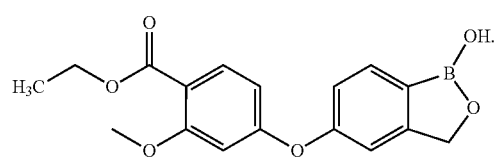 [SMILES: CCOC(=O)c1ccc(Oc2ccc3c(c2)COB3O)cc1OC]

16. The compound of claim 1, or a salt thereof, wherein the compound is

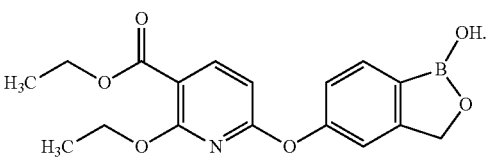 [SMILES: CCOC(=O)c1ccc(Oc2ccc3c(c2)COB3O)nc1OCC]

17. The compound of claim 16, or a salt thereof, wherein the salt is a pharmaceutically acceptable salt.

18. The compound of claim 9, or a salt thereof, wherein $R^4$ is unsubstituted $C_4$ or $C_5$ or $C_6$ alkyl.

19. The compound of claim 9, or a salt thereof, wherein $R^4$ is methyl or ethyl or propyl or isopropyl or isobutyl.

20. The compound of claim 1, or a salt thereof, wherein $R^b$ is $OR^4$, and $R^4$ is straight chain or branched chain alkyl substituted with unsubstituted cycloalkyl.

21. The compound of claim 1, or a salt thereof, wherein $R^b$ is $OR^4$, and $R^4$ is

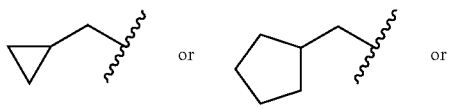

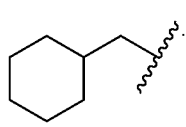

22. The compound of claim 1, or a salt thereof, wherein the compound is

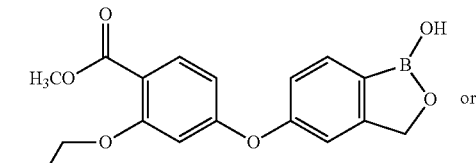

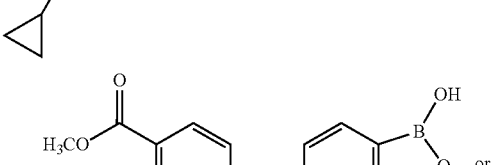

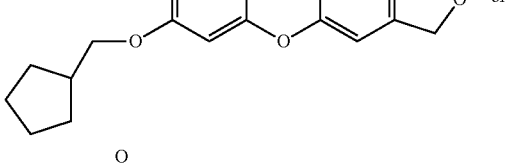

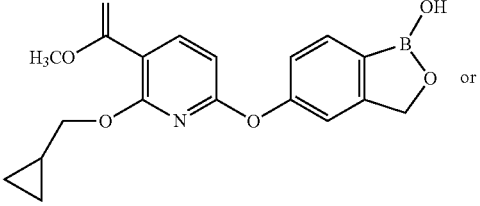

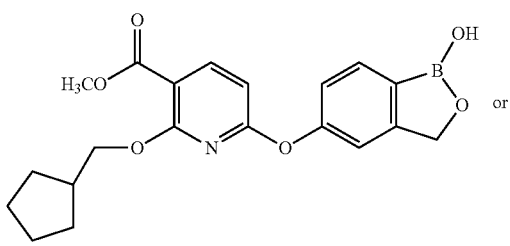

or

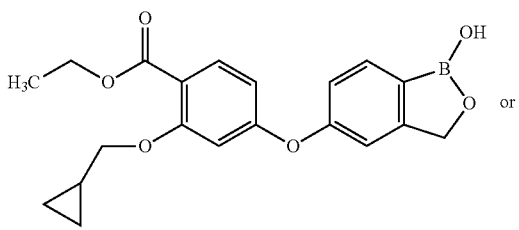

or

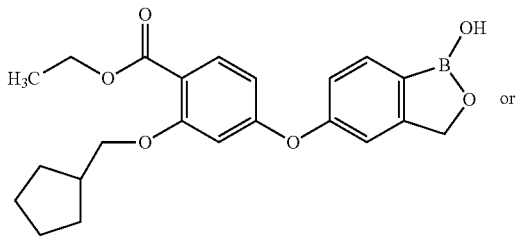

or

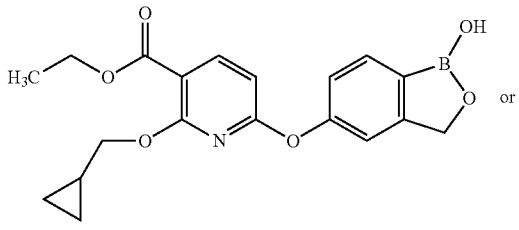

or

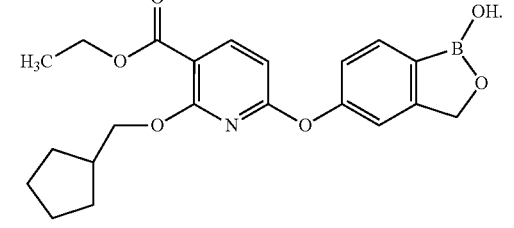

or

23. The compound of claim 1, or a salt thereof, wherein $R^b$ is $OR^4$, and $R^4$ is unsubstituted cycloalkyl.

24. The compound of claim 1, or a salt thereof, wherein $R^b$ is $OR^4$, and $R^4$ is cyclopentyl or cyclohexyl.

25. The compound of claim 1, or a salt thereof, wherein the compound is

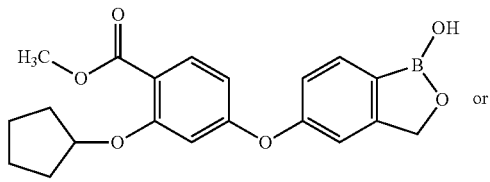

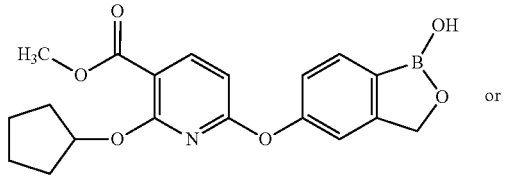

or

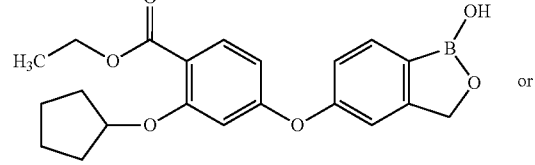

or

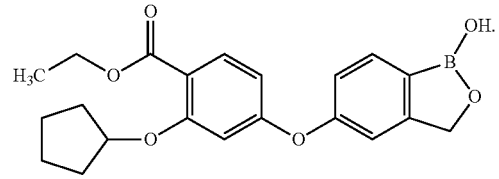

26. A pharmaceutical formulation comprising:
(a) the compound of claim 1, or a pharmaceutically acceptable salt thereof; and
(b) a pharmaceutically acceptable excipient.

27. The formulation of claim 26, wherein the compound is

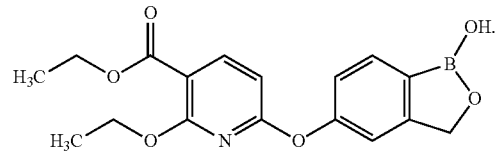 [SMILES: CCOC(=O)c1ccc(Oc2ccc3c(c2)COB3O)nc1OCC]

28. The formulation of claim 26, which is a topical formulation.

29. The formulation of claim 26, wherein the formulation is a lotion or cream or foam or gel or ointment.

30. A method of treating a condition in an animal in need of the treatment, the method comprising administering to the animal a therapeutically effective amount of the compound of claim 1, or a pharmaceutically acceptable salt thereof, thereby treating the condition, wherein said condition is psoriasis or dermatitis.

31. The method of claim 30, wherein the compound is

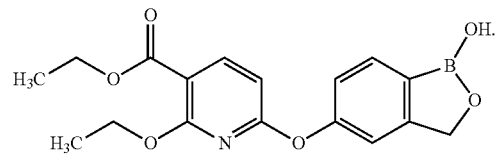

32. The method of claim 31, wherein the condition is psoriasis.

33. The method of claim 31, wherein the condition is psoriasis, and said psoriasis is plaque psoriasis.

34. The method of claim 31, wherein the condition is psoriasis, and said psoriasis is flexural psoriasis.

35. The method of claim 31, wherein the condition is psoriasis, and said psoriasis is guttate psoriasis.

36. The method of claim 31, wherein the condition is psoriasis, and said psoriasis is pustular psoriasis.

37. The method of claim 31, wherein the condition is psoriasis, and said psoriasis is nail psoriasis.

38. The method of claim 31, wherein the condition is psoriasis, and said psoriasis is psoriatic arthritis.

39. The method of claim 31, wherein the condition is psoriasis, and said psoriasis is erythrodermic psoriasis.

40. The method of claim 31, wherein the condition is dermatitis.

41. The method of claim 31, wherein the condition is dermatitis, and said dermatitis is contact dermatitis.

42. The method of claim 31, wherein the condition is dermatitis, and said dermatitis is atopic dermatitis.

43. The method of claim 31, wherein the condition is dermatitis, and said dermatitis is eczema.

\* \* \* \* \*